US012685785B2

(12) United States Patent
Jiang et al.

(10) Patent No.: US 12,685,785 B2
(45) Date of Patent: Jul. 21, 2026

(54) POLYNUCLEOTIDES ENCODING PROPIONYL-CoA CARBOXYLASE ALPHA AND BETA SUBUNITS FOR THE TREATMENT OF PROPIONIC ACIDEMIA

(71) Applicant: ModernaTX, Inc., Cambridge, MA (US)

(72) Inventors: Lei Jiang, Cambridge, MA (US); Lin Tung Guey, Lexington, MA (US); Paolo G. V. Martini, Boston, MA (US); Vladimir Presnyak, Manchester, NH (US)

(73) Assignee: ModernaTX, Inc., Cambridge, MA (US)

( * ) Notice: Subject to any disclaimer, the term of this patent is extended or adjusted under 35 U.S.C. 154(b) by 455 days.

(21) Appl. No.: 18/327,728

(22) Filed: Jun. 1, 2023

(65) Prior Publication Data

US 2024/0024506 A1 Jan. 25, 2024

Related U.S. Application Data

(63) Continuation of application No. 16/765,632, filed as application No. PCT/US2018/062283 on Nov. 21, 2018, now abandoned.

(60) Provisional application No. 62/747,356, filed on Oct. 18, 2018, provisional application No. 62/693,552, filed on Jul. 3, 2018, provisional application No. 62/663,024, filed on Apr. 26, 2018, provisional application No. 62/614,787, filed on Jan. 8, 2018, provisional application No. 62/590,199, filed on Nov. 22, 2017.

(51) Int. Cl.

| | |
|---|---|
| *A61K 48/00* | (2006.01) |
| *A61K 9/1271* | (2025.01) |
| *A61K 38/43* | (2006.01) |
| *A61K 38/53* | (2006.01) |
| *A61P 3/00* | (2006.01) |

(52) U.S. Cl.
CPC ........ *A61K 48/0033* (2013.01); *A61K 9/1271* (2013.01); *A61K 38/53* (2013.01); *A61P 3/00* (2018.01); *C12Y 604/01003* (2013.01)

(58) Field of Classification Search
None
See application file for complete search history.

(56) References Cited

U.S. PATENT DOCUMENTS

| | | | |
|---|---|---|---|
| 8,691,966 B2 | 4/2014 | Kariko et al. | |
| 2014/0155468 A1 | 6/2014 | Gregory et al. | |
| 2018/0126003 A1 | 5/2018 | Ingmar | |
| 2018/0126005 A1 | 5/2018 | Fotin-Mleczek | |
| 2018/0221402 A1 | 8/2018 | Prieve et al. | |
| 2019/0175759 A1 | 6/2019 | Fotin-Mleczek et al. | |

| | | |
|---|---|---|
| 2020/0165593 A1 | 5/2020 | Sobolov-Jaynes |
| 2022/0265856 A1 | 8/2022 | Jiang et al. |
| 2024/0216288 A1 | 7/2024 | Benenato et al. |
| 2024/0316165 A1 | 9/2024 | Attarwala et al. |

FOREIGN PATENT DOCUMENTS

| | | |
|---|---|---|
| WO | WO1995027512 | 10/1995 |
| WO | WO2009030481 | 3/2009 |
| WO | WO2009127230 | 10/2009 |
| WO | WO2013151665 | 10/2013 |
| WO | WO2013151666 | 10/2013 |
| WO | WO2014152513 | 9/2014 |
| WO | WO2014160243 | 10/2014 |
| WO | WO2015017519 | 2/2015 |
| WO | WO2016118697 | 7/2016 |
| WO | WO2016179138 | 11/2016 |
| WO | WO2017049245 | 3/2017 |
| WO | WO2017062513 | 4/2017 |
| WO | WO2017070616 | 4/2017 |
| WO | WO2017070626 | 4/2017 |
| WO | WO2017100551 | 6/2017 |
| WO | WO2017147720 | 9/2017 |
| WO | WO2017153936 | 9/2017 |
| WO | WO2017191274 | 11/2017 |
| WO | WO2017192761 | 11/2017 |
| WO | WO2017201349 | 11/2017 |
| WO | WO2018204603 | 11/2018 |

(Continued)

OTHER PUBLICATIONS

Alignment_SEQ 11 to SEQ 5 in U.S. Appl. No. 18/578,052, filed 2025.*
Alignment_SEQ 25 to SEQ 6 in U.S. Appl. No. 18/578,052, filed 2025.*
Pardi et al., J. Control. Rel., 2015, 217: 345-351.*
Alignment_Flotin-Mleczek_SEQ 25, 2025.*
U.S. Appl. No. 16/765,632, filed May 20, 2020, Lei Jiang.
U.S. Appl. No. 16/631,607, filed Jan. 16, 2020, Susan Sobolov-Jaynes.

(Continued)

*Primary Examiner* — Ileana Popa
(74) *Attorney, Agent, or Firm* — Fish & Richardson P.C.

(57) ABSTRACT

This disclosure relates to mRNA therapy for the treatment of propionic acidemia (PA). mRNAs for use in the invention, when administered in vivo, encode human propionyl-CoA carboxylase alpha (PCCA) and/or human propionyl-CoA carboxylase beta (PCCB), and isoforms thereof, functional fragments thereof, and fusion proteins comprising PCCA and/or PCCB. mRNAs of the invention are preferably encapsulated in lipid nanoparticles (LNPs) to effect efficient delivery to cells and/or tissues in subjects, when administered thereto. mRNA therapies of the invention increase and/or restore deficient levels of propionyl-CoA carboxylase (PCC) expression and/or activity in subjects. mRNA therapies of the invention further decrease levels of disease-associated toxic metabolites associated with deficient PCCA or PCCB activity, in subjects.

42 Claims, 47 Drawing Sheets

Specification includes a Sequence Listing.

(56) References Cited

FOREIGN PATENT DOCUMENTS

| | | |
|---|---|---|
| WO | WO2018232357 | 12/2018 |
| WO | WO2019018765 | 1/2019 |
| WO | WO2020061295 | 3/2020 |
| WO | WO2020072451 | 4/2020 |
| WO | WO2020264353 | 12/2020 |
| WO | WO2021076797 | 4/2021 |
| WO | WO2022204380 | 9/2022 |
| WO | WO2023287751 | 1/2023 |

OTHER PUBLICATIONS

Chandler et al., "Efficacy of Adeno-associated Viral Gene Therapy as a Treatment for Methylmalonic and Propionic Acidemia," Dissertation for the degree of Doctor of Philosophy, The Faculty of the Columbian College of Arts and Sciences of The George Washington University, May 20, 2012, 113 pages.

Charbit-Henrion et al., "Early and Late Complications After Liver Transplantation for Propionic Acidemia in Children: A Two Centers Study," American Journal of Transplantation, Mar. 2015, 15(3):786-791.

Critelli et al., "Liver Transplantation for Propionic Acidemia and Methylmalonic Acidemia: Perioperative Management and Clinical Outcomes," Liver Transplantation, Sep. 2018, 24(9):1260-1270.

GenBank Accession No. NM_000282.3, "*Homo sapiens* propionyl-CoA carboxylase subunit alpha (PCCA), transcript variant 1, mRNA," Oct. 21, 2018, 7 pages.

GenBank Accession No. NM_000532.4, "*Homo sapiens* propionyl-CoA carboxylase subunit beta (PCCB), transcript variant 1, mRNA," Oct. 20, 2018, 5 pages.

GenBank Accession No. NM_001127692.2, "*Homo sapiens* propionyl-CoA carboxylase subunit alpha (PCCA), transcript variant 2, mRNA; nuclear gene for mitochondrial product," Jul. 22, 2020, 4 pages.

GenBank Accession No. NM_001178004.1, "*Homo sapiens* propionyl-CoA carboxylase subunit alpha (PCCA), transcript variant 3, mRNA; nuclear gene for mitochondrial product," Jul. 22, 2020, 5 pages.

GenBank Accession No. NM_001178014.1, "*Homo sapiens* propionyl-CoA carboxylase subunit beta (PCCB), transcript variant 2, mRNA; nuclear gene for mitochondrial product," Jul. 23, 2020, 5 pages.

GenPept Accession No. NP_000273.2, "propionyl-CoA carboxylase alpha chain, mitochondrial isoform a precursor [*Homo sapiens*]," Nov. 17, 2019, 5 pages.

GenPept Accession No. NP_000523.2, "propionyl-CoA carboxylase beta chain, mitochondrial isoform 1 precursor [*Homo sapiens*]," Aug. 22, 2019, 4 pages.

GenPept Accession No. NP_001121164.1, "propionyl-CoA carboxylase alpha chain, mitochondrial isoform b [*Homo sapiens*]," Sep. 21, 2019, 3 pages.

GenPept Accession No. NP_001171475.1, "propionyl-CoA carboxylase alpha chain, mitochondrial isoform c precursor [*Homo sapiens*]," Sep. 21, 2019, 3 pages.

GenPept Accession No. NP_001171485.1, "propionyl-CoA carboxylase beta chain, mitochondrial isoform 2 precursor [*Homo sapiens*]," Aug. 4, 2019, 3 pages.

International Preliminary Report on Patentability in International Application No. PCT/US2022/021713, mailed on Oct. 5, 2023, 7 pages.

International Preliminary Report on Patentability in International Application No. PCT/US2022/036769, mailed on Jan. 25, 2024, 10 pages.

International Search Report and Written Opinion in International Application No. PCT/US2022/021713, mailed on Jul. 22, 2022, 15 pages.

International Search Report and Written Opinion in International Application No. PCT/US2022/036769, mailed on Nov. 22, 2022, 18 pages.

Jiang et al., "Dual mRNA Therapy Restores Metabolic Function in Long-term Studies in Mice with Propionic Acidemia," Nature Communications, Oct. 21, 2020, 11(5339):1-10.

Jiang et al., "Supplementary data to: Dual mRNA Therapy Restores Metabolic Function in Long-term Studies in Mice with Propionic Acidemia," Nature Communications, Oct. 21, 2020, 11(5339), 22 pages.

Lomash et al., "Successfully Navigating Food and Drug Administration Orphan Drug and Rare Pediatric Disease Designations for AAV9-hPCCA Gene Therapy: The National Institutes of Health Platform Vector Gene Therapy Experience," Human Gene Therapy, Mar. 2023, 34(5-6):217-227.

McKusick et al., "OMIM 232000—Ropionyl-CoA Carboxylase, Alpha Subunit; PCCA," Jun. 3, 1986, last updated Dec. 20, 2021, 11 pages.

McKusick et al., "OMIM 232050—Propionyl-CoA Carboxylase, Beta Subunit; PCCB," Jun. 24, 1986, last updated Nov. 28, 2008, 11 pages.

Quintero et al., "The Role of Liver Transplantation in Propionic Acidemia," Liver Transplantation, Dec. 2018, 24(12):1736-1745.

Silva et al., "Liver Transplantation for Propionic Acidemia," Journal of Pediatric Gastroenterology and Nutrition, Mar. 2017, 64(3):e73-76.

Vara et al., "Liver transplantation for propionic acidemia in children," Liver Transplantation, Jun. 2011, 17(6):661-667.

U.S. Appl. No. 16/765,632, 20220265856, May 20, 2020, Jiang.

U.S. Appl. No. 16/631,607, 20200165593, Jan. 16, 2020, Sobolov-Jaynes.

U.S. Appl. No. 18/578,052, filed Jan. 10, 2024, Attarwala.

U.S. Appl. No. 18/282,640, filed Sep. 18, 2023, Benenato.

SCV Search Results Details for U.S. Appl. No. 16/765,632 and Search Result 20240905, "Sequence alignment, BFB44649 standard; RNA; 1620 BP," first entry on Apr. 5, 2018, retrieved on Jan. 1, 2025, 3 pages.

U.S. Appl. No. 18/578,052, 20240316165, Jan. 10, 2024, Attarwala.

U.S. Appl. No. 18/282,640, 20240216288, Sep. 18, 2023, Benenato.

Guenzel et al., "Generation of a Hypomorphic Model of Propionic Acidemia Amenable to Gene Therapy Testing," Molecular Therapy, Jul. 2013, 21(7):1316-1323.

Clavero et al., "Functional characterization of PCCA mutations causing propionic acidemia", Molecular Basis of Disease, Nov. 2002, 1588(2):119-125.

Darvish-Damavandi et al., "Towards the development of an enzyme replacement therapy for the metabolic disorder propionic acidemia", Molecular Genetics and Metabolism Reports, Jul. 2016, 8:51-60.

Dreyfus et al., "The Poly(A) Tail of mRNAs: Bodyguard in Eukaryotes, Scavenger in Bacteria," Cell, Nov. 2002, 111:611-613.

Hanson et al., "Codon optimality, bias and usage in translation and mRNA decay", Nat. Rev. Mol. Cell Biol., Oct. 2017, 19(1):20-30.

Kurokawa et al., "Development of New Treatment Method of Propionic Acidemia (PA)," Talk, 3T21-6, 2008, 3 pages (with English Translation).

Lamhonwah et al., "Correction of the Metabolic Defect in Propionic Acidemia Fibroblasts by Microinjection of a Full-Length cDNA or RNA Transcript Encoding the Propionyl-CoA Carboxylase beta Subunit," Genomics, 1994, 19(3):500-505.

PCT International Preliminary Report on Patentability in International Appln. No. PCT/US2018/043089, dated Jan. 30, 2020, 8 pages.

PCT International Preliminary Report on Patentability in International Appln. No. PCT/US2018/062283, dated Jun. 4, 2020, 20 pages.

PCT International Search Report and Written Opinion in International Appln. No. PCT/US2018/043089, dated Oct. 19, 2018, 16 pages.

PCT International Search Report and Written Opinion in International Appln. No. PCT/US2018/062283, dated May 17, 2019, 35 pages.

Perez-Cerda et al., "Functional analysis of PCCB mutations causing propionic acidemia based on expression studies in deficient human skin fibroblasts", Biochimica Et Biophysica Acta. Molecular Basis of Disease, Apr. 2003, 1638(1):45.

Perez-Cerda et al., "Functional Analysis of PCCB Mutations Causing Propionic Acidemia Based on Expression Studies in Deficient Human Skin Fibroblasts," Biochimica et Biophysica Acta, May 2003, 1638(1):43-49.

(56) References Cited

OTHER PUBLICATIONS

Rodriguez-Pombo et al., "Transfection Screening for Defects in the PCCA and PCCB Genes Encoding Propionyl-CoA Carboxylase Subunits", Molecular Genetics and Metabolism, 2002, 75:276-279.

Shchelochkov et al., "Propionic Acidemia" GeneReviews, 2016, 30 pages.

Tavernier et al., "mRNA as gene therapeutic: How to control protein expression", Journal of Controlled Release, Oct. 2010, 150(3):240-241.

Wongkittichote et al., "Propionyl-CoA carboxylase—A review", Molecular Genetics and Metabolism, Oct. 2017, 122(4):145-152.

Yamamoto et al., "Current prospects for mRNA gene delivery", European Journal of Pharmaceutics and Biopharmaceutics, Oct. 2008, 71(3):484-489.

Youn et al., "Modified mRNA as an alternative to plasmid DNA (pDNA) for transcript replacement and vaccination therapy", Expert Opinion on Biological Therapy, Jun. 2015, 15(9):1337-1348.

\* cited by examiner

PCCA mRNA

FIGURE 5

| mRNA | Ratio to GFP |
| --- | --- |
| PCCA_11 | 40.0 |
| PCCA_12 | 48.9 |
| PCCA_13 | 49.4 |
| PCCA_14 | 51.6 |
| PCCA_15 | 53.3 |
| PCCA_16 | 49.0 |
| PCCA_17 | 55.5 |
| PCCA_18 | 44.1 |
| PCCA_19 | 41.0 |
| PCCA_20 | 53.4 |
| PCCA-014 | 49.4 |

Transfection with 1ug mRNA for ~40hrs
~25ug protein was loaded to the PCC reaction

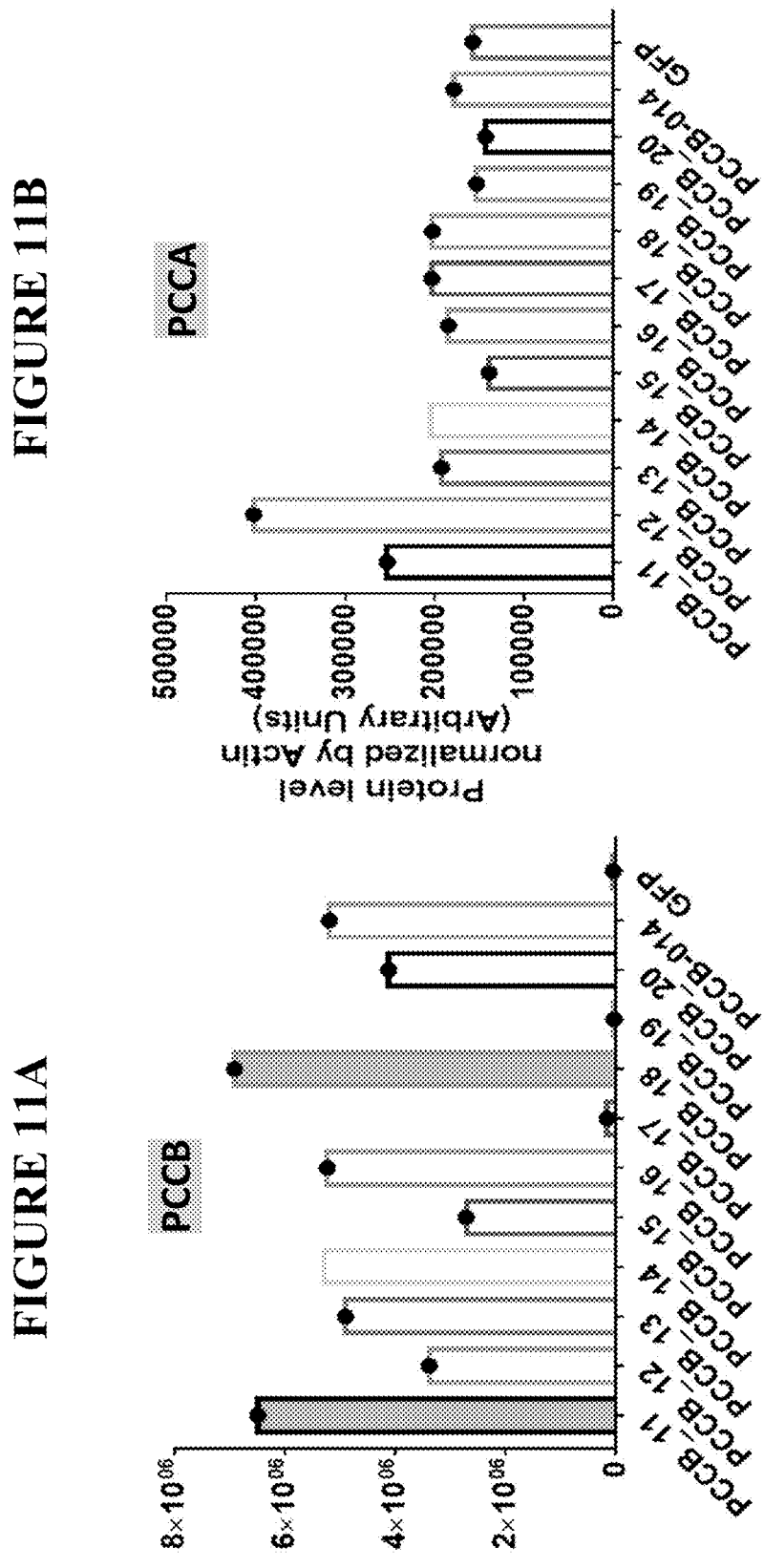

| mRNA | Ratio to GFP |
|---|---|
| PCCA_11 | 1.6 |
| PCCA_12 | 1.5 |
| PCCA_13 | 1.4 |
| PCCA_14 | 1.4 |
| PCCA_15 | 1.2 |
| PCCA_16 | 1.5 |
| PCCA_17 | 1.7 |
| PCCA_18 | 1.7 |
| PCCA_19 | 1.8 |
| PCCA_20 | 1.4 |
| PCCA_014 | 1.5 |

POLYNUCLEOTIDES ENCODING PROPIONYL-CoA CARBOXYLASE ALPHA AND BETA SUBUNITS FOR THE TREATMENT OF PROPIONIC ACIDEMIA

CROSS-REFERENCE TO RELATED APPLICATIONS

This application is a continuation application of U.S. application Ser. No. 16/765,632 filed May 20, 2020, which is a § 371 of International Appln No. PCT/US2018/062283 filed Nov. 21, 2018, which claims priority to U.S. Provisional Appl. No. 62/590,199, filed Nov. 22, 2017, U.S. Provisional Appl. No. 62/614,787, filed Jan. 8, 2018, U.S. Provisional Appl. No. 62/663,024, filed Apr. 26, 2018, U.S. Provisional Appl. No. 62/693,552, filed Jul. 3, 2018, and U.S. Provisional Appl. No. 62/747,356, filed Oct. 18, 2018. The content of the prior applications are incorporated by reference herein in their entirety.

SEQUENCE LISTING

This application contains a Sequence Listing that has been submitted electronically as an XML file named "45817-0024002_SL_ST26.XML." The XML file, created on May 31, 2023, is 334,968 bytes in size. The material in the XML file is hereby incorporated by reference in its entirety.

BACKGROUND

Propionic acidemia (PA), or propionic aciduria, is a rare, autosomal recessive metabolic disorder with significant morbidity and mortality that is caused by a deficiency in propionyl-CoA carboxylase (PCC) that prevents the enzyme from catalyzing the carboxylation of propionyl-CoA to methylmalonyl-CoA. Wongkittichote et al., *Mol. Genet. Metab.*, Epub ahead of print. (2017). Disruption of PCC function causes propionyl-CoA and metabolites of propionate metabolism (breakdown of certain amino acids and fats) to accumulate in the blood, urine and other fluids and tissues/cells, which can lead to metabolic acidosis and hyperammonemia. Propionylcarnitine (C3), the levocarnitine ester of propionyl-CoA, 2-methylcitirc acid (2-MC), 3-hydroxypropionic acid (3OHPA), propionylglycine, glycine, lactate and ammonia are also elevated in individuals with PA, and can serve as biomarkers for the disorder. Classical PA, caused by a complete loss of PCC function, usually presents in neonates in the first few hours or days after birth, with symptoms resulting from metabolic decompensation, including poor feeding, vomiting, hyper- or hypotonia, temperature instability, irritability, and lethargy. In rarer cases, late onset PA can occur after infancy, triggered by physical stress, such as infection. Mistreatment of acute metabolic discompensation, or lack of treatment, can lead to coma or death. The risk of mortality in this disorder is significant, as each acute metabolic decompensation is life-threatening and can lead to irreversible sequelae. Long-term complications of PA include neurodevelopmental sequelae, including significant cognitive deficits and developmental delays in motor and language skills, cardiomyopathy, arrhythmia, and pancreatitis. PA has an estimated incidence of 1:105,000 to 1:130,000 in the United States, but is higher in parts of the Middle East. Shchelochkov et al., GeneReviews (2016).

PCC (E.C. 6.4.1.3) is a heterodecamer composed of six propionyl-CoA carboxylase alpha subunits, encoded by PCCA (OMIM 232000), and 6 propionyl-CoA beta subunits, encoded by PCCB (OMIM 232050). The PCC enzyme is expressed in several tissues, and localizes to mitochondria where it engages with its necessary co-factor, biotin. There are three PCCA isoforms. The first isoform (NM_000282.3) encodes a protein (NP_000273.2) that is 728 amino acids in length, while isoform 2 (NM_001127692.2) encodes a protein (NP_001121164.1) that is 702 amino acids long, and isoform 3 (NM_001178004.1) encodes a protein (NP_001171475.1) that is 681 amino acids long. PCCA null variants, such as R288X and S537X, result in severe phenotypes, while splice type variants can result in milder disease. PCCB isoform 1 (NM_000532.4 encodes a protein (NP_000523.2) that is 539 amino acids in length, while isoform 2 (NM_001178014.1) encodes a protein (NP 001171485.1) that is 559 amino acids long. PCCB requires PCCA for stability, and can be absent in individuals lacking functional PCCA. Some PCCB gene variants disturb the interaction between PCCA and PCCB.

Elevated levels of intermediaries such as C3, 2-MC, 3-OHPA, and/or ammonia can be used as diagnostic markers for PA. Prenatal testing of 2-MC levels in amniotic fluids and newborn screening for elevated levels of C3 in dried blood spot can be used to diagnose PA prior to clinical presentation of the disease postpartum. There are no approved therapies for PA in the U.S., and management of the disorder is limited generally to the strict dietary restriction of amino acids and odd-chain fatty acids, the precursors of propionic acid, while ensuring sufficient essential amino acids and nutrients to the diet, carnitine supplementation, antibiotics to decrease propionate production from gut bacteria, and vigilant medical monitoring. Acutely hyperammonemic individuals may require detoxification using ammonia scavengers such as Carbaglu® (which is approved in Europe for the treatment of hyperammonemia due to PA) and/or sodium benzoate. In severe cases, an individual could receive a liver transplant.

In view of the significant problems associated with existing PA treatments, there is an unmet need for an improved treatment for PA

SUMMARY

The present invention provides messenger RNA (mRNA) therapeutics for the treatment of propionic acidemia (PA). The mRNA therapeutics of the invention are particularly well-suited for the treatment of PA as the technology provides for the intracellular delivery of mRNA encoding PCCA and/or PCCB followed by de novo synthesis of functional PCCA and/or PCCB protein within target cells. The instant invention features the incorporation of modified nucleotides within therapeutic mRNAs to (1) minimize unwanted immune activation (e.g., the innate immune response associated with the in vivo introduction of foreign nucleic acids) and (2) optimize the translation efficiency of mRNA to protein. Exemplary aspects of the invention feature a combination of nucleotide modification to reduce the innate immune response and sequence optimization, in particular, within the open reading frame (ORF) of therapeutic mRNAs encoding PCCA or PCCB to enhance protein expression.

In further embodiments, the mRNA therapeutic technology of the instant invention also features delivery of mRNA encoding PCCA and/or PCCB via a lipid nanoparticle (LNP) delivery system. The instant invention features ionizable lipid-based LNPs, which have improved properties when combined with mRNA encoding PCCA and/or PCCB and administered in vivo, for example, cellular uptake, intracellular transport and/or endosomal release or endosomal escape. The LNP formulations of the invention also demonstrate reduced immunogenicity associated with the in vivo administration of LNPs.

In certain aspects, the invention relates to compositions and delivery formulations comprising a polynucleotide, e.g., a ribonucleic acid (RNA), e.g., a mRNA, encoding PCCA or PCCB and methods for treating PA in a human subject in need thereof by administering the same.

The present disclosure provides a pharmaceutical composition comprising a lipid nanoparticle encapsulated mRNA that comprises an open reading frame (ORF) encoding a PCCA or PCCB polypeptide, wherein the composition is suitable for administration to a human subject in need of treatment for PA.

The present disclosure further provides a pharmaceutical composition comprising: (a) a mRNA that comprises (i) an open reading frame (ORF) encoding a PCCA or PCCB polypeptide, wherein the ORF comprises at least one chemically modified nucleobase, sugar, backbone, or any combination thereof and (ii) an untranslated region (UTR) comprising a microRNA (miRNA) binding site; and (b) a delivery agent, wherein the pharmaceutical composition is suitable for administration to a human subject in need of treatment for PA. In some cases, the pharmaceutical composition comprises (a) an mRNA that comprises an ORF encoding PCCA, and an mRNA that comprises an ORF encoding PCCB, wherein each ORF comprises at least one chemically modified nucleobase, sugar, backbone, or any combination thereof, and an untranslated region (UTR) comprising a microRNA (miRNA) binding site; and (b) a delivery agent.

In one aspect, the disclosure features a pharmaceutical composition comprising an mRNA comprising an open reading frame (ORF) encoding a propionyl-CoA carboxylase alpha (PCCA) polypeptide, wherein the composition when administered as a single intravenous dose to a human subject in need thereof is sufficient to:

(i) increase the level of PCC activity in liver tissue to within at least 2%, at least 5%, at least 10%, at least 20%, at least 30%, at least 40%, at least 50%, at least 60%, at least 70%, at least 80%, at least 90%, or at least 100% of normal PCC activity level for at least 12 hours, at least 24 hours, at least 48 hours, at least 72 hours, at least 96 hours, at least 120 hours, at least 1 week, at least 2 weeks, at least 3 weeks, at least 4 weeks, at least 8 weeks, or at least 12 weeks post-administration;

(ii) increase the level of PCC activity in liver tissue at least 1.5-fold, at least 2-fold, at least 3-fold, at least 4-fold, at least 5-fold, at least 10-fold, at least 20-fold, or at least 50-fold compared to the subject's baseline PCC activity level or a reference PCC activity level in a human subject having propionic academia (PA) for at least 12 hours, at least 24 hours, at least 48 hours, at least 72 hours, at least 96 hours, at least 120 hours, at least 1 week, at least 2 weeks, at least 3 weeks, at least 4 weeks, at least 8 weeks, or at least 12 weeks post-administration;

(iii) reduce plasma, serum, whole blood (including dried blood spot), urine, and/or liver levels of propionic acid at least 30%, at least 40%, at least 50%, at least 60%, at least 70%, at least 80%, at least 90%, or at least 100% compared to the subject's baseline plasma, serum, whole blood, urine, and/or liver levels of propionic acid or a reference plasma, serum, whole blood (including dried blood spot), urine, and/or liver levels of propionic acid in a human subject having propionic acidemia (PA) for at least 12 hours, at least 24 hours, at least 48 hours, at least 72 hours, at least 96 hours, at least 120 hours, at least 1 week, at least 2 weeks, at least 3 weeks, at least 4 weeks, at least 8 weeks, or at least 12 weeks post-administration;

(iv) reduce plasma, serum, whole blood, and/or urine levels of propionyl-L-carnitine (C3), 2-methylcitric acid (2-MC), 3-hydroxypropionic acid, (3OHPA), propionylglycine, glycine, lactate and/or ammonia at least 30%, at least 40%, at least 50%, at least 60%, at least 70%, at least 80%, at least 90%, or at least 100% compared to the subject's baseline plasma, serum, or urine level or a reference plasma, serum, or urine C3, 2-MC, 3OHPA, propionylglycine, glycine, lactate and/or ammonia level in a human subject having PA for at least 12 hours, at least 24 hours, at least 48 hours, at least 72 hours, at least 96 hours, at least 120 hours, at least 1 week, at least 2 weeks, at least 3 weeks, at least 4 weeks, at least 8 weeks, or at least 12 weeks post-administration;

(v) reduce plasma, serum, whole blood, urine, and/or liver levels of propionic acid at least 1.5-fold, at least 2-fold, at least 5-fold, at least 10-fold, at least 20-fold, or at least 50-fold as compared to the subject's baseline plasma, serum, whole blood, urine, and/or liver propionic acid level or a reference plasma, serum, whole blood, urine, and/or liver propionic acid level in a patient with PA for at least 12 hours, at least 24 hours, at least 48 hours, at least 72 hours, at least 96 hours, at least 120 hours, at least 1 week, at least 2 weeks, at least 3 weeks, at least 4 weeks, at least 8 weeks, or at least 12 weeks post-administration; and/or (vi) reduce plasma, serum, and/or urine level of C3, 2-MC, 3OHPA, propionylglycine, glycine, lactate and/or ammonia at least 1.5-fold, at least 2-fold at least 5-fold, at least 10-fold, at least 20-fold or at least 50-fold as compared to the subject's baseline plasma, serum, and/or urine C3, 2-MC, 3OHPA, propionylglycine, glycine, lactate and/or ammonia level or a reference plasma, serum, and/or urine C3, 2-MC, 3OHPA, propionylglycine, glycine, lactate and/or ammonia level in a patient with PA for at least 12 hours, at least 24 hours, at least 48 hours, at least 72 hours, at least 96 hours, at least 120 hours, at least 1 week, at least 2 weeks, at least 3 weeks, at least 4 weeks, at least 8 weeks, or at least 12 weeks post-administration.

In another aspect, the disclosure features a pharmaceutical composition comprising an mRNA comprising an open reading frame (ORF) encoding a propionyl-CoA carboxylase beta (PCCB) polypeptide, wherein the composition when administered as a single intravenous dose to a human subject in need thereof is sufficient to:

(i) increase the level of PCC activity in liver tissue to within at least 2%, at least 5%, at least 10%, at least 20%, at least 30%, at least 40%, at least 50%, at least 60%, at least 70%, at least 80%, at least 90%, or at least 100% of normal PCC activity level for at least 12 hours, at least 24 hours, at least 48 hours, at least 72 hours, at least 96 hours, at least 120 hours, at least 1 week, at least 2 weeks, at least 3 weeks, at least 4 weeks, at least 8 weeks, or at least 12 weeks post-administration;

(ii) increase the level of PCC activity in liver tissue at least 1.5-fold, at least 2-fold, at least 3-fold, at least 4-fold, at least 5-fold, at least 10-fold, at least 20-fold, or at least 50-fold compared to the subject's baseline PCC activity level or a reference PCC activity level in a human subject having propionic academia (PA) for at least 12 hours, at least 24 hours, at least 48 hours, at least 72 hours, at least 96 hours, at least 120 hours, at least 1 week, at least 2 weeks, at least 3 weeks, at least 4 weeks, at least 8 weeks, or at least 12 weeks post-administration;

(iii) reduce plasma, serum, whole blood, urine, and/or liver levels of propionic acid at least 30%, at least 40%, at least 50%, at least 60%, at least 70%, at least 80%, at least 90%, or at least 100% compared to the subject's baseline plasma, serum, whole blood, urine, and/or liver propionic acid level or a reference plasma, serum, whole blood, urine, and/or liver propionic acid level in a human subject having PA for at least 12 hours, at least 24 hours, at least 48 hours, at least 72 hours, at least 96 hours, at least 120 hours, at least 1 week, at least 2 weeks, at least 3 weeks, at least 4 weeks, at least 8 weeks, or at least 12 weeks post-administration;

(iv) reduce plasma, serum, whole blood, and/or urine levels of propionyl-L-carnitine (C3), 2-methylcitric acid (2-MC), 3-hydroxypropionic acid, (3OHPA), propionylglycine, glycine, lactate and/or ammonia at least 30%, at least 40%, at least 50%, at least 60%, at least 70%, at least 80%, at least 90%, or at least 100% compared to the subject's baseline plasma, serum, or urine level or a reference plasma, serum, or urine C3, 2-MC, 3OHPA, propionylglycine, glycine, lactate and/or ammonia level in a human subject having PA for at least 12 hours, at least 24 hours, at least 48 hours, at least 72 hours, at least 96 hours, at least 120 hours, at least 1 week, at least 2 weeks, at least 3 weeks, at least 4 weeks, at least 8 weeks, or at least 12 weeks post-administration;

(v) reduce plasma, serum, whole blood, urine, and/or liver levels of propionic acid at least 1.5-fold, at least 2-fold, at least 5-fold, at least 10-fold, at least 20-fold, or at least 50-fold as compared to the subject's baseline plasma, serum, whole blood, urine, and/or liver propi-onic acid level or a reference plasma, serum, whole blood, urine, and/or liver propionic acid level in a patient with PA for at least 12 hours, at least 24 hours, at least 48 hours, at least 72 hours, at least 96 hours, at least 120 hours, at least 1 week, at least 2 weeks, at least 3 weeks, at least 4 weeks, at least 8 weeks, or at least 12 weeks post-administration; and/or (vi) reduce plasma, serum, and/or urine level of C3, 2-MC, 3OHPA, propionylglycine, glycine, lactate and/or ammonia at least 1.5-fold, at least 2-fold at least 5-fold, at least 10-fold, at least 20-fold or at least 50-fold as compared to the subject's baseline plasma, serum, and/or urine C3, 2-MC, 3OHPA, propionylgly-cine, glycine, lactate and/or ammonia level or a refer-ence plasma, serum, and/or urine C3, 2-MC, 3OHPA, propionylglycine, glycine, lactate and/or ammonia level in a patient with PA for at least 12 hours, at least 24 hours, at least 48 hours, at least 72 hours, at least 96 hours, at least 120 hours, at least 1 week, at least 2 weeks, at least 3 weeks, at least 4 weeks, at least 8 weeks, or at least 12 weeks post-administration.

In another aspect, the disclosure features a pharmaceutical composition comprising an mRNA comprising an open reading frame (ORF) encoding a propionyl-CoA carboxy-lase alpha (PCCA) polypeptide and an mRNA comprising an open reading frame (ORF) encoding a propionyl-CoA car-boxylase beta (PCCB) polypeptide, wherein the composition when administered as a single intravenous dose to a human subject in need thereof is sufficient to:

(i) increase the level of PCC activity in liver tissue to within at least 2%, at least 5%, at least 10%, at least 20%, at least 30%, at least 40%, at least 50%, at least 60%, at least 70%, at least 80%, at least 90%, or at least 100% of normal PCC activity level for at least 12 hours, at least 24 hours, at least 48 hours, at least 72 hours, at least 96 hours, at least 120 hours, at least 1 week, at least 2 weeks, at least 3 weeks, at least 4 weeks, at least 8 weeks, or at least 12 weeks post-administration;

(ii) increase the level of PCC activity in liver tissue at least 1.5-fold, at least 2-fold, at least 3-fold, at least 4-fold, at least 5-fold, at least 10-fold, at least 20-fold, or at least 50-fold compared to the subject's baseline PCC activity level or a reference PCC activity level in a human subject having propionic academia (PA) for at least 12 hours, at least 24 hours, at least 48 hours, at least 72 hours, at least 96 hours, at least 120 hours, at least 1 week, at least 2 weeks, at least 3 weeks, at least 4 weeks, at least 8 weeks, or at least 12 weeks post-administration;

(iii) reduce plasma, serum, whole blood, urine, and/or liver levels of propionic acid at least 30%, at least 40%, at least 50%, at least 60%, at least 70%, at least 80%, at least 90%, or at least 100% compared to the subject's baseline plasma, serum, whole blood, urine, and/or liver propionic acid level or a reference plasma, serum, whole blood, urine, and/or liver propionic acid level in a human subject having PA for at least 12 hours, at least 24 hours, at least 48 hours, at least 72 hours, at least 96 hours, at least 120 hours, at least 1 week, at least 2 weeks, at least 3 weeks, at least 4 weeks, at least 8 weeks, or at least 12 weeks post-administration;

(iv) reduce plasma, serum, whole blood, and/or urine levels of propionyl-L-carnitine (C3), 2-methylcitric acid (2-MC), 3-hydroxypropionic acid, (3OHPA), pro-pionylglycine, glycine, lactate and/or ammonia at least 30%, at least 40%, at least 50%, at least 60%, at least 70%, at least 80%, at least 90%, or at least 100% compared to the subject's baseline plasma, serum, or urine level or a reference plasma, serum, or urine C3, 2-MC, 3OHPA, propionylglycine, glycine, lactate and/or ammonia level in a human subject having PA for at least 12 hours, at least 24 hours, at least 48 hours, at least 72 hours, at least 96 hours, at least 120 hours, at least 1 week, at least 2 weeks, at least 3 weeks, at least 4 weeks, at least 8 weeks, or at least 12 weeks post-administration;

(v) reduce plasma, serum, whole blood, urine, and/or liver levels of propionic acid at least 1.5-fold, at least 2-fold, at least 5-fold, at least 10-fold, at least 20-fold, or at least 50-fold as compared to the subject's baseline plasma, serum, whole blood, urine, and/or liver propi-onic acid level or a reference plasma, serum, whole blood, urine, and/or liver propionic acid level in a patient with PA for at least 12 hours, at least 24 hours, at least 48 hours, at least 72 hours, at least 96 hours, at least 120 hours, at least 1 week, at least 2 weeks, at least 3 weeks, at least 4 weeks, at least 8 weeks, or at least 12 weeks post-administration; and/or (vi) reduce plasma, serum, and/or urine level of C3, 2-MC, 3OHPA, propionylglycine, glycine, lactate and/or ammonia at least 1.5-fold, at least 2-fold at least 5-fold, at least 10-fold, at least 20-fold or at least 50-fold as compared to the subject's baseline plasma, serum, and/or urine C3, 2-MC, 3OHPA, propionylgly-cine, glycine, lactate and/or ammonia level or a reference plasma, serum, and/or urine C3, 2-MC, 3OHPA, propionylglycine, glycine, lactate and/or ammonia level in a patient with PA for at least 12 hours, at least 24 hours, at least 48 hours, at least 72 hours, at least 96 hours, at least 120 hours, at least 1 week, at least 2 weeks, at least 3 weeks, at least 4 weeks, at least 8 weeks, or at least 12 weeks post-administration.

In some embodiments of the aspects, the pharmaceutical composition further comprises a delivery agent. In some embodiments, the delivery agent comprises a lipid nanoparticle comprising: (i) Compound II, (ii) Cholesterol, and (iii) PEG-DMG or Compound I; (i) Compound VI, (ii) Cholesterol, and (iii) PEG-DMG or Compound I; (i) Compound II, (ii) DSPC or DOPE, (iii) Cholesterol, and (iv) PEG-DMG or Compound I; (i) Compound VI, (ii) DSPC or DOPE, (iii) Cholesterol, and (iv) PEG-DMG or Compound I; (i) Compound II, (ii) Cholesterol, and (iii) Compound I; or (i) Compound II, (ii) DSPC or DOPE, (iii) Cholesterol, and (iv) Compound I.

In some embodiments of the aspects, the pharmaceutical composition further comprises a delivery agent. In some embodiments, the delivery agent comprises a lipid nanoparticle comprising (i) Compound II, (ii) Cholesterol, and (iii) Compound I.

In some embodiments of the aspects, the pharmaceutical composition further comprises a delivery agent. In some embodiments, the delivery agent comprises a lipid nanoparticle comprising (i) Compound II, (ii) DSPC or DOPE, (iii) Cholesterol, and (iv) Compound I.

In some embodiments, the PCCA polypeptide comprises the amino acid sequence set forth in SEQ ID NO:1 and the PCCB polypeptide comprises the amino acid sequence set forth in SEQ ID NO:15.

In some embodiments, the ORF has at least 79%, at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from the group consisting of SEQ ID NOs: 2, 5-14, 16-27, 196, 197, and 198.

In some embodiments, the mRNA comprises a microRNA (miR) binding site. In certain instances, the microRNA is expressed in an immune cell of hematopoietic lineage or a cell that expresses TLR7 and/or TLR8 and secretes pro-inflammatory cytokines and/or chemokines. In some instances, the microRNA binding site is for a microRNA selected from the group consisting of miR-126, miR-142, miR-144, miR-146, miR-150, miR-155, miR-16, miR-21, miR-223, miR-24, miR-27, miR-26a, or any combination thereof. In some instances, the microRNA binding site is for a microRNA selected from the group consisting of miR126-3p, miR-142-3p, miR-142-5p, miR-155, or any combination thereof. In some instances, the microRNA binding site is a miR-142-3p binding site. In some instances, the microRNA binding site is located in the 3' UTR of the mRNA.

In some embodiments, the mRNA comprises a 3' UTR comprising a nucleic acid sequence at least about 90%, at least about 95%, at least about 96%, at least about 97%, at least about 98%, at least about 99%, or 100% identical to a 3' UTR sequence of SEQ ID NO:4, SEQ ID NO: 112, or SEQ ID NO:178.

In some embodiments, the mRNA comprises a 3' UTR comprising a nucleic acid sequence at least about 90%, at least about 95%, at least about 96%, at least about 97%, at least about 98%, at least about 99%, or 100% identical to a 3' UTR sequence of SEQ ID NO:4, SEQ ID NO:111, SEQ ID NO:150, SEQ ID NO:175, SEQ ID NO: 177, SEQ ID NO:178, SEQ ID NO:207, or SEQ ID NO:208.

In some embodiments, the mRNA comprises a 5' UTR comprising a nucleic acid sequence at least 90%, at least about 95%, at least about 96%, at least about 97%, at least about 98%, at least about 99%, or 100% identical to a 5' UTR sequence of SEQ ID NO:3, SEQ ID NO:64, or SEQ ID NO:199.

In some embodiments, the mRNA comprises a 5' UTR comprising a nucleic acid sequence at least 90%, at least about 95%, at least about 96%, at least about 97%, at least about 98%, at least about 99%, or 100% identical to a 5' UTR sequence of SEQ ID NO:3, SEQ ID NO:191, SEQ ID NO:199, or SEQ ID NO:206.

In some embodiments, the mRNA comprises a 5' terminal cap. In some instances, the 5' terminal cap comprises a Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof.

In some embodiments, the mRNA comprises a poly-A region. In some instances, the poly-A region is at least about 10, at least about 20, at least about 30, at least about 40, at least about 50, at least about 60, at least about 70, at least about 80, at least about 90 nucleotides in length, or at least about 100 nucleotides in length. In some instances, the poly-A region has about 10 to about 200, about 20 to about 180, about 50 to about 160, about 70 to about 140, or about 80 to about 120 nucleotides in length.

In some embodiments, the mRNA comprises at least one chemically modified nucleobase, sugar, backbone, or any combination thereof. In some instances, the at least one chemically modified nucleobase is selected from the group consisting of pseudouracil ($\psi$), N1 methylpseudouracil (m1$\psi$), 1-ethylpseudouracil, 2-thiouracil (s2U), 4'-thiouracil, 5-methylcytosine, 5-methyluracil, 5-methoxyuracil, and any combination thereof. In some instances, at least about 25%, at least about 30%, at least about 40%, at least about 50%, at least about 60%, at least about 70%, at least about 80%, at least about 90%, at least about 95%, at least about 99%, or 100% of the uracils are chemically modified to N1-methylpseudouracils. In some instances, at least about 25%, at least about 30%, at least about 40%, at least about 50%, at least about 60%, at least about 70%, at least about 80%, at least about 90%, at least about 95%, at least about 99%, or 100% of the guanines are chemically modified. In some instances, at least about 25%, at least about 30%, at least about 40%, at least about 50%, at least about 60%, at least about 70%, at least about 80%, at least about 90%, at least about 95%, at least about 99%, or 100% of the cytosines are chemically modified. In some instances, at least about 25%, at least about 30%, at least about 40%, at least about 50%, at least about 60%, at least about 70%, at least about 80%, at least about 90%, at least about 95%, at least about 99%, or 100% of the adenines are chemically modified.

In some embodiments, the human subject has propionic acidemia (PA).

In some embodiments, the human subject is on a protein restricted diet. In some embodiments, the human subject is not on a protein restricted diet.

In one aspect, the disclosure features a polynucleotide comprising an mRNA comprising: (i) a 5' UTR; (ii) an open reading frame (ORF) encoding a human PCCA polypeptide, wherein the ORF has at least 79%, at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from the group consisting of SEQ ID NOs:2 and 5-14; and (iii) a 3' UTR.

In one aspect, the disclosure features a polynucleotide comprising an mRNA comprising: (i) a 5' UTR; (ii) an open reading frame (ORF) encoding a human PCCA polypeptide, wherein the ORF has at least 79%, at least 80%, at least 85%, at least 90%, at least 91%, at least 92%, at least 93%, at least 94%, at least 95%, at least 96%, at least 97%, at least 98%, at least 99%, or 100% sequence identity to SEQ ID NO: 11; and (iii) a 3' UTR. In some embodiments, the PCCA polypeptide consists of the amino acid sequence of SEQ ID NO:1.

In one aspect, the disclosure features a polynucleotide comprising an mRNA comprising: (i) a 5' UTR; (ii) an open reading frame (ORF) encoding a human PCCA polypeptide, wherein the ORF has at least 80% sequence identity to SEQ ID NO:11; and (iii) a 3' UTR. In some embodiments, the PCCA polypeptide consists of the amino acid sequence of SEQ ID NO:1.

In one aspect, the disclosure features a polynucleotide comprising an mRNA comprising: (i) a 5' UTR; (ii) an open reading frame (ORF) encoding a human PCCA polypeptide, wherein the ORF has at least 85% sequence identity to SEQ ID NO:11; and (iii) a 3' UTR. In some embodiments, the PCCA polypeptide consists of the amino acid sequence of SEQ ID NO:1.

In one aspect, the disclosure features a polynucleotide comprising an mRNA comprising: (i) a 5' UTR; (ii) an open reading frame (ORF) encoding a human PCCA polypeptide, wherein the ORF has at least 90% sequence identity to SEQ ID NO:11; and (iii) a 3' UTR. In some embodiments, the PCCA polypeptide consists of the amino acid sequence of SEQ ID NO:1.

In one aspect, the disclosure features a polynucleotide comprising an mRNA comprising: (i) a 5' UTR; (ii) an open reading frame (ORF) encoding a human PCCA polypeptide, wherein the ORF has at least 95% sequence identity to SEQ ID NO:11; and (iii) a 3' UTR. In some embodiments, the PCCA polypeptide consists of the amino acid sequence of SEQ ID NO:1.

In one aspect, the disclosure features a polynucleotide comprising an mRNA comprising: (i) a 5' UTR; (ii) an open reading frame (ORF) encoding a human PCCA polypeptide, wherein the ORF has at least 98% sequence identity to SEQ ID NO:11; and (iii) a 3' UTR. In some embodiments, the PCCA polypeptide consists of the amino acid sequence of SEQ ID NO:1.

In one aspect, the disclosure features a polynucleotide comprising an mRNA comprising: (i) a 5' UTR; (ii) an open reading frame (ORF) encoding a human PCCA polypeptide, wherein the ORF comprises a nucleic acid sequence selected from the group consisting of SEQ ID NOs:2 and 5-14; and (iii) a 3' UTR.

In one aspect, the disclosure features a polynucleotide comprising an mRNA comprising: (i) a 5' UTR; (ii) an open reading frame (ORF) encoding a human PCCB polypeptide, wherein the ORF has at least 79%, at least 80%, at least 85%, at least 90%, at least 91%, at least 92%, at least 93%, at least 94%, at least 95%, at least 96%, at least 97%, at least 98%, at least 99%, or 100% sequence identity to a nucleic acid sequence selected from the group consisting of SEQ ID NOs: 16-27, 196, 197, and 198; and (iii) a 3' UTR. In some embodiments, the PCCB polypeptide consists of the amino acid sequence of SEQ ID NO:15.

In one aspect, the disclosure features a polynucleotide comprising an mRNA comprising: (i) a 5' UTR; (ii) an open reading frame (ORF) encoding a human PCCB polypeptide, wherein the ORF has at least 94% sequence identity to SEQ ID NO:23; and (iii) a 3' UTR. In some embodiments, the PCCB polypeptide consists of the amino acid sequence of SEQ ID NO:15.

In one aspect, the disclosure features a polynucleotide comprising an mRNA comprising: (i) a 5' UTR; (ii) an open reading frame (ORF) encoding a human PCCB polypeptide, wherein the ORF has at least 95% sequence identity to SEQ ID NO:23; and (iii) a 3' UTR. In some embodiments, the PCCB polypeptide consists of the amino acid sequence of SEQ ID NO:15.

In one aspect, the disclosure features a polynucleotide comprising an mRNA comprising: (i) a 5' UTR; (ii) an open reading frame (ORF) encoding a human PCCB polypeptide, wherein the ORF has at least 96% sequence identity to SEQ ID NO:23; and (iii) a 3' UTR. In some embodiments, the PCCB polypeptide consists of the amino acid sequence of SEQ ID NO:15.

In one aspect, the disclosure features a polynucleotide comprising an mRNA comprising: (i) a 5' UTR; (ii) an open reading frame (ORF) encoding a human PCCB polypeptide, wherein the ORF has at least 97% sequence identity to SEQ ID NO:23; and (iii) a 3' UTR. In some embodiments, the PCCB polypeptide consists of the amino acid sequence of SEQ ID NO:15.

In one aspect, the disclosure features a polynucleotide comprising an mRNA comprising: (i) a 5' UTR; (ii) an open reading frame (ORF) encoding a human PCCB polypeptide, wherein the ORF has at least 98% sequence identity to SEQ ID NO:23; and (iii) a 3' UTR. In some embodiments, the PCCB polypeptide consists of the amino acid sequence of SEQ ID NO:15.

In one aspect, the disclosure features a polynucleotide comprising an mRNA comprising: (i) a 5' UTR; (ii) an open reading frame (ORF) encoding a human PCCB polypeptide, wherein the ORF has at least 99% sequence identity to SEQ ID NO:23; and (iii) a 3' UTR. In some embodiments, the PCCB polypeptide consists of the amino acid sequence of SEQ ID NO:15.

In one aspect, the disclosure features a polynucleotide comprising an mRNA comprising: (i) a 5' UTR; (ii) an open reading frame (ORF) encoding a human PCCB polypeptide, wherein the ORF has at least 94% sequence identity to SEQ ID NO:25; and (iii) a 3' UTR. In some embodiments, the PCCB polypeptide consists of the amino acid sequence of SEQ ID NO:15.

In one aspect, the disclosure features a polynucleotide comprising an mRNA comprising: (i) a 5' UTR; (ii) an open reading frame (ORF) encoding a human PCCB polypeptide, wherein the ORF has at least 95% sequence identity to SEQ ID NO:25; and (iii) a 3' UTR. In some embodiments, the PCCB polypeptide consists of the amino acid sequence of SEQ ID NO:15.

In one aspect, the disclosure features a polynucleotide comprising an mRNA comprising: (i) a 5' UTR; (ii) an open reading frame (ORF) encoding a human PCCB polypeptide, wherein the ORF has at least 96% sequence identity to SEQ ID NO:25; and (iii) a 3' UTR. In some embodiments, the PCCB polypeptide consists of the amino acid sequence of SEQ ID NO:15.

In one aspect, the disclosure features a polynucleotide comprising an mRNA comprising: (i) a 5' UTR; (ii) an open reading frame (ORF) encoding a human PCCB polypeptide, wherein the ORF has at least 97% sequence identity to SEQ ID NO:25; and (iii) a 3' UTR. In some embodiments, the PCCB polypeptide consists of the amino acid sequence of SEQ ID NO:15.

In one aspect, the disclosure features a polynucleotide comprising an mRNA comprising: (i) a 5' UTR; (ii) an open reading frame (ORF) encoding a human PCCB polypeptide, wherein the ORF has at least 98% sequence identity to SEQ ID NO:25; and (iii) a 3' UTR. In some embodiments, the PCCB polypeptide consists of the amino acid sequence of SEQ ID NO:15.

In one aspect, the disclosure features a polynucleotide comprising an mRNA comprising: (i) a 5' UTR; (ii) an open reading frame (ORF) encoding a human PCCB polypeptide, wherein the ORF has at least 99% sequence identity to SEQ ID NO:25; and (iii) a 3' UTR. In some embodiments, the PCCB polypeptide consists of the amino acid sequence of SEQ ID NO:15.

In one aspect, the disclosure features a polynucleotide comprising an mRNA comprising: (i) a 5' UTR; (ii) an open reading frame (ORF) encoding a human PCCB polypeptide, wherein the ORF comprises a nucleic acid sequence selected from the group consisting of SEQ ID NOs:16-27, 196, 197, and 198; and (iii) a 3' UTR.

In some embodiments of the aspects, the mRNA comprises a microRNA (miR) binding site. In some instances, the microRNA is expressed in an immune cell of hematopoietic lineage or a cell that expresses TLR7 and/or TLR8 and secretes pro-inflammatory cytokines and/or chemokines. In some instances, the microRNA binding site is for a microRNA selected from the group consisting of miR-126, miR-142, miR-144, miR-146, miR-150, miR-155, miR-16, miR-21, miR-223, miR-24, miR-27, miR-26a, or any combination thereof. In some instances, the microRNA binding site is for a microRNA selected from the group consisting of miR126-3p, miR-142-3p, miR-142-5p, miR-155, or any combination thereof. In some instances, the microRNA binding site is a miR-142-3p binding site.

In some embodiments, the microRNA binding site is located in the 3' UTR of the mRNA. In some instances, the 3' UTR comprises a nucleic acid sequence at least about 90%, at least about 95%, at least about 96%, at least about 97%, at least about 98%, at least about 99%, or 100% identical to a 3' UTR of SEQ ID NO:4, SEQ ID NO: 112, or SEQ ID NO:178.

In some embodiments, the microRNA binding site is located in the 3' UTR of the mRNA. In some instances, the 3' UTR comprises a nucleic acid sequence at least about 90%, at least about 95%, at least about 96%, at least about 97%, at least about 98%, at least about 99%, or 100% identical to a 3' UTR of SEQ ID NO:4, SEQ ID NO:111, SEQ ID NO:150, SEQ ID NO:175, SEQ ID NO:177, SEQ ID NO:178, SEQ ID NO:207, or SEQ ID NO:208. In some embodiments, the 5' UTR comprises a nucleic acid sequence at least 90%, at least about 95%, at least about 96%, at least about 97%, at least about 98%, at least about 99%, or 100% identical to a 5' UTR sequence of SEQ ID NO:3, SEQ ID NO:64, or SEQ ID NO:199.

In some embodiments, the 5' UTR comprises a nucleic acid sequence at least 90%, at least about 95%, at least about 96%, at least about 97%, at least about 98%, at least about 99%, or 100% identical to a 5' UTR sequence of SEQ ID NO:3, SEQ ID NO: 191, SEQ ID NO: 199, or SEQ ID NO:206. In some embodiments, the mRNA comprises a 5' terminal cap. In some instances, the 5' terminal cap comprises a Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof.

In some embodiments, the mRNA comprises a poly-A region. In some instances, the poly-A region is at least about 10, at least about 20, at least about 30, at least about 40, at least about 50, at least about 60, at least about 70, at least about 80, at least about 90 nucleotides in length, or at least about 100 nucleotides in length. In some instances, the poly-A region has about 10 to about 200, about 20 to about 180, about 50 to about 160, about 70 to about 140, or about 80 to about 120 nucleotides in length.

In some embodiments, the mRNA comprises at least one chemically modified nucleobase, sugar, backbone, or any combination thereof. In some instances, the at least one chemically modified nucleobase is selected from the group consisting of pseudouracil (ψ), N1-methylpseudouracil (m1ψ), 1-ethylpseudouracil, 2-thiouracil (s2U), 4'-thiouracil, 5-methylcytosine, 5-methyluracil, 5-methoxyuracil, and any combination thereof. In some instances, at least about 25%, at least about 30%, at least about 40%, at least about 50%, at least about 60%, at least about 70%, at least about 80%, at least about 90%, at least about 95%, at least about 99%, or 100% of the uracils are chemically modified to N1-methylpseudouracils.

In some embodiments, the polynucleotide comprises a nucleic acid sequence selected from the group consisting of SEQ ID NOs: 28-38, 63, 65, and 203. In some embodiments, the polynucleotide comprises a nucleic acid sequence selected from the group consisting of SEQ ID NOs: 39-50, 66, 67, 200-202, 204, and 205.

In one aspect, the disclosure features a polynucleotide comprising an mRNA comprising: (i) a 5'-terminal cap; (ii) a 5' UTR comprising the nucleic acid sequence of SEQ ID NO:3, SEQ ID NO:64, or SEQ ID NO:199; (iii) an open reading frame (ORF) encoding a human PCCA polypeptide, wherein the ORF comprises a sequence selected from the group consisting of SEQ ID NOs:2 and 5-14; (iv) a 3' UTR comprising the nucleic acid sequence of SEQ ID NO:4, SEQ ID NO: 112, or SEQ ID NO:178; and (v) a poly-A-region.

In one aspect, the disclosure features a polynucleotide comprising an mRNA comprising: (i) a 5'-terminal cap; (ii) a 5' UTR comprising the nucleic acid sequence of SEQ ID NO:3, SEQ ID NO:64, or SEQ ID NO:199; (iii) an open reading frame (ORF) encoding a human PCCB polypeptide, wherein the ORF comprises a sequence selected from the group consisting of SEQ ID NOs: 16-27, 196, 197, and 198; (iv) a 3' UTR comprising the nucleic acid sequence of SEQ ID NO:4, SEQ ID NO: 112, or SEQ ID NO:178; and (v) a poly-A-region.

In one aspect, the disclosure features a polynucleotide comprising an mRNA comprising: (i) a 5'-terminal cap; (ii) a 5' UTR comprising the nucleic acid sequence of SEQ ID NO:3, SEQ ID NO:191, SEQ ID NO:199, or SEQ ID NO:206; (iii) an open reading frame (ORF) encoding a human PCCA polypeptide, wherein the ORF comprises a sequence selected from the group consisting of SEQ ID NOs:2 and 5-14; (iv) a 3' UTR comprising the nucleic acid sequence of SEQ ID NO:4, SEQ ID NO:111, SEQ ID NO:150, SEQ ID NO:175, SEQ ID NO:177, SEQ ID NO:178, SEQ ID NO:207, or SEQ ID NO:208; and (v) a poly-A-region.

In one aspect, the disclosure features a polynucleotide comprising an mRNA comprising: (i) a 5'-terminal cap; (ii) a 5' UTR comprising the nucleic acid sequence of SEQ ID NO:3, SEQ ID NO:191, SEQ ID NO:199, or SEQ ID NO:206; (iii) an open reading frame (ORF) encoding a human PCCB polypeptide, wherein the ORF comprises a sequence selected from the group consisting of SEQ ID NOs: 16-27, 196, 197, and 198; (iv) a 3' UTR comprising the nucleic acid sequence of SEQ ID NO:4, SEQ ID NO:111, SEQ ID NO:150, SEQ ID NO:175, SEQ ID NO:177, SEQ ID NO:178, SEQ ID NO:207, or SEQ ID NO:208; and (v) a poly-A-region.

In some embodiments, the 5' terminal cap comprises a Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof.

In some embodiments, the poly-A region is at least about 10, at least about 20, at least about 30, at least about 40, at least about 50, at least about 60, at least about 70, at least about 80, or at least about 90 nucleotides in length. In some instances, the poly-A region has about 10 to about 200, about 20 to about 180, about 50 to about 160, about 70 to about 140, or about 80 to about 120 nucleotides in length.

In some embodiments, the mRNA comprises at least one chemically modified nucleobase, sugar, backbone, or any combination thereof. In some embodiments, the at least one chemically modified nucleobase is selected from the group consisting of pseudouracil (ψ), N1-methylpseudouracil (m1ψ), 1-ethylpseudouracil, 2-thiouracil (s2U), 4'-thiouracil, 5-methylcytosine, 5-methyluracil, 5-methoxyuracil, and any combination thereof.

In some embodiments, the polynucleotide comprises a nucleic acid sequence selected from the group consisting of SEQ ID NOs: 28-38, 63, 65, and 203. In some embodiments, the polynucleotide comprises a nucleic acid sequence selected from the group consisting of SEQ ID NOs: 39-50, 66, 67, 200-202, 204, and 205. In some of these embodiments, the 5' terminal cap comprises Cap1 and all of the uracils of the polynucleotide are N1-methylpseudouracils. In some of these embodiments, the poly-A-region is 100 nucleotides in length.

In some embodiments, the pharmaceutical composition comprises a polynucleotide described herein, and a delivery agent.

In one aspect, the disclosure features a pharmaceutical composition comprising two polynucleotides, wherein the first polynucleotide comprises an open reading frame (ORF) described herein encoding a human PCCA polypeptide and the second polynucleotide comprises an open reading frame (ORF) described herein encoding a human PCCB polypeptide, and a delivery agent.

In some embodiments of the pharmaceutical composition, the first polynucleotide comprises an mRNA comprising: (i) a 5' UTR; (ii) an open reading frame (ORF) encoding a human PCCA polypeptide (e.g., SEQ ID NO:1), wherein the ORF has at least 80% sequence identity to SEQ ID NO: 11; and (iii) a 3' UTR, and the second polynucleotide comprises an mRNA comprising: (i) a 5' UTR; (ii) an open reading frame (ORF) encoding a human PCCB polypeptide (e.g., SEQ ID NO:15), wherein the ORF has at least 80% sequence identity to SEQ ID NO:23; and (iii) a 3' UTR.

In some embodiments of the pharmaceutical composition, the first polynucleotide comprises an mRNA comprising: (i) a 5' UTR; (ii) an open reading frame (ORF) encoding a human PCCA polypeptide (e.g., SEQ ID NO:1), wherein the ORF has at least 85% sequence identity to SEQ ID NO: 11; and (iii) a 3' UTR, and the second polynucleotide comprises an mRNA comprising: (i) a 5' UTR; (ii) an open reading frame (ORF) encoding a human PCCB polypeptide (e.g., SEQ ID NO:15), wherein the ORF has at least 85% sequence identity to SEQ ID NO:23; and (iii) a 3' UTR.

In some embodiments of the pharmaceutical composition, the first polynucleotide comprises an mRNA comprising: (i) a 5' UTR; (ii) an open reading frame (ORF) encoding a human PCCA polypeptide (e.g., SEQ ID NO:1), wherein the ORF has at least 90% sequence identity to SEQ ID NO: 11; and (iii) a 3' UTR, and the second polynucleotide comprises an mRNA comprising: (i) a 5' UTR; (ii) an open reading frame (ORF) encoding a human PCCB polypeptide (e.g., SEQ ID NO:15), wherein the ORF has at least 90% sequence identity to SEQ ID NO:23; and (iii) a 3' UTR.

In some embodiments of the pharmaceutical composition, the first polynucleotide comprises an mRNA comprising: (i) a 5' UTR; (ii) an open reading frame (ORF) encoding a human PCCA polypeptide (e.g., SEQ ID NO:1), wherein the ORF has at least 95% sequence identity to SEQ ID NO: 11; and (iii) a 3' UTR, and the second polynucleotide comprises an mRNA comprising: (i) a 5' UTR; (ii) an open reading frame (ORF) encoding a human PCCB polypeptide (e.g., SEQ ID NO:15), wherein the ORF has at least 95% sequence identity to SEQ ID NO:23; and (iii) a 3' UTR.

In some embodiments of the pharmaceutical composition, the first polynucleotide comprises an mRNA comprising: (i) a 5' UTR; (ii) an open reading frame (ORF) encoding a human PCCA polypeptide (e.g., SEQ ID NO:1), wherein the ORF has at least 98% sequence identity to SEQ ID NO: 11; and (iii) a 3' UTR, and the second polynucleotide comprises an mRNA comprising: (i) a 5' UTR; (ii) an open reading frame (ORF) encoding a human PCCB polypeptide (e.g., SEQ ID NO:15), wherein the ORF has at least 98% sequence identity to SEQ ID NO:23; and (iii) a 3' UTR.

In some embodiments of the pharmaceutical composition, the first polynucleotide comprises an mRNA comprising: (i) a 5' UTR; (ii) an open reading frame (ORF) encoding a human PCCA polypeptide (e.g., SEQ ID NO:1), wherein the ORF comprises SEQ ID NO:11; and (iii) a 3' UTR, and the second polynucleotide comprises an mRNA comprising: (i) a 5' UTR; (ii) an open reading frame (ORF) encoding a human PCCB polypeptide (e.g., SEQ ID NO:15), wherein the ORF comprises SEQ ID NO:23; and (iii) a 3' UTR.

In some embodiments of the pharmaceutical composition, the first polynucleotide comprises an mRNA comprising: (i) a 5' UTR; (ii) an open reading frame (ORF) encoding a human PCCA polypeptide (e.g., SEQ ID NO:1), wherein the ORF has at least 80% sequence identity to SEQ ID NO: 11; and (iii) a 3' UTR, and the second polynucleotide comprises an mRNA comprising: (i) a 5' UTR; (ii) an open reading frame (ORF) encoding a human PCCB polypeptide (e.g., SEQ ID NO:15), wherein the ORF has at least 80% sequence identity to SEQ ID NO:25; and (iii) a 3' UTR.

In some embodiments of the pharmaceutical composition, the first polynucleotide comprises an mRNA comprising: (i) a 5' UTR; (ii) an open reading frame (ORF) encoding a human PCCA polypeptide (e.g., SEQ ID NO:1), wherein the ORF has at least 85% sequence identity to SEQ ID NO: 11; and (iii) a 3' UTR, and the second polynucleotide comprises an mRNA comprising: (i) a 5' UTR; (ii) an open reading frame (ORF) encoding a human PCCB polypeptide (e.g., SEQ ID NO:15), wherein the ORF has at least 85% sequence identity to SEQ ID NO:25; and (iii) a 3' UTR.

In some embodiments of the pharmaceutical composition, the first polynucleotide comprises an mRNA comprising: (i) a 5' UTR; (ii) an open reading frame (ORF) encoding a human PCCA polypeptide (e.g., SEQ ID NO:1), wherein the ORF has at least 90% sequence identity to SEQ ID NO: 11; and (iii) a 3' UTR, and the second polynucleotide comprises an mRNA comprising: (i) a 5' UTR; (ii) an open reading frame (ORF) encoding a human PCCB polypeptide (e.g., SEQ ID NO:15), wherein the ORF has at least 90% sequence identity to SEQ ID NO:25; and (iii) a 3' UTR.

In some embodiments of the pharmaceutical composition, the first polynucleotide comprises an mRNA comprising: (i) a 5' UTR; (ii) an open reading frame (ORF) encoding a human PCCA polypeptide (e.g., SEQ ID NO:1), wherein the ORF has at least 95% sequence identity to SEQ ID NO: 11; and (iii) a 3' UTR, and the second polynucleotide comprises an mRNA comprising: (i) a 5' UTR; (ii) an open reading frame (ORF) encoding a human PCCB polypeptide (e.g., SEQ ID NO:15), wherein the ORF has at least 95% sequence identity to SEQ ID NO:25; and (iii) a 3' UTR.

In some embodiments of the pharmaceutical composition, the first polynucleotide comprises an mRNA comprising: (i) a 5' UTR; (ii) an open reading frame (ORF) encoding a human PCCA polypeptide (e.g., SEQ ID NO:1), wherein the ORF has at least 98% sequence identity to SEQ ID NO:11; and (iii) a 3' UTR, and the second polynucleotide comprises an mRNA comprising: (i) a 5' UTR; (ii) an open reading frame (ORF) encoding a human PCCB polypeptide (e.g., SEQ ID NO:15), wherein the ORF has at least 98% sequence identity to SEQ ID NO:25; and (iii) a 3' UTR.

In some embodiments of the pharmaceutical composition, the first polynucleotide comprises an mRNA comprising: (i) a 5' UTR; (ii) an open reading frame (ORF) encoding a human PCCA polypeptide (e.g., SEQ ID NO:1), wherein the ORF comprises SEQ ID NO:11; and (iii) a 3' UTR, and the second polynucleotide comprises an mRNA comprising: (i) a 5' UTR; (ii) an open reading frame (ORF) encoding a human PCCB polypeptide (e.g., SEQ ID NO:15), wherein the ORF comprises SEQ ID NO:25; and (iii) a 3' UTR.

In some embodiments, the delivery agent comprises a lipid nanoparticle comprising: (i) Compound II, (ii) Cholesterol, and (iii) PEG-DMG or Compound I; (i) Compound VI, (ii) Cholesterol, and (iii) PEG-DMG or Compound I; (i) Compound II, (ii) DSPC or DOPE, (iii) Cholesterol, and (iv) PEG-DMG or Compound I; (i) Compound VI, (ii) DSPC or DOPE, (iii) Cholesterol, and (iv) PEG-DMG or Compound I; (i) Compound II, (ii) Cholesterol, and (iii) Compound I; or (i) Compound II, (ii) DSPC or DOPE, (iii) Cholesterol, and (iv) Compound I.

In one aspect, the disclosure features a method of expressing a propionyl-CoA carboxylase alpha (PCCA) polypeptide in a human subject in need thereof, comprising administering to the subject an effective amount or a pharmaceutical composition or a polynucleotide described herein.

In one aspect, the disclosure features a method of expressing a propionyl-CoA carboxylase beta (PCCB) polypeptide in a human subject in need thereof, comprising administering to the subject an effective amount of a pharmaceutical composition or a polynucleotide described herein.

In one aspect, the disclosure features a method of expressing a propionyl-CoA carboxylase alpha (PCCA) polypeptide and a propionyl-CoA carboxylase beta (PCCB) polypeptide in a human subject in need thereof, comprising administering to the subject an effective amount of at least one of the pharmaceutical compositions described herein or two polynucleotides described herein, wherein the first polynucleotide comprises an open reading frame (ORF) encoding a human PCCA polypeptide and the second polynucleotide comprises an open reading frame (ORF) encoding a human PCCB polypeptide.

In some embodiments, pharmaceutical composition comprises a first polynucleotide comprising an open reading frame (ORF) described herein encoding a human PCCA polypeptide and a second polynucleotide comprising an open reading frame (ORF) described herein encoding a human PCCB polypeptide.

In some embodiments, the method comprises administering a first pharmaceutical composition and a second pharmaceutical composition, wherein the first pharmaceutical composition comprises a first polynucleotide comprising an open reading frame (ORF) described herein encoding a human PCCA polypeptide, and wherein the second pharmaceutical composition comprises a second polynucleotide comprising an open reading frame (ORF) described herein encoding a human PCCB polypeptide.

In one aspect, the disclosure features a method of treating, preventing, or delaying the onset and/or progression of propionic academia (PA) in a human subject in need thereof, comprising administering to the subject an effective amount of a pharmaceutical composition or a polynucleotide described herein.

In one aspect, the disclosure features a method of treating, preventing, or delaying the onset and/or progression of propionic academia (PA) in a human subject in need thereof, comprising administering to the subject an effective amount of a pharmaceutical composition or a polynucleotide described herein.

In one aspect, the disclosure features a method of treating, preventing, or delaying the onset and/or progression of propionic academia (PA) in a human subject in need thereof, comprising administering to the subject an effective amount of at least one of the pharmaceutical compositions described herein or two polynucleotides described herein, wherein the first polynucleotide comprises an open reading frame (ORF) encoding a human PCCA polypeptide and the second polynucleotide comprises an open reading frame (ORF) encoding a human PCCB polypeptide.

In some embodiments, the method comprises administering a pharmaceutical composition comprising a first polynucleotide comprising an open reading frame (ORF) described herein encoding a human PCCA polypeptide and a second polynucleotide comprising an open reading frame (ORF) described herein encoding a human PCCB polypeptide.

In some embodiments, the method comprises administering a first pharmaceutical composition and a second pharmaceutical composition, wherein the first pharmaceutical composition comprises a first polynucleotide comprising an open reading frame (ORF) described herein encoding a human PCCA polypeptide, and wherein the second pharmaceutical composition comprises a second polynucleotide comprising an open reading frame (ORF) described herein encoding a human PCCB polypeptide.

In one aspect, the disclosure features a method of reducing propionic acid blood level in a human subject in need thereof, comprising administering to the subject an effective amount of a pharmaceutical composition or a polynucleotide described herein.

In one aspect, the disclosure features a method of reducing propionic acid blood level in a human subject in need thereof, comprising administering to the subject an effective amount of a pharmaceutical composition or a polynucleotide described herein.

In one aspect, the discourse features a method of reducing propionic acid blood level in a human subject in need thereof, comprising administering to the subject an effective amount of at least one of the pharmaceutical compositions described herein or two polynucleotides described herein, wherein the first polynucleotide comprises an open reading frame (ORF) encoding a human PCCA polypeptide and the second polynucleotide comprises an open reading frame (ORF) encoding a human PCCB polypeptide.

In some embodiments, the method comprises administering a pharmaceutical composition comprising a first polynucleotide comprising an open reading frame (ORF) described herein encoding a human PCCA polypeptide and a second polynucleotide comprising an open reading frame (ORF) described herein encoding a human PCCB polypeptide.

In some embodiments, the method comprises administering a first pharmaceutical composition and a second pharmaceutical composition, wherein the first pharmaceutical composition comprises a first polynucleotide comprising an open reading frame (ORF) described herein encoding a human PCCA polypeptide, and wherein the second pharmaceutical composition comprises a second polynucleotide comprising an open reading frame (ORF) described herein encoding a human PCCB polypeptide.

In one aspect, the disclosure features a method of reducing C3, 2-MC, 3OHPA, propionylglycine, glycine, lactate and/or ammonia plasma, serum, whole blood, urine, and/or liver level in a human subject in need thereof, comprising administering to the subject an effective amount of a pharmaceutical composition or a polynucleotide described herein.

In one aspect, the disclosure features a method of reducing C3, 2-MC, 3OHPA, propionylglycine, glycine, lactate and/or ammonia plasma, serum, whole blood, urine, and/or liver level in a human subject in need thereof, comprising administering to the subject an effective amount of at least one of the pharmaceutical compositions described herein or two polynucleotides described herein, wherein the first polynucleotide comprises an open reading frame (ORF) encoding a human PCCA polypeptide and the second polynucleotide comprises an open reading frame (ORF) encoding a human PCCB polypeptide.

In some embodiments, the method comprises administering a pharmaceutical composition comprising a first polynucleotide comprising an open reading frame (ORF) described herein encoding a human PCCA polypeptide and a second polynucleotide comprising an open reading frame (ORF) described herein encoding a human PCCB polypeptide.

In some embodiments, the method comprises administering a first pharmaceutical composition and a second pharmaceutical composition, wherein the first pharmaceutical composition comprises a first polynucleotide comprising an open reading frame (ORF) encoding a human PCCA polypeptide, and wherein the second pharmaceutical composition comprises a second polynucleotide comprising an open reading frame (ORF) encoding a human PCCB polypeptide.

In some embodiments of the above methods:

(i) the propionic acid blood and/or liver level is reduced at least 20%, at least 30%, at least 40%, at least 50%, at least 60%, at least 70%, at least 80%, at least 90%, or at least 100% as compared to the human subject's baseline propionic acid blood and/or liver level or a reference propionic acid blood and/or liver level in a patient with PA, for at least 24 hours, at least 48 hours, at least 72 hours, at least 96 hours, at least 120 hours, 6 days, 1 week, 8 days, 9 days, 10 days, 11 days, 12 days, 14 days, 18 days, or 21 days after a single administration;

(ii) the propionic acid plasma, serum, and/or urine level is reduced at least 20%, at least 30%, at least 40%, at least 30%, at least 40%, at least 50%, at least 60%, at least 70%, at least 80%, at least 90%, or at least 100% as compared to the human subject's baseline propionic acid plasma, serum, and/or urine level or a reference propionic acid plasma, serum, and/or urine level in a patient with PA, for at least 24 hours, at least 48 hours, at least 72 hours, at least 96 hours, at least 120 hours, 6 days, 1 week, 8 days, 9 days, 10 days, 11 days, 12 days, 14 days, 18 days, or 21 days after a single administration;

(iii) the propionic acid blood and/or liver level is reduced to at least within 10-fold, at least within 5-fold, at least within 2-fold, or at least within 1.5-fold as compared to a normal propionic acid blood and/or liver level within at least 24 hours, at least 48 hours, at least 72 hours, at least 96 hours, at least 120 hours, 6 days, 1 week, 8 days, 9 days, 10 days, 11 days, 12 days, 14 days, 18 days, or 21 days after a single administration;

(iv) the propionic acid plasma, serum, and/or urine level is reduced to at least within 10-fold, at least within 5-fold, at least within 2-fold, or at least within 1.5-fold, as compared to a normal propionic acid plasma, serum, and/or urine level, for at least 24 hours, at least 48 hours, at least 72 hours, at least 96 hours, at least 120 hours, 6 days, 1 week, 8 days, 9 days, 10 days, 11 days, 12 days, 14 days, 18 days, or 21 days after a single administration;

(v) the C3, 2-MC, 3OHPA, propionylglycine, glycine, lactate and/or ammonia plasma, serum, whole blood, urine, and/or liver level is reduced at least 20%, at least 30%, at least 40%, at least 50%, at least 60%, at least 70%, at least 80%, at least 90%, or at least 100% as compared to the human subject's baseline plasma, serum, whole blood, urine, and/or liver C3, 2-MC, 3OHPA, propionylglycine, glycine, lactate and/or ammonia or a reference C3, 2-MC, 3OHPA, propionylglycine, glycine, lactate and/or ammonia plasma, serum, whole blood, urine, and/or liver level in a patient with PA, for at least 24 hours, at least 48 hours, at least 72 hours, at least 96 hours, at least 120 hours, 6 days, 1 week, 8 days, 9 days, 10 days, 11 days, 12 days, 14 days, 18 days, or 21 days after a single administration; and/or (vi) the C3, 2-MC, 3OHPA, propionylglycine, glycine, lactate and/or ammonia plasma, serum, whole blood, urine, and/or liver level is reduced to at least within 10-fold, at least within 5-fold, at least within 2-fold, or at least within 1.5-fold as compared to a normal C3, 2-MC, 3OHPA, propionylglycine, glycine, lactate and/or ammonia plasma, serum, whole blood, urine, and/or liver level within at least 24 hours, at least 48 hours, at least 72 hours, at least 96 hours, at least 120 hours, 6 days, 1 week, 8 days, 9 days, 10 days, 11 days, 12 days, 14 days, 18 days, or 21 days after a single administration.

In one aspect, the disclosure features a method of increasing PCC activity in a human subject in need thereof, comprising administering to the subject an effective amount of a pharmaceutical composition described herein or a polynucleotide described herein.

In one aspect, the disclosure features a method of increasing PCC activity in a human subject in need thereof, comprising administering to the subject an effective amount of at least one of the pharmaceutical compositions described herein or two polynucleotides described herein, wherein the first polynucleotide comprises an open reading frame (ORF) encoding a human PCCA polypeptide and the second polynucleotide comprises an open reading frame (ORF) encoding a human PCCB polypeptide.

In some embodiments, the disclosure features a method comprising administering a pharmaceutical composition comprising a first polynucleotide comprising an open reading frame (ORF) encoding a human PCCA polypeptide and a second polynucleotide comprising an open reading frame (ORF) encoding a human PCCB polypeptide.

In some embodiments, the method comprises administering a first pharmaceutical composition and a second pharmaceutical composition, wherein the first pharmaceutical composition comprises a first polynucleotide comprising an open reading frame (ORF) encoding a human PCCA polypeptide, and wherein the second pharmaceutical composition comprises a second polynucleotide comprising an open reading frame (ORF) encoding a human PCCB polypeptide.

In certain embodiments of the above methods:

(i) the level of PCC activity in the human subject is increased at least 1.5-fold, at least 2-fold, at least 5-fold, at least 10-fold, at least 20-fold, or at least 50-fold as compared to a reference PCC activity level in a human subject having PA for at least 24 hours, at least 48 hours, at least 72 hours, at least 96 hours, or at least 120 hours after a single administration; and/or (ii) 12 hours after a single administration of the pharmaceutical composition or polynucleotide is administered to the human subject, the PCC activity in the human subject is increased at least 20%, at least 30%, at least 40%, at least 50%, at least 60%, at least 70%, at least 80%, at least 90%, at least 100%, at least 150%, at least 200%, at least 300%, at least 400%, at least 500%, or at least 600% compared to the subject's baseline PCC activity.

In some embodiments of the above methods, the PCC activity is increased in the liver or blood of the human subject.

In some embodiments of the above methods, the administration to the human subject is about once a week, about once every two weeks, about once a month, about once every six weeks, or about once every two months.

In certain embodiments, the pharmaceutical composition or polynucleotide is administered intravenously. In some instances, the pharmaceutical composition or polynucleotide is administered at a dose of 0.1 mg/kg to 2.0 mg/kg. In some instances, the pharmaceutical composition or polynucleotide is administered at a dose of 0.1 mg/kg to 1.5 mg/kg. In some instances, the pharmaceutical composition or polynucleotide is administered at a dose of 0.1 mg/kg to 1.0 mg/kg. In some instances, the pharmaceutical composition or polynucleotide is administered at a dose of 0.1 mg/kg to 0.5 mg/kg.

BRIEF DESCRIPTION OF THE DRAWINGS

FIG. 5 is a bar graph showing PCCA expression levels (Western blots assessed with capillary electrophoresis, normalized to actin levels) in wild-type FVB mice at 72 hours following single intravenous injection of modified human PCCA mRNAs or control mRNA.

FIG. 11A is a bar graph showing PCCB expression levels (Western blots assessed with capillary electrophoresis, normalized to actin levels) in GM1298 PCCB-deficient patient fibroblasts transfected with modified human PCCB mRNAs or control mRNA.

FIG. 11B is a bar graph showing PCCA expression levels (Western blots assessed with capillary electrophoresis, normalized to actin levels) in GM1298 PCCB-deficient patient fibroblasts transfected with modified human PCCB mRNAs or control mRNA.

DETAILED DESCRIPTION

Figure 1A:
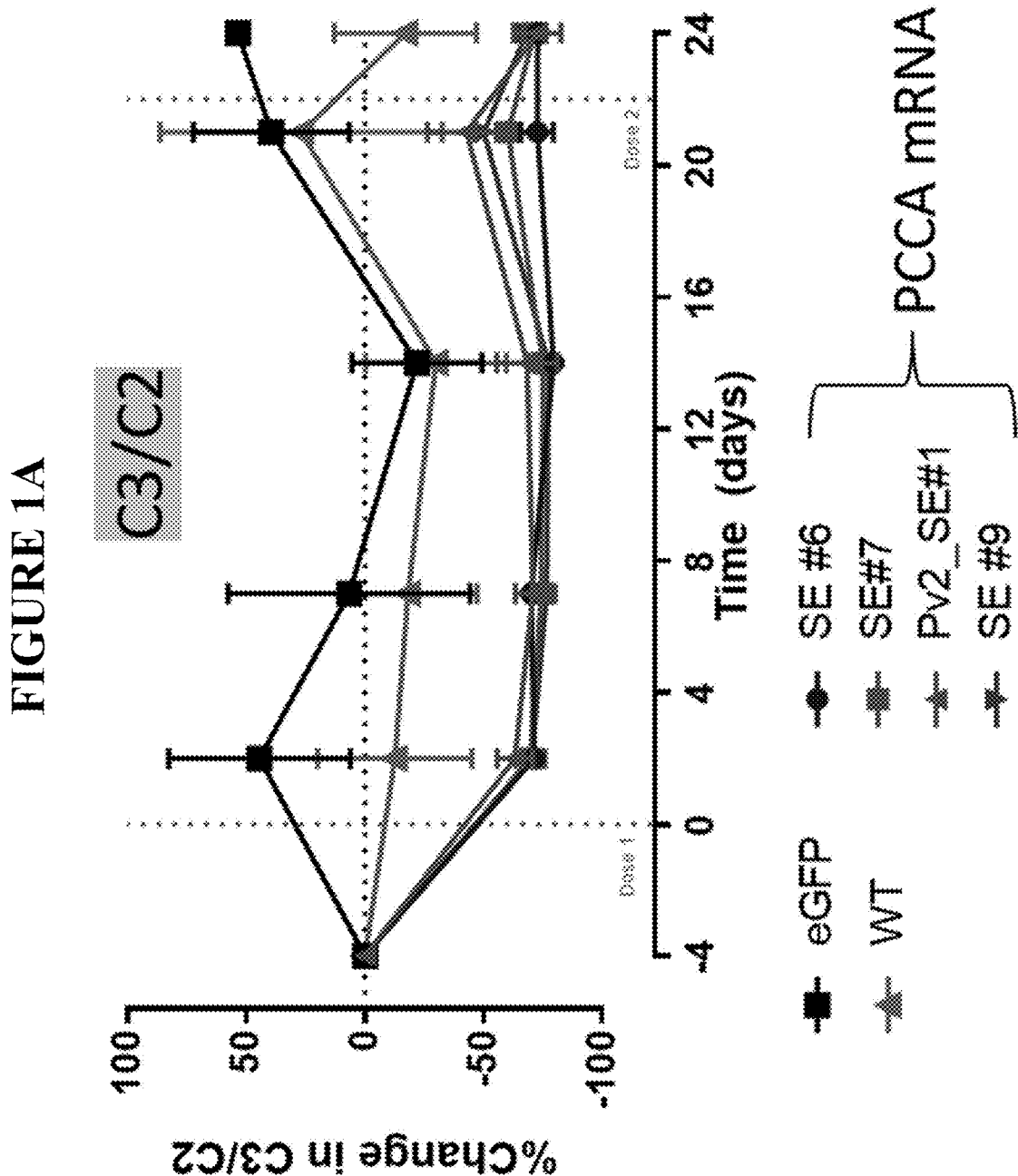
FIG. 1A shows the percent change in propionyl-L-carnitine/acetyl-L-carnitine (C3/C2) levels measured in Pcca$^{-/-}$ (A138T) mice at 2, 7, 14, 21, and 24 days following intravenous injection of modified human PCCA mRNA constructs or eGFP mRNA control.

The present invention provides mRNA therapeutics for the treatment of propionic acidemia (PA). PA is an autosomal recessive metabolic disorder affecting the ability to catalyze carboxylation of propionyl-CoA to methylmalonyl-CoA. As a result, propionyl-CoA and metabolites of propionate metabolism can accumulate in the blood, urine and other fluids, as well as tissues, which can result in metabolic acidosis and hyperammonemia. PA is caused by loss-of-function mutations in the PCCA or PCCB genes, which code for the alpha and beta subunits of propionyl-CoA carboxylase (PCC). mRNA therapeutics are particularly well-suited for the treatment of PA, as the technology provides for the intracellular delivery of mRNA encoding PCCA and/or PCCB, followed by de novo synthesis of functional PCCA and/or PCCB protein capable of assembling into PCC within target cells with the proper subcellular localization. After delivery of mRNA to the target cells, the desired PCCA and/or PCCB protein is expressed by the cells' own translational machinery, and hence, fully functional PCCA and/or PCCB protein replaces the defective or missing protein.

One challenge associated with delivering nucleic acid-based therapeutics (e.g., mRNA therapeutics) in vivo stems from the innate immune response which can occur when the body's immune system encounters foreign nucleic acids. Foreign mRNAs can activate the immune system via recognition through toll-like receptors (TLRs), in particular TLR7/8, which is activated by single-stranded RNA (ssRNA). In nonimmune cells, the recognition of foreign mRNA can occur through the retinoic acid-inducible gene I (RIG-I). Immune recognition of foreign mRNAs can result in unwanted cytokine effects including interleukin-1β (IL-1β) production, tumor necrosis factor-α (TNF-α) distribution and a strong type I interferon (type I IFN) response. This disclosure features the incorporation of different modified nucleotides within therapeutic mRNAs to minimize the immune activation and optimize the translation efficiency of mRNA to protein. Particular aspects feature a combination of nucleotide modification to reduce the innate immune response and sequence optimization, in particular, within the open reading frame (ORF) of therapeutic mRNAs encoding PCCA or PCCB to enhance protein expression.

Certain embodiments of the mRNA therapeutic technology of the instant disclosure also feature delivery of mRNA encoding PCCA and/or PCCB via a lipid nanoparticle (LNP) delivery system. Lipid nanoparticles (LNPs) are an ideal platform for the safe and effective delivery of mRNAs to target cells. LNPs have the unique ability to deliver nucleic acids by a mechanism involving cellular uptake, intracellular transport and endosomal release or endosomal escape. The instant invention features ionizable lipid-based LNPs combined with mRNA encoding PCCA and/or PCCB, which have improved properties when administered in vivo. Without being bound in theory, it is believed that the ionizable lipid-based LNP formulations of the invention have improved properties, for example, cellular uptake, intracellular transport and/or endosomal release or endosomal escape. LNPs administered by systemic route (e.g., intravenous (IV) administration), for example, in a first administration, can accelerate the clearance of subsequently injected LNPs, for example, in further administrations. This phenomenon is known as accelerated blood clearance (ABC) and is a key challenge, in particular, when replacing deficient enzymes (e.g., PCC) in a therapeutic context. This is because repeat administration of mRNA therapeutics is in most instances essential to maintain necessary levels of enzyme in target tissues in human subjects (e.g., human subjects suffering from PA.) Repeat dosing challenges can be addressed on multiple levels. mRNA engineering and/or efficient delivery by LNPs can result in increased levels and or enhanced duration of protein (e.g., PCCA or PCCB) being expressed following a first dose of administration, which in turn, can lengthen the time between first dose and subsequent dosing. It is known that the ABC phenomenon is, at least in part, transient in nature, with the immune responses underlying ABC resolving after sufficient time following systemic administration. As such, increasing the duration of protein expression and/or activity following systemic delivery of an mRNA therapeutic of the disclosure in one aspect, combats the ABC phenomenon. Moreover, LNPs can be engineered to avoid immune sensing and/or recognition and can thus further avoid ABC upon subsequent or repeat dosing. An exemplary aspect of the disclosure features LNPs which have been engineered to have reduced ABC.

1. Propionyl-CoA Carboxylase (PCC)

Propionyl-CoA carboxylase (PCC; EC 6.4.1.3) catalyzes the carboxylation of propionyl-CoA with bicarbonate, producing methylmalonyl-CoA. Methylmalonyl-CoA is then converted to succinyl-CoA, which is an intermediate in the tricarboxylic acid cycle (TCA). In the cell, PCC exists as a heterododecamer composed of six propionyl-CoA carboxylase alpha subunits, encoded by PCCA (OMIM 232000), and 6 propionyl-CoA beta subunits, encoded by PCCB (OMIM 232050).

Propionic Acidemia (PA; OMIM 606054), also known as propionic aciduria, is an autosomal recessive metabolic disorder associated with PCC function. PA results when bi-allelic variants eliminate or reduce the function of the PCCA or PCCB subunits of PCC. Propionyl-CoA accumulates intracellularly in human subjects with PA, which has many metabolic effects, including, e.g., the inhibition of mitochondrial respiratory function and reduced synthesis of citrate, GTP and ATP. A variety of variant PCCA and PCCB proteins have different levels of activity, with the severity of PA being correlated with the severity of the enzymes' mutations. For example, PCCA null mutations, such as R288X and S537X, result in severe phenotypes, while certain splice site variants can result in milder disease. Generally, variations in the PCCA N and C terminal regions can cause PA because regions are necessary for PCC's holocarboxylase synthase interaction. PCCB mutations, e.g., A497V, R512C, L519P, and W531X, often affect the interaction between PCCA and PCCB, thereby disturbing PCC stability and function.

The wild type PCCA canonical mRNA sequence, corresponding to isoform 1, is described at the NCBI Reference Sequence database (RefSeq) under accession number NM_000282.3 ("*Homo sapiens* propionyl-CoA carboxylase alpha subunit (PCCA), transcript variant 1, mRNA"). The wild type PCCA canonical protein sequence, corresponding to isoform 1, is described at the RefSeq database under accession number NP_000273.2 ("propionyl-CoA carboxylase alpha chain, mitochondrial isoform a precursor [*Homo sapiens*]"). The PCCA isoform 1 protein is 728 amino acids long. The specific nucleic acid sequences encoding the reference protein sequence in the Ref Seq sequences are the coding sequence (CDS) as indicated in the respective RefSeq database entry.

PCCA isoform 2 is produced by alternative splicing. The RefSeq protein and mRNA sequences for isoform 2 of PCCA are NP_001121164.1 and NM_001127692.2, respectively. Isoform 2 PCCA is encoded by the CDS disclosed in each one of the above mentioned mRNA RefSeq entries. The isoform 2 polynucleotide is shorter than PCCA isoform 1. The PCCA isoform 2 protein is 702 amino acids long, and lacks amino acids 36-61 of isoform 1.

PCCA isoform 3 is produced by alternative splicing. The RefSeq protein and mRNA sequences for isoform 3 of PCCA are NP_001171475.1 and NM_001178004.1, respectively. Isoform 3 of PCCA is encoded by the CDS disclosed in each one of the above mentioned mRNA RefSeq entries. The isoform 3 polynucleotide is shorter than PCCA isoforms 1 and 2. The PCCA isoform 3 protein is 681 amino acids long, and lacks amino acids 634-680 of isoform 1.

The CDS for wild type PCCB canonical mRNA sequence, corresponding to isoform 1, is described at the NCBI Reference Sequence database (RefSeq) under accession number NM_000532.4 ("*Homo sapiens* propionyl-CoA carboxylase beta subunit (PCCB), transcript variant 1, mRNA"). The wild type PCCB canonical protein sequence, corresponding to isoform 1, is described at the RefSeq database under accession number NP_000523.2 ("propionyl-CoA carboxylase beta chain, mitochondrial isoform 1 precursor [*Homo sapiens*]"). The PCCB isoform 1 protein is 539 amino acids long. It is noted that the specific nucleic acid sequences encoding the reference protein sequence in the Ref Seq sequences are the CDS as indicated in the respective RefSeq database entry.

PCCB isoform 2 is produced by alternative splicing. The RefSeq protein and mRNA sequences for isoform 2 of PCCB are NP_001171485.1 and NM_001178014.1, respectively. Isoform 2 of PCCB is encoded by the CDS disclosed in each one of the above mentioned mRNA RefSeq entries. The isoform 2 polynucleotide is longer than PCCB isoform 1. The PCCB isoform 2 protein is 559 amino acids long, and has an additional 20 amino acids over isoform 1 (amino acids QQIIGWAQWLPLVISALWEAE in place of a Q at position 124 of isoform 1).

The amino acid sequence of wild-type isoform 1 of human PCCA is provided in SEQ ID NO:1. The amino acid sequence of wild-type isoform 1 of human PCCB is provided in SEQ ID NO:15.

In certain aspects, the invention provides a polynucleotide (e.g., a ribonucleic acid (RNA), e.g., a mRNA) comprising a nucleotide sequence (e.g., an open reading frame (ORF)) encoding a PCCA or PCCB polypeptide. In some embodiments, the PCCA polypeptide of the invention is a wild type human PCCA isoform 1, 2 or 3 protein. In some embodiments, the PCCB polypeptide of the invention is a wild type human PCCB isoform 1 or 2 protein. In some embodiments, the PCCA polypeptide or PCCB polypeptide of the invention is a variant, a peptide or a polypeptide containing a substitution, and insertion and/or an addition, a deletion and/or a covalent modification with respect to a wild-type PCCA isoform 1, 2 or 3 sequence or wild-type PCCB isoform 1 or 2 sequence, respectively. In some embodiments, sequence tags or amino acids, can be added to the sequences encoded by the polynucleotides of the invention (e.g., at the N-terminal or C-terminal ends), e.g., for localization. In some embodiments, amino acid residues located at the carboxy, amino terminal, or internal regions of a polypeptide of the invention can optionally be deleted providing for fragments.

In some embodiments, the polynucleotide (e.g., a RNA, e.g., an mRNA) comprising a nucleotide sequence (e.g., an ORF) of the invention encodes a substitutional variant of a human PCCA isoform 1, 2 or 3 sequence, or a human PCCB isoform 1 or 2 sequence, which can comprise one, two, three or more than three substitutions. In some embodiments, the substitutional variant can comprise one or more conservative amino acids substitutions. In other embodiments, the variant is an insertional variant. In other embodiments, the variant is a deletional variant.

PCCA or PCCB protein fragments, functional protein domains, variants, and homologous proteins (orthologs) are also within the scope of the PCCA and PCCB polypeptides of the invention. Nonlimiting examples of polypeptides encoded by the polynucleotides of the invention are shown in SEQ ID NO:1 and SEQ ID NO:15.

Certain compositions and methods presented in this disclosure refer to the protein or polynucleotide sequences of PCCA isoform 1 and/or PCCB isoform 1. Such disclosures are equally applicable to any other isoforms of PCCA and/or PCCB.

2. Polynucleotides and Open Reading Frames (ORFs)

The instant invention features mRNAs for use in treating or preventing propionic academia (PA). The mRNAs featured for use in the invention are administered to human subjects and encode human priopionyl-CoA carboxylase alpha (PCCA) protein or human priopionyl-CoA carboxylase beta (PCCB) protein in vivo. PCCA and PCCB bind to form propionyl-CoA carboxylase (PCC). Accordingly, the invention relates to polynucleotides, e.g., mRNA, comprising an open reading frame of linked nucleosides encoding human PCCA (SEQ ID NO:1) or PCCB (SEQ ID NO: 15), isoforms thereof, functional fragments thereof, and fusion proteins comprising PCCA or PCCB. In some embodiments, the open reading frame is sequence-optimized. In particular embodiments, the invention provides sequence-optimized polynucleotides comprising nucleotides encoding the polypeptide sequence of human PCCA or human PCCB, or sequence having high sequence identity with those sequence optimized polynucleotides.

In certain aspects, the invention provides polynucleotides (e.g., a RNA such as an mRNA) that comprise a nucleotide sequence (e.g., an ORF) encoding one or more PCCA and/or PCCB polypeptides. In some embodiments, the encoded PCCA or PCCB polypeptide of the invention can be selected from:

(i) a full length PCCA or PCCB polypeptide (e.g., having the same or essentially the same length as wild-type PCCA isoform 1, 2 or 3, or wild-type PCCB isoform 1 or 2);

(ii) a functional fragment of PCCA or PCCB described herein (e.g., a truncated (e.g., deletion of carboxy, amino terminal, or internal regions) sequence shorter than wild-type PCCA or PCCB; but still retaining PCC enzymatic activity);

(iii) a variant thereof (e.g., full length or truncated PCCA or PCCB proteins in which one or more amino acids have been replaced, e.g., variants that retain all or most of the PCCA or PCCB activity of the polypeptide with respect to a reference isoform (such as any natural or artificial variants known in the art); or (iv) a fusion protein comprising (i) a full length PCCA (SEQ ID NO:1) or PCCB (SEQ ID NO:15) protein, a functional fragment or a variant thereof, and (ii) a heterologous protein.

In certain embodiments, the encoded PCCA polypeptide is a mammalian PCCA polypeptide, such as a human PCCA polypeptide, a functional fragment or a variant thereof. In certain embodiments, the encoded PCCB polypeptide is a mammalian PCCB polypeptide, such as a human PCCB polypeptide, a functional fragment or a variant thereof.

In some embodiments, the polynucleotide (e.g., a RNA, e.g., an mRNA) of the invention increases PCCA or PCCB protein expression levels and/or detectable PCC enzymatic activity levels in cells when introduced in those cells, e.g., by at least 2%, by at least 5%, by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%, compared to PCCA or PCCB protein expression levels and/or detectable PCC enzymatic activity levels in the cells prior to the administration of the polynucleotide of the invention. PCCA and PCCB protein expression levels and/or PCC enzymatic activity can be measured according to methods know in the art. In some embodiments, the polynucleotide is introduced to the cells in vitro. In some embodiments, the polynucleotide is introduced to the cells in vivo.

In some embodiments, the polynucleotides (e.g., a RNA, e.g., an mRNA) of the invention comprise a nucleotide sequence (e.g., an ORF) that encodes a wild-type human PCCA, e.g., wild-type isoform 1 of human PCCA (SEQ ID NO: 1). In some embodiments, the polynucleotides (e.g., a RNA, e.g., an mRNA) of the invention comprise a nucleotide sequence (e.g., an ORF) that encodes a wild-type human PCCB, e.g., wild-type isoform 1 of human PCCB (SEQ ID NO: 15).

In some embodiments, the polynucleotide (e.g., a RNA, e.g., an mRNA) of the invention comprises a codon optimized nucleic acid sequence, wherein the open reading frame (ORF) of the codon optimized nucleic acid sequence is derived from a wild-type PCCA or PCCB sequence (e.g., wild-type human PCCA or wild-type human PCCB). For example, for polynucleotides of invention comprising a sequence optimized ORF encoding PCCA or PCCB, the corresponding wild type sequence is the native PCCA or PCCB. Similarly, for a sequence optimized mRNA encoding a functional fragment of human PCCA or PCCB, the corresponding wild type sequence is the corresponding fragment from human PCCA or PCCB.

In some embodiments, the polynucleotides (e.g., a RNA, e.g., an mRNA) of the invention comprise a nucleotide sequence encoding PCCA isoform 1 having the full length sequence of human PCCA isoform 1 (i.e., including the initiator methionine; amino acids 1-728). In some embodiments, the polynucleotides (e.g., a RNA, e.g., an mRNA) of the invention comprise a nucleotide sequence encoding PCCB isoform 1 having the full length sequence of human PCCB isoform 1 (i.e., including the initiator methionine; amino acids 1-539). In some embodiments, the polynucleotide (e.g., a RNA, e.g., an mRNA) of the invention comprising a nucleotide sequence encoding PCCA or PCCB having the full length or mature sequence of human PCCA or PCCB is sequence optimized.

In some embodiments, the polynucleotides (e.g., a RNA, e.g., an mRNA) of the invention comprise a nucleotide sequence (e.g., an ORF) encoding a mutant PCCA or PCCB polypeptide. In some embodiments, the polynucleotides of the invention comprise an ORF encoding a PCCA or PCCB polypeptide that comprises at least one point mutation in the PCCA or PCCB sequence and retains PCC enzymatic activity. In some embodiments, the mutant PCCA or PCCB polypeptide causes a PCC activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the PCC activity resulting from the corresponding wild-type PCCA or PCCB (i.e., the same PCCA or PCCB isoform but without the mutation(s)). In some embodiments, the polynucleotide (e.g., a RNA, e.g., an mRNA) of the invention comprising an ORF encoding a mutant PCCA or PCCB polypeptide is sequence optimized.

In some embodiments, the polynucleotide (e.g., a RNA, e.g., an mRNA) of the invention comprises a nucleotide sequence (e.g., an ORF) that encodes a PCCA or PCCB polypeptide with mutations that do not alter PCC enzymatic activity. Such mutant PCCA or PCCB polypeptides can be referred to as function-neutral. In some embodiments, the polynucleotide comprises an ORF that encodes a mutant PCCA or PCCB polypeptide comprising one or more function-neutral point mutations.

In some embodiments, the mutant PCCA or PCCB polypeptide leads to higher PCC enzymatic activity than the corresponding wild-type PCCA or PCCB. In some embodiments, the mutant PCCA or PCCB polypeptide causes a PCC activity that is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% higher than the activity of the corresponding wild-type PCCA or PCCB (i.e., the same PCCA or PCCB isoform but without the mutation(s)).

In some embodiments, the polynucleotides (e.g., a RNA, e.g., an mRNA) of the invention comprise a nucleotide sequence (e.g., an ORF) encoding a functional PCCA or PCCB fragment, e.g., where one or more fragments correspond to a polypeptide subsequence of a wild type PCCA or PCCB polypeptide and retain PCC enzymatic activity. In some embodiments, the PCCA or PCCB fragment causes a PCC activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the PCC activity of the corresponding full length PCCA or PCCB. In some embodiments, the polynucleotides (e.g., a RNA, e.g., an mRNA) of the invention comprising an ORF encoding a functional PCCA or PCCB fragment is sequence optimized.

In some embodiments, the polynucleotide (e.g., a RNA, e.g., an mRNA) of the invention comprises a nucleotide sequence (e.g., an ORF) encoding a PCCA or PCCB fragment that causes higher PCC enzymatic activity than the corresponding full length PCCA or PCCB. Thus, in some embodiments the PCCA or PCCB fragment causes a PCC activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% higher than the PCC activity of the corresponding full length PCCA or PCCB.

In some embodiments, the polynucleotide (e.g., a RNA, e.g., an mRNA) of the invention comprises a nucleotide sequence (e.g., an ORF) encoding a PCCA fragment that is at least 1%, 2%, 3%, 4%, 5%, 6%, 7%, 8%, 9%, 10%, 11%, 12%, 13%1, 4%1, 5%1, 6%1, 7%1, 8%, 19%, 20%, 21%, 22%, 23%, 24% or 25% shorter than wild-type PCCA isoform 1. In some embodiments, the polynucleotide (e.g., a RNA, e.g., an mRNA) of the invention comprises a nucleotide sequence (e.g., an ORF) encoding a PCCB fragment that is at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% shorter than wild-type PCCB isoform 1.

In some embodiments, the polynucleotide (e.g., a RNA, e.g., an mRNA) of the invention comprises a nucleotide sequence (e.g., an ORF) encoding a PCCA polypeptide (e.g., the wild-type sequence, functional fragment, or variant thereof), wherein the nucleotide sequence has at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a sequence selected from the group consisting of SEQ ID NOs: 2 and 5-14. In some embodiments, the polynucleotide (e.g., a RNA, e.g., an mRNA) of the invention comprises a nucleotide sequence (e.g., an ORF) encoding a PCCB polypeptide (e.g., the wild-type sequence, functional fragment, or variant thereof), wherein the nucleotide sequence has at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a sequence selected from the group consisting of SEQ ID NOs: 16-27, 196, 197, and 198.

In some embodiments, the polynucleotide (e.g., a RNA, e.g., an mRNA) of the invention comprises an ORF encoding a PCCA polypeptide (e.g., the wild-type sequence, functional fragment, or variant thereof), wherein the polynucleotide comprises a nucleic acid sequence having 70% to 100%, 75% to 100%, 80% to 100%, 85% to 100%, 70% to 95%, 80% to 95%, 70% to 85%, 75% to 90%, 80% to 95%, 70% to 75%, 75% to 80%, 80% to 85%, 85% to 90%, 90% to 95%, or 95% to 100%, sequence identity to a sequence selected from the group consisting of SEQ ID NOs: 2 and 5-14 In some embodiments, the polynucleotide (e.g., a RNA, e.g., an mRNA) of the invention comprises an ORF encoding a PCCB polypeptide (e.g., the wild-type sequence, functional fragment, or variant thereof), wherein the polynucleotide comprises a nucleic acid sequence having 70% to 100%, 75% to 100%, 80% to 100%, 85% to 100%, 70% to 95%, 80% to 95%, 70% to 85%, 75% to 90%, 80% to 95%, 70% to 75%, 75% to 80%, 80% to 85%, 85% to 90%, 90% to 95%, or 95% to 100%, sequence identity to a sequence selected from the group consisting of SEQ ID NOs: 16-27, 196, 197, and 198.

In some embodiments the polynucleotide (e.g., a RNA, e.g., an mRNA) of the invention comprises a nucleotide sequence (e.g., an ORF) encoding a PCCA polypeptide (e.g., the wild-type sequence, functional fragment, or variant thereof), wherein the nucleotide sequence is between 70% and 90% identical; between 75% and 85% identical; between 76% and 84% identical; between 77% and 83% identical, between 77% and 82% identical, or between 78% and 81% identical to a sequence selected from the group consisting of SEQ ID NO: 2 or 5-14. In some embodiments the polynucleotide (e.g., a RNA, e.g., an mRNA) of the invention comprises a nucleotide sequence (e.g., an ORF) encoding a PCCB polypeptide (e.g., the wild-type sequence, functional fragment, or variant thereof), wherein the nucleotide sequence is between 70% and 90% identical; between 75% and 85% identical; between 76% and 84% identical; between 77% and 83% identical, between 77% and 82% identical, or between 78% and 81% identical to a sequence selected from the group consisting of SEQ ID NO: 16-27, 196, 197, and 198.

In some embodiments, the polynucleotide (e.g., a RNA, e.g., an mRNA) of the invention comprises from about 900 to about 100,000 nucleotides (e.g., from 900 to 1,000, from 900 to 1,100, from 900 to 1,200, from 900 to 1,300, from 900 to 1,400, from 900 to 1,500, from 1,000 to 1,100, from 1,000 to 1,100, from 1,000 to 1,200, from 1,000 to 1,300, from 1,000 to 1,400, from 1,000 to 1,500, from 1,187 to 1,200, from 1,187 to 1,400, from 1,187 to 1,600, from 1,187 to 1,800, from 1,187 to 2,000, from 1,187 to 3,000, from 1,187 to 5,000, from 1,187 to 7,000, from 1,187 to 10,000, from 1,187 to 25,000, from 1,187 to 50,000, from 1,187 to 70,000, or from 1,187 to 100,000).

In some embodiments, the polynucleotide of the invention (e.g., a RNA, e.g., an mRNA) comprises a nucleotide sequence (e.g., an ORF) encoding a PCCA or PCCB polypeptide (e.g., the wild-type sequence, functional fragment, or variant thereof), wherein the length of the nucleotide sequence (e.g., an ORF) is at least 500 nucleotides in length (e.g., at least or greater than about 500, 600, 700, 80, 900, 1,000, 1,050, 1,100, 1,187, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 7,000, 8,000, 9,000, 10,000, 20,000, 30,000, 40,000, 50,000, 60,000, 70,000, 80,000, 90,000 or up to and including 100,000 nucleotides).

In some embodiments, the polynucleotide of the invention (e.g., a RNA, e.g., an mRNA) comprises a nucleotide sequence (e.g., an ORF) encoding a PCCA or PCCB polypeptide (e.g., the wild-type sequence, functional fragment, or variant thereof) further comprises at least one nucleic acid sequence that is noncoding, e.g., a microRNA binding site. In some embodiments, the polynucleotide (e.g., a RNA, e.g., an mRNA) of the invention further comprises a 5'-UTR (e.g., selected from the sequences of SEQ ID NOs: 3, 64, 88-102, 165-167, or 199 or selected from the sequences of SEQ ID NO:3, SEQ ID NO:191, SEQ ID NO:199, or SEQ ID NO:206) and a 3'UTR (e.g., selected from the sequences of SEQ ID NOs: 4, 104-112, 150, or 178 or selected from the sequences of SEQ ID NO:4, SEQ ID NO:111, SEQ ID NO:150, SEQ ID NO:175, SEQ ID NO:177, SEQ ID NO: 178, SEQ ID NO:207, or SEQ ID NO:208). In some embodiments, the polynucleotide (e.g., a RNA, e.g., an mRNA) of the invention comprises a sequence selected from the group consisting of SEQ ID NOs: 2, 5-14, 16-27, 196, 197, and 198. In a further embodiment, the polynucleotide (e.g., a RNA, e.g., an mRNA) comprises a 5' terminal cap (e.g., Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof) and a poly-A-tail region (e.g., about 100 nucleotides in length). In a further embodiment, the polynucleotide (e.g., a RNA, e.g., an mRNA) a comprises a 3' UTR comprising a nucleic acid sequence selected from the group consisting of SEQ ID NOs: 4, 111, 112, or 178 or any combination thereof. In a further embodiment, the polynucleotide (e.g., a RNA, e.g., an mRNA) a comprises a 3' UTR comprising a nucleic acid sequence selected from the group consisting of SEQ ID NO:4, SEQ ID NO:111, SEQ ID NO:150, SEQ ID NO:175, SEQ ID NO:177, SEQ ID NO:178, SEQ ID NO:207, or SEQ ID NO:208 or any combination thereof. In some embodiments, the mRNA comprises a 3' UTR comprising a nucleic acid sequence of SEQ ID NO: 111. In some embodiments, the mRNA comprises a 3' UTR comprising a nucleic acid sequence of SEQ ID NO: 4. In some embodiments, the mRNA comprises a 3' UTR comprising a nucleic acid sequence of SEQ ID NO: 112. In some embodiments, the mRNA comprises a 3' UTR comprising a nucleic acid sequence of SEQ ID NO: 178. In some embodiments, the mRNA comprises a 3' UTR comprising a nucleic acid sequence of SEQ ID NO:150. In some embodiments, the mRNA comprises a 3' UTR comprising a nucleic acid sequence of SEQ ID NO:175. In some embodiments, the mRNA comprises a 3' UTR comprising a nucleic acid sequence of SEQ ID NO:207. In some embodiments, the mRNA comprises a 3' UTR comprising a nucleic acid sequence of SEQ ID NO:208. In some embodiments, the mRNA comprises a 3' UTR comprising a nucleic acid sequence of SEQ ID NO:177.

In some embodiments, the mRNA comprises a polyA tail. In some instances, the poly A tail is 50-150, 75-150, 85-150, 90-150, 90-120, 90-130, or 90-150 nucleotides in length. In some instances, the poly A tail is 100 nucleotides in length.

In some embodiments, the polynucleotide of the invention (e.g., a RNA, e.g., an mRNA) comprises a nucleotide sequence (e.g., an ORF) encoding a PCCA or PCCB polypeptide is single stranded or double stranded.

In some embodiments, the polynucleotide of the invention comprising a nucleotide sequence (e.g., an ORF) encoding a PCCA or PCCB polypeptide (e.g., the wild-type sequence, functional fragment, or variant thereof) is DNA or RNA. In some embodiments, the polynucleotide of the invention is RNA. In some embodiments, the polynucleotide of the invention is, or functions as, a mRNA. In some embodiments, the mRNA comprises a nucleotide sequence (e.g., an ORF) that encodes at least one PCCA or PCCB polypeptide, and is capable of being translated to produce the encoded PCCA or PCCB polypeptide in vitro, in vivo, in situ or ex vivo.

In some embodiments, the polynucleotide of the invention (e.g., a RNA, e.g., an mRNA) comprises a sequence-optimized nucleotide sequence (e.g., an ORF) encoding a PCCA or PCCB polypeptide (e.g., the wild-type sequence, functional fragment, or variant thereof, see e.g., SEQ ID NOs.; 2, 5-14, 16-27, 196, 197, and 198), wherein the polynucleotide comprises at least one chemically modified nucleobase, e.g., N1-methylpseudouracil or 5-methoxyuracil. In certain embodiments, all uracils in the polynucleotide are N1-methylpseudouracils. In other embodiments, all uracils in the polynucleotide are 5-methoxyuracils. In some embodiments, the polynucleotide further comprises a miRNA binding site, e.g., a miRNA binding site that binds to miR-142 and/or a miRNA binding site that binds to miR-126.

In some embodiments, the polynucleotide (e.g., a RNA, e.g., a mRNA) disclosed herein is formulated with a delivery agent comprising, e.g., a compound having the Formula (I), e.g., any of Compounds 1-232, e.g., Compound II; a compound having the Formula (III), (IV), (V), or (VI), e.g., any of Compounds 233-342, e.g., Compound VI; or a compound having the Formula (VIII), e.g., any of Compounds 419-428, e.g., Compound I, or any combination thereof. In some embodiments, the delivery agent comprises Compound II, DSPC, Cholesterol, and Compound I or PEG-DMG, e.g., with a mole ratio of about 50:10:38.5:1.5. In some embodiments, the delivery agent comprises Compound VI, DSPC, Cholesterol, and Compound I or PEG-DMG, e.g., with a mole ratio in the range of about 30 to about 60 mol % Compound II or VI (or related suitable amino lipid) (e.g., 30-40, 40-45, 45-50, 50-55 or 55-60 mol % Compound II or VI (or related suitable amino lipid)), about 5 to about 20 mol % phospholipid (or related suitable phospholipid or "helper lipid") (e.g., 5-10, 10-15, or 15-20 mol % phospholipid (or related suitable phospholipid or "helper lipid")), about 20 to about 50 mol % cholesterol (or related sterol or "non-cationic" lipid) (e.g., about 20-30, 30-35, 35-40, 40-45, or 45-50 mol % cholesterol (or related sterol or "non-cationic" lipid)) and about 0.05 to about 10 mol % PEG lipid (or other suitable PEG lipid) (e.g., 0.05-1, 1-2, 2-3, 3-4, 4-5, 5-7, or 7-10 mol % PEG lipid (or other suitable PEG lipid)). An exemplary delivery agent can comprise mole ratios of, for example, 47.5:10.5:39.0:3.0 or 50:10:38.5:1.5. In certain instances, an exemplary delivery agent can comprise mole ratios of, for example, 47.5:10.5:39.0:3; 47.5:10:39.5:3; 47.5:11:39.5:2; 47.5:10.5:39.5:2.5; 47.5:11:39:2.5; 48.5:10: 38.5:3; 48.5:10.5:39:2; 48.5:10.5:38.5:2.5; 48.5:10.5:39.5: 1.5; 48.5:10.5:38.0:3; 47:10.5:39.5:3; 47:10:40.5:2.5; 47:11: 40:2; 47:10.5:39.5:3; 48:10.5:38.5:3; 48:10:39.5:2.5; 48:11: 39:2; or 48:10.5:38.5:3. In some embodiments, the delivery agent comprises Compound II or VI, DSPC, Cholesterol, and Compound I or PEG-DMG, e.g., with a mole ratio of about 47.5:10.5:39.0:3.0. In some embodiments, the delivery agent comprises Compound II or VI, DSPC, Cholesterol, and Compound I or PEG-DMG, e.g., with a mole ratio of about 50:10:38.5:1.5.

In some embodiments, the polynucleotide of the disclosure is an mRNA that comprises a 5'-terminal cap (e.g., Cap 1), a 5'UTR (e.g., SEQ ID NO:3, SEQ ID NO:64, or SEQ ID NO:199), a ORF sequence selected from the group consisting of SEQ ID NOs.: 2, 5-14, 16-27, 196, 197, and 198, a 3'UTR (e.g., SEQ ID NO:4, SEQ ID NO: 112, or SEQ ID NO: 178), and a poly A tail (e.g., about 100 nt in length), wherein all uracils in the polynucleotide are N1-methylp-seudouracils. In some embodiments, the delivery agent comprises Compound II or Compound VI as the ionizable lipid and PEG-DMG or Compound I as the PEG lipid.

In some embodiments, the polynucleotide of the disclosure is an mRNA that comprises a 5'-terminal cap (e.g., Cap 1), a 5'UTR (e.g., SEQ ID NO:3, SEQ ID NO: 191, SEQ ID NO:199, or SEQ ID NO:206), a ORF sequence selected from the group consisting of SEQ ID NOs.: 2, 5-14, 16-27, 196, 197, and 198, a 3'UTR (e.g., SEQ ID NO:4, SEQ ID NO:111, SEQ ID NO:150, SEQ ID NO:175, SEQ ID NO: 177, SEQ ID NO:178, SEQ ID NO:207, or SEQ ID NO:208), and a poly A tail (e.g., about 100 nt in length), wherein all uracils in the polynucleotide are N1 methylp-seudouracils. In some embodiments, the delivery agent comprises Compound II or Compound VI as the ionizable lipid and PEG-DMG or Compound I as the PEG lipid.

3. Signal Sequences

The polynucleotides (e.g., a RNA, e.g., an mRNA) of the invention can also comprise nucleotide sequences that encode additional features that facilitate trafficking of the encoded polypeptides to therapeutically relevant sites. One such feature that aids in protein trafficking is the signal sequence, or targeting sequence. The peptides encoded by these signal sequences are known by a variety of names, including targeting peptides, transit peptides, and signal peptides. In some embodiments, the polynucleotide (e.g., a RNA, e.g., an mRNA) comprises a nucleotide sequence (e.g., an ORF) that encodes a signal peptide operably linked to a nucleotide sequence that encodes a PCCA or PCCB polypeptide described herein.

In some embodiments, the "signal sequence" or "signal peptide" is a polynucleotide or polypeptide, respectively, which is from about 30-210, e.g., about 45-80 or 15-60 nucleotides (e.g., about 20, 30, 40, 50, 60, or 70 amino acids) in length that, optionally, is incorporated at the 5' (or N-terminus) of the coding region or the polypeptide, respectively. Addition of these sequences results in trafficking the encoded polypeptide to a desired site, such as the endoplasmic reticulum or the mitochondria through one or more targeting pathways. Some signal peptides are cleaved from the protein, for example by a signal peptidase after the proteins are transported to the desired site.

[In some embodiments, the polynucleotide of the invention comprises a nucleotide sequence encoding a PCCA or PCCB polypeptide, wherein the nucleotide sequence further comprises a 5' nucleic acid sequence encoding a heterologous signal peptide.

4. Fusion Proteins

In some embodiments, the polynucleotide of the invention (e.g., a RNA, e.g., an mRNA) can comprise more than one nucleic acid sequence (e.g., an ORF) encoding a polypeptide of interest. In some embodiments, polynucleotides of the invention comprise a single ORF encoding a PCCA or PCCB polypeptide, a functional fragment, or a variant thereof. However, in some embodiments, the polynucleotide of the invention can comprise more than one ORF, for example, a first ORF encoding a PCCA or PCCB polypeptide (a first polypeptide of interest), a functional fragment, or a variant thereof, and a second ORF expressing a second polypeptide of interest. In some embodiments, two or more polypeptides of interest can be genetically fused, i.e., two or more polypeptides can be encoded by the same ORF. In some embodiments, the polynucleotide can comprise a nucleic acid sequence encoding a linker (e.g., a G4S (SEQ ID NO: 86) peptide linker or another linker known in the art) between two or more polypeptides of interest.

In some embodiments, a polynucleotide of the invention (e.g., a RNA, e.g., an mRNA) can comprise two, three, four, or more ORFs, each expressing a polypeptide of interest.

In some embodiments, the polynucleotide of the invention (e.g., a RNA, e.g., an mRNA) can comprise a first nucleic acid sequence (e.g., a first ORF) encoding a PCCA or PCCB polypeptide and a second nucleic acid sequence (e.g., a second ORF) encoding a second polypeptide of interest.

Linkers and Cleavable Peptides

In certain embodiments, the mRNAs of the disclosure encode more than one PCCA OR PCCB domain (e.g., PCCA OR PCCB catalytic domain, PCCA OR PCCB tetrameriza-tion domain) or a heterologous domain, referred to herein as multimer constructs. In certain embodiments of the multimer constructs, the mRNA further encodes a linker located between each domain. The linker can be, for example, a cleavable linker or protease-sensitive linker. In certain embodiments, the linker is selected from the group consisting of F2A linker, P2A linker, T2A linker, E2A linker, and combinations thereof. This family of self-cleaving peptide linkers, referred to as 2A peptides, has been described in the art (see for example, Kim, J. H. et al. (2011) PLoS ONE 6:e18556). In certain embodiments, the linker is an F2A linker. In certain embodiments, the linker is a GGGS (SEQ ID NO: 86) linker. In certain embodiments, the linker is a (GGGS)n (SEQ ID NO: 190) linker, wherein n=2, 3,4, or 5. In certain embodiments, the multimer construct contains three domains with intervening linkers, having the structure: domain-linker-domain-linker-domain e.g., PCCA OR PCCB domain-linker-PCCA OR PCCB domain-linker-PCCA OR PCCB domain.

In one embodiment, the cleavable linker is an F2A linker (e.g., having the amino acid sequence GSGVKQTLNFDLLKLAGDVESNPGP (SEQ ID NO:186)). In other embodiments, the cleavable linker is a T2A linker (e.g., having the amino acid sequence GSGEGRGSLLTCGDVEENPGP (SEQ ID NO:187)), a P2A linker (e.g., having the amino acid sequence GSGATNFSLLKQAGDVEENPGP (SEQ ID NO: 188)) or an E2A linker (e.g., having the amino acid sequence GSGQCTNYALLKLAGDVESNPGP (SEQ ID NO:189)). The skilled artisan will appreciate that other art-recognized linkers may be suitable for use in the constructs of the invention (e.g., encoded by the polynucleotides of the invention). The skilled artisan will likewise appreciate that other multicistronic constructs may be suitable for use in the invention. In exemplary embodiments, the construct design yields approximately equimolar amounts of intrabody and/or domain thereof encoded by the constructs of the invention.

In one embodiment, the self-cleaving peptide may be, but is not limited to, a 2A peptide. A variety of 2A peptides are known and available in the art and may be used, including e.g., the foot and mouth disease virus (FMDV) 2A peptide, the equine rhinitis A virus 2A peptide, the Thosea asigna virus 2A peptide, and the porcine teschovirus-1 2A peptide. 2A peptides are used by several viruses to generate two proteins from one transcript by ribosome-skipping, such that a normal peptide bond is impaired at the 2A peptide sequence, resulting in two discontinuous proteins being produced from one translation event. As a non-limiting example, the 2A peptide may have the protein sequence of SEQ ID NO:188, fragments or variants thereof. In one embodiment, the 2A peptide cleaves between the last glycine and last proline. As another non-limiting example, the polynucleotides of the present invention may include a polynucleotide sequence encoding the 2A peptide having the protein sequence of fragments or variants of SEQ ID NO:188. One example of a polynucleotide sequence encoding the 2A peptide is:GGAAGCGGAGCUACUAAC-UUCAGCCUGCUGAAGCAGGCUGGAGACG UGGAG-GAGAACCCUGGACCU (SEQ ID NO:209). In one illustrative embodiment, a 2A peptide is encoded by the following sequence: 5'-UCCGGACUCAGAUCCGGG-GAUCUCAAAAUUGUCGCUCCUGUCAAACAA ACU-CUUAACUUUGAUUUACUCAAACUGGCUGGGGAU-GUAGAAAGCAAU CCAGGTCCACUC-3'(SEQ ID NO:210). The polynucleotide sequence of the 2A peptide may be modified or codon optimized by the methods described herein and/or are known in the art.

In one embodiment, this sequence may be used to separate the coding regions of two or more polypeptides of interest. As a non-limiting example, the sequence encoding the F2A peptide may be between a first coding region A and a second coding region B (A-F2Apep-B). The presence of the F2A peptide results in the cleavage of the one long protein between the glycine and the proline at the end of the F2A peptide sequence (NPGP is cleaved to result in NPG and P) thus creating separate protein A (with 21 amino acids of the F2A peptide attached, ending with NPG) and separate protein B (with 1 amino acid, P, of the F2A peptide attached). Likewise, for other 2A peptides (P2A, T2A and E2A), the presence of the peptide in a long protein results in cleavage between the glycine and proline at the end of the 2A peptide sequence (NPGP is cleaved to result in NPG and P). Protein A and protein B may be the same or different peptides or polypeptides of interest (e.g., a PCCA OR PCCB polypeptide such as full length human PCCA OR PCCB or a truncated version thereof comprising the catalytic and tetramerization domain of PCCA OR PCCB). In particular embodiments, protein A and protein B are a PCCA OR PCCB catalytic domain, and a PCCA OR PCCB tetramerization domain, in either order. In certain embodiments, the first coding region and the second coding region encode a PCCA OR PCCB catalytic domain and a PCCA OR PCCB tetramerization domain, in either order.

5. Sequence Optimization of Nucleotide Sequence Encoding a PCCA or PCCB Polypeptide In some embodiments, the polynucleotide (e.g., a RNA, e.g., an mRNA) of the invention is sequence optimized. In some embodiments, the polynucleotide (e.g., a RNA, e.g., an mRNA) of the invention comprises a nucleotide sequence (e.g., an ORF) encoding a PCCA or PCCB polypeptide, optionally, a nucleotide sequence (e.g., an ORF) encoding another polypeptide of interest, a 5'-UTR, a 3'-UTR, the 5' UTR or 3' UTR optionally comprising at least one microRNA binding site, optionally a nucleotide sequence encoding a linker, a polyA tail, or any combination thereof), in which the ORF(s) are sequence optimized.

A sequence-optimized nucleotide sequence, e.g., a codon-optimized mRNA sequence encoding a PCCA or PCCB polypeptide, is a sequence comprising at least one synonymous nucleobase substitution with respect to a reference sequence (e.g., a wild type nucleotide sequence encoding a PCCA or PCCB polypeptide).

A sequence-optimized nucleotide sequence can be partially or completely different in sequence from the reference sequence. For example, a reference sequence encoding polyserine uniformly encoded by UCU codons can be sequence-optimized by having 100% of its nucleobases substituted (for each codon, U in position 1 replaced by A, C in position 2 replaced by G, and U in position 3 replaced by C) to yield a sequence encoding polyserine which would be uniformly encoded by AGC codons. The percentage of sequence identity obtained from a global pairwise alignment between the reference polyserine nucleic acid sequence and the sequence-optimized polyserine nucleic acid sequence would be 0%. However, the protein products from both sequences would be 100% identical.

Some sequence optimization (also sometimes referred to codon optimization) methods are known in the art (and discussed in more detail below) and can be useful to achieve one or more desired results. These results can include, e.g., matching codon frequencies in certain tissue targets and/or host organisms to ensure proper folding; biasing G/C content to increase mRNA stability or reduce secondary structures; minimizing tandem repeat codons or base runs that can impair gene construction or expression; customizing transcriptional and translational control regions; inserting or removing protein trafficking sequences; removing/adding post translation modification sites in an encoded protein (e.g., glycosylation sites); adding, removing or shuffling protein domains; inserting or deleting restriction sites; modifying ribosome binding sites and mRNA degradation sites; adjusting translational rates to allow the various domains of the protein to fold properly; and/or reducing or eliminating problem secondary structures within the polynucleotide. Sequence optimization tools, algorithms and services are known in the art, non-limiting examples include services from GeneArt (Life Technologies), DNA2.0 (Menlo Park CA) and/or proprietary methods.

Codon options for each amino acid are given in TABLE 1.

TABLE 1

| Codon Options | | |
| --- | --- | --- |
| Amino Acid | Single Letter Code | Codon Options |
| Isoleucine | I | AUU, AUC, AUA |
| Leucine | L | CUU, CUC, CUA, CUG, UUA, UUG |
| Valine | V | GUU, GUC, GUA, GUG |
| Phenylalanine | F | UUU, UUC |
| Methionine | M | AUG |
| Cysteine | C | UGU, UGC |
| Alanine | A | GCU, GCC, GCA, GCG |
| Glycine | G | GGU, GGC, GGA, GGG |
| Proline | P | CCU, CCC, CCA, CCG |
| Threonine | T | ACU, ACC, ACA, ACG |
| Serine | S | UCU, UCC, UCA, UCG, AGU, AGC |
| Tyrosine | Y | UAU, UAC |
| Tryptophan | W | UGG |
| Glutamine | Q | CAA, CAG |
| Asparagine | N | AAU, AAC |
| Histidine | H | CAU, CAC |

TABLE 1-continued

Codon Options

| Amino Acid | Single Letter Code | Codon Options |
|---|---|---|
| Glutamic acid | E | GAA, GAG |
| Aspartic acid | D | GAU, GAC |
| Lysine | K | AAA, AAG |
| Arginine | R | CGU, CGC, CGA, CGG, AGA, AGG |
| Selenocysteine | Sec | UGA in mRNA in presence of Selenocysteine insertion element (SECIS) |
| Stop codons | Stop | UAA, UAG, UGA |

In some embodiments, a polynucleotide (e.g., a RNA, e.g., an mRNA) of the invention comprises a sequence-optimized nucleotide sequence (e.g., an ORF) encoding a PCCA or PCCB polypeptide, a functional fragment, or a variant thereof, wherein the PCCA or PCCB polypeptide, functional fragment, or a variant thereof encoded by the sequence-optimized nucleotide sequence has improved properties (e.g., compared to a PCCA or PCCB polypeptide, functional fragment, or a variant thereof encoded by a reference nucleotide sequence that is not sequence optimized), e.g., improved properties related to expression efficacy after administration in vivo. Such properties include, but are not limited to, improving nucleic acid stability (e.g., mRNA stability), increasing translation efficacy in the target tissue, reducing the number of truncated proteins expressed, improving the folding or prevent misfolding of the expressed proteins, reducing toxicity of the expressed products, reducing cell death caused by the expressed products, increasing and/or decreasing protein aggregation.

In some embodiments, the sequence-optimized nucleotide sequence (e.g., an ORF) is codon optimized for expression in human subjects, having structural and/or chemical features that avoid one or more of the problems in the art, for example, features which are useful for optimizing formulation and delivery of nucleic acid-based therapeutics while retaining structural and functional integrity; overcoming a threshold of expression; improving expression rates; half-life and/or protein concentrations; optimizing protein localization; and avoiding deleterious bio-responses such as the immune response and/or degradation pathways.

In some embodiments, the polynucleotides of the invention comprise a nucleotide sequence (e.g., a nucleotide sequence (e.g., an ORF) encoding a PCCA or PCCB polypeptide, a nucleotide sequence (e.g., an ORF) encoding another polypeptide of interest, a 5'-UTR, a 3'-UTR, a microRNA binding site, a nucleic acid sequence encoding a linker, or any combination thereof) that is sequence-optimized according to a method comprising:

(i) substituting at least one codon in a reference nucleotide sequence (e.g., an ORF encoding a PCCA or PCCB polypeptide) with an alternative codon to increase or decrease uridine content to generate a uridine-modified sequence;

(ii) substituting at least one codon in a reference nucleotide sequence (e.g., an ORF encoding a PCCA or PCCB polypeptide) with an alternative codon having a higher codon frequency in the synonymous codon set;

(iii) substituting at least one codon in a reference nucleotide sequence (e.g., an ORF encoding a PCCA or PCCB polypeptide) with an alternative codon to increase G/C content; or (iv) a combination thereof.

In some embodiments, the sequence-optimized nucleotide sequence (e.g., an ORF encoding a PCCA or PCCB polypeptide) has at least one improved property with respect to the reference nucleotide sequence.

In some embodiments, the sequence optimization method is multiparametric and comprises one, two, three, four, or more methods disclosed herein and/or other optimization methods known in the art.

Features, which can be considered beneficial in some embodiments of the invention, can be encoded by or within regions of the polynucleotide and such regions can be upstream (5') to, downstream (3') to, or within the region that encodes the PCCA or PCCB polypeptide. These regions can be incorporated into the polynucleotide before and/or after sequence-optimization of the protein encoding region or open reading frame (ORF). Examples of such features include, but are not limited to, untranslated regions (UTRs), microRNA sequences, Kozak sequences, oligo(dT) sequences, poly-A tail, and detectable tags and can include multiple cloning sites that can have XbaI recognition.

In some embodiments, the polynucleotide of the invention comprises a 5' UTR, a 3' UTR and/or a microRNA binding site. In some embodiments, the polynucleotide comprises two or more 5' UTRs and/or 3' UTRs, which can be the same or different sequences. In some embodiments, the polynucleotide comprises two or more microRNA binding sites, which can be the same or different sequences. Any portion of the 5' UTR, 3' UTR, and/or microRNA binding site, including none, can be sequence-optimized and can independently contain one or more different structural or chemical modifications, before and/or after sequence optimization.

In some embodiments, after optimization, the polynucleotide is reconstituted and transformed into a vector such as, but not limited to, plasmids, viruses, cosmids, and artificial chromosomes. For example, the optimized polynucleotide can be reconstituted and transformed into chemically competent *E. coli*, yeast, *neurospora*, maize, *drosophila*, etc. where high copy plasmid-like or chromosome structures occur by methods described herein.

6. Sequence-Optimized Nucleotide Sequences Encoding PCCA or PCCB Polypeptides

In some embodiments, the polynucleotide of the invention comprises a sequence-optimized nucleotide sequence encoding a PCCA or PCCB polypeptide disclosed herein. In some embodiments, the polynucleotide of the invention comprises an open reading frame (ORF) encoding a PCCA or PCCB polypeptide, wherein the ORF has been sequence optimized.

Exemplary sequence-optimized nucleotide sequences encoding human PCCA are set forth as SEQ ID NOs: 2 and 5-14 (PCCA_11, PCCA_12, PCCA_13, PCCA_14, PCCA 15, PCCA 16, PCCA 17, PCCA 18, PCCA 19, PCCA 20, PCCA_21, PCCA_22, PCCA-01-014.2, and SE_P-CCA_018). Exemplary sequence-optimized nucleotide sequences encoding human PCCB are set forth as SEQ ID NOs: 16-27, 196, 197, and 198 (PCCB_11, PCCB_12, PCCB_13, PCCB_14, PCCB_15, PCCB 16, PCCB 17, PCCB 18, PCCB 19, PCCB 20, PCCB 21, PCCB_22, PCCB-01-014, SE_PCCB 026, SE_PCCB 027, SE_PCCB 028, and SE_PCCB_020). In some embodiments, the sequence optimized PCCA or PCCB sequences, fragments, and variants thereof are used to practice the methods disclosed herein.

In some embodiments, a polynucleotide of the present disclosure, for example a polynucleotide comprising an mRNA nucleotide sequence encoding a PCCA or PCCB polypeptide, comprises from 5' to 3' end:

(i) a 5' cap provided herein, for example, Cap1;

(ii) a 5' UTR, such as the sequences provided herein, for example, SEQ ID NO:3, SEQ ID NO:64, or SEQ ID NO:199;

(iii) an open reading frame encoding a PCCA or PCCB polypeptide, e.g., a sequence optimized nucleic acid sequence encoding PCCA or PCCB set forth as SEQ ID NOs: 2, 5-14, 16-27, 196, 197, and 198;

(iv) at least one stop codon (if not present at 5' terminus of 3'UTR);

(v) a 3' UTR, such as the sequences provided herein, for example, SEQ ID NO:4, SEQ ID NO:112, or SEQ ID NO:178; and (vi) a poly-A tail provided above.

In some embodiments, a polynucleotide of the present disclosure, for example a polynucleotide comprising an mRNA nucleotide sequence encoding a PCCA or PCCB polypeptide, comprises from 5' to 3' end:

(i) a 5' cap provided herein, for example, Cap1;

(ii) a 5' UTR, such as the sequences provided herein, for example, SEQ ID NO:3, SEQ ID NO:191, SEQ ID NO:199, or SEQ ID NO:206;

(iii) an open reading frame encoding a PCCA or PCCB polypeptide, e.g., a sequence optimized nucleic acid sequence encoding PCCA or PCCB set forth as SEQ ID NOs: 2, 5-14, 16-27, 196, 197, and 198;

(iv) at least one stop codon (if not present at 5' terminus of 3'UTR);

(v) a 3' UTR, such as the sequences provided herein, for example, SEQ ID NO:4, SEQ ID NO:111, SEQ ID NO:150, SEQ ID NO:175, SEQ ID NO:177, SEQ ID NO:178, SEQ ID NO:207, or SEQ ID NO:208; and (vi) a poly-A tail provided above.

In certain embodiments, all uracils in the polynucleotide are N1-methylpseudouracil (G5). In certain embodiments, all uracils in the polynucleotide are 5-methoxyuracil (G6).

The sequence-optimized nucleotide sequences disclosed herein are distinct from the corresponding wild type nucleotide acid sequences and from other known sequence-optimized nucleotide sequences, e.g., these sequence-optimized nucleic acids have unique compositional characteristics.

In some embodiments, the percentage of uracil or thymine nucleobases in a sequence-optimized nucleotide sequence (e.g., encoding a PCCA or PCCB polypeptide, a functional fragment, or a variant thereof) is modified (e.g., reduced) with respect to the percentage of uracil or thymine nucleobases in the reference wild-type nucleotide sequence. Such a sequence is referred to as a uracil-modified or thymine-modified sequence. The percentage of uracil or thymine content in a nucleotide sequence can be determined by dividing the number of uracils or thymines in a sequence by the total number of nucleotides and multiplying by 100. In some embodiments, the sequence-optimized nucleotide sequence has a lower uracil or thymine content than the uracil or thymine content in the reference wild-type sequence. In some embodiments, the uracil or thymine content in a sequence-optimized nucleotide sequence of the invention is greater than the uracil or thymine content in the reference wild-type sequence and still maintain beneficial effects, e.g., increased expression and/or reduced Toll-Like Receptor (TLR) response when compared to the reference wild-type sequence.

Methods for optimizing codon usage are known in the art. For example, an ORF of any one or more of the sequences provided herein may be codon optimized. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g., glycosylation sites); add, remove or shuffle protein domains; insert or delete restriction sites; modify ribosome binding sites and mRNA degradation sites; adjust translational rates to allow the various domains of the protein to fold properly; or reduce or eliminate problem secondary structures within the polynucleotide. Codon optimization tools, algorithms and services are known in the art—non-limiting examples include services from GeneArt (Life Technologies), DNA2.0 (Menlo Park CA) and/or proprietary methods. In some embodiments, the open reading frame (ORF) sequence is optimized using optimization algorithms.

7. Characterization of Sequence Optimized Nucleic Acids

In some embodiments of the invention, the polynucleotide (e.g., a RNA, e.g., an mRNA) comprising a sequence optimized nucleic acid disclosed herein encoding a PCCA or PCCB polypeptide can be tested to determine whether at least one nucleic acid sequence property (e.g., stability when exposed to nucleases) or expression property has been improved with respect to the non-sequence optimized nucleic acid.

As used herein, "expression property" refers to a property of a nucleic acid sequence either in vivo (e.g., translation efficacy of a synthetic mRNA after administration to a human subject in need thereof) or in vitro (e.g., translation efficacy of a synthetic mRNA tested in an in vitro model system). Expression properties include but are not limited to the amount of protein produced by an mRNA encoding a PCCA or PCCB polypeptide after administration, and the amount of soluble or otherwise functional protein produced. In some embodiments, sequence optimized nucleic acids disclosed herein can be evaluated according to the viability of the cells expressing a protein encoded by a sequence optimized nucleic acid sequence (e.g., a RNA, e.g., an mRNA) encoding a PCCA or PCCB polypeptide disclosed herein.

In a particular embodiment, a plurality of sequence optimized nucleic acids disclosed herein (e.g., a RNA, e.g., an mRNA) containing codon substitutions with respect to the non-optimized reference nucleic acid sequence can be characterized functionally to measure a property of interest, for example an expression property in an in vitro model system, or in vivo in a target tissue or cell.

a. Optimization of Nucleic Acid Sequence Intrinsic Properties

In some embodiments of the invention, the desired property of the polynucleotide is an intrinsic property of the nucleic acid sequence. For example, the nucleotide sequence (e.g., a RNA, e.g., an mRNA) can be sequence optimized for in vivo or in vitro stability. In some embodiments, the nucleotide sequence can be sequence optimized for expression in a particular target tissue or cell. In some embodiments, the nucleic acid sequence is sequence optimized to increase its plasma half-life by preventing its degradation by endo and exonucleases.

In other embodiments, the nucleic acid sequence is sequence optimized to increase its resistance to hydrolysis in solution, for example, to lengthen the time that the sequence optimized nucleic acid or a pharmaceutical composition comprising the sequence optimized nucleic acid can be stored under aqueous conditions with minimal degradation.

In other embodiments, the sequence optimized nucleic acid can be optimized to increase its resistance to hydrolysis in dry storage conditions, for example, to lengthen the time that the sequence optimized nucleic acid can be stored after lyophilization with minimal degradation.

b. Nucleic Acids Sequence Optimized for Protein Expression

In some embodiments of the invention, the desired property of the polynucleotide is the level of expression of a PCCA or PCCB polypeptide encoded by a sequence optimized sequence disclosed herein. Protein expression levels can be measured using one or more expression systems. In some embodiments, expression can be measured in cell culture systems, e.g., CHO cells, HEK293 cells, Hepa1-6 cells, primary fibroblasts. In some embodiments, expression can be measured using in vitro expression systems prepared from extracts of living cells, e.g., rabbit reticulocyte lysates, or in vitro expression systems prepared by assembly of purified individual components. In other embodiments, the protein expression is measured in an in vivo system, e.g., mouse, rabbit, monkey, etc.

In some embodiments, protein expression in solution form can be desirable. Accordingly, in some embodiments, a reference sequence can be sequence optimized to yield a sequence optimized nucleic acid sequence having optimized levels of expressed proteins in soluble form. Levels of protein expression and other properties such as solubility, levels of aggregation, and the presence of truncation products (i.e., fragments due to proteolysis, hydrolysis, or defective translation) can be measured according to methods known in the art, for example, using electrophoresis (e.g., native or SDS-PAGE) or chromatographic methods (e.g., HPLC, size exclusion chromatography, etc.).

c. Optimization of Target Tissue or Target Cell Viability

In some embodiments, the expression of heterologous therapeutic proteins encoded by a nucleic acid sequence can have deleterious effects in the target tissue or cell, reducing protein yield, or reducing the quality of the expressed product (e.g., due to the presence of protein fragments or precipitation of the expressed protein in inclusion bodies), or causing toxicity.

Accordingly, in some embodiments of the invention, the sequence optimization of a nucleic acid sequence disclosed herein, e.g., a nucleic acid sequence encoding a PCCA or PCCB polypeptide, can be used to increase the viability of target cells expressing the protein encoded by the sequence optimized nucleic acid.

Heterologous protein expression can also be deleterious to cells transfected with a nucleic acid sequence for autologous or heterologous transplantation. Accordingly, in some embodiments of the present disclosure the sequence optimization of a nucleic acid sequence disclosed herein can be used to increase the viability of target cells expressing the protein encoded by the sequence optimized nucleic acid sequence. Changes in cell or tissue viability, toxicity, and other physiological reaction can be measured according to methods known in the art.

d. Reduction of Immune and/or Inflammatory Response

In some cases, the administration of a sequence optimized nucleic acid encoding PCCA or PCCB polypeptide or a functional fragment thereof can trigger an immune response, which could be caused by (i) the therapeutic agent (e.g., an mRNA encoding a PCCA or PCCB polypeptide), or (ii) the expression product of such therapeutic agent (e.g., the PCCA or PCCB polypeptide encoded by the mRNA), or (iv) a combination thereof. Accordingly, in some embodiments of the present disclosure the sequence optimization of nucleic acid sequence (e.g., an mRNA) disclosed herein can be used to decrease an immune or inflammatory response triggered by the administration of a nucleic acid encoding a PCCA or PCCB polypeptide or by the expression product of PCCA or PCCB encoded by such nucleic acid.

In some aspects, an inflammatory response can be measured by detecting increased levels of one or more inflammatory cytokines using methods known in the art, e.g., ELISA. The term "inflammatory cytokine" refers to cytokines that are elevated in an inflammatory response. Examples of inflammatory cytokines include interleukin-6 (IL-6), CXCL1 (chemokine (C—X—C motif) ligand 1; also known as GROα, interferon-γ (IFNγ), tumor necrosis factor α (TNFα), interferon γ-induced protein 10 (IP-10), or granulocyte-colony stimulating factor (G-CSF). The term inflammatory cytokines includes also other cytokines associated with inflammatory responses known in the art, e.g., interleukin-1 (IL-1), interleukin-8 (IL-8), interleukin-12 (IL-12), interleukin-13 (11-13), interferon α (IFN-α), etc.

8. Modified Nucleotide Sequences Encoding PCCA or PCCB Polypeptides

In some embodiments, the polynucleotide (e.g., a RNA, e.g., an mRNA) of the invention comprises a chemically modified nucleobase, for example, a chemically modified uracil, e.g., pseudouracil, N1-methylpseudouracil, 5-methoxyuracil, or the like. In some embodiments, the mRNA is a uracil-modified sequence comprising an ORF encoding a PCCA or PCCB polypeptide, wherein the mRNA comprises a chemically modified nucleobase, for example, a chemically modified uracil, e.g., pseudouracil, N1-methylpseudouracil, or 5-methoxyuracil.

In certain aspects of the invention, when the modified uracil base is connected to a ribose sugar, as it is in polynucleotides, the resulting modified nucleoside or nucleotide is referred to as modified uridine. In some embodiments, uracil in the polynucleotide is at least about 25%, at least about 30%, at least about 40%, at least about 50%, at least about 60%, at least about 70%, at least about 80%, at least 90%, at least 95%, at least 99%, or about 100% modified uracil. In one embodiment, uracil in the polynucleotide is at least 95% modified uracil. In another embodiment, uracil in the polynucleotide is 100% modified uracil.

In embodiments where uracil in the polynucleotide is at least 95% modified uracil overall uracil content can be adjusted such that an mRNA provides suitable protein expression levels while inducing little to no immune response. In some embodiments, the uracil content of the ORF is between about 100% and about 150%, between about 100% and about 110%, between about 105% and about 115%, between about 110% and about 120%, between about 115% and about 125%, between about 120% and about 130%, between about 125% and about 135%, between about 130% and about 140%, between about 135% and about 145%, between about 140% and about 150% of the theoretical minimum uracil content in the corresponding wild-type ORF (% $U_{TM}$). In other embodiments, the uracil content of the ORF is between about 121% and about 136% or between 123% and 134% of the % $U_{TM}$. In some embodiments, the uracil content of the ORF encoding a PCCA or PCCB polypeptide is about 115%, about 120%, about 125%, about 130%, about 135%, about 140%, about 145%, or about 150% of the % $U_{TM}$. In this context, the term "uracil" can refer to modified uracil and/or naturally occurring uracil.

In some embodiments, the uracil content in the ORF of the mRNA encoding a PCCA or PCCB polypeptide of the invention is less than about 30%, about 25%, about 20%, about 15%, or about 10% of the total nucleobase content in the ORF. In some embodiments, the uracil content in the ORF is between about 10% and about 20% of the total nucleobase content in the ORF. In other embodiments, the uracil content in the ORF is between about 10% and about 25% of the total nucleobase content in the ORF. In one embodiment, the uracil content in the ORF of the mRNA encoding a PCCA or PCCB polypeptide is less than about 20% of the total nucleobase content in the open reading frame. In this context, the term "uracil" can refer to modified uracil and/or naturally occurring uracil.

In further embodiments, the ORF of the mRNA encoding a PCCA or PCCB polypeptide having modified uracil and adjusted uracil content has increased Cytosine (C), Guanine (G), or Guanine/Cytosine (G/C) content (absolute or relative). In some embodiments, the overall increase in C, G, or G/C content (absolute or relative) of the ORF is at least about 2%, at least about 3%, at least about 4%, at least about 5%, at least about 6%, at least about 7%, at least about 10%, at least about 15%, at least about 20%, at least about 40%, at least about 50%, at least about 60%, at least about 70%, at least about 80%, at least about 90%, at least about 95%, or at least about 100% relative to the G/C content (absolute or relative) of the wild-type ORF. In some embodiments, the G, the C, or the G/C content in the ORF is less than about 100%, less than about 90%, less than about 85%, or less than about 80% of the theoretical maximum G, C, or G/C content of the corresponding wild type nucleotide sequence encoding the PCCA or PCCB polypeptide (% $G_{TMX}$; % $C_{TMX}$, or % G/$C_{TMX}$). In some embodiments, the increases in G and/or C content (absolute or relative) described herein can be conducted by replacing synonymous codons with low G, C, or G/C content with synonymous codons having higher G, C, or G/C content. In other embodiments, the increase in G and/or C content (absolute or relative) is conducted by replacing a codon ending with U with a synonymous codon ending with G or C.

In further embodiments, the ORF of the mRNA encoding a PCCA or PCCB polypeptide of the invention comprises modified uracil and has an adjusted uracil content containing less uracil pairs (UU) and/or uracil triplets (UUU) and/or uracil quadruplets (UUUU) than the corresponding wild-type nucleotide sequence encoding the PCCA or PCCB polypeptide. In some embodiments, the ORF of the mRNA encoding a PCCA or PCCB polypeptide of the invention contains no uracil pairs and/or uracil triplets and/or uracil quadruplets. In some embodiments, uracil pairs and/or uracil triplets and/or uracil quadruplets are reduced below a certain threshold, e.g., no more than 1, 2, 3, 4, 5, 6, 7, 8, 9, 10, 11, 12, 13, 14, 15, 16, 17, 18, 19, or 20 occurrences in the ORF of the mRNA encoding the PCCA or PCCB polypeptide. In a particular embodiment, the ORF of the mRNA encoding the PCCA or PCCB polypeptide of the invention contains less than 20, 19, 18, 17, 16, 15, 14, 13, 12, 11, 10, 9, 8, 7, 6, 5, 4, 3, 2, or 1 non-phenylalanine uracil pairs and/or triplets. In another embodiment, the ORF of the mRNA encoding the PCCA or PCCB polypeptide contains no non-phenylalanine uracil pairs and/or triplets.

In further embodiments, the ORF of the mRNA encoding a PCCA or PCCB polypeptide of the invention comprises modified uracil and has an adjusted uracil content containing less uracil-rich clusters than the corresponding wild-type nucleotide sequence encoding the PCCA or PCCB polypeptide. In some embodiments, the ORF of the mRNA encoding the PCCA or PCCB polypeptide of the invention contains uracil-rich clusters that are shorter in length than corresponding uracil-rich clusters in the corresponding wild-type nucleotide sequence encoding the PCCA or PCCB polypeptide.

In further embodiments, alternative lower frequency codons are employed. At least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100% of the codons in the PCCA or PCCB polypeptide-encoding ORF of the modified uracil-comprising mRNA are substituted with alternative codons, each alternative codon having a codon frequency lower than the codon frequency of the substituted codon in the synonymous codon set. The ORF also has adjusted uracil content, as described above. In some embodiments, at least one codon in the ORF of the mRNA encoding the PCCA or PCCB polypeptide is substituted with an alternative codon having a codon frequency lower than the codon frequency of the substituted codon in the synonymous codon set.

In some embodiments, the adjusted uracil content, PCCA or PCCB polypeptide-encoding ORF of the modified uracil-comprising mRNA exhibits expression levels of PCCA or PCCB when administered to a mammalian cell that are higher than expression levels of PCCA or PCCB from the corresponding wild-type mRNA. In some embodiments, the mammalian cell is a mouse cell, a rat cell, or a rabbit cell. In other embodiments, the mammalian cell is a monkey cell or a human cell. In some embodiments, the human cell is a HeLa cell, a BJ fibroblast cell, or a peripheral blood mononuclear cell (PBMC). In some embodiments, PCCA or PCCB is expressed a level higher than expression levels of PCCA or PCCB from the corresponding wild-type mRNA when the mRNA is administered to a mammalian cell in vivo. In some embodiments, the mRNA is administered to mice, rabbits, rats, monkeys, or humans. In one embodiment, mice are null mice. In some embodiments, the mRNA is administered to mice in an amount of about 0.01 mg/kg, about 0.05 mg/kg, about 0.1 mg/kg, or 0.2 mg/kg or about 0.5 mg/kg. In some embodiments, the mRNA is administered intravenously or intramuscularly. In other embodiments, the PCCA or PCCB polypeptide is expressed when the mRNA is administered to a mammalian cell in vitro. In some embodiments, the expression is increased by at least about 2-fold, at least about 5-fold, at least about 10-fold, at least about 50-fold, at least about 500-fold, at least about 1500-fold, or at least about 3000-fold. In other embodiments, the expression is increased by at least about 10%, about 20%, about 30%, about 40%, about 50%, 60%, about 70%, about 80%, about 90%, or about 100%.

In some embodiments, adjusted uracil content, PCCA or PCCB polypeptide-encoding ORF of the modified uracil-comprising mRNA exhibits increased stability. In some embodiments, the mRNA exhibits increased stability in a cell relative to the stability of a corresponding wild-type mRNA under the same conditions. In some embodiments, the mRNA exhibits increased stability including resistance to nucleases, thermal stability, and/or increased stabilization of secondary structure. In some embodiments, increased stability exhibited by the mRNA is measured by determining the half-life of the mRNA (e.g., in a plasma, serum, cell, or tissue sample) and/or determining the area under the curve (AUC) of the protein expression by the mRNA over time (e.g., in vitro or in vivo). An mRNA is identified as having increased stability if the half-life and/or the AUC is greater than the half-life and/or the AUC of a corresponding wild-type mRNA under the same conditions.

In some embodiments, the mRNA of the present invention induces a detectably lower immune response (e.g., innate or acquired) relative to the immune response induced by a corresponding wild-type mRNA under the same conditions. In other embodiments, the mRNA of the present disclosure induces a detectably lower immune response (e.g., innate or acquired) relative to the immune response induced by an mRNA that encodes for a PCCA or PCCB polypeptide but does not comprise modified uracil under the same conditions, or relative to the immune response induced by an mRNA that encodes for a PCCA or PCCB polypeptide and that comprises modified uracil but that does not have adjusted uracil content under the same conditions. The innate immune response can be manifested by increased expression of pro-inflammatory cytokines, activation of intracellular PRRs (RIG-I, MDA5, etc.), cell death, and/or termination or reduction in protein translation. In some embodiments, a reduction in the innate immune response can be measured by expression or activity level of Type 1 interferons (e.g., IFN-α, IFN-β, IFN-κ, IFN-δ, IFN-ε, IFN-τ, IFN-ω, and IFN-ζ) or the expression of interferon-regulated genes such as the toll-like receptors (e.g., TLR7 and TLR8), and/or by decreased cell death following one or more administrations of the mRNA of the invention into a cell.

In some embodiments, the expression of Type-1 interferons by a mammalian cell in response to the mRNA of the present disclosure is reduced by at least 10%, 20%, 30%, 40%, 50%, 60%, 70%, 80%, 90%, 95%, 99%, 99.9%, or greater than 99.9% relative to a corresponding wild-type mRNA, to an mRNA that encodes a PCCA or PCCB polypeptide but does not comprise modified uracil, or to an mRNA that encodes a PCCA or PCCB polypeptide and that comprises modified uracil but that does not have adjusted uracil content. In some embodiments, the interferon is IFN-β. In some embodiments, cell death frequency caused by administration of mRNA of the present disclosure to a mammalian cell is 10%, 25%, 50%, 75%, 85%, 90%, 95%, or over 95% less than the cell death frequency observed with a corresponding wild-type mRNA, an mRNA that encodes for a PCCA or PCCB polypeptide but does not comprise modified uracil, or an mRNA that encodes for a PCCA or PCCB polypeptide and that comprises modified uracil but that does not have adjusted uracil content. In some embodiments, the mammalian cell is a BJ fibroblast cell. In other embodiments, the mammalian cell is a splenocyte. In some embodiments, the mammalian cell is that of a mouse or a rat. In other embodiments, the mammalian cell is that of a human. In one embodiment, the mRNA of the present disclosure does not substantially induce an innate immune response of a mammalian cell into which the mRNA is introduced.

9. Methods for Modifying Polynucleotides

The disclosure includes modified polynucleotides comprising a polynucleotide described herein (e.g., a polynucleotide, e.g. mRNA, comprising a nucleotide sequence encoding a PCCA or PCCB polypeptide). The modified polynucleotides can be chemically modified and/or structurally modified. When the polynucleotides of the present invention are chemically and/or structurally modified the polynucleotides can be referred to as "modified polynucleotides."

The present disclosure provides for modified nucleosides and nucleotides of a polynucleotide (e.g., RNA polynucleotides, such as mRNA polynucleotides) encoding a PCCA or PCCB polypeptide. A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside including a phosphate group. Modified nucleotides can be synthesized by any useful method, such as, for example, chemically, enzymatically, or recombinantly, to include one or more modified or non-natural nucleosides. Polynucleotides can comprise a region or regions of linked nucleosides. Such regions can have variable backbone linkages. The linkages can be standard phosphodiester linkages, in which case the polynucleotides would comprise regions of nucleotides.

The modified polynucleotides disclosed herein can comprise various distinct modifications. In some embodiments, the modified polynucleotides contain one, two, or more (optionally different) nucleoside or nucleotide modifications. In some embodiments, a modified polynucleotide, introduced to a cell can exhibit one or more desirable properties, e.g., improved protein expression, reduced immunogenicity, or reduced degradation in the cell, as compared to an unmodified polynucleotide.

In some embodiments, a polynucleotide of the present invention (e.g., a polynucleotide comprising a nucleotide sequence encoding a PCCA or PCCB polypeptide) is structurally modified. As used herein, a "structural" modification is one in which two or more linked nucleosides are inserted, deleted, duplicated, inverted or randomized in a polynucleotide without significant chemical modification to the nucleotides themselves. Because chemical bonds will necessarily be broken and reformed to effect a structural modification, structural modifications are of a chemical nature and hence are chemical modifications. However, structural modifications will result in a different sequence of nucleotides. For example, the polynucleotide "ATCG" can be chemically modified to "AT-5meC-G". The same polynucleotide can be structurally modified from "ATCG" to "ATCCCG". Here, the dinucleotide "CC" has been inserted, resulting in a structural modification to the polynucleotide.

Therapeutic compositions of the present disclosure comprise, in some embodiments, at least one nucleic acid (e.g., RNA) having an open reading frame encoding PCCA or PCCB (e.g., SEQ ID NOs: 2, 5-14, 16-27, 196, 197, and 198), wherein the nucleic acid comprises nucleotides and/or nucleosides that can be standard (unmodified) or modified as is known in the art. In some embodiments, nucleotides and nucleosides of the present disclosure comprise modified nucleotides or nucleosides. Such modified nucleotides and nucleosides can be naturally-occurring modified nucleotides and nucleosides or non-naturally occurring modified nucleotides and nucleosides. Such modifications can include those at the sugar, backbone, or nucleobase portion of the nucleotide and/or nucleoside as are recognized in the art.

In some embodiments, a naturally-occurring modified nucleotide or nucleotide of the disclosure is one as is generally known or recognized in the art. Non-limiting examples of such naturally occurring modified nucleotides and nucleotides can be found, inter alia, in the widely recognized MODOMICS database.

In some embodiments, a non-naturally occurring modified nucleotide or nucleoside of the disclosure is one as is generally known or recognized in the art. Non-limiting examples of such non-naturally occurring modified nucleotides and nucleosides can be found, inter alia, in published US application Nos. PCT/US2012/058519; PCT/US2013/075177; PCT/US2014/058897; PCT/US2014/058891; PCT/US2014/070413; PCT/US2015/36773; PCT/US2015/36759; PCT/US2015/36771; or PCT/IB2017/051367 all of which are incorporated by reference herein.

In some embodiments, at least one RNA (e.g., mRNA) of the present disclosure is not chemically modified and comprises the standard ribonucleotides consisting of adenosine, guanosine, cytosine and uridine. In some embodiments, nucleotides and nucleosides of the present disclosure comprise standard nucleoside residues such as those present in transcribed RNA (e.g. A, G, C, or U). In some embodiments, nucleotides and nucleosides of the present disclosure comprise standard deoxyribonucleosides such as those present in DNA (e.g. dA, dG, dC, or dT).

Hence, nucleic acids of the disclosure (e.g., DNA nucleic acids and RNA nucleic acids, such as mRNA nucleic acids) can comprise standard nucleotides and nucleosides, naturally-occurring nucleotides and nucleosides, non-naturally-occurring nucleotides and nucleosides, or any combination thereof.

Nucleic acids of the disclosure (e.g., DNA nucleic acids and RNA nucleic acids, such as mRNA nucleic acids), in some embodiments, comprise various (more than one) different types of standard and/or modified nucleotides and nucleosides. In some embodiments, a particular region of a nucleic acid contains one, two or more (optionally different) types of standard and/or modified nucleotides and nucleosides.

In some embodiments, a modified RNA nucleic acid (e.g., a modified mRNA nucleic acid), introduced to a cell or organism, exhibits reduced degradation in the cell or organism, respectively, relative to an unmodified nucleic acid comprising standard nucleotides and nucleosides.

In some embodiments, a modified RNA nucleic acid (e.g., a modified mRNA nucleic acid), introduced into a cell or organism, may exhibit reduced immunogenicity in the cell or organism, respectively (e.g., a reduced innate response) relative to an unmodified nucleic acid comprising standard nucleotides and nucleosides.

Nucleic acids (e.g., RNA nucleic acids, such as mRNA nucleic acids), in some embodiments, comprise non-natural modified nucleotides that are introduced during synthesis or post-synthesis of the nucleic acids to achieve desired functions or properties. The modifications may be present on intemucleotide linkages, purine or pyrimidine bases, or sugars. The modification may be introduced with chemical synthesis or with a polymerase enzyme at the terminal of a chain or anywhere else in the chain. Any of the regions of a nucleic acid may be chemically modified.

The present disclosure provides for modified nucleosides and nucleotides of a nucleic acid (e.g., RNA nucleic acids, such as mRNA nucleic acids). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside, including a phosphate group. Modified nucleotides may by synthesized by any useful method, such as, for example, chemically, enzymatically, or recombinantly, to include one or more modified or non-natural nucleosides. Nucleic acids can comprise a region or regions of linked nucleosides. Such regions may have variable backbone linkages. The linkages can be standard phosphodiester linkages, in which case the nucleic acids would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures, such as, for example, in those nucleic acids having at least one chemical modification. One example of such non-standard base pairing is the base pairing between the modified nucleotide inosine and adenine, cytosine or uracil. Any combination of base/sugar or linker may be incorporated into nucleic acids of the present disclosure.

In some embodiments, modified nucleobases in nucleic acids (e.g., RNA nucleic acids, such as mRNA nucleic acids) comprise N1-methyl-pseudouridine (m1ψ), 1-ethyl-pseudouridine (e1ψ), 5-methoxy-uridine (mo5U), 5-methyl-cytidine (m5C), and/or pseudouridine (ψ). In some embodiments, modified nucleobases in nucleic acids (e.g., RNA nucleic acids, such as mRNA nucleic acids) comprise 5-methoxymethyl uridine, 5-methylthio uridine, 1-methoxymethyl pseudouridine, 5-methyl cytidine, and/or 5-methoxy cytidine. In some embodiments, the polyribonucleotide includes a combination of at least two (e.g., 2, 3, 4 or more) of any of the aforementioned modified nucleobases, including but not limited to chemical modifications.

In some embodiments, a RNA nucleic acid of the disclosure comprises N1-methyl-pseudouridine (m1ψ) substitutions at one or more or all uridine positions of the nucleic acid.

In some embodiments, a RNA nucleic acid of the disclosure comprises N1-methyl-pseudouridine (m1ψ) substitutions at one or more or all uridine positions of the nucleic acid and 5-methyl cytidine substitutions at one or more or all cytidine positions of the nucleic acid.

In some embodiments, a RNA nucleic acid of the disclosure comprises pseudouridine (ψ) substitutions at one or more or all uridine positions of the nucleic acid.

In some embodiments, a RNA nucleic acid of the disclosure comprises pseudouridine (ψ) substitutions at one or more or all uridine positions of the nucleic acid and 5-methyl cytidine substitutions at one or more or all cytidine positions of the nucleic acid.

In some embodiments, a RNA nucleic acid of the disclosure comprises uridine at one or more or all uridine positions of the nucleic acid.

In some embodiments, nucleic acids (e.g., RNA nucleic acids, such as mRNA nucleic acids) are uniformly modified (e.g., fully modified, modified throughout the entire sequence) for a particular modification. For example, a nucleic acid can be uniformly modified with N1-methyl-pseudouridine, meaning that all uridine residues in the mRNA sequence are replaced with N1-methyl-pseudouridine. Similarly, a nucleic acid can be uniformly modified for any type of nucleoside residue present in the sequence by replacement with a modified residue such as those set forth above.

The nucleic acids of the present disclosure may be partially or fully modified along the entire length of the molecule. For example, one or more or all or a given type of nucleotide (e.g., purine or pyrimidine, or any one or more or all of A, G, U, C) may be uniformly modified in a nucleic acid of the disclosure, or in a predetermined sequence region thereof (e.g., in the mRNA including or excluding the polyA tail). In some embodiments, all nucleotides X in a nucleic acid of the present disclosure (or in a sequence region thereof) are modified nucleotides, wherein X may be any one of nucleotides A, G, U, C, or any one of the combinations A+G, A+U, A+C, G+U, G+C, U+C, A+G+U, A+G+C, G+U+C or A+G+C.

The nucleic acid may contain from about 1% to about 100% modified nucleotides (either in relation to overall nucleotide content, or in relation to one or more types of nucleotide, i.e., any one or more of A, G, U or C) or any intervening percentage (e.g., from 10% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of unmodified A, G, U, or C.

The nucleic acids may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the nucleic acids may contain a modified pyrimidine such as a modified uracil or cytosine. In some embodiments, at least 5%, at least 10%, at least 25%, at least 50%, at least 80%, at least 90% or 100% of the uracil in the nucleic acid is replaced with a modified uracil (e.g., a 5-substituted uracil). The modified uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the nucleic acid is replaced with a modified cytosine (e.g., a 5-substituted cytosine). The modified cytosine can be replaced by a compound having a single unique structure, or can be replaced by a plurality of compounds having different structures (e.g., 2, 3, 4 or more unique structures).

10. Untranslated Regions (UTRs)

Translation of a polynucleotide comprising an open reading frame encoding a polypeptide can be controlled and regulated by a variety of mechanisms that are provided by various cis-acting nucleic acid structures. For example, naturally-occurring, cis-acting RNA elements that form hairpins or other higher-order (e.g., pseudoknot) intramolecular mRNA secondary structures can provide a translational regulatory activity to a polynucleotide, wherein the RNA element influences or modulates the initiation of polynucleotide translation, particularly when the RNA element is positioned in the 5' UTR close to the 5'-cap structure (Pelletier and Sonenberg (1985) Cell 40(3):515-526; Kozak (1986) Proc Natl Acad Sci 83:2850-2854).

Untranslated regions (UTRs) are nucleic acid sections of a polynucleotide before a start codon (5' UTR) and after a stop codon (3' UTR) that are not translated. In some embodiments, a polynucleotide (e.g., a ribonucleic acid (RNA), e.g., a messenger RNA (mRNA)) of the invention comprising an open reading frame (ORF) encoding a PCCA or PCCB polypeptide further comprises UTR (e.g., a 5' UTR or functional fragment thereof, a 3' UTR or functional fragment thereof, or a combination thereof).

Cis-acting RNA elements can also affect translation elongation, being involved in numerous frameshifting events (Namy et al., (2004) Mol Cell 13(2):157-168). Internal ribosome entry sequences (IRES) represent another type of cis-acting RNA element that are typically located in 5' UTRs, but have also been reported to be found within the coding region of naturally-occurring mRNAs (Holcik et al. (2000) Trends Genet 16(10):469-473). In cellular mRNAs, IRES often coexist with the 5'-cap structure and provide mRNAs with the functional capacity to be translated under conditions in which cap-dependent translation is compromised (Gebauer et al., (2012) Cold Spring Harb Perspect Biol 4(7):a012245). Another type of naturally-occurring cis-acting RNA element comprises upstream open reading frames (uORFs). Naturally-occurring uORFs occur singularly or multiply within the 5' UTRs of numerous mRNAs and influence the translation of the downstream major ORF, usually negatively (with the notable exception of GCN4 mRNA in yeast and ATF4 mRNA in mammals, where uORFs serve to promote the translation of the downstream major ORF under conditions of increased eIF2 phosphorylation (Hinnebusch (2005) Annu Rev Microbiol 59:407-450)). Additional exemplary translational regulatory activities provided by components, structures, elements, motifs, and/or specific sequences comprising polynucleotides (e.g., mRNA) include, but are not limited to, mRNA stabilization or destabilization (Baker & Parker (2004) Curr Opin Cell Biol 16(3):293-299), translational activation (Villalba et al., (2011) Curr Opin Genet Dev 21(4):452-457), and translational repression (Blumer et al., (2002) Mech Dev 110(1-2):97-112). Studies have shown that naturally-occurring, cis-acting RNA elements can confer their respective functions when used to modify, by incorporation into, heterologous polynucleotides (Goldberg-Cohen et al., (2002) J Biol Chem 277(16):13635-13640).

Modified Polynucleotides Comprising Functional RNA Elements

The present disclosure provides synthetic polynucleotides comprising a modification (e.g., an RNA element), wherein the modification provides a desired translational regulatory activity. In some embodiments, the disclosure provides a polynucleotide comprising a 5' untranslated region (UTR), an initiation codon, a full open reading frame encoding a polypeptide, a 3' UTR, and at least one modification, wherein the at least one modification provides a desired translational regulatory activity, for example, a modification that promotes and/or enhances the translational fidelity of mRNA translation. In some embodiments, the desired translational regulatory activity is a cis-acting regulatory activity. In some embodiments, the desired translational regulatory activity is an increase in the residence time of the 43S pre-initiation complex (PIC) or ribosome at, or proximal to, the initiation codon. In some embodiments, the desired translational regulatory activity is an increase in the initiation of polypeptide synthesis at or from the initiation codon. In some embodiments, the desired translational regulatory activity is an increase in the amount of polypeptide translated from the full open reading frame. In some embodiments, the desired translational regulatory activity is an increase in the fidelity of initiation codon decoding by the PIC or ribosome. In some embodiments, the desired translational regulatory activity is inhibition or reduction of leaky scanning by the PIC or ribosome. In some embodiments, the desired translational regulatory activity is a decrease in the rate of decoding the initiation codon by the PIC or ribosome. In some embodiments, the desired translational regulatory activity is inhibition or reduction in the initiation of polypeptide synthesis at any codon within the mRNA other than the initiation codon. In some embodiments, the desired translational regulatory activity is inhibition or reduction of the amount of polypeptide translated from any open reading frame within the mRNA other than the full open reading frame. In some embodiments, the desired translational regulatory activity is inhibition or reduction in the production of aberrant translation products. In some embodiments, the desired translational regulatory activity is a combination of one or more of the foregoing translational regulatory activities.

Accordingly, the present disclosure provides a polynucleotide, e.g., an mRNA, comprising an RNA element that comprises a sequence and/or an RNA secondary structure(s) that provides a desired translational regulatory activity as described herein. In some aspects, the mRNA comprises an RNA element that comprises a sequence and/or an RNA secondary structure(s) that promotes and/or enhances the translational fidelity of mRNA translation. In some aspects, the mRNA comprises an RNA element that comprises a sequence and/or an RNA secondary structure(s) that provides a desired translational regulatory activity, such as inhibiting and/or reducing leaky scanning. In some aspects, the disclosure provides an mRNA that comprises an RNA element that comprises a sequence and/or an RNA secondary structure(s) that inhibits and/or reduces leaky scanning thereby promoting the translational fidelity of the mRNA.

In some embodiments, the RNA element comprises natural and/or modified nucleotides. In some embodiments, the RNA element comprises of a sequence of linked nucleotides, or derivatives or analogs thereof, that provides a desired translational regulatory activity as described herein. In some embodiments, the RNA element comprises a sequence of linked nucleotides, or derivatives or analogs thereof, that forms or folds into a stable RNA secondary structure, wherein the RNA secondary structure provides a desired translational regulatory activity as described herein. RNA elements can be identified and/or characterized based on the primary sequence of the element (e.g., GC-rich element), by RNA secondary structure formed by the element (e.g. stem-loop), by the location of the element within the RNA molecule (e.g., located within the 5' UTR of an mRNA), by the biological function and/or activity of the element (e.g., "translational enhancer element"), and any combination thereof.

In some aspects, the disclosure provides an mRNA having one or more structural modifications that inhibits leaky scanning and/or promotes the translational fidelity of mRNA translation, wherein at least one of the structural modifications is a GC-rich RNA element. In some aspects, the disclosure provides a modified mRNA comprising at least one modification, wherein at least one modification is a GC-rich RNA element comprising a sequence of linked nucleotides, or derivatives or analogs thereof, preceding a Kozak consensus sequence in a 5' UTR of the mRNA. In one embodiment, the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA. In another embodiment, the GC-rich RNA element is located 15-30, 15-20, 15-25, 10-15, or 5-10 nucleotides upstream of a Kozak consensus sequence. In another embodiment, the GC-rich RNA element is located immediately adjacent to a Kozak consensus sequence in the 5' UTR of the mRNA.

In any of the foregoing or related aspects, the disclosure provides a GC-rich RNA element which comprises a sequence of 3-30, 5-25, 10-20, 15-20, about 20, about 15, about 12, about 10, about 7, about 6 or about 3 nucleotides, derivatives or analogs thereof, linked in any order, wherein the sequence composition is 70-80% cytosine, 60-70% cytosine, 50%-60% cytosine, 40-50% cytosine, 30-40% cytosine bases. In any of the foregoing or related aspects, the disclosure provides a GC-rich RNA element which comprises a sequence of 3-30, 5-25, 10-20, 15-20, about 20, about 15, about 12, about 10, about 7, about 6 or about 3 nucleotides, derivatives or analogs thereof, linked in any order, wherein the sequence composition is about 80% cytosine, about 70% cytosine, about 60% cytosine, about 50% cytosine, about 40% cytosine, or about 30% cytosine.

In any of the foregoing or related aspects, the disclosure provides a GC-rich RNA element which comprises a sequence of 20, 19, 18, 17, 16, 15, 14, 13, 12, 11, 10, 9, 8, 7, 6, 5, 4, or 3 nucleotides, or derivatives or analogs thereof, linked in any order, wherein the sequence composition is 70-80% cytosine, 60-70% cytosine, 50%-60% cytosine, 40-50% cytosine, or 30-40% cytosine. In any of the foregoing or related aspects, the disclosure provides a GC-rich RNA element which comprises a sequence of 20, 19, 18, 17, 16, 15, 14, 13, 12, 11, 10, 9, 8, 7, 6, 5, 4, or 3 nucleotides, or derivatives or analogs thereof, linked in any order, wherein the sequence composition is about 80% cytosine, about 70% cytosine, about 60% cytosine, about 50% cytosine, about 40% cytosine, or about 30% cytosine.

In some embodiments, the disclosure provides a modified mRNA comprising at least one modification, wherein at least one modification is a GC-rich RNA element comprising a sequence of linked nucleotides, or derivatives or analogs thereof, preceding a Kozak consensus sequence in a 5' UTR of the mRNA, wherein the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA, and wherein the GC-rich RNA element comprises a sequence of 3, 4, 5, 6, 7, 8, 9, 10, 11, 12, 13, 14, 15, 16, 17, 18, 19, or 20 nucleotides, or derivatives or analogs thereof, linked in any order, wherein the sequence composition is >50% cytosine. In some embodiments, the sequence composition is >55% cytosine, >60% cytosine, >65% cytosine, >70% cytosine, >75% cytosine, >80% cytosine, >85% cytosine, or >90% cytosine.

In other aspects, the disclosure provides a modified mRNA comprising at least one modification, wherein at least one modification is a GC-rich RNA element comprising a sequence of linked nucleotides, or derivatives or analogs thereof, preceding a Kozak consensus sequence in a 5' UTR of the mRNA, wherein the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA, and wherein the GC-rich RNA element comprises a sequence of about 3-30, 5-25, 10-20, 15-20 or about 20, about 15, about 12, about 10, about 6 or about 3 nucleotides, or derivatives or analogues thereof, wherein the sequence comprises a repeating GC-motif, wherein the repeating GC-motif is [CCG]n, wherein n=1 to 10, n=2 to 8, n=3 to 6, or n=4 to 5. In some embodiments, the sequence comprises a repeating GC-motif [CCG]n, wherein n=1, 2, 3, 4 or 5. In some embodiments, the sequence comprises a repeating GC-motif [CCG]n, wherein n=1, 2, or 3. In some embodiments, the sequence comprises a repeating GC-motif [CCG]n, wherein n=1. In some embodiments, the sequence comprises a repeating GC-motif [CCG]n, wherein n=2. In some embodiments, the sequence comprises a repeating GC-motif [CCG]n, wherein n=3. In some embodiments, the sequence comprises a repeating GC-motif [CCG]n, wherein n=4. In some embodiments, the sequence comprises a repeating GC-motif [CCG]n, wherein n=5.

In another aspect, the disclosure provides a modified mRNA comprising at least one modification, wherein at least one modification is a GC-rich RNA element comprising a sequence of linked nucleotides, or derivatives or analogs thereof, preceding a Kozak consensus sequence in a 5' UTR of the mRNA, wherein the GC-rich RNA element comprises any one of the sequences set forth in Table 2. In one embodiment, the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA. In another embodiment, the GC-rich RNA element is located about 15-30, 15-20, 15-25, 10-15, or 5-10 nucleotides upstream of a Kozak consensus sequence. In another embodiment, the GC-rich RNA element is located immediately adjacent to a Kozak consensus sequence in the 5' UTR of the mRNA.

In other aspects, the disclosure provides a modified mRNA comprising at least one modification, wherein at least one modification is a GC-rich RNA element comprising the sequence V1 [CCCCGGCGCC (SEQ ID NO: 194)] as set forth in Table 2, or derivatives or analogs thereof, preceding a Kozak consensus sequence in the 5' UTR of the mRNA. In some embodiments, the GC-rich element comprises the sequence V1 as set forth in Table 2 located immediately adjacent to and upstream of the Kozak consensus sequence in the 5' UTR of the mRNA. In some embodiments, the GC-rich element comprises the sequence VI as set forth in Table 2 located 1, 2, 3, 4, 5, 6, 7, 8, 9 or 10 bases upstream of the Kozak consensus sequence in the 5' UTR of the mRNA. In other embodiments, the GC-rich element comprises the sequence V1 as set forth in Table 2 located 1-3, 3-5, 5-7, 7-9, 9-12, or 12-15 bases upstream of the Kozak consensus sequence in the 5' UTR of the mRNA.

In other aspects, the disclosure provides a modified mRNA comprising at least one modification, wherein at least one modification is a GC-rich RNA element comprising the sequence V2 [CCCCGGC (SEQ ID NO: 195)] as set forth in Table 2, or derivatives or analogs thereof, preceding a Kozak consensus sequence in the 5' UTR of the mRNA. In some embodiments, the GC-rich element comprises the sequence V2 as set forth in Table 2 located immediately adjacent to and upstream of the Kozak consensus sequence in the 5' UTR of the mRNA. In some embodiments, the GC-rich element comprises the sequence V2 as set forth in Table 2 located 1, 2, 3, 4, 5, 6, 7, 8, 9 or 10 bases upstream of the Kozak consensus sequence in the 5' UTR of the mRNA. In other embodiments, the GC-rich element comprises the sequence V2 as set forth in Table 2 located 1-3, 3-5, 5-7, 7-9, 9-12, or 12-15 bases upstream of the Kozak consensus sequence in the 5' UTR of the mRNA.

In other aspects, the disclosure provides a modified mRNA comprising at least one modification, wherein at least one modification is a GC-rich RNA element comprising the sequence EK [GCCGCC (SEQ ID NO:193)] as set forth in Table 2, or derivatives or analogs thereof, preceding a Kozak consensus sequence in the 5' UTR of the mRNA. In some embodiments, the GC-rich element comprises the sequence EK as set forth in Table 2 located immediately adjacent to and upstream of the Kozak consensus sequence in the 5' UTR of the mRNA. In some embodiments, the GC-rich element comprises the sequence EK as set forth in Table 2 located 1, 2, 3, 4, 5, 6, 7, 8, 9 or 10 bases upstream of the Kozak consensus sequence in the 5' UTR of the mRNA. In other embodiments, the GC-rich element comprises the sequence EK as set forth in Table 2 located 1-3, 3-5, 5-7, 7-9, 9-12, or 12-15 bases upstream of the Kozak consensus sequence in the 5' UTR of the mRNA.

In yet other aspects, the disclosure provides a modified mRNA comprising at least one modification, wherein at least one modification is a GC-rich RNA element comprising the sequence V1 [CCCCGGCGCC (SEQ ID NO:194)] as set forth in Table 2, or derivatives or analogs thereof, preceding a Kozak consensus sequence in the 5' UTR of the mRNA, wherein the 5' UTR comprises the following sequence shown in Table 2:

GGGAAAUAAGAGAGAAAAGAAGAGUAAGAA-GAAAUAUAAGA (SEQ ID NO:211). The skilled artisan will of course recognize that all Us in the RNA sequences described herein will be Ts in a corresponding template DNA sequence, for example, in DNA templates or constructs from which mRNAs of the disclosure are transcribed, e.g., via IVT.

In some embodiments, the GC-rich element comprises the sequence V1 as set forth in Table 2 located immediately adjacent to and upstream of the Kozak consensus sequence in the 5' UTR sequence shown in Table 2. In some embodiments, the GC-rich element comprises the sequence V1 as set forth in Table 2 located 1, 2, 3, 4, 5, 6, 7, 8, 9 or 10 bases upstream of the Kozak consensus sequence in the 5' UTR of the mRNA, wherein the 5' UTR comprises the following sequence shown in Table 2:

```
                              (SEQ ID NO: 211)
GGGAAAUAAGAGAGAAAAGAAGAGUAAGAAGAAAUAUAAGA.
```

In other embodiments, the GC-rich element comprises the sequence V1 as set forth in Table 2 located 1-3, 3-5, 5-7, 7-9, 9-12, or 12-15 bases upstream of the Kozak consensus sequence in the 5' UTR of the mRNA, wherein the 5' UTR comprises the following sequence shown in Table 2:

```
                              (SEQ ID NO: 211)
GGGAAAUAAGAGAGAAAAGAAGAGUAAGAAGAAAUAUAAGA.
```

In some embodiments, the 5' UTR comprises the following sequence set forth in Table 2:

```
                              (SEQ ID NO: 191)
GGGAAAUAAGAGAGAAAAGAAGAGUAAGAAGAAAUAUAAGACCCCGGCGC
CGCCACC
```

TABLE 2

| 5' UTRs | 5' UTR Sequence |
|---|---|
| Standard | GGGAAAUAAGAGAGAAAAGAAGAGUAAGAAG AAAUAUAAGAGCCACC (SEQ ID NO: 3) |
| V1-UTR | GGGAAAUAAGAGAGAAAAGAAGAGUAAGAAG AAAUAUAAGACCCCGGCGCCGCCACC (SEQ ID NO: 191) |
| V2-UTR | GGGAAAUAAGAGAGAAAAGAAGAGUAAGAAG AAAUAUAAGACCCCGGCGCCACC (SEQ ID NO: 190) |

| GC-Rich RNA Elements | Sequence |
|---|---|
| K0 (Traditional Kozak consensus) | [GCCA/GCC] (SEQ ID NO: 192) |
| EK | [GCCGCC] (SEQ ID NO: 193) |
| V1 | [CCCCGGCGCC] (SEQ ID NO: 194) |
| V2 | [CCCCGGC] (SEQ ID NO: 195) |
| (CCG)$_n$, where n = 1-10 | [CCG]$_n$ |
| (GCC)$_n$, where n = 1-10 | [GCC]$_n$ |

In another aspect, the disclosure provides a modified mRNA comprising at least one modification, wherein at least one modification is a GC-rich RNA element comprising a stable RNA secondary structure comprising a sequence of nucleotides, or derivatives or analogs thereof, linked in an order which forms a hairpin or a stem-loop. In one embodiment, the stable RNA secondary structure is upstream of the Kozak consensus sequence. In another embodiment, the stable RNA secondary structure is located about 30, about 25, about 20, about 15, about 10, or about 5 nucleotides upstream of the Kozak consensus sequence. In another embodiment, the stable RNA secondary structure is located about 20, about 15, about 10 or about 5 nucleotides upstream of the Kozak consensus sequence. In another embodiment, the stable RNA secondary structure is located about 5, about 4, about 3, about 2, about 1 nucleotides upstream of the Kozak consensus sequence. In another embodiment, the stable RNA secondary structure is located about 15-30, about 15-20, about 15-25, about 10-15, or about 5-10 nucleotides upstream of the Kozak consensus sequence. In another embodiment, the stable RNA secondary structure is located 12-15 nucleotides upstream of the Kozak consensus sequence. In another embodiment, the stable RNA secondary structure has a deltaG of about −30 kcal/mol, about −20 to −30 kcal/mol, about −20 kcal/mol, about −10 to −20 kcal/mol, about −10 kcal/mol, about −5 to −10 kcal/mol.

In another embodiment, the modification is operably linked to an open reading frame encoding a polypeptide and wherein the modification and the open reading frame are heterologous.

In another embodiment, the sequence of the GC-rich RNA element is comprised exclusively of guanine (G) and cytosine (C) nucleobases.

RNA elements that provide a desired translational regulatory activity as described herein can be identified and characterized using known techniques, such as ribosome profiling. Ribosome profiling is a technique that allows the determination of the positions of PICs and/or ribosomes bound to mRNAs (see e.g., Ingolia et al., (2009) Science 324(5924):218-23, incorporated herein by reference). The technique is based on protecting a region or segment of mRNA, by the PIC and/or ribosome, from nuclease digestion. Protection results in the generation of a 30-bp fragment of RNA termed a 'footprint'. The sequence and frequency of RNA footprints can be analyzed by methods known in the art (e.g., RNA-seq). The footprint is roughly centered on the A-site of the ribosome. If the PIC or ribosome dwells at a particular position or location along an mRNA, footprints generated at these position would be relatively common. Studies have shown that more footprints are generated at positions where the PIC and/or ribosome exhibits decreased processivity and fewer footprints where the PIC and/or ribosome exhibits increased processivity (Gardin et al., (2014) eLife 3:e03735). In some embodiments, residence time or the time of occupancy of the PIC or ribosome at a discrete position or location along an polynucleotide comprising any one or more of the RNA elements described herein is determined by ribosome profiling.

A UTR can be homologous or heterologous to the coding region in a polynucleotide. In some embodiments, the UTR is homologous to the ORF encoding the PCCA or PCCB polypeptide. In some embodiments, the UTR is heterologous to the ORF encoding the PCCA or PCCB polypeptide. In some embodiments, the polynucleotide comprises two or more 5' UTRs or functional fragments thereof, each of which has the same or different nucleotide sequences. In some embodiments, the polynucleotide comprises two or more 3' UTRs or functional fragments thereof, each of which has the same or different nucleotide sequences.

In some embodiments, the 5' UTR or functional fragment thereof, 3' UTR or functional fragment thereof, or any combination thereof is sequence optimized.

In some embodiments, the 5'UTR or functional fragment thereof, 3' UTR or functional fragment thereof, or any combination thereof comprises at least one chemically modified nucleobase, e.g., N1-methylpseudouracil or 5-methoxyuracil.

UTRs can have features that provide a regulatory role, e.g., increased or decreased stability, localization and/or translation efficiency. A polynucleotide comprising a UTR can be administered to a cell, tissue, or organism, and one or more regulatory features can be measured using routine methods. In some embodiments, a functional fragment of a 5' UTR or 3' UTR comprises one or more regulatory features of a full length 5' or 3' UTR, respectively.

Natural 5'UTRs bear features that play roles in translation initiation. They harbor signatures like Kozak sequences that are commonly known to be involved in the process by which the ribosome initiates translation of many genes. Kozak sequences have the consensus CCR(A/G)CCAUGG (SEQ ID NO:87), where R is a purine (adenine or guanine) three bases upstream of the start codon (AUG), which is followed by another 'G'. 5' UTRs also have been known to form secondary structures that are involved in elongation factor binding.

By engineering the features typically found in abundantly expressed genes of specific target organs, one can enhance the stability and protein production of a polynucleotide. For example, introduction of 5' UTR of liver-expressed mRNA, such as albumin, serum amyloid A, Apolipoprotein A/B/E, transferrin, alpha fetoprotein, erythropoietin, or Factor VIII, can enhance expression of polynucleotides in hepatic cell lines or liver. Likewise, use of 5'UTR from other tissue-specific mRNA to improve expression in that tissue is possible for muscle (e.g., MyoD, Myosin, Myoglobin, Myogenin, Herculin), for endothelial cells (e.g., Tie-1, CD36), for myeloid cells (e.g., C/EBP, AML1, G-CSF, GM-CSF, CDiib, MSR, Fr-1, i-NOS), for leukocytes (e.g., CD45, CD18), for adipose tissue (e.g., CD36, GLUT4, ACRP30, adiponectin) and for lung epithelial cells (e.g., SP-A/B/C/D).

In some embodiments, UTRs are selected from a family of transcripts whose proteins share a common function, structure, feature or property. For example, an encoded polypeptide can belong to a family of proteins (i.e., that share at least one function, structure, feature, localization, origin, or expression pattern), which are expressed in a particular cell, tissue or at some time during development. The UTRs from any of the genes or mRNA can be swapped for any other UTR of the same or different family of proteins to create a new polynucleotide.

In some embodiments, the 5' UTR and the 3' UTR can be heterologous. In some embodiments, the 5' UTR can be derived from a different species than the 3' UTR. In some embodiments, the 3' UTR can be derived from a different species than the 5' UTR.

Co-owned International Patent Application No. PCT/US2014/021522 (Publ. No. WO/2014/164253, incorporated herein by reference in its entirety) provides a listing of exemplary UTRs that can be utilized in the polynucleotide of the present invention as flanking regions to an ORF.

Exemplary UTRs of the application include, but are not limited to, one or more 5'UTR and/or 3'UTR derived from the nucleic acid sequence of: a globin, such as an α- or β-globin (e.g., aXenopus, mouse, rabbit, or human globin); a strong Kozak translational initiation signal; a CYBA (e.g., human cytochrome b-245 α polypeptide); an albumin (e.g., human albumin7); aHSD17B4 (hydroxysteroid (17-β) dehydrogenase); a virus (e.g., a tobacco etch virus (TEV), a Venezuelan equine encephalitis virus (VEEV), a Dengue virus, a cytomegalovirus (CMV) (e.g., CMV immediate early 1 (IE1)), a hepatitis virus (e.g., hepatitis B virus), a sindbis virus, or a PAV barley yellow dwarf virus); a heat shock protein (e.g., hsp70); a translation initiation factor (e.g., elF4G); a glucose transporter (e.g., hGLUTI (human glucose transporter 1)); an actin (e.g., human α or β actin); a GAPDH; a tubulin; a histone; a citric acid cycle enzyme; a topoisomerase (e.g., a 5'UTR of a TOP gene lacking the 5' TOP motif (the oligopyrimidine tract)); a ribosomal protein Large 32 (L32); a ribosomal protein (e.g., human or mouse ribosomal protein, such as, for example, rps9); an ATP synthase (e.g., ATP5A1 or the β subunit of mitochondrial H⁺-ATP synthase); a growth hormone e (e.g., bovine (bGH) or human (hGH)); an elongation factor (e.g., elongation factor 1 α1 (EEF1A1)); a manganese superoxide dismutase (MnSOD); a myocyte enhancer factor 2A (MEF2A); a β-F1-ATPase, a creatine kinase, a myoglobin, a granulocyte-colony stimulating factor (G-CSF); a collagen (e.g., collagen type I, alpha 2 (Col1A2), collagen type I, alpha 1 (Col1A1), collagen type VI, alpha 2 (Col6A2), collagen type VI, alpha 1 (Col6A1)); a ribophorin (e.g., ribophorin I (RPNI)); a low density lipoprotein receptor-related protein (e.g., LRP1); a cardiotrophin-like cytokine factor (e.g., Nnt1); calreticulin (Calr); a procollagen-lysine, 2-oxoglutarate 5-dioxygenase 1 (Plod1); and a nucleobindin (e.g., Nucb1).

In some embodiments, the 5' UTR is selected from the group consisting of a β-globin 5' UTR; a 5'UTR containing a strong Kozak translational initiation signal; a cytochrome b-245 α polypeptide (CYBA) 5' UTR; a hydroxysteroid (17-0) dehydrogenase (HSD17B4) 5' UTR; a Tobacco etch virus (TEV) 5' UTR; a Venezuelen equine encephalitis virus (TEEV) 5' UTR; a 5' proximal open reading frame of rubella virus (RV) RNA encoding nonstructural proteins; a Dengue virus (DEN) 5' UTR; a heat shock protein 70 (Hsp70) 5'

UTR; a eIF4G 5' UTR; a GLUT1 5' UTR; functional fragments thereof and any combination thereof.

In some embodiments, the 3' UTR is selected from the group consisting of a β-globin 3' UTR; a CYBA 3' UTR; an albumin 3' UTR; a growth hormone (GH) 3' UTR; a VEEV 3' UTR; a hepatitis B virus (HBV) 3' UTR; α-globin 3'UTR; a DEN 3' UTR; a PAV barley yellow dwarf virus (BYDV-PAV) 3' UTR; an elongation factor 1 α1 (EEF1A1) 3' UTR; a manganese superoxide dismutase (MnSOD) 3' UTR; a β subunit of mitochondrial H(+)-ATP synthase (β-mRNA) 3' UTR; a GLUT1 3' UTR; a MEF2A 3' UTR; a β-F1-ATPase 3' UTR; functional fragments thereof and combinations thereof.

Wild-type UTRs derived from any gene or mRNA can be incorporated into the polynucleotides of the invention. In some embodiments, a UTR can be altered relative to a wild type or native UTR to produce a variant UTR, e.g., by changing the orientation or location of the UTR relative to the ORF; or by inclusion of additional nucleotides, deletion of nucleotides, swapping or transposition of nucleotides. In some embodiments, variants of 5' or 3' UTRs can be utilized, for example, mutants of wild type UTRs, or variants wherein one or more nucleotides are added to or removed from a terminus of the UTR.

Additionally, one or more synthetic UTRs can be used in combination with one or more non-synthetic UTRs. See, e.g., Mandal and Rossi, Nat. Protoc. 2013 8(3):568-82, the contents of which are incorporated herein by reference in their entirety.

UTRs or portions thereof can be placed in the same orientation as in the transcript from which they were selected or can be altered in orientation or location. Hence, a 5' and/or 3' UTR can be inverted, shortened, lengthened, or combined with one or more other 5' UTRs or 3' UTRs.

In some embodiments, the polynucleotide comprises multiple UTRs, e.g., a double, a triple or a quadruple 5' UTR or 3' UTR. For example, a double UTR comprises two copies of the same UTR either in series or substantially in series. For example, a double beta-globin 3'UTR can be used (see US2010/0129877, the contents of which are incorporated herein by reference in its entirety).

In certain embodiments, the polynucleotides of the invention comprise a 5' UTR and/or a 3' UTR selected from any of the UTRs disclosed herein. In some embodiments, the 5' UTR comprises:

```
5' UTR-001 (Upstream UTR)
                                    (SEQ ID NO: 3)
(GGGAAAUAAGAGAGAAAAGAAGAGUAAGAAGAAAUAUAAGAGCCACC);

5' UTR-002 (Upstream UTR)
                                    (SEQ ID NO: 89)
(GGGAGAUCAGAGAGAAAAGAAGAGUAAGAAGAAAUAUAAGAGCCACC);

5' UTR-003 (Upstream UTR)  (See WO2016/100812)
5' UTR-004 (Upstream UTR)
                                    (SEQ ID NO: 90)
(GGGAGACAAGCUUGGCAUUCCGGUACUGUUGGUAAAGCCACC);

5' UTR-005 (Upstream UTR)
                                    (SEQ ID NO: 89)
(GGGAGAUCAGAGAGAAAAGAAGAGUAAGAAGAAAUAUAAGAGCCACC);

5' UTR-006 (Upstream UTR)  (See WO2016/100812)
5' UTR-007 (Upstream UTR)
                                    (SEQ ID NO: 90)
(GGGAGACAAGCUUGGCAUUCCGGUACUGUUGGUAAAGCCACC);
```

-continued

```
5' UTR-008 (Upstream UTR)
                                     (SEQ ID NO: 93)
(GGGAAUUAACAGAGAAAAGAAGAGUAAGAAGAAAUAUAAGAGCCACC);

5' UTR-009 (Upstream UTR)
                                     (SEQ ID NO: 94)
(GGGAAAUUAGACAGAGAAAAGAAGAGUAAGAAGAAAUAUAAGAGCCACC);

5' UTR-010, Upstream
                                     (SEQ ID NO: 95)
(GGGAAAUAAGAGAGUAAAGAACAGUAAGAAGAAAUAUAAGAGCCACC);

5' UTR-011 (Upstream UTR)
                                     (SEQ ID NO: 96)
(GGGAAAAAAGAGAGAAAAGAAGACUAAGAAGAAAUAUAAGAGCCACC);

5' UTR-012 (Upstream UTR)
                                     (SEQ ID NO: 97)
(GGGAAAUAAGAGAGAAAAGAAGAGUAAGAAGAUAUAUAAGAGCCACC);

5' UTR-013 (Upstream UTR)
                                     (SEQ ID NO: 98)
(GGGAAAUAAGAGACAAAACAAGAGUAAGAAGAAAUAUAAGAGCCACC);

5' UTR-014 (Upstream UTR)
                                     (SEQ ID NO: 99)
(GGGAAAUUAGAGAGUAAAGAACAGUAAGUAGAAUUAAAAGAGCCACC);

5' UTR-015 (Upstream UTR)
                                     (SEQ ID NO: 100)
(GGGAAAUAAGAGAGAAUAGAAGAGUAAGAAGAAAUAUAAGAGCCACC);

5' UTR-016 (Upstream UTR)
                                     (SEQ ID NO: 101)
(GGGAAAUAAGAGAGAAAAGAAGAGUAAGAAGAAAAUUAAGAGCCACC);

5' UTR-017 (Upstream UTR);
                                     (SEQ ID NO: 102)
(GGGAAAUAAGAGAGAAAAGAAGAGUAAGAAGAAAUUUAAGAGCCACC);
or 5' UTR-018 (Upstream UTR) 5' UTR
                                     (SEQ ID NO: 88)
(UCAAGCUUUUGGACCCUCGUACAGAAGCUAAUACGACUCACUAUAGGGA

AAUAAGAGAGAAAAGAAGAGUAAGAAGAAAUAUAAGAGCCACC).

5' UTR-019
                                     (SEQ ID NO: 64)
(GGGAAATAAGAGAGAAAAGAAGAGTAAGAAGAAATATAAGAGCCACC)

5' UTR v1 A Start
                                     (SEQ ID NO: 199)
(AGGAAAUAAGAGAGAAAAGAAGAGUAAGAAGAAAUAUAAGAGCCACC)
```

In some embodiments, the 3' UTR comprises:

```
142-3p 3' UTR (UTR including miR142-3p binding
site)
                                     (SEQ ID NO: 104)
(UGAUAAUAGUCCAUAAAGUAGGAAACACUACAGCUGGAGCCUCGGUGG

CCAUGCUUCUUGCCCCUUGGGCCUCCCCCCAGCCCCUCCUCCCCUUCCU

GCACCCGUACCCCCGUGGUCUUUGAAUAAAGUCUGAGUGGGCGGC);

142-3p 3' UTR (UTR including miR142-3p binding
site)
                                     (SEQ ID NO: 105)
(UGAUAAUAGGCUGGAGCCUCGGUGGCUCCAUAAAGUAGGAAACACUAC

ACAUGCUUCUUGCCCCUUGGGCCUCCCCCCAGCCCCUCCUCCCCUUCCU

GCACCCGUACCCCCGUGGUCUUUGAAUAAAGUCUGAGUGGGCGGC);
or
```

-continued

```
142-3p 3' UTR (UTR including miR142-3p binding
site)
                                     (SEQ ID NO: 106)
(UGAUAAUAGGCUGGAGCCUCGGUGGCCAUGCUUCUUGCCCCUUCCAUA

AAGUAGGAAACACUACAUGGGCCUCCCCCCAGCCCCUCCUCCCCUUCCU

GCACCCGUACCCCCGUGGUCUUUGAAUAAAGUCUGAGUGGGCGGC);

142-3p 3' UTR (UTR including miR142-3p binding
site)
                                     (SEQ ID NO: 107)
(UGAUAAUAGGCUGGAGCCUCGGUGGCCAUGCUUCUUGCCCCUUGGGCC

UCCCCCCAGUCCAUAAAGUAGGAAACACUACACCCCUCCUCCCCUUCCU

GCACCCGUACCCCCGUGGUCUUUGAAUAAAGUCUGAGUGGGCGGC);

142-3p 3' UTR (UTR including miR142-3p binding
site)
                                     (SEQ ID NO: 108)
(UGAUAAUAGGCUGGAGCCUCGGUGGCCAUGCUUCUUGCCCCUUGGGCC

UCCCCCCAGCCCCUCCUCCCCUUCUCCAUAAAGUAGGAAACACUACACU

GCACCCGUACCCCCGUGGUCUUUGAAUAAAGUCUGAGUGGGCGGC);

142-3p 3' UTR (UTR including miR142-3p binding
site)
                                     (SEQ ID NO: 109)
(UGAUAAUAGGCUGGAGCCUCGGUGGCCAUGCUUCUUGCCCCUUGGGCC

UCCCCCCAGCCCCUCCUCCCCUUCCUGCACCCGUACCCCCUCCAUAAAG

UAGGAAACACUACAGUGGUCUUUGAAUAAAGUCUGAGUGGGCGGC).

142-3p 3' UTR (UTR including miR142-3p binding
site)
                                     (SEQ ID NO: 110)
(UGAUAAUAGGCUGGAGCCUCGGUGGCCAUGCUUCUUGCCCCUUGGGCC

UCCCCCCAGCCCCUCCUCCCCUUCCUGCACCCGUACCCCCGUGGUCUUU

GAAUAAAGUUCCAUAAAGUAGGAAACACUACACUGAGUGGGCGGC);

3' UTR-018 (See SEQ ID NO: 150);
3' UTR (miR142 and miR126 binding sites variant 1)
                                     (SEQ ID NO: 111)
(UGAUAAUAGUCCAUAAAGUAGGAAACACUACAGCUGGAGCCUCGGUGG

CCAUGCUUCUUGCCCCUUGGGCCUCCCCCCAGCCCCUCCUCCCCUUCCU

GCACCCGUACCCCCGCAUUAUUACUCACGGUACGAGUGGUCUUUGAAU

AAAGUCUGAGUGGGCGGC)

3' UTR (miR142 and miR126 binding sites variant 2)
                                     (SEQ ID NO: 112)
(UGAUAAUAGUCCAUAAAGUAGGAAACACUACAGCUGGAGCCUCGGUGG

CCUAGCUUCUUGCCCCUUGGGCCUCCCCCCAGCCCCUCCUCCCCUUCCU

GCACCCGUACCCCCCGCAUUAUUACUCACGGUACGAGUGGUCUUUGAAU

AAAGUCUGAGUGGGCGGC);
or

3'UTR (miR142-3p binding site variant 3)
                                     (SEQ ID NO: 4)
UGAUAAUAGGCUGGAGCCUCGGUGGCCUAGCUUCUUGCCCCUUGGGCCU

CCCCCCAGCCCCUCCUCCCCUUCCUGCACCCGUACCCCCUCCAUAAAGU

AGGAAACACUACAGUGGUCUUUGAAUAAAGUCUGAGUGGGCGGC.
```

In certain embodiments, the 5' UTR and/or 3' UTR sequence of the invention comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of 5' UTR sequences comprising any of SEQ ID NOs: 3, 64, 88-102, 165-167, or 199 and/or 3' UTR sequences comprises any of SEQ ID NOs:4, 104-112, 150, or 178, and any combination thereof.

In certain embodiments, the 5' UTR and/or 3' UTR sequence of the invention comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of 5' UTR sequences comprising any of SEQ ID NO:3, SEQ ID NO:191, SEQ ID NO:199, or SEQ ID NO:206 and/or 3' UTR sequences comprises any of SEQ ID NO:4, SEQ ID NO:111, SEQ ID NO:150, SEQ ID NO:175, SEQ ID NO: 177, SEQ ID NO:178, SEQ ID NO:207, or SEQ ID NO:208, and any combination thereof.

In some embodiments, the 5' UTR comprises an amino acid sequence set forth in Table 4B (SEQ ID NO:3, SEQ ID NO:191, SEQ ID NO:199, or SEQ ID NO:206). In some embodiments, the 3' UTR comprises an amino acid sequence set forth in Table 4B (SEQ ID NO:4, SEQ ID NO:111, SEQ ID NO:150, SEQ ID NO:175, SEQ ID NO:177, SEQ ID NO: 178, SEQ ID NO:207, or SEQ ID NO:208). In some embodiments, the 5' UTR comprises an amino acid sequence set forth in Table 4B (SEQ ID NO:3, SEQ ID NO:191, SEQ ID NO:199, or SEQ ID NO:206) and the 3' UTR comprises an amino acid sequence set forth in Table 4B (SEQ ID NO:4, SEQ ID NO:111, SEQ ID NO:150, SEQ ID NO:175, SEQ ID NO:177, SEQ ID NO:178, SEQ ID NO:207, or SEQ ID NO:208).

The polynucleotides of the invention can comprise combinations of features. For example, the ORF can be flanked by a 5'UTR that comprises a strong Kozak translational initiation signal and/or a 3'UTR comprising an oligo(dT) sequence for templated addition of a poly-A tail. A 5'UTR can comprise a first polynucleotide fragment and a second polynucleotide fragment from the same and/or different UTRs (see, e.g., US2010/0293625, herein incorporated by reference in its entirety).

Other non-UTR sequences can be used as regions or subregions within the polynucleotides of the invention. For example, introns or portions of intron sequences can be incorporated into the polynucleotides of the invention. Incorporation of intronic sequences can increase protein production as well as polynucleotide expression levels. In some embodiments, the polynucleotide of the invention comprises an internal ribosome entry site (IRES) instead of or in addition to a UTR (see, e.g., Yakubov et al., Biochem. Biophys. Res. Commun. 2010 394(1):189-193, the contents of which are incorporated herein by reference in their entirety). In some embodiments, the polynucleotide comprises an IRES instead of a 5' UTR sequence. In some embodiments, the polynucleotide comprises an ORF and a viral capsid sequence. In some embodiments, the polynucleotide comprises a synthetic 5' UTR in combination with a non-synthetic 3' UTR.

In some embodiments, the UTR can also include at least one translation enhancer polynucleotide, translation enhancer element, or translational enhancer elements (collectively, "TEE," which refers to nucleic acid sequences that increase the amount of polypeptide or protein produced from a polynucleotide. As a non-limiting example, the TEE can be located between the transcription promoter and the start codon. In some embodiments, the 5' UTR comprises a TEE.

In one aspect, a TEE is a conserved element in a UTR that can promote translational activity of a nucleic acid such as, but not limited to, cap-dependent or cap-independent translation.

11. MicroRNA (miRNA) Binding Sites

Polynucleotides of the invention can include regulatory elements, for example, microRNA (miRNA) binding sites, transcription factor binding sites, structured mRNA sequences and/or motifs, artificial binding sites engineered to act as pseudo-receptors for endogenous nucleic acid binding molecules, and combinations thereof. In some embodiments, polynucleotides including such regulatory elements are referred to as including "sensor sequences".

In some embodiments, a polynucleotide (e.g., a ribonucleic acid (RNA), e.g., a messenger RNA (mRNA)) of the invention comprises an open reading frame (ORF) encoding a polypeptide of interest and further comprises one or more miRNA binding site(s). Inclusion or incorporation of miRNA binding site(s) provides for regulation of polynucleotides of the invention, and in turn, of the polypeptides encoded therefrom, based on tissue-specific and/or cell-type specific expression of naturally-occurring miRNAs.

The present invention also provides pharmaceutical compositions and formulations that comprise any of the polynucleotides described above. In some embodiments, the composition or formulation further comprises a delivery agent.

In some embodiments, the composition or formulation can contain a polynucleotide comprising a sequence optimized nucleic acid sequence disclosed herein which encodes a polypeptide. In some embodiments, the composition or formulation can contain a polynucleotide (e.g., a RNA, e.g., an mRNA) comprising a polynucleotide (e.g., an ORF) having significant sequence identity to a sequence optimized nucleic acid sequence disclosed herein which encodes a polypeptide. In some embodiments, the polynucleotide further comprises a miRNA binding site, e.g., a miRNA binding site that binds A miRNA, e.g., a natural-occurring miRNA, is a 19-25 nucleotide long noncoding RNA that binds to a polynucleotide and down-regulates gene expression either by reducing stability or by inhibiting translation of the polynucleotide. A miRNA sequence comprises a "seed" region, i.e., a sequence in the region of positions 2-8 of the mature miRNA. A miRNA seed can comprise positions 2-8 or 2-7 of the mature miRNA.

microRNAs derive enzymatically from regions of RNA transcripts that fold back on themselves to form short hairpin structures often termed a pre-miRNA (precursor-miRNA). A pre-miRNA typically has a two-nucleotide overhang at its 3' end, and has 3' hydroxyl and 5' phosphate groups. This precursor-mRNA is processed in the nucleus and subsequently transported to the cytoplasm where it is further processed by DICER (a RNase III enzyme), to form a mature microRNA of approximately 22 nucleotides. The mature microRNA is then incorporated into a ribonuclear particle to form the RNA-induced silencing complex, RISC, which mediates gene silencing. Art-recognized nomenclature for mature miRNAs typically designates the arm of the pre-miRNA from which the mature miRNA derives; "5p" means the microRNA is from the 5 prime arm of the pre-miRNA hairpin and "3p" means the microRNA is from the 3 prime end of the pre-miRNA hairpin. A miR referred to by number herein can refer to either of the two mature microRNAs originating from opposite arms of the same pre-miRNA (e.g., either the 3p or 5p microRNA). All miRs referred to herein are intended to include both the 3p and 5p arms/sequences, unless particularly specified by the 3p or 5p designation.

As used herein, the term "microRNA (miRNA or miR) binding site" refers to a sequence within a polynucleotide, e.g., within a DNA or within an RNA transcript, including in the 5'UTR and/or 3'UTR, that has sufficient complementarity to all or a region of a miRNA to interact with, associate with or bind to the miRNA. In some embodiments, a polynucleotide of the invention comprising an ORF encoding a polypeptide of interest and further comprises one or more miRNA binding site(s). In exemplary embodiments, a 5' UTR and/or 3' UTR of the polynucleotide (e.g., a ribonucleic acid (RNA), e.g., a messenger RNA (mRNA)) comprises the one or more miRNA binding site(s).

A miRNA binding site having sufficient complementarity to a miRNA refers to a degree of complementarity sufficient to facilitate miRNA-mediated regulation of a polynucleotide, e.g., miRNA-mediated translational repression or degradation of the polynucleotide. In exemplary aspects of the invention, a miRNA binding site having sufficient complementarity to the miRNA refers to a degree of complementarity sufficient to facilitate miRNA-mediated degradation of the polynucleotide, e.g., miRNA-guided RNA-induced silencing complex (RISC)-mediated cleavage of mRNA. The miRNA binding site can have complementarity to, for example, a 19-25 nucleotide long miRNA sequence, to a 19-23 nucleotide long miRNA sequence, or to a 22 nucleotide long miRNA sequence. A miRNA binding site can be complementary to only a portion of a miRNA, e.g., to a portion less than 1, 2, 3, or 4 nucleotides of the full length of a naturally-occurring miRNA sequence, or to a portion less than 1, 2, 3, or 4 nucleotides shorter than a naturally-occurring miRNA sequence. Full or complete complementarity (e.g., full complementarity or complete complementarity over all or a significant portion of the length of a naturally-occurring miRNA) is preferred when the desired regulation is mRNA degradation.

In some embodiments, a miRNA binding site includes a sequence that has complementarity (e.g., partial or complete complementarity) with an miRNA seed sequence. In some embodiments, the miRNA binding site includes a sequence that has complete complementarity with a miRNA seed sequence. In some embodiments, a miRNA binding site includes a sequence that has complementarity (e.g., partial or complete complementarity) with an miRNA sequence. In some embodiments, the miRNA binding site includes a sequence that has complete complementarity with a miRNA sequence. In some embodiments, a miRNA binding site has complete complementarity with a miRNA sequence but for 1, 2, or 3 nucleotide substitutions, terminal additions, and/or truncations.

In some embodiments, the miRNA binding site is the same length as the corresponding miRNA. In other embodiments, the miRNA binding site is one, two, three, four, five, six, seven, eight, nine, ten, eleven or twelve nucleotide(s) shorter than the corresponding miRNA at the 5' terminus, the 3' terminus, or both. In still other embodiments, the microRNA binding site is two nucleotides shorter than the corresponding microRNA at the 5' terminus, the 3' terminus, or both. The miRNA binding sites that are shorter than the corresponding miRNAs are still capable of degrading the mRNA incorporating one or more of the miRNA binding sites or preventing the mRNA from translation.

In some embodiments, the miRNA binding site binds the corresponding mature miRNA that is part of an active RISC containing Dicer. In another embodiment, binding of the miRNA binding site to the corresponding miRNA in RISC degrades the mRNA containing the miRNA binding site or prevents the mRNA from being translated. In some embodiments, the miRNA binding site has sufficient complementarity to miRNA so that a RISC complex comprising the miRNA cleaves the polynucleotide comprising the miRNA binding site. In other embodiments, the miRNA binding site has imperfect complementarity so that a RISC complex comprising the miRNA induces instability in the polynucleotide comprising the miRNA binding site. In another embodiment, the miRNA binding site has imperfect complementarity so that a RISC complex comprising the miRNA represses transcription of the polynucleotide comprising the miRNA binding site.

In some embodiments, the miRNA binding site has one, two, three, four, five, six, seven, eight, nine, ten, eleven or twelve mismatch(es) from the corresponding miRNA.

In some embodiments, the miRNA binding site has at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one contiguous nucleotides complementary to at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one, respectively, contiguous nucleotides of the corresponding miRNA.

By engineering one or more miRNA binding sites into a polynucleotide of the invention, the polynucleotide can be targeted for degradation or reduced translation, provided the miRNA in question is available. This can reduce off-target effects upon delivery of the polynucleotide. For example, if a polynucleotide of the invention is not intended to be delivered to a tissue or cell but ends up is said tissue or cell, then a miRNA abundant in the tissue or cell can inhibit the expression of the gene of interest if one or multiple binding sites of the miRNA are engineered into the 5' UTR and/or 3' UTR of the polynucleotide. Thus, in some embodiments, incorporation of one or more miRNA binding sites into an mRNA of the disclosure may reduce the hazard of off-target effects upon nucleic acid molecule delivery and/or enable tissue-specific regulation of expression of a polypeptide encoded by the mRNA. In yet other embodiments, incorporation of one or more miRNA binding sites into an mRNA of the disclosure can modulate immune responses upon nucleic acid delivery in vivo. In further embodiments, incorporation of one or more miRNA binding sites into an mRNA of the disclosure can modulate accelerated blood clearance (ABC) of lipid-comprising compounds and compositions described herein.

Conversely, miRNA binding sites can be removed from polynucleotide sequences in which they naturally occur in order to increase protein expression in specific tissues. For example, a binding site for a specific miRNA can be removed from a polynucleotide to improve protein expression in tissues or cells containing the miRNA.

Regulation of expression in multiple tissues can be accomplished through introduction or removal of one or more miRNA binding sites, e.g., one or more distinct miRNA binding sites. The decision whether to remove or insert a miRNA binding site can be made based on miRNA expression patterns and/or their profilings in tissues and/or cells in development and/or disease. Identification of miR- NAs, miRNA binding sites, and their expression patterns and role in biology have been reported (e.g., Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/leu.2011.356); Bartel Cell 2009 136:215-233; Landgraf et al, Cell, 2007 129:1401-1414; Gentner and Naldini, Tissue Antigens. 2012 80:393-403 and all references therein; each of which is incorporated herein by reference in its entirety).

Examples of tissues where miRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-30c), heart (miR-1d, miR-149), kidney (miR-192, miR-194, miR-204), and lung epithelial cells (let-7, miR-133, miR-126).

Specifically, miRNAs are known to be differentially expressed in immune cells (also called hematopoietic cells), such as antigen presenting cells (APCs) (e.g., dendritic cells and macrophages), macrophages, monocytes, B lymphocytes, T lymphocytes, granulocytes, natural killer cells, etc. Immune cell specific miRNAs are involved in immunogenicity, autoimmunity, the immune-response to infection, inflammation, as well as unwanted immune response after gene therapy and tissue/organ transplantation. Immune cells specific miRNAs also regulate many aspects of development, proliferation, differentiation and apoptosis of hematopoietic cells (immune cells). For example, miR-142 and miR-146 are exclusively expressed in immune cells, particularly abundant in myeloid dendritic cells. It has been demonstrated that the immune response to a polynucleotide can be shut-off by adding miR-142 binding sites to the 3'-UTR of the polynucleotide, enabling more stable gene transfer in tissues and cells. miR-142 efficiently degrades exogenous polynucleotides in antigen presenting cells and suppresses cytotoxic elimination of transduced cells (e.g., Annoni A et al., blood, 2009, 114, 5152-5161; Brown B D, et al., Nat med. 2006, 12(5), 585-591; Brown B D, et al., blood, 2007, 110(13): 4144-4152, each of which is incorporated herein by reference in its entirety).

An antigen-mediated immune response can refer to an immune response triggered by foreign antigens, which, when entering an organism, are processed by the antigen presenting cells and displayed on the surface of the antigen presenting cells. T cells can recognize the presented antigen and induce a cytotoxic elimination of cells that express the antigen.

Introducing a miR-142 binding site into the 5' UTR and/or 3'UTR of a polynucleotide of the invention can selectively repress gene expression in antigen presenting cells through miR-142 mediated degradation, limiting antigen presentation in antigen presenting cells (e.g., dendritic cells) and thereby preventing antigen-mediated immune response after the delivery of the polynucleotide. The polynucleotide is then stably expressed in target tissues or cells without triggering cytotoxic elimination.

In one embodiment, binding sites for miRNAs that are known to be expressed in immune cells, in particular, antigen presenting cells, can be engineered into a polynucleotide of the invention to suppress the expression of the polynucleotide in antigen presenting cells through miRNA mediated RNA degradation, subduing the antigen-mediated immune response. Expression of the polynucleotide is maintained in non-immune cells where the immune cell specific miRNAs are not expressed. For example, in some embodiments, to prevent an immunogenic reaction against a liver specific protein, any miR-122 binding site can be removed and a miR-142 (and/or mirR-146) binding site can be engineered into the 5' UTR and/or 3' UTR of a polynucleotide of the invention.

To further drive the selective degradation and suppression in APCs and macrophage, a polynucleotide of the invention can include a further negative regulatory element in the 5' UTR and/or 3' UTR, either alone or in combination with miR-142 and/or miR-146 binding sites. As a non-limiting example, the further negative regulatory element is a Constitutive Decay Element (CDE).

Immune cell specific miRNAs include, but are not limited to, hsa-let-7a-2-3p, hsa-let-7a-3p, hsa-7a-5p, hsa-let-7c, hsa-let-7e-3p, hsa-let-7e-5p, hsa-let-7g-3p, hsa-let-7g-5p, hsa-let-7i-3p, hsa-let-7i-5p, miR-10a-3p, miR-10a-5p, miR-1184, hsa-let-7f-1-3p, hsa-let-7f-2-5p, hsa-let-7f-5p, miR-125b-1-3p, miR-125b-2-3p, miR-125b-5p, miR-1279, miR-130a-3p, miR-130a-5p, miR-132-3p, miR-132-5p, miR-142-3p, miR-142-5p, miR-143-3p, miR-143-5p, miR-146a-3p, miR-146a-5p, miR-146b-3p, miR-146b-5p, miR-147a, miR-147b, miR-148a-5p, miR-148a-3p, miR-150-3p, miR-150-5p, miR-151b, miR-155-3p, miR-155-5p, miR-15a-3p, miR-15a-5p, miR-15b-5p, miR-15b-3p, miR-16-1-3p, miR-16-2-3p, miR-16-5p, miR-17-5p, miR-181a-3p, miR-181a-5p, miR-181a-2-3p, miR-182-3p, miR-182-5p, miR-197-3p, miR-197-5p, miR-21-5p, miR-21-3p, miR-214-3p, miR-214-5p, miR-223-3p, miR-223-5p, miR-221-3p, miR-221-5p, miR-23b-3p, miR-23b-5p, miR-24-1-5p, miR-24-2-5p, miR-24-3p, miR-26a-1-3p, miR-26a-2-3p, miR-26a-5p, miR-26b-3p, miR-26b-5p, miR-27a-3p, miR-27a-5p, miR-27b-3p, miR-27b-5p, miR-28-3p, miR-28-5p, miR-2909, miR-29a-3p, miR-29a-5p, miR-29b-1-5p, miR-29b-2-5p, miR-29c-3p, miR-29c-5p, miR-30e-3p, miR-30e-5p, miR-331-5p, miR-339-3p, miR-339-5p, miR-345-3p, miR-345-5p, miR-346, miR-34a-3p, miR-34a-5p, miR-363-3p, miR-363-5p, miR-372, miR-377-3p, miR-377-5p, miR-493-3p, miR-493-5p, miR-542, miR548b-5p, miR548c-5p, miR-548i, miR-548j, miR-548n, miR-574-3p, miR-598, miR-718, miR-935, miR-99a-3p, miR-99a-5p, miR-99b-3p, and miR-99b-5p. Furthermore, novel miRNAs can be identified in immune cell through micro-array hybridization and microtome analysis (e.g., Jima D D et al, Blood, 2010, 116:e118-e127; Vaz C et al., BMC Genomics, 2010, 11,288, the content of each of which is incorporated herein by reference in its entirety.)

miRNAs that are known to be expressed in the liver include, but are not limited to, miR-107, miR-122-3p, miR-122-5p, miR-1228-3p, miR-1228-5p, miR-1249, miR-129-5p, miR-1303, miR-151a-3p, miR-151a-5p, miR-152, miR-194-3p, miR-194-5p, miR-199a-3p, miR-199a-5p, miR-199b-3p, miR-199b-5p, miR-296-5p, miR-557, miR-581, miR-939-3p, and miR-939-5p. miRNA binding sites from any liver specific miRNA can be introduced to or removed from a polynucleotide of the invention to regulate expression of the polynucleotide in the liver. Liver specific miRNA binding sites can be engineered alone or further in combination with immune cell (e.g., APC) miRNA binding sites in a polynucleotide of the invention.

miRNAs that are known to be expressed in the lung include, but are not limited to, let-7a-2-3p, let-7a-3p, let-7a-5p, miR-126-3p, miR-126-5p, miR-127-3p, miR-127-5p, miR-130a-3p, miR-130a-5p, miR-130b-3p, miR-130b-5p, miR-133a, miR-133b, miR-134, miR-18a-3p, miR-18a-5p, miR-18b-3p, miR-18b-5p, miR-24-1-5p, miR-24-2-5p, miR-24-3p, miR-296-3p, miR-296-5p, miR-32-3p, miR-337-3p, miR-337-5p, miR-381-3p, and miR-381-5p. miRNA binding sites from any lung specific miRNA can be introduced to or removed from a polynucleotide of the invention to regulate expression of the polynucleotide in the lung. Lung specific miRNA binding sites can be engineered alone or further in combination with immune cell (e.g., APC) miRNA binding sites in a polynucleotide of the invention.

miRNAs that are known to be expressed in the heart include, but are not limited to, miR-1, miR-133a, miR-133b, miR-149-3p, miR-149-5p, miR-186-3p, miR-186-5p, miR-208a, miR-208b, miR-210, miR-296-3p, miR-320, miR-451a, miR-451b, miR-499a-3p, miR-499a-5p, miR-499b-3p, miR-499b-5p, miR-744-3p, miR-744-5p, miR-92b-3p, and miR-92b-5p. miRNA binding sites from any heart specific microRNA can be introduced to or removed from a polynucleotide of the invention to regulate expression of the polynucleotide in the heart. Heart specific miRNA binding sites can be engineered alone or further in combination with immune cell (e.g., APC) miRNA binding sites in a polynucleotide of the invention.

miRNAs that are known to be expressed in the nervous system include, but are not limited to, miR-124-5p, miR-125a-3p, miR-125a-5p, miR-125b-1-3p, miR-125b-2-3p, miR-125b-5p, miR-1271-3p, miR-1271-5p, miR-128, miR-132-5p, miR-135a-3p, miR-135a-5p, miR-135b-3p, miR-135b-5p, miR-137, miR-139-5p, miR-139-3p, miR-149-3p, miR-149-5p, miR-153, miR-181c-3p, miR-181c-5p, miR-183-3p, miR-183-5p, miR-190a, miR-190b, miR-212-3p, miR-212-5p, miR-219-1-3p, miR-219-2-3p, miR-23a-3p, miR-23a-5p, miR-30a-5p, miR-30b-3p, miR-30b-5p, miR-30c-1-3p, miR-30c-2-3p, miR-30c-5p, miR-30d-3p, miR-30d-5p, miR-329, miR-342-3p, miR-3665, miR-3666, miR-380-3p, miR-380-5p, miR-383, miR-410, miR-425-3p, miR-425-5p, miR-454-3p, miR-454-5p, miR-483, miR-510, miR-516a-3p, miR-548b-5p, miR-548c-5p, miR-571, miR-7-1-3p, miR-7-2-3p, miR-7-5p, miR-802, miR-922, miR-9-3p, and miR-9-5p. miRNAs enriched in the nervous system further include those specifically expressed in neurons, including, but not limited to, miR-132-3p, miR-132-3p, miR-148b-3p, miR-148b-5p, miR-151a-3p, miR-151a-5p, miR-212-3p, miR-212-5p, miR-320b, miR-320e, miR-323a-3p, miR-323a-5p, miR-324-5p, miR-325, miR-326, miR-328, miR-922 and those specifically expressed in glial cells, including, but not limited to, miR-1250, miR-219-1-3p, miR-219-2-3p, miR-219-5p, miR-23a-3p, miR-23a-5p, miR-3065-3p, miR-3065-5p, miR-30e-3p, miR-30e-5p, miR-32-5p, miR-338-5p, and miR-657. miRNA binding sites from any CNS specific miRNA can be introduced to or removed from a polynucleotide of the invention to regulate expression of the polynucleotide in the nervous system. Nervous system specific miRNA binding sites can be engineered alone or further in combination with immune cell (e.g., APC) miRNA binding sites in a polynucleotide of the invention.

miRNAs that are known to be expressed in the pancreas include, but are not limited to, miR-105-3p, miR-105-5p, miR-184, miR-195-3p, miR-195-5p, miR-196a-3p, miR-196a-5p, miR-214-3p, miR-214-5p, miR-216a-3p, miR-216a-5p, miR-30a-3p, miR-33a-3p, miR-33a-5p, miR-375, miR-7-1-3p, miR-7-2-3p, miR-493-3p, miR-493-5p, and miR-944. miRNA binding sites from any pancreas specific miRNA can be introduced to or removed from a polynucleotide of the invention to regulate expression of the polynucleotide in the pancreas. Pancreas specific miRNA binding sites can be engineered alone or further in combination with immune cell (e.g. APC) miRNA binding sites in a polynucleotide of the invention.

miRNAs that are known to be expressed in the kidney include, but are not limited to, miR-122-3p, miR-145-5p, miR-17-5p, miR-192-3p, miR-192-5p, miR-194-3p, miR-194-5p, miR-20a-3p, miR-20a-5p, miR-204-3p, miR-204-5p, miR-210, miR-216a-3p, miR-216a-5p, miR-296-3p, miR-30a-3p, miR-30a-5p, miR-30b-3p, miR-30b-5p, miR-30c-1-3p, miR-30c-2-3p, miR30c-5p, miR-324-3p, miR-335-3p, miR-335-5p, miR-363-3p, miR-363-5p, and miR-562. miRNA binding sites from any kidney specific miRNA can be introduced to or removed from a polynucleotide of the invention to regulate expression of the polynucleotide in the kidney. Kidney specific miRNA binding sites can be engineered alone or further in combination with immune cell (e.g., APC) miRNA binding sites in a polynucleotide of the invention.

miRNAs that are known to be expressed in the muscle include, but are not limited to, let-7g-3p, let-7g-5p, miR-1, miR-1286, miR-133a, miR-133b, miR-140-3p, miR-143-3p, miR-143-5p, miR-145-3p, miR-145-5p, miR-188-3p, miR-188-5p, miR-206, miR-208a, miR-208b, miR-25-3p, and miR-25-5p. MiRNA binding sites from any muscle specific miRNA can be introduced to or removed from a polynucleotide of the invention to regulate expression of the polynucleotide in the muscle. Muscle specific miRNA binding sites can be engineered alone or further in combination with immune cell (e.g., APC) miRNA binding sites in a polynucleotide of the invention.

miRNAs are also differentially expressed in different types of cells, such as, but not limited to, endothelial cells, epithelial cells, and adipocytes.

miRNAs that are known to be expressed in endothelial cells include, but are not limited to, let-7b-3p, let-7b-5p, miR-100-3p, miR-100-5p, miR-101-3p, miR-101-5p, miR-126-3p, miR-126-5p, miR-1236-3p, miR-1236-5p, miR-130a-3p, miR-130a-5p, miR-17-5p, miR-17-3p, miR-18a-3p, miR-18a-5p, miR-19a-3p, miR-19a-5p, miR-19b-1-5p, miR-19b-2-5p, miR-19b-3p, miR-20a-3p, miR-20a-5p, miR-217, miR-210, miR-21-3p, miR-21-5p, miR-221-3p, miR-221-5p, miR-222-3p, miR-222-5p, miR-23a-3p, miR-23a-5p, miR-296-5p, miR-361-3p, miR-361-5p, miR-421, miR-424-3p, miR-424-5p, miR-513a-5p, miR-92a-1-5p, miR-92a-2-5p, miR-92a-3p, miR-92b-3p, and miR-92b-5p. Many novel miRNAs are discovered in endothelial cells from deep-sequencing analysis (e.g., Voellenkle C et al., RNA, 2012, 18, 472-484, herein incorporated by reference in its entirety). miRNA binding sites from any endothelial cell specific miRNA can be introduced to or removed from a polynucleotide of the invention to regulate expression of the polynucleotide in the endothelial cells.

miRNAs that are known to be expressed in epithelial cells include, but are not limited to, let-7b-3p, let-7b-5p, miR-1246, miR-200a-3p, miR-200a-5p, miR-200b-3p, miR-200b-5p, miR-200c-3p, miR-200c-5p, miR-338-3p, miR-429, miR-451a, miR-451b, miR-494, miR-802 and miR-34a, miR-34b-5p, miR-34c-5p, miR-449a, miR-449b-3p, miR-449b-5p specific in respiratory ciliated epithelial cells, let-7 family, miR-133a, miR-133b, miR-126 specific in lung epithelial cells, miR-382-3p, miR-382-5p specific in renal epithelial cells, and miR-762 specific in corneal epithelial cells. miRNA binding sites from any epithelial cell specific miRNA can be introduced to or removed from a polynucleotide of the invention to regulate expression of the polynucleotide in the epithelial cells.

In addition, a large group of miRNAs are enriched in embryonic stem cells, controlling stem cell self-renewal as well as the development and/or differentiation of various cell lineages, such as neural cells, cardiac, hematopoietic cells, skin cells, osteogenic cells and muscle cells (e.g., Kuppusamy K T et al., Curr. Mol Med, 2013, 13(5), 757-764; Vidigal J A and Ventura A, Semin Cancer Biol. 2012, 22(5-6), 428-436; Goff L A et al., PLoS One, 2009, 4:e7192; Morin R D et al., Genome Res, 2008,18, 610-621; Yoo J K et al., Stem Cells Dev. 2012, 21(11), 2049-2057, each of which is herein incorporated by reference in its entirety). miRNAs abundant in embryonic stem cells include, but are not limited to, let-7a-2-3p, let-a-3p, let-7a-5p, let7d-3p, let-7d-5p, miR-103a-2-3p, miR-103a-5p, miR-106b-3p, miR-106b-5p, miR-1246, miR-1275, miR-138-1-3p, miR-138-2-3p, miR-138-5p, miR-154-3p, miR-154-5p, miR-200c-3p, miR-200c-5p, miR-290, miR-301a-3p, miR-301a-5p, miR-302a-3p, miR-302a-5p, miR-302b-3p, miR-302b-5p, miR-302c-3p, miR-302c-5p, miR-302d-3p, miR-302d-5p, miR-302e, miR-367-3p, miR-367-5p, miR-369-3p, miR-369-5p, miR-370, miR-371, miR-373, miR-380-5p, miR-423-3p, miR-423-5p, miR-486-5p, miR-520c-3p, miR-548e, miR-548f, miR-548g-3p, miR-548g-5p, miR-548i, miR-548k, miR-548l, miR-548m, miR-548n, miR-548o-3p, miR-548o-5p, miR-548p, miR-664a-3p, miR-664a-5p, miR-664b-3p, miR-664b-5p, miR-766-3p, miR-766-5p, miR-885-3p, miR-885-5p, miR-93-3p, miR-93-5p, miR-941, miR-96-3p, miR-96-5p, miR-99b-3p and miR-99b-5p. Many predicted novel miRNAs are discovered by deep sequencing in human embryonic stem cells (e.g., Morin R D et al., Genome Res, 2008,18, 610-621; Goff L A et al., PLoS One, 2009, 4:e7192; Bar M et al., Stem cells, 2008, 26, 2496-2505, the content of each of which is incorporated herein by reference in its entirety).

In some embodiments, miRNAs are selected based on expression and abundance in immune cells of the hematopoietic lineage, such as B cells, T cells, macrophages, dendritic cells, and cells that are known to express TLR7/TLR8 and/or able to secrete cytokines such as endothelial cells and platelets. In some embodiments, the miRNA set thus includes miRs that may be responsible in part for the immunogenicity of these cells, and such that a corresponding miR-site incorporation in polynucleotides of the present invention (e.g., mRNAs) could lead to destabilization of the mRNA and/or suppression of translation from these mRNAs in the specific cell type. Non-limiting representative examples include miR-142, miR-144, miR-150, miR-155 and miR-223, which are specific for many of the hematopoietic cells; miR-142, miR150, miR-16 and miR-223, which are expressed in B cells; miR-223, miR-451, miR-26a, miR-16, which are expressed in progenitor hematopoietic cells; and miR-126, which is expressed in plasmacytoid dendritic cells, platelets and endothelial cells. For further discussion of tissue expression of miRs see e.g., Teruel-Montoya, R. et al. (2014) *PLoS One* 9:e102259; Landgraf, P. et al. (2007) *Cell* 129:1401-1414; Bissels, U. et al. (2009) *RNA* 15:2375-2384. Any one miR-site incorporation in the 3' UTR and/or 5' UTR may mediate such effects in multiple cell types of interest (e.g., miR-142 is abundant in both B cells and dendritic cells).

In some embodiments, it may be beneficial to target the same cell type with multiple miRs and to incorporate binding sites to each of the 3p and 5p arm if both are abundant (e.g., both miR-142-3p and miR142-5p are abundant in hematopoietic stem cells). Thus, in certain embodiments, polynucleotides of the invention contain two or more (e.g., two, three, four or more) miR bindings sites from: (i) the group consisting of miR-142, miR-144, miR-150, miR-155 and miR-223 (which are expressed in many hematopoietic cells); or (ii) the group consisting of miR-142, miR150, miR-16 and miR-223 (which are expressed in B cells); or the group consisting of miR-223, miR-451, miR-26a, miR-16 (which are expressed in progenitor hematopoietic cells).

In some embodiments, it may also be beneficial to combine various miRs such that multiple cell types of interest are targeted at the same time (e.g., miR-142 and miR-126 to target many cells of the hematopoietic lineage and endothelial cells). Thus, for example, in certain embodiments, polynucleotides of the invention comprise two or more (e.g., two, three, four or more) miRNA bindings sites, wherein: (i) at least one of the miRs targets cells of the hematopoietic lineage (e.g., miR-142, miR-144, miR-150, miR-155 or miR-223) and at least one of the miRs targets plasmacytoid dendritic cells, platelets or endothelial cells (e.g., miR-126); or (ii) at least one of the miRs targets B cells (e.g., miR-142, miR150, miR-16 or miR-223) and at least one of the miRs targets plasmacytoid dendritic cells, platelets or endothelial cells (e.g., miR-126); or (iii) at least one of the miRs targets progenitor hematopoietic cells (e.g., miR-223, miR-451, miR-26a or miR-16) and at least one of the miRs targets plasmacytoid dendritic cells, platelets or endothelial cells (e.g., miR-126); or (iv) at least one of the miRs targets cells of the hematopoietic lineage (e.g., miR-142, miR-144, miR-150, miR-155 or miR-223), at least one of the miRs targets B cells (e.g., miR-142, miR150, miR-16 or miR-223) and at least one of the miRs targets plasmacytoid dendritic cells, platelets or endothelial cells (e.g., miR-126); or any other possible combination of the foregoing four classes of miR binding sites (i.e., those targeting the hematopoietic lineage, those targeting B cells, those targeting progenitor hematopoietic cells and/or those targeting plasmacytoid dendritic cells/platelets/endothelial cells).

In one embodiment, to modulate immune responses, polynucleotides of the present invention can comprise one or more miRNA binding sequences that bind to one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells). It has now been discovered that incorporation into an mRNA of one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells) reduces or inhibits immune cell activation (e.g., B cell activation, as measured by frequency of activated B cells) and/or cytokine production (e.g., production of IL-6, IFN-γ and/or TNFα). Furthermore, it has now been discovered that incorporation into an mRNA of one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells) can reduce or inhibit an anti-drug antibody (ADA) response against a protein of interest encoded by the mRNA.

In another embodiment, to modulate accelerated blood clearance of a polynucleotide delivered in a lipid-comprising compound or composition, polynucleotides of the invention can comprise one or more miR binding sequences that bind to one or more miRNAs expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells). It has now been discovered that incorporation into an mRNA of one or more miR binding sites reduces or inhibits accelerated blood clearance (ABC) of the lipid-comprising compound or composition for use in delivering the mRNA. Furthermore, it has now been discovered that incorporation of one or more miR binding sites into an mRNA reduces serum levels of anti-PEG anti-IgM (e.g., reduces or inhibits the acute production of IgMs that recognize polyethylene glycol (PEG) by B cells) and/or reduces or inhibits proliferation and/or activation of plasmacytoid dendritic cells following administration of a lipid-comprising compound or composition comprising the mRNA.

In some embodiments, miR sequences may correspond to any known microRNA expressed in immune cells, including but not limited to those taught in US Publication US2005/0261218 and US Publication US2005/0059005, the contents of which are incorporated herein by reference in their entirety. Non-limiting examples of miRs expressed in immune cells include those expressed in spleen cells, myeloid cells, dendritic cells, plasmacytoid dendritic cells, B cells, T cells and/or macrophages. For example, miR-142-3p, miR-142-5p, miR-16, miR-21, miR-223, miR-24 and miR-27 are expressed in myeloid cells, miR-155 is expressed in dendritic cells, B cells and T cells, miR-146 is upregulated in macrophages upon TLR stimulation and miR-126 is expressed in plasmacytoid dendritic cells. In certain embodiments, the miR(s) is expressed abundantly or preferentially in immune cells. For example, miR-142 (miR-142-3p and/or miR-142-5p), miR-126 (miR-126-3p and/or miR-126-5p), miR-146 (miR-146-3p and/or miR-146-5p) and miR-155 (miR-155-3p and/or miR155-5p) are expressed abundantly in immune cells. These microRNA sequences are known in the art and, thus, one of ordinary skill in the art can readily design binding sequences or target sequences to which these microRNAs will bind based upon Watson-Crick complementarity.

Accordingly, in various embodiments, polynucleotides of the present invention comprise at least one microRNA binding site for a miR selected from the group consisting of miR-142, miR-146, miR-155, miR-126, miR-16, miR-21, miR-223, miR-24 and miR-27. In another embodiment, the mRNA comprises at least two miR binding sites for microRNAs expressed in immune cells. In various embodiments, the polynucleotide of the invention comprises 1-4, one, two, three or four miR binding sites for microRNAs expressed in immune cells. In another embodiment, the polynucleotide of the invention comprises three miR binding sites. These miR binding sites can be for microRNAs selected from the group consisting of miR-142, miR-146, miR-155, miR-126, miR-16, miR-21, miR-223, miR-24, miR-27, and combinations thereof. In one embodiment, the polynucleotide of the invention comprises two or more (e.g., two, three, four) copies of the same miR binding site expressed in immune cells, e.g., two or more copies of a miR binding site selected from the group of miRs consisting of miR-142, miR-146, miR-155, miR-126, miR-16, miR-21, miR-223, miR-24, miR-27.

In one embodiment, the polynucleotide of the invention comprises three copies of the same miRNA binding site. In certain embodiments, use of three copies of the same miR binding site can exhibit beneficial properties as compared to use of a single miRNA binding site. Non-limiting examples of sequences for 3' UTRs containing three miRNA bindings sites are shown in SEQ ID NO: 155 (three miR-142-3p binding sites) and SEQ ID NO: 157 (three miR-142-5p binding sites).

In another embodiment, the polynucleotide of the invention comprises two or more (e.g., two, three, four) copies of at least two different miR binding sites expressed in immune cells. Non-limiting examples of sequences of 3' UTRs containing two or more different miR binding sites are shown in SEQ ID NO: 111 (one miR-142-3p binding site and one miR-126-3p binding site), SEQ ID NO: 158 (two miR-142-5p binding sites and one miR-142-3p binding sites), and SEQ ID NO: 161 (two miR-155-5p binding sites and one miR-142-3p binding sites).

In another embodiment, the polynucleotide of the invention comprises at least two miR binding sites for microRNAs expressed in immune cells, wherein one of the miR binding sites is for miR-142-3p. In various embodiments, the polynucleotide of the invention comprises binding sites for miR-142-3p and miR-155 (miR-155-3p or miR-155-5p), miR-142-3p and miR-146 (miR-146-3 or miR-146-5p), or miR-142-3p and miR-126 (miR-126-3p or miR-126-5p).

In another embodiment, the polynucleotide of the invention comprises at least two miR binding sites for microRNAs expressed in immune cells, wherein one of the miR binding sites is for miR-126-3p. In various embodiments, the polynucleotide of the invention comprises binding sites for miR-126-3p and miR-155 (miR-155-3p or miR-155-5p), miR-126-3p and miR-146 (miR-146-3p or miR-146-5p), or miR-126-3p and miR-142 (miR-142-3p or miR-142-5p).

In another embodiment, the polynucleotide of the invention comprises at least two miR binding sites for microRNAs expressed in immune cells, wherein one of the miR binding sites is for miR-142-5p. In various embodiments, the polynucleotide of the invention comprises binding sites for miR-142-5p and miR-155 (miR-155-3p or miR-155-5p), miR-142-5p and miR-146 (miR-146-3 or miR-146-5p), or miR-142-5p and miR-126 (miR-126-3p or miR-126-5p).

In yet another embodiment, the polynucleotide of the invention comprises at least two miR binding sites for microRNAs expressed in immune cells, wherein one of the miR binding sites is for miR-155-5p. In various embodiments, the polynucleotide of the invention comprises binding sites for miR-155-5p and miR-142 (miR-142-3p or miR-142-5p), miR-155-5p and miR-146 (miR-146-3 or miR-146-5p), or miR-155-5p and miR-126 (miR-126-3p or miR-126-5p).

miRNA can also regulate complex biological processes such as angiogenesis (e.g., miR-132) (Anand and Cheresh Curr Opin Hematol 2011 18:171-176). In the polynucleotides of the invention, miRNA binding sites that are involved in such processes can be removed or introduced, in order to tailor the expression of the polynucleotides to biologically relevant cell types or relevant biological processes. In this context, the polynucleotides of the invention are defined as auxotrophic polynucleotides.

In some embodiments, a polynucleotide of the invention comprises a miRNA binding site, wherein the miRNA binding site comprises one or more nucleotide sequences selected from Table 3, including one or more copies of any one or more of the miRNA binding site sequences. In some embodiments, a polynucleotide of the invention further comprises at least one, two, three, four, five, six, seven, eight, nine, ten, or more of the same or different miRNA binding sites selected from Table 3, including any combination thereof.

In some embodiments, the miRNA binding site binds to miR-142 or is complementary to miR-142. In some embodiments, the miR-142 comprises SEQ ID NO: 114. In some embodiments, the miRNA binding site binds to miR-142-3p or miR-142-5p. In some embodiments, the miR-142-3p binding site comprises SEQ ID NO:116. In some embodiments, the miR-142-5p binding site comprises SEQ ID NO:118. In some embodiments, the miRNA binding site comprises a nucleotide sequence at least 80%, at least 85%, at least 90%, at least 95%, or 100% identical to SEQ ID NO:116 or SEQ ID NO:118.

In some embodiments, the miRNA binding site binds to miR-126 or is complementary to miR-126. In some embodiments, the miR-126 comprises SEQ ID NO: 119. In some embodiments, the miRNA binding site binds to miR-126-3p or miR-126-5p. In some embodiments, the miR-126-3p binding site comprises SEQ ID NO: 121. In some embodiments, the miR-126-5p binding site comprises SEQ ID NO: 123. In some embodiments, the miRNA binding site comprises a nucleotide sequence at least 80%, at least 85%, at least 90%, at least 95%, or 100% identical to SEQ ID NO: 121 or SEQ ID NO: 123.

In one embodiment, the 3' UTR comprises two miRNA binding sites, wherein a first miRNA binding site binds to miR-142 and a second miRNA binding site binds to miR-126. In a specific embodiment, the 3' UTR binding to miR-142 and miR-126 comprises, consists, or consists essentially of the sequence of SEQ ID NO:98 or 105.

binding site is inserted in at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, or at least about 100 nucleotides downstream from the stop codon of an ORF in a polynucleotide of the invention. In some embodiments, a miRNA binding site is inserted in about 10 nucleotides to about 100 nucleotides, about 20 nucleotides to about 90 nucleotides, about 30 nucleotides to about 80 nucleotides, about 40 nucleotides to about 70 nucleotides, about 50 nucleotides to about 60 nucleotides, about 45 nucleotides to about 65 nucleotides downstream from the stop codon of an ORF in a polynucleotide of the invention.

In some embodiments, a miRNA binding site is inserted within the 3' UTR immediately following the stop codon of

TABLE 3

| SEQ ID NO. | Description | Sequence |
| --- | --- | --- |
| 114 | miR-142 | GACAGUGCAGUCACCCAUAAAGUAGAAAGCACUACUAA CAGCACUGGAGGGUGUAGUGUUUCCUACUUUAUGGAUG AGUGUACUGUG |
| 115 | miR-142-3p | UGUAGUGUUUCCUACUUUAUGGA |
| 116 | miR-142-3p binding site | UCCAUAAAGUAGGAAACACUACA |
| 117 | miR-142-5p | CAUAAAGUAGAAAGCACUACU |
| 118 | miR-142-5p binding site | AGUAGUGCUUUCUACUUUAUG |
| 119 | miR-126 | CGCUGGCGACGGGACAUUAUUACUUUUGGUACGCGCUG UGACACUUCAAACUCGUACCGUGAGUAAUAAUGCGCCG UCCACGGCA |
| 120 | miR-126-3p | UCGUACCGUGAGUAAUAAUGCG |
| 121 | miR-126-3p binding site | CGCAUUAUUACUCACGGUACGA |
| 122 | miR-126-5p | CAUUAUUACUUUUGGUACGCG |
| 123 | miR-126-5p binding site | CGCGUACCAAAAGUAAUAAUG |

In some embodiments, a miRNA binding site is inserted in the polynucleotide of the invention in any position of the polynucleotide (e.g., the 5' UTR and/or 3' UTR). In some embodiments, the 5' UTR comprises a miRNA binding site. In some embodiments, the 3' UTR comprises a miRNA binding site. In some embodiments, the 5' UTR and the 3' UTR comprise a miRNA binding site. The insertion site in the polynucleotide can be anywhere in the polynucleotide as long as the insertion of the miRNA binding site in the polynucleotide does not interfere with the translation of a functional polypeptide in the absence of the corresponding miRNA; and in the presence of the miRNA, the insertion of the miRNA binding site in the polynucleotide and the binding of the miRNA binding site to the corresponding miRNA are capable of degrading the polynucleotide or preventing the translation of the polynucleotide.

In some embodiments, a miRNA binding site is inserted in at least about 30 nucleotides downstream from the stop codon of an ORF in a polynucleotide of the invention comprising the ORF. In some embodiments, a miRNA the coding region within the polynucleotide of the invention, e.g., mRNA. In some embodiments, if there are multiple copies of a stop codon in the construct, a miRNA binding site is inserted immediately following the final stop codon. In some embodiments, a miRNA binding site is inserted further downstream of the stop codon, in which case there are 3' UTR bases between the stop codon and the miR binding site(s). In some embodiments, three non-limiting examples of possible insertion sites for a miR in a 3' UTR are shown in SEQ ID NOs: 104, 105, and 164, which show a 3' UTR sequence with a miR-142-3p site inserted in one of three different possible insertion sites, respectively, within the 3' UTR.

In some embodiments, one or more miRNA binding sites can be positioned within the 5' UTR at one or more possible insertion sites. For example, three non-limiting examples of possible insertion sites for a miR in a 5' UTR are shown in SEQ ID NOs: 165, 166, and 167, which show a 5' UTR sequence with a miR-142-3p site inserted into one of three different possible insertion sites, respectively, within the 5' UTR.

In one embodiment, a codon optimized open reading frame encoding a polypeptide of interest comprises a stop codon and the at least one microRNA binding site is located within the 3' UTR 1-100 nucleotides after the stop codon. In one embodiment, the codon optimized open reading frame encoding the polypeptide of interest comprises a stop codon and the at least one microRNA binding site for a miR expressed in immune cells is located within the 3' UTR 30-50 nucleotides after the stop codon. In another embodiment, the codon optimized open reading frame encoding the polypeptide of interest comprises a stop codon and the at least one microRNA binding site for a miR expressed in immune cells is located within the 3' UTR at least 50 nucleotides after the stop codon. In other embodiments, the codon optimized open reading frame encoding the polypeptide of interest comprises a stop codon and the at least one microRNA binding site for a miR expressed in immune cells is located within the 3' UTR immediately after the stop codon, or within the 3' UTR 15-20 nucleotides after the stop codon or within the 3' UTR 70-80 nucleotides after the stop codon. In other embodiments, the 3' UTR comprises more than one miRNA binding site (e.g., 2-4 miRNA binding sites), wherein there can be a spacer region (e.g., of 10-100, 20-70 or 30-50 nucleotides in length) between each miRNA binding site. In another embodiment, the 3' UTR comprises a spacer region between the end of the miRNA binding site(s) and the poly A tail nucleotides. For example, a spacer region of 10-100, 20-70 or 30-50 nucleotides in length can be situated between the end of the miRNA binding site(s) and the beginning of the poly A tail.

In one embodiment, a codon optimized open reading frame encoding a polypeptide of interest comprises a start codon and the at least one microRNA binding site is located within the 5' UTR 1-100 nucleotides before (upstream of) the start codon. In one embodiment, the codon optimized open reading frame encoding the polypeptide of interest comprises a start codon and the at least one microRNA binding site for a miR expressed in immune cells is located within the 5' UTR 10-50 nucleotides before (upstream of) the start codon. In another embodiment, the codon optimized open reading frame encoding the polypeptide of interest comprises a start codon and the at least one microRNA binding site for a miR expressed in immune cells is located within the 5' UTR at least 25 nucleotides before (upstream of) the start codon. In other embodiments, the codon optimized open reading frame encoding the polypeptide of interest comprises a start codon and the at least one microRNA binding site for a miR expressed in immune cells is located within the 5' UTR immediately before the start codon, or within the 5' UTR 15-20 nucleotides before the start codon or within the 5' UTR 70-80 nucleotides before the start codon. In other embodiments, the 5' UTR comprises more than one miRNA binding site (e.g., 2-4 miRNA binding sites), wherein there can be a spacer region (e.g., of 10-100, 20-70 or 30-50 nucleotides in length) between each miRNA binding site.

In one embodiment, the 3' UTR comprises more than one stop codon, wherein at least one miRNA binding site is positioned downstream of the stop codons. For example, a 3' UTR can comprise 1, 2 or 3 stop codons. Non-limiting examples of triple stop codons that can be used include: UGAUAAUAG (SEQ ID NO:124), UGAUAGUAA (SEQ ID NO:125), UAAUGAUAG (SEQ ID NO:126), UGAUAAUAA (SEQ ID NO:127), UGAUAGUAG (SEQ ID NO:128), UAAUGAUGA (SEQ ID NO:129), UAAU-AGUAG (SEQ ID NO:130), UGAUGAUGA (SEQ ID NO:131), UAAUAAUAA (SEQ ID NO:132), and UAGU-AGUAG (SEQ ID NO:133). Within a 3' UTR, for example, 1, 2, 3 or 4 miRNA binding sites, e.g., miR-142-3p binding sites, can be positioned immediately adjacent to the stop codon(s) or at any number of nucleotides downstream of the final stop codon. When the 3' UTR comprises multiple miRNA binding sites, these binding sites can be positioned directly next to each other in the construct (i.e., one after the other) or, alternatively, spacer nucleotides can be positioned between each binding site.

In one embodiment, the 3' UTR comprises three stop codons with a single miR-142-3p binding site located downstream of the 3rd stop codon. Non-limiting examples of sequences of 3' UTR having three stop codons and a single miR-142-3p binding site located at different positions downstream of the final stop codon are shown in SEQ ID NOs: 109, 104, 105, and 164.

TABLE 4A

| 5' UTRs, 3'UTRs, miR sequences, and miR binding sites | |
|---|---|
| SEQ ID NO: | Sequence |
| 134 | GCUGGAGCCUCGGUGGCCAUGCUUCUUGCCCCUUGGGCCUCCCCCCAGCCCC UCCUCCCCUUCCUGCACCCGUACCCCCUCCAUAAAGUAGGAAACACUACAGU GGUCUUUGAAUAAAGUCUGAGUGGGCGGC (3' UTR with miR 142-3p binding site) |
| 116 | UCCAUAAAGUAGGAAACACUACA (miR 142-3p binding site) |
| 115 | UGUAGUGUUUCCUACUUUAUGGA (miR 142-3p sequence) |
| 117 | CAUAAAGUAGAAAGCACUACU (miR 142-5p sequence) |
| 135 | CCUCUGAAAUUCAGUUCUUCAG (miR 146-3p sequence) |
| 136 | UGAGAACUGAAUUCCAUGGGUU (miR 146-5p sequence) |
| 137 | CUCCUACAUAUUAGCAUUAACA (miR 155-3p sequence) |

TABLE 4A-continued

| 5' UTRs, 3'UTRs, miR sequences, and miR binding sites |
| --- |

| SEQ ID NO: | Sequence |
| --- | --- |
| 138 | UUAAUGCUAAUCGUGAUAGGGGU<br>(miR 155-5p sequence) |
| 120 | UCGUACCGUGAGUAAUAAUGCG<br>(miR 126-3p sequence) |
| 122 | CAUUAUUACUUUUGGUACGCG<br>(miR 126-5p sequence) |
| 139 | CCAGUAUUAACUGUGCUGCUGA<br>(miR 16-3p sequence) |
| 140 | UAGCAGCACGUAAAUAUUGGCG<br>(miR 16-5p sequence) |
| 141 | CAACACCAGUCGAUGGGCUGU<br>(miR 21-3p sequence) |
| 142 | UAGCUUAUCAGACUGAUGUUGA<br>(miR 21-5p sequence) |
| 143 | UGUCAGUUUGUCAAAUACCCCA<br>(miR 223-3p sequence) |
| 144 | CGUGUAUUUGACAAGCUGAGUU<br>(miR 223-5p sequence) |
| 145 | UGGCUCAGUUCAGCAGGAACAG<br>(miR 24-3p sequence) |
| 146 | UGCCUACUGAGCUGAUAUCAGU<br>(miR 24-5p sequence) |
| 147 | UUCACAGUGGCUAAGUUCCGC<br>(miR 27-3p sequence) |
| 148 | AGGGCUUAGCUGCUUGUGAGCA<br>(miR 27-5p sequence) |
| 121 | CGCAUUAUUACUCACGGUACGA<br>(miR 126-3p binding site) |
| 149 | UGAUAAUAGGCUGGAGCCUCGGUGGCCAUGCUUCUUGCCCCUUGGGCCUCCC<br>CCCAGCCCCUCCUCCCCUUCCUGCACCCGUACCCCC<u>CGCAUUAUUACUCACG<br>GUACGA</u>GUGGUCUUUGAAUAAAGUCUGAGUGGGCGGC<br>(3' UTR with miR 126-3p binding site) |
| 150 | UGAUAAUAGGCUGGAGCCUCGGUGGCCAUGCUUCUUGCCCCUUGGGCCUCCC<br>CCCAGCCCCUCCUCCCCUUCCUGCACCCGUACCCCCGUGGUCUUUGAAUAAA<br>GUCUGAGUGGGCGGC<br>(3' UTR, no miR binding sites) |
| 109 | UGAUAAUAGGCUGGAGCCUCGGUGGCCAUGCUUCUUGCCCCUUGGGCCUCCC<br>CCCAGCCCCUCCUCCCCUUCCUGCACCCGUACCCCC<u>UCCAUAAAGUAGGAAA<br>CACUACAGUGGUCUUUGAAUAAAGUCUGAGUGGGCGGC</u><br>(3' UTR with miR 142-3p binding site) |
| 111 | UGAUAAUAGU<u>CCAUAAAGUAGGAAACACUAC</u>AGCUGGAGCCUCGGUGGCCAU<br>GCUUCUUGCCCCUUGGGCCUCCCCCCAGCCCCUCCUCCCCUUCCUGCACCCG<br>UACCCC<u>CGCAUUAUUACUCACGGUACGA</u>GUGGUCUUUGAAUAAAGUCUGAG<br>UGGGCGGC<br>(3' UTR with miR 142-3p and miR 126-3p binding sites variant 1) |
| 153 | UUAAUGCUAAUUGUGAUAGGGGU<br>(miR 155-5p sequence) |
| 154 | ACCCCUAUCACAAUUAGCAUUAA<br>(miR 155-5p binding site) |
| 155 | UGAUAAUAGU<u>CCAUAAAGUAGGAAACACUAC</u>AGCUGGAGCCUCGGUGGCCAU<br>GCUUCUUGCCCCUUGGGCCUCC<u>AUAAAGUAGGAAACACUACAUCCCCCC</u>AGC<br>CCCUCCUCCCCUUCCUGCACCCGUACCCCC<u>UCCAUAAAGUAGGAAACACUAC<br>A</u>GUGGUCUUUGAAUAAAGUCUGAGUGGGCGGC<br>(3' UTR with 3 miR 142-3p binding sites) |

TABLE 4A-continued

5' UTRs, 3'UTRs, miR sequences, and miR binding sites

| SEQ ID NO: | Sequence |
|---|---|

156    UGAUAAUAGGCUGGAGCCUCGGUGGCCAUGCUUCUUGCCCCUUGGGCCUCCC
CCCAGCCCCUCCUCCCCUUCCUGCACCCGUACCCCAGUAGUGCUUUCUACU
<u>UUAUG</u>GUGGUCUUUGAAUAAAGUCUGAGUGGGCGGC
(3' UTR with miR 142-5p binding site)

157    UGAUAAUAG<u>AGUAGUGCUUUCUACUUUAUG</u>GCUGGAGCCUCGGUGGCCAUGC
UUCUUGCCCCUUGGGCC<u>AGUAGUGCUUUCUACUUUAUG</u>UCCCCCCAGCCCCU
CCUCCCCUUCCUGCACCCGUACCCC<u>AGUAGUGCUUUCUACUUUAUG</u>GUGGU
CUUUGAAUAAAGUCUGAGUGGGCGGC
(3' UTR with 3 miR 142-5p binding sites)

158    UGAUAAUAG<u>AGUAGUGCUUUCUACUUUAUG</u>GCUGGAGCCUCGGUGGCCAUGC
UUCUUGCCCCUUGGGCC<u>UCCAUAAAGUAGGAAACACUAC</u>AUCCCCCCAGCCC
CUCCUCCCCUUCCUGCACCCGUACCC<u>AGUAGUGCUUUCUACUUUAUG</u>GUG
GUCUUUGAAUAAAGUCUGAGUGGGCGGC
(3' UTR with 2 miR 142-5p binding sites and 1 miR 142-3p binding site)

159    UGAUAAUAGGCUGGAGCCUCGGUGGCCAUGCUUCUUGCCCCUUGGGCCUCCC
CCCAGCCCCUCCUCCCCUUCCUGCACCCGUACCCCC<u>ACCCCUAUCACAAUUA</u>
<u>GCAUUAA</u>GUGGUCUUUGAAUAAAGUCUGAGUGGGCGGC
(3' UTR with miR 155-5p binding site)

160    UGAUAAUAG<u>ACCCCUAUCACAAUUAGCAUUAAG</u>CUGGAGCCUCGGUGGCCAU
GCUUCUUGCCCCUUGGGCC<u>ACCCCUAUCACAAUUAGCAUUAA</u>UCCCCCCAGC
CCCUCCUCCCCUUCCUGCACCCGUACCCCC<u>ACCCCUAUCACAAUUAGCAUUA</u>
<u>A</u>GUGGUCUUUGAAUAAAGUCUGAGUGGGCGGC
(3' UTR with 3 miR 155-5p binding sites)

161    UGAUAAUAG<u>ACCCCUAUCACAAUUAGCAUUAAG</u>CUGGAGCCUCGGUGGCCAU
GCUUCUUGCCCCUUGGGCC<u>UCCAUAAAGUAGGAAACACUAC</u>AUCCCCCCAGC
CCCUCCUCCCCUUCCUGCACCCGUACCCCC<u>ACCCCUAUCACAAUUAGCAUUA</u>
<u>A</u>GUGGUCUUUGAAUAAAGUCUGAGUGGGCGGC
(3' UTR with 2 miR 155-5p binding sites and 1 miR 142-3p binding site)

104    UGAUAAUAG<u>UCCAUAAAGUAGGAAACACUAC</u>AGCUGGAGCCUCGGUGGCCAU
GCUUCUUGCCCCUUGGGCCUCCCCCCAGCCCCUCCUCCCCUUCCUGCACCCG
UACCCCCGUGGUCUUUGAAUAAAGUCUGAGUGGGCGGC
(3' UTR with miR 142-3p binding site, P1 insertion)

105    UGAUAAUAGGCUGGAGCCUCGGUGGC<u>UCCAUAAAGUAGGAAACACUAC</u>ACAU
GCUUCUUGCCCCUUGGGCCUCCCCCC<u>AGCCCCUCCUCCCCUUCCUGCACCCG</u>
UACCCCCGUGGUCUUUGAAUAAAGUCUGAGUGGGCGGC
(3' UTR with miR 142-3p binding site, P2 insertion)

164    UGAUAAUAGGCUGGAGCCUCGGUGGCCAUGCUUCUUGCCCCUUGGGCC<u>UCCA</u>
<u>UAAAGUAGGAAACACUAC</u>AUCCCCCCAGCCCCUCCUCCCCUUCCUGCACCCG
UACCCCCGUGGUCUUUGAAUAAAGUCUGAGUGGGCGGC
(3' UTR with miR 142-3p binding site, P3 insertion)

118    AGUAGUGCUUUCUACUUUAUG
(miR-142-5p binding site)

114    GACAGUGCAGUCACCCAUAAAGUAGAAAGCACUACUAACAGCACUGGAGGGU
GUAGUGUUUCCUACUUUAUGGAUGAGUGUACUGUG
(miR-142)

3    GGGAAAUAAGAGAGAAAAGAAGAGUAAGAAGAAAUAUAAGAGCCACC
(5' UTR)

165    GGGAAAUAAGAG<u>UCCAUAAAGUAGGAAACACUAC</u>AAGAAAAGAAGAGUAAGA
AGAAAUAUAAGAGCCACC
(5' UTR with miR142-3p binding site at position p1)

166    GGGAAAUAAGAGAGAAAAGAAGAGUAA<u>UCCAUAAAGUAGGAAACACUAC</u>AGA
AGAAAUAUAAGAGCCACC
(5' UTR with miR142-3p binding site at position p2)

167    GGGAAAUAAGAGAGAAAAGAAGAGUAAGAAGAAAUAUAA<u>UCCAUAAAGUAGG</u>
<u>AAACACUAC</u>AGAGCCACC
(5' UTR with miR142-3p binding site at position p3)

TABLE 4A-continued

5' UTRs, 3'UTRs, miR sequences, and miR binding sites

SEQ ID NO:      Sequence

169     UGAUAAUAG<u>AGUAGUGCUUUCUACUUUAUG</u>GCUGGAGCCUCGGUGGCCAUGC
        UUCUUGCCCCUUGGGCC<u>AGUAGUGCUUUCUACUUUAUG</u>UCCCCCCAGCCCCU
        CUCCCCUUCCUGCACCCGUACCCCC<u>AGUAGUGCUUUCUACUUUAUG</u>GUGGUC
        UUUGAAUAAAGUCUGAGUGGGCGGC
        (3' UTR with 3 miR 142-5p binding sites)

106     UGAUAAUAGGCUGGAGCCUCGGUGGCCAUGCUUCUUGCCCCUUCCAUAAAGU
        <u>AGGAAACACUAC</u>AUGGGCCUCCCCCCAGCCCCUCCUCCCCUU<u>CCUGCACCCG</u>
        UACCCCCGUGGUCUUUGAAUAAAGUCUGAGUGGGCGGC
        (3'UTR including miR142-3p binding site)

107     UGAUAAUAGGCUGGAGCCUCGGUGGCCAUGCUUCUUGCCCCUUGGGCCUCCC
        CCCAGUCCAUAAAGUAGGAAACACUACACCCCUCCUCUCCCCUUCCUGCACCCG
        UACCCCCGUGGUCUUUGAAUAAAGUCUGAGUGGGCGGC
        (3'UTR including miR142-3p binding site)

108     UGAUAAUAGGCUGGAGCCUCGGUGGCCAUGCUUCUUGCCCCUUGGGCCUCCC
        CCCAGCCCCUCCUCCCCUUC<u>UCCAUAAAGUAGGAAACACUACA</u>CUGCACCCG
        UACCCCCGUGGUCUUUGAAUAAAGUCUGAGUGGGCGGC
        (3'UTR including including miR142-3p binding site)

110     UGAUAAUAGGCUGGAGCCUCGGUGGCCAUGCUUCUUGCCCCUUGGGCCUCCC
        CCCAGCCCCUCCUCCCCUUCCUGCACCCGUACCCCCGUGGUCUUUGAAUAAA
        GUUCCAUAAAGUAGGAAACACUACACUGAGUGGGCGGC
        (3'UTR including including miR142-3p binding site)

112     UGAUAAUAGUCCAUAAAGUAGGAAACACUACAGCUGGAGCCUCGGUGGCCUA
        GCUUCUUGCCCCUUGGGCCUCCCCCCAGCCCCUCCUCCCCUUCCUGCACCCG
        UACCCC<u>CGCAUUAUUACUCACGGUACGA</u>GUGGUCUUUGAAUAAAGUCUGAG
        UGGGCGGC
        (3' UTR with miR 142-3p and miR 126-3p binding sites variant 2)

175     UGAUAAUAGGCUGGAGCCUCGGUGGCCUAGCUUCUUGCCCCUUGGGCCUCCC
        CCCAGCCCCUCCUCCCCUUCCUGCACCCGUACCCCCGUGGUCUUUGAAUAAA
        GUCUGAGUGGGCGGC
        (3' UTR, no miR binding sites variant 2)

4       UGAUAAUAGGCUGGAGCCUCGGUGGCCUAGCUUCUUGCCCCUUGGGCCUCCC
        CCCAGCCCCUCCUCCCCUUCCUGCACCCGUACCCCC<u>UCCAUAAAGUAGGAAA</u>
        <u>CACUACA</u>GUGGUCUUUGAAUAAAGUCUGAGUGGGCGGC
        (3' UTR with miR 142-3p binding site variant 3)

177     UGAUAAUAGGCUGGAGCCUCGGUGGCCUAGCUUCUUGCCCCUUGGGCCUCCC
        CCCAGCCCCUCCUCCCCUUCCUGCACCCGUACCCCC<u>CGCAUUAUUACUCACG</u>
        <u>GUACGA</u>GUGGUCUUUGAAUAAAGUCUGAGUGGGCGGC
        (3' UTR with miR 126-3p binding site variant 3)

178     UGAUAAUAGUCCAUAAAGUAGGAAACACUACAGCUGGAGCCUCGGUGGCCUA
        GCUUCUUGCCCCUUGGGCC<u>UCCAUAAAGUAGGAAACACUAC</u>AUCCCCCCAGC
        CCCUCCUCCCCUUCCUGCACCCGUACCCCC<u>UCCAUAAAGUAGGAAACACUAC</u>
        AGUGGUCUUUGAAUAAAGUCUGAGUGGGCGGC
        (3' UTR with 3 miR 142-3p binding sites variant 2)

179     UGAUAAUAGUCCAUAAAGUAGGAAACACUACAGCUGGAGCCUCGGUGGCCUA
        GCUUCUUGCCCCUUGGGCCUCCCCCCAGCCCCUCCUCCCCUUCCUGCACCCG
        UACCCCCGUGGUCUUUGAAUAAAGUCUGAGUGGGCGGC
        (3'UTR with miR 142-3p binding site, P1 insertion variant 2)

180     UGAUAAUAGGCUGGAGCCUCGGUGGCUCCAUAAAGUAGGAAACACUACACUA
        GCUUCUUGCCCCUUGGGCCUCCCCCCAGCCCCUCCUCCCCUUCCUGCACCCG
        UACCCCCGUGGUCUUUGAAUAAAGUCUGAGUGGGCGGC
        (3'UTR with miR 142-3p binding site, P2 insertion variant 2)

181     UGAUAAUAGGCUGGAGCCUCGGUGGCCUAGCUUCUUGCCCCUUGGGCC<u>UCCA</u>
        <u>UAAAGUAGGAAACACUAC</u>AUCCCCCCAGCCCCUCCUCCCCUUCCUGCACCCG
        UACCCCCGUGGUCUUUGAAUAAAGUCUGAGUGGGCGGC
        (3'UTR with miR 142-3p binding site, P3 insertion variant 2)

182     UGAUAAUAGGCUGGAGCCUCGGUGGCCUAGCUUCUUGCCCCUUGGGCCUCCC
        CCCAGCCCCUCCUCCCCUUCCUGCACCCGUACCCCC<u>ACCCCUAUCACAAUUA</u>
        <u>GCAUUAA</u>GUGGUCUUUGAAUAAAGUCUGAGUGGGCGGC
        (3'UTR with miR 155-5p binding site variant 2)

TABLE 4A-continued

| 5' UTRs, 3'UTRs, miR sequences, and miR binding sites | |
|---|---|
| SEQ ID NO: | Sequence |
| 183 | UGAUAAUAGACCCCUAUCACAAUUAGCAUUAAGCUGGAGCCUCGGUGGCCUA GCUUCUUGCCCCUUGGGCCACCCCUAUCACAAUUAGCAUUAAUCCCCCCAGC CCCUCCUCCCCUUCCUGCACCCGUACCCCCACCCCUAUCACAAUUAGCAUUA AGUGGUCUUUGAAUAAAGUCUGAGUGGGCGGC (3' UTR with 3 miR 155-5p binding sites variant 2) |
| 184 | UGAUAAUAGACCCCUAUCACAAUUAGCAUUAGCUGGAGCCUCGGUGGCCUA GCUUCUUGCCCCUUGGGCCUCCAUAAAGUAGGAAACACUACAUCCCCCCAGC CCCUCCUCCCCUUCCUGCACCCGUACCCCCACCCCUAUCACAAUUAGCAUUA AGUGGUCUUUGAAUAAAGUCUGAGUGGGCGGC (3'UTR with 2 miR 155-5p binding sites and 1 miR 142-3p binding site variant 2) |

Stop codon = bold
miR 142-3p binding site = underline
miR 126-3p binding site = bold underline
miR 155-5p binding site = double underline
miR 142-5p binding site = bold double underline

TABLE 4B

| Exemplary Preferred UTRs | |
|---|---|
| SEQ ID NO: | Sequence |
| 5' UTR (v1) (SEQ ID NO: 3) | GGGAAAUAAGAGAGAAAAGAAGAGUAAGAAGAAAUAUAAGAGCCACC |
| 5'UTR (v1 A) (SEQ ID NO: 199) | AGGAAAUAAGAGAGAAAAGAAGAGUAAGAAGAAAUAUAAGAGCCACC |
| 5' UTR (v1.1) (SEQ ID NO: 191) | GGGAAAUAAGAGAGAAAAGAAGAGUAAGAAGAAAUAUAAGACCCCGGC GCCGCCACC |
| 5' UTR (v1.1 A) (SEQ ID NO: 206) | AGGAAAUAAGAGAGAAAAGAAGAGUAAGAAGAAAUAUAAGACCCCGGC GCCGCCACC |
| 3' UTR (v1) (SEQ ID NO: 150) | UGAUAAUAGGCUGGAGCCUCGGUGGCCAUGCUUCUUGCCCCUUGGGCC UCCCCCCAGCCCCUCCUCCCCUUCCUGCACCCGUACCCCCGUGGUCUU UGAAUAAAGUCUGAGUGGGCGGC |
| 3' UTR (v1.1) (SEQ ID NO: 175) | UGAUAAUAGGCUGGAGCCUCGGUGGCCUAGCUUCUUGCCCCUUGGGCC UCCCCCCAGCCCCUCCUCCCCUUCCUGCACCCGUACCCCCGUGGUCUU UGAAUAAAGUCUGAGUGGGCGGC |
| 3' UTR (miR122) (SEQ ID NO: 207) | UGAUAAUAGGCUGGAGCCUCGGUGGCCAUGCUUCUUGCCCCUUGGGCC UCCCCCCAGCCCCUCCUCCCCUUCCUGCACCCGUACCCCCCAAACACC AUUGUCACACUCCAGUGGUCUUUGAAUAAAGUCUGAGUGGGCGGC |
| 3' UTR (v1.1 miR122) (SEQ ID NO: 208) | UGAUAAUAGGCUGGAGCCUCGGUGGCCUAGCUUCUUGCCCCUUGGGCC UCCCCCCAGCCCCUCCUCCCCUUCCUGCACCCGUACCCCCCAAACACC AUUGUCACACUCCAGUGGUCUUUGAAUAAAGUCUGAGUGGGCGGC |
| 3' UTR (v1.1 mir142-3p) (SEQ ID NO: 4) | UGAUAAUAGGCUGGAGCCUCGGUGGCCUAGCUUCUUGCCCCUUGGGCC UCCCCCCAGCCCCUCCUCCCCUUCCUGCACCCGUACCCCCUCCAUAAA GUAGGAAACACUACAGUGGUCUUUGAAUAAAGUCUGAGUGGGCGGC |
| 3' UTR (v1.1 mir 126-3p) (SEQ ID NO: 177) | UGAUAAUAGGCUGGAGCCUCGGUGGCCUAGCUUCUUGCCCCUUGGGCC UCCCCCCAGCCCCUCCUCCCCUUCCUGCACCCGUACCCCCCGCAUUAU UACUCACGGUACGAGUGGUCUUUGAAUAAAGUCUGAGUGGGCGGC |
| 3' UTR (mir-126, miR-142-3p) (SEQ ID NO: 111) | UGAUAAUAGUCCAUAAAGUAGGAAACACUACAGCUGGAGCCUCGGUGG CCAUGCUUCUUGCCCCUUGGGCCUCCCCCCAGCCCCUCCUCCCCUUCC UGCACCCGUACCCCCCGCAUUAUUACUCACGGUACGAGUGGUCUUUGA AUAAAGUCUGAGUGGGCGGC |
| 3' UTR (v.1.1 3x mir142-3p) (SEQ ID NO: 178) | UGAUAAUAGUCCAUAAAGUAGGAAACACUACAGCUGGAGCCUCGGUGG CCUAGCUUCUUGCCCCUUGGGCCUCCAUAAAGUAGGAAACACUACAUC CCCCCAGCCCCUCCUCCCCUUCCUGCACCCGUACCCCCUCCAUAAAGU AGGAAACACUACAGUGGUCUUUGAAUAAAGUCUGAGUGGGCGGC |

In one embodiment, the polynucleotide of the invention comprises a 5' UTR, a codon optimized open reading frame encoding a polypeptide of interest, a 3' UTR comprising the at least one miRNA binding site for a miR expressed in immune cells, and a 3' tailing region of linked nucleosides. In various embodiments, the 3' UTR comprises 1-4, at least two, one, two, three or four miRNA binding sites for miRs expressed in immune cells, preferably abundantly or preferentially expressed in immune cells.

In one embodiment, the at least one miRNA expressed in immune cells is a miR-142-3p microRNA binding site. In one embodiment, the miR-142-3p microRNA binding site comprises the sequence shown in SEQ ID NO: 116. In one embodiment, the 3' UTR of the mRNA comprising the miR-142-3p microRNA binding site comprises the sequence shown in SEQ ID NO: 134.

In one embodiment, the at least one miRNA expressed in immune cells is a miR-126 microRNA binding site. In one embodiment, the miR-126 binding site is a miR-126-3p binding site. In one embodiment, the miR-126-3p microRNA binding site comprises the sequence shown in SEQ ID NO: 121. In one embodiment, the 3' UTR of the mRNA of the invention comprising the miR-126-3p microRNA binding site comprises the sequence shown in SEQ ID NO: 149.

Non-limiting exemplary sequences for miRs to which a microRNA binding site(s) of the disclosure can bind include the following: miR-142-3p (SEQ ID NO: 115), miR-142-5p (SEQ ID NO: 117), miR-146-3p (SEQ ID NO: 135), miR-146-5p (SEQ ID NO: 136), miR-155-3p (SEQ ID NO: 137), miR-155-5p (SEQ ID NO: 138), miR-126-3p (SEQ ID NO: 120), miR-126-5p (SEQ ID NO: 122), miR-16-3p (SEQ ID NO: 139), miR-16-5p (SEQ ID NO: 140), miR-21-3p (SEQ ID NO: 141), miR-21-5p (SEQ ID NO: 142), miR-223-3p (SEQ ID NO: 143), miR-223-5p (SEQ ID NO: 144), miR-24-3p (SEQ ID NO: 145), miR-24-5p (SEQ ID NO: 146), miR-27-3p (SEQ ID NO: 147) and miR-27-5p (SEQ ID NO: 148). Other suitable miR sequences expressed in immune cells (e.g., abundantly or preferentially expressed in immune cells) are known and available in the art, for example at the University of Manchester's microRNA database, miRBase. Sites that bind any of the aforementioned miRs can be designed based on Watson-Crick complementarity to the miR, typically 100% complementarity to the miR, and inserted into an mRNA construct of the disclosure as described herein.

In another embodiment, a polynucleotide of the present invention (e.g., and mRNA, e.g., the 3' UTR thereof) can comprise at least one miRNA binding site to thereby reduce or inhibit accelerated blood clearance, for example by reducing or inhibiting production of IgMs, e.g., against PEG, by B cells and/or reducing or inhibiting proliferation and/or activation of pDCs, and can comprise at least one miRNA binding site for modulating tissue expression of an encoded protein of interest.

miRNA gene regulation can be influenced by the sequence surrounding the miRNA such as, but not limited to, the species of the surrounding sequence, the type of sequence (e.g., heterologous, homologous, exogenous, endogenous, or artificial), regulatory elements in the surrounding sequence and/or structural elements in the surrounding sequence. The miRNA can be influenced by the 5'UTR and/or 3'UTR. As a non-limiting example, a non-human 3'UTR can increase the regulatory effect of the miRNA sequence on the expression of a polypeptide of interest compared to a human 3' UTR of the same sequence type.

In one embodiment, other regulatory elements and/or structural elements of the 5' UTR can influence miRNA mediated gene regulation. One example of a regulatory element and/or structural element is a structured IRES (Internal Ribosome Entry Site) in the 5' UTR, which is necessary for the binding of translational elongation factors to initiate protein translation. EIF4A2 binding to this secondarily structured element in the 5'-UTR is necessary for miRNA mediated gene expression (Meijer H A et al., Science, 2013, 340, 82-85, herein incorporated by reference in its entirety). The polynucleotides of the invention can further include this structured 5' UTR in order to enhance microRNA mediated gene regulation.

At least one miRNA binding site can be engineered into the 3' UTR of a polynucleotide of the invention. In this context, at least two, at least three, at least four, at least five, at least six, at least seven, at least eight, at least nine, at least ten, or more miRNA binding sites can be engineered into a 3' UTR of a polynucleotide of the invention. For example, 1 to 10, 1 to 9, 1 to 8, 1 to 7, 1 to 6, 1 to 5, 1 to 4, 1 to 3, 2, or 1 miRNA binding sites can be engineered into the 3'UTR of a polynucleotide of the invention. In one embodiment, miRNA binding sites incorporated into a polynucleotide of the invention can be the same or can be different miRNA sites. A combination of different miRNA binding sites incorporated into a polynucleotide of the invention can include combinations in which more than one copy of any of the different miRNA sites are incorporated. In another embodiment, miRNA binding sites incorporated into a polynucleotide of the invention can target the same or different tissues in the body. As a non-limiting example, through the introduction of tissue-, cell-type-, or disease-specific miRNA binding sites in the 3'-UTR of a polynucleotide of the invention, the degree of expression in specific cell types (e.g., myeloid cells, endothelial cells, etc.) can be reduced.

In one embodiment, a miRNA binding site can be engineered near the 5' terminus of the 3'UTR, about halfway between the 5' terminus and 3' terminus of the 3'UTR and/or near the 3' terminus of the 3' UTR in a polynucleotide of the invention. As a non-limiting example, a miRNA binding site can be engineered near the 5' terminus of the 3'UTR and about halfway between the 5' terminus and 3' terminus of the 3'UTR. As another non-limiting example, a miRNA binding site can be engineered near the 3' terminus of the 3'UTR and about halfway between the 5' terminus and 3' terminus of the 3' UTR. As yet another non-limiting example, a miRNA binding site can be engineered near the 5' terminus of the 3' UTR and near the 3' terminus of the 3' UTR.

In another embodiment, a 3'UTR can comprise 1, 2, 3, 4, 5, 6, 7, 8, 9, or 10 miRNA binding sites. The miRNA binding sites can be complementary to a miRNA, miRNA seed sequence, and/or miRNA sequences flanking the seed sequence.

In some embodiments, the expression of a polynucleotide of the invention can be controlled by incorporating at least one sensor sequence in the polynucleotide and formulating the polynucleotide for administration. As a non-limiting example, a polynucleotide of the invention can be targeted to a tissue or cell by incorporating a miRNA binding site and formulating the polynucleotide in a lipid nanoparticle comprising a ionizable lipid, including any of the lipids described herein.

A polynucleotide of the invention can be engineered for more targeted expression in specific tissues, cell types, or biological conditions based on the expression patterns of miRNAs in the different tissues, cell types, or biological conditions. Through introduction of tissue-specific miRNA binding sites, a polynucleotide of the invention can be designed for optimal protein expression in a tissue or cell, or in the context of a biological condition.

In some embodiments, a polynucleotide of the invention can be designed to incorporate miRNA binding sites that either have 100% identity to known miRNA seed sequences or have less than 100% identity to miRNA seed sequences. In some embodiments, a polynucleotide of the invention can be designed to incorporate miRNA binding sites that have at least: 60%, 65%, 70%, 75%, 80%, 85%, 90%, 95%, 96%, 97%, 98%, or 99% identity to known miRNA seed sequences. The miRNA seed sequence can be partially mutated to decrease miRNA binding affinity and as such result in reduced downmodulation of the polynucleotide. In essence, the degree of match or mis-match between the miRNA binding site and the miRNA seed can act as a rheostat to more finely tune the ability of the miRNA to modulate protein expression. In addition, mutation in the non-seed region of a miRNA binding site can also impact the ability of a miRNA to modulate protein expression.

In one embodiment, a miRNA sequence can be incorporated into the loop of a stem loop.

In another embodiment, a miRNA seed sequence can be incorporated in the loop of a stem loop and a miRNA binding site can be incorporated into the 5' or 3' stem of the stem loop.

In one embodiment the miRNA sequence in the 5' UTR can be used to stabilize a polynucleotide of the invention described herein.

In another embodiment, a miRNA sequence in the 5' UTR of a polynucleotide of the invention can be used to decrease the accessibility of the site of translation initiation such as, but not limited to a start codon. See, e.g., Matsuda et al., PLoS One. 2010 11(5):e15057; incorporated herein by reference in its entirety, which used antisense locked nucleic acid (LNA) oligonucleotides and exon-junction complexes (EJCs) around a start codon (−4 to +37 where the A of the AUG codons is +1) in order to decrease the accessibility to the first start codon (AUG). Matsuda showed that altering the sequence around the start codon with an LNA or EJC affected the efficiency, length and structural stability of a polynucleotide. A polynucleotide of the invention can comprise a miRNA sequence, instead of the LNA or EJC sequence described by Matsuda et al, near the site of translation initiation in order to decrease the accessibility to the site of translation initiation. The site of translation initiation can be prior to, after or within the miRNA sequence. As a non-limiting example, the site of translation initiation can be located within a miRNA sequence such as a seed sequence or binding site.

In some embodiments, a polynucleotide of the invention can include at least one miRNA in order to dampen the antigen presentation by antigen presenting cells. The miRNA can be the complete miRNA sequence, the miRNA seed sequence, the miRNA sequence without the seed, or a combination thereof. As a non-limiting example, a miRNA incorporated into a polynucleotide of the invention can be specific to the hematopoietic system. As another non-limiting example, a miRNA incorporated into a polynucleotide of the invention to dampen antigen presentation is miR-142-3p.

In some embodiments, a polynucleotide of the invention can include at least one miRNA in order to dampen expression of the encoded polypeptide in a tissue or cell of interest. As a non-limiting example a polynucleotide of the invention can include at least one miR-142-3p binding site, miR-142-3p seed sequence, miR-142-3p binding site without the seed, miR-142-5p binding site, miR-142-5p seed sequence, miR-142-5p binding site without the seed, miR-146 binding site, miR-146 seed sequence and/or miR-146 binding site without the seed sequence.

In some embodiments, a polynucleotide of the invention can comprise at least one miRNA binding site in the 3'UTR in order to selectively degrade mRNA therapeutics in the immune cells to subdue unwanted immunogenic reactions caused by therapeutic delivery. As a non-limiting example, the miRNA binding site can make a polynucleotide of the invention more unstable in antigen presenting cells. Non-limiting examples of these miRNAs include miR-142-5p, miR-142-3p, miR-146a-5p, and miR-146-3p.

In one embodiment, a polynucleotide of the invention comprises at least one miRNA sequence in a region of the polynucleotide that can interact with a RNA binding protein.

In some embodiments, the polynucleotide of the invention (e.g., a RNA, e.g., an mRNA) comprising (i) a sequence-optimized nucleotide sequence (e.g., an ORF) encoding a PCCA or PCCB polypeptide (e.g., the wild-type sequence, functional fragment, or variant thereof) and (ii) a miRNA binding site (e.g., a miRNA binding site that binds to miR-142) and/or a miRNA binding site that binds to miR-126.

12. 3'UTRs

In certain embodiments, a polynucleotide of the present invention (e.g., a polynucleotide comprising a nucleotide sequence encoding a PCCA or PCCB polypeptide of the invention) further comprises a 3' UTR.

3'-UTR is the section of mRNA that immediately follows the translation termination codon and often contains regulatory regions that post-transcriptionally influence gene expression. Regulatory regions within the 3'-UTR can influence poly adenylation, translation efficiency, localization, and stability of the mRNA. In one embodiment, the 3'-UTR useful for the invention comprises a binding site for regulatory proteins or microRNAs.

In certain embodiments, the 3' UTR useful for the polynucleotides of the invention comprises a 3' UTR selected from the group consisting of SEQ ID NO: 4, 104 to 113, and 178, or any combination thereof. In some embodiments, the 3' UTR comprises a nucleic acid sequence selected from the group consisting of SEQ ID NOs: 111, 112, or 113 or any combination thereof. In certain embodiments, the 3' UTR comprises a 3' UTR selected from the group consisting of SEQ ID NO:4, SEQ ID NO:111, SEQ ID NO:150, SEQ ID NO: 175, SEQ ID NO:177, SEQ ID NO: 178, SEQ ID NO:207, or SEQ ID NO:208, or any combination thereof. In some embodiments, the 3' UTR comprises a nucleic acid sequence of SEQ ID NO: 111. In some embodiments, the 3' UTR comprises a nucleic acid sequence of SEQ ID NO: 112. In some embodiments, the 3' UTR comprises a nucleic acid sequences of SEQ ID NO: 113. In some embodiments, the 3' UTR comprises a nucleic acid sequence of SEQ ID NO: 150. In some embodiments, the 3' UTR comprises a nucleic acid sequence of SEQ ID NO: 175. In some embodiments, the 3' UTR comprises a nucleic acid sequences of SEQ ID NO: 207. In some embodiments, the 3' UTR comprises a nucleic acid sequence of SEQ ID NO: 208. In some embodiments, the 3' UTR comprises a nucleic acid sequence of SEQ ID NO: 4. In some embodiments, the 3' UTR comprises a nucleic acid sequences of SEQ ID NO: 177. In some embodiments, the 3' UTR comprises a nucleic acid sequence of SEQ ID NO: 178.

In certain embodiments, the 3' UTR sequence useful for the invention comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of 3' UTR sequences selected from the group consisting of SEQ ID NOs: 4, 104 to 113, and 178, or any combination thereof.

In certain embodiments, the 3' UTR sequence useful for the invention comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of 3' UTR sequences selected from the group consisting of SEQ ID NO:4, SEQ ID NO:111, SEQ ID NO:150, SEQ ID NO:175, SEQ ID NO:177, SEQ ID NO:178, SEQ ID NO:207, or SEQ ID NO:208, or any combination thereof.

13. Regions Having a 5' Cap

The disclosure also includes a polynucleotide that comprises both a 5' Cap and a polynucleotide of the present invention (e.g., a polynucleotide comprising a nucleotide sequence encoding a PCCA or PCCB polypeptide).

The 5' cap structure of a natural mRNA is involved in nuclear export, increasing mRNA stability and binds the mRNA Cap Binding Protein (CBP), which is responsible for mRNA stability in the cell and translation competency through the association of CBP with poly(A) binding protein to form the mature cyclic mRNA species. The cap further assists the removal of 5' proximal introns during mRNA splicing.

Endogenous mRNA molecules can be 5'-end capped generating a 5'-ppp-5'-triphosphate linkage between a terminal guanosine cap residue and the 5'-terminal transcribed sense nucleotide of the mRNA molecule. This 5'-guanylate cap can then be methylated to generate an N7-methyl-guanylate residue. The ribose sugars of the terminal and/or anteterminal transcribed nucleotides of the 5' end of the mRNA can optionally also be 2'-O-methylated. 5'-decapping through hydrolysis and cleavage of the guanylate cap structure can target a nucleic acid molecule, such as an mRNA molecule, for degradation.

In some embodiments, the polynucleotides of the present invention (e.g., a polynucleotide comprising a nucleotide sequence encoding a PCCA or PCCB polypeptide) incorporate a cap moiety.

In some embodiments, polynucleotides of the present invention (e.g., a polynucleotide comprising a nucleotide sequence encoding a PCCA or PCCB polypeptide) comprise a non-hydrolyzable cap structure preventing decapping and thus increasing mRNA half-life. Because cap structure hydrolysis requires cleavage of 5'-ppp-5' phosphorodiester linkages, modified nucleotides can be used during the capping reaction. For example, a Vaccinia Capping Enzyme from New England Biolabs (Ipswich, MA) can be used with α-thio-guanosine nucleotides according to the manufacturer's instructions to create a phosphorothioate linkage in the 5'-ppp-5' cap. Additional modified guanosine nucleotides can be used such as α-methyl-phosphonate and seleno-phosphate nucleotides.

Additional modifications include, but are not limited to, 2'-O-methylation of the ribose sugars of 5'-terminal and/or 5'-anteterminal nucleotides of the polynucleotide (as mentioned above) on the 2'-hydroxyl group of the sugar ring. Multiple distinct 5'-cap structures can be used to generate the 5'-cap of a nucleic acid molecule, such as a polynucleotide that functions as an mRNA molecule. Cap analogs, which herein are also referred to as synthetic cap analogs, chemical caps, chemical cap analogs, or structural or functional cap analogs, differ from natural (i.e., endogenous, wild-type or physiological) 5'-caps in their chemical structure, while retaining cap function. Cap analogs can be chemically (i.e., non-enzymatically) or enzymatically synthesized and/or linked to the polynucleotides of the invention.

For example, the Anti-Reverse Cap Analog (ARCA) cap contains two guanines linked by a 5'-5'-triphosphate group, wherein one guanine contains an N7 methyl group as well as a 3'-O-methyl group (i.e., N7,3'-O-dimethyl-guanosine-5'-triphosphate-5'-guanosine (m$^7$G-3'mppp-G; which can equivalently be designated 3' O-Me-m7G(5')ppp(5')G). The 3'-O atom of the other, unmodified, guanine becomes linked to the 5'-terminal nucleotide of the capped polynucleotide. The N7- and 3'-O-methlyated guanine provides the terminal moiety of the capped polynucleotide.

Another exemplary cap is mCAP, which is similar to ARCA but has a 2'-O-methyl group on guanosine (i.e., N7,2'-O-dimethyl-guanosine-5'-triphosphate-5'-guanosine, m$^7$Gm-ppp-G).

In some embodiments, the cap is a dinucleotide cap analog. As a non-limiting example, the dinucleotide cap analog can be modified at different phosphate positions with a boranophosphate group or a phosphoroselenoate group such as the dinucleotide cap analogs described in U.S. Pat. No. 8,519,110, the contents of which are herein incorporated by reference in its entirety.

In another embodiment, the cap is a cap analog is a N7-(4-chlorophenoxyethyl) substituted dinucleotide form of a cap analog known in the art and/or described herein. Non-limiting examples of a N7-(4-chlorophenoxyethyl) substituted dinucleotide form of a cap analog include a N7-(4-chlorophenoxyethyl)-G(5')ppp(5')G and a N7-(4-chlorophenoxyethyl)-m$^{3'-O}$G(5')ppp(5')G cap analog (See, e.g., the various cap analogs and the methods of synthesizing cap analogs described in Kore et al. Bioorganic & Medicinal Chemistry 2013 21:4570-4574; the contents of which are herein incorporated by reference in its entirety). In another embodiment, a cap analog of the present invention is a 4-chloro/bromophenoxyethyl analog.

While cap analogs allow for the concomitant capping of a polynucleotide or a region thereof, in an in vitro transcription reaction, up to 20% of transcripts can remain uncapped. This, as well as the structural differences of a cap analog from an endogenous 5'-cap structures of nucleic acids produced by the endogenous, cellular transcription machinery, can lead to reduced translational competency and reduced cellular stability.

Polynucleotides of the invention (e.g., a polynucleotide comprising a nucleotide sequence encoding a PCCA or PCCB polypeptide) can also be capped post-manufacture (whether IVT or chemical synthesis), using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function and/or structure as compared to synthetic features or analogs, etc., of the prior art, or which outperforms the corresponding endogenous, wild-type, natural or physiological feature in one or more respects. Non-limiting examples of more authentic 5'cap structures of the present invention are those that, among other things, have enhanced binding of cap binding proteins, increased half-life, reduced susceptibility to 5' endonucleases and/or reduced 5'decapping, as compared to synthetic 5'cap structures known in the art (or to a wild-type, natural or physiological 5'cap structure). For example, recombinant Vaccinia Virus Capping Enzyme and recombinant 2'-O-methyltransferase enzyme can create a canonical 5'-5'-triphosphate linkage between the 5'-terminal nucleotide of a polynucleotide and a guanine cap nucleotide wherein the cap guanine contains an N7 methylation and the 5'-terminal nucleotide of the mRNA contains a 2'-O-methyl. Such a structure is termed the Cap1 structure. This cap results in a higher translational-competency and cellular stability and a reduced activation of cellular pro-inflammatory cytokines, as compared, e.g., to other 5'cap analog structures known in the art. Cap structures include, but are not limited to, 7mG(5')ppp(5')N, pN2p (cap 0), 7mG(5')ppp (5')NlmpNp (cap 1), and 7mG(5')-ppp(5')NlmpN2mp (cap 2).

As a non-limiting example, capping chimeric polynucleotides post-manufacture can be more efficient as nearly 100% of the chimeric polynucleotides can be capped. This is in contrast to ~80% when a cap analog is linked to a chimeric polynucleotide in the course of an in vitro transcription reaction.

According to the present invention, 5' terminal caps can include endogenous caps or cap analogs. According to the present invention, a 5' terminal cap can comprise a guanine analog. Useful guanine analogs include, but are not limited to, inosine, N1-methyl-guanosine, 2'fluoro-guanosine, 7-deaza-guanosine, 8-oxo-guanosine, 2-amino-guanosine, LNA-guanosine, and 2-azido-guanosine.

14. Poly-A Tails

In some embodiments, the polynucleotides of the present disclosure (e.g., a polynucleotide comprising a nucleotide sequence encoding a PCCA or PCCB polypeptide) further comprise a poly-A tail. In further embodiments, terminal groups on the poly-A tail can be incorporated for stabilization. In other embodiments, a poly-A tail comprises des-3' hydroxyl tails.

During RNA processing, a long chain of adenine nucleotides (poly-A tail) can be added to a polynucleotide such as an mRNA molecule in order to increase stability. Immediately after transcription, the 3' end of the transcript can be cleaved to free a 3' hydroxyl. Then poly-A polymerase adds a chain of adenine nucleotides to the RNA. The process, called polyadenylation, adds a poly-A tail that can be between, for example, approximately 80 to approximately 250 residues long, including approximately 80, 90, 100, 110, 120, 130, 140, 150, 160, 170, 180, 190, 200, 210, 220, 230, 240 or 250 residues long. In one embodiment, the poly-A tail is 100 nucleotides in length.

PolyA tails can also be added after the construct is exported from the nucleus.

According to the present invention, terminal groups on the poly A tail can be incorporated for stabilization. Polynucleotides of the present invention can include des-3' hydroxyl tails. They can also include structural moieties or 2'-Omethyl modifications as taught by Junjie Li, et al. (Current Biology, Vol. 15, 1501-1507, Aug. 23, 2005, the contents of which are incorporated herein by reference in its entirety).

The polynucleotides of the present invention can be designed to encode transcripts with alternative polyA tail structures including histone mRNA. According to Norbury, "Terminal uridylation has also been detected on human replication-dependent histone mRNAs. The turnover of these mRNAs is thought to be important for the prevention of potentially toxic histone accumulation following the completion or inhibition of chromosomal DNA replication. These mRNAs are distinguished by their lack of a 3' poly(A) tail, the function of which is instead assumed by a stable stem-loop structure and its cognate stem-loop binding protein (SLBP); the latter carries out the same functions as those of PABP on polyadenylated mRNAs" (Norbury, "Cytoplasmic RNA: a case of the tail wagging the dog," Nature Reviews Molecular Cell Biology; AOP, published online 29 Aug. 2013; doi:10.1038/nrm3645) the contents of which are incorporated herein by reference in its entirety.

Unique poly-A tail lengths provide certain advantages to the polynucleotides of the present invention. Generally, the length of a poly-A tail, when present, is greater than 30 nucleotides in length. In another embodiment, the poly-A tail is greater than 35 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000 nucleotides).

In some embodiments, the polynucleotide or region thereof includes from about 30 to about 3,000 nucleotides (e.g., from 30 to 50, from 30 to 100, from 30 to 250, from 30 to 500, from 30 to 750, from 30 to 1,000, from 30 to 1,500, from 30 to 2,000, from 30 to 2,500, from 50 to 100, from 50 to 250, from 50 to 500, from 50 to 750, from 50 to 1,000, from 50 to 1,500, from 50 to 2,000, from 50 to 2,500, from 50 to 3,000, from 100 to 500, from 100 to 750, from 100 to 1,000, from 100 to 1,500, from 100 to 2,000, from 100 to 2,500, from 100 to 3,000, from 500 to 750, from 500 to 1,000, from 500 to 1,500, from 500 to 2,000, from 500 to 2,500, from 500 to 3,000, from 1,000 to 1,500, from 1,000 to 2,000, from 1,000 to 2,500, from 1,000 to 3,000, from 1,500 to 2,000, from 1,500 to 2,500, from 1,500 to 3,000, from 2,000 to 3,000, from 2,000 to 2,500, and from 2,500 to 3,000).

In some embodiments, the poly-A tail is designed relative to the length of the overall polynucleotide or the length of a particular region of the polynucleotide. This design can be based on the length of a coding region, the length of a particular feature or region or based on the length of the ultimate product expressed from the polynucleotides.

In this context, the poly-A tail can be 10, 20, 30, 40, 50, 60, 70, 80, 90, or 100% greater in length than the poly-nucleotide or feature thereof. The poly-A tail can also be designed as a fraction of the polynucleotides to which it belongs. In this context, the poly-A tail can be 10, 20, 30, 40, 50, 60, 70, 80, or 90% or more of the total length of the construct, a construct region or the total length of the construct minus the poly-A tail. Further, engineered binding sites and conjugation of polynucleotides for Poly-A binding protein can enhance expression.

Additionally, multiple distinct polynucleotides can be linked together via the PABP (Poly-A binding protein) through the 3'-end using modified nucleotides at the 3'-terminus of the poly-A tail. Transfection experiments can be conducted in relevant cell lines at and protein production can be assayed by ELISA at 12 hr, 24 hr, 48 hr, 72 hr and day 7 post-transfection.

In some embodiments, the polynucleotides of the present invention are designed to include a polyA-G Quartet region. The G-quartet is a cyclic hydrogen bonded array of four guanine nucleotides that can be formed by G-rich sequences in both DNA and RNA. In this embodiment, the G-quartet is incorporated at the end of the poly-A tail. The resultant polynucleotide is assayed for stability, protein production and other parameters including half-life at various time points. It has been discovered that the polyA-G quartet results in protein production from an mRNA equivalent to at least 75% of that seen using a poly-A tail of 120 nucleotides alone.

15. Start Codon Region

The invention also includes a polynucleotide that comprises both a start codon region and the polynucleotide described herein (e.g., a polynucleotide comprising a nucleotide sequence encoding a PCCA or PCCB polypeptide). In some embodiments, the polynucleotides of the present invention can have regions that are analogous to or function like a start codon region.

In some embodiments, the translation of a polynucleotide can initiate on a codon that is not the start codon AUG. Translation of the polynucleotide can initiate on an alternative start codon such as, but not limited to, ACG, AGG, AAG, CTG/CUG, GTG/GUG, ATA/AUA, ATT/AUU, TTG/UUG (see Touriol et al. Biology of the Cell 95 (2003) 169-178 and Matsuda and Mauro PLoS ONE, 2010 5:11; the contents of each of which are herein incorporated by reference in its entirety).

As a non-limiting example, the translation of a polynucleotide begins on the alternative start codon ACG. As another non-limiting example, polynucleotide translation begins on the alternative start codon CTG or CUG. As yet another non-limiting example, the translation of a polynucleotide begins on the alternative start codon GTG or GUG.

Nucleotides flanking a codon that initiates translation such as, but not limited to, a start codon or an alternative start codon, are known to affect the translation efficiency, the length and/or the structure of the polynucleotide. (See, e.g., Matsuda and Mauro PLoS ONE, 2010 5:11; the contents of which are herein incorporated by reference in its entirety). Masking any of the nucleotides flanking a codon that initiates translation can be used to alter the position of translation initiation, translation efficiency, length and/or structure of a polynucleotide.

In some embodiments, a masking agent can be used near the start codon or alternative start codon in order to mask or hide the codon to reduce the probability of translation initiation at the masked start codon or alternative start codon. Non-limiting examples of masking agents include antisense locked nucleic acids (LNA) polynucleotides and exon-junction complexes (EJCs) (See, e.g., Matsuda and Mauro describing masking agents LNA polynucleotides and EJCs (PLoS ONE, 2010 5:11); the contents of which are herein incorporated by reference in its entirety).

In another embodiment, a masking agent can be used to mask a start codon of a polynucleotide in order to increase the likelihood that translation will initiate on an alternative start codon. In some embodiments, a masking agent can be used to mask a first start codon or alternative start codon in order to increase the chance that translation will initiate on a start codon or alternative start codon downstream to the masked start codon or alternative start codon.

In some embodiments, a start codon or alternative start codon can be located within a perfect complement for a miRNA binding site. The perfect complement of a miRNA binding site can help control the translation, length and/or structure of the polynucleotide similar to a masking agent. As a non-limiting example, the start codon or alternative start codon can be located in the middle of a perfect complement for a miRNA binding site. The start codon or alternative start codon can be located after the first nucleotide, second nucleotide, third nucleotide, fourth nucleotide, fifth nucleotide, sixth nucleotide, seventh nucleotide, eighth nucleotide, ninth nucleotide, tenth nucleotide, eleventh nucleotide, twelfth nucleotide, thirteenth nucleotide, fourteenth nucleotide, fifteenth nucleotide, sixteenth nucleotide, seventeenth nucleotide, eighteenth nucleotide, nineteenth nucleotide, twentieth nucleotide or twenty-first nucleotide.

In another embodiment, the start codon of a polynucleotide can be removed from the polynucleotide sequence in order to have the translation of the polynucleotide begin on a codon that is not the start codon. Translation of the polynucleotide can begin on the codon following the removed start codon or on a downstream start codon or an alternative start codon. In a non-limiting example, the start codon ATG or AUG is removed as the first 3 nucleotides of the polynucleotide sequence in order to have translation initiate on a downstream start codon or alternative start codon. The polynucleotide sequence where the start codon was removed can further comprise at least one masking agent for the downstream start codon and/or alternative start codons in order to control or attempt to control the initiation of translation, the length of the polynucleotide and/or the structure of the polynucleotide.

16. Stop Codon Region

The invention also includes a polynucleotide that comprises both a stop codon region and the polynucleotide described herein (e.g., a polynucleotide comprising a nucleotide sequence encoding a PCCA or PCCB polypeptide). In some embodiments, the polynucleotides of the present invention can include at least two stop codons before the 3' untranslated region (UTR). The stop codon can be selected from TGA, TAA and TAG in the case of DNA, or from UGA, UAA and UAG in the case of RNA. In some embodiments, the polynucleotides of the present invention include the stop codon TGA in the case or DNA, or the stop codon UGA in the case of RNA, and one additional stop codon. In a further embodiment the addition stop codon can be TAA or UAA. In another embodiment, the polynucleotides of the present invention include three consecutive stop codons, four stop codons, or more.

17. Polynucleotide Comprising an mRNA Encoding a PCCA or PCCB Polypeptide

In certain embodiments, a polynucleotide of the present disclosure, for example a polynucleotide comprising an mRNA nucleotide sequence encoding a PCCA or PCCB polypeptide, comprises from 5' to 3' end:
  (i) a 5' cap provided above;
  (ii) a 5' UTR, such as the sequences provided above;
  (iii) an open reading frame encoding a PCCA or PCCB polypeptide, e.g., a sequence optimized nucleic acid sequence encoding a PCCA or PCCB disclosed herein;
  (iv) at least one stop codon;
  (v) a 3' UTR, such as the sequences provided above; and
  (vi) a poly-A tail provided above.

In some embodiments, the polynucleotide further comprises a miRNA binding site, e.g., a miRNA binding site that binds to miRNA-142. In some embodiments, the 5' UTR comprises the miRNA binding site. In some embodiments, the 3' UTR comprises the miRNA binding site.

In some embodiments, a polynucleotide of the present disclosure comprises a nucleotide sequence encoding a polypeptide sequence at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the protein sequence of a wild type human PCCA (SEQ ID NO:1) or wild type human PCCB (SEQ ID NO:15).

In some embodiments, a polynucleotide of the present disclosure, for example a polynucleotide comprising an mRNA nucleotide sequence encoding a polypeptide, comprises (1) a 5' cap provided above, for example, CAP1, (2) a 5' UTR, (3) a nucleotide sequence ORF selected from the group consisting of SEQ ID NOs: 2, 5-14, 16-27, 196, 197, and 198, (3) a stop codon, (4) a 3'UTR, and (5) a poly-A tail provided above, for example, a poly-A tail of about 100 residues.

Exemplary PCCA nucleotide constructs are described below:

SEQ ID NO: 28 consists from 5' to 3' end: 5' UTR of SEQ ID NO: 3, PCCA nucleotide ORF of SEQ ID NO: 2, and 3' UTR of SEQ ID NO: 4.

SEQ ID NO: 29 consists from 5' to 3' end: 5' UTR of SEQ ID NO: 3, PCCA nucleotide ORF of SEQ ID NO: 5, and 3' UTR of SEQ ID NO: 4.

SEQ ID NO: 30 consists from 5' to 3' end: 5' UTR of SEQ ID NO: 3, PCCA nucleotide ORF of SEQ ID NO: 6, and 3' UTR of SEQ ID NO: 4.

SEQ ID NO: 31 consists from 5' to 3' end: 5' UTR of SEQ ID NO: 3, PCCA nucleotide ORF of SEQ ID NO: 7, and 3' UTR of SEQ ID NO: 4.

SEQ ID NO: 32 consists from 5' to 3' end: 5' UTR of SEQ ID NO: 3, PCCA nucleotide ORF of SEQ ID NO: 8, and 3' UTR of SEQ ID NO: 4.

SEQ ID NO: 33 consists from 5' to 3' end: 5' UTR of SEQ ID NO: 3, PCCA nucleotide ORF of SEQ ID NO: 9, and 3' UTR of SEQ ID NO: 4.

SEQ ID NO: 34 consists from 5' to 3' end: 5' UTR of SEQ ID NO: 3, PCCA nucleotide ORF of SEQ ID NO: 10, and 3' UTR of SEQ ID NO: 4.

SEQ ID NO: 35 consists from 5' to 3' end: 5' UTR of SEQ ID NO: 3, PCCA nucleotide ORF of SEQ ID NO: 11, and 3' UTR of SEQ ID NO: 4.

SEQ ID NO: 36 consists from 5' to 3' end: 5' UTR of SEQ ID NO: 3, PCCA nucleotide ORF of SEQ ID NO: 12, and 3' UTR of SEQ ID NO: 4.

SEQ ID NO: 37 consists from 5' to 3' end: 5' UTR of SEQ ID NO: 3, PCCA nucleotide ORF of SEQ ID NO: 13, and 3' UTR of SEQ ID NO: 4.

SEQ ID NO: 38 consists from 5' to 3' end: 5' UTR of SEQ ID NO: 3, PCCA nucleotide ORF of SEQ ID NO: 14, and 3' UTR of SEQ ID NO: 150.

SEQ ID NO: 63 consists from 5' to 3' end: 5' UTR of SEQ ID NO: 3, PCCA nucleotide ORF of SEQ ID NO: 11, and 3' UTR of SEQ ID NO: 178.

SEQ ID NO: 65 consists from 5' to 3' end: 5' UTR of SEQ ID NO: 3, PCCA nucleotide ORF of SEQ ID NO: 11, and 3' UTR of SEQ ID NO:112.

SEQ ID NO:203 consists from 5' to 3' end: 5' UTR of SEQ ID NO:199, PCCA nucleotide ORF of SEQ ID NO:11, and 3' UTR of SEQ ID NO:178.

Exemplary PCCB nucleotide constructs are described below:

SEQ ID NO: 39 consists from 5' to 3' end: 5' UTR of SEQ ID NO: 3, PCCB nucleotide ORF of SEQ ID NO: 16, and 3' UTR of SEQ ID NO: 4.

SEQ ID NO: 40 consists from 5' to 3' end: 5' UTR of SEQ ID NO: 3, PCCB nucleotide ORF of SEQ ID NO: 17, and 3' UTR of SEQ ID NO: 4.

SEQ ID NO: 41 consists from 5' to 3' end: 5' UTR of SEQ ID NO: 3, PCCB nucleotide ORF of SEQ ID NO: 18, and 3' UTR of SEQ ID NO: 4.

SEQ ID NO: 42 consists from 5' to 3' end: 5' UTR of SEQ ID NO: 3, PCCB nucleotide ORF of SEQ ID NO: 19, and 3' UTR of SEQ ID NO: 4.

SEQ ID NO: 43 consists from 5' to 3' end: 5' UTR of SEQ ID NO: 3, PCCB nucleotide ORF of SEQ ID NO: 20, and 3' UTR of SEQ ID NO: 4.

SEQ ID NO: 44 consists from 5' to 3' end: 5' UTR of SEQ ID NO: 3, PCCB nucleotide ORF of SEQ ID NO: 21, and 3' UTR of SEQ ID NO: 4.

SEQ ID NO: 45 consists from 5' to 3' end: 5' UTR of SEQ ID NO: 3, PCCB nucleotide ORF of SEQ ID NO: 22, and 3' UTR of SEQ ID NO: 4.

SEQ ID NO: 46 consists from 5' to 3' end: 5' UTR of SEQ ID NO: 3, PCCB nucleotide ORF of SEQ ID NO: 23, and 3' UTR of SEQ ID NO: 4.

SEQ ID NO: 47 consists from 5' to 3' end: 5' UTR of SEQ ID NO: 3, PCCB nucleotide ORF of SEQ ID NO: 24, and 3' UTR of SEQ ID NO: 4.

SEQ ID NO: 48 consists from 5' to 3' end: 5' UTR of SEQ ID NO: 3, PCCB nucleotide ORF of SEQ ID NO: 25, and 3' UTR of SEQ ID NO: 4.

SEQ ID NO: 49 consists from 5' to 3' end: 5' UTR of SEQ ID NO: 3, PCCB nucleotide ORF of SEQ ID NO: 26, and 3' UTR of SEQ ID NO: 150.

SEQ ID NO: 50 consists from 5' to 3' end: 5' UTR of SEQ ID NO: 3, PCCB nucleotide ORF of SEQ ID NO: 27, and 3' UTR of SEQ ID NO: 150.

SEQ ID NO: 66 consists from 5' to 3' end: 5' UTR of SEQ ID NO: 3, PCCB nucleotide ORF of SEQ ID NO: 23, and 3' UTR of SEQ ID NO: 178.

SEQ ID NO: 67 consists from 5' to 3' end: 5' UTR of SEQ ID NO: 64, PCCB nucleotide ORF of SEQ ID NO: 23, and 3' UTR of SEQ ID NO:112.

SEQ ID NO:200 consists from 5' to 3' end: 5' UTR of SEQ ID NO:199, PCCB nucleotide ORF of SEQ ID NO:196, and 3' UTR of SEQ ID NO:178.

SEQ ID NO:201 consists from 5' to 3' end: 5' UTR of SEQ ID NO:199, PCCB nucleotide ORF of SEQ ID NO:197, and 3' UTR of SEQ ID NO:178.

SEQ ID NO:202 consists from 5' to 3' end: 5' UTR of SEQ ID NO:199, PCCB nucleotide ORF of SEQ ID NO:198, and 3' UTR of SEQ ID NO:178.

SEQ ID NO:204 consists from 5' to 3' end: 5' UTR of SEQ ID NO:199, PCCB nucleotide ORF of SEQ ID NO:23, and 3' UTR of SEQ ID NO:178.

SEQ ID NO:205 consists from 5' to 3' end: 5' UTR of SEQ ID NO:199, PCCB nucleotide ORF of SEQ ID NO:25, and 3' UTR of SEQ ID NO:178.

In certain embodiments, in constructs with SEQ ID NOs.: 28-50, 63, 65-67, and 200-205, all uracils therein are replaced by N1-methylpseudouracil. In certain embodiments, in constructs with SEQ ID NOs.: 28-50, 63, 65-67, and 200-205, all uracils therein are replaced by 5-methoxyuracil.

In some embodiments, a polynucleotide of the present disclosure, for example a polynucleotide comprising an mRNA nucleotide sequence encoding a PCCA or PCCB polypeptide, comprises (1) a 5' cap provided above, for example, CAP1, (2) a nucleotide sequence selected from the group consisting of SEQ ID NO: 28-50, 63, 65-67, and 200-205, and (3) a poly-A tail provided above, for example, a poly A tail of ~100 residues.

TABLE 5

Modified mRNA constructs including ORFs encoding human PCCA or PCCB (each of constructs #1 to #33 comprises a Cap1 5' terminal cap and a 3' terminal PolyA region)

| PCCA/PCCB mRNA construct | 5' UTR SEQ ID NO | PCCA/PCCB ORF Name (Chemistry) | SEQ ID NO | 3' UTR SEQ ID NO: |
|---|---|---|---|---|
| #1 (SEQ ID NO: 28) | 3 | PCCA 11 (G5) | 2 | 4 |
| #2 (SEQ ID NO: 29) | 3 | PCCA 12 (G5) | 5 | 4 |
| #3 (SEQ ID NO: 30) | 3 | PCCA 13 (G5) | 6 | 4 |
| #4 (SEQ ID NO: 31) | 3 | PCCA 14 (G5) | 7 | 4 |
| #5 (SEQ ID NO: 32) | 3 | PCCA 15 (G5) | 8 | 4 |
| #6 (SEQ ID NO: 33) | 3 | PCCA 16 (G5) | 9 | 4 |
| #7 (SEQ ID NO: 34) | 3 | PCCA 17 (G5) | 10 | 4 |
| #8 (SEQ ID NO: 35) | 3 | PCCA 18 (G5) | 11 | 4 |
| #9 (SEQ ID NO: 36) | 3 | PCCA 19 (G5) | 12 | 4 |
| #10 (SEQ ID NO: 37) | 3 | PCCA 20 (G5) | 13 | 4 |
| #11 (SEQ ID NO: 38) | 3 | PCCA 01-014.2 (G5) | 14 | 150 |
| #12 (SEQ ID NO: 39) | 3 | PCCB 11 (G5) | 16 | 4 |
| #13 (SEQ ID NO: 40) | 3 | PCCB 12 (G5) | 17 | 4 |
| #14 (SEQ ID NO: 41) | 3 | PCCB 13 (G5) | 18 | 4 |
| #15 (SEQ ID NO: 42) | 3 | PCCB 14 (G5) | 19 | 4 |
| #16 (SEQ ID NO: 43) | 3 | PCCB 15 (G5) | 20 | 4 |
| #17 (SEQ ID NO: 44) | 3 | PCCB 16 (G5) | 21 | 4 |
| #18 (SEQ ID NO: 45) | 3 | PCCB 17 (G5) | 22 | 4 |
| #19 (SEQ ID NO: 46) | 3 | PCCB 18 (G5) | 23 | 4 |
| #20 (SEQ ID NO: 47) | 3 | PCCB 19 (G5) | 24 | 4 |
| #21 (SEQ ID NO: 48) | 3 | PCCB 20 (G5) | 25 | 4 |
| #22 (SEQ ID NO: 49) | 3 | PCCB 01-014 (G5) | 26 | 150 |
| #23 (SEQ ID NO: 63) | 3 | PCCA 21 (G5) | 11 | 178 |
| #24 (SEQ ID NO: 65) | 3 | PCCA 22 (G5) | 11 | 112 |
| #25 (SEQ ID NO: 66) | 3 | PCCB 21 (G5) | 23 | 178 |
| #26 (SEQ ID NO: 67) | 64 | PCCB 22 (G5) | 23 | 112 |
| #27 (SEQ ID NO: 50) | 3 | PCCB 14 (G5) | 27 | 150 |
| #28 (SEQ ID NO: 200) | 199 | SE_PCCB_026 (G5) | 196 | 178 |
| #29 (SEQ ID NO:201) | 199 | SE_PCCB_027 (G5) | 197 | 178 |
| #30 (SEQ ID NO: 202) | 199 | SE_PCCB_028 (G5) | 198 | 178 |
| #31 (SEQ ID NO: 203) | 199 | SE_PCCA_018 (G5) | 11 | 178 |
| #32 (SEQ ID NO: 204) | 199 | SE_PCCB_018 (G5) | 23 | 178 |
| #33 (SEQ ID NO: 205) | 199 | SE_PCCB_020 | 25 | 178 |

18. Methods of Making Polynucleotides

The present disclosure also provides methods for making a polynucleotide of the invention (e.g., a polynucleotide comprising a nucleotide sequence encoding a PCCA or PCCB polypeptide) or a complement thereof.

In some aspects, a polynucleotide (e.g., a RNA, e.g., an mRNA) disclosed herein, and encoding a PCCA or PCCB polypeptide, can be constructed using in vitro transcription (IVT). In other aspects, a polynucleotide (e.g., a RNA, e.g., an mRNA) disclosed herein, and encoding a PCCA or PCCB polypeptide, can be constructed by chemical synthesis using an oligonucleotide synthesizer.

In other aspects, a polynucleotide (e.g., a RNA, e.g., an mRNA) disclosed herein, and encoding a PCCA or PCCB polypeptide is made by using a host cell. In certain aspects, a polynucleotide (e.g., a RNA, e.g., an mRNA) disclosed herein, and encoding a PCCA or PCCB polypeptide is made by one or more combination of the IVT, chemical synthesis, host cell expression, or any other methods known in the art.

Naturally occurring nucleosides, non-naturally occurring nucleosides, or combinations thereof, can totally or partially naturally replace occurring nucleosides present in the candidate nucleotide sequence and can be incorporated into a sequence-optimized nucleotide sequence (e.g., a RNA, e.g., an mRNA) encoding a PCCA or PCCB polypeptide. The resultant polynucleotides, e.g., mRNAs, can then be examined for their ability to produce protein and/or produce a therapeutic outcome.

a. In Vitro Transcription/Enzymatic Synthesis

The polynucleotides of the present invention disclosed herein (e.g., a polynucleotide comprising a nucleotide sequence encoding a PCCA or PCCB polypeptide) can be transcribed using an in vitro transcription (IVT) system. The system typically comprises a transcription buffer, nucleotide triphosphates (NTPs), an RNase inhibitor and a polymerase. The NTPs can be selected from, but are not limited to, those described herein including natural and unnatural (modified) NTPs. The polymerase can be selected from, but is not limited to, T7 RNA polymerase, T3 RNA polymerase and mutant polymerases such as, but not limited to, polymerases able to incorporate polynucleotides disclosed herein. See U.S. Publ. No. US20130259923, which is herein incorporated by reference in its entirety.

Any number of RNA polymerases or variants can be used in the synthesis of the polynucleotides of the present invention. RNA polymerases can be modified by inserting or deleting amino acids of the RNA polymerase sequence. As a non-limiting example, the RNA polymerase can be modified to exhibit an increased ability to incorporate a 2'-modified nucleotide triphosphate compared to an unmodified RNA polymerase (see International Publication WO2008078180 and U.S. Pat. No. 8,101,385; herein incorporated by reference in their entireties).

Variants can be obtained by evolving an RNA polymerase, optimizing the RNA polymerase amino acid and/or nucleic acid sequence and/or by using other methods known in the art. As a non-limiting example, T7 RNA polymerase variants can be evolved using the continuous directed evolution system set out by Esvelt et al. (Nature 472:499-503 (2011); herein incorporated by reference in its entirety) where clones of T7 RNA polymerase can encode at least one mutation such as, but not limited to, lysine at position 93 substituted for threonine (K93T), 14M, A7T, E63V, V64D, A65E, D66Y, T76N, C125R, S128R, A136T, N165S, G175R, H176L, Y178H, F182L, L196F, G198V, D208Y, E222K, S228A, Q239R, T243N, G259D, M2671, G280C, H300R, D351A, A354S, E356D, L360P, A383V, Y385C, D388Y, S397R, M401T, N410S, K450R, P451T, G452V, E484A, H523L, H524N, G542V, E565K, K577E, K577M, N601S, S684Y, L6991, K713E, N748D, Q754R, E775K, A827V, D851N or L864F. As another non-limiting example, T7 RNA polymerase variants can encode at least mutation as described in U.S. Pub. Nos. 20100120024 and 20070117112; herein incorporated by reference in their entireties. Variants of RNA polymerase can also include, but are not limited to, substitutional variants, conservative amino acid substitution, insertional variants, and/or deletional variants.

In one aspect, the polynucleotide can be designed to be recognized by the wild type or variant RNA polymerases. In doing so, the polynucleotide can be modified to contain sites or regions of sequence changes from the wild type or parent chimeric polynucleotide.

Polynucleotide or nucleic acid synthesis reactions can be carried out by enzymatic methods utilizing polymerases. Polymerases catalyze the creation of phosphodiester bonds between nucleotides in a polynucleotide or nucleic acid chain. Currently known DNA polymerases can be divided into different families based on amino acid sequence comparison and crystal structure analysis. DNA polymerase I (pol I) or A polymerase family, including the Klenow fragments of *E. coli, Bacillus* DNA polymerase I, *Thermus aquaticus* (Taq) DNA polymerases, and the T7 RNA and DNA polymerases, is among the best studied of these families. Another large family is DNA polymerase α (pol α) or B polymerase family, including all eukaryotic replicating DNA polymerases and polymerases from phages T4 and RB69. Although they employ similar catalytic mechanism, these families of polymerases differ in substrate specificity, substrate analog-incorporating efficiency, degree and rate for primer extension, mode of DNA synthesis, exonuclease activity, and sensitivity against inhibitors.

DNA polymerases are also selected based on the optimum reaction conditions they require, such as reaction temperature, pH, and template and primer concentrations. Sometimes a combination of more than one DNA polymerases is employed to achieve the desired DNA fragment size and synthesis efficiency. For example, Cheng et al. increase pH, add glycerol and dimethyl sulfoxide, decrease denaturation times, increase extension times, and utilize a secondary thermostable DNA polymerase that possesses a 3' to 5' exonuclease activity to effectively amplify long targets from cloned inserts and human genomic DNA. (Cheng et al., PNAS 91:5695-5699 (1994), the contents of which are incorporated herein by reference in their entirety). RNA polymerases from bacteriophage T3, T7, and SP6 have been widely used to prepare RNAs for biochemical and biophysical studies. RNA polymerases, capping enzymes, and poly-A polymerases are disclosed in the co-pending International Publication No. WO2014/028429, the contents of which are incorporated herein by reference in their entirety.

In one aspect, the RNA polymerase which can be used in the synthesis of the polynucleotides of the present invention is a Syn5 RNA polymerase. (see Zhu et al. Nucleic Acids Research 2013, doi:10.1093/nar/gkt1193, which is herein incorporated by reference in its entirety). The Syn5 RNA polymerase was recently characterized from marine cyanophage Syn5 by Zhu et al. where they also identified the promoter sequence (see Zhu et al. Nucleic Acids Research 2013, the contents of which is herein incorporated by reference in its entirety). Zhu et al. found that Syn5 RNA polymerase catalyzed RNA synthesis over a wider range of temperatures and salinity as compared to T7 RNA polymerase. Additionally, the requirement for the initiating nucleotide at the promoter was found to be less stringent for Syn5 RNA polymerase as compared to the T7 RNA polymerase making Syn5 RNA polymerase promising for RNA synthesis.

In one aspect, a Syn5 RNA polymerase can be used in the synthesis of the polynucleotides described herein. As a non-limiting example, a Syn5 RNA polymerase can be used in the synthesis of the polynucleotide requiring a precise 3'-terminus.

In one aspect, a Syn5 promoter can be used in the synthesis of the polynucleotides. As a non-limiting example, the Syn5 promoter can be 5'-ATTGGGCACCCGTAAGGG-3' (SEQ ID NO: 185 as described by Zhu et al. (Nucleic Acids Research 2013).

In one aspect, a Syn5 RNA polymerase can be used in the synthesis of polynucleotides comprising at least one chemical modification described herein and/or known in the art (see e.g., the incorporation of pseudo-UTP and 5Me-CTP described in Zhu et al. Nucleic Acids Research 2013).

In one aspect, the polynucleotides described herein can be synthesized using a Syn5 RNA polymerase which has been purified using modified and improved purification procedure described by Zhu et al. (Nucleic Acids Research 2013).

Various tools in genetic engineering are based on the enzymatic amplification of a target gene which acts as a template. For the study of sequences of individual genes or specific regions of interest and other research needs, it is necessary to generate multiple copies of a target gene from a small sample of polynucleotides or nucleic acids. Such methods can be applied in the manufacture of the polynucleotides of the invention.

For example, polymerase chain reaction (PCR), strand displacement amplification (SDA), nucleic acid sequence-based amplification (NASBA), also called transcription mediated amplification (TMA), and/or rolling-circle amplification (RCA) can be utilized in the manufacture of one or more regions of the polynucleotides of the present invention. Assembling polynucleotides or nucleic acids by a ligase is also widely used.

b. Chemical Synthesis

Standard methods can be applied to synthesize an isolated polynucleotide sequence encoding an isolated polypeptide of interest, such as a polynucleotide of the invention (e.g., a polynucleotide comprising a nucleotide sequence encoding a PCCA or PCCB polypeptide). For example, a single DNA or RNA oligomer containing a codon-optimized nucleotide sequence coding for the particular isolated polypeptide can be synthesized. In other aspects, several small oligonucleotides coding for portions of the desired polypeptide can be synthesized and then ligated. In some aspects, the individual oligonucleotides typically contain 5' or 3' overhangs for complementary assembly.

A polynucleotide disclosed herein (e.g., a RNA, e.g., an mRNA) can be chemically synthesized using chemical synthesis methods and potential nucleobase substitutions known in the art. See, for example, International Publication Nos. WO2014093924, WO2013052523; WO2013039857, WO2012135805, WO2013151671; U.S. Publ. No. US20130115272; or U.S. Pat. Nos. U.S. Pat. No. 8,999,380 or U.S. Pat. No. 8,710,200, all of which are herein incorporated by reference in their entireties.

c. Purification of Polynucleotides Encoding PCCA or PCCB

Purification of the polynucleotides described herein (e.g., a polynucleotide comprising a nucleotide sequence encoding a PCCA or PCCB polypeptide) can include, but is not limited to, polynucleotide clean-up, quality assurance and quality control. Clean-up can be performed by methods known in the arts such as, but not limited to, AGEN-COURT® beads (Beckman Coulter Genomics, Danvers, MA), poly-T beads, LNA™ oligo-T capture probes (EX-IQON® Inc., Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC).

The term "purified" when used in relation to a polynucleotide such as a "purified polynucleotide" refers to one that is separated from at least one contaminant. As used herein, a "contaminant" is any substance that makes another unfit, impure or inferior. Thus, a purified polynucleotide (e.g., DNA and RNA) is present in a form or setting different from that in which it is found in nature, or a form or setting different from that which existed prior to subjecting it to a treatment or purification method.

In some embodiments, purification of a polynucleotide of the invention (e.g., a polynucleotide comprising a nucleotide sequence encoding a PCCA or PCCB polypeptide) removes impurities that can reduce or remove an unwanted immune response, e.g., reducing cytokine activity.

In some embodiments, the polynucleotide of the invention (e.g., a polynucleotide comprising a nucleotide sequence encoding a PCCA or PCCB polypeptide) is purified prior to administration using column chromatography (e.g., strong anion exchange HPLC, weak anion exchange HPLC, reverse phase HPLC (RP-HPLC), and hydrophobic interaction HPLC (HIC-HPLC), or (LCMS)).

In some embodiments, the polynucleotide of the invention (e.g., a polynucleotide comprising a nucleotide sequence a PCCA or PCCB polypeptide) purified using column chromatography (e.g., strong anion exchange HPLC, weak anion exchange HPLC, reverse phase HPLC (RP-HPLC, hydrophobic interaction HPLC (HIC-HPLC), or (LCMS)) presents increased expression of the encoded PCCA or PCCB protein compared to the expression level obtained with the same polynucleotide of the present disclosure purified by a different purification method.

In some embodiments, a column chromatography (e.g., strong anion exchange HPLC, weak anion exchange HPLC, reverse phase HPLC (RP-HPLC), hydrophobic interaction HPLC (HIC-HPLC), or (LCMS)) purified polynucleotide comprises a nucleotide sequence encoding a PCCA or PCCB polypeptide comprising one or more of the point mutations known in the art.

In some embodiments, the use of RP-HPLC purified polynucleotide increases PCCA or PCCB protein expression levels in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the expression levels of PCCA or PCCB protein in the cells before the RP-HPLC purified polynucleotide was introduced in the cells, or after a non-RP-HPLC purified polynucleotide was introduced in the cells.

In some embodiments, the use of RP-HPLC purified polynucleotide increases functional PCCA or PCCB protein expression levels in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the functional expression levels of PCCA or PCCB protein in the cells before the RP-HPLC purified polynucleotide was introduced in the cells, or after a non-RP-HPLC purified polynucleotide was introduced in the cells.

In some embodiments, the use of RP-HPLC purified polynucleotide increases detectable PCCA or PCCB activity in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the activity levels of functional PCCA or PCCB in the cells before the RP-HPLC purified polynucleotide was introduced in the cells, or after a non-RP-HPLC purified polynucleotide was introduced in the cells.

In some embodiments, the purified polynucleotide is at least about 80% pure, at least about 85% pure, at least about 90% pure, at least about 95% pure, at least about 96% pure, at least about 97% pure, at least about 98% pure, at least about 99% pure, or about 100% pure.

A quality assurance and/or quality control check can be conducted using methods such as, but not limited to, gel electrophoresis, UV absorbance, or analytical HPLC. In another embodiment, the polynucleotide can be sequenced by methods including, but not limited to reverse-transcriptase-PCR.

d. Quantification of Expressed Polynucleotides Encoding PCCA or PCCB

In some embodiments, the polynucleotides of the present invention (e.g., a polynucleotide comprising a nucleotide sequence encoding a PCCA or PCCB polypeptide), their expression products, as well as degradation products and metabolites can be quantified according to methods known in the art.

In some embodiments, the polynucleotides of the present invention can be quantified in exosomes or when derived from one or more bodily fluid. As used herein "bodily fluids" include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes can be retrieved from an organ selected from the group consisting of lung, heart, pancreas, stomach, intestine, bladder, kidney, ovary, testis, skin, colon, breast, prostate, brain, esophagus, liver, and placenta.

In the exosome quantification method, a sample of not more than 2 mL is obtained from the human subject and the exosomes isolated by size exclusion chromatography, density gradient centrifugation, differential centrifugation, nanomembrane ultrafiltration, immunoabsorbent capture, affinity purification, microfluidic separation, or combinations thereof. In the analysis, the level or concentration of a polynucleotide can be an expression level, presence, absence, truncation or alteration of the administered construct. It is advantageous to correlate the level with one or more clinical phenotypes or with an assay for a human disease biomarker.

The assay can be performed using construct specific probes, cytometry, qRT-PCR, real-time PCR, PCR, flow cytometry, electrophoresis, mass spectrometry, or combinations thereof while the exosomes can be isolated using immunohistochemical methods such as enzyme linked immunosorbent assay (ELISA) methods. Exosomes can also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of polynucleotides remaining or delivered. This is possible because the polynucleotides of the present invention differ from the endogenous forms due to the structural or chemical modifications.

In some embodiments, the polynucleotide can be quantified using methods such as, but not limited to, ultraviolet visible spectroscopy (UV/Vis). A non-limiting example of a UV/Vis spectrometer is a NANODROP® spectrometer (ThermoFisher, Waltham, MA). The quantified polynucleotide can be analyzed in order to determine if the polynucleotide can be of proper size, check that no degradation of the polynucleotide has occurred. Degradation of the polynucleotide can be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

19. Pharmaceutical Compositions and Formulations

The present invention provides pharmaceutical compositions and formulations that comprise any of the polynucleotides described above. In some embodiments, the composition or formulation further comprises a delivery agent.

In some embodiments, the composition or formulation can contain a polynucleotide comprising a sequence optimized nucleic acid sequence disclosed herein which encodes a PCCA or PCCB polypeptide. In some embodiments, the composition or formulation can contain a polynucleotide (e.g., a RNA, e.g., an mRNA) comprising a polynucleotide (e.g., an ORF) having significant sequence identity to a sequence optimized nucleic acid sequence disclosed herein which encodes a PCCA or PCCB polypeptide. In some embodiments, the polynucleotide further comprises a miRNA binding site, e.g., a miRNA binding site that binds miR-126, miR-142, miR-144, miR-146, miR-150, miR-155, miR-16, miR-21, miR-223, miR-24, miR-27 and miR-26a.

Pharmaceutical compositions or formulation can optionally comprise one or more additional active substances, e.g., therapeutically and/or prophylactically active substances. Pharmaceutical compositions or formulation of the present invention can be sterile and/or pyrogen-free. General considerations in the formulation and/or manufacture of pharmaceutical agents can be found, for example, in *Remington: The Science and Practice of Pharmacy* 21$^{st}$ ed., Lippincott Williams & Wilkins, 2005 (incorporated herein by reference in its entirety). In some embodiments, compositions are administered to humans, human patients or subjects. For the purposes of the present disclosure, the phrase "active ingredient" generally refers to polynucleotides to be delivered as described herein.

Formulations and pharmaceutical compositions described herein can be prepared by any method known or hereafter developed in the art of pharmacology. In general, such preparatory methods include the step of associating the active ingredient with an excipient and/or one or more other accessory ingredients, and then, if necessary and/or desirable, dividing, shaping and/or packaging the product into a desired single- or multi-dose unit.

A pharmaceutical composition or formulation in accordance with the present disclosure can be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient that would be administered to a human subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure can vary, depending upon the identity, size, and/or condition of the human subject being treated and further depending upon the route by which the composition is to be administered.

In some embodiments, the compositions and formulations described herein can contain at least one polynucleotide of the invention. As a non-limiting example, the composition or formulation can contain 1, 2, 3, 4 or 5 polynucleotides of the invention. In some embodiments, the compositions or formulations described herein can comprise more than one type of polynucleotide. In some embodiments, the composition or formulation can comprise a polynucleotide in linear and circular form. In another embodiment, the composition or formulation can comprise a circular polynucleotide and an in vitro transcribed (IVT) polynucleotide. In yet another embodiment, the composition or formulation can comprise an IVT polynucleotide, a chimeric polynucleotide and a circular polynucleotide.

Although the descriptions of pharmaceutical compositions and formulations provided herein are principally directed to pharmaceutical compositions and formulations that are suitable for administration to humans, it will be understood by the skilled artisan that such compositions are generally suitable for administration to any other animal, e.g., to non-human animals, e.g. non-human mammals.

The present invention provides pharmaceutical formulations that comprise a polynucleotide described herein (e.g., a polynucleotide comprising a nucleotide sequence encoding a PCCA or PCCB polypeptide). The polynucleotides described herein can be formulated using one or more excipients to: (1) increase stability; (2) increase cell transfection; (3) permit the sustained or delayed release (e.g., from a depot formulation of the polynucleotide); (4) alter the biodistribution (e.g., target the polynucleotide to specific tissues or cell types); (5) increase the translation of encoded protein in vivo; and/or (6) alter the release profile of encoded protein in vivo. In some embodiments, the pharmaceutical formulation further comprises a delivery agent comprising, e.g., a compound having the Formula (I), e.g., any of Compounds 1-232, e.g., Compound II; a compound having the Formula (III), (IV), (V), or (VI), e.g., any of Compounds 233-342, e.g., Compound VI; or a compound having the Formula (VIII), e.g., any of Compounds 419-428, e.g., Compound I, or any combination thereof. In some embodiments, the delivery agent comprises Compound II, DSPC, Cholesterol, and Compound I or PEG-DMG, e.g., with a mole ratio of about 50:10:38.5:1.5. In some embodiments, the delivery agent comprises Compound II, DSPC, Cholesterol, and Compound I or PEG-DMG, e.g., with a mole ratio of about 47.5:10.5:39.0:3.0. In some embodiments, the delivery agent comprises Compound VI, DSPC, Cholesterol, and Compound I or PEG-DMG, e.g., with a mole ratio of about 50:10:38.5:1.5. In some embodiments, the delivery agent comprises Compound VI, DSPC, Cholesterol, and Compound I or PEG-DMG, e.g., with a mole ratio of about 47.5:10.5:39.0:3.0.

A pharmaceutically acceptable excipient, as used herein, includes, but are not limited to, any and all solvents, dispersion media, or other liquid vehicles, dispersion or suspension aids, diluents, granulating and/or dispersing agents, surface active agents, isotonic agents, thickening or emulsifying agents, preservatives, binders, lubricants or oil, coloring, sweetening or flavoring agents, stabilizers, antioxidants, antimicrobial or antifungal agents, osmolality adjusting agents, pH adjusting agents, buffers, chelants, cyoprotectants, and/or bulking agents, as suited to the particular dosage form desired. Various excipients for formulating pharmaceutical compositions and techniques for preparing the composition are known in the art (see Remington: The Science and Practice of Pharmacy, 21st Edition, A. R. Gennaro (Lippincott, Williams & Wilkins, Baltimore, M D, 2006; incorporated herein by reference in its entirety).

Exemplary diluents include, but are not limited to, calcium or sodium carbonate, calcium phosphate, calcium hydrogen phosphate, sodium phosphate, lactose, sucrose, cellulose, microcrystalline cellulose, kaolin, mannitol, sorbitol, etc., and/or combinations thereof.

Exemplary granulating and/or dispersing agents include, but are not limited to, starches, pregelatinized starches, or microcrystalline starch, alginic acid, guar gum, agar, poly (vinyl-pyrrolidone), (providone), cross-linked poly(vinyl-pyrrolidone) (crospovidone), cellulose, methylcellulose, carboxymethyl cellulose, cross-linked sodium carboxymethyl cellulose (croscarmellose), magnesium aluminum silicate (VEEGUM®), sodium lauryl sulfate, etc., and/or combinations thereof.

Exemplary surface active agents and/or emulsifiers include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), sorbitan fatty acid esters (e.g., polyoxyethylene sorbitan monooleate [TWEEN®80], sorbitan monopalmitate [SPAN®40], glyceryl monooleate, polyoxyethylene esters, polyethylene glycol fatty acid esters (e.g., CREMOPHOR®), polyoxyethylene ethers (e.g., polyoxyethylene lauryl ether [BRIJ®30]), PLUORINC®F 68, POLOXAMER®188, etc. and/or combinations thereof.

Exemplary binding agents include, but are not limited to, starch, gelatin, sugars (e.g., sucrose, glucose, dextrose, dextrin, molasses, lactose, lactitol, mannitol), amino acids (e.g., glycine), natural and synthetic gums (e.g., acacia, sodium alginate), ethylcellulose, hydroxyethylcellulose, hydroxypropyl methylcellulose, etc., and combinations thereof.

Oxidation is a potential degradation pathway for mRNA, especially for liquid mRNA formulations. In order to prevent oxidation, antioxidants can be added to the formulations. Exemplary antioxidants include, but are not limited to, alpha tocopherol, ascorbic acid, ascorbyl palmitate, benzyl alcohol, butylated hydroxyanisole, m-cresol, methionine, butylated hydroxytoluene, monothioglycerol, sodium or potassium metabisulfite, propionic acid, propyl gallate, sodium ascorbate, etc., and combinations thereof.

Exemplary chelating agents include, but are not limited to, ethylenediaminetetraacetic acid (EDTA), citric acid monohydrate, disodium edetate, fumaric acid, malic acid, phosphoric acid, sodium edetate, tartaric acid, trisodium edetate, etc., and combinations thereof.

Exemplary antimicrobial or antifungal agents include, but are not limited to, benzalkonium chloride, benzethonium chloride, methyl paraben, ethyl paraben, propyl paraben, butyl paraben, benzoic acid, hydroxybenzoic acid, potassium or sodium benzoate, potassium or sodium sorbate, sodium propionate, sorbic acid, etc., and combinations thereof.

Exemplary preservatives include, but are not limited to, vitamin A, vitamin C, vitamin E, beta-carotene, citric acid, ascorbic acid, butylated hydroxyanisol, ethylenediamine, sodium lauryl sulfate (SLS), sodium lauryl ether sulfate (SLES), etc., and combinations thereof.

In some embodiments, the pH of polynucleotide solutions is maintained between pH 5 and pH 8 to improve stability. Exemplary buffers to control pH can include, but are not limited to sodium phosphate, sodium citrate, sodium succinate, histidine (or histidine-HCl), sodium malate, sodium carbonate, etc., and/or combinations thereof.

Exemplary lubricating agents include, but are not limited to, magnesium stearate, calcium stearate, stearic acid, silica, talc, malt, hydrogenated vegetable oils, polyethylene glycol, sodium benzoate, sodium or magnesium lauryl sulfate, etc., and combinations thereof.

The pharmaceutical composition or formulation described here can contain a cryoprotectant to stabilize a polynucleotide described herein during freezing. Exemplary cryoprotectants include, but are not limited to mannitol, sucrose, trehalose, lactose, glycerol, dextrose, etc., and combinations thereof.

The pharmaceutical composition or formulation described here can contain a bulking agent in lyophilized polynucleotide formulations to yield a "pharmaceutically elegant" cake, stabilize the lyophilized polynucleotides during long term (e.g., 36 month) storage. Exemplary bulking agents of the present invention can include, but are not limited to sucrose, trehalose, mannitol, glycine, lactose, raffinose, and combinations thereof.

In some embodiments, the pharmaceutical composition or formulation further comprises a delivery agent. The delivery agent of the present disclosure can include, without limitation, liposomes, lipid nanoparticles, lipidoids, polymers, lipoplexes, microvesicles, exosomes, peptides, proteins, cells transfected with polynucleotides, hyaluronidase, nanoparticle mimics, nanotubes, conjugates, and combinations thereof.

20. Delivery Agents a. Lipid Compound

The present disclosure provides pharmaceutical compositions with advantageous properties. The lipid compositions described herein may be advantageously used in lipid nanoparticle compositions for the delivery of therapeutic and/or prophylactic agents, e.g., mRNAs, to mammalian cells or organs. For example, the lipids described herein have little or no immunogenicity. For example, the lipid compounds disclosed herein have a lower immunogenicity as compared to a reference lipid (e.g., MC3, KC2, or DLinDMA). For example, a formulation comprising a lipid disclosed herein and a therapeutic or prophylactic agent, e.g., mRNA, has an increased therapeutic index as compared to a corresponding formulation which comprises a reference lipid (e.g., MC3, KC2, or DLinDMA) and the same therapeutic or prophylactic agent.

In certain embodiments, the present application provides pharmaceutical compositions comprising:

(a) a polynucleotide comprising a nucleotide sequence encoding a PCCA or PCCB polypeptide; and (b) a delivery agent.

Lipid Nanoparticle Formulations

In some embodiments, nucleic acids of the invention (e.g. PCCA or PCCB mRNA) are formulated in a lipid nanoparticle (LNP). Lipid nanoparticles typically comprise ionizable cationic lipid, non-cationic lipid, sterol and PEG lipid components along with the nucleic acid cargo of interest. The lipid nanoparticles of the invention can be generated using components, compositions, and methods as are generally known in the art, see for example PCT/US2016/052352; PCT/US2016/068300; PCT/US2017/037551; PCT/

US2015/027400; PCT/US2016/047406; PCT/US2016000129; PCT/US2016/014280; PCT/US2016/014280; PCT/US2017/038426; PCT/US2014/027077; PCT/US2014/055394; PCT/US2016/52117; PCT/US2012/069610; PCT/US2017/027492; PCT/US2016/059575 and PCT/US2016/069491 all of which are incorporated by reference herein in their entirety.

Nucleic acids of the present disclosure (e.g. PCCA or PCCB mRNA) are typically formulated in lipid nanoparticle. In some embodiments, the lipid nanoparticle comprises at least one ionizable cationic lipid, at least one non-cationic lipid, at least one sterol, and/or at least one polyethylene glycol (PEG)-modified lipid.

In some embodiments, the lipid nanoparticle comprises a molar ratio of 20-60% ionizable cationic lipid. For example, the lipid nanoparticle may comprise a molar ratio of 20-50%, 20-40%, 20-30%, 30-60%, 30-50%, 30-40%, 40-60%, 40-50%, or 50-60% ionizable cationic lipid. In some embodiments, the lipid nanoparticle comprises a molar ratio of 20%, 30%, 40%, 50, or 60% ionizable cationic lipid.

In some embodiments, the lipid nanoparticle comprises a molar ratio of 5-25% non-cationic lipid. For example, the lipid nanoparticle may comprise a molar ratio of 5-20%, 5-15%, 5-10%, 10-25%, 10-20%, 10-25%, 15-25%, 15-20%, or 20-25% non-cationic lipid. In some embodiments, the lipid nanoparticle comprises a molar ratio of 5%, 10%, 15%, 20%, or 25% non-cationic lipid.

In some embodiments, the lipid nanoparticle comprises a molar ratio of 25-55% sterol. For example, the lipid nanoparticle may comprise a molar ratio of 25-50%, 25-45%, 25-40%, 25-35%, 25-30%, 30-55%, 30-50%, 30-45%, 30-40%, 30-35%, 35-55%, 35-50%, 35-45%, 35-40%, 40-55%, 40-50%, 40-45%, 45-55%, 45-50%, or 50-55% sterol. In some embodiments, the lipid nanoparticle comprises a molar ratio of 25%, 30%, 35%, 40%, 45%, 50%, or 55% sterol.

In some embodiments, the lipid nanoparticle comprises a molar ratio of 0.5-15% PEG-modified lipid. For example, the lipid nanoparticle may comprise a molar ratio of 0.5-10%, 0.5-5%, 1-15%, 1-10%, 1-5%, 2-15%, 2-10%, 2-5%, 5-15%, 5-10%, or 10-15%. In some embodiments, the lipid nanoparticle comprises a molar ratio of 0.5%, 1%, 2%, 3%, 4%, 5%, 6%, 7%, 8%, 9%, 10%, 11%, 12%, 13%, 14%, or 15% PEG-modified lipid.

In some embodiments, the lipid nanoparticle comprises a molar ratio of 20-60% ionizable cationic lipid, 5-25% non-cationic lipid, 25-55% sterol, and 0.5-15% PEG-modified lipid.

Ionizable Lipids

In some aspects, the ionizable lipids of the present disclosure may be one or more of compounds of Formula (I):

$$(I)$$

or their N-oxides, or salts or isomers thereof, wherein:

$R^1$ is selected from the group consisting of $C_{5-30}$ alkyl, $C_{5-20}$ alkenyl, —R*YR", —YR", and —R"M'R';

$R^2$ and $R^3$ are independently selected from the group consisting of H, $C_{1-14}$ alkyl, $C_{2-14}$ alkenyl, —R*YR", —YR", and —R*OR", or $R^2$ and $R^3$, together with the atom to which they are attached, form a heterocycle or carbocycle;

$R^4$ is selected from the group consisting of hydrogen, a $C_{3-6}$ carbocycle, —$(CH_2)_nQ$, —$(CH_2)_n$CHQR, CHQR, —$CQ(R)_2$, and unsubstituted $C_{1-6}$ alkyl, where Q is selected from a carbocycle, heterocycle, —OR, —$O(CH_2)_nN(R)_2$, —C(O)OR, —OC(O)R, —$CX_3$, —$CX_2H$, —$CXH_2$, —CN, —$N(R)_2$, —$C(O)N(R)_2$, —N(R)C(O)R, —$N(R)S(O)_2R$, —$N(R)C(O)N(R)_2$, —$N(R)C(S)N(R)_2$, —$N(R)R^8$, —$N(R)S(O)_2R_8$, —$O(CH_2)_nOR$, —N(R)C(=NR_9)N(R)_2$, —N(R)C(=CHR_9)N(R)_2$, —OC(O)N (R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —N(OR)C(=NR_9)N(R)_2$, —N(OR)C(=CHR_9)N(R)_2$, —$C(=NR_9)N(R)_2$ $C(=NR_9)R$, —C(O)N(R)OR, and —$C(R)N(R)_2C(O)$ OR, and each n is independently selected from 1, 2, 3, 4, and 5;

each $R^5$ is independently selected from the group consisting of $C_{1-3}$ alkyl, $C_{2-3}$ alkenyl, and H;

each $R^6$ is independently selected from the group consisting of $C_{1-3}$ alkyl, $C_{2-3}$ alkenyl, and H;

M and M' are independently selected from —C(O)O—, —OC(O)—, —OC(O)-M"-C(O) O—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group, in which M" is a bond, $C_{1-13}$ alkyl or $C_{2-13}$ alkenyl;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-15}$ alkyl and $C_{3-15}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and wherein when $R^4$ is —$(CH_2)_nQ$, —$(CH_2)_n$CHQR, —CHQR, or —$CQ(R)_2$, then (i) Q is not —$N(R)_2$ when n is 1, 2, 3, 4 or 5, or (ii) Q is not 5, 6, or 7-membered heterocycloalkyl when n is 1 or 2.

In certain embodiments, a subset of compounds of Formula (I) includes those of Formula (IA):

$$(IA)$$

or its N-oxide, or a salt or isomer thereof, wherein 1 is selected from 1, 2, 3, 4, and 5; m is selected from 5, 6, 7, 8, and 9; $M_1$ is a bond or M'; $R^4$ is hydrogen, unsubstituted $C_{1-3}$ alkyl, or —$(CH_2)_n$Q, in which Q is OH, —NHC(S)N(R)$_2$, —NHC(O)N(R)$_2$, —N(R)C(O) R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O) OR, heteroaryl or heterocycloalkyl; M and M' are independently selected from —C(O)O—, —OC(O)—, —OC(O)-M''-C(O)O—, —C(O)N(R')—, —P(O)(OR') O—, —S—S—, an aryl group, and a heteroaryl group; and $R_2$ and $R_3$ are independently selected from the group consisting of H, $C_{1-14}$ alkyl, and $C_{2-14}$ alkenyl. For example, m is 5, 7, or 9. For example, Q is OH, —NHC(S)N(R)$_2$, or —NHC(O)N(R)$_2$. For example, Q is —N(R)C(O)R, or —N(R)S(O)$_2$R.

In certain embodiments, a subset of compounds of Formula (I) includes those of Formula (IB):

(IB)

or its N-oxide, or a salt or isomer thereof in which all variables are as defined herein. For example, m is selected from 5, 6, 7, 8, and 9; $R_4$ is hydrogen, unsubstituted $C_{1-3}$ alkyl, or —$(CH_2)_n$Q, in which Q is OH, —NHC(S)N(R)$_2$, —NHC(O)N(R)$_2$, —N(R)C(O)R, —N(R)S(O)$_2$R, —N(R) R$_8$, —NHC(=NR$_9$)N(R)$_2$, —NHC(=CHR$_9$)N(R)$_2$, —OC (O)N(R)$_2$, —N(R)C(O)OR, heteroaryl or heterocycloalkyl; M and M' are independently selected from —C(O)O—, —OC(O)—, —OC(O)-M''-C(O)O—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl. For example, m is 5, 7, or 9. For example, Q is OH, —NHC(S) N(R)$_2$, or —NHC(O)N(R)$_2$. For example, Q is —N(R)C(O) R, or —N(R)S(O)$_2$R.

In certain embodiments, a subset of compounds of Formula (I) includes those of Formula (II):

(II)

or its N-oxide, or a salt or isomer thereof, wherein 1 is selected from 1, 2, 3, 4, and 5; $M_1$ is a bond or M'; $R_4$ is hydrogen, unsubstituted $C_{1-3}$ alkyl, or —$(CH_2)_n$Q, in which n is 2, 3, or 4, and Q is OH, —NHC(S)N(R)$_2$, —NHC(O) N(R)$_2$, —N(R)C(O)R, —N(R)S(O)$_2$R, —N(R)R$_8$, —NHC (=NR$_9$)N(R)$_2$, —NHC(=CHR$_9$)N(R)$_2$, —OC(O)N(R)$_2$, —N(R)C(O)OR, heteroaryl or heterocycloalkyl; M and M' are independently selected from —C(O)O—, —OC(O)—, —OC(O)-M''-C(O)O—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In one embodiment, the compounds of Formula (I) are of Formula (IIa), (IIa)

or their N-oxides, or salts or isomers thereof, wherein $R_4$ is as described herein.

In another embodiment, the compounds of Formula (I) are of Formula (IIb), (IIb)

or their N-oxides, or salts or isomers thereof, wherein $R_4$ is as described herein.

In another embodiment, the compounds of Formula (I) are of Formula (IIc) or (IIe):

(IIc)

or (IIe)

or their N-oxides, or salts or isomers thereof, wherein $R_4$ is as described herein.

In another embodiment, the compounds of Formula (I) are of Formula (IIf):

(IIf)

or their N-oxides, or salts or isomers thereof, wherein M is —C(O)O— or —OC(O)—, M" is $C_{1-6}$ alkyl or $C_{2-6}$ alkenyl, $R_2$ and $R_3$ are independently selected from the group consisting of $C_{5-14}$ alkyl and $C_{5-14}$ alkenyl, and n is selected from 2, 3, and 4.

In a further embodiment, the compounds of Formula (I) are of Formula (IId), (IId)

or their N-oxides, or salts or isomers thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In a further embodiment, the compounds of Formula (I) are of Formula (IIg), (IIg)

or their N-oxides, or salts or isomers thereof, wherein 1 is selected from 1, 2, 3, 4, and 5; m is selected from 5, 6, 7, 8, and 9; $M_1$ is a bond or M'; M and M' are independently selected from —C(O)O—, —OC(O)—, —OC(O)-M"-C(O)O—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl. For example, M" is $C_{1-6}$ alkyl (e.g., $C_{1-4}$ alkyl) or $C_{2-6}$ alkenyl (e.g. $C_{2-4}$ alkenyl). For example, $R_2$ and $R_3$ are independently selected from the group consisting of $C_{5-14}$ alkyl and $C_{5-14}$ alkenyl.

In some embodiments, the ionizable lipids are one or more of the compounds described in U.S. Application Nos. 62/220,091, 62/252,316, 62/253,433, 62/266,460, 62/333, 557, 62/382,740, 62/393,940, 62/471,937, 62/471,949, 62/475,140, and 62/475,166, and PCT Application No. PCT/US2016/052352.

In some embodiments, the ionizable lipids are selected from Compounds 1-280 described in U.S. Application No. 62/475,166.

In some embodiments, the ionizable lipid is (Compound II)

or a salt thereof.

In some embodiments, the ionizable lipid is (Compound III)

or a salt thereof.

In some embodiments, the ionizable lipid is (Compound IV)

or a salt thereof.

In some embodiments, the ionizable lipid is (Compound V)

or a salt thereof.

The central amine moiety of a lipid according to Formula (I), (IA), (IB), (II), (IIa), (IIb), (IIc), (IId), (IIe), (IIf), or (IIg) may be protonated at a physiological pH. Thus, a lipid may have a positive or partial positive charge at physiological pH. Such lipids may be referred to as cationic or ionizable (amino)lipids. Lipids may also be zwitterionic, i.e., neutral molecules having both a positive and a negative charge.

In some aspects, the ionizable lipids of the present disclosure may be one or more of compounds of formula (III), (III)

or salts or isomers thereof, wherein

W is ring A is $t$ is 1 or 2;

$A_1$ and $A_2$ are each independently selected from CH or N;

Z is $CH_2$ or absent wherein when Z is $CH_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of $C_{5-20}$ alkyl, $C_{5-20}$ alkenyl, —R"MR', —R*YR", —YR", and —R*OR";

$R_{X1}$ and $R_{X2}$ are each independently H or $C_{1-3}$ alkyl;

each M is independently selected from the group consisting of —C(O)O—, —OC(O)—, —OC(O)O—, —C(O)N(R')—, —N(R')C(O)—, —C(O)—, —C(S)—, —C(S)S—, —SC(S)—, —CH(OH)—, —P(O)(OR')O—, —S(O)$_2$—, —C(O)S—, —SC(O)—, an aryl group, and a heteroaryl group;

M* is $C_1$-$C_6$ alkyl, $W^1$ and $W^2$ are each independently selected from the group consisting of —O— and —N(R$_6$)—;

each $R_6$ is independently selected from the group consisting of H and $C_{1-5}$ alkyl;

$X^1$, $X^2$, and $X^3$ are independently selected from the group consisting of a bond, —CH$_2$—, —(CH$_2$)$_2$—, —CHR—, —CHY—, —C(O)—, —C(O)O—, —OC(O)—, —(CH$_2$)n-C(O)—, —C(O)—(CH$_2$)$_n$—, —(CH$_2$)n-C(O)O—, —OC(O)—(CH$_2$)$_n$—, —(CH$_2$)n-OC(O)—, —C(O)O—(CH$_2$)$_n$—, —CH(OH)—, —C(S)—, and —CH(SH)—;

each Y is independently a C$_{3-6}$ carbocycle;

each R* is independently selected from the group consisting of C$_{1-12}$ alkyl and C$_{2-12}$ alkenyl;

each R is independently selected from the group consisting of C$_{1-3}$ alkyl and a C$_{3-6}$ carbocycle;

each R' is independently selected from the group consisting of C$_{1-12}$ alkyl, C$_{2-12}$ alkenyl, and H;

each R" is independently selected from the group consisting of C$_{3-12}$ alkyl, C$_{3-12}$ alkenyl and —R*MR'; and n is an integer from 1-6;

when ring A is then i) at least one of X$^1$, X$^2$, and X$^3$ is not —CH$_2$—; and/or ii) at least one of R$_1$, R$_2$, R$_3$, R$_4$, and R$_5$ is —R"MR'.

In some embodiments, the compound is of any of formulae (IIIa1)-(IIa8).

(IIIa1)

(IIIa2)

(IIIa3)

-continued (IIIa4)

(IIIa5')

(IIIa6)

(IIIa7)

(IIIa8)

In some embodiments, the ionizable lipids are one or more of the compounds described in U.S. Application Nos. 62/271,146, 62/338,474, 62/413,345, and 62/519,826, and PCT Application No. PCT/US2016/068300.

In some embodiments, the ionizable lipids are selected from Compounds 1-156 described in U.S. Application No. 62/519,826.

In some embodiments, the ionizable lipids are selected from Compounds 1-16, 42-66, 68-76, and 78-156 described in U.S. Application No. 62/519,826.

In some embodiments, the ionizable lipid is (Compound VI)

or a salt thereof.

In some embodiments, the ionizable lipid is (Compound VII), or a salt thereof.

The central amine moiety of a lipid according to Formula (III), (IIIa1), (IIIa2), (IIIa3), (IIIa4), (IIIa5), (IIIa6), (IIIa7), or (IIIa8) may be protonated at a physiological pH. Thus, a lipid may have a positive or partial positive charge at physiological pH. Such lipids may be referred to as cationic or ionizable (amino)lipids. Lipids may also be zwitterionic, i.e., neutral molecules having both a positive and a negative charge.

Phospholipids

The lipid composition of the lipid nanoparticle composition disclosed herein can comprise one or more phospholipids, for example, one or more saturated or (poly)unsaturated phospholipids or a combination thereof. In general, phospholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Particular phospholipids can facilitate fusion to a membrane. For example, a cationic phospholipid can interact with one or more negatively charged phospholipids of a membrane (e.g., a cellular or intracellular membrane). Fusion of a phospholipid to a membrane can allow one or more elements (e.g., a therapeutic agent) of a lipid-containing composition (e.g., LNPs) to pass through the membrane permitting, e.g., delivery of the one or more elements to a target tissue.

Non-natural phospholipid species including natural species with modifications and substitutions including branching, oxidation, cyclization, and alkynes are also contemplated. For example, a phospholipid can be functionalized with or cross-linked to one or more alkynes (e.g., an alkenyl group in which one or more double bonds is replaced with a triple bond). Under appropriate reaction conditions, an alkyne group can undergo a copper-catalyzed cycloaddition upon exposure to an azide. Such reactions can be useful in functionalizing a lipid bilayer of a nanoparticle composition to facilitate membrane permeation or cellular recognition or in conjugating a nanoparticle composition to a useful component such as a targeting or imaging moiety (e.g., a dye).

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin.

In some embodiments, a phospholipid of the invention comprises 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-gly cero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine,1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

In certain embodiments, a phospholipid useful or potentially useful in the present invention is an analog or variant of DSPC. In certain embodiments, a phospholipid useful or potentially useful in the present invention is a compound of Formula (IV):

$$\text{(IV)}$$

or a salt thereof, wherein:

each $R^1$ is independently optionally substituted alkyl; or optionally two $R^1$ are joined together with the intervening atoms to form optionally substituted monocyclic carbocyclyl or optionally substituted monocyclic heterocyclyl; or optionally three $R^1$ are joined together with the intervening atoms to form optionally substituted bicyclic carbocyclyl or optionally substitute bicyclic heterocyclyl;

n is 1, 2, 3, 4, 5, 6, 7, 8, 9, or 10;

m is 0, 1, 2, 3, 4, 5, 6, 7, 8, 9, or 10;

A is of the formula:

each instance of $L^2$ is independently a bond or optionally substituted $C_{1-6}$ alkylene, wherein one methylene unit of the optionally substituted $C_{1-6}$ alkylene is optionally replaced with O, $N(R^N)$, S, C(O), $C(O)N(R^N)$, $NR^NC(O)$, C(O)O, OC(O), OC(O)O, —OC(O)N(R^N), $NR^NC(O)O$, or $NR^NC(O)N(R^N)$;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, $N(R^N)$, O, S, C(O), $C(O)N(R^N)$, —NR^NC(O), NR^NC(O)N(R^N), C(O)O, OC(O), OC(O)O, OC(O)N(R^N), $NR^NC(O)O$, —C(O)S, SC(O), C(=NR^N), C(=NR^N)N(R^N), NR^NC(=NR^N), NR^NC(=NR^N)N(R^N), —C(S), C(S)N(R^N), NR^NC(S), NR^NC(S)N(R^N), S(O), OS(O), S(O)O, OS(O)O, —OS(O)_2,

119

S(O)$_2$O, OS(O)$_2$O, N(R$^N$)S(O), S(O)N(R$^N$), N(R$^N$)S
(O)N(R$^N$), OS(O)N(R$^N$), N(R$^N$)S(O)O, S(O)$_2$, N(R$^N$)S
(O)$_2$, S(O)$_2$N(R$^N$), N(R$^N$)S(O)$_2$N(R$^N$), OS(O)$_2$N(R$^N$),
or N(R$^N$)S(O)$_2$O;

each instance of R$^N$ is independently hydrogen, optionally
substituted alkyl, or a nitrogen protecting group;

Ring B is optionally substituted carbocyclyl, optionally
substituted heterocyclyl, optionally substituted aryl, or
optionally substituted heteroaryl; and p is 1 or 2;

provided that the compound is not of the formula:

wherein each instance of R$^2$ is independently unsubstituted alkyl, unsubstituted alkenyl, or unsubstituted
alkynyl.

In some embodiments, the phospholipids may be one or
more of the phospholipids described in U.S. Application No.
62/520,530.

i) Phospholipid Head Modifications

In certain embodiments, a phospholipid useful or potentially useful in the present invention comprises a modified
phospholipid head (e.g., a modified choline group). In
certain embodiments, a phospholipid with a modified head
is DSPC, or analog thereof, with a modified quaternary
amine. For example, in embodiments of Formula (IV), at
least one of R$^1$ is not methyl. In certain embodiments, at
least one of R$^1$ is not hydrogen or methyl. In certain
embodiments, the compound of Formula (IV) is of one of
the following formulae:

120

-continued or a salt thereof, wherein:

each t is independently 1, 2, 3, 4, 5, 6, 7, 8, 9, or 10;

each t is independently 0, 1, 2, 3, 4, 5, 6, 7, 8, 9, or 10;
and each v is independently 1, 2, or 3.

In certain embodiments, a compound of Formula (IV) is
of Formula (IV-a):

(IV-a)

or a salt thereof.

In certain embodiments, a phospholipid useful or potentially useful in the present invention comprises a cyclic
moiety in place of the glyceride moiety. In certain embodiments, a phospholipid useful in the present invention is
DSPC, or analog thereof, with a cyclic moiety in place of the
glyceride moiety. In certain embodiments, the compound of
Formula (IV) is of Formula (IV-b):

(IV-b)

or a salt thereof.

(ii) Phospholipid Tail Modifications

In certain embodiments, a phospholipid useful or potentially useful in the present invention comprises a modified
tail. In certain embodiments, a phospholipid useful or potentially useful in the present invention is DSPC, or analog
thereof, with a modified tail. As described herein, a "modified tail" may be a tail with shorter or longer aliphatic chains,
aliphatic chains with branching introduced, aliphatic chains
with substituents introduced, aliphatic chains wherein one or
more methylenes are replaced by cyclic or heteroatom
groups, or any combination thereof. For example, in certain
embodiments, the compound of (IV) is of Formula (IV-a), or
a salt thereof, wherein at least one instance of R$^2$ is each
instance of R$^2$ is optionally substituted C$_{1-30}$ alkyl, wherein
one or more methylene units of R$^2$ are independently
replaced with optionally substituted carbocyclylene, optionally substituted heterocyclylene, optionally substituted
arylene, optionally substituted heteroarylene, N(R$^N$), O, S,
—C(O), C(O)N(R$^N$), NR$^N$C(O), NR$^N$C(O)N(R$^N$), C(O)O,
OC(O), OC(O)O, —OC(O)N(R$^N$), NR$^N$C(O)O, C(O)S,
SC(O), C(=NR$^N$), C(=NR$^N$)N(R$^N$), NR$^N$C(=NR$^N$),
NR$^N$C(=NR$^N$)N(R$^N$), C(S), C(S)N(R$^N$), NR$^N$C(S), NR$^N$C
(S)N(R$^N$), S(O), OS(O), —S(O)O, OS(O)O, OS(O)$_2$, S(O)$_2$
O, OS(O)$_2$O, N(R$^N$)S(O), S(O)N(R$^N$), —N(R$^N$)S(O)N(R$^N$),

121

$OS(O)N(R^N)$, $N(R^N)S(O)O$, $S(O)_2$, $N(R^N)S(O)_2$, $S(O)_2N(R^N)$, $-N(R^N)S(O)_2N(R^N)$, $OS(O)_2N(R^N)$, or $N(R^N)S(O)_2O$.

In certain embodiments, the compound of Formula (IV) is of Formula (IV-c):

(IV-c)

or a salt thereof, wherein:

each x is independently an integer between 0-30, inclusive; and each instance is G is independently selected from the group consisting of optionally substituted carbocyclylene, optionally substituted heterocyclylene, optionally substituted arylene, optionally substituted heteroarylene, $N(R^N)$, O, S, C(O), $-C(O)N(R^N)$, $NR^NC(O)$, $NR^NC(O)N(R^N)$, C(O)O, OC(O), OC(O)O, OC(O)N(R^N) $-NR^NC(O)O$, C(O)S, SC(O), $C(=NR^N)$, $C(=NR^N)N(R^N)$, $NR^NC(=NR^N)$, $-NR^NC(=NR^N)N(R^N)$, C(S), C(S)N(R^N), $NR^NC(S)$, $NR^NC(S)N(R^N)$, S(O) OS(O), $-S(O)O$, OS(O)O, OS(O)_2, S(O)_2O, OS(O)_2O, $N(R^N)S(O)$, S(O)N(R^N), $-N(R^N)S(O)N(R^N)$, OS(O)N(R^N), $N(R^N)S(O)O$, S(O)_2, N(R^N)S(O)_2, $S(O)_2N(R^N)$ $-N(R^N)S(O)_2N(R^N)$, $OS(O)_2N(R^N)$, or $N(R^N)S(O)_2O$. Each possibility represents a separate embodiment of the present invention.

In certain embodiments, a phospholipid useful or potentially useful in the present invention comprises a modified phosphocholine moiety, wherein the alkyl chain linking the quaternary amine to the phosphoryl group is not ethylene (e.g., n is not 2). Therefore, in certain embodiments, a phospholipid useful or potentially useful in the present invention is a compound of Formula (IV), wherein n is 1, 3, 4, 5, 6, 7, 8, 9, or 10. For example, in certain embodiments, a compound of Formula (IV) is of one of the following formulae:

or a salt thereof.

Alternative Lipids

In certain embodiments, a phospholipid useful or potentially useful in the present invention comprises a modified phosphocholine moiety, wherein the alkyl chain linking the quaternary amine to the phosphoryl group is not ethylene (e.g., n is not 2). Therefore, in certain embodiments, a phospholipid useful.

In certain embodiments, an alternative lipid is used in place of a phospholipid of the present disclosure.

In certain embodiments, an alternative lipid of the invention is oleic acid.

In certain embodiments, the alternative lipid is one of the following:

-continued

Structural Lipids

The lipid composition of a pharmaceutical composition disclosed herein can comprise one or more structural lipids. As used herein, the term "structural lipid" refers to sterols and also to lipids containing sterol moieties.

Incorporation of structural lipids in the lipid nanoparticle may help mitigate aggregation of other lipids in the particle. Structural lipids can be selected from the group including but not limited to, cholesterol, fecosterol, sitosterol, ergosterol, campesterol, stigmasterol, brassicasterol, tomatidine, tomatine, ursolic acid, alpha-tocopherol, hopanoids, phytosterols, steroids, and mixtures thereof. In some embodiments, the structural lipid is a sterol. As defined herein, "sterols" are a subgroup of steroids consisting of steroid alcohols. In certain embodiments, the structural lipid is a steroid. In certain embodiments, the structural lipid is cholesterol. In certain embodiments, the structural lipid is an analog of cholesterol. In certain embodiments, the structural lipid is alpha-tocopherol.

In some embodiments, the structural lipids may be one or more of the structural lipids described in U.S. Application Ser. No. 62/520,530.

Polyethylene Glycol (PEG)-Lipids

The lipid composition of a pharmaceutical composition disclosed herein can comprise one or more a polyethylene glycol (PEG) lipid.

As used herein, the term "PEG-lipid" refers to polyethylene glycol (PEG)-modified lipids. Non-limiting examples of PEG-lipids include PEG-modified phosphatidyletha-nolamine and phosphatidic acid, PEG-ceramide conjugates (e.g., PEG-CerC14 or PEG-CerC20), PEG-modified dialky-lamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG-DMPE, PEG-DPPC, or a PEG-DSPE lipid.

In some embodiments, the PEG-lipid includes, but not limited to 1,2-dimyristoyl-sn-glycerol methoxypolyethylene glycol (PEG-DMG), 1,2-distearoyl-sn-glycero-3-phospho-ethanolamine-N-[amino(polyethylene glycol)] (PEG-DSPE), PEG-disteryl glycerol (PEG-DSG), PEG-dipalme-toleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

In one embodiment, the PEG-lipid is selected from the group consisting of a PEG-modified phosphatidyletha-nolamine, a PEG-modified phosphatidic acid, a PEG-modi-fied ceramide, a PEG-modified dialkylamine, a PEG-modi-fied diacylglycerol, a PEG-modified dialkylglycerol, and mixtures thereof.

In some embodiments, the lipid moiety of the PEG-lipids includes those having lengths of from about $C_{14}$ to about $C_{22}$, preferably from about $C_{14}$ to about $C_{16}$. In some embodiments, a PEG moiety, for example an mPEG-NH$_2$, has a size of about 1000, 2000, 5000, 10,000, 15,000 or 20,000 daltons. In one embodiment, the PEG-lipid is PEG$_{2k}$-DMG.

In one embodiment, the lipid nanoparticles described herein can comprise a PEG lipid which is a non-diffusible PEG. Non-limiting examples of non-diffusible PEGs include PEG-DSG and PEG-DSPE.

PEG-lipids are known in the art, such as those described in U.S. Pat. No. 8,158,601 and International Publ. No. WO 2015/130584 A2, which are incorporated herein by reference in their entirety.

In general, some of the other lipid components (e.g., PEG lipids) of various formulae, described herein may be synthesized as described International Patent Application No. PCT/US2016/000129, filed Dec. 10, 2016, entitled "Compositions and Methods for Delivery of Therapeutic Agents," which is incorporated by reference in its entirety.

The lipid component of a lipid nanoparticle composition may include one or more molecules comprising polyethylene glycol, such as PEG or PEG-modified lipids. Such species may be alternately referred to as PEGylated lipids. A PEG lipid is a lipid modified with polyethylene glycol. A PEG lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

In some embodiments the PEG-modified lipids are a modified form of PEG DMG. PEG-DMG has the following structure:

$L^1$ is optionally substituted $C_{1-10}$ alkylene, wherein at least one methylene of the optionally substituted $C_{1-10}$ alkylene is independently replaced with optionally substituted carbocyclylene, optionally substituted heterocyclylene, optionally substituted arylene, optionally substituted heteroarylene, O, N($R^N$), S, C(O), —C(O)N($R^N$), NR$^N$C(O), C(O)O, OC(O), OC(O)O, OC(O)N($R^N$), NR$^N$C(O)O, or —NR$^N$C(O)N($R^N$);

D is a moiety obtained by click chemistry or a moiety cleavable under physiological conditions;

m is 0, 1, 2, 3, 4, 5, 6, 7, 8, 9, or 10;

A is of the formula:

each instance of $L^2$ is independently a bond or optionally substituted $C_{1-6}$ alkylene, wherein one methylene unit of the optionally substituted $C_{1-6}$ alkylene is optionally replaced with O, N($R^N$), S, C(O), C(O)N($R^N$), NR$^N$C(O), C(O)O, OC(O), OC(O)O, OC(O)N($R^N$), NR$^N$C(O)O, or NR$^N$C(O)N($R^N$);

each instance of $R^2$ is independently optionally substituted $C_{1-30}$ alkyl, optionally substituted $C_{1-30}$ alkenyl, or optionally substituted $C_{1-30}$ alkynyl; optionally In one embodiment, PEG lipids useful in the present invention can be PEGylated lipids described in International Publication No. WO2012099755, the contents of which is herein incorporated by reference in its entirety. Any of these exemplary PEG lipids described herein may be modified to comprise a hydroxyl group on the PEG chain. In certain embodiments, the PEG lipid is a PEG-OH lipid. As generally defined herein, a "PEG-OH lipid" (also referred to herein as "hydroxy-PEGylated lipid") is a PEGylated lipid having one or more hydroxyl (—OH) groups on the lipid. In certain embodiments, the PEG-OH lipid includes one or more hydroxyl groups on the PEG chain. In certain embodiments, a PEG-OH or hydroxy-PEGylated lipid comprises an —OH group at the terminus of the PEG chain. Each possibility represents a separate embodiment of the present invention.

In certain embodiments, a PEG lipid useful in the present invention is a compound of Formula (V). Provided herein are compounds of Formula (V):

or salts thereof, wherein:

$R^3$ is —OR$^O$;

$R^O$ is hydrogen, optionally substituted alkyl, or an oxygen protecting group; r is an integer between 1 and 100, inclusive;

wherein one or more methylene units of $R^2$ are independently replaced with optionally substituted carbocyclylene, optionally substituted heterocyclylene, optionally substituted arylene, optionally substituted heteroarylene, N($R^N$), O, S, C(O), —C(O)N($R^N$), NR$^N$C(O), NR$^N$C(O)N($R^N$), C(O)O, OC(O), OC(O)O, OC(O)N($R^N$), —NR$^N$C(O)O, C(O)S, SC(O), C(=NR$^N$), C(=NR$^N$)N($R^N$), NR$^N$C(=NR$^N$), —NR$^N$C(=NR$^N$)N($R^N$), C(S), C(S)N($R^N$), NR$^N$C(S), NR$^N$C(S)N($R^N$), S(O), OS(O), —S(O)O, OS(O)O, OS(O)$_2$, S(O)$_2$O, OS(O)$_2$O, N($R^N$)S(O), S(O)N($R^N$), —N($R^N$)S(O)N($R^N$), OS(O)N($R^N$), N($R^N$)S(O)O, S(O)$_2$, N($R^N$)S(O)$_2$, S(O)$_2$N($R^N$), —N($R^N$)S(O)$_2$N($R^N$), OS(O)$_2$N($R^N$), or N($R^N$)S(O)$_2$O;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2.

In certain embodiments, the compound of Formula (V) is a PEG-OH lipid (i.e., $R^3$ is —OR$^O$, and $R^O$ is hydrogen). In certain embodiments, the compound of Formula (V) is of Formula (V—OH):

or a salt thereof.

In certain embodiments, a PEG lipid useful in the present invention is a PEGylated fatty acid. In certain embodiments, a PEG lipid useful in the present invention is a compound of Formula (VI). Provided herein are compounds of Formula (VI):

(VI)

or a salts thereof, wherein:

$R^3$ is-$OR^O$;

$R^1$ is hydrogen, optionally substituted alkyl or an oxygen protecting group; r is an integer between 1 and 100, inclusive;

$R^5$ is optionally substituted $C_{10-40}$ alkyl, optionally substituted $C_{10-40}$ alkenyl, or optionally substituted $C_{10-40}$ alkynyl; and optionally one or more methylene groups of $R^5$ are replaced with optionally substituted carbocyclylene, optionally substituted heterocyclylene, optionally substituted arylene, optionally substituted heteroarylene, $N(R^N)$, O, S, C(O), C(O)N($R^N$), $NR^N$C(O), $NR^N$C(O)N($R^N$), C(O)O, OC(O), —OC(O)O, OC(O)N($R^N$), $NR^N$C(O)O, C(O)S, SC(O), C(=$NR^N$), C(=$NR^N$)N($R^N$), —$NR^N$C(=$NR^N$), $NR^N$C(=$NR^N$)N($R^N$), C(S), C(S)N($R^N$), $NR^N$C(S), $NR^N$C(S)N($R^N$), S(O), OS(O), S(O)O, OS(O)O, OS(O)$_2$, S(O)$_2$O, OS(O)$_2$O, N($R^N$)S(O), S(O)N($R^N$), N($R^N$)S(O)N($R^N$), OS(O)N($R^N$), N($R^N$)S(O)O, S(O)$_2$, N($R^N$)S(O)$_2$, S(O)$_2$N($R^N$), —N($R^N$)S(O)$_2$N($R^N$), OS(O)$_2$N($R^N$), or N($R^N$)S(O)$_2$O; and each instance of $R^N$ is independently hydrogen, optionally substituted alkyl, or a nitrogen protecting group.

In certain embodiments, the compound of Formula (VI) is of Formula (VI—OH):

(VI-OH)

or a salt thereof. In some embodiments, r is 45.

In yet other embodiments the compound of Formula (VI) is:

or a salt thereof.

In one embodiment, the compound of Formula (VI) is

In some aspects, the lipid composition of the pharmaceutical compositions disclosed herein does not comprise a PEG-lipid.

In some embodiments, the PEG-lipids may be one or more of the PEG lipids described in U.S. Application No. 62/520,530.

In some embodiments, a PEG lipid of the invention comprises a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In some embodiments, the PEG-modified lipid is PEG-DMG, PEG-c-DOMG (also referred to as PEG-DOMG), PEG-DSG and/or PEG-DPG.

In some embodiments, a LNP of the invention comprises an ionizable cationic lipid of any of Formula I, II or III, a phospholipid comprising DSPC, a structural lipid, and a PEG lipid comprising PEG-DMG.

In some embodiments, a LNP of the invention comprises an ionizable cationic lipid of any of Formula I, II or III, a phospholipid comprising DSPC, a structural lipid, and a PEG lipid comprising a compound having Formula VI.

In some embodiments, a LNP of the invention comprises an ionizable cationic lipid of Formula I, II or III, a phospholipid comprising a compound having Formula IV, a structural lipid, and the PEG lipid comprising a compound having Formula V or VI.

In some embodiments, a LNP of the invention comprises an ionizable cationic lipid of Formula I, II or III, a phospholipid comprising a compound having Formula IV, a structural lipid, and the PEG lipid comprising a compound having Formula V or VI.

In some embodiments, a LNP of the invention comprises an ionizable cationic lipid of Formula I, II or III, a phospholipid having Formula IV, a structural lipid, and a PEG lipid comprising a compound having Formula VI.

In some embodiments, a LNP of the invention comprises an ionizable cationic lipid of (Compound I)

and a PEG lipid comprising Formula VI.

In some embodiments, a LNP of the invention comprises an ionizable cationic lipid of and an alternative lipid comprising oleic acid.

In some embodiments, a LNP of the invention comprises an ionizable cationic lipid of an alternative lipid comprising oleic acid, a structural lipid comprising cholesterol, and a PEG lipid comprising a compound having Formula VI.

In some embodiments, a LNP of the invention comprises an ionizable cationic lipid of a phospholipid comprising DOPE, a structural lipid comprising cholesterol, and a PEG lipid comprising a compound having Formula VI.

In some embodiments, a LNP of the invention comprises an ionizable cationic lipid of a phospholipid comprising DOPE, a structural lipid comprising cholesterol, and a PEG lipid comprising a compound having Formula VII.

In some embodiments, a LNP of the invention comprises an N:P ratio of from about 2:1 to about 30:1.

In some embodiments, a LNP of the invention comprises an N:P ratio of about 6:1.

In some embodiments, a LNP of the invention comprises an N:P ratio of about 3:1.

In some embodiments, a LNP of the invention comprises a wt/wt ratio of the ionizable cationic lipid component to the RNA of from about 10:1 to about 100:1.

In some embodiments, a LNP of the invention comprises a wt/wt ratio of the ionizable cationic lipid component to the RNA of about 20:1.

In some embodiments, a LNP of the invention comprises a wt/wt ratio of the ionizable cationic lipid component to the RNA of about 10:1.

In some embodiments, a LNP of the invention has a mean diameter from about 50 nm to about 150 nm.

In some embodiments, a LNP of the invention has a mean diameter from about 70 nm to about 120 nm.

As used herein, the term "alkyl", "alkyl group", or "alkylene" means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms), which is optionally substituted. The notation "C1-14 alkyl" means an optionally substituted linear or branched, saturated hydrocarbon including 1 14 carbon atoms. Unless otherwise specified, an alkyl group described herein refers to both unsubstituted and substituted alkyl groups.

As used herein, the term "alkenyl", "alkenyl group", or "alkenylene" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond, which is optionally substituted. The notation "C2-14 alkenyl" means an optionally substituted linear or branched hydrocarbon including 2 14 carbon atoms and at least one carbon-carbon double bond. An alkenyl group may include one, two, three, four, or more carbon-carbon double bonds. For example, C18 alkenyl may include one or more double bonds. A C18 alkenyl group including two double bonds may be a linoleyl group. Unless otherwise specified, an alkenyl group described herein refers to both unsubstituted and substituted alkenyl groups.

As used herein, the term "alkynyl", "alkynyl group", or "alkynylene" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one carbon-carbon triple bond, which is optionally substituted. The notation "C2-14 alkynyl" means an optionally substituted linear or branched hydrocarbon including 2 14 carbon atoms and at least one carbon-carbon triple bond. An alkynyl group may include one, two, three, four, or more carbon-carbon triple bonds. For example, C18 alkynyl may include one or more carbon-carbon triple bonds. Unless otherwise specified, an alkynyl group described herein refers to both unsubstituted and substituted alkynyl groups.

As used herein, the term "carbocycle" or "carbocyclic group" means an optionally substituted mono- or multi-cyclic system including one or more rings of carbon atoms. Rings may be three, four, five, six, seven, eight, nine, ten, eleven, twelve, thirteen, fourteen, fifteen, sixteen, seventeen, eighteen, nineteen, or twenty membered rings. The notation "C3-6 carbocycle" means a carbocycle including a single ring having 3-6 carbon atoms. Carbocycles may include one or more carbon-carbon double or triple bonds and may be non-aromatic or aromatic (e.g., cycloalkyl or aryl groups). Examples of carbocycles include cyclopropyl, cyclopentyl, cyclohexyl, phenyl, naphthyl, and 1,2 dihydronaphthyl groups. The term "cycloalkyl" as used herein means a non-aromatic carbocycle and may or may not include any double or triple bond. Unless otherwise specified, carbocycles described herein refers to both unsubstituted and substituted carbocycle groups, i.e., optionally substituted carbocycles.

As used herein, the term "heterocycle" or "heterocyclic group" means an optionally substituted mono- or multi-cyclic system including one or more rings, where at least one ring includes at least one heteroatom. Heteroatoms may be, for example, nitrogen, oxygen, or sulfur atoms. Rings may be three, four, five, six, seven, eight, nine, ten, eleven, twelve, thirteen, or fourteen membered rings. Heterocycles may include one or more double or triple bonds and may be non-aromatic or aromatic (e.g., heterocycloalkyl or heteroaryl groups). Examples of heterocycles include imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl groups. The term "heterocycloalkyl" as used herein means a non-aromatic heterocycle and may or may not include any double or triple bond. Unless otherwise specified, heterocycles described herein refers to both unsubstituted and substituted heterocycle groups, i.e., optionally substituted heterocycles.

As used herein, the term "heteroalkyl", "heteroalkenyl", or "heteroalkynyl", refers respectively to an alkyl, alkenyl, alkynyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. Unless otherwise specified, heteroalkyls, heteroalkenyls, or heteroalkynyls described herein refers to both unsubstituted and substituted heteroalkyls, heteroalkenyls, or heteroalkynyls, i.e., optionally substituted heteroalkyls, heteroalkenyls, or heteroalkynyls.

As used herein, a "biodegradable group" is a group that may facilitate faster metabolism of a lipid in a mammalian entity. A biodegradable group may be selected from the group consisting of, but is not limited to, $-C(O)O-$, $-OC(O)-$, $-C(O)N(R')-$, $-N(R')C(O)-$, $-C(O)-$, $-C(S)-$, $-C(S)S-$, $-SC(S)-$, $-CH(OH)-$, $-P(O)(OR')O-$, $-S(O)_2-$, an aryl group, and a heteroaryl group. As used herein, an "aryl group" is an optionally substituted carbocyclic group including one or more aromatic rings. Examples of aryl groups include phenyl and naphthyl groups. As used herein, a "heteroaryl group" is an optionally substituted heterocyclic group including one or more aromatic rings. Examples of heteroaryl groups include pyrrolyl, furyl, thiophenyl, imidazolyl, oxazolyl, and thiazolyl. Both aryl and heteroaryl groups may be optionally substituted. For example, M and M' can be selected from the non-limiting group consisting of optionally substituted phenyl, oxazole, and thiazole. In the formulas herein, M and M' can be independently selected from the list of biodegradable groups above. Unless otherwise specified, aryl or heteroaryl groups described herein refers to both unsubstituted and substituted groups, i.e., optionally substituted aryl or heteroaryl groups.

Alkyl, alkenyl, and cyclyl (e.g., carbocyclyl and heterocyclyl) groups may be optionally substituted unless otherwise specified. Optional substituents may be selected from the group consisting of, but are not limited to, a halogen atom (e.g., a chloride, bromide, fluoride, or iodide group), a carboxylic acid (e.g., C(O)OH), an alcohol (e.g., a hydroxyl, OH), an ester (e.g., C(O)OR OC(O)R), an aldehyde (e.g., C(O)H), a carbonyl (e.g., C(O)R, alternatively represented by C═O), an acyl halide (e.g., C(O)X, in which X is a halide selected from bromide, fluoride, chloride, and iodide), a carbonate (e.g., OC(O)OR), an alkoxy (e.g., OR), an acetal (e.g., C(OR)$_2$R"", in which each OR are alkoxy groups that can be the same or different and R"" is an alkyl or alkenyl group), a phosphate (e.g., P(O)43-), a thiol (e.g., SH), a sulfoxide (e.g., S(O)R), a sulfinic acid (e.g., S(O)OH), a sulfonic acid (e.g., S(O)2OH), a thial (e.g., C(S)H), a sulfate (e.g., S(O)42-), a sulfonyl (e.g., S(O)2), an amide (e.g., C(O)NR2, or N(R)C(O)R), an azido (e.g., N3), a nitro (e.g., NO2), a cyano (e.g., CN), an isocyano (e.g., NC), an acyloxy (e.g., OC(O)R), an amino (e.g., NR2, NRH, or NH2), a carbamoyl (e.g., OC(O)NR2, OC(O)NRH, or OC(O)NH2), a sulfonamide (e.g., S(O)2NR2, S(O)2NRH, S(O)2NH2, N(R)S(O)2R, N(H)S(O)2R, N(R)S(O)2H, or N(H)S(O)2H), an alkyl group, an alkenyl group, and a cyclyl (e.g., carbocyclyl or heterocyclyl) group. In any of the preceding, R is an alkyl or alkenyl group, as defined herein. In some embodiments, the substituent groups themselves may be further substituted with, for example, one, two, three, four, five, or six substituents as defined herein. For example, a C1 6 alkyl group may be further substituted with one, two, three, four, five, or six substituents as described herein.

Compounds of the disclosure that contain nitrogens can be converted to N-oxides by treatment with an oxidizing agent (e.g., 3-chloroperoxybenzoic acid (mCPBA) and/or hydrogen peroxides) to afford other compounds of the disclosure. Thus, all shown and claimed nitrogen-containing compounds are considered, when allowed by valency and structure, to include both the compound as shown and its N-oxide derivative (which can be designated as N□O or N+—O—). Furthermore, in other instances, the nitrogens in the compounds of the disclosure can be converted to N-hydroxy or N-alkoxy compounds. For example, N-hydroxy compounds can be prepared by oxidation of the parent amine by an oxidizing agent such as m CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted C1-C 6 alkyl, C1-C6 alkenyl, C1-C6 alkynyl, 3-14-membered carbocycle or 3-14-membered heterocycle) derivatives.

(vi) Other Lipid Composition Components

The lipid composition of a pharmaceutical composition disclosed herein can include one or more components in addition to those described above. For example, the lipid composition can include one or more permeability enhancer molecules, carbohydrates, polymers, surface altering agents (e.g., surfactants), or other components. For example, a permeability enhancer molecule can be a molecule described by U.S. Patent Application Publication No. 2005/0222064. Carbohydrates can include simple sugars (e.g., glucose) and polysaccharides (e.g., glycogen and derivatives and analogs thereof).

A polymer can be included in and/or used to encapsulate or partially encapsulate a pharmaceutical composition disclosed herein (e.g., a pharmaceutical composition in lipid nanoparticle form). A polymer can be biodegradable and/or biocompatible. A polymer can be selected from, but is not limited to, polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates.

The ratio between the lipid composition and the polynucleotide range can be from about 10:1 to about 60:1 (wt/wt).

In some embodiments, the ratio between the lipid composition and the polynucleotide can be about 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1 or 60:1 (wt/wt). In some embodiments, the wt/wt ratio of the lipid composition to the polynucleotide encoding a therapeutic agent is about 20:1 or about 15:1.

In some embodiments, the pharmaceutical composition disclosed herein can contain more than one polypeptides. For example, a pharmaceutical composition disclosed herein can contain two or more polynucleotides (e.g., RNA, e.g., mRNA).

In one embodiment, the lipid nanoparticles described herein can comprise polynucleotides (e.g., mRNA) in a lipid:polynucleotide weight ratio of 5:1, 10:1, 15:1, 20:1, 25:1, 30:1, 35:1, 40:1, 45:1, 50:1, 55:1, 60:1 or 70:1, or a range or any of these ratios such as, but not limited to, 5:1 to about 10:1, from about 5:1 to about 15:1, from about 5:1 to about 20:1, from about 5:1 to about 25:1, from about 5:1 to about 30:1, from about 5:1 to about 35:1, from about 5:1 to about 40:1, from about 5:1 to about 45:1, from about 5:1 to about 50:1, from about 5:1 to about 55:1, from about 5:1 to about 60:1, from about 5:1 to about 70:1, from about 10:1 to about 15:1, from about 10:1 to about 20:1, from about 10:1 to about 25:1, from about 10:1 to about 30:1, from about 10:1 to about 35:1, from about 10:1 to about 40:1, from about 10:1 to about 45:1, from about 10:1 to about 50:1, from about 10:1 to about 55:1, from about 10:1 to about 60:1, from about 10:1 to about 70:1, from about 15:1 to about 20:1, from about 15:1 to about 25:1, from about 15:1 to about 30:1, from about 15:1 to about 35:1, from about 15:1 to about 40:1, from about 15:1 to about 45:1, from about 15:1 to about 50:1, from about 15:1 to about 55:1, from about 15:1 to about 60:1 or from about 15:1 to about 70:1.

In one embodiment, the lipid nanoparticles described herein can comprise the polynucleotide in a concentration from approximately 0.1 mg/ml to 2 mg/ml such as, but not limited to, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml or greater than 2.0 mg/ml.

(vii) Nanoparticle Compositions

In some embodiments, the pharmaceutical compositions disclosed herein are formulated as lipid nanoparticles (LNP). Accordingly, the present disclosure also provides nanoparticle compositions comprising (i) a lipid composition comprising a delivery agent such as compound as described herein, and (ii) a polynucleotide encoding a PCCA or PCCB polypeptide. In such nanoparticle composition, the lipid composition disclosed herein can encapsulate the polynucleotide encoding a PCCA or PCCB polypeptide.

Nanoparticle compositions are typically sized on the order of micrometers or smaller and can include a lipid bilayer. Nanoparticle compositions encompass lipid nanoparticles (LNPs), liposomes (e.g., lipid vesicles), and lipoplexes. For example, a nanoparticle composition can be a liposome having a lipid bilayer with a diameter of 500 nm or less.

Nanoparticle compositions include, for example, lipid nanoparticles (LNPs), liposomes, and lipoplexes. In some embodiments, nanoparticle compositions are vesicles including one or more lipid bilayers. In certain embodiments, a nanoparticle composition includes two or more concentric bilayers separated by aqueous compartments. Lipid bilayers can be functionalized and/or crosslinked to one another. Lipid bilayers can include one or more ligands, proteins, or channels.

In one embodiment, a lipid nanoparticle comprises an ionizable lipid, a structural lipid, a phospholipid, and mRNA. In some embodiments, the LNP comprises an ionizable lipid, a PEG-modified lipid, a sterol and a structural lipid. In some embodiments, the LNP has a molar ratio of about 20-60% ionizable lipid:about 5-25% structural lipid: about 25-55% sterol; and about 0.5-15% PEG-modified lipid.

In some embodiments, the LNP has a polydispersity value of less than 0.4. In some embodiments, the LNP has a net neutral charge at a neutral pH. In some embodiments, the LNP has a mean diameter of 50-150 nm. In some embodiments, the LNP has a mean diameter of 80-100 nm.

As generally defined herein, the term "lipid" refers to a small molecule that has hydrophobic or amphiphilic properties. Lipids may be naturally occurring or synthetic. Examples of classes of lipids include, but are not limited to, fats, waxes, sterol-containing metabolites, vitamins, fatty acids, glycerolipids, glycerophospholipids, sphingolipids, saccharolipids, and polyketides, and prenol lipids. In some instances, the amphiphilic properties of some lipids leads them to form liposomes, vesicles, or membranes in aqueous media.

In some embodiments, a lipid nanoparticle (LNP) may comprise an ionizable lipid. As used herein, the term "ionizable lipid" has its ordinary meaning in the art and may refer to a lipid comprising one or more charged moieties. In some embodiments, an ionizable lipid may be positively charged or negatively charged. An ionizable lipid may be positively charged, an which case it can be referred to as "cationic lipid". In certain embodiments, an ionizable lipid molecule may comprise an amine group, and can be referred to as an ionizable amino lipid. As used herein, a "charged moiety" is a chemical moiety that carries a formal electronic charge, e.g., monovalent (+1, or −1), divalent (+2, or −2), trivalent (+3, or −3), etc. The charged moiety may be anionic (i.e., negatively charged) or cationic (i.e., positively charged). Examples of positively-charged moieties include amine groups (e.g., primary, secondary, and/or tertiary amines), ammonium groups, pyridinium groups, guanidine groups, and imidizolium groups. In a particular embodiment, the charged moieties comprise amine groups. Examples of negatively-charged groups or precursors thereof, include carboxylate groups, sulfonate groups, sulfate groups, phosphonate groups, phosphate groups, hydroxyl groups, and the like. The charge of the charged moiety may vary, in some cases, with the environmental conditions, for example, changes in pH may alter the charge of the moiety, and/or cause the moiety to become charged or uncharged. In general, the charge density of the molecule may be selected as desired.

It should be understood that the terms "charged" or "charged moiety" does not refer to a "partial negative charge" or "partial positive charge" on a molecule. The terms "partial negative charge" and "partial positive charge" are given its ordinary meaning in the art. A "partial negative charge" may result when a functional group comprises a bond that becomes polarized such that electron density is pulled toward one atom of the bond, creating a partial negative charge on the atom. Those of ordinary skill in the art will, in general, recognize bonds that can become polarized in this way.

In some embodiments, the ionizable lipid is an ionizable amino lipid, sometimes referred to in the art as an "ionizable cationic lipid". In one embodiment, the ionizable amino lipid may have a positively charged hydrophilic head and a hydrophobic tail that are connected via a linker structure.

In addition to these, an ionizable lipid may also be a lipid including a cyclic amine group.

In one embodiment, the ionizable lipid may be selected from, but not limited to, a ionizable lipid described in International Publication Nos. WO2013086354 and WO2013116126; the contents of each of which are herein incorporated by reference in their entirety.

In yet another embodiment, the ionizable lipid may be selected from, but not limited to, formula CLI-CLXXXXII of U.S. Pat. No. 7,404,969; each of which is herein incorporated by reference in their entirety.

In one embodiment, the lipid may be a cleavable lipid such as those described in International Publication No. WO2012170889, herein incorporated by reference in its entirety. In one embodiment, the lipid may be synthesized by methods known in the art and/or as described in International Publication Nos. WO2013086354; the contents of each of which are herein incorporated by reference in their entirety.

Nanoparticle compositions can be characterized by a variety of methods. For example, microscopy (e.g., transmission electron microscopy or scanning electron microscopy) can be used to examine the morphology and size distribution of a nanoparticle composition. Dynamic light scattering or potentiometry (e.g., potentiometric titrations) can be used to measure zeta potentials. Dynamic light scattering can also be utilized to determine particle sizes. Instruments such as the Zetasizer Nano ZS (Malvern Instruments Ltd, Malvern, Worcestershire, UK) can also be used to measure multiple characteristics of a nanoparticle composition, such as particle size, polydispersity index, and zeta potential.

The size of the nanoparticles can help counter biological reactions such as, but not limited to, inflammation, or can increase the biological effect of the polynucleotide.

As used herein, "size" or "mean size" in the context of nanoparticle compositions refers to the mean diameter of a nanoparticle composition.

In one embodiment, the polynucleotide encoding a PCCA or PCCB polypeptide are formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm, about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In one embodiment, the nanoparticles have a diameter from about 10 to 500 nm. In one embodiment, the nanoparticle has a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the largest dimension of a nanoparticle composition is 1 μm or shorter (e.g., 1 μm, 900 nm, 800 nm, 700 nm, 600 nm, 500 nm, 400 nm, 300 nm, 200 nm, 175 nm, 150 nm, 125 nm, 100 nm, 75 nm, 50 nm, or shorter).

A nanoparticle composition can be relatively homogenous. A polydispersity index can be used to indicate the homogeneity of a nanoparticle composition, e.g., the particle size distribution of the nanoparticle composition. A small (e.g., less than 0.3) polydispersity index generally indicates a narrow particle size distribution. A nanoparticle composition can have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition disclosed herein can be from about 0.10 to about 0.20.

The zeta potential of a nanoparticle composition can be used to indicate the electrokinetic potential of the composition. For example, the zeta potential can describe the surface charge of a nanoparticle composition. Nanoparticle compositions with relatively low charges, positive or negative, are generally desirable, as more highly charged species can interact undesirably with cells, tissues, and other elements in the body. In some embodiments, the zeta potential of a nanoparticle composition disclosed herein can be from about −10 mV to about +20 mV, from about −10 mV to about +15 mV, from about 10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

In some embodiments, the zeta potential of the lipid nanoparticles can be from about 0 mV to about 100 mV, from about 0 mV to about 90 mV, from about 0 mV to about 80 mV, from about 0 mV to about 70 mV, from about 0 mV to about 60 mV, from about 0 mV to about 50 mV, from about 0 mV to about 40 mV, from about 0 mV to about 30 mV, from about 0 mV to about 20 mV, from about 0 mV to about 10 mV, from about 10 mV to about 100 mV, from about 10 mV to about 90 mV, from about 10 mV to about 80 mV, from about 10 mV to about 70 mV, from about 10 mV to about 60 mV, from about 10 mV to about 50 mV, from about 10 mV to about 40 mV, from about 10 mV to about 30 mV, from about 10 mV to about 20 mV, from about 20 mV to about 100 mV, from about 20 mV to about 90 mV, from about 20 mV to about 80 mV, from about 20 mV to about 70 mV, from about 20 mV to about 60 mV, from about 20 mV to about 50 mV, from about 20 mV to about 40 mV, from about 30 mV to about 100 mV, from about 30 mV to about 90 mV, from about 30 mV to about 80 mV, from about 30 mV to about 70 mV, from about 30 mV to about 60 mV, from about 30 mV to about 50 mV, from about 30 mV to about 40 mV, from about 40 mV to about 100 mV, from about 40 mV to about 90 mV, from about 40 mV to about 80 mV, from about 40 mV to about 70 mV, from about 40 mV to about 60 mV, and from about 40 mV to about 50 mV. In some embodiments, the zeta potential of the lipid nanoparticles can be from about 10 mV to about 50 mV, from about 15 mV to about 45 mV, from about 20 mV to about 40 mV, and from about 25 mV to about 35 mV. In some embodiments, the zeta potential of the lipid nanoparticles can be about 10 mV, about 20 mV, about 30 mV, about 40 mV, about 50 mV, about 60 mV, about 70 mV, about 80 mV, about 90 mV, and about 100 mV.

The term "encapsulation efficiency" of a polynucleotide describes the amount of the polynucleotide that is encapsulated by or otherwise associated with a nanoparticle composition after preparation, relative to the initial amount provided. As used herein, "encapsulation" can refer to complete, substantial, or partial enclosure, confinement, surrounding, or encasement.

Encapsulation efficiency is desirably high (e.g., close to 100%). The encapsulation efficiency can be measured, for example, by comparing the amount of the polynucleotide in a solution containing the nanoparticle composition before and after breaking up the nanoparticle composition with one or more organic solvents or detergents.

Fluorescence can be used to measure the amount of free polynucleotide in a solution. For the nanoparticle compositions described herein, the encapsulation efficiency of a polynucleotide can be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency can be at least 80%. In certain embodiments, the encapsulation efficiency can be at least 90%.

The amount of a polynucleotide present in a pharmaceutical composition disclosed herein can depend on multiple factors such as the size of the polynucleotide, desired target and/or application, or other properties of the nanoparticle composition as well as on the properties of the polynucleotide.

For example, the amount of an mRNA useful in a nanoparticle composition can depend on the size (expressed as length, or molecular mass), sequence, and other characteristics of the mRNA. The relative amounts of a polynucleotide in a nanoparticle composition can also vary.

The relative amounts of the lipid composition and the polynucleotide present in a lipid nanoparticle composition of the present disclosure can be optimized according to considerations of efficacy and tolerability. For compositions including an mRNA as a polynucleotide, the N:P ratio can serve as a useful metric.

As the N:P ratio of a nanoparticle composition controls both expression and tolerability, nanoparticle compositions with low N:P ratios and strong expression are desirable. N:P ratios vary according to the ratio of lipids to RNA in a nanoparticle composition.

In general, a lower N:P ratio is preferred. The one or more RNA, lipids, and amounts thereof can be selected to provide an N:P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In certain embodiments, the N:P ratio can be from about 2:1 to about 8:1. In other embodiments, the N:P ratio is from about 5:1 to about 8:1. In certain embodiments, the N:P ratio is between 5:1 and 6:1. In one specific aspect, the N:P ratio is about is about 5.67:1.

In addition to providing nanoparticle compositions, the present disclosure also provides methods of producing lipid nanoparticles comprising encapsulating a polynucleotide. Such method comprises using any of the pharmaceutical compositions disclosed herein and producing lipid nanoparticles in accordance with methods of production of lipid nanoparticles known in the art. See, e.g., Wang et al. (2015) "Delivery of oligonucleotides with lipid nanoparticles" Adv. Drug Deliv. Rev. 87:68-80; Silva et al. (2015) "Delivery Systems for Biopharmaceuticals. Part I: Nanoparticles and Microparticles" Curr. Pharm. Technol. 16: 940-954; Naseri et al. (2015) "Solid Lipid Nanoparticles and Nanostructured Lipid Carriers: Structure, Preparation and Application" Adv. Pharm. Bull. 5:305-13; Silva et al. (2015) "Lipid nanoparticles for the delivery of biopharmaceuticals" Curr. Pharm. Biotechnol. 16:291-302, and references cited therein.

21. Other Delivery Agents a. Liposomes, Lipoplexes, and Lipid Nanoparticles

In some embodiments, the compositions or formulations of the present disclosure comprise a delivery agent, e.g., a liposome, a lioplexes, a lipid nanoparticle, or any combination thereof. The polynucleotides described herein (e.g., a polynucleotide comprising a nucleotide sequence encoding a PCCA or PCCB polypeptide) can be formulated using one or more liposomes, lipoplexes, or lipid nanoparticles. Liposomes, lipoplexes, or lipid nanoparticles can be used to improve the efficacy of the polynucleotides directed protein production as these formulations can increase cell transfection by the polynucleotide; and/or increase the translation of encoded protein. The liposomes, lipoplexes, or lipid nanoparticles can also be used to increase the stability of the polynucleotides.

Liposomes are artificially-prepared vesicles that can primarily be composed of a lipid bilayer and can be used as a delivery vehicle for the administration of pharmaceutical formulations. Liposomes can be of different sizes. A multilamellar vesicle (MLV) can be hundreds of nanometers in diameter, and can contain a series of concentric bilayers separated by narrow aqueous compartments. A small unicellular vesicle (SUV) can be smaller than 50 nm in diameter, and a large unilamellar vesicle (LUV) can be between 50 and 500 nm in diameter. Liposome design can include, but is not limited to, opsonins or ligands to improve the attachment of liposomes to unhealthy tissue or to activate events such as, but not limited to, endocytosis. Liposomes can contain a low or a high pH value in order to improve the delivery of the pharmaceutical formulations.

The formation of liposomes can depend on the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimal size, polydispersity and the shelf-life of the vesicles for the intended application, and the batch-to-batch reproducibility and scale up production of safe and efficient liposomal products, etc.

As a non-limiting example, liposomes such as synthetic membrane vesicles can be prepared by the methods, apparatus and devices described in U.S. Pub. Nos. US20130177638, US20130177637, US20130177636, US20130177635, US20130177634, US20130177633, US20130183375, US20130183373, and US20130183372. In some embodiments, the polynucleotides described herein can be encapsulated by the liposome and/or it can be contained in an aqueous core that can then be encapsulated by the liposome as described in, e.g., Intl. Pub. Nos. WO2012031046, WO2012031043, WO2012030901, WO2012006378, and WO2013086526; and U.S. Pub. Nos. US20130189351, US20130195969 and US20130202684. Each of the references in herein incorporated by reference in its entirety.

In some embodiments, the polynucleotides described herein can be formulated in a cationic oil-in-water emulsion where the emulsion particle comprises an oil core and a cationic lipid that can interact with the polynucleotide anchoring the molecule to the emulsion particle. In some embodiments, the polynucleotides described herein can be formulated in a water-in-oil emulsion comprising a continuous hydrophobic phase in which the hydrophilic phase is dispersed. Exemplary emulsions can be made by the methods described in Intl. Pub. Nos. WO2012006380 and WO201087791, each of which is herein incorporated by reference in its entirety.

In some embodiments, the polynucleotides described herein can be formulated in a lipid-polycation complex. The formation of the lipid-polycation complex can be accomplished by methods as described in, e.g., U.S. Pub. No. US20120178702. As a non-limiting example, the polycation can include a cationic peptide or a polypeptide such as, but not limited to, polylysine, polyornithine and/or polyarginine and the cationic peptides described in Intl. Pub. No. WO2012013326 or U.S. Pub. No. US20130142818. Each of the references is herein incorporated by reference in its entirety.

In some embodiments, the polynucleotides described herein can be formulated in a lipid nanoparticle (LNP) such as those described in Intl. Pub. Nos. WO2013123523, WO2012170930, WO2011127255 and WO2008103276; and U.S. Pub. No. US20130171646, each of which is herein incorporated by reference in its entirety.

Lipid nanoparticle formulations typically comprise one or more lipids. In some embodiments, the lipid is an ionizable lipid (e.g., an ionizable amino lipid), sometimes referred to in the art as an "ionizable cationic lipid". In some embodiments, lipid nanoparticle formulations further comprise other components, including a phospholipid, a structural lipid, and a molecule capable of reducing particle aggregation, for example a PEG or PEG-modified lipid.

Exemplary ionizable lipids include, but not limited to, any one of Compounds 1-342 disclosed herein, DLin-MC3-DMA (MC3), DLin-DMA, DLenDMA, DLin-D-DMA, DLin-K-DMA, DLin-M-C2-DMA, DLin-K-DMA, DLin-KC2-DMA, DLin-KC3-DMA, DLin-KC4-DMA, DLin-C2K-DMA, DLin-MP-DMA, DODMA, 98N12-5, C12-200, DLin-C-DAP, DLin-DAC, DLinDAP, DLinAP, DLin-EG-DMA, DLin-2-DMAP, KL10, KL22, KL25, Octyl-CLinDMA, Octyl-CLinDMA (2R), Octyl-CLinDMA (2S), and any combination thereof. Other exemplary ionizable lipids include, (13Z,16Z)—N,N-dimethyl-3-nonyldocosa-13,16-dien-1-amine (L608), (20Z,23Z)—N,N-dimethyl-nonacosa-20,23-dien-10-amine, (17Z,20Z)-N,N-dimemyl-hexacosa-17,20-dien-9-amine, (16Z,19Z)-N5N-dimethylpentacosa-16,19-dien-8-amine, (13Z,16Z)-N,N-dimethyldocosa-13,16-dien-5-amine, (12Z,15Z)-N,N-dimethylhenicosa-12,15-dien-4-amine, (14Z,17Z)-N,N-dimethyltricosa-14,17-dien-6-amine, (15Z,18Z)-N,N-dimethyltetracosa-15,18-dien-7-amine, (18Z,21Z)-N,N-dimethylheptacosa-18,21-dien-10-amine, (15Z,18Z)-N,N-dimethyltetracosa-15,18-dien-5-amine, (14Z,17Z)-N,N-dimethyltricosa-14,17-dien-4-amine, (19Z,22Z)-N,N-dimeihyloctacosa-19,22-dien-9-amine, (18Z,21Z)-N,N- dimethylheptacosa-18,21-dien-8-amine, (17Z,20Z)-N,N-dimethylhexacosa-17,20-dien-7-amine, (16Z,19Z)-N,N-dimethylpentacosa-16,19-dien-6-amine, (22Z,25Z)-N,N-dimethylhentriaconta-22,25-dien-10-amine, (21Z,24Z)-N,N-dimethyltriaconta-21,24-dien-9-amine, (18Z)-N,N-dimetylheptacos-18-en-10-amine, (17Z)-N,N-dimethylhexacos-17-en-9-amine, (19Z,22Z)-N,N-dimethyloctacosa-19,22-dien-7-amine, N,N-dimethylheptacosan-10-amine, (20Z,23Z)-N-ethyl-N-methylnonacosa-20,23-dien-10-amine, 1-[(11Z,14Z)-1-nonylicosa-11,14-dien-1-yl]pyrrolidine, (20Z)-N,N-dimethylheptacos-20-en-10-amine, (15Z)-N,N-dimethyl eptacos-15-en-10-amine, (14Z)-N,N-dimethylnonacos-14-en-10-amine, (17Z)-N,N-dimethylnonacos-17-en-10-amine, (24Z)-N,N-dimethyltritriacont-24-en-10-amine, (20Z)-N,N-dimethylnonacos-20-en-10-amine, (22Z)-N,N-dimethylhentriacont-22-en-10-amine, (16Z)-N,N-dimethylpentacos-16-en-8-amine, (12Z,15Z)—N,N-dimethyl-2-nonylhenicosa-12,15-dien-1-amine, N,N-dimethyl-1-[(1S,2R)-2-octylcyclopropyl] eptadecan-8-amine, 1-[(1S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl] henicosan-10-amine, N,N-dimethyl-1-[(1S,2S)-2-{[(1R,2R)-2-pentylcyclopropyl]methyl}cyclopropyl]nonadecan-10-amine, N,N-dimethyl-1-[(1S,2R)-2-octylcyclopropyl] hexadecan-8-amine, N,N-dimethyl-[(1R,2S)-2-undecylcyclopropyl]tetradecan-5-amine, N,N-dimethyl-3-{7-[(1S,2R)-2-octylcyclopropyl]heptyl}dodecan-1-amine, 1-[(1R,2S)-2-heptylcyclopropyl]-N,N-dimethyloctadecan-9-amine, 1-[(1S,2R)-2-decylcyclopropyl]-N,N-dimethyl-pentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy)propan-2-amine, 1-{2-[(9Z,12Z)-octadeca-9,12-dien-1-yloxy]-1-[(octyloxy)methyl] ethyl}pyrrolidine, (2S)—N,N-dimethyl-1-[(9Z,12Z)-octadeca-9,12-dien-1-yloxy]-3-[(5Z)-oct-5-en-1-yloxy] propan-2-amine, 1-{2-[(9Z,12Z)-octadeca-9,12-dien-1-yloxy]-1-[(octyloxy)methyl]ethyl}azetidine, (2S)-1-(hexyloxy)-N,N-dimethyl-3-[(9Z,12Z)-octadeca-9,12-dien-1-yloxy]propan-2-amine, (2S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy) propan-2-amine; (2S)—N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(11Z,14Z)-icosa-11,14-dien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy)propan-2-amine, (2S)-1-[(13Z, 16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoyloctyl)oxy]-3-[(9Z,12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-dien-1-yloxy]propan-2-amine, N,N-dimethyl-1-(octyloxy)-3-({8-[(1S,2S)-2-{[(1R,2R)-2-pentyl-cyclopropyl]methyl}cyclopropyl]octyl}oxy)propan-2- amine, N,N-dimethyl-1-{[8-(2-oclylcyclopropyl)octyl] oxy}-3-(octyloxy)propan-2-amine, and (11E,20Z,23Z)-N,N-dimethylnonacosa-11,20,2-trien-10-amine, and any combination thereof.

Phospholipids include, but are not limited to, glycero-phospholipids such as phosphatidylcholines, phosphatidyle-thanolamines, phosphatidylserines, phosphatidylinositols, phosphatidy glycerols, and phosphatidic acids. Phospholipids also include phosphosphingolipid, such as sphingomy-elin. In some embodiments, the phospholipids are DLPC, DMPC, DOPC, DPPC, DSPC, DUPC, 18:0 Diether PC, DLnPC, DAPC, DHAPC, DOPE, 4ME 16:0 PE, DSPE, DLPE, DLnPE, DAPE, DHAPE, DOPG, and any combination thereof. In some embodiments, the phospholipids are MPPC, MSPC, PMPC, PSPC, SMPC, SPPC, DHAPE, DOPG, and any combination thereof. In some embodiments, the amount of phospholipids (e.g., DSPC) in the lipid composition ranges from about 1 mol % to about 20 mol %.

The structural lipids include sterols and lipids containing sterol moieties. In some embodiments, the structural lipids include cholesterol, fecosterol, sitosterol, ergosterol, camp-esterol, stigmasterol, brassicasterol, tomatidine, tomatine, ursolic acid, alpha-tocopherol, and mixtures thereof. In some embodiments, the structural lipid is cholesterol. In some embodiments, the amount of the structural lipids (e.g., cholesterol) in the lipid composition ranges from about 20 mol % to about 60 mol %.

The PEG-modified lipids include PEG-modified phospha-tidylethanolamine and phosphatidic acid, PEG-ceramide conjugates (e.g., PEG-CerC14 or PEG-CerC20), PEG-modi-fied dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG DMPE, PEG-DPPC, or a PEG-DSPE lipid. In some embodiments, the PEG-lipid are 1,2-dimyristoyl-sn-glycerol methoxypolyethylene glycol (PEG-DMG), 1,2-distearoyl-sn-glycero-3-phosphoetha-nolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA). In some embodiments, the PEG moiety has a size of about 1000, 2000, 5000, 10,000, 15,000 or 20,000 daltons. In some embodiments, the amount of PEG-lipid in the lipid composition ranges from about 0 mol % to about 5 mol %.

In some embodiments, the LNP formulations described herein can additionally comprise a permeability enhancer molecule. Non-limiting permeability enhancer molecules are described in U.S. Pub. No. US20050222064, herein incorporated by reference in its entirety.

The LNP formulations can further contain a phosphate conjugate. The phosphate conjugate can increase in vivo circulation times and/or increase the targeted delivery of the nanoparticle. Phosphate conjugates can be made by the methods described in, e.g., Intl. Pub. No. WO2013033438 or U.S. Pub. No. US20130196948. The LNP formulation can also contain a polymer conjugate (e.g., a water soluble conjugate) as described in, e.g., U.S. Pub. Nos. US20130059360, US20130196948, and US20130072709. Each of the references is herein incorporated by reference in its entirety.

The LNP formulations can comprise a conjugate to enhance the delivery of nanoparticles of the present invention in a human subject. Further, the conjugate can inhibit phagocytic clearance of the nanoparticles in a human subject. In some embodiments, the conjugate can be a "self"

peptide designed from the human membrane protein CD47 (e.g., the "self" particles described by Rodriguez et al, Science 2013 339, 971-975, herein incorporated by reference in its entirety). As shown by Rodriguez et al. the self peptides delayed macrophage-mediated clearance of nanoparticles which enhanced delivery of the nanoparticles.

The LNP formulations can comprise a carbohydrate carrier. As a non-limiting example, the carbohydrate carrier can include, but is not limited to, an anhydride-modified phytoglycogen or glycogen-type material, phytoglycogen octenyl succinate, phytoglycogen beta-dextrin, anhydride-modified phytoglycogen beta-dextrin (e.g., Intl. Pub. No. WO2012109121, herein incorporated by reference in its entirety).

The LNP formulations can be coated with a surfactant or polymer to improve the delivery of the particle. In some embodiments, the LNP can be coated with a hydrophilic coating such as, but not limited to, PEG coatings and/or coatings that have a neutral surface charge as described in U.S. Pub. No. US20130183244, herein incorporated by reference in its entirety.

The LNP formulations can be engineered to alter the surface properties of particles so that the lipid nanoparticles can penetrate the mucosal barrier as described in U.S. Pat. No. 8,241,670 or Intl. Pub. No. WO2013110028, each of which is herein incorporated by reference in its entirety.

The LNP engineered to penetrate mucus can comprise a polymeric material (i.e., a polymeric core) and/or a polymer-vitamin conjugate and/or a ti-block co-polymer. The polymeric material can include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, poly acrylonitriles, and polyarylates.

LNP engineered to penetrate mucus can also include surface altering agents such as, but not limited to, polynucleotides, anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin β4 dornase alfa, neltenexine, erdosteine) and various DNases including rhDNase.

In some embodiments, the mucus penetrating LNP can be a hypotonic formulation comprising a mucosal penetration enhancing coating. The formulation can be hypotonic for the epithelium to which it is being delivered. Non-limiting examples of hypotonic formulations can be found in, e.g., Intl. Pub. No. WO2013110028, herein incorporated by reference in its entirety.

In some embodiments, the polynucleotide described herein is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, MA), and polyethylenimine (PEI) or protamine-based targeted and non-targeted delivery of nucleic acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al.

Microvasc Res 2010 80:286-293Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132; all of which are incorporated herein by reference in its entirety).

In some embodiments, the polynucleotides described herein are formulated as a solid lipid nanoparticle (SLN), which can be spherical with an average diameter between 10 to 1000 nm. SLN possess a solid lipid core matrix that can solubilize lipophilic molecules and can be stabilized with surfactants and/or emulsifiers. Exemplary SLN can be those as described in Intl. Pub. No. WO2013105101, herein incorporated by reference in its entirety.

In some embodiments, the polynucleotides described herein can be formulated for controlled release and/or targeted delivery. As used herein, "controlled release" refers to a pharmaceutical composition or compound release profile that conforms to a particular pattern of release to effect a therapeutic outcome. In one embodiment, the polynucleotides can be encapsulated into a delivery agent described herein and/or known in the art for controlled release and/or targeted delivery. As used herein, the term "encapsulate" means to enclose, surround or encase. As it relates to the formulation of the compounds of the invention, encapsulation can be substantial, complete or partial. The term "substantially encapsulated" means that at least greater than 50, 60, 70, 80, 85, 90, 95, 96, 97, 98, 99, or greater than 99% of the pharmaceutical composition or compound of the invention can be enclosed, surrounded or encased within the delivery agent. "Partially encapsulation" means that less than 10, 10, 20, 30, 40 50 or less of the pharmaceutical composition or compound of the invention can be enclosed, surrounded or encased within the delivery agent.

Advantageously, encapsulation can be determined by measuring the escape or the activity of the pharmaceutical composition or compound of the invention using fluorescence and/or electron micrograph. For example, at least 1, 5, 10, 20, 30, 40, 50, 60, 70, 80, 85, 90, 95, 96, 97, 98, 99, 99.9, or greater than 99% of the pharmaceutical composition or compound of the invention are encapsulated in the delivery agent.

In some embodiments, the polynucleotides described herein can be encapsulated in a therapeutic nanoparticle, referred to herein as "therapeutic nanoparticle polynucleotides." Therapeutic nanoparticles can be formulated by methods described in, e.g., Intl. Pub. Nos. WO2010005740, WO2010030763, WO2010005721, WO2010005723, and WO2012054923; and U.S. Pub. Nos. US20110262491, US20100104645, US20100087337, US20100068285, US20110274759, US20100068286, US20120288541, US20120140790, US20130123351 and US20130230567; and U.S. Pat. Nos. 8,206,747, 8,293,276, 8,318,208 and 8,318,211, each of which is herein incorporated by reference in its entirety.

In some embodiments, the therapeutic nanoparticle polynucleotide can be formulated for sustained release. As used herein, "sustained release" refers to a pharmaceutical composition or compound that conforms to a release rate over a specific period of time. The period of time can include, but is not limited to, hours, days, weeks, months and years. As a non-limiting example, the sustained release nanoparticle of the polynucleotides described herein can be formulated as disclosed in Intl. Pub. No. WO2010075072 and U.S. Pub.

Nos. US20100216804, US20110217377, US20120201859 and US20130150295, each of which is herein incorporated by reference in their entirety.

In some embodiments, the therapeutic nanoparticle polynucleotide can be formulated to be target specific, such as those described in Intl. Pub. Nos. WO2008121949, WO2010005726, WO2010005725, WO2011084521 and WO2011084518; and U.S. Pub. Nos. US20100069426, US20120004293 and US20100104655, each of which is herein incorporated by reference in its entirety.

The LNPs can be prepared using microfluidic mixers or micromixers. Exemplary microfluidic mixers can include, but are not limited to, a slit interdigital micromixer including, but not limited to those manufactured by Microinnova (Allerheiligen bei Wildon, Austria) and/or a staggered herringbone micromixer (SHM) (see Zhigaltsev et al., "Bottom-up design and synthesis of limit size lipid nanoparticle systems with aqueous and triglyceride cores using millisecond microfluidic mixing," Langmuir 28:3633-40 (2012); Belliveau et al., "Microfluidic synthesis of highly potent limit-size lipid nanoparticles for in vivo delivery of siRNA," Molecular Therapy-Nucleic Acids. 1:e37 (2012); Chen et al., "Rapid discovery of potent siRNA-containing lipid nanoparticles enabled by controlled microfluidic formulation," J. Am. Chem. Soc. 134(16):6948-51 (2012); each of which is herein incorporated by reference in its entirety). Exemplary micromixers include Slit Interdigital Microstructured Mixer (SIMM-V2) or a Standard Slit Interdigital Micro Mixer (SSIMM) or Caterpillar (CPMM) or Impinging-jet (IJMM,) from the Institut für Mikrotechnik Mainz GmbH, Mainz Germany. In some embodiments, methods of making LNP using SHM further comprise mixing at least two input streams wherein mixing occurs by microstructure-induced chaotic advection (MICA). According to this method, fluid streams flow through channels present in a herringbone pattern causing rotational flow and folding the fluids around each other. This method can also comprise a surface for fluid mixing wherein the surface changes orientations during fluid cycling. Methods of generating LNPs using SHM include those disclosed in U.S. Pub. Nos. US20040262223 and US20120276209, each of which is incorporated herein by reference in their entirety.

In some embodiments, the polynucleotides described herein can be formulated in lipid nanoparticles using microfluidic technology (see Whitesides, George M., "The Origins and the Future of Microfluidics," Nature 442: 368-373 (2006); and Abraham et al., "Chaotic Mixer for Microchannels," Science 295: 647-651 (2002); each of which is herein incorporated by reference in its entirety). In some embodiments, the polynucleotides can be formulated in lipid nanoparticles using a micromixer chip such as, but not limited to, those from Harvard Apparatus (Holliston, MA) or Dolomite Microfluidics (Royston, UK). A micromixer chip can be used for rapid mixing of two or more fluid streams with a split and recombine mechanism.

In some embodiments, the polynucleotides described herein can be formulated in lipid nanoparticles having a diameter from about 1 nm to about 100 nm such as, but not limited to, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from about 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In some embodiments, the lipid nanoparticles can have a diameter from about 10 to 500 nm. In one embodiment, the lipid nanoparticle can have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the polynucleotides can be delivered using smaller LNPs. Such particles can comprise a diameter from below 0.1 μm up to 100 nm such as, but not limited to, less than 0.1 μm, less than 1.0 μm, less than 5 μm, less than 10 μm, less than 15 um, less than 20 um, less than 25 um, less than 30 um, less than 35 um, less than 40 um, less than 50 um, less than 55 um, less than 60 um, less than 65 um, less than 70 um, less than 75 um, less than 80 um, less than 85 um, less than 90 um, less than 95 um, less than 100 um, less than 125 um, less than 150 um, less than 175 um, less than 200 um, less than 225 um, less than 250 um, less than 275 um, less than 300 um, less than 325 um, less than 350 um, less than 375 um, less than 400 um, less than 425 um, less than 450 um, less than 475 um, less than 500 um, less than 525 um, less than 550 um, less than 575 um, less than 600 um, less than 625 um, less than 650 um, less than 675 um, less than 700 um, less than 725 um, less than 750 um, less than 775 um, less than 800 um, less than 825 um, less than 850 um, less than 875 um, less than 900 um, less than 925 um, less than 950 um, or less than 975 um.

The nanoparticles and microparticles described herein can be geometrically engineered to modulate macrophage and/or the immune response. The geometrically engineered particles can have varied shapes, sizes and/or surface charges to incorporate the polynucleotides described herein for targeted delivery such as, but not limited to, pulmonary delivery (see, e.g., Intl. Pub. No. WO2013082111, herein incorporated by reference in its entirety). Other physical features the geometrically engineering particles can include, but are not limited to, fenestrations, angled arms, asymmetry and surface roughness, charge that can alter the interactions with cells and tissues.

In some embodiment, the nanoparticles described herein are stealth nanoparticles or target-specific stealth nanoparticles such as, but not limited to, those described in U.S. Pub. No. US20130172406, herein incorporated by reference in its entirety. The stealth or target-specific stealth nanoparticles can comprise a polymeric matrix, which can comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates, or combinations thereof.

b. Lipidoids

In some embodiments, the compositions or formulations of the present disclosure comprise a delivery agent, e.g., a lipidoid. The polynucleotides described herein (e.g., a polynucleotide comprising a nucleotide sequence encoding a PCCA or PCCB polypeptide) can be formulated with lipidoids. Complexes, micelles, liposomes or particles can be prepared containing these lipidoids and therefore to achieve an effective delivery of the polynucleotide, as judged by the production of an encoded protein, following the injection of a lipidoid formulation via localized and/or systemic routes of administration. Lipidoid complexes of polynucleotides can be administered by various means including, but not limited to, intravenous, intramuscular, or subcutaneous routes.

The synthesis of lipidoids is described in literature (see Mahon et al., Bioconjug. Chem. 2010 21:1448-1454; Schroeder et al., J Intern Med. 2010 267:9-21; Akinc et al., Nat Biotechnol. 2008 26:561-569; Love et al., Proc Natl Acad Sci USA. 2010 107:1864-1869; Siegwart et al., Proc Natl Acad Sci USA. 2011 108:12996-3001; all of which are incorporated herein in their entireties).

Formulations with the different lipidoids, including, but not limited to penta[3-(1-laurylaminopropionyl)]-triethylenetetramine hydrochloride (TETA-5LAP; also known as 98N12-5, see Murugaiah et al., Analytical Biochemistry, 401:61 (2010)), C12-200 (including derivatives and variants), and MD1, can be tested for in vivo activity. The lipidoid "98N12-5" is disclosed by Akinc et al., Mol Ther. 2009 17:872-879. The lipidoid "C12-200" is disclosed by Love et al., Proc Natl Acad Sci USA. 2010 107:1864-1869 and Liu and Huang, Molecular Therapy. 2010 669-670. Each of the references is herein incorporated by reference in its entirety.

In one embodiment, the polynucleotides described herein can be formulated in an aminoalcohol lipidoid. Aminoalcohol lipidoids can be prepared by the methods described in U.S. Pat. No. 8,450,298 (herein incorporated by reference in its entirety).

The lipidoid formulations can include particles comprising either 3 or 4 or more components in addition to polynucleotides. Lipidoids and polynucleotide formulations comprising lipidoids are described in Intl. Pub. No. WO 2015051214 (herein incorporated by reference in its entirety.

c. Hyaluronidase

In some embodiments, the polynucleotides described herein (e.g., a polynucleotide comprising a nucleotide sequence encoding a PCCA or PCCB polypeptide) and hyaluronidase for injection (e.g., intramuscular or subcutaneous injection). Hyaluronidase catalyzes the hydrolysis of hyaluronan, which is a constituent of the interstitial barrier. Hyaluronidase lowers the viscosity of hyaluronan, thereby increases tissue permeability (Frost, Expert Opin. Drug Deliv. (2007) 4:427-440). Alternatively, the hyaluronidase can be used to increase the number of cells exposed to the polynucleotides administered intramuscularly, or subcutaneously.

d. Nanoparticle Mimics

In some embodiments, the polynucleotides described herein (e.g., a polynucleotide comprising a nucleotide sequence encoding a PCCA or PCCB polypeptide) is encapsulated within and/or absorbed to a nanoparticle mimic. A nanoparticle mimic can mimic the delivery function organisms or particles such as, but not limited to, pathogens, viruses, bacteria, fungus, parasites, prions and cells. As a non-limiting example, the polynucleotides described herein can be encapsulated in a non-viron particle that can mimic the delivery function of a virus (see e.g., Intl. Pub. No. WO2012006376 and U.S. Pub. Nos. US20130171241 and US20130195968, each of which is herein incorporated by reference in its entirety).

e. Self-Assembled Nanoparticles, or Self-Assembled Macromolecules

In some embodiments, the compositions or formulations of the present disclosure comprise the polynucleotides described herein (e.g., a polynucleotide comprising a nucleotide sequence encoding a PCCA or PCCB polypeptide) in self-assembled nanoparticles, or amphiphilic macromolecules (AMs) for delivery. AMs comprise biocompatible amphiphilic polymers that have an alkylated sugar backbone covalently linked to poly(ethylene glycol). In aqueous solution, the AMs self-assemble to form micelles. Nucleic acid self-assembled nanoparticles are described in Intl. Appl. No. PCT/US2014/027077, and AMs and methods of forming AMs are described in U.S. Pub. No. US20130217753, each of which is herein incorporated by reference in its entirety.

f. Cations and Anions

In some embodiments, the compositions or formulations of the present disclosure comprise the polynucleotides described herein (e.g., a polynucleotide comprising a nucleotide sequence encoding a PCCA or PCCB polypeptide) and a cation or anion, such as $Zn2+$, $Ca2+$, $Cu2+$, $Mg2+$ and combinations thereof. Exemplary formulations can include polymers and a polynucleotide complexed with a metal cation as described in, e.g., U.S. Pat. Nos. 6,265,389 and 6,555,525, each of which is herein incorporated by reference in its entirety. In some embodiments, cationic nanoparticles can contain a combination of divalent and monovalent cations. The delivery of polynucleotides in cationic nanoparticles or in one or more depot comprising cationic nanoparticles can improve polynucleotide bioavailability by acting as a long-acting depot and/or reducing the rate of degradation by nucleases.

g. Amino Acid Lipids

In some embodiments, the compositions or formulations of the present disclosure comprise the polynucleotides described herein (e.g., a polynucleotide comprising a nucleotide sequence encoding a PCCA or PCCB polypeptide) that is formulation with an amino acid lipid. Amino acid lipids are lipophilic compounds comprising an amino acid residue and one or more lipophilic tails. Non-limiting examples of amino acid lipids and methods of making amino acid lipids are described in U.S. Pat. No. 8,501,824. The amino acid lipid formulations can deliver a polynucleotide in releasable form that comprises an amino acid lipid that binds and releases the polynucleotides. As a non-limiting example, the release of the polynucleotides described herein can be provided by an acid-labile linker as described in, e.g., U.S. Pat. Nos. 7,098,032, 6,897,196, 6,426,086, 7,138,382, 5,563,250, and 5,505,931, each of which is herein incorporated by reference in its entirety.

h. Interpolyelectrolyte Complexes

In some embodiments, the compositions or formulations of the present disclosure comprise the polynucleotides described herein (e.g., a polynucleotide comprising a nucleotide sequence encoding a PCCA or PCCB polypeptide) in an interpolyelectrolyte complex. Interpolyelectrolyte complexes are formed when charge-dynamic polymers are complexed with one or more anionic molecules. Non-limiting examples of charge-dynamic polymers and interpolyelectrolyte complexes and methods of making interpolyelectrolyte complexes are described in U.S. Pat. No. 8,524,368, herein incorporated by reference in its entirety.

i. Crystalline Polymeric Systems

In some embodiments, the compositions or formulations of the present disclosure comprise the polynucleotides described herein (e.g., a polynucleotide comprising a nucleotide sequence encoding a PCCA or PCCB polypeptide) in crystalline polymeric systems. Crystalline polymeric systems are polymers with crystalline moieties and/or terminal units comprising crystalline moieties. Exemplary polymers are described in U.S. Pat. No. 8,524,259 (herein incorporated by reference in its entirety).

j. Polymers, Biodegradable Nanoparticles, and Core-Shell Nanoparticles

In some embodiments, the compositions or formulations of the present disclosure comprise the polynucleotides described herein (e.g., a polynucleotide comprising a nucleotide sequence encoding a PCCA or PCCB polypeptide) and a natural and/or synthetic polymer. The polymers include, but not limited to, polyethenes, polyethylene glycol (PEG), poly(l-lysine)(PLL), PEG grafted to PLL, cationic lipopolymer, biodegradable cationic lipopolymer, polyethyleneimine (PEI), cross-linked branched poly(alkylene imines), a polyamine derivative, a modified poloxamer, elastic biodegradable polymer, biodegradable copolymer, biodegradable polyester copolymer, biodegradable polyester copolymer, multiblock copolymers, poly[α-(4-aminobutyl)-L-glycolic acid) (PAGA), biodegradable cross-linked cationic multi-block copolymers, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyureas, polystyrenes, polyamines, polylysine, poly(ethylene imine), poly(serine ester), poly(L-lactide-co-L-lysine), poly(4-hydroxy-L-proline ester), amine-containing polymers, dextran polymers, dextran polymer derivatives or combinations thereof.

Exemplary polymers include, DYNAMIC POLYCONJUGATE® (Arrowhead Research Corp., Pasadena, CA) formulations from MIRUS® Bio (Madison, WI) and Roche Madison (Madison, WI), PHASERX™ polymer formulations such as, without limitation, SMARTT POLYMER TECHNOLOGY™ (PHASERX@, Seattle, WA), DMRI/DOPE, poloxamer, VAXFECTIN® adjuvant from Vical (San Diego, CA), chitosan, cyclodextrin from Calando Pharmaceuticals (Pasadena, CA), dendrimers and poly(lactic-co-glycolic acid) (PLGA) polymers. RONDEL™ (RNAi/Oligonucleotide Nanoparticle Delivery) polymers (Arrowhead Research Corporation, Pasadena, CA) and pH responsive co-block polymers such as PHASERX® (Seattle, WA).

The polymer formulations allow a sustained or delayed release of the polynucleotide (e.g., following intramuscular or subcutaneous injection). The altered release profile for the polynucleotide can result in, for example, translation of an encoded protein over an extended period of time. The polymer formulation can also be used to increase the stability of the polynucleotide. Sustained release formulations can include, but are not limited to, PLGA microspheres, ethylene vinyl acetate (EVAc), poloxamer, GELSITE® (Nanotherapeutics, Inc. Alachua, FL), HYLENEX® (Halozyme Therapeutics, San Diego CA), surgical sealants such as fibrinogen polymers (Ethicon Inc. Cornelia, GA), TISSELL® (Baxter International, Inc. Deerfield, IL), PEG-based sealants, and COSEAL® (Baxter International, Inc. Deerfield, IL).

As a non-limiting example modified mRNA can be formulated in PLGA microspheres by preparing the PLGA microspheres with tunable release rates (e.g., days and weeks) and encapsulating the modified mRNA in the PLGA microspheres while maintaining the integrity of the modified mRNA during the encapsulation process. EVAc are non-biodegradable, biocompatible polymers that are used extensively in pre-clinical sustained release implant applications (e.g., extended release products Ocusert a pilocarpine ophthalmic insert for glaucoma or progestasert a sustained release progesterone intrauterine device; transdermal delivery systems Testoderm, Duragesic and Selegiline; catheters). Poloxamer F-407 NF is a hydrophilic, non-ionic surfactant triblock copolymer of polyoxyethylene-polyoxypropylene-polyoxyethylene having a low viscosity at temperatures less than 5° C. and forms a solid gel at temperatures greater than 15° C.

As a non-limiting example, the polynucleotides described herein can be formulated with the polymeric compound of PEG grafted with PLL as described in U.S. Pat. No. 6,177,274. As another non-limiting example, the polynucleotides described herein can be formulated with a block copolymer such as a PLGA-PEG block copolymer (see e.g., U.S. Pub. No. US20120004293 and U.S. Pat. Nos. 8,236,330 and 8,246,968), or a PLGA-PEG-PLGA block copolymer (see e.g., U.S. Pat. No. 6,004,573). Each of the references is herein incorporated by reference in its entirety.

In some embodiments, the polynucleotides described herein can be formulated with at least one amine-containing polymer such as, but not limited to polylysine, polyethylene imine, poly(amidoamine) dendrimers, poly(amine-co-esters) or combinations thereof. Exemplary polyamine polymers and their use as delivery agents are described in, e.g., U.S. Pat. Nos. 8,460,696, 8,236,280, each of which is herein incorporated by reference in its entirety.

In some embodiments, the polynucleotides described herein can be formulated in a biodegradable cationic lipopolymer, a biodegradable polymer, or a biodegradable copolymer, a biodegradable polyester copolymer, a biodegradable polyester polymer, a linear biodegradable copolymer, PAGA, a biodegradable cross-linked cationic multi-block copolymer or combinations thereof as described in, e.g., U.S. Pat. Nos. 6,696,038, 6,517,869, 6,267,987, 6,217,912, 6,652,886, 8,057,821, and 8,444,992; U.S. Pub. Nos. US20030073619, US20040142474, US20100004315, US2012009145 and US20130195920; and Intl Pub. Nos. WO2006063249 and WO2013086322, each of which is herein incorporated by reference in its entirety.

In some embodiments, the polynucleotides described herein can be formulated in or with at least one cyclodextrin polymer as described in U.S. Pub. No. US20130184453. In some embodiments, the polynucleotides described herein can be formulated in or with at least one crosslinked cation-binding polymers as described in Intl. Pub. Nos. WO2013106072, WO2013106073 and WO2013106086. In some embodiments, the polynucleotides described herein can be formulated in or with at least PEGylated albumin polymer as described in U.S. Pub. No. US20130231287. Each of the references is herein incorporated by reference in its entirety.

In some embodiments, the polynucleotides disclosed herein can be formulated as a nanoparticle using a combination of polymers, lipids, and/or other biodegradable agents, such as, but not limited to, calcium phosphate. Components can be combined in a core-shell, hybrid, and/or layer-by-layer architecture, to allow for fine-tuning of the nanoparticle for delivery (Wang et al., Nat Mater. 2006 5:791-796; Fuller et al., Biomaterials. 2008 29:1526-1532; DeKoker et al., Adv Drug Deliv Rev. 2011 63:748-761; Endres et al., Biomaterials. 2011 32:7721-7731; Su et al., Mol Pharm. 2011 Jun. 6; 8(3):774-87; herein incorporated by reference in their entireties). As a non-limiting example, the nanoparticle can comprise a plurality of polymers such as, but not limited to hydrophilic-hydrophobic polymers (e.g., PEG-PLGA), hydrophobic polymers (e.g., PEG) and/ or hydrophilic polymers (Intl. Pub. No. WO20120225129, herein incorporated by reference in its entirety).

The use of core-shell nanoparticles has additionally focused on a high-throughput approach to synthesize cationic cross-linked nanogel cores and various shells (Siegwart et al., Proc Natl Acad Sci USA. 2011 108:12996-13001; herein incorporated by reference in its entirety). The complexation, delivery, and internalization of the polymeric nanoparticles can be precisely controlled by altering the chemical composition in both the core and shell components of the nanoparticle. For example, the core-shell nanoparticles can efficiently deliver siRNA to mouse hepatocytes after they covalently attach cholesterol to the nanoparticle.

In some embodiments, a hollow lipid core comprising a middle PLGA layer and an outer neutral lipid layer containing PEG can be used to delivery of the polynucleotides as described herein. In some embodiments, the lipid nanoparticles can comprise a core of the polynucleotides disclosed herein and a polymer shell, which is used to protect the polynucleotides in the core. The polymer shell can be any of the polymers described herein and are known in the art. The polymer shell can be used to protect the polynucleotides in the core.

Core-shell nanoparticles for use with the polynucleotides described herein are described in U.S. Pat. No. 8,313,777 or Intl. Pub. No. WO2013124867, each of which is herein incorporated by reference in their entirety.

k. Peptides and Proteins

In some embodiments, the compositions or formulations of the present disclosure comprise the polynucleotides described herein (e.g., a polynucleotide comprising a nucleotide sequence encoding a PCCA or PCCB polypeptide) that is formulated with peptides and/or proteins to increase transfection of cells by the polynucleotide, and/or to alter the biodistribution of the polynucleotide (e.g., by targeting specific tissues or cell types), and/or increase the translation of encoded protein (e.g., Intl. Pub. Nos. WO2012110636 and WO2013123298. In some embodiments, the peptides can be those described in U.S. Pub. Nos. US20130129726, US20130137644 and US20130164219. Each of the references is herein incorporated by reference in its entirety.

l. Conjugates

In some embodiments, the compositions or formulations of the present disclosure comprise the polynucleotides described herein (e.g., a polynucleotide comprising a nucleotide sequence encoding a PCCA or PCCB polypeptide) that is covalently linked to a carrier or targeting group, or including two encoding regions that together produce a fusion protein (e.g., bearing a targeting group and therapeutic protein or peptide) as a conjugate. The conjugate can be a peptide that selectively directs the nanoparticle to neurons in a tissue or organism, or assists in crossing the blood-brain barrier.

The conjugates include a naturally occurring substance, such as a protein (e.g., human serum albumin (HSA), low-density lipoprotein (LDL), high-density lipoprotein (HDL), or globulin); an carbohydrate (e.g., a dextran, pullulan, chitin, chitosan, inulin, cyclodextrin or hyaluronic acid); or a lipid. The ligand can also be a recombinant or synthetic molecule, such as a synthetic polymer, e.g., a synthetic polyamino acid, an oligonucleotide (e.g., an aptamer). Examples of polyamino acids include polyamino acid is a polylysine (PLL), poly L-aspartic acid, poly L-glutamic acid, styrene-maleic acid anhydride copolymer, poly (L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

In some embodiments, the conjugate can function as a carrier for the polynucleotide disclosed herein. The conjugate can comprise a cationic polymer such as, but not limited to, polyamine, polylysine, poly alkylenimine, and polyethylenimine that can be grafted to with poly(ethylene glycol). Exemplary conjugates and their preparations are described in U.S. Pat. No. 6,586,524 and U.S. Pub. No. US20130211249, each of which herein is incorporated by reference in its entirety.

The conjugates can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Targeting groups can be proteins, e.g., glycoproteins, or peptides, e.g., molecules having a specific affinity for a co-ligand, or antibodies e.g., an antibody, that binds to a specified cell type such as an endothelial cell or bone cell. Targeting groups can also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, multivalent frucose, or aptamers. The ligand can be, for example, a lipopolysaccharide, or an activator of p38 MAP kinase.

The targeting group can be any ligand that is capable of targeting a specific receptor. Examples include, without limitation, folate, GalNAc, galactose, mannose, mannose-6P, apatamers, integrin receptor ligands, chemokine receptor ligands, transferrin, biotin, serotonin receptor ligands, PSMA, endothelin, GCPII, somatostatin, LDL, and HDL ligands. In particular embodiments, the targeting group is an aptamer. The aptamer can be unmodified or have any combination of modifications disclosed herein. As a non-limiting example, the targeting group can be a glutathione receptor (GR)-binding conjugate for targeted delivery across the blood-central nervous system barrier as described in, e.g., U.S. Pub. No. US2013021661012 (herein incorporated by reference in its entirety).

In some embodiments, the conjugate can be a synergistic biomolecule-polymer conjugate, which comprises a long-acting continuous-release system to provide a greater therapeutic efficacy. The synergistic biomolecule-polymer conjugate can be those described in U.S. Pub. No. US20130195799. In some embodiments, the conjugate can be an aptamer conjugate as described in Intl. Pat. Pub. No. WO2012040524. In some embodiments, the conjugate can be an amine containing polymer conjugate as described in U.S. Pat. No. 8,507,653. Each of the references is herein incorporated by reference in its entirety. In some embodiments, the polynucleotides can be conjugated to SMARTT POLYMER TECHNOLOGY@(PHASERX®, Inc. Seattle, WA).

In some embodiments, the polynucleotides described herein are covalently conjugated to a cell penetrating polypeptide, which can also include a signal sequence or a targeting sequence. The conjugates can be designed to have increased stability, and/or increased cell transfection; and/or altered the biodistribution (e.g., targeted to specific tissues or cell types).

In some embodiments, the polynucleotides described herein can be conjugated to an agent to enhance delivery. In some embodiments, the agent can be a monomer or polymer such as a targeting monomer or a polymer having targeting blocks as described in Intl. Pub. No. WO2011062965. In some embodiments, the agent can be a transport agent covalently coupled to a polynucleotide as described in, e.g., U.S. Pat. Nos. 6,835.393 and 7,374,778. In some embodiments, the agent can be a membrane barrier transport enhancing agent such as those described in U.S. Pat. Nos. 7,737,108 and 8,003,129. Each of the references is herein incorporated by reference in its entirety.

22. Accelerated Blood Clearance

The disclosure provides compounds, compositions and methods of use thereof for reducing the effect of ABC on a repeatedly administered active agent such as a biologically active agent. As will be readily apparent, reducing or eliminating altogether the effect of ABC on an administered active agent effectively increases its half-life and thus its efficacy.

In some embodiments the term reducing ABC refers to any reduction in ABC in comparison to a positive reference control ABC inducing LNP such as an MC3 LNP. ABC inducing LNPs cause a reduction in circulating levels of an active agent upon a second or subsequent administration within a given time frame. Thus a reduction in ABC refers to less clearance of circulating agent upon a second or subsequent dose of agent, relative to a standard LNP. The reduction may be, for instance, at least 10%, 15%, 20%, 25%, 30%, 35%, 40%, 45%, 50%, 55%, 60%, 65%, 70%, 75%, 80%, 85%, 90%, 95%, 98%, or 100%. In some embodiments the reduction is 10-100%, 10-50%, 20-100%, 20-50%, 30-100%, 30-50%, 40%-100%, 40-80%, 50-90%, or 50-100%. Alternatively the reduction in ABC may be characterized as at least a detectable level of circulating agent following a second or subsequent administration or at least a 2 fold, 3 fold, 4 fold, 5 fold increase in circulating agent relative to circulating agent following administration of a standard LNP. In some embodiments the reduction is 2-100 fold, 2-50 fold, 3-100 fold, 3-50 fold, 3-20 fold, 4-100 fold, 4-50 fold, 4-40 fold, 4-30 fold, 4-25 fold, 4-20 fold, 4-15 fold, 4-10 fold, 4-5 fold, 5-100 fold, 5-50 fold, 5-40 fold, 5-30 fold, 5-25 fold, 5-20 fold, 5-15 fold, 5-10 fold, 6-100 fold, 6-50 fold, 6-40 fold, 6-30 fold, 6-25 fold, 6-20 fold, 6-15 fold, 6-10 fold, 8-100 fold, 8-50 fold, 8-40 fold, 8-30 fold, 8-25 fold, 8-20 fold, 8-15 fold, 8-10 fold, 10-100 fold, 10-50 fold, 10-40 fold, 10-30 fold, 10-25 fold, 10-20 fold, 10-15 fold, 20-100 fold, 20-50 fold, 20-40 fold, 20-30 fold, or 20-25 fold.

The disclosure provides lipid-comprising compounds and compositions that are less susceptible to clearance and thus have a longer half-life in vivo. This is particularly the case where the compositions are intended for repeated including chronic administration, and even more particularly where such repeated administration occurs within days or weeks.

Significantly, these compositions are less susceptible or altogether circumvent the observed phenomenon of accelerated blood clearance (ABC). ABC is a phenomenon in which certain exogenously administered agents are rapidly cleared from the blood upon second and subsequent administrations. This phenomenon has been observed, in part, for a variety of lipid-containing compositions including but not limited to lipidated agents, liposomes or other lipid-based delivery vehicles, and lipid-encapsulated agents. Heretofore, the basis of ABC has been poorly understood and in some cases attributed to a humoral immune response and accordingly strategies for limiting its impact in vivo particularly in a clinical setting have remained elusive.

This disclosure provides compounds and compositions that are less susceptible, if at all susceptible, to ABC. In some important aspects, such compounds and compositions are lipid-comprising compounds or compositions. The lipid-containing compounds or compositions of this disclosure, surprisingly, do not experience ABC upon second and subsequent administration in vivo. This resistance to ABC renders these compounds and compositions particularly suitable for repeated use in vivo, including for repeated use within short periods of time, including days or 1-2 weeks. This enhanced stability and/or half-life is due, in part, to the inability of these compositions to activate B1a and/or B1b cells and/or conventional B cells, pDCs and/or platelets.

This disclosure therefore provides an elucidation of the mechanism underlying accelerated blood clearance (ABC). It has been found, in accordance with this disclosure and the inventions provided herein, that the ABC phenomenon at least as it relates to lipids and lipid nanoparticles is mediated, at least in part an innate immune response involving B1a and/or Bib cells, pDC and/or platelets. B1a cells are normally responsible for secreting natural antibody, in the form of circulating IgM. This IgM is poly-reactive, meaning that it is able to bind to a variety of antigens, albeit with a relatively low affinity for each.

It has been found in accordance with the invention that some lipidated agents or lipid-comprising formulations such as lipid nanoparticles administered in vivo trigger and are subject to ABC. It has now been found in accordance with the invention that upon administration of a first dose of the LNP, one or more cells involved in generating an innate immune response (referred to herein as sensors) bind such agent, are activated, and then initiate a cascade of immune factors (referred to herein as effectors) that promote ABC and toxicity. For instance, B1a and B1b cells may bind to LNP, become activated (alone or in the presence of other sensors such as pDC and/or effectors such as IL6) and secrete natural IgM that binds to the LNP. Pre-existing natural IgM in the human subject may also recognize and bind to the LNP, thereby triggering complement fixation. After administration of the first dose, the production of natural IgM begins within 1-2 hours of administration of the LNP. Typically, by about 2-3 weeks the natural IgM is cleared from the system due to the natural half-life of IgM. Natural IgG is produced beginning around 96 hours after administration of the LNP. The agent, when administered in a naïve setting, can exert its biological effects relatively unencumbered by the natural IgM produced post-activation of the B1a cells or Bib cells or natural IgG. The natural IgM and natural IgG are non-specific and thus are distinct from anti-PEG IgM and anti-PEG IgG.

Although Applicant is not bound by mechanism, it is proposed that LNPs trigger ABC and/or toxicity through the following mechanisms. It is believed that when an LNP is administered to a human subject the LNP is rapidly transported through the blood to the spleen. The LNPs may encounter immune cells in the blood and/or the spleen. A rapid innate immune response is triggered in response to the presence of the LNP within the blood and/or spleen. Applicant has shown herein that within hours of administration of an LNP several immune sensors have reacted to the presence of the LNP. These sensors include but are not limited to immune cells involved in generating an immune response, such as B cells, pDC, and platelets. The sensors may be present in the spleen, such as in the marginal zone of the spleen and/or in the blood. The LNP may physically interact with one or more sensors, which may interact with other sensors. In such a case the LNP is directly or indirectly interacting with the sensors. The sensors may interact directly with one another in response to recognition of the LNP. For instance, many sensors are located in the spleen and can easily interact with one another. Alternatively, one or more of the sensors may interact with LNP in the blood and become activated. The activated sensor may then interact directly with other sensors or indirectly (e.g., through the stimulation or production of a messenger such as a cytokine e.g., IL6).

In some embodiments the LNP may interact directly with and activate each of the following sensors: pDC, B1a cells, Bib cells, and platelets. These cells may then interact directly or indirectly with one another to initiate the production of effectors which ultimately lead to the ABC and/or toxicity associated with repeated doses of LNP. For instance, Applicant has shown that LNP administration leads to pDC activation, platelet aggregation and activation and B cell activation. In response to LNP platelets also aggregate and are activated and aggregate with B cells. pDC cells are activated. LNP has been found to interact with the surface of platelets and B cells relatively quickly. Blocking the activation of any one or combination of these sensors in response to LNP is useful for dampening the immune response that would ordinarily occur. This dampening of the immune response results in the avoidance of ABC and/or toxicity.

The sensors once activated produce effectors. An effector, as used herein, is an immune molecule produced by an immune cell, such as a B cell. Effectors include but are not limited to immunoglobulin such as natural IgM and natural IgG and cytokines such as IL6. B1a and B1b cells stimulate the production of natural IgMs within 2-6 hours following administration of an LNP. Natural IgG can be detected within 96 hours. IL6 levels are increased within several hours. The natural IgM and IgG circulate in the body for several days to several weeks. During this time the circulating effectors can interact with newly administered LNPs, triggering those LNPs for clearance by the body. For instance, an effector may recognize and bind to an LNP. The Fc region of the effector may be recognized by and trigger uptake of the decorated LNP by macrophage. The macrophage are then transported to the spleen. The production of effectors by immune sensors is a transient response that correlates with the timing observed for ABC.

If the administered dose is the second or subsequent administered dose, and if such second or subsequent dose is administered before the previously induced natural IgM and/or IgG is cleared from the system (e.g., before the 2-3 window time period), then such second or subsequent dose is targeted by the circulating natural IgM and/or natural IgG or Fc which trigger alternative complement pathway activation and is itself rapidly cleared. When LNP are administered after the effectors have cleared from the body or are reduced in number, ABC is not observed.

Thus, it is useful according to aspects of the invention to inhibit the interaction between LNP and one or more sensors, to inhibit the activation of one or more sensors by LNP (direct or indirect), to inhibit the production of one or more effectors, and/or to inhibit the activity of one or more effectors. In some embodiments the LNP is designed to limit or block interaction of the LNP with a sensor. For instance the LNP may have an altered PC and/or PEG to prevent interactions with sensors. Alternatively or additionally an agent that inhibits immune responses induced by LNPs may be used to achieve any one or more of these effects.

It has also been determined that conventional B cells are also implicated in ABC. Specifically, upon first administration of an agent, conventional B cells, referred to herein as CD19(+), bind to and react against the agent. Unlike B1a and B1b cells though, conventional B cells are able to mount first an IgM response (beginning around 96 hours after administration of the LNPs) followed by an IgG response (beginning around 14 days after administration of the LNPs) concomitant with a memory response. Thus conventional B cells react against the administered agent and contribute to IgM (and eventually IgG) that mediates ABC. The IgM and IgG are typically anti-PEG IgM and anti-PEG IgG.

It is contemplated that in some instances, the majority of the ABC response is mediated through B1a cells and B1a-mediated immune responses. It is further contemplated that in some instances, the ABC response is mediated by both IgM and IgG, with both conventional B cells and B1a cells mediating such effects. In yet still other instances, the ABC response is mediated by natural IgM molecules, some of which are capable of binding to natural IgM, which may be produced by activated B1a cells. The natural IgMs may bind to one or more components of the LNPs, e.g., binding to a phospholipid component of the LNPs (such as binding to the PC moiety of the phospholipid) and/or binding to a PEG-lipid component of the LNPs (such as binding to PEG-DMG, in particular, binding to the PEG moiety of PEG-DMG). Since B1a expresses CD36, to which phosphatidylcholine is a ligand, it is contemplated that the CD36 receptor may mediate the activation of B1a cells and thus production of natural IgM. In yet still other instances, the ABC response is mediated primarily by conventional B cells.

It has been found in accordance with the invention that the ABC phenomenon can be reduced or abrogated, at least in part, through the use of compounds and compositions (such as agents, delivery vehicles, and formulations) that do not activate B1a cells. Compounds and compositions that do not activate B1a cells may be referred to herein as B1a inert compounds and compositions. It has been further found in accordance with the invention that the ABC phenomenon can be reduced or abrogated, at least in part, through the use of compounds and compositions that do not activate conventional B cells. Compounds and compositions that do not activate conventional B cells may in some embodiments be referred to herein as CD19-inert compounds and compositions. Thus, in some embodiments provided herein, the compounds and compositions do not activate B1a cells and they do not activate conventional B cells. Compounds and compositions that do not activate B1a cells and conventional B cells may in some embodiments be referred to herein as B1a/CD19-inert compounds and compositions.

These underlying mechanisms were not heretofore understood, and the role of B1a and B1b cells and their interplay with conventional B cells in this phenomenon was also not appreciated.

Accordingly, this disclosure provides compounds and compositions that do not promote ABC. These may be further characterized as not capable of activating B1a and/or B1b cells, platelets and/or pDC, and optionally conventional B cells also. These compounds (e.g., agents, including biologically active agents such as prophylactic agents, therapeutic agents and diagnostic agents, delivery vehicles, including liposomes, lipid nanoparticles, and other lipid-based encapsulating structures, etc.) and compositions (e.g., formulations, etc.) are particularly desirable for applications requiring repeated administration, and in particular repeated administrations that occur within with short periods of time (e.g., within 1-2 weeks). This is the case, for example, if the agent is a nucleic acid based therapeutic that is provided to a human subject at regular, closely-spaced intervals. The findings provided herein may be applied to these and other agents that are similarly administered and/or that are subject to ABC.

Of particular interest are lipid-comprising compounds, lipid-comprising particles, and lipid-comprising compositions as these are known to be susceptible to ABC. Such lipid-comprising compounds particles, and compositions have been used extensively as biologically active agents or as delivery vehicles for such agents. Thus, the ability to improve their efficacy of such agents, whether by reducing the effect of ABC on the agent itself or on its delivery vehicle, is beneficial for a wide variety of active agents.

Also provided herein are compositions that do not stimulate or boost an acute phase response (ARP) associated with repeat dose administration of one or more biologically active agents.

The composition, in some instances, may not bind to IgM, including but not limited to natural IgM.

The composition, in some instances, may not bind to an acute phase protein such as but not limited to C-reactive protein.

The composition, in some instances, may not trigger a CD5(+) mediated immune response. As used herein, a CD5(+) mediated immune response is an immune response that is mediated by B1a and/or B1b cells. Such a response may include an ABC response, an acute phase response, induction of natural IgM and/or IgG, and the like.

The composition, in some instances, may not trigger a CD19(+) mediated immune response. As used herein, a CD19(+) mediated immune response is an immune response that is mediated by conventional CD19(+), CD5(−) B cells. Such a response may include induction of IgM, induction of IgG, induction of memory B cells, an ABC response, an anti-drug antibody (ADA) response including an anti-protein response where the protein may be encapsulated within an LNP, and the like.

B1a cells are a subset of B cells involved in innate immunity. These cells are the source of circulating IgM, referred to as natural antibody or natural serum antibody. Natural IgM antibodies are characterized as having weak affinity for a number of antigens, and therefore they are referred to as "poly-specific" or "poly-reactive", indicating their ability to bind to more than one antigen. B1a cells are not able to produce IgG. Additionally, they do not develop into memory cells and thus do not contribute to an adaptive immune response. However, they are able to secrete IgM upon activation. The secreted IgM is typically cleared within about 2-3 weeks, at which point the immune system is rendered relatively naïve to the previously administered antigen. If the same antigen is presented after this time period (e.g., at about 3 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic agents unsuitable for use.

In humans, B1a cells are CD19(+), CD20(+), CD27(+), CD43(+), CD70(−) and CD5(+). In mice, B1a cells are CD19(+), CD5(+), and CD45 B cell isoform B220(+). It is the expression of CD5 which typically distinguishes B1a cells from other convention B cells. B1a cells may express high levels of CD5, and on this basis may be distinguished from other B-1 cells such as B-1b cells which express low or undetectable levels of CD5. CD5 is a pan-T cell surface glycoprotein. B1a cells also express CD36, also known as fatty acid translocase. CD36 is a member of the class B scavenger receptor family. CD36 can bind many ligands, including oxidized low density lipoproteins, native lipoproteins, oxidized phospholipids, and long-chain fatty acids.

B1b cells are another subset of B cells involved in innate immunity. These cells are another source of circulating natural IgM. Several antigens, including PS, are capable of inducing T cell independent immunity through B1b activation. CD27 is typically upregulated on B1b cells in response to antigen activation. Similar to B1a cells, the B1b cells are typically located in specific body locations such as the spleen and peritoneal cavity and are in very low abundance in the blood. The B1b secreted natural IgM is typically cleared within about 2-3 weeks, at which point the immune system is rendered relatively naïve to the previously administered antigen. If the same antigen is presented after this time period (e.g., at about 3 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic agents unsuitable for use.

In some embodiments it is desirable to block B1a and/or B1b cell activation. One strategy for blocking B1a and/or B1b cell activation involves determining which components of a lipid nanoparticle promote B cell activation and neutralizing those components. It has been discovered herein that at least PEG and phosphatidylcholine (PC) contribute to B1a and B1b cell interaction with other cells and/or activation. PEG may play a role in promoting aggregation between B1 cells and platelets, which may lead to activation. PC (a helper lipid in LNPs) is also involved in activating the B1 cells, likely through interaction with the CD36 receptor on the B cell surface. Numerous particles have PEG-lipid alternatives, PEG-less, and/or PC replacement lipids (e.g. oleic acid or analogs thereof) have been designed and tested. Applicant has established that replacement of one or more of these components within an LNP that otherwise would promote ABC upon repeat administration, is useful in preventing ABC by reducing the production of natural IgM and/or B cell activation. Thus, the invention encompasses LNPs that have reduced ABC as a result of a design which eliminates the inclusion of B cell triggers.

Another strategy for blocking Bia and/or B1b cell activation involves using an agent that inhibits immune responses induced by LNPs. These types of agents are discussed in more detail below. In some embodiments these agents block the interaction between B1a/B1b cells and the LNP or platelets or pDC. For instance, the agent may be an antibody or other binding agent that physically blocks the interaction. An example of this is an antibody that binds to CD36 or CD6. The agent may also be a compound that prevents or disables the B1a/B1b cell from signaling once activated or prior to activation. For instance, it is possible to block one or more components in the B1a/B1b signaling cascade the results from B cell interaction with LNP or other immune cells. In other embodiments the agent may act one or more effectors produced by the B1a/B1b cells following activation. These effectors include for instance, natural IgM and cytokines.

It has been demonstrated according to aspects of the invention that when activation of pDC cells is blocked, B cell activation in response to LNP is decreased. Thus, in order to avoid ABC and/or toxicity, it may be desirable to prevent pDC activation. Similar to the strategies discussed above, pDC cell activation may be blocked by agents that interfere with the interaction between pDC and LNP and/or B cells/platelets. Alternatively, agents that act on the pDC to block its ability to get activated or on its effectors can be used together with the LNP to avoid ABC.

Platelets may also play an important role in ABC and toxicity. Very quickly after a first dose of LNP is administered to a human subject platelets associate with the LNP, aggregate and are activated. In some embodiments it is desirable to block platelet aggregation and/or activation. One strategy for blocking platelet aggregation and/or activation involves determining which components of a lipid nanoparticle promote platelet aggregation and/or activation and neutralizing those components. It has been discovered herein that at least PEG contribute to platelet aggregation, activation and/or interaction with other cells. Numerous particles have PEG-lipid alternatives and PEG-less have been designed and tested. Applicant has established that replacement of one or more of these components within an LNP that otherwise would promote ABC upon repeat administration, is useful in preventing ABC by reducing the production of natural IgM and/or platelet aggregation. Thus, the invention encompasses LNPs that have reduced ABC as a result of a design which eliminates the inclusion of platelet triggers. Alternatively agents that act on the platelets to block its activity once it is activated or on its effectors can be used together with the LNP to avoid ABC.

(i) Measuring ABC Activity and Related Activities

Various compounds and compositions provided herein, including LNPs, do not promote ABC activity upon administration in vivo. These LNPs may be characterized and/or identified through any of a number of assays, such as but not limited to those described below, as well as any of the assays disclosed in the Examples section, include the methods subsection of the Examples.

In some embodiments the methods involve administering an LNP without producing an immune response that promotes ABC. An immune response that promotes ABC involves activation of one or more sensors, such as B1 cells, pDC, or platelets, and one or more effectors, such as natural IgM, natural IgG or cytokines such as IL6. Thus administration of an LNP without producing an immune response that promotes ABC, at a minimum involves administration of an LNP without significant activation of one or more sensors and significant production of one or more effectors. Significant used in this context refers to an amount that would lead to the physiological consequence of accelerated blood clearance of all or part of a second dose with respect to the level of blood clearance expected for a second dose of an ABC triggering LNP. For instance, the immune response should be dampened such that the ABC observed after the second dose is lower than would have been expected for an ABC triggering LNP.

(ii) B1a or B1b Activation Assay

Certain compositions provided in this disclosure do not activate B cells, such as B1a or B1b cells (CD19+CD5+) and/or conventional B cells (CD19+CD5−). Activation of B1a cells, Bib cells, or conventional B cells may be determined in a number of ways, some of which are provided below. B cell population may be provided as fractionated B cell populations or unfractionated populations of splenocytes or peripheral blood mononuclear cells (PBMC). If the latter, the cell population may be incubated with the LNP of choice for a period of time, and then harvested for further analysis. Alternatively, the supernatant may be harvested and analyzed.

(iii) Upregulation of Activation Marker Cell Surface Expression

Activation of B1a cells, B1b cells, or conventional B cells may be demonstrated as increased expression of B cell activation markers including late activation markers such as CD86. In an exemplary non-limiting assay, unfractionated B cells are provided as a splenocyte population or as a PBMC population, incubated with an LNP of choice for a particular period of time, and then stained for a standard B cell marker such as CD19 and for an activation marker such as CD86, and analyzed using for example flow cytometry. A suitable negative control involves incubating the same population with medium, and then performing the same staining and visualization steps. An increase in CD86 expression in the test population compared to the negative control indicates B cell activation.

(iv) Pro-Inflammatory Cytokine Release

B cell activation may also be assessed by cytokine release assay. For example, activation may be assessed through the production and/or secretion of cytokines such as IL-6 and/or TNF-alpha upon exposure with LNPs of interest.

Such assays may be performed using routine cytokine secretion assays well known in the art. An increase in cytokine secretion is indicative of B cell activation.

(v) LNP Binding/Association to and/or Uptake by B Cells

LNP association or binding to B cells may also be used to assess an LNP of interest and to further characterize such LNP. Association/binding and/or uptake/internalization may be assessed using a detectably labeled, such as fluorescently labeled, LNP and tracking the location of such LNP in or on B cells following various periods of incubation.

The invention further contemplates that the compositions provided herein may be capable of evading recognition or detection and optionally binding by downstream mediators of ABC such as circulating IgM and/or acute phase response mediators such as acute phase proteins (e.g., C-reactive protein (CRP).

(vi) Methods of Use for Reducing ABC

Also provided herein are methods for delivering LNPs, which may encapsulate an agent such as a therapeutic agent, to a human subject without promoting ABC.

In some embodiments, the method comprises administering any of the LNPs described herein, which do not promote ABC, for example, do not induce production of natural IgM binding to the LNPs, do not activate B1a and/or B1b cells. As used herein, an LNP that "does not promote ABC" refers to an LNP that induces no immune responses that would lead to substantial ABC or a substantially low level of immune responses that is not sufficient to lead to substantial ABC. An LNP that does not induce the production of natural IgMs binding to the LNP refers to LNPs that induce either no natural IgM binding to the LNPs or a substantially low level of the natural IgM molecules, which is insufficient to lead to substantial ABC. An LNP that does not activate Bia and/or B1b cells refer to LNPs that induce no response of B1a and/or B1b cells to produce natural IgM binding to the LNPs or a substantially low level of B1a and/or B1b responses, which is insufficient to lead to substantial ABC.

In some embodiments the terms do not activate and do not induce production are a relative reduction to a reference value or condition. In some embodiments the reference value or condition is the amount of activation or induction of production of a molecule such as IgM by a standard LNP such as an MC3 LNP. In some embodiments the relative reduction is a reduction of at least 30%, for example at least 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%. In other embodiments the terms do not activate cells such as B cells and do not induce production of a protein such as IgM may refer to an undetectable amount of the active cells or the specific protein.

(vii) Platelet Effects and Toxicity

The invention is further premised in part on the elucidation of the mechanism underlying dose-limiting toxicity associated with LNP administration. Such toxicity may involve coagulopathy, disseminated intravascular coagulation (DIC, also referred to as consumptive coagulopathy), whether acute or chronic, and/or vascular thrombosis. In some instances, the dose-limiting toxicity associated with LNPs is acute phase response (APR) or complement activation-related pseudoallergy (CARPA).

As used herein, coagulopathy refers to increased coagulation (blood clotting) in vivo. The findings reported in this disclosure are consistent with such increased coagulation and significantly provide insight on the underlying mechanism. Coagulation is a process that involves a number of different factors and cell types, and heretofore the relationship between and interaction of LNPs and platelets has not been understood in this regard. This disclosure provides evidence of such interaction and also provides compounds and compositions that are modified to have reduced platelet effect, including reduced platelet association, reduced platelet aggregation, and/or reduced platelet aggregation. The ability to modulate, including preferably down-modulate, such platelet effects can reduce the incidence and/or severity of coagulopathy post-LNP administration. This in turn will reduce toxicity relating to such LNP, thereby allowing higher doses of LNPs and importantly their cargo to be administered to patients in need thereof.

CARPA is a class of acute immune toxicity manifested in hypersensitivity reactions (HSRs), which may be triggered by nanomedicines and biologicals. Unlike allergic reactions, CARPA typically does not involve IgE but arises as a consequence of activation of the complement system, which is part of the innate immune system that enhances the body's abilities to clear pathogens. One or more of the following pathways, the classical complement pathway (CP), the alternative pathway (AP), and the lectin pathway (LP), may be involved in CARPA. Szebeni, Molecular Immunology, 61:163-173 (2014).

The classical pathway is triggered by activation of the C1-complex, which contains. C1q, C1r, C1s, or C1qr2s2. Activation of the C1-complex occurs when C1q binds to IgM or IgG complexed with antigens, or when C1q binds directly to the surface of the pathogen. Such binding leads to conformational changes in the C1q molecule, which leads to the activation of C1r, which in turn, cleave C1s. The C1r2s2 component now splits C4 and then C2, producing C4a, C4b, C2a, and C2b. C4b and C2b bind to form the classical pathway C3-convertase (C4b2b complex), which promotes cleavage of C3 into C3a and C3b. C3b then binds the C3 convertase to from the C5 convertase (C4b2b3b complex). The alternative pathway is continuously activated as a result of spontaneous C3 hydrolysis. Factor P (properdin) is a positive regulator of the alternative pathway. Oligomerization of properdin stabilizes the C3 convertase, which can then cleave much more C3. The C3 molecules can bind to surfaces and recruit more B, D, and P activity, leading to amplification of the complement activation.

Acute phase response (APR) is a complex systemic innate immune responses for preventing infection and clearing potential pathogens. Numerous proteins are involved in APR and C-reactive protein is a well-characterized one.

It has been found, in accordance with the invention, that certain LNP are able to associate physically with platelets almost immediately after administration in vivo, while other LNP do not associate with platelets at all or only at background levels. Significantly, those LNPs that associate with platelets also apparently stabilize the platelet aggregates that are formed thereafter. Physical contact of the platelets with certain LNPs correlates with the ability of such platelets to remain aggregated or to form aggregates continuously for an extended period of time after administration. Such aggregates comprise activated platelets and also innate immune cells such as macrophages and B cells.

23. Methods of Use

The polynucleotides, pharmaceutical compositions and formulations described herein are used in the preparation, manufacture and therapeutic use of to treat and/or prevent PCC-related diseases, disorders or conditions. In some embodiments, the polynucleotides, compositions and formulations of the invention are used to treat and/or prevent metabolic acidosis (e.g., acidosis of the blood and tissues), hyperammonemia, and/or hyperglycinemia. In some embodiments, the polynucleotides, compositions and formulations of the invention are used to treat and/or prevent the accumulation of propionyl-CoA and/or metabolites of branched-chain amino acid catabolism, e.g., accumulation in the tissue (e.g., liver), whole blood (e.g., in dried blood spots), plasma, serum, RBCs, urine, and/or other fluids.

In some embodiments, the polynucleotides, pharmaceutical compositions and formulations of the invention are used in methods for reducing the levels of propionic acid in a human subject in need thereof. For instance, one aspect of the invention provides a method of alleviating the symptoms of propionic acidemia in a human subject comprising the administration of a composition or formulation comprising a polynucleotide encoding PCCA and/or PCCA to that human subject (e.g., an mRNA encoding a PCCA polypeptide) and/or a PCCB polypeptide. In some embodiments, the invention provides a method of alleviating the symptoms of propionic acidemia in a human subject comprising the co-administration of a composition or formulation comprising a polynucleotide encoding PCCA and a composition or formulation comprising a polynucleotide encoding PCCB to that human subject In some embodiments, the polynucleotides, pharmaceutical compositions and formulations of the invention are used to reduce the level of propionic acid, the method comprising administering to the human subject an effective amount of a polynucleotide encoding a PCCA polypeptide and/or PCCB polypeptide. In some embodiments, the administration of the polynucleotide, pharmaceutical composition or formulation of the invention results in reduction in the level of propionic acid to less than 1,200 μM (e.g., 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175 μM), within a short period of time (e.g., within about 6 hours, within about 8 hours, within about 12 hours, within about 16 hours, within about 20 hours, or within about 24 hours) after administration of the polynucleotide, pharmaceutical composition or formulation of the invention.

In some embodiments, the administration of the polynucleotide, pharmaceutical composition or formulation of the invention results in reduction in the level of propionic acid over the course of at least 12 hours, at least 1 day, at least 5 days, at least 10 days, at least 12 days, at least 14 days, at least 16 days, at least 18 days, at least 20 days, at least 21 days, at least 22 days, at least 24 days, at least 26 days, at least 28 days, at least 30 days, at least 32 days, at least 35 days, at least 40 days, at least 45 days, at least 50 days, or at least 60 days. In some embodiments, the administration of the polynucleotide, pharmaceutical composition or formulation of the invention results in reduction in the level of propionic acid over the course of between 1 day and 30 days, between 15 days and 45 days, or between 30 days and 60 days.

In some embodiments, the administration of an effective amount of a polynucleotide, pharmaceutical composition or formulation of the invention reduces the levels of at least one biomarker of PA, e.g., propionyl-L-carnitine (C3), 2-methylcitric acid (2-MC), 3-hydroxypropionic acid, (3OHPA), propionylglycine, glycine, lactate and/or ammonia. In some embodiments, the administration of an effective amount of a polynucleotide, pharmaceutical composition or formulation of the invention reduces the levels of propionyl-L-carnitine (C3), 2-methylcitric acid (2-MC), 3-hydroxypropionic acid, (3OHPA), propionylglycine, glycine, lactate and/or ammonia in the tissue (e.g., liver), whole blood (e.g., in dried blood spots), plasma, serum, RBCs, urine, and/or other fluids. In one embodiment, the administration of an effective amount of a polynucleotide, pharmaceutical composition or formulation of the invention reduces the levels of ammonia in a tissue of the human subject and further reduces the level of at least one additional biomarker.

In some embodiments, the administration of the polynucleotide, pharmaceutical composition or formulation of the invention results in reduction in the level of one or more biomarkers of PA (e.g., at least one biomarker of PA in addition to ammonia), within a short period of time (e.g., within about 6 hours, within about 8 hours, within about 12 hours, within about 16 hours, within about 20 hours, or within about 24 hours) after administration of the polynucleotide, pharmaceutical composition or formulation of the invention. In some embodiments, the administration of the polynucleotide, pharmaceutical composition or formulation of the invention results in reduction in the level of one or more biomarkers of PA over the course of at least 12 hours, at least 1 day, at least 5 days, at least 10 days, at least 12 days, at least 14 days, at least 16 days, at least 18 days, at least 20 days, at least 21 days, at least 22 days, at least 24 days, at least 26 days, at least 28 days, at least 30 days, at least 32 days, at least 35 days, at least 40 days, at least 45 days, at least 50 days, or at least 60 days. In some embodiments, the administration of the polynucleotide, pharmaceutical composition or formulation of the invention results in reduction in the level of one or more biomarkers of PA over the course of between 1 day and 30 days, between 15 days and 45 days, or between 30 and 60 days.

In some embodiments, the administration of the polynucleotide, pharmaceutical composition or formulation of the invention results in reduction in the level of ammonia. In some embodiments, the administration of the polynucleotide, pharmaceutical composition or formulation of the invention results in reduction in the level of ammonia in a human subject having PA, e.g., reduction in plasma ammonia levels to normal or about normal levels of ammonia. In some embodiments, the effects of co-administering PCCA and PCCB mRNAs on plasma ammonia levels can be compared to the effects on ammonia levels that result from administering Carbaglu® to a human subject, e.g., a mammal such as a human. Carbaglu® is a drug approved by the European Medicines Agency (EMA)- to treat hyperammonemia due to PA. The polynucleotides described herein can have serveral advantages over Carbaglu®. For example, Carbaglu® has a relatively short half-life of approximately 5-6 hours, so patients must take 2-4 doses of Carbaglu daily for the drug to be effective. By contrast, in some cases the polynucleotides described herein (mRNA-expressed human PCCA and PCCB) have a liver residence time of 21 days or more following administration of mRNAs in some mammals, so patients could be dosed less frequently with these polynucleotides relative to Carbaglu®. In addition, Carbaglu®only has an impact on ammonia levels by activating ureagenesis, whereas mRNAs encoding PCCA and PCCB restore functional PCC enzyme and propionate metabolism in the liver, and thus should have an impact on other disease-associated metabolites in addition to ammonia.

Replacement therapy is a potential treatment for PA. Thus, in certain aspects of the invention, the polynucleotides, e.g., mRNA, disclosed herein comprise one or more sequences encoding a PCCA and/or PCCB polypeptide that is suitable for use in gene replacement therapy for PA. In some embodiments, the present disclosure treats a lack of PCCA and/or PCCB or PCC activity, or decreased or abnormal PCC activity in a human subject by providing at least one polynucleotide, e.g., mRNA, that encodes a PCCA polypeptide and/or a PCCB polypeptide to the human subject. In some embodiments, the polynucleotide is sequence-optimized. In some embodiments, the at least one polynucleotide (e.g., an mRNA) comprises a nucleic acid sequence (e.g., an ORF) encoding a PCCA polypeptide and/or PCCB polypeptide, wherein the at least one nucleic acid is sequence-optimized, e.g., by modifying its G/C, uridine, or thymidine content, and/or the at least one polynucleotide comprises at least one chemically modified nucleoside. In some embodiments, the at least one polynucleotide comprises a miRNA binding site, e.g., a miRNA binding site that binds miRNA-142 and/or a miRNA binding site that binds miRNA-126.

In some embodiments, the administration of a composition or formulation comprising at least one polynucleotide, pharmaceutical composition or formulation of the invention to a human subject results in a decrease in propionic acid in blood/plasma to a level at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or to 100% lower than the level observed prior to the administration of the composition or formulation.

In some embodiments, the administration of the at least one polynucleotide, pharmaceutical composition or formulation of the invention results in expression of PCCA and/or PCCB in cells of the human subject. In some embodiments, administering the at least one polynucleotide, pharmaceutical composition or formulation of the invention results in an increase of PCCA and/or PCCB expression and/or enzymatic activity in the human subject. For example, in some embodiments, the polynucleotides of the present invention are used in methods of administering a composition or formulation comprising at least one mRNA encoding a PCCA and/or PCCB polypeptide to a human subject, wherein the method results in an increase of PCCA and/or PCCB expression and/or enzymatic activity in at least some cells of a human subject.

In some embodiments, the administration of a composition or formulation comprising at least one mRNA encoding a PCCA and/or PCCB polypeptide to a human subject results in an increase of PCCA and/or PCCB expression and/or PCC enzymatic activity (e.g., as measured by reduction in at least one biomarker of disease, such as at least one biomarker in addition to ammonia levels) in cells subject to a level at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or to 100% or more of the expression and/or activity level expected in a normal human subject, e.g., a human not suffering from PA. In one embodiment, such administration results in an increase in PCCA and/or PCCB expression and/or PCC enzymatic activity as soon as 1-2 days post administration and which lasts as long as 3-4 weeks after a single intravenous dose. In another embodiment, repeat dosing results in sustained PCCA and/or PCCB expression and/or PCC enzymatic activity. In yet another embodiment, such administration results in expression of PCCA and/or PCCB in the human subject's liver cells, e.g., in mitochondria.

In some embodiments, the administration of the polynucleotide, pharmaceutical composition or formulation of the invention results in expression of PCCA and/or PCCB protein in at least some of the cells of a human subject that persists for a period of time sufficient to allow significant propionic acid metabolism to occur.

In some embodiments, the expression of the encoded polypeptide is increased. In some embodiments, the at least one polynucleotide increases PCCA and/or PCCB expression and/or PCC enzymatic activity levels in cells when introduced into those cells, e.g., by at least 2%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or to 100% with respect to the PCCA and/or PCCB expression and/or PCC enzymatic activity level in the cells before the at least one polypeptide is introduced in the cells.

In some embodiments, the method or use comprises administering at least one polynucleotide, e.g., mRNA, comprising at least one nucleotide sequence having sequence similarity to a polynucleotide selected from the group of SEQ ID NOs: 2, 5-14, 16-27, 196, 197, and 198 or a at least one polynucleotide selected from the group of SEQ ID NOs: 28-50, 63, 65-67, and 200-205, wherein the at least one polynucleotide encodes a PCCA and/or PCCB polypeptide.

Other aspects of the present disclosure relate to transplantation of cells containing polynucleotides to a mammalian subject. Administration of cells to human subjects is known to those of ordinary skill in the art, and includes, but is not limited to, local implantation (e.g., topical or subcutaneous administration), organ delivery or systemic injection (e.g., intravenous injection or inhalation), and the formulation of cells in pharmaceutically acceptable carriers.

In some embodiments, the polynucleotides (e.g., mRNA), pharmaceutical compositions and formulations used in the methods of the invention comprise a uracil-modified sequence encoding a PCCA and/or PCCB polypeptide disclosed herein and a miRNA binding site disclosed herein, e.g., a miRNA binding site that binds to miR-142 and/or a miRNA binding site that binds to miR-126. In some embodiments, the uracil-modified sequence encoding a PCCA and/or PCCB polypeptide comprises at least one chemically modified nucleobase, e.g., N1-methylpseudouracil or 5-methoxyuracil. In some embodiments, at least 95% of a type of nucleobase (e.g., uracil) in a uracil-modified sequence encoding a PCCA and/or PCCB polypeptide of the invention are modified nucleobases. In some embodiments, at least 95% of uracil in a uracil-modified sequence encoding a PCCA and/or PCCB polypeptide is 1-N-methylpseudouridine or 5-methoxyuridine. In some embodiments, the polynucleotide (e.g., a RNA, e.g., a mRNA) disclosed herein is formulated with a delivery agent comprising, e.g., a compound having the Formula (I), e.g., any of Compounds 1-232, e.g., Compound II; a compound having the Formula (III), (IV), (V), or (VI), e.g., any of Compounds 233-342, e.g., Compound VI; or a compound having the Formula (VIII), e.g., any of Compounds 419-428, e.g., Compound I, or any combination thereof. In some embodiments, the delivery agent comprises Compound II, DSPC, Cholesterol, and Compound I or PEG-DMG, e.g., with a mole ratio of about 47.5:10.5:39.0:3.0 or about 50:10:38.5:1.5. In some embodiments, the delivery agent comprises Compound VI, DSPC, Cholesterol, and Compound I or PEG-DMG, e.g., with a mole ratio in the range of about 30 to about 60 mol % Compound II or VI (or related suitable amino lipid) (e.g., 30-40, 40-45, 45-50, 50-55 or 55-60 mol % Compound II or VI (or related suitable amino lipid)), about 5 to about 20 mol % phospholipid (or related suitable phospholipid or "helper lipid") (e.g., 5-10, 10-15, or 15-20 mol % phospholipid (or related suitable phospholipid or "helper lipid")), about 20 to about 50 mol % cholesterol (or related sterol or "non-cationic" lipid) (e.g., about 20-30, 30-35, 35-40, 40-45, or 45-50 mol % cholesterol (or related sterol or "non-cationic" lipid)) and about 0.05 to about 10 mol % PEG lipid (or other suitable PEG lipid) (e.g., 0.05-1, 1-2, 2-3, 3-4, 4-5, 5-7, or 7-10 mol % PEG lipid (or other suitable PEG lipid)). An exemplary delivery agent can comprise mole ratios of, for example, 47.5:10.5:39.0:3.0 or 50:10:38.5:1.5. In certain instances, an exemplary delivery agent can comprise mole ratios of, for example, 47.5:10.5:39.0:3; 47.5:10:39.5:3;

47.5:11:39.5:2; 47.5:10.5:39.5:2.5; 47.5:11:39:2.5; 48.5:10: 38.5:3; 48.5:10.5:39:2; 48.5:10.5:38.5:2.5; 48.5:10.5:39.5: 1.5; 48.5:10.5:38.0:3; 47:10.5:39.5:3; 47:10:40.5:2.5; 47:11: 40:2; 47:10.5:39.5:3; 48:10.5:38.5:3; 48:10:39.5:2.5; 48:11: 39:2; or 48:10.5:38.5:3. In some embodiments, the delivery agent comprises Compound II or VI, DSPC, Cholesterol, and Compound I or PEG-DMG, e.g., with a mole ratio of about 47.5:10.5:39.0:3.0. In some embodiments, the delivery agent comprises Compound II or VI, DSPC, Cholesterol, and Compound I or PEG-DMG, e.g., with a mole ratio of about 47.5:10.5:39.0:3.0 or about 50:10:38.5:1.5.

The skilled artisan will appreciate that the therapeutic effectiveness of a drug or a treatment of the instant invention can be characterized or determined by measuring the level of expression of an encoded protein (e.g., enzyme) in a sample or in samples taken from a subject (e.g., from a preclinical test subject (rodent, primate, etc.) or from a clinical subject (human). Likewise, the therapeutic effectiveness of a drug or a treatment of the instant invention can be characterized or determined by measuring the level of activity of an encoded protein (e.g., enzyme) in a sample or in samples taken from a subject (e.g., from a preclinical test subject (rodent, primate, etc.) or from a clinical subject (human). Furthermore, the therapeutic effectiveness of a drug or a treatment of the instant invention can be characterized or determined by measuring the level of an appropriate biomarker in sample(s) taken from a subject. Levels of protein and/or biomarkers can be determined post-administration with a single dose of an mRNA therapeutic of the invention or can be determined and/or monitored at several time points following administration with a single dose or can be determined and/or monitored throughout a course of treatment, e.g., a multi-dose treatment.

PA is associated with an impaired ability to catalyze the carboxylation of propionyl-CoA to methylmalonyl-CoA. Accordingly, PA patients commonly show high levels of propionic acid in their blood.

PA is an autosomal recessive inborn metabolic disorder characterized by the inability to catalyze the carboxylation of propionyl-CoA to methylmalonyl-CoA. Accordingly, PA patients can be asymptomatic carriers of the disorder or suffer from the various symptoms associated with the disease. PA patients commonly show high levels of propionic acid in their whole blood, plasma, serum, urine, and/or tissue (e.g., liver). Unless otherwise specified, the methods of treating PA patients or human subjects disclosed herein include treatment of both asymptomatic carriers and those individuals with abnormal levels of biomarkers.

PCCA or PCCB Protein Expression Levels

Certain aspects of the invention feature measurement, determination and/or monitoring of the expression level or levels of propionyl-CoA carboxylase alpha (PCCA) protein and/or propionyl-CoA carboxylase beta (PCCB) in a subject, for example, in an animal (e.g., rodents, primates, and the like) or in a human subject. Animals include normal, healthy or wild type animals, as well as animal models for use in understanding PA and treatments thereof. Exemplary animal models include rodent models, for example, PCCA deficient mice (null or hypomorphic) also referred to as PCCA mice.

PCCA or PCCB protein expression levels can be measured or determined by any art-recognized method for determining protein levels in biological samples, e.g., from blood samples or a needle biopsy. The term "level" or "level of a protein" as used herein, preferably means the weight, mass or concentration of the protein within a sample or a human subject. It will be understood by the skilled artisan that in certain embodiments the sample may be subjected, e.g., to any of the following: purification, precipitation, separation, e.g. centrifugation and/or HPLC, and subsequently subjected to determining the level of the protein, e.g., using mass and/or spectrometric analysis. In exemplary embodiments, enzyme-linked immunosorbent assay (ELISA) can be used to determine protein expression levels. In other exemplary embodiments, protein purification, separation and LC-MS can be used as a means for determining the level of a protein according to the invention. In some embodiments, an mRNA therapy of the invention (e.g., a single intravenous dose) results in increased PCCA and/or PCCB protein expression levels in the liver tissue of the human subject (e.g., 2-fold, 3-fold, 4-fold, 5-fold, 6-fold, 7-fold, 8-fold, 9-fold, 10-fold, 20-fold, 30-fold, 40-fold, 50-fold increase and/or increased to at least 50%, at least 60%, at least 70%, at least 75%, 80%, at least 85%, at least 90%, at least 95%, or at least 100% of normal levels) for at least 6 hours, at least 12 hours, at least 24 hours, at least 36 hours, at least 48 hours, at least 60 hours, at least 72 hours, at least 84 hours, at least 96 hours, at least 108 hours, at least 122 hours, at least 1 week, at least 2 weeks, at least 3 weeks, at least 4 weeks after administration of a single dose of the mRNA therapy. In some embodiments, an mRNA therapy of the invention (e.g., a single intravenous dose) results in decreased propionic acid expression levels in the blood, plasma, serum or liver tissue of the human subject (e.g., less than 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175 or 1,200 μM) for at least 6 hours, at least 12 hours, at least 24 hours, at least 36 hours, at least 48 hours, at least 60 hours, at least 72 hours, at least 84 hours, at least 96 hours, at least 108 hours, at least 122 hours, at least 1 week, at least 2 weeks, at least 3 weeks, at least 4 weeks after administration of a single dose of the mRNA therapy.

PCC Protein Activity

In PA patients, PCC enzymatic activity is reduced compared to a normal physiological activity level. Further aspects of the invention feature measurement, determination and/or monitoring of the activity level(s) (i.e., enzymatic activity level(s)) of PCCA or PCCB protein in a subject, for example, in an animal (e.g., rodent, primate, and the like) or in a human subject. Activity levels can be measured or determined by any art-recognized method for determining enzymatic activity levels in biological samples. The term "activity level" or "enzymatic activity level" as used herein, preferably means the activity of the enzyme per volume, mass or weight of sample or total protein within a sample. In exemplary embodiments, the "activity level" or "enzymatic activity level" is described in terms of units per milliliter of fluid (e.g., bodily fluid, e.g., serum, plasma, urine and the like) or is described in terms of units per weight of tissue or per weight of protein (e.g., total protein) within a sample. Units ("U") of enzyme activity can be described in terms of weight or mass of substrate hydrolyzed per unit time. In certain embodiments of the invention feature PCC activity described in terms of U/ml plasma or U/mg protein (tissue), where units ("U") are described in terms of nmol substrate hydrolyzed per hour (or nmol/hr).

In certain embodiments, an mRNA therapy of the invention features a pharmaceutical composition comprising a dose of mRNA effective to result in at least 5 U/mg, at least 10 U/mg, at least 20 U/mg, at least 30 U/mg, at least 40 U/mg, at least 50 U/mg, at least 60 U/mg, at least 70 U/mg, at least 80 U/mg, at least 90 U/mg, at least 100 U/mg, or at least 150 U/mg of PCCA or PCCB activity in tissue (e.g., liver) between 6 and 12 hours, or between 12 and 24, between 24 and 48, or between 48 and 72 hours post administration (e.g., at 48 or at 72 hours post administration).

In exemplary embodiments, an mRNA therapy of the invention features a pharmaceutical composition comprising a single intravenous dose of mRNA that results in the above-described levels of activity. In another embodiment, an mRNA therapy of the invention features a pharmaceutical composition which can be administered in multiple single unit intravenous doses of mRNA that maintain the above-described levels of activity.

PA Biomarkers

Further aspects of the invention feature determining the level (or levels) of a biomarker determined in a sample as compared to a level (e.g., a reference level) of the same or another biomarker in another sample, e.g., from the same patient, from another patient, from a control and/or from the same or different time points, and/or a physiologic level, and/or an elevated level, and/or a supraphysiologic level, and/or a level of a control. The skilled artisan will be familiar with physiologic levels of biomarkers, for example, levels in normal or wildtype animals, normal or healthy subjects, and the like, in particular, the level or levels characteristic of subjects who are healthy and/or normal functioning. As used herein, the phrase "elevated level" means amounts greater than normally found in a normal or wildtype preclinical animal or in a normal or healthy subject, e.g. a human subject. As used herein, the term "supraphysiologic" means amounts greater than normally found in a normal or wildtype preclinical animal or in a normal or healthy subject, e.g. a human subject, optionally producing a significantly enhanced physiologic response. As used herein, the term "comparing" or "compared to" preferably means the mathematical comparison of the two or more values, e.g., of the levels of the biomarker(s). It will thus be readily apparent to the skilled artisan whether one of the values is higher, lower or identical to another value or group of values if at least two of such values are compared with each other. Comparing or comparison to can be in the context, for example, of comparing to a control value, e.g., as compared to a reference blood (e.g., dried blood spot), serum, plasma, urine and/or tissue (e.g., liver) propionyl-L-carnitine (C3), 2-methylcitric acid (2-MC), 3-hydroxypropionic acid, (3OHPA), propionylglycine, glycine, lactate or ammonia level, in said subject prior to administration (e.g., in a person suffering from PA) or in a normal or healthy subject.

As used herein, a "control" is preferably a sample from a human subject wherein the PA status of said human subject is known. In one embodiment, a control is a sample of a healthy patient. In another embodiment, the control is a sample from at least one human subject having a known PA status, for example, a severe, mild, or healthy PA status, e.g. a control patient. In another embodiment, the control is a sample from a human subject not being treated for PA. In a still further embodiment, the control is a sample from a single human subject or a pool of samples from different human subjects and/or samples taken from the human subject(s) at different time points.

The term "level" or "level of a biomarker" as used herein, preferably means the mass, weight or concentration of a biomarker of the invention within a sample or a human subject. It will be understood by the skilled artisan that in certain embodiments the sample may be subjected to, e.g., one or more of the following: substance purification, precipitation, separation, e.g. centrifugation and/or HPLC and subsequently subjected to determining the level of the biomarker, e.g. using mass spectrometric analysis. In certain embodiments, LC-MS can be used as a means for determining the level of a biomarker according to the invention.

The term "determining the level" of a biomarker as used herein can mean methods which include quantifying an amount of at least one substance in a sample from a human subject, for example, in a bodily fluid from the human subject (e.g., blood, serum, plasma, urine, lymph, etc.) or in a tissue of the human subject (e.g., liver, etc.).

The term "reference level" as used herein can refer to levels (e.g., of a biomarker) in a human subject prior to administration of an mRNA therapy of the invention (e.g., in a person suffering from PA) or in a normal or healthy human subject.

As used herein, the term "normal subject" or "healthy subject" refers to a human subject not suffering from symptoms associated with PA. Moreover, a human subject will be considered to be normal (or healthy) if it has no mutation of the functional portions or domains of the PCCA and PCCB genes and/or no mutation of the PCCA and PCCB genes resulting in a reduction of or deficiency of the enzyme PCC or the activity thereof, resulting in symptoms associated with PA. Said mutations will be detected if a sample from the subject is subjected to a genetic testing for such PCCA and/or PCCB mutations. In certain embodiments of the present invention, a sample from a healthy subject is used as a control sample, or the known or standardized value for the level of biomarker from samples of healthy or normal subjects is used as a control.

In some embodiments, comparing the level of the biomarker in a sample from a human subject in need of treatment for PA or in a human subject being treated for PA to a control level of the biomarker comprises comparing the level of the biomarker in the sample from the subject (in need of treatment or being treated for PA) to a baseline or reference level, wherein if a level of the biomarker in the sample from the subject (in need of treatment or being treated for PA) is elevated, increased or higher compared to the baseline or reference level, this is indicative that the subject is suffering from PA and/or is in need of treatment; and/or wherein if a level of the biomarker in the sample from the subject (in need of treatment or being treated for PA) is decreased or lower compared to the baseline level this is indicative that the subject is not suffering from, is successfully being treated for PA, or is not in need of treatment for PA. The stronger the reduction (e.g., at least 2-fold, at least 3-fold, at least 4-fold, at least 5-fold, at least 6-fold, at least 7-fold, at least 8-fold, at least 10-fold, at least 20-fold, at least-30 fold, at least 40-fold, at least 50-fold reduction and/or at least 10%, at least 20%, at least 30% at least 40%, at least 50%, at least 60%, at least 70%, at least 80%, at least 90%, or at least 100% reduction) of the level of a biomarker, within a certain time period, e.g., within 6 hours, within 12 hours, 24 hours, 36 hours, 48 hours, 60 hours, or 72 hours, and/or for a certain duration of time, e.g., 48 hours, 72 hours, 96 hours, 120 hours, 144 hours, 1 week, 2 weeks, 3 weeks, 4 weeks, 1 month, 2 months, 3 months, 4 months, 5 months, 6 months, 7 months, 8 months, 9 months, 10 months, 11 months, 12 months, 18 months, 24 months, etc. the more successful is a therapy, such as for example an mRNA therapy of the invention (e.g., a single dose or a multiple regimen).

A reduction of at least about 20%, at least about 30%, at least about 40%, at least about 50%, at least about 60%, at least about 70%, at least about 80%, at least about 90%, at least 100% or more of the level of biomarker, in particular, in bodily fluid (e.g., whole blood, plasma, serum, urine, e.g., urinary sediment) or in tissue(s) in a human subject (e.g., liver), within 1, 2, 3, 4, 5, 6, 7, 8, 9, 10, 11, 12, 13, 14, 15, 16, 17, 18, 19, 20, 21, 22, 23, 24, 25, or more days following administration is indicative of a dose suitable for successful treatment PA, wherein reduction as used herein, preferably means that the level of biomarker determined at the end of a specified time period (e.g., post-administration, for example, of a single intravenous dose) is compared to the level of the same biomarker determined at the beginning of said time period (e.g., pre-administration of said dose). Exemplary time periods include 12, 24, 48, 72, 96, 120 or 144 hours, 5 days, 8 days, 10 days, 12 days, 14 days, 16 days, 18 days, 20 days, 21 days, 22 days, 23 days, 25 days, 30 days, 32 days, 35 days, 40 days, 45 days, 50 days, 55 days, or 60 days post administration, in particular 24, 48, 72 or 96 hours post administration.

A sustained reduction in substrate levels (e.g., biomarkers) is particularly indicative of mRNA therapeutic dosing and/or administration regimens successful for treatment of PA. Such sustained reduction can be referred to herein as "duration" of effect. In exemplary embodiments, a reduction of at least about 20%, at least about 30%, at least about 40%, at least about 50%, at least about 60%, at least about 65%, at least about 70%, at least about 75%, at least about 80%, at least about 85%, at least about 90%, or at least about 95% at least about 96%, at least about 97%, at least about 98%, at least about 99%, at least about 100% or more of the level of biomarker, in particular, in a bodily fluid (e.g., whole blood, plasma, serum, urine, e.g., urinary sediment) or in tissue(s) in a human subject (e.g., liver), within 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 or more days following administration is indicative of a successful therapeutic approach. In exemplary embodiments, sustained reduction in substrate (e.g., biomarker) levels in one or more samples (e.g., fluids and/or tissues) is preferred. For example, mRNA therapies resulting in sustained reduction in a biomarker, optionally in combination with sustained reduction of said biomarker in at least one tissue, preferably two, three, four, five or more tissues, is indicative of successful treatment.

In some embodiments, a single dose of an mRNA therapy of the invention is about 0.2 to about 0.8 mpk, about 0.3 to about 0.7 mpk, about 0.4 to about 0.8 mpk, or about 0.5 mpk. In another embodiment, a single dose of an mRNA therapy of the invention is less than 1.5 mpk, less than 1.25 mpk, less than 1 mpk, or less than 0.75 mpk. In some embodiments, a single dose of an mRNA therapy described herein is between 0.1 mpk to 2.5 mpk, e.g., 0.5 mpk to 2.0 mpk, 0.75 mpk to 2.0 mpk, 0.8 mpk to 2.0 mpk, 0.9 mpk to 2.0 mpk, 1 mpk to 1.75 mpk, 1.0 mpk to 1.5 mpk, 1.1 mpk to 1.5 mpk, or 1.2 mpk to 1.4 mpk.

24. Compositions and Formulations for Use

Certain aspects of the invention are directed to compositions or formulations comprising any of the polynucleotides disclosed above.

In some embodiments, the composition or formulation comprises:

(i) a polynucleotide (e.g., a RNA, e.g., an mRNA) comprising a sequence-optimized nucleotide sequence (e.g., an ORF) encoding a PCCA or PCCB polypeptide (e.g., the wild-type sequence, functional fragment, or variant thereof), wherein the polynucleotide comprises at least one chemically modified nucleobase, e.g., N1-methylpseudouracil or 5-methoxyuracil (e.g., wherein at least about 25%, at least about 30%, at least about 40%, at least about 50%, at least about 60%, at least about 70%, at least about 80%, at least about 90%, at least about 95%, at least about 99%, or 100% of the uracils are N1-methylpseudouracils or 5-methoxyuracils), and wherein the polynucleotide further comprises a miRNA binding site, e.g., a miRNA binding site that binds to miR-142 (e.g., a miR-142-3p or miR-142-5p binding site) and/or a miRNA binding site that binds to miR-126 (e.g., a miR-126-3p or miR-126-5p binding site); and (ii) a delivery agent comprising, e.g., a compound having the Formula (I), e.g., any of Compounds 1-232, e.g., Compound II; a compound having the Formula (III), (IV), (V), or (VI), e.g., any of Compounds 233-342, e.g., Compound VI; or a compound having the Formula (VIII), e.g., any of Compounds 419-428, e.g., Compound I, or any combination thereof. In some embodiments, the delivery agent is a lipid nanoparticle comprising Compound II, Compound VI, a salt or a stereoisomer thereof, or any combination thereof. In some embodiments, the delivery agent comprises Compound II, DSPC, Cholesterol, and Compound I or PEG-DMG, e.g., with a mole ratio of about 50:10:38.5: 1.5. In some embodiments, the delivery agent comprises Compound II, DSPC, Cholesterol, and Compound I or PEG-DMG, e.g., with a mole ratio of about 47.5:10.5:39.0:3.0. In some embodiments, the delivery agent comprises Compound VI, DSPC, Cholesterol, and Compound I or PEG-DMG, e.g., with a mole ratio of about 50:10:38.5:1.5. In some embodiments, the delivery agent comprises Compound VI, DSPC, Cholesterol, and Compound I or PEG-DMG, e.g., with a mole ratio of about 47.5:10.5:39.0:3.0.

In some embodiments, the uracil or thymine content of the ORF relative to the theoretical minimum uracil or thymine content of a nucleotide sequence encoding the PCCA or PCCB polypeptide (% $U_{TM}$ or % $T_{TM}$), is between about 100% and about 150%.

In some embodiments, the polynucleotides, compositions or formulations above are used to treat and/or prevent PCCA- or PCCB-related diseases, disorders or conditions, e.g., PA.

25. Forms of Administration

The polynucleotides, pharmaceutical compositions and formulations of the invention described above can be administered by any route that results in a therapeutically effective outcome. These include, but are not limited to enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intraabdominal, intra-amniotic, intra-articular, intrabiliary, intrabronchial, intrabursal, intracartilaginous (within a cartilage), intracaudal (within the cauda equine), intracistemal (within the cisterna *magna* cerebellomedularis), intracorneal (within the cornea), dental intracornal, intracoronary (within the coronary arteries), intracorporus cavernosum (within the dilatable spaces of the corporus cavemosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intraocular (within the eye), intraovarian (within the ovary), intraperi-cardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration that is then covered by a dressing that occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), intramyocardial (entering the myocardium), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis or spinal. In specific embodiments, compositions can be administered in a way that allows them cross the blood-brain barrier, vascular barrier, or other epithelial barrier. In some embodiments, a formulation for a route of administration can include at least one inactive ingredient.

The polynucleotides of the present invention (e.g., a polynucleotide comprising a nucleotide sequence encoding a—polypeptide or a functional fragment or variant thereof) can be delivered to a cell naked. As used herein in, "naked" refers to delivering polynucleotides free from agents that promote transfection. The naked polynucleotides can be delivered to the cell using routes of administration known in the art and described herein.

The polynucleotides of the present invention (e.g., a polynucleotide comprising a nucleotide sequence encoding a PCCA or PCCB polypeptide or a functional fragment or variant thereof) can be formulated, using the methods described herein. The formulations can contain polynucleotides that can be modified and/or unmodified. The formulations can further include, but are not limited to, cell penetration agents, a pharmaceutically acceptable carrier, a delivery agent, a bioerodible or biocompatible polymer, a solvent, and a sustained-release delivery depot. The formulated polynucleotides can be delivered to the cell using routes of administration known in the art and described herein.

A pharmaceutical composition for parenteral administration can comprise at least one inactive ingredient. Any or none of the inactive ingredients used can have been approved by the US Food and Drug Administration (FDA). A non-exhaustive list of inactive ingredients for use in pharmaceutical compositions for parenteral administration includes hydrochloric acid, mannitol, nitrogen, sodium acetate, sodium chloride and sodium hydroxide.

Injectable preparations, for example, sterile injectable aqueous or oleaginous suspensions can be formulated according to the known art using suitable dispersing agents, wetting agents, and/or suspending agents. Sterile injectable preparations can be sterile injectable solutions, suspensions, and/or emulsions in nontoxic parenterally acceptable diluents and/or solvents, for example, as a solution in 1,3-butanediol. Among the acceptable vehicles and solvents that can be employed are water, Ringer's solution, U.S.P., and isotonic sodium chloride solution. Sterile, fixed oils are conventionally employed as a solvent or suspending medium. For this purpose, any bland fixed oil can be employed including synthetic mono- or diglycerides. Fatty acids such as oleic acid can be used in the preparation of injectables. The sterile formulation can also comprise adjuvants such as local anesthetics, preservatives and buffering agents.

Injectable formulations can be sterilized, for example, by filtration through a bacterial-retaining filter, and/or by incorporating sterilizing agents in the form of sterile solid compositions that can be dissolved or dispersed in sterile water or other sterile injectable medium prior to use.

Injectable formulations can be for direct injection into a region of a tissue, organ and/or human subject. As a non-limiting example, a tissue, organ and/or human subject can be directly injected a formulation by intramyocardial injection into the ischemic region. (See, e.g., Zangi et al. Nature Biotechnology 2013; the contents of which are herein incorporated by reference in its entirety).

In order to prolong the effect of an active ingredient, it is often desirable to slow the absorption of the active ingredient from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions that are compatible with body tissues.

26. Kits and Devices a. Kits

The invention provides a variety of kits for conveniently and/or effectively using the claimed nucleotides of the present invention. Typically, kits will comprise sufficient amounts and/or numbers of components to allow a user to perform multiple treatments of a human subject(s) and/or to perform multiple experiments.

In one aspect, the present invention provides kits comprising the molecules (polynucleotides) of the invention.

Said kits can be for protein production, comprising a first polynucleotides comprising a translatable region. The kit can further comprise packaging and instructions and/or a delivery agent to form a formulation composition. The delivery agent can comprise a saline, a buffered solution, a lipidoid or any delivery agent disclosed herein.

In some embodiments, the buffer solution can include sodium chloride, calcium chloride, phosphate and/or EDTA. In another embodiment, the buffer solution can include, but is not limited to, saline, saline with 2 mM calcium, 5% sucrose, 5% sucrose with 2 mM calcium, 5% Mannitol, 5% Mannitol with 2 mM calcium, Ringer's lactate, sodium chloride, sodium chloride with 2 mM calcium and mannose (See, e.g., U.S. Pub. No. 20120258046; herein incorporated by reference in its entirety). In a further embodiment, the buffer solutions can be precipitated or it can be lyophilized. The amount of each component can be varied to enable consistent, reproducible higher concentration saline or simple buffer formulations. The components can also be varied in order to increase the stability of modified RNA in the buffer solution over a period of time and/or under a variety of conditions. In one aspect, the present invention provides kits for protein production, comprising: a polynucleotide comprising a translatable region, provided in an amount effective to produce a desired amount of a protein encoded by the translatable region when introduced into a target cell; a second polynucleotide comprising an inhibitory nucleic acid, provided in an amount effective to substantially inhibit the innate immune response of the cell; and packaging and instructions.

In one aspect, the present invention provides kits for protein production, comprising a polynucleotide comprising a translatable region, wherein the polynucleotide exhibits reduced degradation by a cellular nuclease, and packaging and instructions.

In one aspect, the present invention provides kits for protein production, comprising a polynucleotide comprising a translatable region, wherein the polynucleotide exhibits reduced degradation by a cellular nuclease, and a mammalian cell suitable for translation of the translatable region of the first nucleic acid.

b. Devices

The present invention provides for devices that can incorporate polynucleotides that encode polypeptides of interest. These devices contain in a stable formulation the reagents to synthesize a polynucleotide in a formulation available to be immediately delivered to a subject in need thereof, such as a human patient.

Devices for administration can be employed to deliver the polynucleotides of the present invention according to single, multi- or split-dosing regimens taught herein. Such devices are taught in, for example, International Application Publ.

No. WO2013151666, the contents of which are incorporated herein by reference in their entirety.

Method and devices known in the art for multi-administration to cells, organs and tissues are contemplated for use in conjunction with the methods and compositions disclosed herein as embodiments of the present invention. These include, for example, those methods and devices having multiple needles, hybrid devices employing for example lumens or catheters as well as devices utilizing heat, electric current or radiation driven mechanisms.

According to the present invention, these multi-administration devices can be utilized to deliver the single, multi- or split doses contemplated herein. Such devices are taught for example in, International Application Publ. No. WO2013151666, the contents of which are incorporated herein by reference in their entirety.

In some embodiments, the polynucleotide is administered subcutaneously or intramuscularly via at least 3 needles to three different, optionally adjacent, sites simultaneously, or within a 60 minutes period (e.g., administration to 4, 5, 6, 7, 8, 9, or 10 sites simultaneously or within a 60 minute period).

c. Methods and Devices Utilizing Catheters and/or Lumens

Methods and devices using catheters and lumens can be employed to administer the polynucleotides of the present invention on a single, multi- or split dosing schedule. Such methods and devices are described in International Application Publication No. WO2013151666, the contents of which are incorporated herein by reference in their entirety.

d. Methods and Devices Utilizing Electrical Current

Methods and devices utilizing electric current can be employed to deliver the polynucleotides of the present invention according to the single, multi- or split dosing regimens taught herein. Such methods and devices are described in International Application Publication No. WO2013151666, the contents of which are incorporated herein by reference in their entirety.

27. Definitions

In order that the present disclosure can be more readily understood, certain terms are first defined. As used in this application, except as otherwise expressly provided herein, each of the following terms shall have the meaning set forth below. Additional definitions are set forth throughout the application.

The invention includes embodiments in which exactly one member of the group is present in, employed in, or otherwise relevant to a given product or process. The invention includes embodiments in which more than one, or all of the group members are present in, employed in, or otherwise relevant to a given product or process.

In this specification and the appended claims, the singular forms "a", "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Wherever aspects are described herein with the language "comprising," otherwise analogous aspects described in terms of "consisting of" and/or "consisting essentially of" are also provided.

Units, prefixes, and symbols are denoted in their Système International de Unites (SI) accepted form. Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value is explicitly recited, it is to be understood that values which are about the same quantity or amount as the recited value are also within the scope of the invention. Where a combination is disclosed, each subcombination of the elements of that combination is also specifically disclosed and is within the scope of the invention. Conversely, where different elements or groups of elements are individually disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Nucleotides are referred to by their commonly accepted single-letter codes. Unless otherwise indicated, nucleic acids are written left to right in 5' to 3' orientation. Nucleobases are referred to herein by their commonly known one-letter symbols recommended by the IUPAC-IUB Biochemical Nomenclature Commission. Accordingly, A represents adenine, C represents cytosine, G represents guanine, T represents thymine, U represents uracil.

Amino acids are referred to herein by either their commonly known three letter symbols or by the one-letter symbols recommended by the IUPAC-IUB Biochemical Nomenclature Commission. Unless otherwise indicated, amino acid sequences are written left to right in amino to carboxy orientation.

About: The term "about" as used in connection with a numerical value throughout the specification and the claims denotes an interval of accuracy, familiar and acceptable to a person skilled in the art, such interval of accuracy is ±10%.

Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

Administered in combination: As used herein, the term "administered in combination" or "combined administration" means that two or more agents are administered to a human subject at the same time or within an interval such that there can be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

Amino acid substitution: The term "amino acid substitution" refers to replacing an amino acid residue present in a parent or reference sequence (e.g., a wild type PCCA or PCCB sequence) with another amino acid residue. An amino acid can be substituted in a parent or reference sequence (e.g., a wild type PCCA or PCCB polypeptide sequence), for example, via chemical peptide synthesis or through recombinant methods known in the art. Accordingly, a reference to a "substitution at position X" refers to the substitution of an amino acid present at position X with an alternative amino acid residue. In some aspects, substitution patterns can be described according to the schema AnY, wherein A is the single letter code corresponding to the amino acid naturally or originally present at position n, and Y is the substituting amino acid residue. In other aspects, substitution patterns can be described according to the schema An(YZ), wherein A is the single letter code corresponding to the amino acid residue substituting the amino acid naturally or originally present at position X, and Y and Z are alternative substituting amino acid residue.

In the context of the present disclosure, substitutions (even when they referred to as amino acid substitution) are conducted at the nucleic acid level, i.e., substituting an amino acid residue with an alternative amino acid residue is conducted by substituting the codon encoding the first amino acid with a codon encoding the second amino acid.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately," as applied to one or more values of interest, refers to a value that is similar to a stated reference value. In certain embodiments, the term "approximately" refers to a range of values that fall within 25%, 20%, 19%, 18%, 17%, 16%, 15%, 14%, 13%, 12%, 11%, 1%, 90%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein with respect to a disease, the term "associated with" means that the symptom, measurement, characteristic, or status in question is linked to the diagnosis, development, presence, or progression of that disease. As association can, but need not, be causatively linked to the disease. For example, symptoms, sequelae, or any effects causing a decrease in the quality of life of a patient of PA are considered associated with PA and in some embodiments of the present invention can be treated, ameliorated, or prevented by administering the polynucleotides of the present invention to a human subject in need thereof.

When used with respect to two or more moieties, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It can also suggest ionic or hydrogen bonding or a hybridization based connectivity sufficiently stable such that the "associated" entities remain physically associated.

Bifunctional: As used herein, the term "bifunctional" refers to any substance, molecule or moiety that is capable of or maintains at least two functions. The functions can affect the same outcome or a different outcome. The structure that produces the function can be the same or different. For example, bifunctional modified RNAs of the present invention can encode a PCCA or PCCB peptide (a first function) while those nucleosides that comprise the encoding RNA are, in and of themselves, capable of extending the half-life of the RNA (second function). In this example, delivery of the bifunctional modified RNA to a human subject suffereing from a protein defficiency would produce not only a peptide or protein molecule that can ameliorate or treat a disease or conditions, but would also maintain a population modified RNA present in the human subject for a prolonged period of time. In other aspects, a bifunction modified mRNA can be a chimeric or quimeric molecule comprising, for example, an RNA encoding a PCCA or PCCB peptide (a first function) and a second protein either fused to first protein or co-expressed with the first protein.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, a polynucleotide of the present invention can be considered biologically active if even a portion of the polynucleotide is biologically active or mimics an activity considered biologically relevant.

Chimera: As used herein, "chimera" is an entity having two or more incongruous or heterogeneous parts or regions. For example, a chimeric molecule can comprise a first part comprising a PCCA or PCCB polypeptide, and a second part (e.g., genetically fused to the first part) comprising a second therapeutic protein (e.g., a protein with a distinct enzymatic activity, an antigen binding moiety, or a moiety capable of extending the plasma half life of PCCA or PCCB, for example, an Fc region of an antibody).

Sequence Optimization: The term "sequence optimization" refers to a process or series of processes by which nucleobases in a reference nucleic acid sequence are replaced with alternative nucleobases, resulting in a nucleic acid sequence with improved properties, e.g., improved protein expression or decreased immunogenicity.

In general, the goal in sequence optimization is to produce a synonymous nucleotide sequence than encodes the same polypeptide sequence encoded by the reference nucleotide sequence. Thus, there are no amino acid substitutions (as a result of codon optimization) in the polypeptide encoded by the codon optimized nucleotide sequence with respect to the polypeptide encoded by the reference nucleotide sequence.

Codon substitution: The terms "codon substitution" or "codon replacement" in the context of sequence optimization refer to replacing a codon present in a reference nucleic acid sequence with another codon. A codon can be substituted in a reference nucleic acid sequence, for example, via chemical peptide synthesis or through recombinant methods known in the art. Accordingly, references to a "substitution" or "replacement" at a certain location in a nucleic acid sequence (e.g., an mRNA) or within a certain region or subsequence of a nucleic acid sequence (e.g., an mRNA) refer to the substitution of a codon at such location or region with an alternative codon.

As used herein, the terms "coding region" and "region encoding" and grammatical variants thereof, refer to an Open Reading Frame (ORF) in a polynucleotide that upon expression yields a polypeptide or protein.

Compound: As used herein, the term "compound," is meant to include all stereoisomers and isotopes of the structure depicted. As used herein, the term "stereoisomer" means any geometric isomer (e.g., cis- and trans-isomer), enantiomer, or diastereomer of a compound. The present disclosure encompasses any and all stereoisomers of the compounds described herein, including stereomerically pure forms (e.g., geometrically pure, enantiomerically pure, or diastereomerically pure) and enantiomeric and stereoisomeric mixtures, e.g., racemates. Enantiomeric and stereomeric mixtures of compounds and means of resolving them into their component enantiomers or stereoisomers are well-known. "Isotopes" refers to atoms having the same atomic number but different mass numbers resulting from a different number of neutrons in the nuclei. For example, isotopes of hydrogen include tritium and deuterium. Further, a compound, salt, or complex of the present disclosure can be prepared in combination with solvent or water molecules to form solvates and hydrates by routine methods.

Contacting: As used herein, the term "contacting" means establishing a physical connection between two or more entities. For example, contacting a mammalian cell with a nanoparticle composition means that the mammalian cell and a nanoparticle are made to share a physical connection. Methods of contacting cells with external entities both in vivo and ex vivo are well known in the biological arts. For example, contacting a nanoparticle composition and a mammalian cell disposed within a mammal can be performed by varied routes of administration (e.g., intravenous, intramuscular, intradermal, and subcutaneous) and can involve varied amounts of nanoparticle compositions. Moreover, more than one mammalian cell can be contacted by a nanoparticle composition.

Conservative amino acid substitution: A "conservative amino acid substitution" is one in which the amino acid residue in a protein sequence is replaced with an amino acid residue having a similar side chain. Families of amino acid residues having similar side chains have been defined in the art, including basic side chains (e.g., lysine, arginine, or histidine), acidic side chains (e.g., aspartic acid or glutamic acid), uncharged polar side chains (e.g., glycine, asparagine, glutamine, serine, threonine, tyrosine, or cysteine), nonpolar side chains (e.g., alanine, valine, leucine, isoleucine, proline, phenylalanine, methionine, or tryptophan), beta-branched side chains (e.g., threonine, valine, isoleucine) and aromatic side chains (e.g., tyrosine, phenylalanine, tryptophan, or histidine). Thus, if an amino acid in a polypeptide is replaced with another amino acid from the same side chain family, the amino acid substitution is considered to be conservative. In another aspect, a string of amino acids can be conservatively replaced with a structurally similar string that differs in order and/or composition of side chain family members.

Non-conservative amino acid substitution: Non-conservative amino acid substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, His, Ile or Trp) is substituted for, or by, one having a smaller side chain (e.g., Ala or Ser) or no side chain (e.g., Gly).

Other amino acid substitutions can be readily identified by workers of ordinary skill. For example, for the amino acid alanine, a substitution can be taken from any one of D-alanine, glycine, beta-alanine, L-cysteine and D-cysteine. For lysine, a replacement can be any one of D-lysine, arginine, D-arginine, homo-arginine, methionine, D-methionine, omithine, or D-omithine. Generally, substitutions in functionally important regions that can be expected to induce changes in the properties of isolated polypeptides are those in which (i) a polar residue, e.g., serine or threonine, is substituted for (or by) a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine. The likelihood that one of the foregoing non-conservative substitutions can alter functional properties of the protein is also correlated to the position of the substitution with respect to functionally important regions of the protein: some non-conservative substitutions can accordingly have little or no effect on biological properties.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence can apply to the entire length of an polynucleotide or polypeptide or can apply to a portion, region or feature thereof.

Controlled Release: As used herein, the term "controlled release" refers to a pharmaceutical composition or compound release profile that conforms to a particular pattern of release to effect a therapeutic outcome.

Cyclic or Cyclized: As used herein, the term "cyclic" refers to the presence of a continuous loop. Cyclic molecules need not be circular, only joined to form an unbroken chain of subunits. Cyclic molecules such as the engineered RNA or mRNA of the present invention can be single units or multimers or comprise one or more components of a complex or higher order structure.

Cytotoxic: As used herein, "cytotoxic" refers to killing or causing injurious, toxic, or deadly effect on a cell (e.g., a mammalian cell (e.g., a human cell)), bacterium, virus, fungus, protozoan, parasite, prion, or a combination thereof.

Delivering: As used herein, the term "delivering" means providing an entity to a destination. For example, delivering a polynucleotide to a human subject can involve administering a nanoparticle composition including the polynucleotide to the human subject (e.g., by an intravenous, intramuscular, intradermal, or subcutaneous route). Administration of a nanoparticle composition to a mammal or mammalian cell can involve contacting one or more cells with the nanoparticle composition.

Delivery Agent: As used herein, "delivery agent" refers to any substance that facilitates, at least in part, the in vivo, in vitro, or ex vivo delivery of a polynucleotide to targeted cells.

Destabilized: As used herein, the term "destable," "destabilize," or "destabilizing region" means a region or molecule that is less stable than a starting, wild-type or native form of the same region or molecule.

Diastereomer: As used herein, the term "diastereomer," means stereoisomers that are not mirror images of one another and are non-superimposable on one another.

Digest: As used herein, the term "digest" means to break apart into smaller pieces or components. When referring to polypeptides or proteins, digestion results in the production of peptides.

Distal: As used herein, the term "distal" means situated away from the center or away from a point or region of interest.

Domain: As used herein, when referring to polypeptides, the term "domain" refers to a motif of a polypeptide having one or more identifiable structural or functional characteristics or properties (e.g., binding capacity, serving as a site for protein-protein interactions).

Dosing regimen: As used herein, a "dosing regimen" or a "dosing regimen" is a schedule of administration or physician determined regimen of treatment, prophylaxis, or palliative care.

Effective Amount: As used herein, the term "effective amount" of an agent is that amount sufficient to effect beneficial or desired results, for example, clinical results, and, as such, an "effective amount" depends upon the context in which it is being applied. For example, in the context of administering an agent that treats a protein deficiency (e.g., a PCC deficiency), an effective amount of an agent is, for example, an amount of mRNA expressing sufficient PCCA and/or PCCB to ameliorate, reduce, eliminate, or prevent the symptoms associated with the PCC deficiency, as compared to the severity of the symptom observed without administration of the agent. The term "effective amount" can be used interchangeably with "effective dose," "therapeutically effective amount," or "therapeutically effective dose."

Enantiomer: As used herein, the term "enantiomer" means each individual optically active form of a compound of the invention, having an optical purity or enantiomeric excess (as determined by methods standard in the art) of at least 80% (i.e., at least 90% of one enantiomer and at most 10% of the other enantiomer), at least 90%, or at least 98%.

Encapsulate: As used herein, the term "encapsulate" means to enclose, surround or encase.

Encapsulation Efficiency: As used herein, "encapsulation efficiency" refers to the amount of a polynucleotide that becomes part of a nanoparticle composition, relative to the initial total amount of polynucleotide used in the preparation of a nanoparticle composition. For example, if 97 mg of polynucleotide are encapsulated in a nanoparticle composition out of a total 100 mg of polynucleotide initially provided to the composition, the encapsulation efficiency can be given as 97%. As used herein, "encapsulation" can refer to complete, substantial, or partial enclosure, confinement, surrounding, or encasement.

Encoded protein cleavage signal: As used herein, "encoded protein cleavage signal" refers to the nucleotide sequence that encodes a protein cleavage signal.

Engineered: As used herein, embodiments of the invention are "engineered" when they are designed to have a feature or property, whether structural or chemical, that varies from a starting point, wild type or native molecule.

Enhanced Delivery: As used herein, the term "enhanced delivery" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a polynucleotide by a nanoparticle to a target tissue of interest (e.g., mammalian liver) compared to the level of delivery of a polynucleotide by a control nanoparticle to a target tissue of interest (e.g., MC3, KC2, or DLinDMA). The level of delivery of a nanoparticle to a particular tissue can be measured by comparing the amount of protein produced in a tissue to the weight of said tissue, comparing the amount of polynucleotide in a tissue to the weight of said tissue, comparing the amount of protein produced in a tissue to the amount of total protein in said tissue, or comparing the amount of polynucleotide in a tissue to the amount of total polynucleotide in said tissue. It will be understood that the enhanced delivery of a nanoparticle to a target tissue need not be determined in a human subject being treated, it can be determined in a surrogate such as an animal model (e.g., a rat model).

Exosome: As used herein, "exosome" is a vesicle secreted by mammalian cells or a complex involved in RNA degradation.

Expression: As used herein, "expression" of a nucleic acid sequence refers to one or more of the following events: (1) production of an mRNA template from a DNA sequence (e.g., by transcription); (2) processing of an mRNA transcript (e.g., by splicing, editing, 5' cap formation, and/or 3' end processing); (3) translation of an mRNA into a polypeptide or protein; and (4) post-translational modification of a polypeptide or protein.

Ex Vivo: As used herein, the term "ex vivo" refers to events that occur outside of an organism (e.g., animal, plant, or microbe or cell or tissue thereof). Ex vivo events can take place in an environment minimally altered from a natural (e.g., in vivo) environment.

Feature: As used herein, a "feature" refers to a characteristic, a property, or a distinctive element. When referring to polypeptides, "features" are defined as distinct amino acid sequence-based components of a molecule. Features of the polypeptides encoded by the polynucleotides of the present invention include surface manifestations, local conformational shape, folds, loops, half-loops, domains, half-domains, sites, termini or any combination thereof.

Formulation: As used herein, a "formulation" includes at least a polynucleotide and one or more of a carrier, an excipient, and a delivery agent.

Fragment: A "fragment," as used herein, refers to a portion. For example, fragments of proteins can comprise polypeptides obtained by digesting full-length protein isolated from cultured cells. In some embodiments, a fragment is a subsequences of a full length protein (e.g., PCCA or PCCB) wherein N-terminal, and/or C-terminal, and/or internal subsequences have been deleted. In some preferred aspects of the present invention, the fragments of a protein are functional fragments.

Functional: As used herein, a "functional" biological molecule is a biological molecule in a form in which it exhibits a property and/or activity by which it is characterized. Thus, a functional fragment of a polynucleotide of the present invention is a polynucleotide capable of expressing a functional PCCA or PCCB fragment. As used herein, a functional fragment of PCCA or PCCB refers to a fragment of wild type PCCA or PCCB (i.e., a fragment of any of its naturally occurring isoforms), or a mutant or variant thereof, wherein the fragment retains a least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the biological activity of the corresponding full length protein.

PCC Associated Disease: As use herein the terms "PCC-associated disease" or "PCC-associated disorder" refer to diseases or disorders, respectively, which result from aberrant PCC activity (e.g., decreased activity or increased activity). As a non-limiting example, PA is a PCC associated disease.

The terms "PCC enzymatic activity" and "PCC activity," are used interchangeably in the present disclosure and refer to PCC's ability to catalyze the carboxylation of propionyl-CoA to methylmalonyl-CoA. Accordingly, a fragment or variant retaining or having PCC enzymatic activity or PC activity refers to a fragment or variant that has measurable enzymatic activity in catalyzing the carboxylation of propionyl-CoA to methylmalonyl-CoA.

Helper Lipid: As used herein, the term "helper lipid" refers to a compound or molecule that includes a lipidic moiety (for insertion into a lipid layer, e.g., lipid bilayer) and a polar moiety (for interaction with physiologic solution at the surface of the lipid layer). Typically the helper lipid is a phospholipid. A function of the helper lipid is to "complement" the amino lipid and increase the fusogenicity of the bilayer and/or to help facilitate endosomal escape, e.g., of nucleic acid delivered to cells. Helper lipids are also believed to be a key structural component to the surface of the LNP.

Homology: As used herein, the term "homology" refers to the overall relatedness between polymeric molecules, e.g. between nucleic acid molecules (e.g. DNA molecules and/or RNA molecules) and/or between polypeptide molecules. Generally, the term "homology" implies an evolutionary relationship between two molecules. Thus, two molecules that are homologous will have a common evolutionary ancestor. In the context of the present invention, the term homology encompasses both to identity and similarity.

In some embodiments, polymeric molecules are considered to be "homologous" to one another if at least 25%, 30%, 35%, 40%, 45%, 50%, 55%, 60%, 65%, 70%, 75%, 80%, 85%, 90%, 95%, or 99% of the monomers in the molecule are identical (exactly the same monomer) or are similar (conservative substitutions). The term "homologous" necessarily refers to a comparison between at least two sequences (polynucleotide or polypeptide sequences).

Identity: As used herein, the term "identity" refers to the overall monomer conservation between polymeric molecules, e.g., between polynucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. When comparing DNA and RNA, thymine (T) and uracil (U) can be considered equivalent.

Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Sequence alignments can be conducted using methods known in the art such as MAFFT, Clustal (ClustalW, Clustal X or Clustal Omega), MUSCLE, etc.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain aspects, the percentage identity "% ID" of a first amino acid sequence (or nucleic acid sequence) to a second amino acid sequence (or nucleic acid sequence) is calculated as % ID=100×(Y/Z), where Y is the number of amino acid residues (or nucleobases) scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity can be curated either automatically or manually.

Immune response: The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues. In some cases, the administration of a nanoparticle comprising a lipid component and an encapsulated therapeutic agent can trigger an immune response, which can be caused by (i) the encapsulated therapeutic agent (e.g., an mRNA), (ii) the expression product of such encapsulated therapeutic agent (e.g., a polypeptide encoded by the mRNA), (iii) the lipid component of the nanoparticle, or (iv) a combination thereof.

Inflammatory response: "Inflammatory response" refers to immune responses involving specific and non-specific defense systems. A specific defense system reaction is a specific immune system reaction to an antigen. Examples of specific defense system reactions include antibody responses. A non-specific defense system reaction is an inflammatory response mediated by leukocytes generally incapable of immunological memory, e.g., macrophages, eosinophils and neutrophils. In some aspects, an immune response includes the secretion of inflammatory cytokines, resulting in elevated inflammatory cytokine levels.

Inflammatory cytokines: The term "inflammatory cytokine" refers to cytokines that are elevated in an inflammatory response. Examples of inflammatory cytokines include interleukin-6 (IL-6), CXCL1 (chemokine (C—X—C motif) ligand 1; also known as GROα, interferon-γ (IFNγ), tumor necrosis factor α (TNFα), interferon γ-induced protein 10 (IP-10), or granulocyte-colony stimulating factor (G-CSF).

The term inflammatory cytokines includes also other cytokines associated with inflammatory responses known in the art, e.g., interleukin-1 (IL-1), interleukin-8 (IL-8), interleukin-12 (IL-12), interleukin-13 (11-13), interferon α (IFN-α), etc.

In Vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In Vivo: As used herein, the term "in vivo" refers to events that occur within an organism (e.g., animal, plant, or microbe or cell or tissue thereof).

Insertional and deletional variants: "Insertional variants" when referring to polypeptides are those with one or more amino acids inserted immediately adjacent to an amino acid at a particular position in a native or starting sequence. "Immediately adjacent" to an amino acid means connected to either the alpha-carboxy or alpha-amino functional group of the amino acid. "Deletional variants" when referring to polypeptides are those with one or more amino acids in the native or starting amino acid sequence removed. Ordinarily, deletional variants will have one or more amino acids deleted in a particular region of the molecule.

Intact: As used herein, in the context of a polypeptide, the term "intact" means retaining an amino acid corresponding to the wild type protein, e.g., not mutating or substituting the wild type amino acid. Conversely, in the context of a nucleic acid, the term "intact" means retaining a nucleobase corresponding to the wild type nucleic acid, e.g., not mutating or substituting the wild type nucleobase.

Ionizable amino lipid: The term "ionizable amino lipid" includes those lipids having one, two, three, or more fatty acid or fatty alkyl chains and a pH-titratable amino head group (e.g., an alkylamino or dialkylamino head group). An ionizable amino lipid is typically protonated (i.e., positively charged) at a pH below the pKa of the amino head group and is substantially not charged at a pH above the pKa. Such ionizable amino lipids include, but are not limited to DLin-MC3-DMA (MC3) and (13Z,165Z)—N,N-dimethyl-3-nonydocosa-13-16-dien-1-amine (L608).

Isolated: As used herein, the term "isolated" refers to a substance or entity that has been separated from at least some of the components with which it was associated (whether in nature or in an experimental setting). Isolated substances (e.g., polynucleotides or polypeptides) can have varying levels of purity in reference to the substances from which they have been isolated. Isolated substances and/or entities can be separated from at least about 10%, about 20%, about 30%, about 40%, about 50%, about 60%, about 70%, about 80%, about 90%, or more of the other components with which they were initially associated. In some embodiments, isolated substances are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof.

A polynucleotide, vector, polypeptide, cell, or any composition disclosed herein which is "isolated" is a polynucleotide, vector, polypeptide, cell, or composition which is in a form not found in nature. Isolated polynucleotides, vectors, polypeptides, or compositions include those which have been purified to a degree that they are no longer in a form in which they are found in nature. In some aspects, a polynucleotide, vector, polypeptide, or composition which is isolated is substantially pure.

Isomer: As used herein, the term "isomer" means any tautomer, stereoisomer, enantiomer, or diastereomer of any compound of the invention. It is recognized that the compounds of the invention can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

Linker: As used herein, a "linker" refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to a modified nucleoside or nucleotide on the nucleobase or sugar moiety at a first end, and to a payload, e.g., a detectable or therapeutic agent, at a second end. The linker can be of sufficient length as to not interfere with incorporation into a nucleic acid sequence. The linker can be used for any useful purpose, such as to form polynucleotide multimers (e.g., through linkage of two or more chimeric polynucleotides molecules or IVT polynucleotides) or polynucleotides conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers and derivatives thereof, Other examples include, but are not limited to, cleavable moieties within the linker, such as, for example, a disulfide bond (—S—S—) or an azo bond (—N═N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

Methods of Administration: As used herein, "methods of administration" can include intravenous, intramuscular, intradermal, subcutaneous, or other methods of delivering a composition to a subject. A method of administration can be selected to target delivery (e.g., to specifically deliver) to a specific region or system of a body.

Modified: As used herein "modified" refers to a changed state or structure of a molecule of the invention. Molecules can be modified in many ways including chemically, structurally, and functionally. In some embodiments, the mRNA molecules of the present invention are modified by the introduction of non-natural nucleosides and/or nucleotides, e.g., as it relates to the natural ribonucleotides A, U, G, and C. Noncanonical nucleotides such as the cap structures are not considered "modified" although they differ from the chemical structure of the A, C, G, U ribonucleotides.

Mucus: As used herein, "mucus" refers to the natural substance that is viscous and comprises mucin glycoproteins.

Nanoparticle Composition: As used herein, a "nanoparticle composition" is a composition comprising one or more lipids. Nanoparticle compositions are typically sized on the order of micrometers or smaller and can include a lipid bilayer. Nanoparticle compositions encompass lipid nanoparticles (LNPs), liposomes (e.g., lipid vesicles), and lipoplexes. For example, a nanoparticle composition can be a liposome having a lipid bilayer with a diameter of 500 nm or less.

Naturally occurring: As used herein, "naturally occurring" means existing in nature without artificial aid.

Non-human vertebrate: As used herein, a "non-human vertebrate" includes all vertebrates except *Homo sapiens*, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

Nucleic acid sequence: The terms "nucleic acid sequence," "nucleotide sequence," or "polynucleotide sequence" are used interchangeably and refer to a contiguous nucleic acid sequence. The sequence can be either single stranded or double stranded DNA or RNA, e.g., an mRNA.

The term "nucleic acid," in its broadest sense, includes any compound and/or substance that comprises a polymer of nucleotides. These polymers are often referred to as polynucleotides. Exemplary nucleic acids or polynucleotides of the invention include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or hybrids or combinations thereof.

The phrase "nucleotide sequence encoding" refers to the nucleic acid (e.g., an mRNA or DNA molecule) coding sequence which encodes a polypeptide. The coding sequence can further include initiation and termination signals operably linked to regulatory elements including a promoter and polyadenylation signal capable of directing expression in the cells of an individual or mammal to which the nucleic acid is administered. The coding sequence can further include sequences that encode signal peptides.

Off-target: As used herein, "off target" refers to any unintended effect on any one or more target, gene, or cellular transcript.

Open reading frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like.

Optionally substituted: Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g., alkyl)per se is optional.

Part: As used herein, a "part" or "region" of a polynucleotide is defined as any portion of the polynucleotide that is less than the entire length of the polynucleotide.

Patient: As used herein, "patient" refers to a subject who can seek or be in need of treatment, requires treatment, is receiving treatment, will receive treatment, or a subject who is under care by a trained professional for a particular disease or condition. In some embodiments, the treatment is needed, required, or received to prevent or decrease the risk of developing acute disease, i.e., it is a prophylactic treatment.

Pharmaceutically acceptable: The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients can include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfonate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are used. Lists of suitable salts are found in *Remington's Pharmaceutical Sciences*, 17$^{th}$ ed., Mack Publishing Company, Easton, Pa., 1985, p. 1418, *Pharmaceutical Salts: Properties, Selection, and Use*, P. H. Stahl and C. G. Wermuth (eds.), Wiley-VCH, 2008, and Berge et al., *Journal of Pharmaceutical Science*, 66, 1-19 (1977), each of which is incorporated herein by reference in its entirety.

Pharmaceutically acceptable solvate: The term "pharmaceutically acceptable solvate," as used herein, means a compound of the invention wherein molecules of a suitable solvent are incorporated in the crystal lattice. A suitable solvent is physiologically tolerable at the dosage administered. For example, solvates can be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion.

This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Physicochemical: As used herein, "physicochemical" means of or relating to a physical and/or chemical property.

Polynucleotide: The term "polynucleotide" as used herein refers to polymers of nucleotides of any length, including ribonucleotides, deoxyribonucleotides, analogs thereof, or mixtures thereof. This term refers to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the term "polynucleotide" includes poly deoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids "PNAs") and polymorpholino polymers, and other synthetic sequence-specific nucleic acid polymers providing that the polymers contain nucleobases in a configuration which allows for base pairing and base stacking, such as is found in DNA and RNA. In particular aspects, the polynucleotide comprises an mRNA. In other aspect, the mRNA is a synthetic mRNA. In some aspects, the synthetic mRNA comprises at least one unnatural nucleobase. In some aspects, all nucleobases of a certain class have been replaced with unnatural nucleobases (e.g., all uridines in a polynucleotide disclosed herein can be replaced with an unnatural nucleobase, e.g., 5-methoxyuridine). In some aspects, the polynucleotide (e.g., a synthetic RNA or a synthetic DNA) comprises only natural nucleobases, i.e., A (adenosine), G (guanosine), C (cytidine), and T (thymidine) in the case of a synthetic DNA, or A, C, G, and U (uridine) in the case of a synthetic RNA.

The skilled artisan will appreciate that the T bases in the codon maps disclosed herein are present in DNA, whereas the T bases would be replaced by U bases in corresponding RNAs. For example, a codon-nucleotide sequence disclosed herein in DNA form, e.g., a vector or an in-vitro translation (IVT) template, would have its T bases transcribed as U based in its corresponding transcribed mRNA. In this respect, both codon-optimized DNA sequences (comprising T) and their corresponding mRNA sequences (comprising U) are considered codon-optimized nucleotide sequence of the present invention. A skilled artisan would also understand that equivalent codon-maps can be generated by replaced one or more bases with non-natural bases. Thus, e.g., a TTC codon (DNA map) would correspond to a UUC codon (RNA map), which in turn would correspond to a ΨΨ codon (RNA map in which U has been replaced with pseudouridine).

Standard A-T and G-C base pairs form under conditions which allow the formation of hydrogen bonds between the N3-H and C4-oxy of thymidine and the N1 and C6-NH2, respectively, of adenosine and between the C2-oxy, N3 and C4-NH2, of cytidine and the C2-NH2, N'—H and C6-oxy, respectively, of guanosine. Thus, for example, guanosine (2-amino-6-oxy-9-β-D-ribofuranosyl-purine) can be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine-) results in a modified nucleotide which will not effectively base pair with guanosine but will form a base pair with isoguanosine (U.S. Pat. No. 5,681,702 to Collins et al.). Isocytosine is available from Sigma Chemical Co. (St. Louis, Mo.); isocytidine can be prepared by the method described by Switzer et al. (1993) Biochemistry 32:10489-10496 and references cited therein; 2'-deoxy-5-methyl-iso-cytidine can be prepared by the method of Tor et al., 1993, J. Am. Chem. Soc. 115:4461-4467 and references cited therein; and isoguanine nucleotides can be prepared using the method described by Switzer et al., 1993, supra, and Mantsch et al., 1993, Biochem. 14:5593-5601, or by the method described in U.S. Pat. No. 5,780,610 to Collins et al. Other nonnatural base pairs can be synthesized by the method described in Piccirilli et al., 1990, Nature 343:33-37, for the synthesis of 2,6-diaminopyrimidine and its complement (1-methylpyrazolo-[4,3]pyrimidine-5,7-(4H,6H)-di-one. Other such modified nucleotide units which form unique base pairs are known, such as those described in Leach et al. (1992) J. Am. Chem. Soc. 114:3675-3683 and Switzer et al., supra.

Polypeptide: The terms "polypeptide," "peptide," and "protein" are used interchangeably herein to refer to polymers of amino acids of any length. The polymer can comprise modified amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids such as homocysteine, ornithine, p-acetylphenylalanine, D-amino acids, and creatine), as well as other modifications known in the art.

The term, as used herein, refers to proteins, polypeptides, and peptides of any size, structure, or function. Polypeptides include encoded polynucleotide products, naturally occurring polypeptides, synthetic polypeptides, homologs, orthologs, paralogs, fragments and other equivalents, variants, and analogs of the foregoing. A polypeptide can be a monomer or can be a multi-molecular complex such as a dimer, trimer or tetramer. They can also comprise single chain or multichain polypeptides. Most commonly disulfide linkages are found in multichain polypeptides. The term polypeptide can also apply to amino acid polymers in which one or more amino acid residues are an artificial chemical analogue of a corresponding naturally occurring amino acid. In some embodiments, a "peptide" can be less than or equal to 50 amino acids long, e.g., about 5, 10, 15, 20, 25, 30, 35, 40, 45, or 50 amino acids long.

Polypeptide variant: As used herein, the term "polypeptide variant" refers to molecules that differ in their amino acid sequence from a native or reference sequence. The amino acid sequence variants can possess substitutions, deletions, and/or insertions at certain positions within the amino acid sequence, as compared to a native or reference sequence. Ordinarily, variants will possess at least about 50% identity, at least about 60% identity, at least about 70% identity, at least about 80% identity, at least about 90% identity, at least about 95% identity, at least about 99% identity to a native or reference sequence. In some embodiments, they will be at least about 80%, or at least about 90% identical to a native or reference sequence.

Polypeptide per unit drug (PUD): As used herein, a PUD or product per unit drug, is defined as a subdivided portion of total daily dose, usually 1 mg, pg, kg, etc., of a product (such as a polypeptide) as measured in body fluid or tissue, usually defined in concentration such as pmol/mL, mmol/mL, etc. divided by the measure in the body fluid.

Preventing: As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Prophylactic: As used herein, "prophylactic" refers to a therapeutic or course of action used to prevent the spread of disease.

Prophylaxis: As used herein, a "prophylaxis" refers to a measure taken to maintain health and prevent the spread of disease. An "immune prophylaxis" refers to a measure to produce active or passive immunity to prevent the spread of disease.

Protein cleavage site: As used herein, "protein cleavage site" refers to a site where controlled cleavage of the amino acid chain can be accomplished by chemical, enzymatic or photochemical means.

Protein cleavage signal: As used herein "protein cleavage signal" refers to at least one amino acid that flags or marks a polypeptide for cleavage.

Protein of interest: As used herein, the terms "proteins of interest" or "desired proteins" include those provided herein and fragments, mutants, variants, and alterations thereof.

Proximal: As used herein, the term "proximal" means situated nearer to the center or to a point or region of interest.

Pseudouridine: As used herein, pseudouridine (W) refers to the C-glycoside isomer of the nucleoside uridine. A "pseudouridine analog" is any modification, variant, isoform or derivative of pseudouridine. For example, pseudouridine analogs include but are not limited to 1-carboxymethyl-pseudouridine, 1-propynyl-pseudouridine, 1-taurinomethyl-pseudouridine, 1-taurinomethyl-4-thio-pseudouridine, 1-methylpseudouridine ($m^1\psi$) (also known as N1-methyl-pseudouridine), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydropseudouridine, 2-thio-dihydropseudouridine, 2-methoxyuridine, 2-methoxy-4-thio-uridine, 4-methoxy-pseudouridine, 4-methoxy-2-thio-pseudouridine, 1-methyl-3-(3-amino-3-carboxypropyl)pseudouridine ($acp^3\psi$), and 2'-O-methyl-pseudouridine (Wm).

Purified: As used herein, "purify," "purified," "purification" means to make substantially pure or clear from unwanted components, material defilement, admixture or imperfection.

Reference Nucleic Acid Sequence: The term "reference nucleic acid sequence" or "reference nucleic acid" or "reference nucleotide sequence" or "reference sequence" refers to a starting nucleic acid sequence (e.g., a RNA, e.g., an mRNA sequence) that can be sequence optimized. In some embodiments, the reference nucleic acid sequence is a wild type nucleic acid sequence, a fragment or a variant thereof. In some embodiments, the reference nucleic acid sequence is a previously sequence optimized nucleic acid sequence.

Salts: In some aspects, the pharmaceutical composition for delivery disclosed herein and comprises salts of some of their lipid constituents. The term "salt" includes any anionic and cationic complex. Non-limiting examples of anions include inorganic and organic anions, e.g., fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfite, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof.

Sample: As used herein, the term "sample" or "biological sample" refers to a subset of its tissues, cells or component parts (e.g., body fluids, including but not limited to blood, mucus, lymphatic fluid, synovial fluid, cerebrospinal fluid, saliva, amniotic fluid, amniotic cord blood, urine, vaginal fluid and semen). A sample further can include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. A sample further refers to a medium, such as a nutrient broth or gel, which can contain cellular components, such as proteins or nucleic acid molecule.

Signal Sequence: As used herein, the phrases "signal sequence," "signal peptide," and "transit peptide" are used interchangeably and refer to a sequence that can direct the transport or localization of a protein to a certain organelle, cell compartment, or extracellular export. The term encompasses both the signal sequence polypeptide and the nucleic acid sequence encoding the signal sequence. Thus, references to a signal sequence in the context of a nucleic acid refer in fact to the nucleic acid sequence encoding the signal sequence polypeptide.

Signal transduction pathway: A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Single unit dose: As used herein, a "single unit dose" is a dose of any therapeutic administered in one dose/at one time/single route/single point of contact, i.e., single administration event.

Split dose: As used herein, a "split dose" is the division of single unit dose or total daily dose into two or more doses.

Specific delivery: As used herein, the term "specific delivery," "specifically deliver," or "specifically delivering" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a polynucleotide by a nanoparticle to a target tissue of interest (e.g., mammalian liver) compared to an off-target tissue (e.g., mammalian spleen). The level of delivery of a nanoparticle to a particular tissue can be measured by comparing the amount of protein produced in a tissue to the weight of said tissue, comparing the amount of polynucleotide in a tissue to the weight of said tissue, comparing the amount of protein produced in a tissue to the amount of total protein in said tissue, or comparing the amount of polynucleotide in a tissue to the amount of total polynucleotide in said tissue. For example, for renovascular targeting, a polynucleotide is specifically provided to a mammalian kidney as compared to the liver and spleen if 1.5, 2-fold, 3-fold, 5-fold, 10-fold, 15 fold, or 20 fold more polynucleotide per 1 g of tissue is delivered to a kidney compared to that delivered to the liver or spleen following systemic administration of the polynucleotide. It will be understood that the ability of a nanoparticle to specifically deliver to a target tissue need not be determined in a subject being treated, it can be determined in a surrogate such as an animal model (e.g., a rat model).

Stable: As used herein "stable" refers to a compound that is sufficiently robust to survive isolation to a useful degree of purity from a reaction mixture, and in some cases capable of formulation into an efficacious therapeutic agent.

Stabilized: As used herein, the term "stabilize," "stabilized," "stabilized region" means to make or become stable.

Stereoisomer: As used herein, the term "stereoisomer" refers to all possible different isomeric as well as conformational forms that a compound can possess (e.g., a compound of any formula described herein), in particular all possible stereochemically and conformationally isomeric forms, all diastereomers, enantiomers and/or conformers of the basic molecular structure. Some compounds of the present invention can exist in different tautomeric forms, all of the latter being included within the scope of the present invention.

Subject: By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; bears, food animals such as cows, pigs, and sheep; ungulates such as deer and giraffes; rodents such as mice, rats, hamsters and guinea pigs; and so on. In certain embodiments, the mammal is a human subject. In other embodiments, a subject is a human patient. In a particular embodiment, a subject is a human patient in need of treatment.

Substantially: As used herein, the term "substantially" refers to the qualitative condition of exhibiting total or near-total extent or degree of a characteristic or property of interest. One of ordinary skill in the biological arts will understand that biological and chemical characteristics rarely, if ever, go to completion and/or proceed to completeness or achieve or avoid an absolute result. The term "substantially" is therefore used herein to capture the potential lack of completeness inherent in many biological and chemical characteristics.

Substantially equal: As used herein as it relates to time differences between doses, the term means plus/minus 2%.

Substantially simultaneous: As used herein and as it relates to plurality of doses, the term means within 2 seconds.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with and/or cannot exhibit symptoms of the disease, disorder, and/or condition but harbors a propensity to develop a disease or its symptoms. In some embodiments, an individual who is susceptible to a disease, disorder, and/or condition (for example, PA) can be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Sustained release: As used herein, the term "sustained release" refers to a pharmaceutical composition or compound release profile that conforms to a release rate over a specific period of time.

Synthetic: The term "synthetic" means produced, prepared, and/or manufactured by the hand of man. Synthesis of polynucleotides or other molecules of the present invention can be chemical or enzymatic.

Targeted Cells: As used herein, "targeted cells" refers to any one or more cells of interest. The cells can be found in vitro, in vivo, in situ or in the tissue or organ of an organism. The organism can be an animal, for example a mammal, a human, a subject or a patient.

Target tissue: As used herein "target tissue" refers to any one or more tissue types of interest in which the delivery of a polynucleotide would result in a desired biological and/or pharmacological effect. Examples of target tissues of interest include specific tissues, organs, and systems or groups thereof. In particular applications, a target tissue can be a liver, a kidney, a lung, a spleen, or a vascular endothelium in vessels (e.g., intra-coronary or intra-femoral). An "off-target tissue" refers to any one or more tissue types in which the expression of the encoded protein does not result in a desired biological and/or pharmacological effect.

The presence of a therapeutic agent in an off-target issue can be the result of: (i) leakage of a polynucleotide from the administration site to peripheral tissue or distant off-target tissue via diffusion or through the bloodstream (e.g., a polynucleotide intended to express a polypeptide in a certain tissue would reach the off-target tissue and the polypeptide would be expressed in the off-target tissue); or (ii) leakage of an polypeptide after administration of a polynucleotide encoding such polypeptide to peripheral tissue or distant off-target tissue via diffusion or through the bloodstream (e.g., a polynucleotide would expressed a polypeptide in the target tissue, and the polypeptide would diffuse to peripheral tissue).

Targeting sequence: As used herein, the phrase "targeting sequence" refers to a sequence that can direct the transport or localization of a protein or polypeptide.

Terminus: As used herein the terms "termini" or "terminus," when referring to polypeptides, refers to an extremity of a peptide or polypeptide. Such extremity is not limited only to the first or final site of the peptide or polypeptide but can include additional amino acids in the terminal regions. The polypeptide based molecules of the invention can be characterized as having both an N-terminus (terminated by an amino acid with a free amino group ($NH_2$)) and a C-terminus (terminated by an amino acid with a free carboxyl group (COOH)). Proteins of the invention are in some cases made up of multiple polypeptide chains brought together by disulfide bonds or by non-covalent forces (multimers, oligomers). These sorts of proteins will have multiple N- and C-termini. Alternatively, the termini of the polypeptides can be modified such that they begin or end, as the case can be, with a non-polypeptide based moiety such as an organic conjugate.

Therapeutic Agent: The term "therapeutic agent" refers to an agent that, when administered to a subject, has a therapeutic, diagnostic, and/or prophylactic effect and/or elicits a desired biological and/or pharmacological effect. For example, in some embodiments, an mRNA encoding a PCCA or PCCB polypeptide can be a therapeutic agent.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

Total daily dose: As used herein, a "total daily dose" is an amount given or prescribed in 24 hr. period. The total daily dose can be administered as a single unit dose or a split dose.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors can regulate transcription of a target gene alone or in a complex with other molecules.

Transcription: As used herein, the term "transcription" refers to methods to produce mRNA (e.g., an mRNA sequence or template) from DNA (e.g., a DNA template or sequence)

Transfection: As used herein, "transfection" refers to the introduction of a polynucleotide (e.g., exogenous nucleic acids) into a cell wherein a polypeptide encoded by the polynucleotide is expressed (e.g., mRNA) or the polypeptide modulates a cellular function (e.g., siRNA, miRNA). As used herein, "expression" of a nucleic acid sequence refers to translation of a polynucleotide (e.g., an mRNA) into a polypeptide or protein and/or post-translational modification of a polypeptide or protein. Methods of transfection include, but are not limited to, chemical methods, physical treatments and cationic lipids or mixtures.

Treating, treatment, therapy: As used herein, the term "treating" or "treatment" or "therapy" refers to partially or completely alleviating, ameliorating, improving, relieving, delaying onset of, inhibiting progression of, reducing severity of, and/or reducing incidence of one or more symptoms or features of a disease, e.g., metabolic acidosis (e.g., acidosis of the blood and tissues), hyperammonemia, hyperglycinemia, PA. For example, "treating" PA can refer to diminishing symptoms associate with the disease, prolong the lifespan (increase the survival rate) of patients, reducing the severity of the disease, preventing or delaying the onset of the disease, etc. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unmodified: As used herein, "unmodified" refers to any substance, compound or molecule prior to being changed in some way. Unmodified can, but does not always, refer to the wild type or native form of a biomolecule. Molecules can undergo a series of modifications whereby each modified molecule can serve as the "unmodified" starting molecule for a subsequent modification.

Uracil: Uracil is one of the four nucleobases in the nucleic acid of RNA, and it is represented by the letter U. Uracil can be attached to a ribose ring, or more specifically, a ribofuranose via a $\beta$-$N_1$-glycosidic bond to yield the nucleoside uridine. The nucleoside uridine is also commonly abbreviated according to the one letter code of its nucleobase, i.e., U. Thus, in the context of the present disclosure, when a monomer in a polynucleotide sequence is U, such U is designated interchangeably as a "uracil" or a "uridine."

Uridine Content: The terms "uridine content" or "uracil content" are interchangeable and refer to the amount of uracil or uridine present in a certain nucleic acid sequence. Uridine content or uracil content can be expressed as an absolute value (total number of uridine or uracil in the sequence) or relative (uridine or uracil percentage respect to the total number of nucleobases in the nucleic acid sequence).

Uridine-Modified Sequence: The terms "uridine-modified sequence" refers to a sequence optimized nucleic acid (e.g., a synthetic mRNA sequence) with a different overall or local uridine content (higher or lower uridine content) or with different uridine patterns (e.g., gradient distribution or clustering) with respect to the uridine content and/or uridine patterns of a candidate nucleic acid sequence. In the content of the present disclosure, the terms "uridine-modified sequence" and "uracil-modified sequence" are considered equivalent and interchangeable.

A "high uridine codon" is defined as a codon comprising two or three uridines, a "low uridine codon" is defined as a codon comprising one uridine, and a "no uridine codon" is a codon without any uridines. In some embodiments, a uridine-modified sequence comprises substitutions of high uridine codons with low uridine codons, substitutions of high uridine codons with no uridine codons, substitutions of low uridine codons with high uridine codons, substitutions of low uridine codons with no uridine codons, substitution of no uridine codons with low uridine codons, substitutions of no uridine codons with high uridine codons, and combinations thereof. In some embodiments, a high uridine codon can be replaced with another high uridine codon. In some embodiments, a low uridine codon can be replaced with another low uridine codon. In some embodiments, a no uridine codon can be replaced with another no uridine codon. A uridine-modified sequence can be uridine enriched or uridine rarefied.

Uridine Enriched: As used herein, the terms "uridine enriched" and grammatical variants refer to the increase in uridine content (expressed in absolute value or as a percentage value) in an sequence optimized nucleic acid (e.g., a synthetic mRNA sequence) with respect to the uridine content of the corresponding candidate nucleic acid sequence. Uridine enrichment can be implemented by substituting codons in the candidate nucleic acid sequence with synonymous codons containing less uridine nucleobases. Uridine enrichment can be global (i.e., relative to the entire length of a candidate nucleic acid sequence) or local (i.e., relative to a subsequence or region of a candidate nucleic acid sequence).

Uridine Rarefied: As used herein, the terms "uridine rarefied" and grammatical variants refer to a decrease in uridine content (expressed in absolute value or as a percentage value) in an sequence optimized nucleic acid (e.g., a synthetic mRNA sequence) with respect to the uridine content of the corresponding candidate nucleic acid sequence. Uridine rarefication can be implemented by substituting codons in the candidate nucleic acid sequence with synonymous codons containing less uridine nucleobases. Uridine rarefication can be global (i.e., relative to the entire length of a candidate nucleic acid sequence) or local (i.e., relative to a subsequence or region of a candidate nucleic acid sequence).

Variant: The term variant as used in present disclosure refers to both natural variants (e.g., polymorphisms, isoforms, etc) and artificial variants in which at least one amino acid residue in a native or starting sequence (e.g., a wild type sequence) has been removed and a different amino acid inserted in its place at the same position. These variants can de described as "substitutional variants." The substitutions can be single, where only one amino acid in the molecule has been substituted, or they can be multiple, where two or more amino acids have been substituted in the same molecule. If amino acids are inserted or deleted, the resulting variant would be an "insertional variant" or a "deletional variant" respectively.

Initiation Codon: As used herein, the term "initiation codon", used interchangeably with the term "start codon", refers to the first codon of an open reading frame that is translated by the ribosome and is comprised of a triplet of linked adenine-uracil-guanine nucleobases. The initiation codon is depicted by the first letter codes of adenine (A), uracil (U), and guanine (G) and is often written simply as "AUG". Although natural mRNAs may use codons other than AUG as the initiation codon, which are referred to herein as "alternative initiation codons", the initiation codons of polynucleotides described herein use the AUG codon. During the process of translation initiation, the sequence comprising the initiation codon is recognized via complementary base-pairing to the anticodon of an initiator tRNA (Met-tRNA$_i^{Met}$) bound by the ribosome. Open reading frames may contain more than one AUG initiation codon, which are referred to herein as "alternate initiation codons".

The initiation codon plays a critical role in translation initiation. The initiation codon is the first codon of an open reading frame that is translated by the ribosome. Typically, the initiation codon comprises the nucleotide triplet AUG, however, in some instances translation initiation can occur at other codons comprised of distinct nucleotides. The initiation of translation in eukaryotes is a multistep biochemical process that involves numerous protein-protein, protein-RNA, and RNA-RNA interactions between messenger RNA molecules (mRNAs), the 40S ribosomal subunit, other components of the translation machinery (e.g., eukaryotic initiation factors; eIFs). The current model of mRNA translation initiation postulates that the pre-initiation complex (alternatively "43S pre-initiation complex"; abbreviated as "PIC") translocates from the site of recruitment on the mRNA (typically the 5' cap) to the initiation codon by scanning nucleotides in a 5' to 3' direction until the first AUG codon that resides within a specific translation-promotive nucleotide context (the Kozak sequence) is encountered (Kozak (1989) J Cell Biol 108:229-241). Scanning by the PIC ends upon complementary base-pairing between nucleotides comprising the anticodon of the initiator Met-tRNA$_i^{Met}$ transfer RNA and nucleotides comprising the initiation codon of the mRNA. Productive base-pairing between the AUG codon and the Met-tRNA$_i^{Met}$ anticodon elicits a series of structural and biochemical events that culminate in the joining of the large 60S ribosomal subunit to the PIC to form an active ribosome that is competent for translation elongation.

Kozak Sequence: The term "Kozak sequence" (also referred to as "Kozak consensus sequence") refers to a translation initiation enhancer element to enhance expression of a gene or open reading frame, and which in eukaryotes, is located in the 5' UTR. The Kozak consensus sequence was originally defined as the sequence GCCRCC, where R=a purine, following an analysis of the effects of single mutations surrounding the initiation codon (AUG) on translation of the preproinsulin gene (Kozak (1986) Cell 44:283-292). Polynucleotides disclosed herein comprise a Kozak consensus sequence, or a derivative or modification thereof (Examples of translational enhancer compositions and methods of use thereof, see U.S. Pat. No. 5,807,707 to Andrews et al., incorporated herein by reference in its entirety; U.S. Pat. No. 5,723,332 to Chemajovsky, incorporated herein by reference in its entirety; U.S. Pat. No. 5,891,665 to Wilson, incorporated herein by reference in its entirety.)

Modified: As used herein "modified" or "modification" refers to a changed state or a change in composition or structure of a polynucleotide (e.g., mRNA). Polynucleotides may be modified in various ways including chemically, structurally, and/or functionally. For example, polynucleotides may be structurally modified by the incorporation of one or more RNA elements, wherein the RNA element comprises a sequence and/or an RNA secondary structure(s) that provides one or more functions (e.g., translational regulatory activity). Accordingly, polynucleotides of the disclosure may be comprised of one or more modifications (e.g., may include one or more chemical, structural, or functional modifications, including any combination thereof).

Nucleobase: As used herein, the term "nucleobase" (alternatively "nucleotide base" or "nitrogenous base") refers to a purine or pyrimidine heterocyclic compound found in nucleic acids, including any derivatives or analogs of the naturally occurring purines and pyrimidines that confer improved properties (e.g., binding affinity, nuclease resistance, chemical stability) to a nucleic acid or a portion or segment thereof. Adenine, cytosine, guanine, thymine, and uracil are the nucleobases predominately found in natural nucleic acids. Other natural, non-natural, and/or synthetic nucleobases, as known in the art and/or described herein, can be incorporated into nucleic acids.

Nucleoside Nucleotide: As used herein, the term "nucleoside" refers to a compound containing a sugar molecule (e.g., a ribose in RNA or a deoxyribose in DNA), or derivative or analog thereof, covalently linked to a nucleobase (e.g., a purine or pyrimidine), or a derivative or analog thereof (also referred to herein as "nucleobase"), but lacking an internucleoside linking group (e.g., a phosphate group). As used herein, the term "nucleotide" refers to a nucleoside covalently bonded to an internucleoside linking group (e.g., a phosphate group), or any derivative, analog, or modification thereof that confers improved chemical and/or functional properties (e.g., binding affinity, nuclease resistance, chemical stability) to a nucleic acid or a portion or segment thereof.

Nucleic acid: As used herein, the term "nucleic acid" is used in its broadest sense and encompasses any compound and/or substance that includes a polymer of nucleotides, or derivatives or analogs thereof. These polymers are often referred to as "polynucleotides". Accordingly, as used herein the terms "nucleic acid" and "polynucleotide" are equivalent and are used interchangeably. Exemplary nucleic acids or polynucleotides of the disclosure include, but are not limited to, ribonucleic acids (RNAs), deoxyribonucleic acids (DNAs), DNA-RNA hybrids, RNAi-inducing agents, RNAi agents, siRNAs, shRNAs, mRNAs, modified mRNAs, miRNAs, antisense RNAs, ribozymes, catalytic DNA, RNAs that induce triple helix formation, threose nucleic acids (TNAs), glycol nucleic acids (GNAs), peptide nucleic acids (PNAs), locked nucleic acids (LNAs, including LNA having a β-D-ribo configuration, μ-LNA having an α-L-ribo configuration (a diastereomer of LNA), 2'-amino-LNA having a 2'-amino functionalization, and 2'-amino-α-LNA having a 2'-amino functionalization) or hybrids thereof.

Nucleic Acid Structure: As used herein, the term "nucleic acid structure" (used interchangeably with "polynucleotide structure") refers to the arrangement or organization of atoms, chemical constituents, elements, motifs, and/or sequence of linked nucleotides, or derivatives or analogs thereof, that comprise a nucleic acid (e.g., an mRNA). The term also refers to the two-dimensional or three-dimensional state of a nucleic acid. Accordingly, the term "RNA structure" refers to the arrangement or organization of atoms, chemical constituents, elements, motifs, and/or sequence of linked nucleotides, or derivatives or analogs thereof, comprising an RNA molecule (e.g., an mRNA) and/or refers to a two-dimensional and/or three dimensional state of an RNA molecule. Nucleic acid structure can be further demarcated into four organizational categories referred to herein as "molecular structure", "primary structure", "secondary structure", and "tertiary structure" based on increasing organizational complexity.

Open Reading Frame: As used herein, the term "open reading frame", abbreviated as "ORF", refers to a segment or region of an mRNA molecule that encodes a polypeptide. The ORF comprises a continuous stretch of non-overlapping, in-frame codons, beginning with the initiation codon and ending with a stop codon, and is translated by the ribosome.

Pre-Initiation Complex (PIC): As used herein, the term "pre-initiation complex" (alternatively "43S pre-initiation complex"; abbreviated as "PIC") refers to a ribonucleoprotein complex comprising a 40S ribosomal subunit, eukaryotic initiation factors (eIF1, eIF1A, eIF3, eIF5), and the eIF2-GTP-Met-tRNA$_i^{Met}$ ternary complex, that is intrinsically capable of attachment to the 5' cap of an mRNA molecule and, after attachment, of performing ribosome scanning of the 5' UTR.

RNA element: As used herein, the term "RNA element" refers to a portion, fragment, or segment of an RNA molecule that provides a biological function and/or has biological activity (e.g., translational regulatory activity). Modification of a polynucleotide by the incorporation of one or more RNA elements, such as those described herein, provides one or more desirable functional properties to the modified polynucleotide. RNA elements, as described herein, can be naturally-occurring, non-naturally occurring, synthetic, engineered, or any combination thereof. For example, naturally-occurring RNA elements that provide a regulatory activity include elements found throughout the transcriptomes of viruses, prokaryotic and eukaryotic organisms (e.g., humans). RNA elements in particular eukaryotic mRNAs and translated viral RNAs have been shown to be involved in mediating many functions in cells. Exemplary natural RNA elements include, but are not limited to, translation initiation elements (e.g., internal ribosome entry site (IRES), see Kieft et al., (2001) RNA 7(2):194-206), translation enhancer elements (e.g., the APP mRNA translation enhancer element, see Rogers et al., (1999) J Biol Chem 274(10):6421-6431), mRNA stability elements (e.g., AU-rich elements (AREs), see Garneau et al., (2007) Nat Rev Mol Cell Biol 8(2):113-126), translational repression element (see e.g., Blumer et al., (2002) Mech Dev 110(1-2):97-112), protein-binding RNA elements (e.g., iron-responsive element, see Selezneva et al., (2013) J Mol Biol 425(18):3301-3310), cytoplasmic polyadenylation elements (Villalba et al., (2011) Curr Opin Genet Dev 21(4):452-457), and catalytic RNA elements (e.g., ribozymes, see Scott et al., (2009) Biochim Biophys Acta 1789(9-10):634-641).

Residence time: As used herein, the term "residence time" refers to the time of occupancy of a pre-initiation complex (PIC) or a ribosome at a discrete position or location along an mRNA molecule.

Translational Regulatory Activity: As used herein, the term "translational regulatory activity" (used interchangeably with "translational regulatory function") refers to a biological function, mechanism, or process that modulates (e.g., regulates, influences, controls, varies) the activity of the translational apparatus, including the activity of the PIC and/or ribosome. In some aspects, the desired translation regulatory activity promotes and/or enhances the translational fidelity of mRNA translation. In some aspects, the desired translational regulatory activity reduces and/or inhibits leaky scanning.

28. Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" can mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art can be explicitly excluded from any one or more of the claims. Since such embodiments are deemed to be known to one of ordinary skill in the art, they can be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

CONSTRUCT SEQUENCES

By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| SEQ ID NO: | 1 | 2 | 3 | 4 | 28 |
| PCCA_11 (hPCCA; G5) Cap: C1 PolyA tail: 100 nt | MAGFWVGTAPLVAA GRRGRWPPQQLMLS AALRTLKHVLYYSR QCLMVSRNLGSVGY DPNEKTFDKILVANR GEIACRVIRTCKKMG | AUGGCCGGAUUCUG GGUCGGCACAGCCC CUCUUGUGGCCGCA GGGAGGCGCGGCCG CUGGCCACCACAGC AGCUGAUGCUGUCU | GGGAAA UAAGAG AGAAA GAAGAG UAAGAA GAAAUA | UGAUAA UAGGCU GGAGCC UCGGUG GCCUAG CUUCUU | SEQ ID NO: 28 consists from 5' to 3' end: 5' UTR of SEQ ID NO: 3, |

-continued

CONSTRUCT SEQUENCES
By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | IKTVAIHSDVDASSV | GCCGCCCUGCGGAC | UAAGAG | GCCCCU | ORF |
| | HVKMADEAVCVGPA | CCUGAAGCACGUGC | CCACC | UGGGCC | Sequence of |
| | PTSKSYLNMDAIMEA | UGUACUAUAGCAGA | | UCCCCC | SEQ ID NO: 2, |
| | IKKTRAQAVHPGYGF | CAGUGUCUGAUGGU | | CAGCCC | and |
| | LSENKEFARCLAAED | GUCCAGAAACCUCG | | CUCCUC | 3' UTR of |
| | VVFIGPDTHAIQAMG | GAAGCGUGGGCUAC | | CCCUUC | SEQ ID NO: 4 |
| | DKIESKLLAKKAEVN | GACCCCAACGAGAA | | CUGCAC | |
| | TIPGFDGVVKDAEEA | GACCUUCGACAAGA | | CCGUAC | |
| | VRIAREIGYPVMIKAS | UCCUGGUCGCCAAC | | CCCCUC | |
| | AGGGGKGMRIAWDD | CGCGGCGAGAUCGC | | CAUAAA | |
| | EETRDGFRLSSQEAA | UUGCCGGGUGAUCA | | GUAGGA | |
| | SSFGDDRLLIEKFIDN | GGACCUGUAAGAAG | | AACACU | |
| | PRHIEIQVLGDKHGN | AUGGGCAUCAAGAC | | ACAGUG | |
| | ALWLNERECSIQRRN | CGUGGCCAUCCACA | | GUCUUU | |
| | QKVVEEAPSIFLDAE | GCGACGUAGACGCC | | GAAUAA | |
| | TRRAMGEQAVALAR | AGCAGCGUGCACGU | | AGUCUG | |
| | AVKYSSAGTVEFLVD | CAAGAUGGCCGACG | | AGUGGG | |
| | SKKNFYFLEMNTRLQ | AAGCGGUGUGCGUG | | CGGC | |
| | VEHPVTECITGLDLV | GGGCCCGCCCCUAC | | | |
| | QEMIRVAKGYPLRH | AUCCAAGUCCUAUC | | | |
| | KQADIRINGWAVECR | UUAACAUGGACGCC | | | |
| | VYAEDPYKSFGLPSI | AUCAUGGAGGCCAU | | | |
| | GRLSQYQEPLHLPGV | CAAGAAGACUAGAG | | | |
| | RVDSGIQPGSDISIYY | CCCAAGCCGUUCAU | | | |
| | DPMISKLITYGSDRTE | CCGGGGUACGGAUU | | | |
| | ALKRMADALDNYVI | UCUGUCCGAGAACA | | | |
| | RGVTHNIALLREVIIN | AAGAGUUCGCUAGG | | | |
| | SRFVKGDISTKFLSDV | UGCCUCGCCGCCGA | | | |
| | YPDGFKGHMLTKSE | AGACGUUGUCUUCA | | | |
| | KNQLLAIASSLFVAF | UUGGUCCAGACACC | | | |
| | QLRAQHFQENSRMP | CACGCCAUCCAGGC | | | |
| | VIKPDIANWELSVKL | UAUGGGCGAUAAGA | | | |
| | HDKVHTVVASNNGS | UCGAGAGCAAGCUG | | | |
| | VFSVEVDGSKLNVTS | CUGGCUAAGAAGGC | | | |
| | TWNLASPLLSVSVDG | AGAGGUGAACACCA | | | |
| | TQRTVQCLSREAGGN | UCCCCGGAUUCGAC | | | |
| | MSIQFLGTVYKVNIL | GGAGUGGUCAAAGA | | | |
| | TRLAAELNKFMLEK | CGCGGAGGAGGCCG | | | |
| | VTEDTSSVLRSPMPG | UGAGGAUCGCGAGA | | | |
| | VVVAVSVKPGDAVA | GAGAUCGGAUACCC | | | |
| | EGQEICVIEAMKMQN | GGUGAUGAUCAAGG | | | |
| | SMTAGKTGTVKSVH | CCUCAGCAGGCGGC | | | |
| | CQAGDTVGEGDLLV | GGCGGAAAGGGAAU | | | |
| | ELE | GAGAAUUGCCUGGG | | | |
| | | ACGACGAGGAAACC | | | |
| | | CGCGACGGCUUCCG | | | |
| | | GCUCAGCUCCCAGG | | | |
| | | AAGCAGCUUCUAGC | | | |
| | | UUUGGCGACGAUCG | | | |
| | | GCUGCUGAUUGAGA | | | |
| | | AAUUCAUCGAUAAC | | | |
| | | CCCAGACACAUAGA | | | |
| | | GAUCCAGGUGCUGG | | | |
| | | GUGACAAGCACGGC | | | |
| | | AACGCCCUGUGGCU | | | |
| | | GAACGAGAGAGAGU | | | |
| | | GCUCCAUUCAGAGG | | | |
| | | AGGAACCAGAAGGU | | | |
| | | GGUUGAGGAGGCGC | | | |
| | | CUAGCAUCUUCCUG | | | |
| | | GACGCUGAAACAAG | | | |
| | | GAGAGCCAUGGGUG | | | |
| | | AGCAGGCCGUGGCC | | | |
| | | CUGGCUCGCGCCGU | | | |
| | | UAAGUAUAGCAGCG | | | |
| | | CCGGCACCGUCGAG | | | |
| | | UUCCUGGUGGACUC | | | |
| | | CAAGAAGAACUUCU | | | |
| | | AUUUCCUGGAGAUG | | | |
| | | AACACCCGCCUGCA | | | |
| | | GGUGGAGCACCCCG | | | |
| | | UCACUGAGUGUAUU | | | |
| | | ACCGGCCUCGACCU | | | |

-continued

| CONSTRUCT SEQUENCES | | | | | |
|---|---|---|---|---|---|
| By "G5" is meant that all uracils (U) in the mRNA are replaced by N1-methylpseudouracils. | | | | | |
| mRNA<br>Name | ORF Sequence<br>(Amino Acid) | ORF Sequence<br>(Nucleotide) | 5' UTR<br>Sequence | 3' UTR<br>Sequence | Construct<br>Sequence |
| | | GGUCCAGGAGAUGA | | | |
| | | UCAGAGUCGCCAAG | | | |
| | | GGGUAUCCCCUGCG | | | |
| | | GCACAAGCAGGCAG | | | |
| | | ACAUCCGCAUCAAC | | | |
| | | GGCUGGGCCGUGGA | | | |
| | | GUGCAGAGUGUACG | | | |
| | | CCGAGGACCCCUAC | | | |
| | | AAGAGCUUCGGCCU | | | |
| | | GCCAAGCAUCGGCA | | | |
| | | GACUGUCUCAGUAC | | | |
| | | CAAGAACCCCUGCA | | | |
| | | CCUGCCCGGCGUGA | | | |
| | | GAGUAGACAGCGGC | | | |
| | | AUUCAGCCUGGAAG | | | |
| | | CGACAUUAGCAUCU | | | |
| | | ACUACGACCCUAUG | | | |
| | | AUCAGCAAGCUCAU | | | |
| | | CACCUACGGUUCUG | | | |
| | | ACCGGACCGAGGCC | | | |
| | | CUGAAACGGAUGGC | | | |
| | | UGACGCCUGGACA | | | |
| | | ACUACGUGAUCCGG | | | |
| | | GGCGUGACUCACAA | | | |
| | | CAUCGCCCUCCUGA | | | |
| | | GGGAAGUCAUCAUC | | | |
| | | AACAGCCGAUUCGU | | | |
| | | GAAGGGAGACAUCU | | | |
| | | CCACCAAGUUCCUG | | | |
| | | AGCGACGUGUACCC | | | |
| | | UGACGGCUUCAAAG | | | |
| | | GCCACAUGCUGACC | | | |
| | | AAGAGCGAGAAGAA | | | |
| | | CCAGCUCCUGGCCA | | | |
| | | UCGCCAGUAGCCUG | | | |
| | | UUCGUGGCCUUCCA | | | |
| | | GCUGAGGGCCCAGC | | | |
| | | ACUUUCAGGAGAAC | | | |
| | | AGCAGGAUGCCAGU | | | |
| | | GAUUAAGCCUGACA | | | |
| | | UCGCCAACUGGGAG | | | |
| | | CUGUCAGUCAAGCU | | | |
| | | GCACGAUAAGGUGC | | | |
| | | ACACAGUGGUGGCC | | | |
| | | AGCAAUAACGGCUC | | | |
| | | CGUGUUCAGCGUCG | | | |
| | | AGGUGGACGGCUCC | | | |
| | | AAACUGAACGUCAC | | | |
| | | CAGCACCUGGAAUC | | | |
| | | UGGCCUCACCCUUA | | | |
| | | CUGAGCGUGUCUGU | | | |
| | | GGACGGCACCCAGA | | | |
| | | GAACCGUGCAGUGU | | | |
| | | UUGUCUAGGGAGGC | | | |
| | | AGGCGGCAACAUGU | | | |
| | | CCAUCCAGUUUCUG | | | |
| | | GGAACAGUGUACAA | | | |
| | | AGUGAAUAUCCUGA | | | |
| | | CCAGACUGGCCGCU | | | |
| | | GAGCUGAACAAGUU | | | |
| | | CAUGCUUGAGAAGG | | | |
| | | UGACCGAGGAUACU | | | |
| | | AGCUCCGUUCUGAG | | | |
| | | AUCCCCUAUGCCCG | | | |
| | | GUGUGGUCGUGGCA | | | |
| | | GUGAGCGUGAAGCC | | | |
| | | UGGUGACGCGGUGG | | | |
| | | CAGAGGGUCAGGAG | | | |
| | | AUCUGUGUCAUUGA | | | |
| | | GGCUAUGAAGAUGC | | | |
| | | AGAAUAGCAUGACA | | | |
| | | GCCGGUAAGACCGG | | | |
| | | GACGGUUAAAUCCG | | | |

-continued

CONSTRUCT SEQUENCES
By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | UUCACUGCCAGGCU GGCGACACCGUGGG CGAGGGCGAUCUGU UAGUGGAGCUUGAG | | | |

| SEQ ID NO: | 1 | 5 | 3 | 4 | 29 |
|---|---|---|---|---|---|
| PCCA_12 (hPCCA; G5) Cap: C1 PolyA tail: 100 nt | MAGFWVGTAPLVAA GRRGRWPPQQLMLS AALRTLKHVLYYSR QCLMVSRNLGSVGY DPNEKTFDKILVANR GEIACRVIRTCKKMG IKTVAIHSDVDASSV HVKMADEAVCVGPA PTSKSYLNMDAIMEA IKKTRAQAVHPGYGF LSENKEFARCLAAED VVFIGPDTHAIQAMG DKIESKLLAKKAEVN TIPGFDGVVKDAEEA VRIAREIGYPVMIKAS AGGGGKGMRIAWDD EETRDGFRLSSQEAA SSFGDDRLLIEKFIDN PRHIEIQVLGDKHGN ALWLNERECSIQRRN QKVVEEAPSIFLDAE TRRAMGEQAVALAR AVKYSSAGTVEFLVD SKKNFYFLEMNTRLQ VEHPVTECITGLDLV QEMIRVAKGYPLRH KQADIRINGWAVECR VYAEDPYKSFGLPSI GRLSQYQEPLHLPGV RVDSGIQPGSDISIYY DPMISKLITYGSDRTE ALKRMADALDNYVI RGVTHNIALLREVIIN SRFVKGDISTKFLSDV YPDGFKGHMLTKSE KNQLLAIASSLFVAF QLRAQHFQENSRMP VIKPDIANWELSVKL HDKVHTVVASNNGS VFSVEVDGSKLNVTS TWNLASPLLSVSVDG TQRTVQCLSREAGGN MSIQFLGTVYKVNIL TRLAAELNKFMLEK VTEDTSSVLRSPMPG VVVAVSVKPGDAVA EGQEICVIEAMKMQN SMTAGKTGTVKSVH CQAGDTVGEGDLLV ELE | AUGGCGGGCUUUUG GGUGGGCACCGCCC CACUGGUCGCUGCC GGCAGGAGAGGACG GUGGCCACCCCAGC AGCUCAUGCUGAGC GCCGCACUCAGAAC CCUGAAGCACGUGC UGUACUACUCGCGA CAGUGCCUUAUGGU GUCUAGGAACCUGG GCUCUGUCGGCUAC GAUCCGAACGAGAA GACCUUCGACAAGA UCCUGGUCGCCAAC AGGGGCGAAAUCGC CUGUAGAGUCAUAA GGACCUGUAAGAAG AUGGGCAUCAAGAC CGUGGCUAUCCACA GCGACGUGGACGCU AGCUCCGUACACGU GAAGAUGGCCGACG AGGCAGUGUGCGUG GGUCCGGCUCCCAC CUCCAAGUCCUACC UGAACAUGGACGCC AUCAUGGAAGCCAU CAAGAAGACUAGAG CCCAGGCCGUGCAC CCAGGCUACGGGUU UCUCUCCGAGAAUA AAGAGUUCGCCAGG UGCCUGGCUGCCGA GGACGUGGUGUUUA UCGGACCCGAUACU CACGCCAUCCAGGC CAUGGGCGACAAGA UAGAGUCUAAGCUG UUGGCCAAGAAAGC UGAGGUGAACACCA UCCCCGGCUUCGAC GGUGUGGUUAAGG ACGCCGAGGAAGCU GUGCGCAUCGCCAG GGAAAUCGGCUACC CCGUGAUGAUCAAG GCAAGUGCAGGAGG AGGCGGCAAAGGGA UGAGAAUCGCCUGG GACGACGAAGAAAC UAGAGACGGUUUCC GGCUGUCUUCCCAG GAGGCUGCAUCAUC UUUUGGAGACGAUC GGUUGCUGAUUGAG AAGUUUAUUGACAA CCCGCGGCACAUCG AGAUCCAGGUGCUC GGUGACAAGCACGG CAACGCCCUCUGGC UCAACGAAAGAGAG UGCAGCAUUCAGCG CCGGAACCAGAAAG UGGUGGAGGAGGCU | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 29 consists from 5' to 3' end: 5' UTR of SEQ ID NO: 3, ORF Sequence of SEQ ID NO: 5, and 3' UTR of SEQ ID NO: 4 |

-continued

CONSTRUCT SEQUENCES
By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | CCCAGUAUUUUCCU | | | |
| | | GGACGCCGAAACCC | | | |
| | | GGAGAGCCAUGGGA | | | |
| | | GAGCAGGCUGUGGC | | | |
| | | UCUCGCUAGGGCGG | | | |
| | | UGAAGUACAGCUCC | | | |
| | | GCCGGCACAGUCGA | | | |
| | | GUUCCUGGUGGACU | | | |
| | | CCAAGAAGAACUUC | | | |
| | | UACUUCCUGGAGAU | | | |
| | | GAACACAAGACUGC | | | |
| | | AGGUGGAGCAUCCC | | | |
| | | GUUACCGAGUGUAU | | | |
| | | AACCGGCCUGGAUC | | | |
| | | UGGUCCAGGAGAUG | | | |
| | | AUCAGAGUCGCCAA | | | |
| | | GGGAUAUCCCCUUA | | | |
| | | GGCAUAAACAGGCC | | | |
| | | GACAUCAGGAUCAA | | | |
| | | CGGCUGGGCCGUCG | | | |
| | | AGUGCCGGGUGUAC | | | |
| | | GCUGAGGACCCUUA | | | |
| | | UAAGAGCUUCGGCU | | | |
| | | UACCAUCCAUUGGC | | | |
| | | AGACUGUCCCAGUA | | | |
| | | CCAGGAACCUCUGC | | | |
| | | ACUUGCCCGGAGUG | | | |
| | | AGAGUCGACAGCGG | | | |
| | | CAUCCAGCCCGGCA | | | |
| | | GCGACAUCUCCAUC | | | |
| | | UACUACGACCCCAU | | | |
| | | GAUAUCAAAGCUGA | | | |
| | | UCACCUACGGCUCG | | | |
| | | GAUAGAACAGAGGC | | | |
| | | UCUGAAGAGGAUGG | | | |
| | | CUGACGCCCUGGAC | | | |
| | | AACUACGUGAUCCG | | | |
| | | GGGUGUGACACACA | | | |
| | | ACAUUGCCCUGCUG | | | |
| | | AGGGAGGUGAUCAU | | | |
| | | CAAUAGCCGGUUUG | | | |
| | | UGAAGGGUGAUAU | | | |
| | | UUCCACCAAGUUCC | | | |
| | | UGUCUGACGUGUAU | | | |
| | | CCGGACGGAUUCAA | | | |
| | | GGGCCACAUGCUGA | | | |
| | | CAAAGUCCGAGAAG | | | |
| | | AAUCAGCUGCUGGC | | | |
| | | CAUAGCUUCUUCAC | | | |
| | | UGUUCGUGGCCUUU | | | |
| | | CAGCUGAGAGCUCA | | | |
| | | GCACUUCCAGGAGA | | | |
| | | ACUCAAGAAUGCCC | | | |
| | | GUGAUCAAGCCUGA | | | |
| | | UAUCGCCAAUUGGG | | | |
| | | AGCUGAGCGUGAAG | | | |
| | | CUGCACGACAAGGU | | | |
| | | ACACACAGUGGUGG | | | |
| | | CCAGCAACAACGGC | | | |
| | | AGCGUGUUUUCCGU | | | |
| | | GGAGGUAGACGGAA | | | |
| | | GCAAACUGAACGUG | | | |
| | | ACAUCUACCUGGAA | | | |
| | | UCUGGCCUCUCCUC | | | |
| | | UGCUGAGUGUUAGC | | | |
| | | GUCGACGGCACGCA | | | |
| | | GAGAACUGUGCAGU | | | |
| | | GCCUGAGCCGGGAG | | | |
| | | GCGGGCGGAAACAU | | | |
| | | GUCAAUCCAGUUUC | | | |
| | | UCGGCACUGUCUAC | | | |
| | | AAGGUCAACAUCCU | | | |
| | | GACCAGACUGGCUG | | | |

| CONSTRUCT SEQUENCES | | | | | |
|---|---|---|---|---|---|
| By "G5" is meant that all uracils (U) in the mRNA are replaced by N1-methylpseudouracils. | | | | | |
| mRNA Name | ORF Sequence (Amino Acid) | ORF Sequence (Nucleotide) | 5' UTR Sequence | 3' UTR Sequence | Construct Sequence |
| | | CUGAGCUGAAUAAA UUCAUGCUCGAGAA GGUGACCGAGGACA CAAGCUCGGUGCUC AGAAGCCCAAUGCC CGGCGUGGUGGUCG CCGUCAGCGUCAAG CCCGGCGACGCUGU GGCCGAAGGCCAGG AAAUCUGCGUCAUC GAGGCGAUGAAGAU GCAGAAUUCAAUGA CUGCCGGGAAGACC GGCACCGUCAAGAG CGUGCAUUGCCAGG CAGGGGACACCGUG GGCGAAGGGGACCU UCUGGUGGAGCUCG AG | | | |

| SEQ ID NO: | 1 | 6 | 3 | 4 | 30 |
|---|---|---|---|---|---|
| PCCA_13 (hPCCA; G5) Cap: C1 PolyA tail: 100 nt | MAGFWVGTAPLVAA GRRGRWPPQQLMLS AALRTLKHVLYYSR QCLMVSRNLGSVGY DPNEKTFDKILVANR GEIACRVIRTCKKMG IKTVAIHSDVDASSV HVKMADEAVCVGPA PTSKSYLNMDAIMEA IKKTRAQAVHPGYGF LSENKEFARCLAAED VVFIGPDTHAIQAMG DKIESKLLAKKAEVN TIPGFDGVVKDAEEA VRIAREIGYPVMIKAS AGGGGKGMRIAWDD EETRDGFRLSSQEAA SSFGDDRLLIEKFIDN PRHIEIQVLGDKHGN ALWLNERECSIQRRN QKVVEEAPSIFLDAE TRRAMGEQAVALAR AVKYSSAGTVEFLVD SKKNFYFLEMNTRLQ VEHPVTECITGLDLV QEMIRVAKGYPLRH KQADIRINGWAVECR VYAEDPYKSFGLPSI GRLSQYQEPLHLPGV RVDSGIQPGSDISIYY DPMISKLITYGSDRTE ALKRMADALDNYVI RGVTHNIALLREVIIN SRFVKGDISTKFLSDV YPDGFKGHMLTKSE KNQLLAIASSLFVAF QLRAQHFQENSRMP VIKPDIANWELSVKL HDKVHTVVASNNGS VFSVEVDGSKLNVTS TWNLASPLLSVSVDG TQRTVQCLSREAGGN MSIQFLGTVYKVNIL TRLAAELNKFMLEK VTEDTSSVLRSPMPG VVVAVSVKPGDAVA EGQEICVIEAMKMQN SMTAGKTGTVKSVH CQAGDTVGEGDLLV ELE | AUGGCCGGCUUCUG GGUGGGCACCGCAC CCCUCGUGGCCGCC GGCAGAAGAGGCAG GUGGCCUCCCCAGC AGCUGAUGCUGAGC GCCGCCCUGCGGAC CCUGAAGCACGUGC UGUACUACAGCCGG CAGUGCCUGAUGGU GAGCCGGAACCUGG GCAGCGUGGGCUAC GACCCCAACGAGAA GACCUUCGACAAGA UUUUGGUGGCAAAC CGGGGGCGAGAUCGC CUGCCGGGUGAUCC GGACCUGCAAGAAG AUGGGCAUCAAGAC CGUGGCCAUCCACA GCGACGUGGACGCC AGCAGCGUGCACGU GAAGAUGGCCGACG AGGCCGUGUGCGUC GGCCCCGCCCCUAC CAGCAAGAGCUACC UGAACAUGGACGCG AUCAUGGAGGCCAU CAAGAAGACCCGGG CCCAGGCCGUGCAC CCCGGCUACGGCUU CCUGAGCGAGAACA AGGAGUUCGCCCGG UGCCUGGCCGCAGA GGACGUGGUGUUCA UCGGCCCCGACACC CACGCCAUCCAGGC CAUGGGCGACAAGA UCGAGAGCAAGCUG CUGGCCAAGAAGGC CGAGGUGAACACCA UCCCCGGCUUCGAC GGCGUGGUGAAGGA CGCCGAGGAAGCUG UGCGGAUCGCCCGG GAGAUCGGCUACCC CGUGAUGAUCAAGG CCAGCGCCGGAGGC GGAGGCAAGGGCAU GAGAAUCGCUUGGG | GGGAAA UAAGAG AGAAA GAAGAG UAAGAA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 30 consists from 5' to 3' end: 5' UTR of SEQ ID NO: 3, ORF Sequence of SEQ ID NO: 6, and 3' UTR of SEQ ID NO: 4 |

CONSTRUCT SEQUENCES

By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | ACGACGAGGAGACA | | | |
| | | AGAGACGGCUUUCG | | | |
| | | GCUGAGCAGCCAGG | | | |
| | | AGGCAGCGAGCAGC | | | |
| | | UUCGGCGACGACCG | | | |
| | | GCUGCUGAUCGAGA | | | |
| | | AGUUCAUCGACAAC | | | |
| | | CCUCGGCACAUCGA | | | |
| | | GAUCCAGGUGCUGG | | | |
| | | GAGACAAGCACGGC | | | |
| | | AACGCCCUGUGGCU | | | |
| | | GAACGAGCGGGAGU | | | |
| | | GCAGCAUCCAGCGG | | | |
| | | CGGAACCAGAAGGU | | | |
| | | GGUGGAGGAGGCCC | | | |
| | | CUAGCAUCUUCCUG | | | |
| | | GACGCUGAAACCAG | | | |
| | | GAGAGCCAUGGGAG | | | |
| | | AGCAGGCCGUUGCC | | | |
| | | CUGGCCCGGGCCGU | | | |
| | | GAAGUACUCUAGCG | | | |
| | | CUGGCACCGUGGAG | | | |
| | | UUCCUGGUUGACUC | | | |
| | | UAAGAAGAACUUCU | | | |
| | | AUUUUCUGGAGAUG | | | |
| | | AACACCCGGCUGCA | | | |
| | | GGUGGAGCACCCCG | | | |
| | | UCACCGAGUGCAUC | | | |
| | | ACCGGCCUGGACCU | | | |
| | | GGUGCAGGAGAUGA | | | |
| | | UCCGCGUGGCUAAG | | | |
| | | GGCUACCCUCUGCG | | | |
| | | GCACAAGCAGGCUG | | | |
| | | ACAUCCGGAUCAAC | | | |
| | | GGCUGGGCCGUAGA | | | |
| | | GUGCCGUGUCUACG | | | |
| | | CCGAGGACCCCUAC | | | |
| | | AAGUCCUUCGGCCU | | | |
| | | GCCAUCCAUCGGCA | | | |
| | | GGCUGUCCCAGUAC | | | |
| | | CAGGAGCCCCUGCA | | | |
| | | CCUGCCCGGCGUGC | | | |
| | | GAGUGGAUAGCGGC | | | |
| | | AUUCAGCCCGGCAG | | | |
| | | CGACAUCAGCAUCU | | | |
| | | ACUACGACCCUAUG | | | |
| | | AUCUCCAAGCUAAU | | | |
| | | CACCUACGGCAGCG | | | |
| | | AUCGGACCGAGGCC | | | |
| | | CUGAAGAGAAUGGC | | | |
| | | UGACGCCCUGGACA | | | |
| | | ACUACGUGAUCAGA | | | |
| | | GGCGUGACCCACAA | | | |
| | | CAUCGCCCUGCUGC | | | |
| | | GGGAGGUGAUCAUC | | | |
| | | AACAGCCGGUUCGU | | | |
| | | GAAGGGCGAUAUCA | | | |
| | | GCACCAAGUUUCUG | | | |
| | | UCCGACGUUUACCC | | | |
| | | CGACGGCUUCAAGG | | | |
| | | GCCACAUGCUGACC | | | |
| | | AAGAGCGAGAAGAA | | | |
| | | CCAGCUGCUCGCCA | | | |
| | | UCGCAAGCUCCCUG | | | |
| | | UUCGUGGCCUUCCA | | | |
| | | GCUGCGAGCACAGC | | | |
| | | ACUUCCAGGAGAAU | | | |
| | | AGUAGAAUGCCCGU | | | |
| | | GAUCAAGCCCGACA | | | |
| | | UCGCCAACUGGGAG | | | |
| | | CUGAGCGUGAAGCU | | | |
| | | GCACGACAAGGUGC | | | |
| | | ACACCGUUGUGGCU | | | |

-continued

| CONSTRUCT SEQUENCES |
| --- |

By "G5" is meant that all uracils (U) in the mRNA are replaced by N1-methylpseudouracils.

| mRNA<br>Name | ORF Sequence<br>(Amino Acid) | ORF Sequence<br>(Nucleotide) | 5' UTR<br>Sequence | 3' UTR<br>Sequence | Construct<br>Sequence |
| --- | --- | --- | --- | --- | --- |
| | | AGCAACAACGGUUC | | | |
| | | UGUGUUCAGCGUGG | | | |
| | | AGGUGGACGGUAGC | | | |
| | | AAACUGAACGUGAC | | | |
| | | CAGCACCUGGAACC | | | |
| | | UCGCCUCACCACUG | | | |
| | | CUCAGCGUGAGCGU | | | |
| | | GGACGGAACCCAGC | | | |
| | | GGACCGUGCAGUGC | | | |
| | | CUCAGCCGGGAAGC | | | |
| | | CGGCGGCAACAUGA | | | |
| | | GCAUUCAGUUUCUC | | | |
| | | GGCACUGUGUACAA | | | |
| | | GGUGAAUAUCCUGA | | | |
| | | CCAGGCUGGCCGCU | | | |
| | | GAGCUGAACAAGUU | | | |
| | | CAUGCUGGAGAAGG | | | |
| | | UGACAGAGGACACU | | | |
| | | AGCAGCGUUCUGCG | | | |
| | | GAGCCCCAUGCCAG | | | |
| | | GGGUGGUGGUCGCC | | | |
| | | GUUAGCGUCAAGCC | | | |
| | | UGGCGACGCUGUGG | | | |
| | | CCGAGGGCCAGGAG | | | |
| | | AUCUGCGUGAUCGA | | | |
| | | GGCCAUGAAGAUGC | | | |
| | | AGAACAGCAUGACC | | | |
| | | GCCGGCAAGACUGG | | | |
| | | CACAGUGAAGUCAG | | | |
| | | UGCACUGCCAGGCC | | | |
| | | GGCGACACCGUGGG | | | |
| | | CGAGGGCGACCUGC | | | |
| | | UGGUGGAGCUGGAG | | | |
| SEQ ID<br>NO: | 1 | 7 | 3 | 4 | 31 |
| PCCA_14<br>(hPCCA;<br>G5)<br>Cap: C1<br>PolyA tail:<br>100 nt | MAGFWVGTAPLVAA<br>GRRGRWPPQQLMLS<br>AALRTLKHVLYYSR<br>QCLMVSRNLGSVGY<br>DPNEKTFDKILVANR<br>GEIACRVIRTCKKMG<br>IKTVAIHSDVDASSV<br>HVKMADEAVCVGPA<br>PTSKSYLNMDAIMEA<br>IKKTRAQAVHPGYGF<br>LSENKEFARCLAAED<br>VVFIGPDTHAIQAMG<br>DKIESKLLAKKAEVN<br>TIPGFDGVVKDAEEA<br>VRIAREIGYPVMIKAS<br>AGGGGKGMRIAWDD<br>EETRDGFRLSSQEAA<br>SSFGDDRLLIEKFIDN<br>PRHIEIQVLGDKHGN<br>ALWLNERECSIQRRN<br>QKVVEEAPSIFLDAE<br>TRRAMGEQAVALAR<br>AVKYSSAGTVEFLVD<br>SKKNFYFLEMNTRLQ<br>VEHPVTECITGLDLV<br>QEMIRVAKGYPLRH<br>KQADIRINGWAVECR<br>VYAEDPYKSFGLPSI<br>GRLSQYQEPLHLPGV<br>RVDSGIQPGSDISIYY<br>DPMISKLITYGSDRTE<br>ALKRMADALDNYVI<br>RGVTHNIALLREVIIN<br>SRFVKGDISTKFLSDV<br>YPDGFKGHMLTKSE<br>KNQLLAIASSLFVAF | AUGGCCGGCUUCUG<br>GGUGGGCACCGCAC<br>CCCUGGUGGCUGCU<br>GGGAGACGGGGACG<br>GUGGCCUCCUCAGC<br>AGCUGAUGCUGAGC<br>GCCGCCCUGCGGAC<br>CCUGAAGCACGUGC<br>UGUACUACAGCCGG<br>CAGUGCCUGAUGGU<br>GAGCCGGAACCUGG<br>GCAGCGUGGGCUAC<br>GACCCCAACGAGAA<br>GACCUUCGACAAGA<br>UCCUGGUCGCCAAC<br>CGGGGCGAGAUCGC<br>CUGCCGGGUGAUCC<br>GGACCUGCAAGAAG<br>AUGGGCAUCAAGAC<br>CGUGGCCAUCCACA<br>GCGACGUGGACGCC<br>AGCAGCGUGCACGU<br>GAAGAUGGCCGACG<br>AGGCCGUGUGCGUG<br>GGCCCUGCGCCUAC<br>CAGCAAGAGCUACC<br>UGAACAUGGACGCU<br>AUCAUGGAGGCCAU<br>CAAGAAGACCCGGG<br>CCCAGGCCGUGCAC<br>CCCGGCUACGGCUU<br>CCUGAGCGAGAACA<br>AGGAGUUCGCCCGG<br>UGCCUGGCAGCAGA<br>GGACGUGGUGUUCA<br>UCGGCCCCGACACC | GGGAAA<br>UAAGAG<br>AGAAAA<br>GAAGAG<br>UAAGAA<br>GAAAUA<br>UAAGAG<br>CCACC | UGAUAA<br>UAGGCU<br>GGAGCC<br>UCGGUG<br>GCCUAG<br>CUUCUU<br>GCCCCU<br>UGGGCC<br>UCCCCU<br>CAGCCC<br>CUCCUC<br>CCCUUC<br>CUGCAC<br>CCGUAC<br>CCCCUC<br>CAUAAA<br>GUAGGA<br>AACACU<br>ACAGUG<br>GUCUUU<br>GAAUAA<br>AGUCUG<br>AGUGGG<br>CGGC | SEQ ID NO: 31<br>consists<br>from 5' to<br>3' end: 5'<br>UTR of<br>SEQ ID NO: 3,<br>ORF<br>Sequence of<br>SEQ ID NO: 7,<br>and<br>3' UTR of<br>SEQ ID NO: 4 |

-continued

| CONSTRUCT SEQUENCES | | | | | |
|---|---|---|---|---|---|
| By "G5" is meant that all uracils (U) in the mRNA are replaced by N1-methylpseudouracils. | | | | | |
| mRNA Name | ORF Sequence (Amino Acid) | ORF Sequence (Nucleotide) | 5' UTR Sequence | 3' UTR Sequence | Construct Sequence |
| | QLRAQHFQENSRMP VIKPDIANWELSVKL HDKVHTVVASNNGS VFSVEVDGSKLNVTS TWNLASPLLSVSVDG TQRTVQCLSREAGGN MSIQFLGTVYKVNIL TRLAAELNKFMLEK VTEDTSSVLRSPMPG VVVAVSVKPGDAVA EGQEICVIEAMKMQN SMTAGKTGTVKSVH CQAGDTVGEGDLLV ELE | CACGCCAUCCAGGC CAUGGGAGACAAGA UUGAGAGCAAGCUG CUGGCCAAGAAGGC CGAGGUGAACACCA UCCCCGGCUUCGAC GGCGUGGUGAAGGA CGCCGAAGAGGCCG UCCGGAUCGCCCGG GAGAUCGGCUACCC CGUGAUGAUCAAGG CCUCCGCCGGUGGA GGCGGCAAGGGCAU GAGGAUCGCUUGGG ACGACGAGGAGACU AGAGACGGCUUUCG GCUGAGCAGCCAGG AGGCAGCCAGCUCA UUCGGCGACGACCG GCUGCUGAUCGAGA AGUUCAUCGACAAU CCACGGCACAUCGA GAUCCAGGUGCUGG GCGAUAAACACGGC AACGCCCUGUGGCU GAACGAGCGGGAGU GCAGCAUCCAGCGG CGGAACCAGAAGGU GGUGGAGGAGGCUC CUAGCAUCUUCCUU GACGCCGAGACACG CAGAGCUAUGGGCG AGCAGGCUGUGGCC CUGGCCCGGGCCGU GAAGUACUCCAGUG CUGGCACCGUGGAG UUCCUCGUGGACAG CAAGAAGAACUUCU ACUUCCUCGAGAUG AACACCCGGCUGCA GGUGGAGCACCCCG UCACCGAGUGCAUC ACCGGCCUGGACCU GGUGCAGGAGAUGA UCCGUGUGGCUAAG GGCUACCCUCUGCG GCACAAACAGGCCG ACAUCCGGAUCAAC GGCUGGGCCGUCGA GUGCAGGGUGUACG CCGAGGACCCCUAC AAGAGCUUCGGGCU GCCUAGCAUUGGCA GGCUCAGCCAGUAC CAGGAGCCCCUGCA CCUGCCCGGCGUGA GGGUCGACUCUGGC AUACAGCCCGGCAG CGACAUCAGCAUCU AUUACGAUCCCAUG AUCAGCAAACUGAU CACCUACGGUAGCG ACCGGACCGAGGCU CUGAAGAGAAUGGC CGACGCCCUGGACA ACUACGUGAUACGG GGCGUGACCCACAA CAUCGCCCUGCUGC GGGAGGUGAUCAUC AACAGCCGGUUCGU GAAGGGCGAUAUCU CUACCAAGUUCCUG UCCGACGUGUACCC | | | |

-continued

| CONSTRUCT SEQUENCES | | | | | |
|---|---|---|---|---|---|
| By "G5" is meant that all uracils (U) in the mRNA are replaced by N1-methylpseudouracils. | | | | | |
| mRNA Name | ORF Sequence (Amino Acid) | ORF Sequence (Nucleotide) | 5' UTR Sequence | 3' UTR Sequence | Construct Sequence |
| | | CGACGGGUUUAAGG GCCACAUGCUGACC AAGAGUGAGAAGA ACCAACUGCUUGCC AUCGCAAGCAGCCU GUUCGUGGCCUUCC AGCUGCGAGCCCAG CACUUCCAGGAGAA CUCCCGGAUGCCCG UGAUCAAGCCCGAC AUCGCCAACUGGGA GCUGAGCGUGAAGC UGCACGACAAGGUG CACACCGUGGUUGC CAGCAACAACGGCU CAGUGUUCAGCGUG GAGGUGGACGGCUC UAAGCUCAACGUGA CCAGCACCUGGAAU CUGGCCAGCCCGCU GCUGUCUGUCAGCG UCGACGGCACCCAG CGGACCGUGCAGUG UCUGAGCCGGGAGG CCGGCGGUAACAUG AGCAUUCAGUUCCU GGGCACUGUGUACA AAGUGAACAUCCUG ACCCGCCUGGCUGC AGAGCUGAACAAGU UCAUGCUGGAGAAG GUGACCGAAGACAC AUCAAGCGUGCUGC GGAGCCCCAUGCCU GGCGUCGUGGUAGC CGUGUCCGUGAAGC CCGGCGACGCGGUU GCCGAGGGCCAGGA GAUCUGCGUGAUCG AGGCCAUGAAGAUG CAGAACAGCAUGAC CGCCGGCAAGACGG GAACCGUUAAGUCC GUCCACUGCCAGGC UGGCGAUACUGUGG GCGAGGGCGACCUG CUGGUGGAGCUGGA G | | | |

| SEQ ID NO: | 1 | 8 | 3 | 4 | 32 |
|---|---|---|---|---|---|
| PCCA_15 (hPCCA; G5) Cap: C1 PolyA tail: 100 nt | MAGFWVGTAPLVAA GRRGRWPPQQLMLS AALRTLKHVLYYSR QCLMVSRNLGSVGY DPNEKTFDKILVANR GEIACRVIRTCKKMG IKTVAIHSDVDASSV HVKMADEAVCVGPA PTSKSYLNMDAIMEA IKKTRAQAVHPGYGF LSENKEFARCLAAED VVFIGPDTHAIQAMG DKIESKLLAKKAEVN TIPGFDGVVKDAEEA VRIAREIGYPVMIKAS AGGGGKGMRIAWDD EETRDGFRLSSQEAA SSFGDDRLLIEKFIDN PRHIEIQVLGDKHGN ALWLNERECSIQRRN QKVVEEAPSIFLDAE | AUGGCCGGCUUCUG GGUGGGCACCGCCC CACUGGUGGCUGCG GGCAGGAGGGGCAG GUGGCCUCCUCAGC AGCUGAUGCUGAGC GCCGCCCUCCGCAC CCUCAAGCACGUCC UCUACUACUCCCGC CAGUGCCUCAUGGU GUCCCGCAACCUCG GCUCCGUCGGCUAC GACCCCAACGAGAA GACCUUCGACAAGA UCCUCGUCGCCAAC CGCGGCGAGAUCGC CUGCCGCGUCAUCC GCACCUGCAAGAAG AUGGGCAUCAAGAC CGUCGCCAUCCACU CCGACGUCGACGCC | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA | SEQ ID NO: 32 consists from 5' to 3' end: 5' UTR of SEQ ID NO: 3, ORF Sequence of SEQ ID NO: 8, and 3' UTR of SEQ ID NO: 4 |

-continued

CONSTRUCT SEQUENCES

By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | TRRAMGEQAVALAR | UCCUCCGUCCACGU | | AGUCUG | |
| | AVKYSSAGTVEFLVD | CAAGAUGGCCGACG | | AGUGGG | |
| | SKKNFYFLEMNTRLQ | AGGCCGUCUGCGUU | | CGGC | |
| | VEHPVTECITGLDLV | GGACCCGCCCCUAC | | | |
| | QEMIRVAKGYPLRH | CUCCAAGUCCUACC | | | |
| | KQADIRINGWAVECR | UCAACAUGGACGCC | | | |
| | VYAEDPYKSFGLPSI | AUCAUGGAGGCCAU | | | |
| | GRLSQYQEPLHLPGV | CAAGAAGACCCGCG | | | |
| | RVDSGIQPGSDISIYY | CCCAGGCCGUCCAC | | | |
| | DPMISKLITYGSDRTE | CCCGGCUACGGCUU | | | |
| | ALKRMADALDNYVI | CCUCUCCGAGAACA | | | |
| | RGVTHNIALLREVIIN | AGGAGUUCGCCAGA | | | |
| | SRFVKGDISTKFLSDV | UGCCUGGCUGCCGA | | | |
| | YPDGFKGHMLTKSE | GGACGUCGUCUUCA | | | |
| | KNQLLAIASSLFVAF | UCGGCCCUGACACC | | | |
| | QLRAQHFQENSRMP | CACGCUAUCCAGGC | | | |
| | VIKPDIANWELSVKL | CAUGGGCGACAAGA | | | |
| | HDKVHTVVASNNGS | UAGAGUCCAAGCUC | | | |
| | VFSVEVDGSKLNVTS | CUCGCCAAGAAGGC | | | |
| | TWNLASPLLSVSVDG | CGAGGUCAACACCA | | | |
| | TQRTVQCLSREAGGN | UCCCCGGCUUCGAC | | | |
| | MSIQFLGTVYKVNIL | GGCGUCGUCAAGGA | | | |
| | TRLAAELNKFMLEK | CGCGGAAGAGGCCG | | | |
| | VTEDTSSVLRSPMPG | UUCGCAUCGCCCGG | | | |
| | VVVAVSVKPGDAVA | GAAAUCGGCUACCC | | | |
| | EGQEICVIEAMKMQN | CGUCAUGAUCAAGG | | | |
| | SMTAGKTGTVKSVH | CCUCCGCCGGUGGA | | | |
| | CQAGDTVGEGDLLV | GGCGGCAAGGGCAU | | | |
| | ELE | GAGGAUUGCCUGGG | | | |
| | | ACGACGAGGAAACG | | | |
| | | AGAGACGGUUUCCG | | | |
| | | CCUCUCCUCCCAGG | | | |
| | | AAGCCGCAAGCUCA | | | |
| | | UUCGGCGACGAUAG | | | |
| | | ACUGCUGAUCGAGA | | | |
| | | AGUUCAUCGACAAU | | | |
| | | CCUCGCCACAUCGA | | | |
| | | GAUCCAGGUCCUCG | | | |
| | | GCGACAAACACGGC | | | |
| | | AACGCCCUCUGGCU | | | |
| | | CAACGAGCGCGAGU | | | |
| | | GCUCCAUCCAGCGC | | | |
| | | CGCAACCAGAAGGU | | | |
| | | CGUCGAGGAGGCAC | | | |
| | | CCUCCAUCUUCCUC | | | |
| | | GACGCCGAAACCAG | | | |
| | | GCGCGCCAUGGGUG | | | |
| | | AGCAGGCCGUGGCC | | | |
| | | CUGGCCCGAGCCGU | | | |
| | | CAAGUACAGCUCCG | | | |
| | | CUGGGACCGUCGAG | | | |
| | | UUUCUGGUUGACUC | | | |
| | | CAAGAAGAACUUCU | | | |
| | | ACUUCCUGGAGAUG | | | |
| | | AACACCCGCCUCCA | | | |
| | | GGUCGAGCAUCCUG | | | |
| | | UGACCGAGUGCAUC | | | |
| | | ACCGGCCUCGACCU | | | |
| | | CGUCCAGGAGAUGA | | | |
| | | UCCGAGUGGCCAAG | | | |
| | | GGAUACCCGCUCCG | | | |
| | | CCACAAGCAGGCUG | | | |
| | | ACAUCCGCAUCAAC | | | |
| | | GGCUGGGCGGUUGA | | | |
| | | GUGUAGGGUGUACG | | | |
| | | CUGAAGACCCCUAC | | | |
| | | AAGUCUUUCGGCCU | | | |
| | | GCCCAGCAUCGGCA | | | |
| | | GACUGUCCCAGUAC | | | |
| | | CAGGAGCCCCUCCA | | | |
| | | CCUCCCCGGCGUGA | | | |
| | | GGGUGGACUCUGGC | | | |
| | | AUCCAGCCCGGCUC | | | |

-continued

---

CONSTRUCT SEQUENCES

By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | CGACAUCUCCAUCU | | | |
| | | AUUACGAUCCUAUG | | | |
| | | AUCUCAAAGCUGAU | | | |
| | | CACCUACGGUUCCG | | | |
| | | AUCGCACCGAGGCU | | | |
| | | CUGAAGCGCAUGGC | | | |
| | | UGACGCCCUCGACA | | | |
| | | ACUACGUAAUCAGA | | | |
| | | GGCGUCACCCACAA | | | |
| | | CAUCGCCCUCCUGA | | | |
| | | GAGAGGUCAUCAUC | | | |
| | | AACUCCCGCUUCGU | | | |
| | | GAAGGGUGAUAUCU | | | |
| | | CUACCAAGUUUCUG | | | |
| | | AGCGACGUGUACCC | | | |
| | | UGACGGGUUCAAGG | | | |
| | | GCCACAUGCUCACC | | | |
| | | AAGUCCGAGAAGAA | | | |
| | | CCAGCUGCUGGCCA | | | |
| | | UAGCCAGCAGCCUC | | | |
| | | UUCGUCGCCUUCCA | | | |
| | | GCUGAGAGCCCAGC | | | |
| | | ACUUCCAAGAGAAU | | | |
| | | UCUCGUAUGCCCGU | | | |
| | | CAUCAAGCCCGACA | | | |
| | | UCGCCAACUGGGAG | | | |
| | | CUCUCCGUCAAGCU | | | |
| | | CCACGACAAGGUCC | | | |
| | | ACACCGUGGUUGCA | | | |
| | | UCCAACAACGGCAG | | | |
| | | CGUGUUCUCCGUCG | | | |
| | | AGGUCGACGGAAGC | | | |
| | | AAGCUGAACGUCAC | | | |
| | | CUCUACCUGGAACC | | | |
| | | UCGCCUCUCCCCUU | | | |
| | | CUGUCUGUGAGCGU | | | |
| | | GGACGGCACCCAGC | | | |
| | | GCACCGUGCAGUGC | | | |
| | | CUGUCCCGCGAGGC | | | |
| | | UGGCGGCAACAUGU | | | |
| | | CCAUUCAAUUCCUG | | | |
| | | GGCACUGUGUACAA | | | |
| | | GGUGAACAUCCUGA | | | |
| | | CACGGCUCGCAGCC | | | |
| | | GAACUCAACAAGUU | | | |
| | | CAUGCUCGAGAAGG | | | |
| | | UGACCGAAGACACC | | | |
| | | AGCUCCGUGCUCCG | | | |
| | | CAGCCCUAUGCCCG | | | |
| | | GGGUGGUCGUGGCC | | | |
| | | GUGUCCGUCAAACC | | | |
| | | CGGCGACGCUGUGG | | | |
| | | CGGAGGGACAGGAG | | | |
| | | AUCUGCGUCAUCGA | | | |
| | | GGCCAUGAAGAUGC | | | |
| | | AGAACUCCAUGACG | | | |
| | | GCGGGGAAGACCGG | | | |
| | | AACAGUCAAGAGCG | | | |
| | | UGCAUUGCCAAGCC | | | |
| | | GGCGAUACCGUCGG | | | |
| | | CGAGGGCGACUUGC | | | |
| | | UGGUGGAGCUCGAG | | | |

---

| SEQ ID NO: | 1 | 9 | 3 | 4 | 33 |
|---|---|---|---|---|---|

---

| PCCA 16 (hPCCA; G5) Cap: C1 PolyA tail: 100 nt | MAGFWVGTAPLVAA GRRGRWPPQQLMLS AALRTLKHVLYYSR QCLMVSRNLGSVGY DPNEKTFDKILVANR GEIACRVIRTCKKMG IKTVAIHSDVDASSV | AUGGCCGGCUUCUG GGUGGGCACCGCGC CCCUGGUGGCCGCC GGCCGGCGGGGCCG GUGGCCACCCCAGC AGCUGAUGCUGAGC GCCGCCCUGCGGAC | GGGAAA UAAGAG AGAAAA GAAGAG UAAGAA GAAAUA UAAGAG | UGAUAA UAGGCU GGAGCC UCGGUG GCCUAG CUUCUU GCCCCU | SEQ ID NO: 33 consists from 5' to 3' end: 5' UTR of SEQ ID |

-continued

| | | | | | |
|---|---|---|---|---|---|
| | | CONSTRUCT SEQUENCES | | | |
| | By "G5" is meant that all uracils (U) in the mRNA are replaced by N1-methylpseudouracils. | | | | |
| mRNA Name | ORF Sequence (Amino Acid) | ORF Sequence (Nucleotide) | 5' UTR Sequence | 3' UTR Sequence | Construct Sequence |
| | HVKMADEAVCVGPA | CCUGAAGCACGUGC | CCACC | UGGGCC | NO: 3, |
| | PTSKSYLNMDAIMEA | UGUACUACAGCCGG | | UCCCCC | ORF |
| | IKKTRAQAVHPGYGF | CAGUGCCUGAUGGU | | CAGCCC | Sequence |
| | LSENKEFARCLAAED | GAGCCGGAACCUGG | | CUCCUC | of SEQ ID |
| | VVFIGPDTHAIQAMG | GCAGCGUGGGCUAC | | CCCUUC | NO: 9, and |
| | DKIESKLLAKKAEVN | GACCCCAACGAGAA | | CUGCAC | 3' UTR of |
| | TIPGFDGVVKDAEEA | GACCUUCGACAAGA | | CCGUAC | SEQ ID |
| | VRIAREIGYPVMIKAS | UCCUGGUGGCCAAC | | CCCCUC | NO: 4 |
| | AGGGGKGMRIAWDD | CGGGGCGAGAUCGC | | CAUAAA | |
| | EETRDGFRLSSQEAA | CUGCCGGGUGAUCC | | GUAGGA | |
| | SSFGDDRLLIEKFIDN | GGACCUGCAAGAAG | | AACACU | |
| | PRHIEIQVLGDKHGN | AUGGGCAUCAAGAC | | ACAGUG | |
| | ALWLNERECSIQRRN | CGUGGCCAUCCACA | | GUCUUU | |
| | QKVVEEAPSIFLDAE | GCGACGUGGACGCC | | GAAUAA | |
| | TRRAMGEQAVALAR | AGCAGCGUGCACGU | | AGUCUG | |
| | AVKYSSAGTVEFLVD | GAAGAUGGCCGACG | | AGUGGG | |
| | SKKNFYFLEMNTRLQ | AGGCCGUGUGCGUG | | CGGC | |
| | VEHPVTECITGLDLV | GGCCCCGCGCCCAC | | | |
| | QEMIRVAKGYPLRH | CAGCAAGAGCUACC | | | |
| | KQADIRINGWAVECR | UGAACAUGGACGCC | | | |
| | VYAEDPYKSFGLPSI | AUCAUGGAGGCCAU | | | |
| | GRLSQYQEPLHLPGV | CAAGAAGACCCGGG | | | |
| | RVDSGIQPGSDISIYY | CCCAGGCCGUGCAC | | | |
| | DPMISKLITYGSDRTE | CCCGGCUACGGCUU | | | |
| | ALKRMADALDNYVI | CCUGAGCGAGAACA | | | |
| | RGVTHNIALLREVIIN | AGGAGUUCGCCCGG | | | |
| | SRFVKGDISTKFLSDV | UGCCUGGCCGCCGA | | | |
| | YPDGFKGHMLTKSE | GGACGUGGUGUUCA | | | |
| | KNQLLAIASSLFVAF | UCGGCCCCGACACC | | | |
| | QLRAQHFQENSRMP | CACGCCAUCCAGGC | | | |
| | VIKPDIANWELSVKL | CAUGGGCGACAAGA | | | |
| | HDKVHTVVASNNGS | UCGAGAGCAAGCUG | | | |
| | VFSVEVDGSKLNVTS | CUGGCCAAGAAGGC | | | |
| | TWNLASPLLSVSVDG | CGAGGUGAACACCA | | | |
| | TQRTVQCLSREAGGN | UCCCCGGCUUCGAC | | | |
| | MSIQFLGTVYKVNIL | GGCGUGGUGAAGGA | | | |
| | TRLAAELNKFMLEK | CGCCGAGGAGGCCG | | | |
| | VTEDTSSVLRSPMPG | UGCGGAUCGCCCGG | | | |
| | VVVAVSVKPGDAVA | GAGAUCGGCUACCC | | | |
| | EGQEICVIEAMKMQN | CGUGAUGAUCAAGG | | | |
| | SMTAGKTGTVKSVH | CCAGCGCCGGCGGC | | | |
| | CQAGDTVGEGDLLV | GGCGGCAAGGGCAU | | | |
| | ELE | GCGGAUCGCCUGGG | | | |
| | | ACGACGAGGAGACC | | | |
| | | CGGGACGGCUUCCG | | | |
| | | GCUGAGCAGCCAGG | | | |
| | | AGGCCGCCAGCAGC | | | |
| | | UUCGGCGACGACCG | | | |
| | | GCUGCUGAUCGAGA | | | |
| | | AGUUCAUCGACAAC | | | |
| | | CCACGGCACAUCGA | | | |
| | | GAUCCAGGUGCUGG | | | |
| | | GCGACAAGCACGGC | | | |
| | | AACGCCCUGUGGCU | | | |
| | | GAACGAGCGGGAGU | | | |
| | | GCAGCAUCCAGCGG | | | |
| | | CGGAACCAGAAGGU | | | |
| | | GGUGGAGGAGGCGC | | | |
| | | CCAGCAUCUUCCUG | | | |
| | | GACGCCGAGACCCG | | | |
| | | GCGGGCCAUGGGCG | | | |
| | | AGCAGGCCGUGGCC | | | |
| | | CUGGCCCGGGCCGU | | | |
| | | GAAGUACAGCAGCG | | | |
| | | CCGGCACCGUGGAG | | | |
| | | UUCCUGGUGGACAG | | | |
| | | CAAGAAGAACUUCU | | | |
| | | ACUUCCUGGAGAUG | | | |
| | | AACACCCGGCUGCA | | | |
| | | GGUGGAGCACCCCG | | | |
| | | UGACCGAGUGCAUC | | | |
| | | ACCGGCCUGGACCU | | | |
| | | GGUGCAGGAGAUGA | | | |

CONSTRUCT SEQUENCES
By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | UCCGGGUGGCCAAG | | | |
| | | GGCUACCCGCUGCG | | | |
| | | GCACAAGCAGGCCG | | | |
| | | ACAUCCGGAUCAAC | | | |
| | | GGCUGGGCCGUGGA | | | |
| | | GUGCCGGGUGUACG | | | |
| | | CCGAGGACCCCUAC | | | |
| | | AAGAGCUUCGGCCU | | | |
| | | GCCCAGCAUCGGCC | | | |
| | | GGCUGAGCCAGUAC | | | |
| | | CAGGAGCCCCUGCA | | | |
| | | CCUGCCCGGCGUGC | | | |
| | | GGGUGGACAGCGGC | | | |
| | | AUCCAGCCCGGCAG | | | |
| | | CGACAUCAGCAUCU | | | |
| | | ACUACGACCCCAUG | | | |
| | | AUCAGCAAGCUGAU | | | |
| | | CACCUACGGCAGCG | | | |
| | | ACCGGACCGAGGCC | | | |
| | | CUGAAGCGGAUGGC | | | |
| | | CGACGCCCUGGACA | | | |
| | | ACUACGUGAUCCGG | | | |
| | | GGCGUGACCCACAA | | | |
| | | CAUCGCCCUGCUGC | | | |
| | | GGGAGGUGAUCAUC | | | |
| | | AACAGCCGGUUCGU | | | |
| | | GAAGGGCGACAUCA | | | |
| | | GCACCAAGUUCCUG | | | |
| | | AGCGACGUGUACCC | | | |
| | | CGACGGCUUCAAGG | | | |
| | | GCCACAUGCUGACC | | | |
| | | AAGAGCGAGAAGAA | | | |
| | | CCAGCUGCUGGCCA | | | |
| | | UCGCCAGCAGCCUG | | | |
| | | UUCGUGGCCUUCCA | | | |
| | | GCUGCGGGCCCAGC | | | |
| | | ACUUCCAGGAGAAC | | | |
| | | AGCCGGAUGCCCGU | | | |
| | | GAUCAAGCCCGACA | | | |
| | | UCGCCAACUGGGAG | | | |
| | | CUGAGCGUGAAGCU | | | |
| | | GCACGACAAGGUGC | | | |
| | | ACACCGUGGUGGCC | | | |
| | | AGCAACAACGGCAG | | | |
| | | CGUGUUCAGCGUGG | | | |
| | | AGGUGGACGGCAGC | | | |
| | | AAGCUGAACGUGAC | | | |
| | | CAGCACCUGGAACC | | | |
| | | UGGCCAGCCCUCUG | | | |
| | | CUGAGCGUGAGCGU | | | |
| | | GGACGGCACCCAGC | | | |
| | | GGACCGUGCAGUGC | | | |
| | | CUGAGCCGGGAGGC | | | |
| | | CGGCGGCAACAUGA | | | |
| | | GCAUCCAGUUCCUG | | | |
| | | GGCACCGUGUACAA | | | |
| | | GGUGAACAUCCUGA | | | |
| | | CCCGGCUGGCCGCC | | | |
| | | GAGCUGAACAAGUU | | | |
| | | CAUGCUGGAGAAGG | | | |
| | | UGACCGAGGACACC | | | |
| | | AGCAGCGUGCUGCG | | | |
| | | GAGCCCCAUGCCCG | | | |
| | | GCGUGGUGGUGGCC | | | |
| | | GUGAGCGUGAAGCC | | | |
| | | CGGCGACGCCGUGG | | | |
| | | CCGAGGGCCAGGAG | | | |
| | | AUCUGCGUGAUCGA | | | |
| | | GGCCAUGAAGAUGC | | | |
| | | AGAACAGCAUGACC | | | |
| | | GCCGGCAAGACCGG | | | |
| | | CACCGUGAAGAGCG | | | |
| | | UGCACUGCCAGGCC | | | |

-continued

| CONSTRUCT SEQUENCES | | | | | |
|---|---|---|---|---|---|
| By "G5" is meant that all uracils (U) in the mRNA are replaced by N1-methylpseudouracils. | | | | | |
| mRNA Name | ORF Sequence (Amino Acid) | ORF Sequence (Nucleotide) | 5' UTR Sequence | 3' UTR Sequence | Construct Sequence |
|  |  | GGCGACACCGUGGG CGAGGGCGACCUGC UGGUGGAGCUGGAG |  |  |  |
| SEQ ID NO: | 1 | 10 | 3 | 4 | 34 |
| PCCA_17 (hPCCA; G5) Cap: C1 PolyA tail: 100 nt | MAGFWVGTAPLVAA GRRGRWPPQQLMLS AALRTLKHVLYYSR QCLMVSRNLGSVGY DPNEKTFDKILVANR GEIACRVIRTCKKMG IKTVAIHSDVDASSV HVKMADEAVCVGPA PTSKSYLNMDAIMEA IKKTRAQAVHPGYGF LSENKEFARCLAAED VVFIGPDTHAIQAMG DKIESKLLAKKAEVN TIPGFDGVVKDAEEA VRIAREIGYPVMIKAS AGGGGKGMRIAWDD EETRDGFRLSSQEAA SSFGDDRLLIEKFIDN PRHIEIQVLGDKHGN ALWLNERECSIQRRN QKVVEEAPSIFLDAE TRRAMGEQAVALAR AVKYSSAGTVEFLVD SKKNFYFLEMNTRLQ VEHPVTECITGLDLV QEMIRVAKGYPLRH KQADIRINGWAVECR VYAEDPYKSFGLPSI GRLSQYQEPLHLPGV RVDSGIQPGSDISIYY DPMISKLITYGSDRTE ALKRMADALDNYVI RGVTHNIALLREVIIN SRFVKGDISTKFLSDV YPDGFKGHMLTKSE KNQLLAIASSLFVAF QLRAQHFQENSRMP VIKPDIANWELSVKL HDKVHTVVASNNGS VFSVEVDGSKLNVTS TWNLASPLLSVSVDG TQRTVQCLSREAGGN MSIQFLGTVYKVNIL TRLAAELNKFMLEK VTEDTSSVLRSPMPG VVVAVSVKPGDAVA EGQEICVIEAMKMQN SMTAGKTGTVKSVH CQAGDTVGEGDLLV ELE | AUGGCCGGCUUCUG GGUCGGCACCGCCC CACUCGUGGCAGCC GGCAGAAGAGGCCG GUGGCCUCCCCAGC AGCUGAUGCUGAGC GCCGCCCUGAGAAC CCUGAAGCACGUGC UGUACUACAGCAGA CAGUGCCUGAUGGU GAGCAGAAAUCUGG GAUCUGUCGGGUAC GACCCCAACGAGAA GACCUUCGACAAGA UCCUGGUGGCCAAC AGAGGCGAGAUCGC CUGCAGAGUGAUCA GAACCUGCAAGAAG AUGGGCAUCAAGAC CGUGGCCAUCCACA GCGACGUGGACGCG UCCAGCGUGCACGU GAAGAUGGCCGACG AGGCCGUGUGCGUA GGCCCCGCUCCCAC CAGCAAGAGCUACC UGAACAUGGACGCC AUCAUGGAGGCCAU CAAGAAGACCAGAG CCCAGGCUGUGCAU CCCGGCUACGGCUU CCUGAGCGAGAACA AGGAGUUCGCCAGG UGUCUGGCUGCCGA AGACGUCGUGUUCA UCGGCCCCGACACC CACGCGAUCCAGGC CAUGGGUGAUAAGA UCGAGAGCAAACUG CUGGCCAAGAAGGC CGAGGUGAACACCA UCCCCGGCUUCGAC GGCGUGGUGAAAGA CGCCGAGGAGGCAG UGAGAAUCGCCAGA GAGAUCGGCUACCC CGUGAUGAUCAAGG CCAGCGCAGGUGGC GGAGGCAAGGGCAU GAGGAUUGCCUGGG ACGACGAAGAGACG AGGGACGGGUUCCG ACUGAGCAGCCAGG AGGCCGCCAGCUCC UUCGGCGACGACAG ACUGCUGAUCGAGA AGUUCAUCGACAAC CCCAGACACAUCGA GAUACAGGUGCUCG GAGACAAGCACGGC AACGCCCUGUGGCU GAACGAGAGAGAGU GCAGCAUCCAGAGA AGAAACCAGAAGGU GGUGGAGGAGGCCC CAUCAAUCUUCCUC | GGGAAA UAAGAG AGAAAA GAAGAG UAAGAA GAAAUA UAAGAG CCACC | UGAUAA UAGGCU GGAGCC UCGGUG GCCUAG GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 34 consists from 5' to 3' end: 5' UTR of SEQ ID NO: 3, ORF Sequence of SEQ ID NO: 10, and 3' UTR of SEQ ID NO: 4 |

-continued

| CONSTRUCT SEQUENCES | | | | | |
| By "G5" is meant that all uracils (U) in the mRNA are replaced by N1-methylpseudouracils. | | | | | |
| mRNA<br>Name | ORF Sequence<br>(Amino Acid) | ORF Sequence<br>(Nucleotide) | 5' UTR<br>Sequence | 3' UTR<br>Sequence | Construct<br>Sequence |
| --- | --- | --- | --- | --- | --- |
| | | GACGCCGAAACCAG | | | |
| | | ACGGGCCAUGGGAG | | | |
| | | AGCAAGCCGUGGCA | | | |
| | | CUGGCUAGGGCCGU | | | |
| | | GAAGUACAGCUCCG | | | |
| | | CCGGAACCGUGGAG | | | |
| | | UUUCUGGUCGACUC | | | |
| | | CAAGAAGAACUUCU | | | |
| | | ACUUCCUGGAGAUG | | | |
| | | AAUACCCGUCUGCA | | | |
| | | GGUGGAGCACCCCG | | | |
| | | UGACCGAGUGCAUC | | | |
| | | ACCGGUCUGGACCU | | | |
| | | GGUGCAGGAGAUGA | | | |
| | | UCAGAGUGGCCAAG | | | |
| | | GGCUACCCUCUGAG | | | |
| | | ACACAAGCAGGCCG | | | |
| | | ACAUCAGAAUCAAC | | | |
| | | GGCUGGGCCGUGGA | | | |
| | | GUGCAGAGUGUACG | | | |
| | | CCGAGGACCCCUAC | | | |
| | | AAGAGCUUCGGCCU | | | |
| | | GCCCAGCAUCGGCA | | | |
| | | GACUGAGCCAGUAC | | | |
| | | CAGGAGCCCCUGCA | | | |
| | | CCUGCCCGGCGUGA | | | |
| | | GAGUGGACAGCGGC | | | |
| | | AUCCAGCCCGGCUC | | | |
| | | UGACAUCUCCAUAU | | | |
| | | ACUACGACCCCAUG | | | |
| | | AUCAGCAAGCUCAU | | | |
| | | CACCUACGGCAGCG | | | |
| | | ACAGAACCGAGGCC | | | |
| | | CUGAAGAGAAUGGC | | | |
| | | CGACGCCCUGGACA | | | |
| | | ACUACGUGAUCAGA | | | |
| | | GGCGUGACCCACAA | | | |
| | | CAUCGCCCUGCUGA | | | |
| | | GAGAGGUGAUCAUC | | | |
| | | AACAGCAGAUUCGU | | | |
| | | GAAGGGCGACAUCA | | | |
| | | GCACCAAGUUCCUG | | | |
| | | AGCGACGUGUACCC | | | |
| | | CGACGGCUUCAAGG | | | |
| | | GCCACAUGCUGACC | | | |
| | | AAGAGCGAGAAGAA | | | |
| | | CCAGCUUCUGGCAA | | | |
| | | UCGCCUCCAGCCUG | | | |
| | | UUCGUGGCCUUCCA | | | |
| | | GCUGAGAGCCCAGC | | | |
| | | ACUUCCAGGAGAAC | | | |
| | | AGCAGAAUGCCCGU | | | |
| | | GAUCAAGCCCGACA | | | |
| | | UCGCCAACUGGGAG | | | |
| | | CUGAGCGUGAAGCU | | | |
| | | GCACGACAAGGUCC | | | |
| | | AUACGGUGGUCGCC | | | |
| | | AGCAACAACGGCAG | | | |
| | | CGUGUUCAGCGUGG | | | |
| | | AGGUGGACGGCAGC | | | |
| | | AAGCUGAACGUGAC | | | |
| | | CAGCACCUGGAACC | | | |
| | | UCGCCUCACCCCUC | | | |
| | | CUGAGCGUCAGCGU | | | |
| | | CGACGGCACCCAGA | | | |
| | | GAACCGUGCAGUGU | | | |
| | | CUGAGCAGAGAGGC | | | |
| | | AGGCGGCAACAUGA | | | |
| | | GCAUCCAGUUCCUG | | | |
| | | GGCACCGUGUACAA | | | |
| | | GGUGAACAUCCUGA | | | |
| | | CCAGACUGGCCGCC | | | |
| | | GAGCUGAACAAGUU | | | |

-continued

| CONSTRUCT SEQUENCES | | | | | |
|---|---|---|---|---|---|
| By "G5" is meant that all uracils (U) in the mRNA are replaced by N1-methylpseudouracils. | | | | | |
| mRNA Name | ORF Sequence (Amino Acid) | ORF Sequence (Nucleotide) | 5' UTR Sequence | 3' UTR Sequence | Construct Sequence |
| | | CAUGCUGGAGAAGG UGACCGAGGACACC AGCAGCGUGCUGAG AAGCCCCAUGCCCG GAGUGGUGGUGGCC GUGAGCGUGAAACC GGGUGACGCAGUGG CCGAGGGCCAGGAG AUCUGCGUGAUCGA GGCCAUGAAGAUGC AGAACAGCAUGACG GCCGGAAAGACCGG CACCGUGAAGUCCG UGCACUGCCAAGCC GGCGAUACCGUGGG CGAGGGCGACCUCC UCGUCGAGCUGGAG | | | |
| SEQ ID NO: | 1 | 11 | 3 | 4 | 35 |
| PCCA_18 (hPCCA; G5) Cap: C1 PolyA tail: 100 nt | MAGFWVGTAPLVAA GRRGRWPPQQLMLS AALRTLKHVLYYSR QCLMVSRNLGSVGY DPNEKTFDKILVANR GEIACRVIRTCKKMG IKTVAIHSDVDASSV HVKMADEAVCVGPA PTSKSYLNMDAIMEA IKKTRAQAVHPGYGF LSENKEFARCLAAED VVFIGPDTHAIQAMG DKIESKLLAKKAEVN TIPGFDGVVKDAEEA VRIAREIGYPVMIKAS AGGGGKGMRIAWDD EETRDGFRLSSQEAA SSFGDDRLLIEKFIDN PRHIEIQVLGDKHGN ALWLNERECSIQRRN QKVVEEAPSIFLDAE TRRAMGEQAVALAR AVKYSSAGTVEFLVD SKKNFYFLEMNTRLQ VEHPVTECITGLDLV QEMIRVAKGYPLRH KQADIRINGWAVECR VYAEDPYKSFGLPSI GRLSQYQEPLHLPGV RVDSGIQPGSDISIYY DPMISKLITYGSDRTE ALKRMADALDNYVI RGVTHNIALLREVIIN SRFVKGDISTKFLSDV YPDGFKGHMLTKSE KNQLLAIASSLFVAF QLRAQHFQENSRMP VIKPDIANWELSVKL HDKVHTVVASNNGS VFSVEVDGSKLNVTS TWNLASPLLSVSVDG TQRTVQCLSREAGGN MSIQFLGTVYKVNIL TRLAAELNKFMLEK VTEDTSSVLRSPMPG VVVAVSVKPGDAVA EGQEICVIEAMKMQN SMTAGKTGTVKSVH CQAGDTVGEGDLLV ELE | AUGGCCGGCUUCUG GGUCGGCACAGCCC CUCUGGUGGCAGCC GGCAGAAGAGGACG GUGGCCUCCCCAGC AACUGAUGCUGAGC GCCGCCCUGAGAAC CCUGAAGCACGUGC UGUACUACAGCAGA CAGUGCCUGAUGGU GAGCAGAAAUCUGG GCAGCGUGGGGUAC GAUCCCAACGAGAA GACCUUCGAUAAGA UUCUGGUCGCGAAU AGAGGCGAGAUCGC CUGCAGGGUGAUCA GAACCUGCAAGAAG AUGGGCAUCAAGAC CGUGGCCAUCCAUU CGGACGUCGACGCG AGCAGCGUUCACGU GAAGAUGGCAGACG AGGCCGUGUGCGUG GGACCCGCCCCGAC CAGCAAGAGCUACC UGAACAUGGACGCC AUCAUGGAGGCCAU CAAGAAGACCCGCG CUCAAGCCGUGCAC CCGGGCUACGGCUU UCUGAGCGAGAACA AGGAAUUCGCCAGG UGUCUCGCCGCCGA GGACGUAGUCUUCA UCGGCCCUGAUACG CACGCGAUCCAGGC CAUGGGCGACAAGA UCGAGAGCAAACUG CUGGCCAAGAAAGC AGAAGUCAACACCA UCCCCGGCUUCGAC GGCGUGGUGAAGGA CGCCGAAGAGGCUG UCCGCAUCGCCAGA GAGAUCGGCUACCC UGUGAUGAUAAAG GCUAGCGCUGGAGG UGGCGGAAAGGGCA UGAGAAUCGCCUGG GACGACGAGGAGAC UAGAGACGGCUUCA | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 35 consists from 5' to 3' end: 5' UTR of SEQ ID NO: 3, ORF Sequence of SEQ ID NO: 11, and 3' UTR of SEQ ID NO: 4 |

-continued

CONSTRUCT SEQUENCES
By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | GACUGUCCUCCCAG | | | |
| | | GAGGCCGCCAGCUC | | | |
| | | CUUCGGAGACGACA | | | |
| | | GACUGCUGAUCGAG | | | |
| | | AAGUUCAUCGACAA | | | |
| | | CCCCAGACACAUCG | | | |
| | | AAAUCCAGGUGCUC | | | |
| | | GGUGACAAGCACGG | | | |
| | | GAACGCCCUGUGGC | | | |
| | | UGAACGAGAGAGAG | | | |
| | | UGCAGCAUCCAGAG | | | |
| | | AAGAAACCAGAAGG | | | |
| | | UGGUGGAGGAGGCG | | | |
| | | CCGAGCAUCUUUCU | | | |
| | | GGACGCGGAGACAA | | | |
| | | GGAGAGCGAUGGGC | | | |
| | | GAACAGGCCGUCGC | | | |
| | | CCUAGCAAGAGCCG | | | |
| | | UGAAGUACUCCAGU | | | |
| | | GCCGGAACCGUCGA | | | |
| | | GUUUCUUGUCGACA | | | |
| | | GCAAGAAGAAUUUC | | | |
| | | UACUUCCUGGAGAU | | | |
| | | GAACACCAGGCUGC | | | |
| | | AGGUGGAGCAUCCC | | | |
| | | GUGACAGAGUGCAU | | | |
| | | CACUGGACUGGAUC | | | |
| | | UGGUGCAGGAGAUG | | | |
| | | AUCAGGGUGGCCAA | | | |
| | | GGGCUAUCCCCUGA | | | |
| | | GACACAAGCAGGCC | | | |
| | | GACAUCAGAAUCAA | | | |
| | | CGGCUGGGCCGUGG | | | |
| | | AGUGCAGAGUGUAC | | | |
| | | GCCGAGGACCCCUA | | | |
| | | CAAGAGCUUCGGCC | | | |
| | | UGCCCAGCAUCGGC | | | |
| | | AGACUGAGCCAGUA | | | |
| | | CCAGGAGCCCCUGC | | | |
| | | ACCUGCCCGGCGUG | | | |
| | | AGAGUGGACAGCGG | | | |
| | | CAUCCAACCGGGGA | | | |
| | | GCGAUAUCAGCAUC | | | |
| | | UACUACGACCCCAU | | | |
| | | GAUCAGCAAGCUGA | | | |
| | | UAACCUACGGCAGC | | | |
| | | GACAGAACCGAGGC | | | |
| | | CCUGAAGAGAAUGG | | | |
| | | CCGACGCCCUGGAC | | | |
| | | AACUACGUGAUCAG | | | |
| | | AGGCGUGACCCACA | | | |
| | | ACAUCGCCCUGCUG | | | |
| | | AGAGAGGUGAUCAU | | | |
| | | CAACUCGAGGUUCG | | | |
| | | UGAAAGGCGACAUC | | | |
| | | AGCACCAAGUUCCU | | | |
| | | GAGCGACGUGUAUC | | | |
| | | CCGACGGAUUCAAA | | | |
| | | GGUCACAUGCUGAC | | | |
| | | CAAGAGCGAGAAGA | | | |
| | | ACCAGCUGCUGGCC | | | |
| | | AUCGCCUCAUCCCU | | | |
| | | GUUCGUGGCCUUCC | | | |
| | | AGCUGAGAGCCCAG | | | |
| | | CACUUCCAGGAGAA | | | |
| | | CAGCAGAAUGCCCG | | | |
| | | UGAUCAAGCCCGAC | | | |
| | | AUCGCCAACUGGGA | | | |
| | | GCUGAGCGUGAAGC | | | |
| | | UGCACGACAAGGUG | | | |
| | | CACACUGUCGUUGC | | | |
| | | CAGCAACAACGGCU | | | |
| | | CCGUGUUCAGCGUA | | | |

| CONSTRUCT SEQUENCES | | | | | |
|---|---|---|---|---|---|
| By "G5" is meant that all uracils (U) in the mRNA are replaced by N1-methylpseudouracils. | | | | | |
| mRNA Name | ORF Sequence (Amino Acid) | ORF Sequence (Nucleotide) | 5' UTR Sequence | 3' UTR Sequence | Construct Sequence |
| | | GAGGUGGACGGAUC UAAGCUGAACGUGA CCUCCACCUGGAAC CUGGCAAGCCCUCU CCUGUCAGUGAGCG UGGACGGCACCCAG AGAACCGUGCAGUG UCUGUCCCGCGAGG CCGGCGGAAACAUG AGCAUCCAGUUCCU GGGCACCGUGUACA AGGUGAACAUCCUG ACCAGACUGGCCGC CGAGCUGAACAAGU UCAUGCUGGAGAAA GUGACGGAGGAUAC CAGCUCCGUGCUGA GAAGCCCCAUGCCC GGAGUGGUGGUGGC CGUUUCCGUGAAAC CUGGUGACGCCGUG GCCGAGGGGCAAGA GAUCUGCGUGAUCG AGGCCAUGAAGAUG CAGAAUUCCAUGAC CGCCGGAAAGACCG GCACCGUCAAAUCA GUGCACUGCCAGGC GGGCGACACAGUGG GUGAGGGCGACCUG CUGGUGGAGCUGGA G | | | |

| SEQ ID NO: | | | | | |
|---|---|---|---|---|---|
| | 1 | 12 | 3 | 4 | 36 |

| PCCA_19 (hPCCA; G5) Cap: C1 PolyA tail: 100 nt | MAGFWVGTAPLVAA GRRGRWPPQQLMLS AALRTLKHVLYYSR QCLMVSRNLGSVGY DPNEKTFDKILVANR GEIACRVIRTCKKMG IKTVAIHSDVDASSV HVKMADEAVCVGPA PTSKSYLNMDAIMEA IKKTRAQAVHPGYGF LSENKEFARCLAAED VVFIGPDTHAIQAMG DKIESKLLAKKAEVN TIPGFDGVVKDAEEA VRIAREIGYPVMIKAS AGGGGKGMRIAWDD EETRDGFRLSSQEAA SSFGDDRLLIEKFIDN PRHIEIQVLGDKHGN ALWLNERECSIQRRN QKVVEEAPSIFLDAE TRRAMGEQAVALAR AVKYSSAGTVEFLVD SKKNFYFLEMNTRLQ VEHPVTECITGLDLV QEMIRVAKGYPLRH KQADIRINGWAVECR VYAEDPYKSFGLPSI GRLSQYQEPLHLPGV RVDSGIQPGSDISIYY DPMISKLITYGSDRTE ALKRMADALDNYVI RGVTHNIALLREVIIN SRFVKGDISTKFLSDV YPDGFKGHMLTKSE KNQLLAIASSLFVAF QLRAQHFQENSRMP | AUGGCCGGGUUCUG GGUGGGGACCGCCC CACUCGUGGCCGCC GGGAGGAGAGGGA GGUGGCCACCGCAA CAACUAAUGCUAAG CGCCGCCCUACGGA CCCUAAAGCACGUA CUAUACUACAGCAG GCAGUGCCUAAUGG UGAGCAGGAACCUA GGGAGCGUGGGGUA CGAUCCAAACGAGA AGACCUUCGAUAAG AUACUAGUGGCCAA UAGAGGGGAGAUCG CCUGCAGAGUGAUA AGGACCUGCAAGAA GAUGGGGAUCAAGA CCGUGGCCAUACAC AGCGACGUGGCCGC CAGCAGCGUGCACG UGAAGAUGGCCGAC GAGGCCGUGUGUGU GGGGCCAGCCCCAA CCAGCAAGAGCUAC CUAAACAUGGACGC GAUAAUGGAGGCAA UCAAGAAGACCAGA GCGCAAGCCGUGCA CCCUGGGUACGGGU UCCUAUCCGAGAAC AAGGAGUUCGCCAG GUGCCUAGCCGCGG AGGACGUGGUUUUC AUAGGGCCAGAUAC GCACGCCAUCCAAG | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 36 consists from 5' to 3' end: 5' UTR of SEQ ID NO: 3, ORF Sequence of SEQ ID NO: 12, and 3' UTR of SEQ ID NO: 4 |

-continued

CONSTRUCT SEQUENCES
By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | VIKPDIANWELSVKL | CCAUGGGAGAUAAG | | | |
| | HDKVHTVVASNNGS | AUCGAGAGCAAGCU | | | |
| | VFSVEVDGSKLNVTS | ACUAGCCAAGAAGG | | | |
| | TWNLASPLLSVSVDG | CCGAGGUGAACACC | | | |
| | TQRTVQCLSREAGGN | AUACCAGGGUUCGA | | | |
| | MSIQFLGTVYKVNIL | CGGGGUGGUGAAGG | | | |
| | TRLAAELNKFMLEK | ACGCCGAGGAGGCC | | | |
| | VTEDTSSVLRSPMPG | GUGAGGAUUGCCAG | | | |
| | VVVAVSVKPGDAVA | GGAGAUAGGGUACC | | | |
| | EGQEICVIEAMKMQN | CAGUGAUGAUAAAG | | | |
| | SMTAGKTGTVKSVH | GCCUCUGCCGGUGG | | | |
| | CQAGDTVGEGDLLV | AGGAGGGAAGGGG | | | |
| | ELE | AUGCGGAUAGCCUG | | | |
| | | GGACGACGAGGAGA | | | |
| | | CGAGGGACGGCUUC | | | |
| | | AGGCUAAGCAGCCA | | | |
| | | AGAGGCCGCCUCUA | | | |
| | | GCUUCGGGGACGAU | | | |
| | | AGGCUACUAAUAGA | | | |
| | | GAAGUUCAUAGAUA | | | |
| | | ACCCAAGGCACAUA | | | |
| | | GAGAUACAAGUACU | | | |
| | | AGGGGAUAAACACG | | | |
| | | GUAACGCCCUGUGG | | | |
| | | CUCAACGAGAGAGA | | | |
| | | GUGCAGCAUACAAA | | | |
| | | GGAGGAACCAGAAG | | | |
| | | GUGGUUGAGGAGGC | | | |
| | | GCCAAGCAUCUUCC | | | |
| | | UAGACGCCGAGACA | | | |
| | | CGGAGGGCGAUGGG | | | |
| | | AGAACAGGCCGUGG | | | |
| | | CCCUAGCCAGGGCC | | | |
| | | GUUAAGUACUCAAG | | | |
| | | CGCAGGGACCGUGG | | | |
| | | AGUUCCUAGUGGAU | | | |
| | | AGCAAGAAGAACUU | | | |
| | | CUACUUCCUCGAGA | | | |
| | | UGAAUACCAGGCUA | | | |
| | | CAAGUGGAGCACCC | | | |
| | | AGUAACCGAGUGCA | | | |
| | | UCACGGGGCUCGAU | | | |
| | | CUAGUGCAAGAGAU | | | |
| | | GAUAAGGGUGGCCA | | | |
| | | AGGGGUAUCCACUA | | | |
| | | AGGCACAAGCAAGC | | | |
| | | GGAUAUAAGGAUA | | | |
| | | AACGGGUGGGCCGU | | | |
| | | UGAGUGCAGGGUGU | | | |
| | | ACGCCGAGGAUCCC | | | |
| | | UACAAGUCCUUCGG | | | |
| | | GCUACCAAGCAUAG | | | |
| | | GGAGGCUAUCUCAA | | | |
| | | UACCAAGAGCCACU | | | |
| | | ACACCUACCAGGGG | | | |
| | | UGAGGGUUGAUAGC | | | |
| | | GGGAUCCAACCAGG | | | |
| | | GUCUGAUAUAAGCA | | | |
| | | UCUACUACGAUCCC | | | |
| | | AUGAUAUCUAAGCU | | | |
| | | AAUAACCUACGGGA | | | |
| | | GCGACAGGACGGAG | | | |
| | | GCCCUAAAGAGGAU | | | |
| | | GGCGGACGCCCUAG | | | |
| | | AUAACUACGUGAUA | | | |
| | | CGCGGGGUGACCCA | | | |
| | | CAACAUUGCCCUAC | | | |
| | | UAAGGGAGGUGAUC | | | |
| | | AUAAAUUCUAGGUU | | | |
| | | CGUGAAGGGAGAUA | | | |
| | | UAUCAACGAAGUUU | | | |
| | | CUAAGCGACGUUUA | | | |
| | | CCCAGACGGGUUCA | | | |

-continued

| CONSTRUCT SEQUENCES | | | | | |
|---|---|---|---|---|---|
| By "G5" is meant that all uracils (U) in the mRNA are replaced by N1-methylpseudouracils. | | | | | |
| mRNA Name | ORF Sequence (Amino Acid) | ORF Sequence (Nucleotide) | 5' UTR Sequence | 3' UTR Sequence | Construct Sequence |
| | | AGGGGCACAUGCUA ACCAAGAGCGAGAA GAAUCAACUGCUCG CCAUCGCCUCAUCA CUAUUCGUGGCCUU CCAACUAAGGGCCC AACACUUCCAAGAG AAUAGCCGGAUGCC UGUGAUAAAGCCAG AUAUAGCCAAUUGG GAACUAAGCGUGAA GCUCCACGAUAAGG UGCACACCGUGGUG GCCAGCAACAACGG AUCUGUGUUCAGCG UGGAGGUGGACGGU AGCAAGCUCAACGU GACCAGCACCUGGA AUCUAGCCAGCCCA CUACUGAGCGUCAG CGUUGACGGGACCC AAAGGACCGUGCAG UGCUUGAGCAGGGA GGCCGGAGGGAAUA UGUCCAUUCAAUUC CUAGGGACGGUCUA CAAGGUAAACAUAC UAACCCGACUAGCC GCCGAGCUCAACAA GUUCAUGCUAGAGA AGGUGACCGAGGAU ACGUCUAGCGUGCU ACGUAGCCCAAUGC CAGGAGUGGUAGUU GCCGUGUCAGUGAA GCCAGGGGACGCCG UAGCCGAGGGACAA GAGAUCUGCGUGAU CGAGGCCAUGAAGA UGCAGAAUAGCAUG ACCGCAGGGAAGAC GGGGACGGUGAAGU CUGUUCACUGCCAA GCCGGGGAUACCGU AGGGGAGGGAGAUC UACUCGUGGAGCUA GAG | | | |

| SEQ ID NO: | 1 | 13 | 3 | 4 | 37 |
|---|---|---|---|---|---|

| | | | | | |
|---|---|---|---|---|---|
| PCCA_20 (hPCCA; G5) | MAGFWVGTAPLVAA GRRGRWPPQQLMLS AALRTLKHVLYYSR QCLMVSRNLGSVGY DPNEKTFDKILVANR GEIACRVIRTCKKMG IKTVAIHSDVDASSV HVKMADEAVCVGPA PTSKSYLNMDAIMEA IKKTRAQAVHPGYGF LSENKEFARCLAAED VVFIGPDTHAIQAMG DKIESKLLAKKAEVN TIPGFDGVVKDAEEA VRIAREIGYPVMIKAS AGGGGKGMRIAWDD EETRDGFRLSSQEAA SSFGDDRLLIEKFIDN PRHIEIQVLGDKHGN ALWLNERECSIQRRN QKVVEEAPSIFLDAE TRRAMGEQAVALAR | AUGGCCGGCUUCUG GGUGGGCACCGCGC CCCUGGUGGCCGCC GGCAGAAGAGGCAG GUGGCCGCCCCAGC AGCUGAUGCUGAGC GCCGCCCUGAGAAC CCUGAAGCACGUGC UGUACUACAGCAGA CAGUGCCUGAUGGU GAGCAGAAACCUGG GCAGCGUGGGCUAC GACCCCAACGAGAA GACCUUCGACAAGA UCCUGGUGGCCAAC AGAGGCGAGAUCGC CUGCAGAGUGAUCA GAACCUGCAAGAAG AUGGGCAUCAAGAC CGUGGCCAUCCACA GCGACGUGGACGCC AGCAGCGUGCACGU | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG | SEQ ID NO: 37 consists from 5' to 3' end: 5' UTR of SEQ ID NO: 3, ORF Sequence of SEQ ID NO: 13, and 3' UTR of SEQ ID NO: 4 |

-continued

| CONSTRUCT SEQUENCES | | | | | |
|---|---|---|---|---|---|
| By "G5" is meant that all uracils (U) in the mRNA are replaced by N1-methylpseudouracils. | | | | | |
| mRNA Name | ORF Sequence (Amino Acid) | ORF Sequence (Nucleotide) | 5' UTR Sequence | 3' UTR Sequence | Construct Sequence |
| | AVKYSSAGTVEFLVD | GAAGAUGGCCGACG | | AGUGGG | |
| | SKKNFYFLEMNTRLQ | AGGCCGUGUGCGUG | | CGGC | |
| | VEHPVTECITGLDLV | GGCCCCGCGCCCAC | | | |
| | QEMIRVAKGYPLRH | CAGCAAGAGCUACC | | | |
| | KQADIRINGWAVECR | UGAACAUGGACGCC | | | |
| | VYAEDPYKSFGLPSI | AUCAUGGAGGCCAU | | | |
| | GRLSQYQEPLHLPGV | CAAGAAGACCAGAG | | | |
| | RVDSGIQPGSDISIYY | CCCAGGCCGUGCAC | | | |
| | DPMISKLITYGSDRTE | CCCGGCUACGGCUU | | | |
| | ALKRMADALDNYVI | CCUGAGCGAGAACA | | | |
| | RGVTHNIALLREVIIN | AGGAGUUCGCCAGG | | | |
| | SRFVKGDISTKFLSDV | UGCCUGGCCGCCGA | | | |
| | YPDGFKGHMLTKSE | GGACGUGGUGUUCA | | | |
| | KNQLLAIASSLFVAF | UCGGCCCCGACACC | | | |
| | QLRAQHFQENSRMP | CACGCCAUCCAGGC | | | |
| | VIKPDIANWELSVKL | CAUGGGCGACAAGA | | | |
| | HDKVHTVVASNNGS | UCGAGAGCAAGCUG | | | |
| | VFSVEVDGSKLNVTS | CUGGCCAAGAAGGC | | | |
| | TWNLASPLLSVSVDG | CGAGGUGAACACCA | | | |
| | TQRTVQCLSREAGGN | UCCCCGGCUUCGAC | | | |
| | MSIQFLGTVYKVNIL | GGCGUGGUGAAGGA | | | |
| | TRLAAELNKFMLEK | CGCCGAGGAGGCCG | | | |
| | VTEDTSSVLRSPMPG | UGAGAAUCGCCAGA | | | |
| | VVVAVSVKPGDAVA | GAGAUCGGCUACCC | | | |
| | EGQEICVIEAMKMQN | CGUGAUGAUCAAGG | | | |
| | SMTAGKTGTVKSVH | CCAGCGCCGGCGGC | | | |
| | CQAGDTVGEGDLLV | GGCGGCAAGGGCAU | | | |
| | ELE | GAGAAUCGCCUGGG | | | |
| | | ACGACGAGGAGACC | | | |
| | | AGAGACGGCUUCAG | | | |
| | | ACUGAGCAGCCAGG | | | |
| | | AGGCCGCCAGCAGC | | | |
| | | UUCGGCGACGACAG | | | |
| | | ACUGCUGAUCGAGA | | | |
| | | AGUUCAUCGACAAC | | | |
| | | CCCAGACACAUCGA | | | |
| | | GAUCCAGGUGCUGG | | | |
| | | GCGACAAGCACGGC | | | |
| | | AACGCCCUGUGGCU | | | |
| | | GAACGAGAGAGAGU | | | |
| | | GCAGCAUCCAGAGA | | | |
| | | AGAAACCAGAAGGU | | | |
| | | GGUGGAGGAGGCGC | | | |
| | | CCAGCAUCUUCCUG | | | |
| | | GACGCCGAGACCAG | | | |
| | | AAGAGCCAUGGGCG | | | |
| | | AGCAGGCCGUGGCC | | | |
| | | CUGGCCAGAGCCGU | | | |
| | | GAAGUACAGCAGCG | | | |
| | | CCGGCACCGUGGAG | | | |
| | | UUCCUGGUGGACAG | | | |
| | | CAAGAAGAACUUCU | | | |
| | | ACUUCCUGGAGAUG | | | |
| | | AACACCAGACUGCA | | | |
| | | GGUGGAGCACCCCG | | | |
| | | UGACCGAGUGCAUC | | | |
| | | ACCGGCCUGGACCU | | | |
| | | GGUGCAGGAGAUGA | | | |
| | | UCAGAGUGGCCAAG | | | |
| | | GGCUACCCACUGAG | | | |
| | | ACACAAGCAGGCCG | | | |
| | | ACAUCAGAAUCAAC | | | |
| | | GGCUGGGCCGUGGA | | | |
| | | GUGCAGAGUGUACG | | | |
| | | CCGAGGACCCCUAC | | | |
| | | AAGAGCUUCGGCCU | | | |
| | | GCCCAGCAUCGGCA | | | |
| | | GACUGAGCCAGUAC | | | |
| | | CAAGAACCGUUACA | | | |
| | | UCUACCUGGUGUCC | | | |
| | | GAGUGGACAGCGGC | | | |
| | | AUCCAGCCCGGCAG | | | |
| | | CGACAUCAGCAUCU | | | |

-continued

| CONSTRUCT SEQUENCES | | | | | |
|---|---|---|---|---|---|
| By "G5" is meant that all uracils (U) in the mRNA are replaced by N1-methylpseudouracils. | | | | | |
| mRNA Name | ORF Sequence (Amino Acid) | ORF Sequence (Nucleotide) | 5' UTR Sequence | 3' UTR Sequence | Construct Sequence |
| | | ACUACGACCCCAUG | | | |
| | | AUCAGCAAGCUGAU | | | |
| | | CACCUACGGCAGCG | | | |
| | | ACAGAACCGAGGCC | | | |
| | | CUGAAGAGAAUGGC | | | |
| | | CGACGCCCUGGACA | | | |
| | | ACUACGUGAUCAGA | | | |
| | | GGCGUGACCCACAA | | | |
| | | CAUCGCCCUGCUGA | | | |
| | | GAGAGGUGAUCAUC | | | |
| | | AACAGCAGAUUCGU | | | |
| | | GAAGGGCGACAUCA | | | |
| | | GCACCAAGUUCCUG | | | |
| | | AGCGACGUGUACCC | | | |
| | | CGACGGCUUCAAGG | | | |
| | | GCCACAUGCUGACC | | | |
| | | AAGAGCGAGAAGAA | | | |
| | | CCAGCUGCUGGCCA | | | |
| | | UCGCCAGCAGCCUG | | | |
| | | UUCGUGGCCUUCCA | | | |
| | | GCUGAGAGCCCAGC | | | |
| | | ACUUCCAGGAGAAC | | | |
| | | AGCAGAAUGCCCGU | | | |
| | | GAUCAAGCCCGACA | | | |
| | | UCGCCAACUGGGAG | | | |
| | | CUGAGCGUGAAGCU | | | |
| | | GCACGACAAGGUGC | | | |
| | | ACACCGUGGUGGCC | | | |
| | | AGCAACAACGGCAG | | | |
| | | CGUGUUCAGCGUGG | | | |
| | | AGGUGGACGGCAGC | | | |
| | | AAGCUGAACGUGAC | | | |
| | | CAGCACCUGGAACC | | | |
| | | UGGCCAGCCCACUG | | | |
| | | CUGAGCGUGAGCGU | | | |
| | | GGACGGCACCCAGA | | | |
| | | GAACCGUGCAGUGC | | | |
| | | CUGAGCAGAGAGGC | | | |
| | | CGGCGGCAACAUGA | | | |
| | | GCAUCCAGUUCCUG | | | |
| | | GGCACCGUGUACAA | | | |
| | | GGUGAACAUCCUGA | | | |
| | | CCAGACUGGCCGCC | | | |
| | | GAGCUGAACAAGUU | | | |
| | | CAUGCUGGAGAAGG | | | |
| | | UGACCGAGGACACC | | | |
| | | AGCAGCGUGCUGAG | | | |
| | | AAGCCCCAUGCCCG | | | |
| | | GCGUGGUGGUGGCC | | | |
| | | GUGAGCGUGAAGCC | | | |
| | | CGGCGACGCCGUGG | | | |
| | | CCGAGGGCCAGGAG | | | |
| | | AUCUGCGUGAUCGA | | | |
| | | GGCCAUGAAGAUGC | | | |
| | | AGAACAGCAUGACC | | | |
| | | GCCGGCAAGACCGG | | | |
| | | CACCGUGAAGAGCG | | | |
| | | UGCACUGCCAGGCC | | | |
| | | GGCGACACCGUGGG | | | |
| | | CGAGGGCGACCUGC | | | |
| | | UGGUGGAGCUGGAG | | | |

| SEQ ID NO: | 1 | 14 | 3 | 150 | 38 |
|---|---|---|---|---|---|
| PCCA-014 (hPCCA; G5) Cap: C1 PolyA tail: 100 nt | MAGFWVGTAPLVAA GRRGRWPPQQLMLS AALRTLKHVLYYSR QCLMVSRNLGSVGY DPNEKTFDKILVANR GEIACRVIRTCKKMG IKTVAIHSDVDASSV HVKMADEAVCVGPA | AUGGCAGGCUUCUG GGUUGGCACUGCCC CACUCGUGGCCGCC GGCAGAAGGGGAAG GUGGCCUCCCCAGC AGCUCAUGCUGUCC GCCGCUCUGCGCAAC CCUGAAGCACGUGC | GGGAAA UAAGAG AGAAA GAAGAG UAAGAA GAAAUA UAAGAG CCACC | UGAUAA UAGGCU GGAGCC UCGGUG GCCAUG CUUCUU GCCCCU UGGGCC | SEQ ID NO: 38 consists from 5' to 3' end: 5' UTR of SEQ ID NO: 3, |

-continued

CONSTRUCT SEQUENCES
By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | PTSKSYLNMDAIMEA | UGUAUUAUAGCAGG | | UCCCCC | ORF |
| | IKKTRAQAVHPGYGF | CAGUGCCUCAUGGU | | CAGCCC | Sequence |
| | LSENKEFARCLAAED | UUCCCGGAACCUGG | | CUCCUC | of SEQ ID |
| | VVFIGPDTHAIQAMG | GGAGCGUGGGCUAU | | CCCUUC | NO: 14, |
| | DKIESKLLAKKAEVN | GACCCUAAUGAGAA | | CUGCAC | and 3' |
| | TIPGFDGVVKDAEEA | GACUUUCGACAAGA | | CCGUAC | UTR of |
| | VRIAREIGYPVMIKAS | UCCUGGUCGCUAAC | | CCCCGU | SEQ ID |
| | AGGGGKGMRIAWDD | AGAGGCGAGAUCGC | | GGUCUU | NO: 150 |
| | EETRDGFRLSSQEAA | CUGCAGGGUGAUCA | | UGAAUA | |
| | SSFGDDRLLIEKFIDN | GAACAUGCAAGAAG | | AAGUCU | |
| | PRHIEIQVLGDKHGN | AUGGGCAUCAAGAC | | GAGUGG | |
| | ALWLNERECSIQRRN | CGUCGCGAUCCAUA | | GCGGC | |
| | QKVVEEAPSIFLDAE | GCGACGUGGAUGCC | | | |
| | TRRAMGEQAVALAR | AGCAGCGUUCACGU | | | |
| | AVKYSSAGTVEFLVD | CAAGAUGGCCGACG | | | |
| | SKKNFYFLEMNTRLQ | AGGCUGUGUGCGUC | | | |
| | VEHPVTECITGLDLV | GGCCCCGCCCCAAC | | | |
| | QEMIRVAKGYPLRH | UUCCAAGAGCUAUC | | | |
| | KQADIRINGWAVECR | UGAACAUGGACGCC | | | |
| | VYAEDPYKSFGLPSI | AUAAUGGAGGCUAU | | | |
| | GRLSQYQEPLHLPGV | CAAGAAGACCAGAG | | | |
| | RVDSGIQPGSDISIYY | CCCAGGCAGUUCAU | | | |
| | DPMISKLITYGSDRTE | CCCGGCUACGGAUU | | | |
| | ALKRMADALDNYVI | CCUGAGCGAGAACA | | | |
| | RGVTHNIALLREVIIN | AGGAGUUCGCUAGA | | | |
| | SRFVKGDISTKFLSDV | UGUCUGGCCGCCGA | | | |
| | YPDGFKGHMLTKSE | AGACGUGGUUUUCA | | | |
| | KNQLLAIASSLFVAF | UCGGUCCAGACACC | | | |
| | QLRAQHFQENSRMP | CAUGCCAUCCAAGC | | | |
| | VIKPDIANWELSVKL | CAUGGGCGAUAAGA | | | |
| | HDKVHTVVASNNGS | UCGAGAGCAAGCUC | | | |
| | VFSVEVDGSKLNVTS | CUGGCCAAGAAGGC | | | |
| | TWNLASPLLSVSVDG | CGAGGUGAACACCA | | | |
| | TQRTVQCLSREAGGN | UCCCCGGCUUCGAU | | | |
| | MSIQFLGTVYKVNIL | GGCGUGGUGAAGGA | | | |
| | TRLAAELNKFMLEK | CGCGGAGGAGGCAG | | | |
| | VTEDTSSVLRSPMPG | UGCGCAUUGCCAGG | | | |
| | VVVAVSVKPGDAVA | GAGAUCGGCUACCC | | | |
| | EGQEICVIEAMKMQN | CGUGAUGAUCAAGG | | | |
| | SMTAGKTGTVKSVH | CUUCCGCAGGGGGA | | | |
| | CQAGDTVGEGDLLV | GGCGGCAAAGGCAU | | | |
| | ELE | GCGGAUUGCCUGGG | | | |
| | | AUGAUGAAGAAACC | | | |
| | | AGAGAUGGCUUCAG | | | |
| | | ACUGUCAAGCCAGG | | | |
| | | AGGCCGCCAGCAGC | | | |
| | | UUCGGCGACGACAG | | | |
| | | ACUGCUGAUCGAGA | | | |
| | | AGUUUAUAGAUAAC | | | |
| | | CCCCGACACAUAGA | | | |
| | | AAUCCAGGUGCUGG | | | |
| | | GAGACAAGCACGGC | | | |
| | | AACGCUCUGUGGCU | | | |
| | | GAACGAGCGGGAAU | | | |
| | | GCAGUAUCCAGAGG | | | |
| | | AGAAACCAGAAGGU | | | |
| | | GGUUGAGGAGGCCC | | | |
| | | CCUCAAUCUUCCUG | | | |
| | | GAUGCCGAGACAAG | | | |
| | | ACGCGCCAUGGGUG | | | |
| | | AGCAGGCUGUAGCC | | | |
| | | CUCGCCCGUGCCGU | | | |
| | | GAAGUAUAGCAGCG | | | |
| | | CCGGGACAGUGGAG | | | |
| | | UUCUUGGUCGACUC | | | |
| | | CAAGAAGAAUUUCU | | | |
| | | AUUUUCUGGGAGAUG | | | |
| | | AACACUCGGCUCCA | | | |
| | | AGUAGAGCACCCCG | | | |
| | | UGACUGAGUGCAUU | | | |
| | | ACAGGCCUUGAUCU | | | |
| | | GGUGCAGGAGAUGA | | | |
| | | UUAGGGUUGCCAAG | | | |

-continued

CONSTRUCT SEQUENCES
By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | GGCUACCCUCUGCG CCACAAGCAGGCCG ACAUCAGGAUCAAU GGCUGGGCUGUCGA GUGUAGGGUGUACG CAGAGGACCCGUAC AAGAGCUUCGGCCU UCCCUCUAUUGGCA GGCUGAGCCAGUAC CAGGAGCCUCUGCA CCUACCCGGCGUUC GCGUGGACAGCGGU AUCCAACCAGGCUC UGAUAUCAGCAUUU AUUACGACCCAAUG AUCUCAAAGCUGAU CACAUACGGCAGCG ACAGAACCGAGGCC CUGAAGCGAAUGGC CGACGCCCUGGACA ACUACGUGAUCCGG GGCGUCACACAUAA CAUUGCCCUGCUGA GAGAGGUGAUCAUU AAUUCUCGGUUCGU CAAAGGCGACAUCA GCACUAAGUUUCUG AGCGACGUGUACCC CGACGGGUUUAAAG GCCACAUGCUGACA AAGAGCGAGAAGAA CCAGUUGCUGGCCA UCGCCUCUAGCCUG UUCGUAGCCUUCCA GCUGCGAGCACAGC ACUUCCAGGAGAAU AGCAGAAUGCCAGU GAUCAAGCCCGACA UCGCUAACUGGGAG CUGAGCGUGAAGCU CCAUGAUAAGGUCC ACACAGUUGUGGCC AGCAACAACGGCUC AGUGUUCAGCGUGG AGGUAGACGGCUCC AAGCUGAACGUGAC CAGCACUUGGAAUC UGGCCAGCCCCCUG CUGAGCGUGUCCGU GGACGGCACCCAGA GAACCGUGCAGUGC CUGAGCAGGGAGGC CGGGGGCAACAUGU CCAUCCAGUUUCUG GGGACCGUCUAUAA GGUUAACAUCCUGA CUAGACUGGCGGCU GAGCUUAACAAGUU UAUGUUAGAGAAA GUGACCGAGGAUAC AAGCAGCGUGCUGC GUAGCCCCAUGCCU GGCGUGGUCGUGGC CGUGAGCGUCAAGC CAGGCGAUGCAGUG GCUGAGGGCCAGGA GAUUUGUGUGAUA GAGGCCAUGAAGAU GCAGAACUCUAUGA CCGCCGGAAAGACU GGCACCGUGAAGUC UGUCCAUUGUCAGG CCGGAGACACCGUG | | | |

-continued

| CONSTRUCT SEQUENCES | | | | | |
|---|---|---|---|---|---|
| By "G5" is meant that all uracils (U) in the mRNA are replaced by N1-methylpseudouracils. | | | | | |
| mRNA Name | ORF Sequence (Amino Acid) | ORF Sequence (Nucleotide) | 5' UTR Sequence | 3' UTR Sequence | Construct Sequence |
| | | GGGGAAGGAGACCU GCUCGUCGAGCUGG AG | | | |

SEQ ID NO:

| SEQ ID NO: | 1 | 11 | 3 | 178 | 63 |
|---|---|---|---|---|---|
| PCCA_21 (hPCCA; G5) Cap: C1 PolyA tail: 100 nt | MAGFWVGTAPLVAA GRRGRWPPQQLMLS AALRTLKHVLYYSR QCLMVSRNLGSVGY DPNEKTFDKILVANR GEIACRVIRTCKKMG IKTVAIHSDVDASSV HVKMADEAVCVGPA PTSKSYLNMDAIMEA IKKTRAQAVHPGYGF LSENKEFARCLAAED VVFIGPDTHAIQAMG DKIESKLLAKKAEVN TIPGFDGVVKDAEEA VRIAREIGYPVMIKAS AGGGGKGMRIAWDD EETRDGFRLSSQEAA SSFGDDRLLIEKFIDN PRHIEIQVLGDKHGN ALWLNERECSIQRRN QKVVEEAPSIFLDAE TRRAMGEQAVALAR AVKYSSAGTVEFLVD SKKNFYFLEMNTRLQ VEHPVTECITGLDLV QEMIRVAKGYPLRH KQADIRINGWAVECR VYAEDPYKSFGLPSI GRLSQYQEPLHLPGV RVDSGIQPGSDISIYY DPMISKLITYGSDRTE ALKRMADALDNYVI RGVTHNIALLREVIIN SRFVKGDISTKFLSDV YPDGFKGHMLTKSE KNQLLAIASSLFVAF QLRAQHFQENSRMP VIKPDIANWELSVKL HDKVHTVVASNNGS VFSVEVDGSKLNVTS TWNLASPLLSVSVDG TQRTVQCLSREAGGN MSIQFLGTVYKVNIL TRLAAELNKFMLEK VTEDTSSVLRSPMPG VVVAVSVKPGDAVA EGQEICVIEAMKMQN SMTAGKTGTVKSVH CQAGDTVGEGDLLV ELE | AUGGCCGGCUUCUG GGUCGGCACAGCCC CUCUGGUGGCAGCC GGCAGAAGAGGACG GUGGCCUCCCCAGC AACUGAUGCUGAGC GCCGCCCUGAGAAC CCUGAAGCACGUGC UGUACUACAGCAGA CAGUGCCUGAUGGU GAGCAGAAAUCUGG GCAGCGUGGGGUAC GAUCCCAACGAGAA GACCUUCGAUAAGA UUCUGGUCGCGAAU AGAGGCGAGAUCGC CUGCAGGGUGAUCA GAACCUGCAAGAAG AUGGGCAUCAAGAC CGUGGCCAUCCAUU CGGACGUCGACGCG AGCAGCGUUCACGU GAAGAUGGCAGACG AGGCCGUGUGCGUG GGACCCGCCCCGAC CAGCAAGAGCUACC UGAACAUGGACGCC AUCAUGGAGGCCAU CAAGAAGACCCGCG CUCAAGCCGUGCAC CCGGGCUACGGCUU UCUGAGCGAGAACA AGGAAUUCGCCAGG UGUCUCGCCGCCGA GGACGUAGUCUUCA UCGGCCCUGAUACG CACGCGAUCCAGGC CAUGGGCGACAAGA UCGAGAGCAAACUG CUGGCCAAGAAAGC AGAAGUCAACACCA UCCCCGGCUUCGAC GGCGUGGUGAAGGA CGCCGAAGAGGCUG UCCGCAUCGCCAGA GAGAUCGGCUACCC UGUGAUGAUAAAG GCUAGCGCUGGAGG UGGCGGAAAGGGCA UGAGAAUCGCCUGG GACGACGAGGAGAC UAGAGACGGCUUCA GACUGUCCUCCCAG GAGGCCGCCAGCUC CUUCGGAGACGACA GACUGCUGAUCGAG AAGUUCAUCGACAA CCCCAGACACAUCG AAAUCCAGGUGCUC GGUGACAAGCACGG GAACGCCCUGUGGC UGAACGAGAGAGAG UGCAGCAUCCAGAG AAGAAACCAGAAGG UGGUGGAGGAGGCG CCGAGCAUCUUUCU | GGGAAA UAAGAG AGAAAA GAAGAG UAAGAA GAAAUA UAAGAG CCACC | UGAUAA UAGUCC AUAAAG UAGGAA ACACUA CAGCUG GAGCCU CGGUGG CCUAGC UUCUUG CCCCUU GGGCCU CCAUAA AGUAGG AAACAC UACAUC CCCCCA GCCCCU CCUCCC CUUCCU GCACCC GUACCC CCUCCA UAAAGU AGGAAA CACUAC AGUGGU CUUUGA AUAAAG UCUGAG UGGGCG GC | SEQ ID NO: 63 consists from 5' to 3' end: 5' UTR of SEQ ID NO: 3, ORF Sequence of SEQ ID NO: 11, and 3' UTR of SEQ ID NO: 178 |

-continued

| CONSTRUCT SEQUENCES By "G5" is meant that all uracils (U) in the mRNA are replaced by N1-methylpseudouracils. | | | | | |
|---|---|---|---|---|---|
| mRNA Name | ORF Sequence (Amino Acid) | ORF Sequence (Nucleotide) | 5' UTR Sequence | 3' UTR Sequence | Construct Sequence |
| | | GGACGCGGAGACAA | | | |
| | | GGAGAGCGAUGGGC | | | |
| | | GAACAGGCCGUCGC | | | |
| | | CCUAGCAAGAGCCG | | | |
| | | UGAAGUACUCCAGU | | | |
| | | GCCGGAACCGUCGA | | | |
| | | GUUUCUUGUCGACA | | | |
| | | GCAAGAAGAAUUUC | | | |
| | | UACUUCCUGGAGAU | | | |
| | | GAACACCAGGCUGC | | | |
| | | AGGUGGAGCAUCCC | | | |
| | | GUGACAGAGUGCAU | | | |
| | | CACUGGACUGGAUC | | | |
| | | UGGUGCAGGAGAUG | | | |
| | | AUCAGGGUGGCCAA | | | |
| | | GGGCUAUCCCCUGA | | | |
| | | GACACAAGCAGGCC | | | |
| | | GACAUCAGAAUCAA | | | |
| | | CGGCUGGGCCGUGG | | | |
| | | AGUGCAGAGUGUAC | | | |
| | | GCCGAGGACCCCUA | | | |
| | | CAAGAGCUUCGGCC | | | |
| | | UGCCCAGCAUCGGC | | | |
| | | AGACUGAGCCAGUA | | | |
| | | CCAGGAGCCCCUGC | | | |
| | | ACCUGCCCGGCGUG | | | |
| | | AGAGUGGACAGCGG | | | |
| | | CAUCCAACCGGGGA | | | |
| | | GCGAUAUCAGCAUC | | | |
| | | UACUACGACCCCAU | | | |
| | | GAUCAGCAAGCUGA | | | |
| | | UAACCUACGGCAGC | | | |
| | | GACAGAACCGAGGC | | | |
| | | CCUGAAGAGAAUGG | | | |
| | | CCGACGCCCUGGAC | | | |
| | | AACUACGUGAUCAG | | | |
| | | AGGCGUGACCCACA | | | |
| | | ACAUCGCCCUGCUG | | | |
| | | AGAGAGGUGAUCAU | | | |
| | | CAACUCGAGGUUCG | | | |
| | | UGAAAGGCGACAUC | | | |
| | | AGCACCAAGUUCCU | | | |
| | | GAGCGACGUGUAUC | | | |
| | | CCGACGGAUUCAAA | | | |
| | | GGUCACAUGCUGAC | | | |
| | | CAAGAGCGAGAAGA | | | |
| | | ACCAGCUGCUGGCC | | | |
| | | AUCGCCUCAUCCCU | | | |
| | | GUUCGUGGCCUUCC | | | |
| | | AGCUGAGAGCCCAG | | | |
| | | CACUUCCAGGAGAA | | | |
| | | CAGCAGAAUGCCCG | | | |
| | | UGAUCAAGCCCGAC | | | |
| | | AUCGCCAACUGGGA | | | |
| | | GCUGAGCGUGAAGC | | | |
| | | UGCACGACAAGGUG | | | |
| | | CACACUGUCGUUGC | | | |
| | | CAGCAACAACGGCU | | | |
| | | CCGUGUUCAGCGUA | | | |
| | | GAGGUGGACGGAUC | | | |
| | | UAAGCUGAACGUGA | | | |
| | | CCUCCACCUGGAAC | | | |
| | | CUGGCAAGCCCUCU | | | |
| | | CCUGUCAGUGAGCG | | | |
| | | UGGACGGCACCCAG | | | |
| | | AGAACCGUGCAGUG | | | |
| | | UCUGUCCCGCGAGG | | | |
| | | CCGGCGGAAACAUG | | | |
| | | AGCAUCCAGUUCCU | | | |
| | | GGGCACCGUGUACA | | | |
| | | AGGUGAACAUCCUG | | | |
| | | ACCAGACUGGCCGC | | | |
| | | CGAGCUGAACAAGU | | | |

CONSTRUCT SEQUENCES
By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | UCAUGCUGGAGAAA GUGACGGAGGAUAC CAGCUCCGUGCUGA GAAGCCCCAUGCCC GGAGUGGUGGUGGC CGUUUCCGUGAAAC CUGGUGACGCCGUG GCCGAGGGGCAAGA GAUCUGCGUGAUCG AGGCCAUGAAGAUG CAGAAUUCCAUGAC CGCCGGAAAGACCG GCACCGUCAAAUCA GUGCACUGCCAGGC GGGCGACACAGUGG GUGAGGGCGACCUG CUGGUGGAGCUGGA G | | | |

SEQ ID NO: | 1 | 11 | 3 | 112 | 65

| PCCA_22 (hPCCA; G5) Cap: C1 PolyA tail: 100 nt | MAGFWVGTAPLVAA GRRGRWPPQQLMLS AALRTLKHVLYYSR QCLMVSRNLGSVGY DPNEKTIFDKILVANR GEIACRVIRTCKKMG IKTVAIHSDVDASSV HVKMADEAVCVGPA PTSKSYLNMDAIMEA IKKTRAQAVHPGYGF LSENKEFARCLAAED VVFIGPDTHAIQAMG DKIESKLLAKKAEVN TIPGFDGVVKDAEEA VRIAREIGYPVMIKAS AGGGGKGMRIAWDD EETRDGFRLSSQEAA SSFGDDRLLIEKFIDN PRHIEIQVLGDKHGN ALWLNERECSIQRRN QKVVEEAPSIFLDAE TRRAMGEQAVALAR AVKYSSAGTVEFLVD SKKNFYFLEMNTRLQ VEHPVTECITGLDLV QEMIRVAKGYPLRH KQADIRINGWAVECR VYAEDPYKSFGLPSI GRLSQYQEPLHLPGV RVDSGIQPGSDISIYY DPMISKLITYGSDRTE ALKRMADALDNYVI RGVTHNIALLREVIIN SRFVKGDISTKFLSDV YPDGFKGHMLTKSE KNQLLAIASSLFVAF QLRAQHFQENSRMP VIKPDIANWELSVKL HDKVHTVVASNNGS VFSVEVDGSKLNVTS TWNLASPLLSVSVDG TQRTVQCLSREAGGN MSIQFLGTVYKVNIL TRLAAELNKFMLEK VTEDTSSVLRSPMPG VVVAVSVKPGDAVA EGQEICVIEAMKMQN SMTAGKTGTVKSVH CQAGDTVGEGDLLV ELE | AUGGCCGGCUUCUG GGUCGGCACAGCCC CUCUGGUGGCAGCC GGCAGAAGAGGACG GUGGCCUCCCCAGC AACUGAUGCUGAGC GCCGCCCUGAGAAC CCUGAAGCACGUGC UGUACUACAGCAGA CAGUGCCUGAUGGU GAGCAGAAAUCUGG GCAGCGUGGGGUAC GAUCCCAACGAGAA GACCUUCGAUAAGA UUCUGGUCGCGAAU AGAGGCGAGAUCGC CUGCAGGGUGAUCA GAACCUGCAAGAAG AUGGGCAUCAAGAC CGUGGCCAUCCAUU CGGACGUCGACGCG AGCAGCGUUCACGU GAAGAUGGCAGACG AGGCCGUGUGCGUG GGACCCGCCCCGAC CAGCAAGAGCUACC AUCAUGGAGGCCAU CAAGAAGACCCGCG CUCAAGCCGUGCAC CCGGGCUACGGCUU UCUGAGCGAGAACA AGGAAUUCGCCAGG UGUCUCGCCGCCGA GGACGUAGUCUUCA UCGGCCCUGAUACG CACGCGAUCCAGGC CAUGGGCGACAAGA UCGAGAGCAAACUG CUGGCCAAGAAAGC AGAAGUCAACACCA UCCCCGGCUUCGAC GGCGUGGUGAAGGA CGCCGAAGAGGCUG UCCGCAUCGCCAGA GAGAUCGGCUACCC UGUGAUGAUAAAG GCUAGCGCUGGAGG UGGCGGAAAGGGCA UGAGAAUCGCCUGG GACGACGAGGAGAC | GGGAAA UAAGAG AGAAA GAAGAG GAAAUA UAAGAG CCACC | UGAUAA UAGUCC AUAAAG UAGGAA CAGCUG GAGCCU CGGUGG CCUAGC UUCUUG CCCCUU GGGCCU CCCCCC AGCCCC UCCUCC CCUUCC UGCACC CGUACC CCCCGC AUUAUU ACUCAC GGUACG AGUGGU CUUUGA AUAAAG UCUGAG UGGGCG GC | SEQ ID NO: 65 consists from 5' to 3' end: 5' UTR of SEQ ID NO: 3, ORF Sequence of SEQ ID NO: 11, and 3' UTR of SEQ ID NO: 112 |

-continued

| | | CONSTRUCT SEQUENCES | | | |
| | By "G5" is meant that all uracils (U) in the mRNA are replaced by N1-methylpseudouracils. | | | | |
| mRNA<br>Name | ORF Sequence<br>(Amino Acid) | ORF Sequence<br>(Nucleotide) | 5' UTR<br>Sequence | 3' UTR<br>Sequence | Construct<br>Sequence |
|---|---|---|---|---|---|
| | | UAGAGACGGCUUCA | | | |
| | | GACUGUCCUCCCAG | | | |
| | | GAGGCCGCCAGCUC | | | |
| | | CUUCGGAGACGACA | | | |
| | | GACUGCUGAUCGAG | | | |
| | | AAGUUCAUCGACAA | | | |
| | | CCCCAGACACAUCG | | | |
| | | AAAUCCAGGUGCUC | | | |
| | | GGUGACAAGCACGG | | | |
| | | GAACGCCCUGUGGC | | | |
| | | UGAACGAGAGAGAG | | | |
| | | UGCAGCAUCCAGAG | | | |
| | | AAGAAACCAGAAGG | | | |
| | | UGGUGGAGGAGGCG | | | |
| | | CCGAGCAUCUUUCU | | | |
| | | GGACGCGGAGACAA | | | |
| | | GGAGAGCGAUGGGC | | | |
| | | GAACAGGCCGUCGC | | | |
| | | CCUAGCAAGAGCCG | | | |
| | | UGAAGUACUCCAGU | | | |
| | | GCCGGAACCGUCGA | | | |
| | | GUUUCUUGUCGACA | | | |
| | | GCAAGAAGAAUUUC | | | |
| | | UACUUCCUGGAGAU | | | |
| | | GAACACCAGGCUGC | | | |
| | | AGGUGGAGCAUCCC | | | |
| | | GUGACAGAGUGCAU | | | |
| | | CACUGGACUGGAUC | | | |
| | | UGGUGCAGGAGAUG | | | |
| | | AUCAGGGUGGCCAA | | | |
| | | GGGCUAUCCCCUGA | | | |
| | | GACACAAGCAGGCC | | | |
| | | GACAUCAGAAUCAA | | | |
| | | CGGCUGGGCCGUGG | | | |
| | | AGUGCAGAGUGUAC | | | |
| | | GCCGAGGACCCCUA | | | |
| | | CAAGAGCUUCGGCC | | | |
| | | UGCCCAGCAUCGGC | | | |
| | | AGACUGAGCCAGUA | | | |
| | | CCAGGAGCCCCUGC | | | |
| | | ACCUGCCCGGCGUG | | | |
| | | AGAGUGGACAGCGG | | | |
| | | CAUCCAACCGGGGA | | | |
| | | GCGAUAUCAGCAUC | | | |
| | | UACUACGACCCCAU | | | |
| | | GAUCAGCAAGCUGA | | | |
| | | UAACCUACGGCAGC | | | |
| | | GACAGAACCGAGGC | | | |
| | | CCUGAAGAGAAUGG | | | |
| | | CCGACGCCCUGGAC | | | |
| | | AACUACGUGAUCAG | | | |
| | | AGGCGUGACCCACA | | | |
| | | ACAUCGCCCUGCUG | | | |
| | | AGAGAGGUGAUCAU | | | |
| | | CAACUCGAGGUUCG | | | |
| | | UGAAAGGCGACAUC | | | |
| | | AGCACCAAGUUCCU | | | |
| | | GAGCGACGUGUAUC | | | |
| | | CCGACGGAUUCAAA | | | |
| | | GGUCACAUGCUGAC | | | |
| | | CAAGAGCGAGAAGA | | | |
| | | ACCAGCUGCUGGCC | | | |
| | | AUCGCCUCAUCCCU | | | |
| | | GUUCGUGGCCUUCC | | | |
| | | AGCUGAGAGCCCAG | | | |
| | | CACUUCCAGGAGAA | | | |
| | | CAGCAGAAUGCCCG | | | |
| | | UGAUCAAGCCCGAC | | | |
| | | AUCGCCAACUGGGA | | | |
| | | GCUGAGCGUGAAGC | | | |
| | | UGCACGACAAGGUG | | | |
| | | CACACUGUCGUUGC | | | |
| | | CAGCAACAACGGCU | | | |

| CONSTRUCT SEQUENCES |
| By "G5" is meant that all uracils (U) in the mRNA are replaced by N1-methylpseudouracils. |

| mRNA Name | ORF Sequence (Amino Acid) | ORF Sequence (Nucleotide) | 5' UTR Sequence | 3' UTR Sequence | Construct Sequence |
|---|---|---|---|---|---|
| | | CCGUGUUCAGCGUA GAGGUGGACGGAUC UAAGCUGAACGUGA CCUCCACCUGGAAC CUGGCAAGCCCUCU CCUGUCAGUGAGCG UGGACGGCACCCAG AGAACCGUGCAGUG UCUGUCCCGCGAGG CCGGCGGAAACAUG AGCAUCCAGUUCCU GGGCACCGUGUACA AGGUGAACAUCCUG ACCAGACUGGCCGC CGAGCUGAACAAGU UCAUGCUGGAGAAA GUGACGGAGGAUAC CAGCUCCGUGCUGA GAAGCCCCAUGCCC GGAGUGGUGGUGGC CGUUUCCGUGAAAC CUGGUGACGCCGUG GCCGAGGGGCAAGA GAUCUGCGUGAUCG AGGCCAUGAAGAUG CAGAAUUCCAUGAC CGCCGGAAAGACCG GCACCGUCAAAUCA GUGCACUGCCAGGC GGGCGACACAGUGG GUGAGGGCGACCUG CUGGUGGAGCUGGA G | | | |
| SEQ ID NO: | 15 | 16 | 3 | 4 | 39 |
| PCCB_11 (hPCCB; G5) Cap: C1 PolyA tail: 100 nt | MAAALRVAAVGARL SVLASGLRAAVRSLC SQATSVNERIENKRR TALLGGGQRRIDAQH KRGKLTARERISLLL DPGSFVESDMFVEHR CADFGMAADKNKFP GDSVVTGRGRINGRL VYVFSQDFTVFGGSL SGAHAQKICKIMDQA ITVGAPVIGLNDSGG ARIQEGVESLAGYAD IFLRNVTASGVIPQISL IMGPCAGGAVYSPAL TDFTFMVKDTSYLFI TGPDVVKSVTNEDVT QEELGGAKTHTTMS GVAHRAFENDVDAL CNLRDFFNYLPLSSQ DPAPVRECHDPSDRL VPELDTIVPLESTKAY NMVDIIHSVVDEREF FEIMPNYAKNIIVGFA RMNGRTVGIVGNQP KVASGCLDINSSVKG ARFVRFCDAFNIPLIT FVDVPGFLPGTAQEY GGIIRHGAKLLYAFA EATVPKVTVITRKAY GGAYDVMSSKHLCG DTNYAWPTAEIAVM GAKGAVEIIFKGHEN VEAAQAEYIEKFANP FPAAVRGFVDDIIQPS STRARICCDLDVLAS KKVQRPWRKHANIP | AUGGCCGCCGCCCU UAGGGUCGCAGCCG UGGGCGCUAGACUG UCAGUGCUGGCCAG CGGCCUAAGAGCCG CCGUUAGGAGCCUG UGCAGCCAGGCUAC UAGCGUGAACGAGA GAAUAGAGAACAAA CGCCGUACAGCUCU GCUAGGAGGAGGCC AGAGACGUAUCGAC GCCCAGCACAAGCG GGGCAAGCUGACCG CCCGGGAGCGCAUC AGCCUCCUGCUUGA CCCCGGCAGCUUUG UUGAGUCGGACAUG UUCGUGGAGCACCG GUGCGCUGACUUCG GCAUGGCUGCCGAC AAGAACAAGUUCCC CGGCGACUCCGUGG UGACAGGAAGGGGA CGGAUCAACGGCCG GCUGGUGUACGUGU UCUCUCAGGACUUC ACUGUGUUCGGCGG CUCCCUUUCUGGCG CCCACGCCCAGAAG AUCUGUAAGAUUAU GGACCAGGCAAUCA CCGUGGGAGCUCCC GUCAUCGGCCUGAA CGACUCAGGCGGCG CCCGAAUCCAGGAG | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 39 consists from 5' to 3' end: 5' UTR of SEQ ID NO: 3 , ORF Sequence of SEQ ID NO: 16, and 3' UTR of SEQ ID NO: 4 |

-continued

CONSTRUCT SEQUENCES
By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | L | GGCGUGGAGAGCCU | | | |
| | | GGCCGGGUACGCAG | | | |
| | | ACAUUUUCCUGAGA | | | |
| | | AACGUGACCGCUAG | | | |
| | | CGGCGUUAUCCCAC | | | |
| | | AGAUCAGCCUGAUC | | | |
| | | AUGGGACCUUGCGC | | | |
| | | UGGAGGAGCAGUCU | | | |
| | | ACAGCCCAGCCCUG | | | |
| | | ACUGAUUUUACCUU | | | |
| | | CAUGGUGAAAGACA | | | |
| | | CAAGCUACCUGUUC | | | |
| | | AUCACUGGGCCGGA | | | |
| | | CGUAGUUAAGAGUG | | | |
| | | UGACUAACGAGGAC | | | |
| | | GUGACCCAGGAGGA | | | |
| | | GCUGGGCGGAGCCA | | | |
| | | AGACCCAUACGACU | | | |
| | | AUGAGCGGUGUGGC | | | |
| | | GCACCGCGCCUUCG | | | |
| | | AGAACGACGUGGAC | | | |
| | | GCCCUGUGCAAUCU | | | |
| | | GCGCGACUUCUUCA | | | |
| | | AUUACCUGCCCUUA | | | |
| | | AGCAGCCAAGAUCC | | | |
| | | CGCACCCGUGCGGG | | | |
| | | AGUGCCACGAUCCA | | | |
| | | AGCGAUAGGCUGGU | | | |
| | | GCCCGAGCUGGACA | | | |
| | | CCAUUGUGCCUCUG | | | |
| | | GAGUCAACUAAGGC | | | |
| | | UUACAACAUGGUUG | | | |
| | | ACAUCAUCCACAGC | | | |
| | | GUGGUCGACGAGCG | | | |
| | | CGAGUUCUUCGAGA | | | |
| | | UCAUGCCCAACUAC | | | |
| | | GCGAAGAAUAUCAU | | | |
| | | CGUGGGCUUUGCCC | | | |
| | | GCAUGAACGGCCGG | | | |
| | | ACCGUCGGGAUCGU | | | |
| | | CGGCAAUCAACCUA | | | |
| | | AGGUCGCCAGCGGU | | | |
| | | UGCCUGGACAUCAA | | | |
| | | CAGCUCGGUGAAGG | | | |
| | | GCGCCAGGUUCGUU | | | |
| | | AGAUUCUGCGACGC | | | |
| | | UUUCAACAUCCCUC | | | |
| | | UGAUCACUUUCGUA | | | |
| | | GACGUUCCCGGCUU | | | |
| | | CCUCCCUGGGACCG | | | |
| | | CACAGGAGUACGGA | | | |
| | | GGAAUCAUUAGGCA | | | |
| | | CGGCGCCAAGCUGC | | | |
| | | UCUACGCCUUCGCU | | | |
| | | GAGGCUACCGUGCC | | | |
| | | UAAGGUGACCGUGA | | | |
| | | UCACUAGGAAGGCC | | | |
| | | UACGGUGGCGCCUA | | | |
| | | CGACGUCAUGAGCA | | | |
| | | GCAAGCACCUGUGU | | | |
| | | GGAGACACAAACUA | | | |
| | | CGCCUGGCCCACAG | | | |
| | | CUGAGAUUGCGGUU | | | |
| | | AUGGGAGCCAAGGG | | | |
| | | CGCCGUGGAGAUUA | | | |
| | | UUUUCAAGGGCCAC | | | |
| | | GAGAACGUGGAGGC | | | |
| | | CGCCCAGGCCGAGU | | | |
| | | ACAUCGAGAAGUUU | | | |
| | | GCCAACCCCUUCCC | | | |
| | | UGCCGCCGUGAGAG | | | |
| | | GAUUUGUGGACGAU | | | |
| | | AUUAUCCAGCCCUC | | | |

-continued

CONSTRUCT SEQUENCES
By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | CUCCACCAGAGCCA GGAUCUGCUGCGAC CUCGACGUUUUGGC CUCGAAGAAGGUGC AACGGCCCUGGCGC AAACACGCAAACAU CCCGCUG | | | |

| SEQ ID NO: | 15 | 17 | 3 | 4 | 40 |
|---|---|---|---|---|---|
| PCCB_12 (hPCCB; G5) Cap: C1 PolyA tail: 100 nt | MAAALRVAAVGARL SVLASGLRAAVRSLC SQATSVNERIENKRR TALLGGGQRRIDAQH KRGKLTARERISLLL DPGSFVESDMFVEHR CADFGMAADKNKFP GDSVVTGRGRINGRL VYVFSQDFTVFGGSL SGAHAQKICKIMDQA ITVGAPVIGLNDSGG ARIQEGVESLAGYAD IFLRNVTASGVIPQISL IMGPCAGGAVYSPAL TDFTFMVKDTSYLFI TGPDVVKSVTNEDVT QEELGGAKTHTTMS GVAHRAFENDVDAL CNLRDFFNYLPLSSQ DPAPVRECHDPSDRL VPELDTIVPLESTKAY NMVDIIHSVVDEREF FEIMPNYAKNIIVGFA RMNGRTVGIVGNQP KVASGCLDINSSVKG ARFVRFCDAFNIPLIT FVDVPGFLPGTAQEY GGIIRHGAKLLYAFA EATVPKVTVITRKAY GGAYDVMSSKHLCG DTNYAWPTAEIAVM GAKGAVEIIFKGHEN VEAAQAEYIEKFANP FPAAVRGFVDDIIQPS STRARICCDLDVLAS KKVQRPWRKHANIP L | AUGGCCGCCGCCCU GAGGGUGGCCGCAG UCGGCGCACGACUC UCCGUGCUGGCUAG CGGCCUGAGAGCCG CUGUGCGGAGCCUG UGCUCUCAGGCUAC GUCGGUUAACGAGC GUAUAGAGAACAAG CGGCGCACCGCUCU CCUUGGCGGCGGCC AGAGGAGAAUAGAC GCCCAGCAUAAGCG UGGAAAGCUGACCG CCAGAGAGAGAAUA UCCCUUCUCCUGGA UCCCGGGUCUUUCG UGGAGAGCGACAUG UUCGUCGAACACAG GUGCGCCGACUUUG GGAUGGCUGCUGAC AAGAACAAGUUCCC UGGAGAUUCAGUAG UGACAGGUAGGGGC AGGAUCAACGGCAG ACUGGUCUACGUGU UUUCCCAAGAUUUC ACCGUGUUCGGCGG CAGCCUGAGCGGCG CUCACGCACAGAAG AUCUGCAAGAUCAU GGAUCAGGCAAUUA CAGUGGGCGCCCCU GUGAUCGGCCUGAA CGACAGUGGCGGCG CGAGAAUUCAGGAG GGAGUGGAAUCUCU GGCUGGGUACGCCG ACAUUUUCCUGCGA AACGUCACAGCCAG CGGGGUUAUUCCCC AAAUUUCGCUCAUC AUGGGGCCUUGCGC CGGCGGUGCUGUGU ACAGCCCUGCCCUC ACCGACUUCACCUU CAUGGUGAAAGACA CCUCCUAUCUGUUC AUUACAGGACCCGA CGUGGUGAAAUCCG UGACAAACGAGGAC GUGACCCAGGAGGA ACUCGGCGGCGCUA AGACCCACACAACC AUGUCAGGCGUUGC CCACAGAGCGUUCG AGAACGACGUGGAC GCUCUGUGCAACCU GAGAGACUUCUUCA ACUACCUGCCUCUG AGCUCGCAGGACCC AGCUCCCGUGCGGG | GGGAAA UAAGAG AGAAAA GAAGAG GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 40 consists from 5' to 3' end: 5' UTR of SEQ ID NO: 3, ORF Sequence of SEQ ID NO: 17, and 3' UTR of SEQ ID NO: 4 |

-continued

| CONSTRUCT SEQUENCES | | | | | |
|---|---|---|---|---|---|
| By "G5" is meant that all uracils (U) in the mRNA are replaced by N1-methylpseudouracils. | | | | | |
| mRNA Name | ORF Sequence (Amino Acid) | ORF Sequence (Nucleotide) | 5' UTR Sequence | 3' UTR Sequence | Construct Sequence |
| | | AGUGUCACGAUCCC | | | |
| | | AGCGAUCGUCUGGU | | | |
| | | GCCUGAACUGGACA | | | |
| | | CAAUCGUUCCACUG | | | |
| | | GAGUCCACCAAGGC | | | |
| | | CUAUAAUAUGGUGG | | | |
| | | ACAUUAUCCACAGC | | | |
| | | GUGGUGGACGAAAG | | | |
| | | GGAAUUCUUCGAGA | | | |
| | | UCAUGCCCAAUUAC | | | |
| | | GCCAAGAAUAUCAU | | | |
| | | CGUGGGCUUCGCCA | | | |
| | | GAAUGAACGGCCGC | | | |
| | | ACCGUGGGCAUCGU | | | |
| | | UGGCAAUCAACCUA | | | |
| | | AGGUGGCCAGCGGC | | | |
| | | UGCCUCGACAUUAA | | | |
| | | CAGCAGUGUGAAAG | | | |
| | | GCGCCAGAUUCGUG | | | |
| | | CGGUUUUGCGACGC | | | |
| | | CUUUAAUAUCCCUC | | | |
| | | UGAUCACCUUCGUG | | | |
| | | GACGUGCCCGGGUU | | | |
| | | UCUGCCGGGCACCG | | | |
| | | CCCAGGAGUACGGA | | | |
| | | GGGAUCAUUAGACA | | | |
| | | CGGUGCUAAGCUGC | | | |
| | | UGUACGCCUUCGCC | | | |
| | | GAGGCCACAGUGCC | | | |
| | | CAAGGUUACCGUUA | | | |
| | | UCACACGCAAAGCC | | | |
| | | UACGGCGGAGCCUA | | | |
| | | CGACGUGAUGAGCA | | | |
| | | GCAAACACCUCUGU | | | |
| | | GGCGACACCAACUA | | | |
| | | CGCUUGGCCCACAG | | | |
| | | CCGAGAUUGCCGUG | | | |
| | | AUGGGCGCCAAGGG | | | |
| | | CGCUGUGGAGAUCA | | | |
| | | UUUUCAAAGGCCAC | | | |
| | | GAGAACGUGGAGGC | | | |
| | | UGCCCAGGCCGAGU | | | |
| | | AUAUCGAGAAGUUC | | | |
| | | GCAAACCCCUUCCC | | | |
| | | AGCAGCAGUGCGGG | | | |
| | | GCUUCGUCGACGAC | | | |
| | | AUCAUCCAGCCUUC | | | |
| | | UAGCACCAGGGCAA | | | |
| | | GAAUCUGCUGUGAC | | | |
| | | CUUGACGUGCUCGC | | | |
| | | CAGUAAGAAGGUCC | | | |
| | | AGAGGCCGUGGAGA | | | |
| | | AAGCACGCUAACAU | | | |
| | | UCCCCUG | | | |
| SEQ ID NO: | 15 | 18 | 3 | 4 | 41 |
| PCCB_13 (hPCCB; G5) Cap: C1 PolyA tail: 100 nt | MAAALRVAAVGARL SVLASGLRAAVRSLC SQATSVNERIENKRR TALLGGGQRRIDAQH KRGKLTARERISLLL DPGSFVESDMFVEHR CADFGMAADKNKFP GDSVVTGRGRINGRL VYVFSQDFTVFGGSL SGAHAQKICKIMDQA ITVGAPVIGLNDSGG ARIQEGVESLAGYAD IFLRNVTASGVIPQISL IMGPCAGGAVYSPAL TDFTFMVKDTSYLFI | AUGGCCGCCGCCCU GCGGGUUGCAGCCG UGGGCGCCCGGCUG AGCGUGUUGGCCUC AGGGCUGAGAGCCG CUGUGCGGAGCCUG UGCAGCCAGGCCAC CAGCGUGAACGAGC GGAUCGAGAACAAG CGGCGGACUGCCCU GCUGGGCGGCGGGC AGAGGAGAAUCGAC GCCCAGCACAAGCG GGGCAAGCUGACCG CCCGGGAGAGGAUU | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGC UCCCCC CAGCCC CUCCUC CCCUUC CUGCAC CCGUAC CCCCUC | SEQ ID NO: 41 consists from 5' to 3' end: 5' UTR of SEQ ID NO: 3, ORF Sequence of SEQ ID NO: 18, and 3' UTR of SEQ ID |

-continued

CONSTRUCT SEQUENCES
By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | TGPDVVKSVTNEDVT | AGCCUGCUGCUGGA | | CAUAAA | NO: 4 |
| | QEELGGGAKTHTTMS | CCCCGGCAGCUUCG | | GUAGGA | |
| | GVAHRAFENDVDAL | UGGAGAGCGACAUG | | AACACU | |
| | CNLRDFFNYLPLSSQ | UUCGUCGAGCACCG | | ACAGUG | |
| | DPAPVRECHDPSDRL | GUGCGCCGACUUCG | | GUCUUU | |
| | VPELDTIVPLESTKAY | GCAUGGCAGCUGAC | | GAAUAA | |
| | NMVDIIHSVVDEREF | AAGAACAAGUUCCC | | AGUCUG | |
| | FEIMPNYAKNIIVGFA | CGGCGACAGCGUGG | | AGUGGG | |
| | RMNGRTVGIVGNQP | UGACCGGCCGGGGC | | CGGC | |
| | KVASGCLDINSSVKG | CGGAUCAACGGCCG | | | |
| | ARFVRFCDAFNIPLIT | GCUGGUGUACGUGU | | | |
| | FVDVPGFLPGTAQEY | UCAGCCAGGACUUC | | | |
| | GGIIRHGAKLLYAFA | ACCGUGUUCGGCGG | | | |
| | EATVPKVTVITRKAY | CAGCCUGAGCGGCG | | | |
| | GGAYDVMSSKHLCG | CCCACGCCCAGAAG | | | |
| | DTNYAWPTAEIAVM | AUCUGCAAGAUCAU | | | |
| | GAKGAVEIIFKGHEN | GGACCAGGCCAUCA | | | |
| | VEAAQAEYIEKFANP | CUGUCGGCGCACCC | | | |
| | FPAAVRGFVDDIIQPS | GUGAUCGGCCUGAA | | | |
| | STRARICCDLDVLAS | CGACAGCGGCGGCG | | | |
| | KKVQRPWRKHANIP | CACGUAUCCAGGAG | | | |
| | L | GGUGUAGAAUCUCU | | | |
| | | GGCCGGCUACGCCG | | | |
| | | ACAUCUUCCUGCGG | | | |
| | | AACGUGACCGCCUC | | | |
| | | AGGGGUGAUUCCUC | | | |
| | | AGAUCUCGCUGAUC | | | |
| | | AUGGGCCCCUGCGC | | | |
| | | CGGAGGUGCUGUGU | | | |
| | | ACAGCCCCGCCCUG | | | |
| | | ACCGACUUCACAUU | | | |
| | | CAUGGUGAAGGACA | | | |
| | | CCAGCUACCUGUUC | | | |
| | | AUCACCGGCCCCGA | | | |
| | | CGUGGUGAAAUCUG | | | |
| | | UGACCAACGAGGAC | | | |
| | | GUGACCCAGGAGGA | | | |
| | | GUUAGGAGGCGCCA | | | |
| | | AGACCCACACCACC | | | |
| | | AUGAGUGGCGUGGC | | | |
| | | CCACCGGGCCUUCG | | | |
| | | AGAACGACGUGGAC | | | |
| | | GCCCUGUGCAACCU | | | |
| | | GCGGGACUUCUUCA | | | |
| | | ACUACCUGCCCCUG | | | |
| | | UCAAGUCAGGACCC | | | |
| | | CGCUCCGGUACGGG | | | |
| | | AGUGCCACGACCCC | | | |
| | | AGCGAUAGACUGGU | | | |
| | | GCCCGAGCUGGACA | | | |
| | | CCAUCGUGCCCCUG | | | |
| | | GAGAGCACCAAGGC | | | |
| | | CUACAACAUGGUGG | | | |
| | | ACAUCAUCCACUCU | | | |
| | | GUGGUAGACGAGCG | | | |
| | | GGAGUUCUUCGAGA | | | |
| | | UCAUGCCCAACUAC | | | |
| | | GCCAAGAACAUCAU | | | |
| | | CGUGGGCUUUGCUC | | | |
| | | GCAUGAACGGUCGU | | | |
| | | ACCGUUGGUAUCGU | | | |
| | | CGGAAACCAGCCCA | | | |
| | | AGGUGGCCUCCGGU | | | |
| | | UGCCUCGAUAUCAA | | | |
| | | CUCCAGCGUAAAGG | | | |
| | | GCGCUCGGUUCGUG | | | |
| | | CGGUUCUGCGACGC | | | |
| | | CUUCAACAUUCCAC | | | |
| | | UGAUCACAUUCGUG | | | |
| | | GACGUGCCCGGCUU | | | |
| | | CCUGCCCGGCACCG | | | |
| | | CCCAGGAGUACGGC | | | |
| | | GGCAUCAUCCGGCA | | | |

| | | CONSTRUCT SEQUENCES | | | |
|---|---|---|---|---|---|
| | By "G5" is meant that all uracils (U) in the mRNA are replaced by N1-methylpseudouracils. | | | | |
| mRNA Name | ORF Sequence (Amino Acid) | ORF Sequence (Nucleotide) | 5' UTR Sequence | 3' UTR Sequence | Construct Sequence |
| | | CGGAGCAAAGCUGC UGUACGCCUUCGCC GAGGCCACCGUGCC UAAGGUGACCGUGA UCACCCGGAAGGCC UACGGCGGCGCAUA CGACGUGAUGAGCA GCAAGCACCUGUGC GGCGACACAAAUUA CGCUUGGCCCACUG CCGAGAUCGCCGUG AUGGGUGCUAAGGG AGCCGUGGAGAUCA UCUUCAAGGGCCAC GAGAACGUGGAGGC AGCCCAGGCCGAGU ACAUCGAGAAGUUC GCCAACCCCUUCCC CGCCGCGGUCCGCG GAUUUGUUGACGAU AUCAUCCAGCCCAG CAGCACCCGGGCCC GAAUCUGCUGCGAC CUAGACGUAUUGGC CUCUAAGAAGGUGC AGCGGCCCUGGCGG AAGCACGCAAACAU CCCACUG | | | |
| SEQ ID NO: | 15 | 19 | 3 | 4 | 42 |
| PCCB_14 (hPCBB; G5) | MAAALRVAAVGARL SVLASGLRAAVRSLC SQATSVNERIENKRR TALLGGGQRRIDAQH KRGKLTARERISLLL DPGSFVESDMFVEHR CADFGMAADKNKFP GDSVVTGRGRINGRL VYVFSQDFTVFGGSL SGAHAQKICKIMDQA ITVGAPVIGLNDSGG ARIQEGVESLAGYAD IFLRNVTASGVIPQISL IMGPCAGGAVYSPAL TDFTFMVKDTSYLFI TGPDVVKSVTNEDVT QEELGGAKTHTTMS GVAHRAFENDVDAL CNLRDFFNYLPLSSQ DPAPVRECHDPSDRL VPELDTIVPLESTKAY NMVDIIHSVVDEREF FEIMPNYAKNIIVGFA RMNGRTVGIVGNQP KVASGCLDINSSVKG ARFVRFCDAFNIPLIT FVDVPGFLPGTAQEY GGIIRHGAKLLYAFA EATVPKVTVITRKAY GGAYDVMSSKHLCG DTNYAWPTAEIAVM GAKGAVEIIFKGHEN VEAAQAEYIEKFANP FPAAVRGFVDDIIQPS STRARICCDLDVLAS KKVQRPWRKHANIP L | AUGGCCGCCGCGCU CAGAGUUGCCGCGG UCGGCGCACGCCUG AGCGUGCUGGCCAG CGGCCUGCGUGCAG CAGUCCGGAGCCUG UGCAGCCAGGCCAC CAGCGUGAACGAGC GGAUCGAGAACAAG CGGCGGACCGCACU CCUGGGCGGCGGUC AACGCAGGAUUGAC GCCCAGCACAAGCG GGGCAAGCUGACCG CCCGGGAGCGGAUU AGCCUGCUGCUGGA CCCCGGCAGCUUCG UGGAGAGCGACAUG UUUGUCGAACACCG GUGCGCCGACUUCG GCAUGGCCGCUGAC AAGAACAAGUUCCC CGGCGACAGCGUGG UGACCGGCCGGGGC CGGAUCAACGGCCG GCUGGUGUACGUGU UCAGCCAGGACUUC ACCGUGUUCGGCGG CAGCCUGAGCGGCG CCCACGCCCAGAAG AUCUGCAAGAUCAU GGACCAGGCCAUCA CCGUGGGUGCUCCG GUGAUCGGCCUGAA CGACUCAGGAGGUG CCCGGAUCCAGGAG GGAGUGGAAUCUCU GGCCGGCUACGCCG ACAUCUUCCUGCGG AACGUGACCGCUAG CGGCGUGAUACCUC | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 42 consists from 5' to 3' end: 5' UTR of SEQ ID NO: 3, ORF Sequence of SEQ ID NO: 19, and 3' UTR of SEQ ID NO: 4 |

-continued

| CONSTRUCT SEQUENCES | | | | | |
| By "G5" is meant that all uracils (U) in the mRNA are replaced by N1-methylpseudouracils. | | | | | |
| mRNA Name | ORF Sequence (Amino Acid) | ORF Sequence (Nucleotide) | 5' UTR Sequence | 3' UTR Sequence | Construct Sequence |
| | | AAAUUUCUCUGAUC | | | |
| | | AUGGGACCAUGCGC | | | |
| | | UGGCGGGGCCGUGU | | | |
| | | ACAGCCCCGCCCUG | | | |
| | | ACCGACUUUACGUU | | | |
| | | CAUGGUGAAGGACA | | | |
| | | CCAGCUACCUGUUC | | | |
| | | AUCACCGGCCCCGA | | | |
| | | CGUGGUCAAGUCCG | | | |
| | | UGACCAACGAGGAC | | | |
| | | GUGACCCAGGAGGA | | | |
| | | ACUCGGUGGGGCCA | | | |
| | | AGACCCACACCACC | | | |
| | | AUGUCCGGCGUUGC | | | |
| | | CCACCGGGCCUUCG | | | |
| | | AGAACGACGUGGAC | | | |
| | | GCCCUGUGCAACCU | | | |
| | | GCGGGACUUCUUCA | | | |
| | | ACUACCUGCCCCUG | | | |
| | | UCUUCACAAGAUCC | | | |
| | | UGCUCCAGUGCGGG | | | |
| | | AGUGCCACGACCCC | | | |
| | | AGCGACCGUUUGGU | | | |
| | | GCCCGAGCUGGACA | | | |
| | | CCAUCGUGCCCCUG | | | |
| | | GAGAGCACCAAGGC | | | |
| | | CUACAACAUGGUGG | | | |
| | | ACAUCAUCCACUCC | | | |
| | | GUUGUAGACGAGCG | | | |
| | | GGAGUUCUUCGAGA | | | |
| | | UCAUGCCCAACUAC | | | |
| | | GCCAAGAACAUCAU | | | |
| | | CGUGGGCUUCGCCC | | | |
| | | GUAUGAACGGCCGU | | | |
| | | ACCGUCGGGAUUGU | | | |
| | | GGGGAACCAGCCCA | | | |
| | | AGGUUGCUUCUGGG | | | |
| | | UGCCUAGACAUCAA | | | |
| | | CUCAAGCGUCAAAG | | | |
| | | GGGCCCGGUUCGUG | | | |
| | | CGGUUCUGCGACGC | | | |
| | | CUUCAACAUUCCCC | | | |
| | | UGAUCACGUUCGUU | | | |
| | | GACGUGCCCGGCUU | | | |
| | | CCUGCCCGGCACCG | | | |
| | | CCCAGGAGUACGGC | | | |
| | | GGCAUCAUCCGGCA | | | |
| | | CGGUGCCAAACUGC | | | |
| | | UGUACGCCUUCGCC | | | |
| | | GAGGCCACCGUUCC | | | |
| | | CAAGGUGACCGUGA | | | |
| | | UCACCCGGAAAGCU | | | |
| | | UACGGAGGGGCUUA | | | |
| | | CGACGUGAUGAGCA | | | |
| | | GCAAGCACCUGUGC | | | |
| | | GGCGACACAAAUUA | | | |
| | | CGCUUGGCCUACCG | | | |
| | | CCGAGAUCGCCGUG | | | |
| | | AUGGGCGCAAAGGG | | | |
| | | CGCUGUUGAGAUCA | | | |
| | | UCUUCAAGGGCCAC | | | |
| | | GAGAACGUGGAGGC | | | |
| | | UGCUCAGGCCGAGU | | | |
| | | ACAUCGAGAAGUUC | | | |
| | | GCCAACCCCUUCCC | | | |
| | | CGCUGCCGUGCGGG | | | |
| | | GUUUCGUGGACGAU | | | |
| | | AUUAUUCAGCCCAG | | | |
| | | CAGCACCCGGGCCA | | | |
| | | GAAUCUGCUGCGAC | | | |
| | | CUGGACGUUUUGGC | | | |
| | | AUCAAAGAAGGUGC | | | |
| | | AGCGGCCCUGGCGG | | | |

-continued

| CONSTRUCT SEQUENCES | | | | | |
|---|---|---|---|---|---|
| By "G5" is meant that all uracils (U) in the mRNA are replaced by N1-methylpseudouracils. | | | | | |
| mRNA Name | ORF Sequence (Amino Acid) | ORF Sequence (Nucleotide) | 5' UTR Sequence | 3' UTR Sequence | Construct Sequence |
| | | AAGCACGCCAAUAU CCCUCUG | | | |
| SEQ ID NO: | 15 | 20 | 3 | 4 | 43 |
| PCCB_15 (hPCCB; G5) Cap: C1 PolyA tail: 100 nt | MAAALRVAAVGARL SVLASGLRAAVRSLC SQATSVNERIENKRR TALLGGGQRRIDAQH KRGKLTARERISLLL DPGSFVESDMFVEHR CADFGMAADKNKFP GDSVVTGRGRINGRL VYVFSQDFTVFGGSL SGAHAQKICKIMDQA ITVGAPVIGLNDSGG ARIQEGVESLAGYAD IFLRNVTASGVIPQISL IMGPCAGGAVYSPAL TDFTFMVKDTSYLFI TGPDVVKSVTNEDVT QEELGGAKTHTTMS GVAHRAFENDVDAL CNLRDFFNYLPLSSQ DPAPVRECHDPSDRL VPELDTIVPLESTKAY NMVDIIHSVVDEREF FEIMPNYAKNIIVGFA RMNGRTVGIVGNQP KVASGCLDINSSVKG ARFVRFCDAFNIPLIT FVDVPGFLPGTAQEY GGIIRHGAKLLYAFA EATVPKVTVITRKAY GGAYDVMSSKHLCG DTNYAWPTAEIAVM GAKGAVEIIFKGHEN VEAAQAEYIEKFANP FPAAVRGFVDDIIQPS STRARICCDLDVLAS KKVQRPWRKHANIP L | AUGGCCGCCGCCCU UCGGGUUGCAGCGG UCGGUGCUCGGCUG AGCGUGCUCGCUUC CGGUCUUAGGGCUG CUGUGCGGAGCCUG UGCAGCCAGGCCAC CUCCGUCAACGAGC GCAUCGAGAACAAG CGCCGCACUGCCCU GCUGGGCGGAGGCC AGAGGCGAAUCGAC GCCCAGCACAAGCG CGGCAAGCUCACCG CCAGGGAACGGAUC UCCCUCCUCCUCGA CCCCGGCUCCUUCG UCGAGUCCGACAUG UUCGUAGAACACCG CUGCGCCGACUUCG GCAUGGCCGCAGAC AAGAACAAGUUCCC CGGCGACUCCGUCG UCACCGGCCGCGGC CGCAUCAACGGCCG CCUCGUCUACGUCU UCUCCCAGGACUUC ACCGUCUUCGGCGG CUCCCUCUCCGGCG CCCACGCCCAGAAG AUCUGCAAGAUCAU GGACCAGGCCAUCA CCGUCGGCGCCCCG GUCAUCGGCCUCAA CGACUCCGGCGGCG CCCGCAUCCAGGAG GGAGUCGAAUCCCU CGCCGGCUACGCCG ACAUCUUCCUCCGC AACGUCACCGCCUC CGGCGUCAUCCCGC AGAUCAGCCUUAUC AUGGGCCCCUGCGC CGGUGGUGCUGUCU ACAGUCCGGCCCUC ACCGACUUUACGUU CAUGGUCAAGGACA CCUCCUACCUCUUC AUCACUGGCCCCGA CGUCGUCAAGUCCG UCACCAACGAGGAC GUCACCCAGGAGGA GCUGGGAGGCGCCA AGACCCACACCACC AUGUCCGGUGUGGC CCACCGCGCCUUCG AGAACGACGUUGAC GCCCUCUGCAACCU CCGCGACUUCUUCA ACUACCUUCCACUC AGCUCACAGGACCC UGCUCCUGUACGCG AGUGCCACGACCCC UCCGACAGGCUGGU UCCCGAGCUCGACA CCAUCGUGCCGCUC GAGUCCACCAAGGC | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 43 consists from 5' to 3' end: 5' UTR of SEQ ID NO: 3 ORF Sequence of SEQ ID NO: 20, and 3' UTR of SEQ ID NO: 4 |

-continued

| CONSTRUCT SEQUENCES |
| --- |
| By "G5" is meant that all uracils (U) in the mRNA are replaced by N1-methylpseudouracils. |

| mRNA Name | ORF Sequence (Amino Acid) | ORF Sequence (Nucleotide) | 5' UTR Sequence | 3' UTR Sequence | Construct Sequence |
| --- | --- | --- | --- | --- | --- |
| | | CUACAACAUGGUCG | | | |
| | | ACAUCAUCCAUAGC | | | |
| | | GUGGUCGACGAGCG | | | |
| | | CGAGUUCUUCGAGA | | | |
| | | UCAUGCCCAACUAC | | | |
| | | GCCAAGAACAUCAU | | | |
| | | CGUCGGCUUCGCGC | | | |
| | | GGAUGAACGGCAGG | | | |
| | | ACCGUCGGUAUAGU | | | |
| | | CGGCAACCAGCCCA | | | |
| | | AGGUCGCCAGCGGG | | | |
| | | UGCCUAGAUAUUAA | | | |
| | | CUCCUCCGUUAAAG | | | |
| | | GGGCAAGAUUCGUC | | | |
| | | CGCUUCUGCGACGC | | | |
| | | CUUCAACAUCCCCU | | | |
| | | UGAUUACCUUCGUG | | | |
| | | GACGUCCCCGGCUU | | | |
| | | CCUCCCCGGAACAG | | | |
| | | CCCAGGAGUACGGC | | | |
| | | GGCAUCAUCCGCCA | | | |
| | | CGGUGCCAAACUCC | | | |
| | | UCUACGCCUUCGCC | | | |
| | | GAGGCCACCGUCCC | | | |
| | | CAAAGUGACCGUCA | | | |
| | | UCACCCGAAAGGCC | | | |
| | | UACGGAGGCGCUUA | | | |
| | | CGACGUCAUGUCCU | | | |
| | | CCAAGCACCUCUGC | | | |
| | | GGCGACACCAAUUA | | | |
| | | CGCUUGGCCUACUG | | | |
| | | CCGAGAUCGCCGUC | | | |
| | | AUGGGCGCUAAAGG | | | |
| | | AGCUGUUGAGAUAA | | | |
| | | UCUUCAAGGGCCAC | | | |
| | | GAGAACGUCGAGGC | | | |
| | | CGCGCAGGCCGAGU | | | |
| | | ACAUUGAGAAGUUC | | | |
| | | GCCAACCCCUUCCC | | | |
| | | CGCAGCCGUCCGCG | | | |
| | | GUUUCGUGGACGAC | | | |
| | | AUUAUUCAACCUUC | | | |
| | | UUCUACCCGUGCCC | | | |
| | | GUAUCUGCUGCGAC | | | |
| | | CUGGACGUGCUCGC | | | |
| | | CUCCAAGAAGGUCC | | | |
| | | AGCGCCCCUGGCGC | | | |
| | | AAGCACGCCAAUAU | | | |
| | | CCCACUC | | | |

| SEQ ID NO: | 15 | 21 | 3 | 4 | 44 |
| --- | --- | --- | --- | --- | --- |
| PCCB_16 (hPCCB; G5) Cap: C1 PolyA tail: 100 nt | MAAALRVAAVGARL SVLASGLRAAVRSLC SQATSVNERIENKRR TALLGGGQRRIDAQH KRGKLTARERISLLL DPGSFVESDMFVEHR CADFGMAADKNKFP GDSVVTGRGRINGRL VYVFSQDFTVFGGSL SGAHAQKICKIMDQA ITVGAPVIGLNDSGG ARIQEGVESLAGYAD IFLRNVTASGVIPQISL IMGPCAGGAVYSPAL TDFTFMVKDTSYLFI TGPDVVKSVTNEDVT QEELGGAKTHTTMS GVAHRAFENDVDAL CNLRDFFNYLPLSSQ DPAPVRECHDPSDRL | AUGGCCGCCGCCCU GCGGGUGGCCGCCG UGGGCGCCCGGCUG AGCGUGCUGGCCAG CGGCCUGCGGGCCG CCGUGCGGAGCCUG UGCAGCCAGGCCAC CAGCGUGAACGAGC GGAUCGAGAACAAG CGGCGGACCGCCCU GCUGGGCGGCGGCC AGCGGCGGAUCGAC GCCCAGCACAAGCG GGGCAAGCUGACCG CCCGGGAGCGGAUC AGCCUGCUGCUGGA CCCCGGCAGCUUCG UGGAGAGCGACAUG UUCGUGGAGCACCG GUGCGCCGACUUCG | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU | SEQ ID NO: 44 consists from 5' to 3' end: 5' UTR of SEQ ID NO: 3, ORF Sequence of SEQ ID NO: 21, and 3' UTR of SEQ ID NO: 4 |

-continued

| CONSTRUCT SEQUENCES |
| By "G5" is meant that all uracils (U) in the mRNA are replaced by N1-methylpseudouracils. |

| mRNA Name | ORF Sequence (Amino Acid) | ORF Sequence (Nucleotide) | 5' UTR Sequence | 3' UTR Sequence | Construct Sequence |
|---|---|---|---|---|---|
| | VPELDTIVPLESTKAY | GCAUGGCCGCCGAC | | GAAUAA | |
| | NMVDIIHSVVDEREF | AAGAACAAGUUCCC | | AGUCUG | |
| | FEIMPNYAKNIIVGFA | CGGCGACAGCGUGG | | AGUGGG | |
| | RMNGRTVGIVGNQP | UGACCGGCCGGGGC | | CGGC | |
| | KVASGCLDINSSVKG | CGGAUCAACGGCCG | | | |
| | ARFVRFCDAFNIPLIT | GCUGGUGUACGUGU | | | |
| | FVDVPGFLPGTAQEY | UCAGCCAGGACUUC | | | |
| | GGIIRHGAKLLYAFA | ACCGUGUUCGGCGG | | | |
| | EATVPKVTVITRKAY | CAGCCUGAGCGGCG | | | |
| | GGAYDVMSSKHLCG | CCCACGCCCAGAAG | | | |
| | DTNYAWPTAEIAVM | AUCUGCAAGAUCAU | | | |
| | GAKGAVEIIFKGHEN | GGACCAGGCCAUCA | | | |
| | VEAAQAEYIEKFANP | CCGUGGGCGCGCCC | | | |
| | FPAAVRGFVDDIIQPS | GUGAUCGGCCUGAA | | | |
| | STRARICCDLDVLAS | CGACAGCGGCGGCG | | | |
| | KKVQRPWRKHANIP | CCCGGAUCCAGGAG | | | |
| | L | GGCGUGGAGAGCCU | | | |
| | | GGCCGGCUACGCCG | | | |
| | | ACAUCUUCCUGCGG | | | |
| | | AACGUGACCGCCAG | | | |
| | | CGGCGUGAUCCCGC | | | |
| | | AGAUCAGCCUGAUC | | | |
| | | AUGGGCCCCUGCGC | | | |
| | | CGGCGGCGCCGUGU | | | |
| | | ACAGCCCCGCCCUG | | | |
| | | ACCGACUUCACCUU | | | |
| | | CAUGGUGAAGGACA | | | |
| | | CCAGCUACCUGUUC | | | |
| | | AUCACCGGCCCCGA | | | |
| | | CGUGGUGAAGAGCG | | | |
| | | UGACCAACGAGGAC | | | |
| | | GUGACCCAGGAGGA | | | |
| | | GCUGGGCGGCGCCA | | | |
| | | AGACCCACACCACC | | | |
| | | AUGAGCGGCGUGGC | | | |
| | | CCACCGGGCCUUCG | | | |
| | | AGAACGACGUGGAC | | | |
| | | GCCCUGUGCAACCU | | | |
| | | GCGGGACUUCUUCA | | | |
| | | ACUACCUGCCCCUG | | | |
| | | AGCAGCCAGGACCC | | | |
| | | CGCGCCCGUGCGGG | | | |
| | | AGUGCCACGACCCC | | | |
| | | AGCGACCGGCUGGU | | | |
| | | GCCCGAGCUGGACA | | | |
| | | CCAUCGUGCCCCUG | | | |
| | | GAGAGCACCAAGGC | | | |
| | | CUACAACAUGGUGG | | | |
| | | ACAUCAUCCACAGC | | | |
| | | GUGGUGGACGAGCG | | | |
| | | GGAGUUCUUCGAGA | | | |
| | | UCAUGCCCAACUAC | | | |
| | | GCCAAGAACAUCAU | | | |
| | | CGUGGGCUUCGCCC | | | |
| | | GGAUGAACGGCCGG | | | |
| | | ACCGUGGGCAUCGU | | | |
| | | GGGCAACCAGCCCA | | | |
| | | AGGUGGCCAGCGGC | | | |
| | | UGCCUGGACAUCAA | | | |
| | | CAGCAGCGUGAAGG | | | |
| | | GCGCCCGGUUCGUG | | | |
| | | CGGUUCUGCGACGC | | | |
| | | CUUCAACAUCCCAC | | | |
| | | UGAUCACCUUCGUG | | | |
| | | GACGUGCCCGGCUU | | | |
| | | CCUGCCCGGCACCG | | | |
| | | CCCAGGAGUACGGC | | | |
| | | GGCAUCAUCCGGCA | | | |
| | | CGGCGCCAAGCUGC | | | |
| | | UGUACGCCUUCGCC | | | |
| | | GAGGCCACCGUGCC | | | |
| | | CAAGGUGACCGUGA | | | |
| | | UCACCCGGAAGGCC | | | |

-continued

| CONSTRUCT SEQUENCES | | | | | |
|---|---|---|---|---|---|
| By "G5" is meant that all uracils (U) in the mRNA are replaced by N1-methylpseudouracils. | | | | | |
| mRNA Name | ORF Sequence (Amino Acid) | ORF Sequence (Nucleotide) | 5' UTR Sequence | 3' UTR Sequence | Construct Sequence |
| | | UACGGCGGCGCCUA CGACGUGAUGAGCA GCAAGCACCUGUGC GGCGACACCAACUA CGCCUGGCCCACCG CCGAGAUCGCCGUG AUGGGCGCCAAGGG CGCCGUGGAGAUCA UCUUCAAGGGCCAC GAGAACGUGGAGGC CGCCCAGGCCGAGU ACAUCGAGAAGUUC GCCAACCCCUUCCC CGCCGCCGUGCGGG GCUUCGUGGACGAC AUCAUCCAGCCCAG CAGCACCCGGGCCC GGAUCUGCUGCGAC CUGGACGUGCUGGC CAGCAAGAAGGUGC AGCGGCCCUGGCGG AAGCACGCCAACAU CCCGCUG | | | |
| SEQ ID NO: | 15 | 22 | 3 | 4 | 45 |
| PCCB_17 (hPCCB; G5) | MAAALRVAAVGARL SVLASGLRAAVRSLC SQATSVNERIENKRR TALLGGGQRRIDAQH KRGKLTARERISLLL DPGSFVESDMFVEHR CADFGMAADKNKFP GDSVVTGRGRINGRL VYVFSQDFTVFGGSL SGAHAQKICKIMDQA ITVGAPVIGLNDSGG ARIQEGVESLAGYAD IFLRNVTASGVIPQISL IMGPCAGGAVYSPAL TDFTFMVKDTSYLFI TGPDVVKSVTNEDVT QEELGGAKTHTTMS GVAHRAFENDVDAL CNLRDFFNYLPLSSQ DPAPVRECHDPSDRL VPELDTIVPLESTKAY NMVDIIHSVVDEREF FEIMPNYAKNIIVGFA RMNGRTVGIVGNQP KVASGCLDINSSVKG ARFVRFCDAFNIPLIT FVDVPGFLPGTAQEY GGIIRHGAKLLYAFA EATVPKVTVITRKAY GGAYDVMSSKHLCG DTNYAWPTAEIAVM GAKGAVEIIFKGHEN VEAAQAEYIEKFANP FPAAVRGFVDDIIQPS STRARICCDLDVLAS KKVQRPWRKHANIP L | AUGGCCGCGGCCCU GCGGGUCGCGGCCG UGGGAGCCAGACUG UCCGUGCUAGCCUC AGGGCUGCGCGCCG CUGUGAGAAGCCUG UGCAGCCAGGCCAC CAGCGUGAACGAGA GAAUCGAGAACAAG AGAAGAACCGCUCU GCUGGGUGGCGGCC AGAGAAGAAUCGAC GCCCAGCACAAGAG AGGCAAGCUGACCG CCAGAGAGAGAAUC AGCCUGCUGCUGGA CCCCGGCAGCUUCG UGGAGAGCGACAUG UUCGUGGAGCACCG CUGCGCCGACUUCG GCAUGGCCGCCGAC AAGAACAAGUUCCC CGGCGACAGCGUGG UGACCGGCAGAGGC AGAAUCAACGGCAG ACUGGUGUACGUGU UCAGCCAGGACUUC ACCGUGUUCGGCGG CUCCCUGAGCGGGG CCCACGCCCAGAAG AUCUGCAAGAUCAU GGACCAAGCCAUUA CCGUGGGCGCUCCU GUGAUCGGCCUGAA CGACUCCGGCGGCG CGAGGAUCCAGGAG GGCGUGGAAAGCCU GGCGGGUUACGCCG ACAUCUUCCUGAGA AACGUCACCGCAUC CGGAGUGAUUCCCC AGAUCAGCCUGAUC AUGGGUCCCUGCGC GGGCGGAGCCGUGU ACAGCCCCGCCCUG ACCGACUUCACCUU | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 45 consists from 5' to 3' end: 5' UTR of SEQ ID NO: 3, ORF Sequence of SEQ ID NO: 22, and 3' UTR SEQ ID NO: 4 |

-continued

CONSTRUCT SEQUENCES
By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | CAUGGUGAAGGACA | | | |
| | | CCAGCUACCUGUUC | | | |
| | | AUCACCGGCCCCGA | | | |
| | | CGUGGUCAAGAGCG | | | |
| | | UGACCAACGAGGAC | | | |
| | | GUGACCCAAGAGGA | | | |
| | | GCUCGGAGGCGCCA | | | |
| | | AGACCCACACCACC | | | |
| | | AUGAGCGGCGUGGC | | | |
| | | CCACAGAGCCUUCG | | | |
| | | AGAACGACGUGGAC | | | |
| | | GCCCUGUGCAACCU | | | |
| | | GAGAGACUUCUUCA | | | |
| | | ACUACCUGCCCCUG | | | |
| | | AGUUCUCAGGAUCC | | | |
| | | UGCACCCGUGAGAG | | | |
| | | AGUGCCACGACCCC | | | |
| | | AGCGACAGACUGGU | | | |
| | | GCCCGAGCUGGACA | | | |
| | | CCAUCGUGCCCCUG | | | |
| | | GAGAGCACCAAGGC | | | |
| | | CUACAACAUGGUGG | | | |
| | | ACAUCAUCCACAGC | | | |
| | | GUUGUGGACGAGAG | | | |
| | | AGAGUUCUUCGAGA | | | |
| | | UCAUGCCCAACUAC | | | |
| | | GCCAAGAACAUCAU | | | |
| | | CGUGGGCUUCGCCA | | | |
| | | GAAUGAACGGCAGG | | | |
| | | ACUGUGGGAAUCGU | | | |
| | | GGGCAACCAGCCCA | | | |
| | | AGGUGGCCAGCGGC | | | |
| | | UGCCUGGACAUCAA | | | |
| | | CAGCAGCGUGAAGG | | | |
| | | GCGCCAGAUUCGUG | | | |
| | | AGAUUCUGCGACGC | | | |
| | | CUUCAACAUCCCGC | | | |
| | | UGAUCACAUUCGUG | | | |
| | | GACGUUCCCGGCUU | | | |
| | | CCUGCCCGGCACAG | | | |
| | | CCCAGGAGUACGGC | | | |
| | | GGCAUCAUCAGACA | | | |
| | | CGGCGCCAAGCUGC | | | |
| | | UGUACGCCUUCGCC | | | |
| | | GAGGCCACCGUGCC | | | |
| | | CAAGGUGACCGUGA | | | |
| | | UCACCAGAAAGGCC | | | |
| | | UACGGCGGAGCUUA | | | |
| | | CGACGUGAUGAGCA | | | |
| | | GCAAGCACCUGUGC | | | |
| | | GGUGACACUAACUA | | | |
| | | CGCCUGGCCGACCG | | | |
| | | CCGAGAUCGCCGUG | | | |
| | | AUGGGCGCCAAAGG | | | |
| | | GGCCGUGGAGAUCA | | | |
| | | UCUUCAAGGGCCAC | | | |
| | | GAGAACGUGGAGGC | | | |
| | | CGCCCAGGCCGAGU | | | |
| | | ACAUCGAGAAGUUC | | | |
| | | GCCAACCCCUUCCC | | | |
| | | CGCCGCCGUCAGGG | | | |
| | | GUUUCGUGGACGAC | | | |
| | | AUCAUCCAGCCCUC | | | |
| | | CUCCACCAGAGCCA | | | |
| | | GAAUCUGCUGCGAC | | | |
| | | CUGGACGUACUGGC | | | |
| | | CAGCAAGAAGGUGC | | | |
| | | AACGUCCCUGGAGA | | | |
| | | AAGCACGCCAACAU | | | |
| | | CCCUCUG | | | |

| CONSTRUCT SEQUENCES | | | | | |
|---|---|---|---|---|---|
| By "G5" is meant that all uracils (U) in the mRNA are replaced by N1-methylpseudouracils. | | | | | |
| mRNA Name | ORF Sequence (Amino Acid) | ORF Sequence (Nucleotide) | 5' UTR Sequence | 3' UTR Sequence | Construct Sequence |
| SEQ ID NO: | 15 | 23 | 3 | 4 | 46 |
| PCCB_18 (hPCCB; G5) Cap: C1 PolyA tail: 100 nt | MAAALRVAAVGARL SVLASGLRAAVRSLC SQATSVNERIENKRR TALLGGGQRRIDAQH KRGKLTARERISLLL DPGSFVESDMFVEHR CADFGMAADKNKFP GDSVVTGRGRINGRL VYVFSQDFTVFGGSL SGAHAQKICKIMDQA ITVGAPVIGLNDSGG ARIQEGVESLAGYAD IFLRNVTASGVIPQISL IMGPCAGGAVYSPAL TDFTFMVKDTSYLFI TGPDVVKSVTNEDVT QEELGGAKTHTTMS GVAHRAFENDVDAL CNLRDFFNYLPLSSQ DPAPVRECHDPSDRL VPELDTIVPLESTKAY NMVDIIHSVVDEREF FEIMPNYAKNIIVGFA RMNGRTVGIVGNQP KVASGCLDINSSVKG ARFVRFCDAFNIPLIT FVDVPGFLPGTAQEY GGIIRHGAKLLYAFA EATVPKVTVITRKAY GGAYDVMSSKHLCG DTNYAWPTAEIAVM GAKGAVEIIFKGHEN VEAAQAEYIEKFANP FPAAVRGFVDDIIQPS STRARICCDLDVLAS KKVQRPWRKHANIP L | AUGGCCGCAGCCCU CAGAGUGGCUGCCG UGGGAGCCAGACUC AGCGUGCUCGCCUC AGGCCUGCGGGCCG CAGUCAGAAGCCUG UGCAGCCAGGCAAC CUCAGUGAACGAGA GAAUCGAGAACAAG AGACGGACCGCCCU GCUGGGUGGCGGGC AAAGAAGAAUUGAC GCCCAGCACAAGAG AGGCAAGCUGACCG CCCGCGAGCGCAUC AGCCUGCUGCUGGA CCCCGGCAGCUUCG UGGAGAGCGACAUG UUCGUGGAGCAUCG GUGUGCCGACUUCG GCAUGGCCGCCGAC AAGAACAAGUUCCC CGGCGACAGCGUGG UGACCGGCAGAGGC AGAAUCAACGGCAG ACUGGUGUACGUGU UCUCACACAAGACUUU ACCGUCUUCGGAGG AUCCCUGUCAGGGG CUCACGCCCAGAAG AUCUGCAAGAUCAU GGACCAGGCCAUCA CCGUGGGCGCUCCC GUGAUCGGCCUGAA CGACAGCGGAGGCG CCAGGAUCCAAGAG GGAGUGGAGUCCCU GGCCGGCUACGCCG ACAUCUUCCUGAGA AACGUGACCGCCUC GGGCGUGAUCCCAC AGAUCUCCCUGAUC AUGGGACCCUGCGC CGGCGGGGCCGUCU ACAGCCCUGCCCUG ACCGACUUCACCUU CAUGGUGAAGGACA CCAGCUACCUGUUC AUCACCGGCCCCGA CGUGGUCAAGAGCG UGACCAACGAGGAC GUGACCCAGGAGGA GCUCGGCGGAGCCA AGACUCACACAACC AUGUCCGGCGUCGC UCAUAGGGCCUUCG AGAACGACGUGGAC GCCCUGUGCAACCU GAGAGACUUCUUCA ACUACCUGCCAUUG AGCAGCCAGGAUCC CGCCCCUGUGAGAG AGUGCCACGACCCC AGCGACAGACUGGU GCCCGAGCUGGACA CCAUCGUGCCCCUG GAGAGCACCAAGGC CUACAACAUGGUGG ACAUCAUCCACAGC GUGGUGGACGAGAG | GGGAAA UAAGAG AGAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 46 consists from 5' to 3' end: 5' UTR of SEQ ID NO: 3, ORF Sequence of SEQ ID NO: 23, and 3' UTR of SEQ ID NO: 4 |

CONSTRUCT SEQUENCES

By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | AGAGUUCUUCGAGA UCAUGCCCAACUAC GCCAAGAACAUCAU CGUGGGCUUCGCCA GAAUGAACGGCAGA ACCGUGGGCAUUGU GGGCAACCAGCCCA AGGUCGCCAGCGGC UGCCUCGACAUCAA CAGCAGCGUGAAGG GCGCCAGAUUCGUG AGAUUCUGCGACGC CUUCAACAUACCUC UGAUCACCUUUGUG GACGUGCCUGGUUU CCUCCCGGGCACCG CCCAAGAAUACGGU GGCAUCAUCAGACA CGGCGCCAAGCUGC UGUACGCCUUCGCC GAGGCCACCGUGCC CAAGGUGACCGUUA UCACCCGCAAAGCC UACGGCGGCGCCUA CGACGUGAUGAGCA GCAAGCACCUGUGU GGCGACACCAAUUA CGCCUGGCCCACCG CCGAGAUCGCCGUC AUGGGCGCGAAAGG AGCCGUGGAGAUCA UCUUCAAGGGCCAC GAGAACGUGGAGGC CGCCCAGGCCGAGU ACAUCGAGAAGUUC GCCAACCCCUUCCC UGCCGCCGUGAGGG GCUUCGUCGACGAU AUCAUCCAGCCCAG CUCCACCCGCGCCA GAAUCUGUUGCGAC CUGGACGUGCUGGC CAGCAAGAAGGUGC AAAGACCCUGGAGA AAGCACGCCAACAU CCCGCUG | | | |

| SEQ ID NO: | 15 | 24 | 3 | 4 | 47 |
|---|---|---|---|---|---|
| PCCB_19 (hPCCB; G5) Cap: C1 PolyA tail: 100 nt | MAAALRVAAVGARL SVLASGLRAAVRSLC SQATSVNERIENKRR TALLGGGQRRIDAQH KRGKLTARERISLLL DPGSFVESDMFVEHR CADFGMAADKNKFP GDSVVTGRGRINGRL VYVFSQDFTVFGGSL SGAHAQKICKIMDQA ITVGAPVIGLNDSGG ARIQEGVESLAGYAD IFLRNVTASGVIPQISL IMGPCAGGAVYSPAL TDFTFMVKDTSYLFI TGPDVVKSVTNEDVT QEELGGAKTHTTMS GVAHRAFENDVDAL CNLRDFFNYLPLSSQ DPAPVRECHDPSDRL VPELDTIVPLESTKAY NMVDIIHSVVDEREF FEIMPNYAKNIIVGFA | AUGGCCGCCGCCCU AAGGGUUGCCGCAG UUGGUGCCAGGCUA AGCGUGCUAGCCAG CGGGCUACGGGCGG CGGUAAGGAGCCUG UGCAGCCAAGCCAC CAGCGUGAACGAGA GGAUAGAGAACAAG AGGAGGACCGCCCU ACUAGGCGGUGGGC AACGCCGGAUCGAC GCCCAACACAAGAG GGGAAAGCUAACCG CCAGGGAAAGAAUA AGCCUACUACUAGA UCCAGGGAGCUUCG UGGAGAGCGAUAUG UUUGUGGAGCACAG GUGCGCCGAUUUCG GGAUGGCCGCAGAU AAGAACAAGUUCCC AGGGGAUAGCGUGG | GGGAAA UAAGAG AGAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG | SEQ ID NO: 47 consists from 5' to 3' end: 5' UTR of SEQ ID NO: 3, ORF Sequence of SEQ ID NO: 24, and 3' UTR of SEQ ID NO: 4 |

-continued

CONSTRUCT SEQUENCES
By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | RMNGRTVGIVGNQP KVASGCLDINSSVKG ARFVRFCDAFNIPLIT FVDVPGFLPGTAQEY GGIIRHGAKLLYAFA EATVPKVTVITRKAY GGAYDVMSSKHLCG DTNYAWPTAEIAVM GAKGAVEIIFKGHEN VEAAQAEYIEKFANP FPAAVRGFVDDIIQPS STRARICCDLDVLAS KKVQRPWRKHANIP L | UGACCGGGAGAGGA AGGAUAAACGGGAG GCUAGUGUACGUGU UCAGCCAAGAUUUC ACCGUGUUCGGAGG GAGCCUAAGCGGGG CCCACGCCCAGAAG AUUUGCAAGAUAAU GGAUCAAGCCAUAA CCGUUGGAGCGCCA GUGAUAGGGCUAAA CGAUAGCGGUGGAG CCCGGAUCCAAGAG GGCGUGGAAUCUCU AGCCGGGUACGCCG AUAUAUUCCUAAGG AACGUGACCGCGUC UGGUGUGAUACCAC AAAUUAGUCUCAUA AUGGGGCCUUGCGC AGGAGGGGCUGUGU ACAGCCCAGCCCUA ACCGAUUUCACGUU CAUGGUGAAGGAUA CCAGCUACCUAUUC AUAACCGGGCCAGA CGUGGUAAAGUCCG UGACCAACGAGGAC GUGACCCAAGAGGA AUUAGGAGGAGCCA AGACCCACACCACC AUGUCCGGGGUUGC CCACAGGGCCUUCG AGAACGACGUGGAC GCCCUGUGCAACCU AAGGGAUUUCUUCA ACUACCUACCACUA UCUUCCCAAGAUCC UGCCCCAGUGAGGG AGUGCCACGAUCCA AGCGAUAGACUGGU CCCAGAGCUAGAUA CCAUAGUGCCACUA GAGAGCACCAAGGC CUACAACAUGGUGG AUAUAAUACACUCC GUGGUGGACGAGAG GGAGUUCUUCGAGA UAAUGCCAAACUAC GCCAAGAACAUAAU AGUGGGGUUCGCCA GGAUGAACGGGCGU ACCGUGGGGAUAGU AGGAAACCAACCAA AGGUGGCCUCUGGG UGCCUAGAUAUAAA CAGCUCUGUCAAGG GAGCCCGCUUCGUG AGGUUCUGCGACGC CUUCAACAUACCUC UAAUAACAUUCGUU GACGUGCCAGGGUU CCUACCAGGGACGG CACAAGAGUACGGA GGGAUAAUAAGGCA CGGGGCGAAGCUAC UAUACGCCUUCGCC GAGGCCACCGUGCC UAAGGUGACCGUGA UAACCAGGAAGGCU UACGGAGGGGCCUA CGACGUGAUGAGCA GCAAGCACCUGUGC | | CGGC | |

-continued

| CONSTRUCT SEQUENCES | | | | | |
|---|---|---|---|---|---|
| By "G5" is meant that all uracils (U) in the mRNA are replaced by N1-methylpseudouracils. | | | | | |
| mRNA Name | ORF Sequence (Amino Acid) | ORF Sequence (Nucleotide) | 5' UTR Sequence | 3' UTR Sequence | Construct Sequence |
| | | GGGGAUACCAACUA CGCGUGGCCAACCG CCGAGAUAGCCGUG AUGGGUGCAAAGGG UGCUGUGGAGAUAA UAUUCAAGGGGCAC GAGAACGUGGAGGC CGCGCAGGCCGAGU ACAUAGAGAAGUUC GCCAACCCAUUCCC AGCAGCGGUACGGG GAUUUGUUGACGAU AUCAUUCAACCAAG CAGCACCCGCGCGA GAAUUUGCUGCGAC UUAGACGUGUUAGC GAGCAAGAAGGUAC AACGGCCCUGGAGG AAGCACGCUAACAU CCCACUA | | | |
| SEQ ID NO: | 15 | 25 | 3 | 4 | 48 |
| PCCB_20 (hPCCB; G5) Cap: C1 PolyA tail: 100 nt | MAAALRVAAVGARL SVLASGLRAAVRSLC SQATSVNERIENKRR TALLGGGQRRIDAQH KRGKLTARERISLLL DPGSFVESDMFVEHR CADFGMAADKNKFP GDSVVTGRGRINGRL VYVFSQDFTVFGGSL SGAHAQKICKIMDQA ITVGAPVIGLNDSGG ARIQEGVESLAGYAD IFLRNVTASGVIPQISL IMGPCAGGAVYSPAL TDFTFMVKDTSYLFI TGPDVVKSVTNEDVT QEELGGAKTHTTMS GVAHRAFENDVDAL CNLRDFFNYLPLSSQ DPAPVRECHDPSDRL VPELDTIVPLESTKAY NMVDIIHSVVDEREF FEIMPNYAKNIIVGFA RMNGRTVGIVGNQP KVASGCLDINSSVKG ARFVRFCDAFNIPLIT FVDVPGFLPGTAQEY GGIIRHGAKLLYAFA EATVPKVTVITRKAY GGAYDVMSSKHLCG DTNYAWPTAEIAVM GAKGAVEIIFKGHEN VEAAQAEYIEKFANP FPAAVRGFVDDIIQPS STRARICCDLDVLAS KKVQRPWRKHANIP L | AUGGCGGCGGCAUU ACGGGUGGCGGCGG UCGGGGCAAGGCUC AGCGUGCUGGCCAG CGGCCUGAGAGCCG CCGUGAGAAGCCUG UGCAGCCAGGCCAC CAGCGUGAACGAGA GAAUCGAGAACAAG AGAAGAACCGCCCU GCUGGGCGGCGGCC AGAGAAGAAUCGAC GCCCAGCACAAGAG AGGCAAGCUGACCG CCAGAGAGAGAAUC AGCCUGCUGCUGGA CCCCGGCAGCUUCG UGGAGAGCGACAUG UUCGUGGAGCACAG GUGCGCCGACUUCG GCAUGGCCGCCGAC AAGAACAAGUUCCC CGGCGACAGCGUGG UGACCGGCAGAGGC AGAAUCAACGGCAG ACUGGUGUACGUGU UCAGCCAGGACUUC ACCGUGUUCGGCGG CAGCCUGAGCGGCG CCCACGCCCAGAAG AUCUGCAAGAUCAU GGACCAGGCCAUCA CCGUGGGCGCGCCC GUGAUCGGCCUGAA CGACAGCGGCGGCG CCAGAAUCCAGGAG GGCGUGGAGAGCCU GGCCGGCUACGCCG ACAUCUUCCUGAGA AACGUGACCGCCAG CGGCGUGAUCCCAC AGAUCAGCCUGAUC AUGGGCCCCUGCGC CGGCGGCGCCGUGU ACAGCCCCGCCCUG ACCGACUUCACCUU CAUGGUGAAGGACA CCAGCUACCUGUUC AUCACCGGCCCCGA | GGGAAA UAAGAG AGAAAA GAAGAG UAAGAA GAAAUA UAAGAG CCACC | UGAUAA UAGGCU GGAGCC UCGGUG GCCUAG CUUCUU GCCCCU UGGGCC UCCCCC CAGCCC CUCCUC CCCUUC CUGCAC CCGUAC CCCCUC CAUAAA GUAGGA AACACU ACAGUG GUCUUU GAAUAA AGUCUG AGUGGG CGGC | SEQ ID NO: 48 consists from 5' to 3' end: 5' UTR of SEQ ID NO: 3, ORF Sequence of SEQ ID NO: 25, and 3' UTR of SEQ ID NO: 4 |

-continued

| CONSTRUCT SEQUENCES | | | | | |
| By "G5" is meant that all uracils (U) in the mRNA are replaced by N1-methylpseudouracils. | | | | | |
| mRNA Name | ORF Sequence (Amino Acid) | ORF Sequence (Nucleotide) | 5' UTR Sequence | 3' UTR Sequence | Construct Sequence |
| | | CGUGGUGAAGAGCG UGACCAACGAGGAC GUGACCCAGGAGGA GCUGGGCGGCGCCA AGACCCACACCACC AUGAGCGGCGUGGC CCACAGAGCCUUCG AGAACGACGUGGAC GCCCUGUGCAACCU GAGAGACUUCUUCA ACUACCUGCCCCUG AGCAGCCAGGACCC CGCGCCCGUGAGAG AGUGCCACGACCCC AGCGACAGACUGGU GCCCGAGCUGGACA CCAUCGUGCCCCUG GAGAGCACCAAGGC CUACAACAUGGUGG ACAUCAUCCACAGC GUGGUGGACGAGAG AGAGUUCUUCGAGA UCAUGCCCAACUAC GCCAAGAACAUCAU CGUGGGCUUCGCCA GAAUGAACGGCAGA ACCGUGGGCAUCGU GGGCAACCAGCCCA AGGUGGCCAGCGGC UGCCUGGACAUCAA CAGCAGCGUGAAGG GCGCCAGAUUCGUG AGAUUCUGCGACGC CUUCAACAUCCCUC UGAUCACCUUCGUG GACGUGCCCGGCUU CCUGCCCGGCACCG CCCAGGAGUACGGC GGCAUCAUCAGACA CGGCGCCAAGCUGC UGUACGCCUUCGCC GAGGCCACCGUGCC CAAGGUGACCGUGA UCACCAGAAAGGCC UACGGCGGCGCCUA CGACGUGAUGAGCA GCAAGCACCUGUGC GGCGACACCAACUA CGCCUGGCCCACCG CCGAGAUCGCCGUG AUGGGCGCCAAGGG CGCCGUGGAGAUCA UCUUCAAGGGCCAC GAGAACGUGGAGGC CGCCCAGGCCGAGU ACAUCGAGAAGUUC GCCAACCCCUUCCC CGCCGCCGUGAGAG GCUUCGUGGACGAC AUCAUCCAGCCCAG CAGCACCAGAGCCA GAAUCUGCUGCGAC CUGGACGUGCUGGC CAGCAAGAAGGUGC AGAGACCCUGGAGA AAGCACGCCAACAU CCCUCUG | | | |
| SEQ ID NO: | 15 | 23 | 3 | 178 | 66 |
| PCCB_21 (hPCCB; | MAAALRVAAVGARL SVLASGLRAAVRSLC | AUGGCCGCAGCCCU CAGAGUGGCUGCCG | GGGAAA UAAGAG | UGAUAA UAGUCC | SEQ ID NO: 66 |

-continued

| CONSTRUCT SEQUENCES | | | | | |
| --- | --- | --- | --- | --- | --- |
| By "G5" is meant that all uracils (U) in the mRNA are replaced by N1-methylpseudouracils. | | | | | |
| mRNA<br>Name | ORF Sequence<br>(Amino Acid) | ORF Sequence<br>(Nucleotide) | 5' UTR<br>Sequence | 3' UTR<br>Sequence | Construct<br>Sequence |
| G5)<br>Cap: C1<br>PolyA tail:<br>100 nt | SQATSVNERIENKRR<br>TALLGGGQRRIDAQH<br>KRGKLTARERISLLL<br>DPGSFVESDMFVEHR<br>CADFGMAADKNKFP<br>GDSVVTGRGRINGRL<br>VYVFSQDFTVFGGSL<br>SGAHAQKICKIMDQA<br>ITVGAPVIGLNDSGG<br>ARIQEGVESLAGYAD<br>IFLRNVTASGVIPQISL<br>IMGPCAGGAVYSPAL<br>TDFTFMVKDTSYLFI<br>TGPDVVKSVTNEDVT<br>QEELGGAKTHTTMS<br>GVAHRAFENDVDAL<br>CNLRDFFNYLPLSSQ<br>DPAPVRECHDPSDRL<br>VPELDTIVPLESTKAY<br>NMVDIIHSVVDEREF<br>FEIMPNYAKNIIVGFA<br>RMNGRTVGIVGNQP<br>KVASGCLDINSSVKG<br>ARFVRFCDAFNIPLIT<br>FVDVPGFLPGTAQEY<br>GGIIRHGAKLLYAFA<br>EATVPKVTVITRKAY<br>GGAYDVMSSKHLCG<br>DTNYAWPTAEIAVM<br>GAKGAVEIIFKGHEN<br>VEAAQAEYIEKFANP<br>FPAAVRGFVDDIIQPS<br>STRARICCDLDVLAS<br>KKVQRPWRKHANIP<br>L | UGGGAGCCAGACUC<br>AGCGUGCUCGCCUC<br>AGGCCUGCGGGCCG<br>CAGUCAGAAGCCUG<br>UGCAGCCAGGCAAC<br>CUCAGUGAACGAGA<br>GAAUCGAGAACAAG<br>AGACGGACCGCCCU<br>GCUGGGUGGCGGGC<br>AAAGAAGAAUUGAC<br>GCCCAGCACAAGAG<br>AGGCAAGCUGACCG<br>CCCGCGAGCGCAUC<br>AGCCUGCUGCUGGA<br>CCCCGGCAGCUUCG<br>UGGAGAGCGACAUG<br>UUCGUGGAGCAUCG<br>GUGUGCCGACUUCG<br>GCAUGGCCGCCGAC<br>AAGAACAAGUUCCC<br>CGGCGACAGCGUGG<br>UGACCGGCAGAGGC<br>AGAAUCAACGGCAG<br>ACUGGUGUACGUGU<br>UCUCACAAGACUUU<br>ACCGUCUUCGGAGG<br>AUCCCUGUCAGGGG<br>CUCACGCCCAGAAG<br>AUCUGCAAGAUCAU<br>GGACCAGGCCAUCA<br>CCGUGGGCGCUCCC<br>GUGAUCGGCCUGAA<br>CGACAGCGGAGGCG<br>CCAGGAUCCAAGAG<br>GGAGUGGAGUCCCU<br>GGCCGGCUACGCCG<br>ACAUCUUCCUGAGA<br>AACGUGACCGCCUC<br>GGGCGUGAUCCCAC<br>AGAUCUCCCUGAUC<br>AUGGGACCCUGCGC<br>CGGCGGGGCCGUCU<br>ACAGCCCUGCCCUG<br>ACCGACUUCACCUU<br>CAUGGUGAAGGACA<br>CCAGCUACCUGUUC<br>AUCACCGGCCCCGA<br>CGUGGUCAAGAGCG<br>UGACCAACGAGGAC<br>GUGACCCAGGAGGA<br>GCUCGGCGGAGCCA<br>AGACUCACACAACC<br>AUGUCCGGCGUCGC<br>UCAUAGGGCCUUCG<br>AGAACGACGUGGAC<br>GCCCUGUGCAACCU<br>GAGAGACUUCUUCA<br>ACUACCUGCCAUUG<br>AGCAGCCAGGAUCC<br>CGCCCCUGUGAGAG<br>AGUGCCACGACCCC<br>AGCGACAGACUGGU<br>GCCCGAGCUGGACA<br>CCAUCGUGCCCCUG<br>GAGAGCACCAAGGC<br>CUACAACAUGGUGG<br>ACAUCAUCCACAGC<br>GUGGUGGACGAGAG<br>AGAGUUCUUCGAGA<br>UCAUGCCCAACUAC<br>GCCAAGAACAUCAU<br>CGUGGGCUUCGCCA<br>GAAUGAACGGCAGA | AGAAAA<br>GAAGAG<br>UAAGAA<br>GAAAUA<br>UAAGAG<br>CCACC | AUAAAG<br>UAGGAA<br>ACACUA<br>CAGCUG<br>GAGCCU<br>CGGUGG<br>CCUAGC<br>UUCUUG<br>CCCCUU<br>GGGCCU<br>CCAUAA<br>AGUAGG<br>AAACAC<br>UACAUC<br>CCCCCA<br>GCCCCU<br>CCUCCC<br>CUUCCU<br>GCACCC<br>GUACCC<br>CCUCCA<br>UAAAGU<br>AGGAAA<br>CACUAC<br>AGUGGU<br>CUUUGA<br>AUAAAG<br>UCUGAG<br>UGGGCG<br>GC | consists<br>from 5' to<br>3' end: 5'<br>UTR of<br>SEQ ID<br>NO: 3,<br>ORF<br>Sequence<br>of SEQ ID<br>NO: 23,<br>and 3'<br>UTR of<br>SEQ ID<br>NO: 178 |

-continued

| CONSTRUCT SEQUENCES |
| By "G5" is meant that all uracils (U) in the mRNA are replaced by N1-methylpseudouracils. |

| mRNA Name | ORF Sequence (Amino Acid) | ORF Sequence (Nucleotide) | 5' UTR Sequence | 3' UTR Sequence | Construct Sequence |
|---|---|---|---|---|---|
| | | ACCGUGGGCAUUGU GGGCAACCAGCCCA AGGUCGCCAGCGGC UGCCUCGACAUCAA CAGCAGCGUGAAGG GCGCCAGAUUCGUG AGAUUCUGCGACGC CUUCAACAUACCUC UGAUCACCUUUGUG GACGUGCCUGGUUU CCUCCCGGGCACCG CCCAAGAAUACGGU GGCAUCAUCAGACA CGGCGCCAAGCUGC UGUACGCCUUCGCC GAGGCCACCGUGCC CAAGGUGACCGUUA UCACCCGCAAAGCC UACGGCGGCGCCUA CGACGUGAUGAGCA GCAAGCACCUGUGU GGCGACACCAAUUA CGCCUGGCCCACCG CCGAGAUCGCCGUC AUGGGCGCGAAAGG AGCCGUGGAGAUCA UCUUCAAGGGCCAC GAGAACGUGGAGGC CGCCCAGGCCGAGU ACAUCGAGAAGUUC GCCAACCCCUUCCC UGCCGCCGUGAGGG GCUUCGUCGACGAU AUCAUCCAGCCCAG CUCCACCCGCGCCA GAAUCUGUUGCGAC CUGGACGUGCUGGC CAGCAAGAAGGUGC AAAGACCCUGGAGA AAGCACGCCAACAU CCCGCUG | | | |

| SEQ ID NO: | 15 | 23 | 64 | 112 | 67 |
|---|---|---|---|---|---|
| PCCB_22 (hPCCB; G5) Cap: C1 PolyA tail: 100 nt | MAAALRVAAVGARL SVLASGLRAAVRSLC SQATSVNERIENKRR TALLGGGQRRIDAQH KRGKLTARERISLLL DPGSFVESDMFVEHR CADFGMAADKNKFP GDSVVTGRGRINGRL VYVFSQDFTVFGGSL SGAHAQKICKIMDQA ITVGAPVIGLNDSGG ARIQEGVESLAGYAD IFLRNVTASGVIPQISL IMGPCAGGAVYSPAL TDFTFMVKDTSYLFI TGPDVVKSVTNEDVT QEELGGAKTHTTMS GVAHRAFENDVDAL CNLRDFFNYLPLSSQ DPAPVRECHDPSDRL VPELDTIVPLESTKAY NMVDIIHSVVDEREF FEIMPNYAKNIIVGFA RMNGRTVGIVGNQP KVASGCLDINSSVKG ARFVRFCDAFNIPLIT FVDVPGFLPGTAQEY GGIIRHGAKLLYAFA | AUGGCCGCAGCCCU CAGAGUGGCUGCCG UGGGAGCCAGACUC AGCGUGCUCGCCUC AGGCCUGCGGGCCG CAGUCAGAAGCCUG UGCAGCCAGGCAAC CUCAGUGAACGAGA GAAUCGAGAACAAG AGACGGACCGCCCU GCUGGGUGGCGGGC AAAGAAGAAUUGAC GCCCAGCACAAGAG AGGCAAGCUGACCG CCCGCGAGCGCAUC AGCCUGCUGCUGGA CCCCGGCAGCUUCG UGGAGAGCGACAUG UUCGUGGAGCAUCG GUGUGCCGACUUCG GCAUGGCCGCCGAC AAGAACAAGUUCCC CGGCGACAGCGUGG UGACCGGCAGAGGC AGAAUCAACGGCAG ACUGGUGUACGUGU UCUCACAAGACUUU ACCGUCUUCGGAGG | GGGAAA TAAGAG AGAAAA GAAGAG TAAGAA GAAATA TAAGAG CCACC | UGAUAA UAGUCC AUAAAG CAGCUG GAGCCU CGGUGG CCUAGC UUCUUG CCCCUU GGGCCU CCCCCC AGCCCC UCCUCC CCUUCC UGCACC CGUACC CCCCGC AUUAUU ACUCAC GGUACG AGUGGU CUUUGA AUAAAG UCUGAG UGGGCG GC | SEQ ID NO: 67 consists from 5' to 3' end: 5' UTR of SEQ ID NO: 64, ORF Sequence of SEQ ID NO: 23, and 3' UTR of SEQ ID NO: 112 |

-continued

| | CONSTRUCT SEQUENCES | | | | |
| --- | --- | --- | --- | --- | --- |
| | By "G5" is meant that all uracils (U) in the mRNA are replaced by N1-methylpseudouracils. | | | | |
| mRNA Name | ORF Sequence (Amino Acid) | ORF Sequence (Nucleotide) | 5' UTR Sequence | 3' UTR Sequence | Construct Sequence |
| | EATVPKVTVITRKAY GGAYDVMSSKHLCG DTNYAWPTAEIAVM GAKGAVEIIFKGHEN VEAAQAEYIEKFANP FPAAVRGFVDDIIQPS STRARICCDLDVLAS KKVQRPWRKHANIP L | AUCCCUGUCAGGGG CUCACGCCCAGAAG AUCUGCAAGAUCAU GGACCAGGCCAUCA CCGUGGGCGCUCCC GUGAUCGGCCUGAA CGACAGCGGAGGCG CCAGGAUCCAAGAG GGAGUGGAGUCCCU GGCCGGCUACGCCG ACAUCUUCCUGAGA AACGUGACCGCCUC GGGCGUGAUCCCAC AGAUCUCCCUGAUC AUGGGACCCUGCGC CGGCGGGGCCGUCU ACAGCCCUGCCCUG ACCGACUUCACCUU CAUGGUGAAGGACA CCAGCUACCUGUUC AUCACCGGCCCCGA CGUGGUCAAGAGCG UGACCAACGAGGAC GUGACCCAGGAGGA GCUCGGCGGAGCCA AGACUCACACAACC AUGUCCGGCGUCGC UCAUAGGGCCUUCG AGAACGACGUGGAC GCCCUGUGCAACCU GAGAGACUUCUUCA ACUACCUGCCAUUG AGCAGCCAGGAUCC CGCCCCUGUGAGAG AGUGCCACGACCCC AGCGACAGACUGGU GCCCGAGCUGGACA CCAUCGUGCCCCUG GAGAGCACCAAGGC CUACAACAUGGUGG ACAUCAUCCACAGC GUGGUGGACGAGAG AGAGUUCUUCGAGA UCAUGCCCAACUAC GCCAAGAACAUCAU CGUGGGCUUCGCCA GAAUGAACGGCAGA ACCGUGGGCAUUGU GGGCAACCAGCCCA AGGUCGCCAGCGGC UGCCUCGACAUCAA CAGCAGCGUGAAGG GCGCCAGAUUCGUG AGAUUCUGCGACGC CUUCAACAUACCUC UGAUCACCUUUGUG GACGUGCCUGGUUU CCUCCCGGGCACCG CCCAAGAAUACGGU GGCAUCAUCAGACA CGGCGCCAAGCUGC UGUACGCCUUCGCC GAGGCCACCGUGCC CAAGGUGACCGUUA UCACCCGCAAAGCC UACGGCGGCGCCUA CGACGUGAUGAGCA GCAAGCACCUGUGU GGCGACACCAAUUA CGCCUGGCCCACCG CCGAGAUCGCCGUC AUGGGCGCGAAAGG AGCCGUGGAGAUCA | | | |

CONSTRUCT SEQUENCES
By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | UCUUCAAGGGCCAC GAGAACGUGGAGGC CGCCCAGGCCGAGU ACAUCGAGAAGUUC GCCAACCCCUUCCC UGCCGCCGUGAGGG GCUUCGUCGACGAU AUCAUCCAGCCCAG CUCCACCCGCGCCA GAAUCUGUUGCGAC CUGGACGUGCUGGC CAGCAAGAAGGUGC AAAGACCCUGGAGA AAGCACGCCAACAU CCCGCUG | | | |

SEQ ID
NO:                15                26               3         150          49

| PCCB-014 (hPCCB; G5) Cap: C1 PolyA tail: 100 nt | MAAALRVAAVGARL SVLASGLRAAVRSLC SQATSVNERIENKRR TALLGGGQRRIDAQH KRGKLTARERISLLL DPGSFVESDMFVEHR CADFGMAADKNKFP GDSVVTGRGRINGRL VYVFSQDFTVFGGSL SGAHAQKICKIMDQA ITVGAPVIGLNDSGG ARIQEGVESLAGYAD IFLRNVTASGVIPQISL IMGPCAGGAVYSPAL TDFTFMVKDTSYLFI TGPDVVKSVTNEDVT QEELGGAKTHTTMS GVAHRAFENDVDAL CNLRDFFNYLPLSSQ DPAPVRECHDPSDRL VPELDTIVPLESTKAY NMVDIIHSVVDEREF FEIMPNYAKNIIVGFA RMNGRTVGIVGNQP KVASGCLDINSSVKG ARFVRFCDAFNIPLIT FVDVPGFLPGTAQEY GGIIRHGAKLLYAFA EATVPKVTVITRKAY GGAYDVMSSKHLCG DTNYAWPTAEIAVM GAKGAVEIIFKGHEN VEAAQAEYIEKFANP FPAAVRGFVDDIIQPS STRARICCDLDVLAS KKVQRPWRKHANIP L | AUGGCCGCCGCCCU GAGAGUGGCCGCUG UGGGCGCCCAGGCUG AGCGUGCUCGCUAG CGGCCUGAGAGCCG CCGUUAGAAGCCUG UGCAGCCAGGCCAC CUCCGUGAACGAGA GGAUCGAGAAUAAG AGACGAACCGCCCU GCUCGGCGGCGGCC AGAGACGCAUCGAC GCCCAGCACAAGCG AGGUAAGCUGACAG CCAGGGAGCGAAUC AGCCUGCUCCUGGA CCCCGGAAGCUUCG UGGAAUCCGACAUG UUCGUUGAGCACAG AUGCGCCGACUUCG GCAUGGCCGCCGAC AAGAACAAGUUUCC AGGGGACUCAGUGG UCACCGGAAGAGGC CGCAUCAACGGCCG CCUGGUCUACGUGU UCUCACAGGACUUU ACAGUGUUCGGCGG CAGCCUGUCAGGCG CCCAUGCCCAGAAG AUCUGCAAGAUCAU GGAUCAGGCCAUCA CAGUGGGCGCCCCC GUGAUCGGUCUGAA CGACUCUGGCGGCG CCAGAAUUCAAGAG GGCGUGGAGAGCCU GGCCGGUUACGCCG ACAUUUUCCUGAGG AACGUCACCGCCAG CGGCGUCAUCCCCC AGAUCUCUCUGAUC AUGGGCCCCUGCGC UGGCGGCGCCGUGU ACAGCCCCGCCCUG ACCGAUUUCACCUU CAUGGUGAAGGAUA CCAGCUAUCUGUUC AUCACCGGCCCGGA UGUGGUGAAGAGU GUGACCAACGAGGA CGUGACCCAGGAGG AGCUGGGUGGAGCC AAGACUCACACAAC | GGGAAA UAAGAG AGAAAA GAAGAG UAAGAA GAAAUA UAAGAG CCACC | UGAUAA UAGGCU GGAGCC UCGGUG GCCAUG CUUCUU GCCCCU UGGGCC UCCCCC CAGCCC CUCCUC CCCUUC CUGCAC CCGUAC CCCCGU GGUCUU UGAAUA AAGUCU GAGUGG GCGGC | SEQ ID NO: 49 consists from 5' to 3' end: 5' UTR of SEQ ID NO: 3, ORF Sequence of SEQ ID NO: 26, and 3' UTR of SEQ ID NO: 150 |

-continued

CONSTRUCT SEQUENCES

By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | CAUGUCCGGCGUGG | | | |
| | | CCCAUCGAGCCUUU | | | |
| | | GAGAACGACGUCGA | | | |
| | | CGCCCUGUGUAACC | | | |
| | | UGAGAGACUUCUUC | | | |
| | | AAUUACCUGCCCCU | | | |
| | | GAGCUCCCAGGACC | | | |
| | | CCGCCCCAGUUAGG | | | |
| | | GAGUGCCACGAUCC | | | |
| | | CUCCGACCGCCUGG | | | |
| | | UGCCCGAGCUGGAC | | | |
| | | ACCAUCGUGCCCCU | | | |
| | | GGAGAGCACCAAGG | | | |
| | | CCUACAACAUGGUG | | | |
| | | GAUAUCAUCCAUAG | | | |
| | | CGUCGUCGACGAGC | | | |
| | | GCGAGUUCUUCGAG | | | |
| | | AUCAUGCCCAACUA | | | |
| | | CGCCAAGAACAUCA | | | |
| | | UCGUGGGCUUUGCC | | | |
| | | AGGAUGAACGGCCG | | | |
| | | CACCGUGGGCAUUG | | | |
| | | UGGGCAACCAGCCC | | | |
| | | AAGGUGGCCUCUGG | | | |
| | | CUGCCUGGACAUCA | | | |
| | | ACAGCAGCGUGAAG | | | |
| | | GGUGCUAGGUUCGU | | | |
| | | GAGGUUCUGCGAUG | | | |
| | | CCUUUAACAUCCCA | | | |
| | | CUUAUCACCUUCGU | | | |
| | | UGAUGUCCCUGGCU | | | |
| | | UCCUGCCUGGCACC | | | |
| | | GCCCAGGAGUACGG | | | |
| | | CGGCAUCAUCAGAC | | | |
| | | AUGGUGCCAAGCUG | | | |
| | | CUGUACGCCUUCGC | | | |
| | | CGAGGCCACCGUGC | | | |
| | | CCAAGGUGACCGUG | | | |
| | | AUUACCCGGAAAGC | | | |
| | | CUACGGCGGCGCCU | | | |
| | | ACGACGUCAUGAGC | | | |
| | | AGCAAGCACCUGUG | | | |
| | | CGGCGACACCAACU | | | |
| | | ACGCCUGGCCCACC | | | |
| | | GCCGAGAUCGCCGU | | | |
| | | CAUGGGCGCCAAGG | | | |
| | | GGGCCGUCGAGAUC | | | |
| | | AUCUUCAAGGGACA | | | |
| | | CGAGAACGUGGAGG | | | |
| | | CCGCUCAGGCCGAG | | | |
| | | UACAUCGAGAAGUU | | | |
| | | CGCUAACCCUUUCC | | | |
| | | CCGCCGCUGUUAGA | | | |
| | | GGAUUCGUGGAUGA | | | |
| | | CAUCAUCCAGCCAA | | | |
| | | GCAGCACCCGGGCC | | | |
| | | AGGAUCUGCUGUGA | | | |
| | | CCUGGAUGUGCUGG | | | |
| | | CUAGCAAGAAGGUG | | | |
| | | CAGAGACCCUGGAG | | | |
| | | AAAGCACGCCAACA | | | |
| | | UUCCCCUG | | | |

| SEQ ID NO: | 15 | 27 | 3 | 150 | 50 |
|---|---|---|---|---|---|
| PCCB-014 (hPCCB; G5) Cap: C1 PolyA tail: 100 nt | MAAALRVAAVGARL SVLASGLRAAVRSLC SQATSVNERIENKRR TALLGGGQRRIDAQH KRGKLTARERISLLL DPGSFVESDMFVEHR CADFGMAADKNKFP | AUGGCCGCCGCCCU GAGAGUGGCCGCUG UGGGCGCCAGGCUG AGCGUGCUCGCUAG CGGCCUGAGAGCCG CCGUUAGAAGCCUG UGCAGCCAGGCCAC | GGGAAA UAAGAG AGAAAA GAAGAG UAAGAA GAAAUA UAAGAG | UGAUAA UAGGCU GGAGCC UCGGUG GCCAUG CUUCUU GCCCCU | SEQ ID NO: 50 consists from 5' to 3' end: 5' UTR of SEQ ID |

-continued

CONSTRUCT SEQUENCES
By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | GDSVVTGRGRINGRL | CUCCGUGAACGAGA | CCACC | UGGGCC | NO: 3, |
| | VYVFSQDFTVFGGSL | GGAUCGAGAAUAAG | | UCCCCC | ORF |
| | SGAHAQKICKIMDQA | AGACGAACCGCCCU | | CAGCCC | Sequence |
| | ITVGAPVIGLNDSGG | GCUCGGCGGCGGCC | | CUCCUC | of SEQ ID |
| | ARIQEGVESLAGYAD | AGAGACGCAUCGAC | | CCCUUC | NO: 27, |
| | IFLRNVTASGVIPQISL | GCCCAGCACAAGCG | | CUGCAC | and 3' |
| | IMGPCAGGAVYSPAL | AGGUAAGCUGACAG | | CCGUAC | UTR of |
| | TDFTFMVKDTSYLFI | CCAGGGAGCGAAUC | | CCCCGU | SEQ ID |
| | TGPDVVKSVTNEDVT | AGCCUGCUCCUGGA | | GGUCUU | NO: 150 |
| | QEELGGAKTHTTMS | CCCCGGAAGCUUCG | | UGAAUA | |
| | GVAHRAFENDVDAL | UGGAAUCCGACAUG | | AAGUCU | |
| | CNLRDFFNYLPLSSQ | UUCGUUGAGCACAG | | GAGUGG | |
| | DPAPVRECHDPSDRL | AUGCGCCGACUUCG | | GCGGC | |
| | VPELDTIVPLESTKAY | GCAUGGCCGCCGAC | | | |
| | NMVDIIHSVVDEREF | AAGAACAAGUUUCC | | | |
| | FEIMPNYAKNIIVGFA | AGGGGACUCAGUGG | | | |
| | RMNGRTVGIVGNQP | UCACCGGAAGAGGC | | | |
| | KVASGCLDINSSVKG | CGCAUCAACGGCCG | | | |
| | ARFVRFCDAFNIPLIT | CCUGGUCUACGUGU | | | |
| | FVDVPGFLPGTAQEY | UCUCACAGGACUUU | | | |
| | GGIIRHGAKLLYAFA | ACAGUGUUCGGCGG | | | |
| | EATVPKVTVITRKAY | CAGCCUGUCAGGCG | | | |
| | GGAYDVMSSKHLCG | CCCAUGCCCAGAAG | | | |
| | DTNYAWPTAEIAVM | AUCUGCAAGAUCAU | | | |
| | GAKGAVEIIFKGHEN | GGAUCAGGCCAUCA | | | |
| | VEAAQAEYIEKFANP | CAGUGGGCGCCCCC | | | |
| | FPAAVRGFVDDIIQPS | GUGAUCGGUCUGAA | | | |
| | STRARICCDLDVLAS | CGACUCUGGCGGCG | | | |
| | KKVQRPWRKHANIP | CCAGAAUUCAAGAG | | | |
| | L | GGCGUGGAGAGCCU | | | |
| | | GGCCGGUUACGCCG | | | |
| | | ACAUUUUCCUGAGG | | | |
| | | AACGUCACCGCCAG | | | |
| | | CGGCGUCAUCCCCC | | | |
| | | AGAUCUCUCUGAUC | | | |
| | | AUGGGCCCCUGCGC | | | |
| | | UGGCGGCGCCGUGU | | | |
| | | ACAGCCCCGCCCUG | | | |
| | | ACCGAUUUCACCUU | | | |
| | | CAUGGUGAAGGAUA | | | |
| | | CCAGCUAUCUGUUC | | | |
| | | AUCACCGGCCCGGA | | | |
| | | UGUGGUGAAGAGU | | | |
| | | GUGACCAACGAGGA | | | |
| | | CGUGACCCAGGAGG | | | |
| | | AGCUGGGUGGAGCC | | | |
| | | AAGACUCACACAAC | | | |
| | | CAUGUCCGGCGUGG | | | |
| | | CCCAUCGAGCCUUU | | | |
| | | GAGAACGACGUCGA | | | |
| | | CGCCCUGUGUAACC | | | |
| | | UGAGAGACUUCUUC | | | |
| | | AAUUACCUGCCCCU | | | |
| | | GAGCUCCCAGGACC | | | |
| | | CCGCCCCAGUUAGG | | | |
| | | GAGUGCCACGAUCC | | | |
| | | CUCCGACCGCCUGG | | | |
| | | UGCCCGAGCUGGAC | | | |
| | | ACCAUCGUGCCCCU | | | |
| | | GGAGAGCACCAAGG | | | |
| | | CCUACAACAUGGUG | | | |
| | | GAUAUCAUCCAUAG | | | |
| | | CGUCGUCGACGAGC | | | |
| | | GCGAGUUCUUCGAG | | | |
| | | AUCAUGCCCAACUA | | | |
| | | CGCCAAGAACAUCA | | | |
| | | UCGUGGGCUUUGCC | | | |
| | | AGGAUGAACGGCCG | | | |
| | | CACCGUGGGCAUUG | | | |
| | | UGGGCAACCAGCCC | | | |
| | | AAGGUGGCCUCUGG | | | |
| | | CUGCCUGGACAUCA | | | |
| | | ACAGCAGCGUGAAG | | | |

-continued

| CONSTRUCT SEQUENCES | | | | | |
|---|---|---|---|---|---|
| By "G5" is meant that all uracils (U) in the mRNA are replaced by N1-methylpseudouracils. | | | | | |
| mRNA Name | ORF Sequence (Amino Acid) | ORF Sequence (Nucleotide) | 5' UTR Sequence | 3' UTR Sequence | Construct Sequence |
| | | GGUGCUAGGUUCGU GAGGUUCUGCGAUG CCUUUAACAUCCCA CUUAUCACCUUCGU UGAUGUCCCUGGCU UCCUGCCUGGCACC GCCCAGGAGUACGG CGGCAUCAUCAGAC AUGGUGCCAAGCUG CUGUACGCCUUCGC CGAGGCCACCGUGC CCAAGGUGACCGUG AUUACCCGGAAAGC CUACGGCGGCGCCU ACGACGUCAUGAGC AGCAAGCACCUGUG CGGCGACACCAACU ACGCCUGGCCCACC GCCGAGAUCGCCGU CAUGGGCGCCAAGG GGGCCGUCGAGAUC AUCUUCAAGGGACA CGAGAACGUGGAGG CCGCUCAGGCCGAG UACAUCGAGAAGUU CGCUAACCCUUUCC CCGCCGCUGUUAGA GGAUUCGUGGAUGA CAUCAUCCAGCCAA GCAGCACCCGGGCC AGGAUCUGCUGUGA CCUGGAUGUGCUGG CUAGCAAGAAGGUG CAGAGACCCUGGAG AAAGCACGCCAACA UUCCCCUG | | | |
| SEQ ID NO: | 1 | 51 | 3 | 150 | 57 |
| LX- hPCCA- 01-015.2 (hPCCA; G5; SE#7) Cap: C1 PolyA tail: 100 nt | MAGFWVGTAPLVAA GRRGRWPPQQLMLS AALRTLKHVLYYSR QCLMVSRNLGSVGY DPNEKTFDKILVANR GEIACRVIRTCKKMG IKTVAIHSDVDASSV HVKMADEAVCVGPA PTSKSYLNMDAIMEA IKKTRAQAVHPGYGF LSENKEFARCLAAED VVFIGPDTHAIQAMG DKIESKLLAKKAEVN TIPGFDGVVKDAEEA VRIAREIGYPVMIKAS AGGGGKGMRIAWDD EETRDGFRLSSQEAA SSFGDDRLLIEKFIDN PRHIEIQVLGDKHGN ALWLNERECSIQRRN QKVVEEAPSIFLDAE TRRAMGEQAVALAR AVKYSSAGTVEFLVD SKKNFYFLEMNTRLQ VEHPVTECITGLDLV QEMIRVAKGYPLRH KQADIRINGWAVECR VYAEDPYKSFGLPSI GRLSQYQEPLHLPGV RVDSGIQPGSDISIYY DPMISKLITYGSDRTE ALKRMADALDNYVI RGVTHNIALLREVIIN | AUGGCCGGGUUCUG GGUGGGCACCGCCC CCCUGGUCGCUGCA GGCCGGAGGGGCAG GUGGCCCCCUCAGC AGCUGAUGCUGAGC GCCGCUCUUCGGAC ACUCAAACACGUGC UGUACUAUAGCAGA CAGUGCCUGAUGGU GAGUAGGAACCUCG GCAGCGUGGGGUAU GAUCCCAACGAGAA GACCUUCGACAAGA UCCUGGUGGCAAAU CGGGGCGAGAUCGC CUGCAGGGUGAUCA GAACCUGCAAGAAG AUGGGCAUCAAGAC CGUCGCUAUUCACA GCGACGUGGAUGCC UCAAGCGUGCACGU GAAGAUGGCAGACG AAGCAGUGUGUGUG GGCCCCGCCCCUAC UUCAAAGUCCUACC UUAAUAUGGACGCA AUUAUGGAGGCAAU CAAGAAGACCAGGG CUCAAGCUGUGCAU CCAGGAUAUGGCUU CCUGUCCGAGAACA AGGAGUUCGCCAGA | GGGAAA UAAGAG AGAAAA GAAGAG UAAGAA GAAAUA UAAGAG CCACC | UGAUAA UAGGCU GGAGCC UCGGUG CUUCUU GCCAUG GCCCCU UGGGCC UCCCCC CAGCCC CUCCUC CCCUUC CUGCAC CCGUAC CCCCGU GGUCUU UGAAUA AAGUCU GAGUGG GCGGC | SEQ ID NO: 57 consists from 5' to 3' end: 5' UTR of SEQ ID NO: 3, ORF Sequence of SEQ ID NO: 51, and 3' UTR of SEQ ID NO: 150 |

-continued

CONSTRUCT SEQUENCES
By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | SRFVKGDISTKFLSDV YPDGFKGHMLTKSE KNQLLAIASSLFVAF QLRAQHFQENSRMP VIKPDIANWELSVKL IIDKVHTVVASNNGS VFSVEVDGSKLNVTS TWNLASPLLSVSVDG TQRTVQCLSREAGGN MSIQFLGTVYKVNIL TRLAAELNKFMLEK VTEDTSSVLRSPMPG VVVAVSVKPGDAVA EGQEICVIEAMKMQN SMTAGKTGTVKSVH CQAGDTVGEGDLLV ELE | UGCCUGGCAGCCGA GGAUGUGGUCUUUA UCGGCCCUGAUACA CACGCCAUCCAGGC UAUGGGGGAUAAG AUCGAGAGUAAGCU GCUGGCGAAGAAAG CCGAGGUGAACACC AUUCCGGGCUUUGA CGGCGUGGUGAAGG ACGCCGAGGAGGCC GUGCGGAUCGCUAG GGAGAUCGGCUACC CUGUGAUGAUCAAG GCUUCUGCCGGCGG AGGCGGAAAGGGCA UGCGUAUUGCUUGG GACGACGAGGAAAC CCGCGACGGCUUUC GGCUGAGCAGCCAG GAAGCCGCCAGUAG CUUUGGCGAUGACC GGCUUCUUAUAGAG AAGUUUAUCGACAA CCCCAGACACAUUG AGAUCCAGGUAUUG GGCGAUAAACACGG AAAUGCCCUUUGGC UGAAUGAGAGAGA AUGCUCCAUCCAGA GAAGGAACCAGAAG GUGGUGGAGGAGGC CCCCUCAAUCUUCC UGGACGCCGAGACC CGUAGAGCCAUGGG CGAGCAGGCCGUGG CCCUCGCCAGAGCU GUGAAGUAUUCCUC UGCUGGCACCGUGG AGUUCUUAGUGGAU UCCAAGAAGAACUU CUACUUCCUCGAGA UGAAUACCAGACUC CAGGUGGAGCAUCC CGUCACCGAAUGCA UCACUGGCCUGGAC CUGGUGCAGGAGAU GAUCAGAGUUGCUA AGGGUUACCCACUG CGCCACAAGCAGGC UGACAUCAGGAUCA ACGGGUGGGCAGUG GAGUGCAGAGUGUA UGCUGAGGACCCCU ACAAGAGCUUCGGC CUGCCGAGCAUCGG CCGGCUGAGCCAGU ACCAGGAACCCCUC CACCUGCCUGGCGU ACGGGUGGACAGUG GAAUCCAGCCCGGC AGCGACAUCAGCAU UUAUUACGAUCCCA UGAUCUCGAAGUUG AUCACCUAUGGGUC UGACAGAACCGAGG CCCUGAAGAGAAUG GCCGACGCGCUGGA UAACUACGUGAUUC GGGGAGUGACUCAC AACAUAGCUCUACU GCGUGAGGUCAUCA UCAAUAGCAGAUUC | | | |

-continued

| CONSTRUCT SEQUENCES |
| By "G5" is meant that all uracils (U) in the mRNA are replaced by N1-methylpseudouracils. |

| mRNA Name | ORF Sequence (Amino Acid) | ORF Sequence (Nucleotide) | 5' UTR Sequence | 3' UTR Sequence | Construct Sequence |
|---|---|---|---|---|---|
| | | GUAAAGGGCGACAU | | | |
| | | UAGCACCAAGUUUC | | | |
| | | UUUCCGACGUGUAC | | | |
| | | CCAGACGGUUUUAA | | | |
| | | GGGACACAUGCUGA | | | |
| | | CAAAGUCUGAGAAG | | | |
| | | AACCAGCUGCUGGC | | | |
| | | CAUAGCCAGCAGCC | | | |
| | | UGUUCGUGGCCUUU | | | |
| | | CAGCUCCGAGCCCA | | | |
| | | ACACUUCCAGGAGA | | | |
| | | ACAGCAGAAUGCCA | | | |
| | | GUGAUCAAGCCUGA | | | |
| | | CAUCGCCAACUGGG | | | |
| | | AGCUGUCUGUGAAA | | | |
| | | CUGCACGACAAGGU | | | |
| | | GCAUACCGUCGUGG | | | |
| | | CCAGCAACAAUGGC | | | |
| | | UCCGUGUUCUCCGU | | | |
| | | GGAGGUGGAUGGCU | | | |
| | | CAAAGCUGAACGUG | | | |
| | | ACCUCGACAUGGAA | | | |
| | | CCUCGCCUCUCCCC | | | |
| | | UGCUGAGUGUGAGC | | | |
| | | GUGGACGGCACACA | | | |
| | | GAGAACCGUGCAGU | | | |
| | | GCCUGAGUAGAGAA | | | |
| | | GCAGGGGGCAACAU | | | |
| | | GUCCAUUCAGUUUC | | | |
| | | UCGGCACCGUGUAC | | | |
| | | AAGGUCAAUAUUCU | | | |
| | | CACCAGACUCGCCG | | | |
| | | CCGAGCUGAACAAG | | | |
| | | UUCAUGCUUGAGAA | | | |
| | | GGUGACCGAGGAUA | | | |
| | | CUAGUUCCGUGCUC | | | |
| | | AGAUCCCCUAUGCC | | | |
| | | CGGCGUGGUGGUCG | | | |
| | | CUGUGUCCGUCAAG | | | |
| | | CCCGGCGACGCCGU | | | |
| | | GGCCGAGGGACAGG | | | |
| | | AGAUUUGCGUGAUU | | | |
| | | GAGGCUAUGAAGAU | | | |
| | | GCAGAAUAGCAUGA | | | |
| | | CUGCUGGCAAGACG | | | |
| | | GGCACAGUGAAGAG | | | |
| | | CGUGCAUUGCCAGG | | | |
| | | CAGGCGACACAGUG | | | |
| | | GGCGAAGGAGACCU | | | |
| | | GCUGGUCGAGUUAG | | | |
| | | AG | | | |

| SEQ ID NO: | | 1 | 52 | 3 | 150 | 58 |
|---|---|---|---|---|---|---|
| LX-hPCCA-10-002 (hPPCA; G5; Pv2-SE#1) Cap: C1 PolyA tail: 100 nt | | MAGFWVGTAPLVAA GRRGRWPPQQLMLS AALRTLKHVLYYSR QCLMVSRNLGSVGY DPNEKTFDKILIANRG EIACRVIRTCKKMGI KTVAIHSDVDASSVH VKMADEAVCVGPAP TSKSYLNMDAIMEAI KKTRAQAVHPGYGF LSENKEFARCLAAED VVFIGPDTHAIQAMG DKIESKLLAKKAEVN TIPGFDGVVKDAEEA VRIAREIGYPVMIKAS AGGGGKGMRIAWDD EETRDGFRLSSQEAA SSFGDDRLLIEKFIDN | AUGGCAGGCUUCUG GGUUGGCACUGCCC CACUCGUGGCCGCC GGCAGAAGGGGAAG GUGGCCUCCCCAGC AGCUCAUGCUGUCC GCCGCUGCUGCAAC CCUGAAGCACGUGC UGUAUUAUAGCAGG CAGUGCCUCAUGGU UUCCCGGAACCUGG GGAGCGUGGGCUAU GACCCUAAUGAGAA GACUUUCGACAAGA UCCUGAUCGCUAAC AGAGGCGAGAUCGC CUGCAGGGUGAUCA GAACAUGCAAGAAG | GGGAAA UAAGAG AGAAAA GAAGAG UAAGAA GAAAUA UAAGAG CCACC | UGAUAA UAGGCU GGAGCC UCGGUG GCCAUG CUUCUU GCCCCU GCCAUG UGGGCC UCCCCC CAGCCC CUCCUC CCCUUC CUGCAC CCGUAC CCCCGU GGUCUU UGAAUA AAGUCU | SEQ ID NO: 58 consists from 5' to 3' end: 5' UTR of SEQ ID NO: 3, ORF Sequence of SEQ ID NO: 52, and 3' UTR of SEQ ID NO: 150 |

-continued

| CONSTRUCT SEQUENCES |
| --- |

By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
| --- | --- | --- | --- | --- | --- |
| | PRHIEIQVLGDKHGN | AUGGGCAUCAAGAC | | GAGUGG | |
| | ALWLNERECSIQRRN | CGUCGCGAUCCAUA | | GCGGC | |
| | QKVVEEAPSIFLDAE | GCGACGUGGAUGCC | | | |
| | TRRAMGEQAVALAR | AGCAGCGUUCACGU | | | |
| | AVKYSSAGTVEFLVD | CAAGAUGGCCGACG | | | |
| | SKKNFYFLEMNTRLQ | AGGCUGUGUGCGUC | | | |
| | VEHPVTECITGLDLV | GGCCCCGCCCCAAC | | | |
| | QEMIRVAKGYPLRH | UUCCAAGAGCUAUC | | | |
| | KQADIRINGWAVECR | UGAACAUGGACGCC | | | |
| | VYAEDPYKSFGLPSI | AUAAUGGAGGCUAU | | | |
| | GRLSQYQEPLHLPGV | CAAGAAGACCAGAG | | | |
| | RVDSGIQPGSDISIYY | CCCAGGCAGUUCAU | | | |
| | DPMISKLITYGSDRTE | CCCGGCUACGGAUU | | | |
| | ALKRMEDALDNYVI | CCUGAGCGAGAACA | | | |
| | RGVTHNIALLREVIIN | AGGAGUUCGCUAGA | | | |
| | SRFVKGDISTKFLSDV | UGUCUGGCCGCCGA | | | |
| | YPDGFKGHMLTKSE | AGACGUGGUUUUCA | | | |
| | KNQLLAIASSLFVAF | UCGGUCCAGACACC | | | |
| | QLRAQHFQENSRVPV | CAUGCCAUCCAAGC | | | |
| | IKPDIANWELSVKLH | CAUGGGCGAUAAGA | | | |
| | DKVHTVVASNNGSV | UCGAGAGCAAGCUC | | | |
| | FSVEVDGSKLNVTST | CUGGCCAAGAAGGC | | | |
| | WNLASPLLSVSVDGT | CGAGGUGAACACCA | | | |
| | QRTVQCLSREAGGN | UCCCCGGCUUCGAU | | | |
| | MSIQFLGTVYKVNIL | GGCGUGGUGAAGGA | | | |
| | TRLAAELNKFMLEK | CGCGGAGGAGGCAG | | | |
| | VTEDTSSVLRSPMPG | UGCGCAUUGCCAGG | | | |
| | VVVAVSVKPGDAVA | GAGAUCGGCUACCC | | | |
| | EGQEICVIEAMKMQN | CGUGAUGAUCAAGG | | | |
| | SMTAGKTGTVKSVH | CUUCCGCAGGGGGA | | | |
| | CQAGDTVGEGDLLV | GGCGGCAAAGGCAU | | | |
| | ELE | GCGGAUUGCCUGGG | | | |
| | | AUGAUGAAGAAACC | | | |
| | | AGAGAUGGCUUCAG | | | |
| | | ACUGUCAAGCCAGG | | | |
| | | AGGCCGCCAGCAGC | | | |
| | | UUCGGCGACGACAG | | | |
| | | ACUGCUGAUCGAGA | | | |
| | | AGUUUAUAGAUAAC | | | |
| | | CCCCGACACAUAGA | | | |
| | | AAUCCAGGUGCUGG | | | |
| | | GAGACAAGCACGGC | | | |
| | | AACGCUCUGUGGCU | | | |
| | | GAACGAGCGGGAAU | | | |
| | | GCAGUAUCCAGAGG | | | |
| | | AGAAACCAGAAGGU | | | |
| | | GGUUGAGGAGGCCC | | | |
| | | CCUCAAUCUUCCUG | | | |
| | | GAUGCCGAGACAAG | | | |
| | | ACGCGCCAUGGGUG | | | |
| | | AGCAGGCUGUAGCC | | | |
| | | CUCGCCCGUGCCGU | | | |
| | | GAAGUAUAGCAGCG | | | |
| | | CCGGGACAGUGGAG | | | |
| | | UUCUUGGUCGACUC | | | |
| | | CAAGAAGAAUUUCU | | | |
| | | AUUUUCUGGAGAUG | | | |
| | | AACACUCGGCUCCA | | | |
| | | AGUAGAGCACCCCG | | | |
| | | UGACUGAGUGCAUU | | | |
| | | ACAGGCCUUGAUCU | | | |
| | | GGUGCAGGAGAUGA | | | |
| | | UUAGGGUUGCCAAG | | | |
| | | GGCUACCCUCUGCG | | | |
| | | CCACAAGCAGGCCG | | | |
| | | ACAUCAGGAUCAAU | | | |
| | | GGCUGGGCUGUCGA | | | |
| | | GUGUAGGGUGUACG | | | |
| | | CAGAGGACCCGUAC | | | |
| | | AAGAGCUUCGGCCU | | | |
| | | UCCCUCUAUUGGCA | | | |
| | | GGCUGAGCCAGUAC | | | |
| | | CAGGAGCCUCUGCA | | | |

-continued

CONSTRUCT SEQUENCES
By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | CCUACCCGGCGUUC GCGUGGACAGCGGU AUCCAACCAGGCUC UGAUAUCAGCAUUU AUUACGACCCAAUG AUCUCAAAGCUGAU CACAUACGGCAGCG ACAGAACCGAGGCC CUGAAGCGAAUGGA GGACGCCCUGGACA ACUACGUGAUCCGG GGCGUCACACAUAA CAUUGCCCUGCUGA GAGAGGUGAUCAUU AAUUCUCGGUUCGU CAAAGGCGACAUCA GCACUAAGUUUCUG AGCGACGUGUACCC CGACGGGUUUAAAG GCCACAUGCUGACA AAGAGCGAGAAGAA CCAGUUGCUGGCCA UCGCCUCUAGCCUG UUCGUAGCCUUCCA GCUGCGAGCACAGC ACUUCCAGGAGAAU AGCAGAGUGCCAGU GAUCAAGCCCGACA UCGCUAACUGGGAG CUGAGCGUGAAGCU CCAUGAUAAGGUCC ACACAGUUGUGGCC AGCAACAACGGCUC AGUGUUCAGCGUGG AGGUAGACGGCUCC AAGCUGAACGUGAC CAGCACUUGGAAUC UGGCCAGCCCCCUG CUGAGCGUGUCCGU GGACGGCACCCAGA GAACCGUGCAGUGC CUGAGCAGGGAGGC CGGGGGCAACAUGU CCAUCCAGUUUCUG GGGACCGUCUAUAA GGUUAACAUCCUGA CUAGACUGGCGGCU GAGCUUAACAAGUU UAUGUUAGAGAAA GUGACCGAGGAUAC AAGCAGCGUGCUGC GUAGCCCCAUGCCU GGCGUGGUCGUGGC CGUGAGCGUCAAGC CAGGCGAUGCAGUG GCUGAGGGCCAGGA GAUUUGUGUGAUA GAGGCCAUGAAGAU GCAGAACUCUAUGA CCGCCGGAAAGACU GGCACCGUGAAGUC UGUCCAUUGUCAGG CCGGAGACACCGUG GGGGAAGGAGACCU GCUCGUCGAGCUGG AG | | | |

| SEQ ID NO: | 1 | 53 | 3 | 150 | 59 |
|---|---|---|---|---|---|
| LX- hPCCA- 01-018 | MAGFWVGTAPLVAA GRRGRWPPQQLMLS AALRTLKHVLYYSR | AUGGCCGGCUUCUG GGUGGGCACCGCUC CAUUGGUGGCCGCC | GGGAAA UAAGAG AGAAAA | UGAUAA UAGGCU GGAGCC | SEQ ID NO: 59 consists |

-continued

CONSTRUCT SEQUENCES
By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| (hPCCA; G5; SE#9) Cap: C1 PolyA tail: 100 nt | QCLMVSRNLGSVGY DPNEKTFDKILVANR GEIACRVIRTCKKMG IKTVAIHSDVDASSV HVKMADEAVCVGPA PTSKSYLNMDAIMEA IKKTRAQAVHPGYGF LSENKEFARCLAAED VVFIGPDTHAIQAMG DKIESKLLAKKAEVN TIPGFDGVVKDAEEA VRIAREIGYPVMIKAS AGGGGKGMRIAWDD EETRDGFRLSSQEAA SSFGDDRLLIEKFIDN PRHIEIQVLGDKHGN ALWLNERECSIQRRN QKVVEEAPSIFLDAE TRRAMGEQAVALAR AVKYSSAGTVEFLVD SKKNFYFLEMNTRLQ VEHPVTECITGLDLV QEMIRVAKGYPLRH KQADIRINGWAVECR VYAEDPYKSFGLPSI GRLSQYQEPLHLPGV RVDSGIQPGSDISIYY DPMISKLITYGSDRTE ALKRMADALDNYVI RGVTHNIALLREVIIN SRFVKGDISTKFLSDV YPDGFKGHMLTKSE KNQLLAIASSLFVAF QLRAQHFQENSRMP VIKPDIANWELSVKL HDKVHTVVASNNGS VFSVEVDGSKLNVTS TWNLASPLLSVSVDG TQRTVQCLSREAGGN MSIQFLGTVYKVNIL TRLAAELNKFMLEK VTEDTSSVLRSPMPG VVVAVSVKPGDAVA EGQEICVIEAMKMQN SMTAGKTGTVKSVH CQAGDTVGEGDLLV ELE | GGCAGACGGGGCCG CUGGCCUCCUCAAC AGCUUAUGUUAUCA GCCGCUUUGCGGAC CUUGAAGCACGUGC UUUACUAUAGCAGG CAGUGCCUCAUGGU GUCCAGGAAUCUCG GCAGCGUGGGUUAC GAUCCUAACGAGAA GACCUUCGAUAAGA UCCUGGUAGCAAAC CGCGGCGAGAUCGC CUGUAGGGUGAUCA GGACCUGCAAGAAG AUGGGAAUAAAGAC CGUGGCCAUUCACU CCGAUGUGGACGCC AGCAGCGUGCACGU UAAGAUGGCCGACG AGGCCGUGUGCGUG GGCCCUGCCCCUAC UAGCAAGUCUUACC UGAACAUGGACGCC AUCAUGGAGGCCAU CAAGAAGACCAGAG CCCAGGCCGUUCAU CCAGGAUACGGCUU CCUGAGCGAGAACA AGGAAUUCGCCAGG UGCCUGGCGGCCGA AGAUGUGGUGUUCA UCGGUCCAGACACA CACGCCAUCCAAGC CAUGGGCGACAAGA UCGAGAGCAAGCUG CUGGCUAAGAAGGC CGAGGUCAACACAA UCCCUGGCUUCGAC GGUGUCGUGAAGGA UGCCGAGGAGGCCG UGCGGAUCGCCCGU GAGAUUGGCUAUCC AGUGAUGAUCAAGG CCUCCGCCGGAGGA GGCGGCAAGGGCAU GAGAAUCGCGUGGG ACGACGAGGAAACU AGAGACGGAUUCCG CCUGAGCAGUCAGG AGGCCGCUAGCAGC UUCGGCGACGAUAG ACUGCUGAUCGAGA AGUUCAUCGACAAC CCAAGACACAUCGA GAUCCAAGUGUUAG GCGAUAAGCACGGC AAUGCCCUCUGGCU GAAUGAGCGGGAGU GCAGCAUUCAGCGG AGAAAUCAGAAGGU GGUGGAGGAGGCUC CAUCCAUUUUCCUC GACGCCGAGACUAG AAGGGCAAUGGGCG AACAAGCUGUUGCC CUGGCAAGAGCCGU GAAGUACUCUAGCG CCGGCACCGUCGAG UUCCUGGUCGACAG CAAGAAGAACUUCU ACUUCCUGGAGAUG AACACAAGACUGCA | GAAGAG UAAGAA GAAAUA UAAGAG CCACC | UCGGUG GCCAUG CUUCUU GCCCCU UGGGCC UCCCCC CAGCCC CUCCUC CCCUUC CUGCAC CCGUAC CCCCGU GGUCUU UGAAUA AAGUCU GAGUGG GCGGC | from 5' to 3' end: 5' UTR of SEQ ID NO: 3, ORF Sequence of SEQ ID NO: 53, and 3' UTR of SEQ ID NO: 150 |

| | | CONSTRUCT SEQUENCES | | | |
|---|---|---|---|---|---|
| | By "G5" is meant that all uracils (U) in the mRNA are replaced by N1-methylpseudouracils. | | | | |
| mRNA Name | ORF Sequence (Amino Acid) | ORF Sequence (Nucleotide) | 5' UTR Sequence | 3' UTR Sequence | Construct Sequence |
| | | GGUGGAACACCCUG | | | |
| | | UCACCGAGUGCAUA | | | |
| | | ACAGGCCUGGACCU | | | |
| | | UGUGCAGGAGAUGA | | | |
| | | UUAGGGUGGCCAAG | | | |
| | | GGAUACCCUCUGCG | | | |
| | | CCACAAGCAGGCCG | | | |
| | | ACAUCCGGAUCAAC | | | |
| | | GGCUGGGCCGUGGA | | | |
| | | GUGCCGAGUCUACG | | | |
| | | CCGAGGAUCCUUAC | | | |
| | | AAGAGCUUCGGCUU | | | |
| | | GCCUAGCAUCGGCA | | | |
| | | GGCUGAGCCAGUAU | | | |
| | | CAGGAGCCGCUGCA | | | |
| | | CCUGCCUGGUGUUA | | | |
| | | GAGUGGACUCAGGA | | | |
| | | AUCCAGCCGGGCAG | | | |
| | | CGACAUCAGCAUCU | | | |
| | | ACUAUGACCCGAUG | | | |
| | | AUCUCCAAGCUCAU | | | |
| | | UACCUACGGCUCUG | | | |
| | | ACAGAACAGAAGCU | | | |
| | | CUGAAGCGCAUGGC | | | |
| | | UGACGCCCUGGACA | | | |
| | | ACUACGUGAUCAGA | | | |
| | | GGCGUGACCCACAA | | | |
| | | UAUCGCCCUGCUGC | | | |
| | | GGGAGGUGAUCAUC | | | |
| | | AAUUCCCGUUUCGU | | | |
| | | GAAGGGCGAUAUCA | | | |
| | | GCACAAAGUUCCUU | | | |
| | | AGCGAUGUCUACCC | | | |
| | | UGACGGCUUCAAGG | | | |
| | | GCCACAUGCUGACU | | | |
| | | AAGAGCGAGAAGAA | | | |
| | | CCAGCUCCUGGCCA | | | |
| | | UCGCAUCAAGCCUC | | | |
| | | UUCGUCGCCUUCCA | | | |
| | | GCUGCGGGCUCAGC | | | |
| | | ACUUCCAGGAGAAC | | | |
| | | AGCCGGAUGCCAGU | | | |
| | | GAUCAAGCCAGACA | | | |
| | | UCGCCAACUGGGAG | | | |
| | | CUUUCUGUCAAGCU | | | |
| | | GCACGACAAGGUGC | | | |
| | | AUACAGUCGUGGCU | | | |
| | | UCUAACAAUGGCAG | | | |
| | | CGUCUUCUCCGUGG | | | |
| | | AGGUCGACGGAUCA | | | |
| | | AAGCUGAACGUGAC | | | |
| | | CAGCACCUGGAAUC | | | |
| | | UGGCCAGCCCUCUU | | | |
| | | CUCAGCGUGUCCGU | | | |
| | | GGACGGAACCCAGA | | | |
| | | GAACCGUGCAGUGU | | | |
| | | CUGAGUAGAGAGGC | | | |
| | | CGGCGGCAACAUGA | | | |
| | | GCAUACAGUUCCUG | | | |
| | | GGCACCGUGUACAA | | | |
| | | GGUCAACAUCCUGA | | | |
| | | CCAGGCUGGCUGCG | | | |
| | | GAGCUGAACAAGUU | | | |
| | | CAUGUUGGAGAAGG | | | |
| | | UGACGGAGGACACC | | | |
| | | UCUAGCGUGCUGCG | | | |
| | | AAGCCCUAUGCCGG | | | |
| | | GUGUCGUAGUGGCU | | | |
| | | GUGAGCGUGAAGCC | | | |
| | | AGGCGACGCCGUGG | | | |
| | | CAGAGGGCCAAGAG | | | |
| | | AUUUGUGUUAUUG | | | |
| | | AGGCAAUGAAGAUG | | | |

-continued

| CONSTRUCT SEQUENCES | | | | | |
|---|---|---|---|---|---|
| By "G5" is meant that all uracils (U) in the mRNA are replaced by N1-methylpseudouracils. | | | | | |
| mRNA Name | ORF Sequence (Amino Acid) | ORF Sequence (Nucleotide) | 5' UTR Sequence | 3' UTR Sequence | Construct Sequence |
| | | CAGAAUAGCAUGAC CGCCGGCAAGACCG GCACUGUGAAGUCC GUUCACUGCCAGGC CGGCGAUACCGUGG GUGAGGGCGACUUG CUCGUGGAGUUGGA A | | | |

| SEQ ID NO: | 1 | 54 | 3 | 150 | 60 |
|---|---|---|---|---|---|
| LX-hPCCA-10-003 (hPCCA; G5; Pv2_SE#4) Cap: C1 PolyA tail: 100 nt | MAGFWVGTAPLVAA GRRGRWPPQQLMLS AALRTLKHVLYYSR QCLMVSRNLGSVGY DPNEKTFDKILIANRG EIACRVIRTCKKMGI KTVAIHSDVDASSVH VKMADEAVCVGPAP TSKSYLNMDAIMEAI KKTRAQAVHPGYGF LSENKEFARCLAAED VVFIGPDTHAIQAMG DKIESKLLAKKAEVN TIPGFDGVVKDAEEA VRIAREIGYPVMIKAS AGGGGKGMRIAWDD EETRDGFRLSSQEAA SSFGDDRLLIEKFIDN PRHIEIQVLGDKHGN ALWLNERECSIQRRN QKVVEEAPSIFLDAE TRRAMGEQAVALAR AVKYSSAGTVEFLVD SKKNFYFLEMNTRLQ VEHPVTECITGLDLV QEMIRVAKGYPLRH KQADIRINGWAVECR VYAEDPYKSFGLPSI GRLSQYQEPLHLPGV RVDSGIQPGSDISIYY DPMISKLITYGSDRTE ALKRMEDALDNYVI RGVTHNIALLREVIIN SRFVKGDISTKFLSDV YPDGFKGHMLTKSE KNQLLAIASSLFVAF QLRAQHFQENSRVPV IKPDIANWELSVKLH DKVHTVVASNNGSV FSVEVDGSKLNVTST WNLASPLLSVSVDGT QRTVQCLSREAGGN MSIQFLGTVYKVNIL TRLAAELNKFMLEK VTEDTSSVLRSPMPG VVVAVSVKPGDAVA EGQEICVIEAMKMQN SMTAGKTGTVKSVH CQAGDTVGEGDLLV ELE | AUGGCCGGGUUCUG GGUGGGCACCGCCC CCCUGGUCGCUGCA GGCCGGAGGGGCAG GUGGCCCCCUCAGC AGCUGAUGCUGAGC GCCGCUCUUCGGAC ACUCAAACACGUGC UGUACUAUAGCAGA CAGUGCCUGAUGGU GAGUAGGAACCUCG GCAGCGUGGGGUAU GAUCCCAACGAGAA GACCUUCGACAAGA UCCUGAUCGCAAAU CGGGGCGAGAUCGC CUGCAGGGUGAUCA GAACCUGCAAGAAG AUGGGCAUCAAGAC CGUCGCUAUUCACA GCGACGUGGAUGCC UCAAGCGUGCACGU GAAGAUGGCAGACG AAGCAGUGUGUGUG GGCCCCGCCCCUAC UUCAAAGUCCUACC UUAAUAUGGACGCA AUUAUGGAGGCAAU CAAGAAGACCAGGG CUCAAGCUGUGCAU CCAGGAUAUGGCUU CCUGUCCGAGAACA AGGAGUUCGCCAGA UGCCUGGCAGCCGA GGAUGUGGUCUUUA UCGGCCCUGAUACA CACGCCAUCCAGGC UAUGGGGGAUAAG AUCGAGAGUAAGCU GCUGGCGAAGAAAG CCGAGGUGAACACC AUUCCGGGCUUUGA CGGCGUGGUGAAGG ACGCCGAGGAGGCC GUGCGGAUCGCUAG GGAGAUCGGCUACC CUGUGAUGAUCAAG GCUUCUGCCGGCGG AGGCGGAAAGGGCA UGCGUAUUGCUUGG GACGACGAGGAAAC CCGCGACGGCUUUC GGCUGAGCAGCCAG GAAGCCGCCAGUAG CUUUGGCGAUGACC GGCUUCUUAUAGAG AAGUUUAUCGACAA CCCCAGACACAUUG AGAUCCAGGUAUUG GGCGAUAAACACGG AAAUGCCCUUUGGC | GGGAAA UAAGAG AGAAAA GAAGAG UAAGAA GAAAUA UAAGAG CCACC | UGAUAA UAGGCU GGAGCC UCGGUG GCCAUG CUUCUU GCCCCU UGGGCC UCCCCC CAGCCC CUCCUC CCCUUC CUGCAC CCGUAC CCCCGU GGUCUU UGAAUA AAGUCU GAGUGG GCGGC | SEQ ID NO: 60 consists from 5' to 3' end: 5' UTR of SEQ ID NO: 3, ORF Sequence of SEQ ID NO: 54, and 3' UTR of SEQ ID NO: 150 |

-continued

| CONSTRUCT SEQUENCES | | | | | |
| By "G5" is meant that all uracils (U) in the mRNA are replaced by N1-methylpseudouracils. | | | | | |
| mRNA Name | ORF Sequence (Amino Acid) | ORF Sequence (Nucleotide) | 5' UTR Sequence | 3' UTR Sequence | Construct Sequence |
| --- | --- | --- | --- | --- | --- |
| | | UGAAUGAGAGAGA | | | |
| | | AUGCUCCAUCCAGA | | | |
| | | GAAGGAACCAGAAG | | | |
| | | GUGGUGGAGGAGGC | | | |
| | | CCCCUCAAUCUUCC | | | |
| | | UGGACGCCGAGACC | | | |
| | | CGUAGAGCCAUGGG | | | |
| | | CGAGCAGGCCGUGG | | | |
| | | CCCUCGCCAGAGCU | | | |
| | | GUGAAGUAUUCCUC | | | |
| | | UGCUGGCACCGUGG | | | |
| | | AGUUCUUAGUGGAU | | | |
| | | UCCAAGAAGAACUU | | | |
| | | CUACUUCCUCGAGA | | | |
| | | UGAAUACCAGACUC | | | |
| | | CAGGUGGAGCAUCC | | | |
| | | CGUCACCGAAUGCA | | | |
| | | UCACUGGCCUGGAC | | | |
| | | CUGGUGCAGGAGAU | | | |
| | | GAUCAGAGUUGCUA | | | |
| | | AGGGUUACCCACUG | | | |
| | | CGCCACAAGCAGGC | | | |
| | | UGACAUCAGGAUCA | | | |
| | | ACGGGUGGGCAGUG | | | |
| | | GAGUGCAGAGUGUA | | | |
| | | UGCUGAGGACCCCU | | | |
| | | ACAAGAGCUUCGGC | | | |
| | | CUGCCGAGCAUCGG | | | |
| | | CCGGCUGAGCCAGU | | | |
| | | ACCAGGAACCCCUC | | | |
| | | CACCUGCCUGGCGU | | | |
| | | ACGGGUGGACAGUG | | | |
| | | GAAUCCAGCCCGGC | | | |
| | | AGCGACAUCAGCAU | | | |
| | | UUAUUACGAUCCCA | | | |
| | | UGAUCUCGAAGUUG | | | |
| | | AUCACCUAUGGGUC | | | |
| | | UGACAGAACCGAGG | | | |
| | | CCCUGAAGAGAAUG | | | |
| | | GAGGACGCGCUGGA | | | |
| | | UAACUACGUGAUUC | | | |
| | | GGGGAGUGACUCAC | | | |
| | | AACAUAGCUCUACU | | | |
| | | GCGUGAGGUCAUCA | | | |
| | | UCAAUAGCAGAUUC | | | |
| | | GUAAAGGGCGACAU | | | |
| | | UAGCACCAAGUUUC | | | |
| | | UUUCCGACGUGUAC | | | |
| | | CCAGACGGUUUUAA | | | |
| | | GGGACACAUGCUGA | | | |
| | | CAAAGUCUGAGAAG | | | |
| | | AACCAGCUGCUGGC | | | |
| | | CAUAGCCAGCAGCC | | | |
| | | UGUUCGUGGCCUUU | | | |
| | | CAGCUCCGAGCCCA | | | |
| | | ACACUUCCAGGAGA | | | |
| | | ACAGCAGAGUGCCA | | | |
| | | GUGAUCAAGCCUGA | | | |
| | | CAUCGCCAACUGGG | | | |
| | | AGCUGUCUGUGAAA | | | |
| | | CUGCACGACAAGGU | | | |
| | | GCAUACCGUCGUGG | | | |
| | | CCAGCAACAAUGGC | | | |
| | | UCCGUGUUCUCCGU | | | |
| | | GGAGGUGGAUGGCU | | | |
| | | CAAAGCUGAACGUG | | | |
| | | ACCUCGACAUGGAA | | | |
| | | CCUCGCCUCUCCCC | | | |
| | | UGCUGAGUGUGAGC | | | |
| | | GUGGACGGCACACA | | | |
| | | GAGAACCGUGCAGU | | | |
| | | GCCUGAGUAGAGAA | | | |
| | | GCAGGGGGCAACAU | | | |

-continued

| CONSTRUCT SEQUENCES | | | | | |
|---|---|---|---|---|---|
| By "G5" is meant that all uracils (U) in the mRNA are replaced by N1-methylpseudouracils. | | | | | |
| mRNA Name | ORF Sequence (Amino Acid) | ORF Sequence (Nucleotide) | 5' UTR Sequence | 3' UTR Sequence | Construct Sequence |
| | | GUCCAUUCAGUUUC UCGGCACCGUGUAC AAGGUCAAUAUUCU CACCAGACUCGCCG CCGAGCUGAACAAG UUCAUGCUUGAGAA GGUGACCGAGGAUA CUAGUUCCGUGCUC AGAUCCCCUAUGCC CGGCGUGGUGGUCG CUGUGUCCGUCAAG CCCGGCGACGCCGU GGCCGAGGGACAGG AGAUUUGCGUGAUU GAGGCUAUGAAGAU GCAGAAUAGCAUGA CUGCUGGCAAGACG GGCACAGUGAAGAG CGUGCAUUGCCAGG CAGGCGACACAGUG GGCGAAGGAGACCU GCUGGUCGAGUUAG AG | | | |
| SEQ ID NO: | 1 | 55 | 3 | 150 | 61 |
| LX- hPCCA- 01-017 (hPCCA; G5; SE#8) Cap: C1 PolyA tail: 100 nt | MAGFWVGTAPLVAA GRRGRWPPQQLMLS AALRTLKHVLYYSR QCLMVSRNLGSVGY DPNEKTFDKILVANR GEIACRVIRTCKKMG IKTVAIHSDVDASSV HVKMADEAVCVGPA PTSKSYLNMDAIMEA IKKTRAQAVHPGYGF LSENKEFARCLAAED VVFIGPDTHAIQAMG DKIESKLLAKKAEVN TIPGFDGVVKDAEEA VRIAREIGYPVMIKAS AGGGGKGMRIAWDD EETRDGFRLSSQEAA SSFGDDRLLIEKFIDN PRHIEIQVLGDKHGN ALWLNERECSIQRRN QKVVEEAPSIFLDAE TRRAMGEQAVALAR AVKYSSAGTVEFLVD SKKNFYFLEMNTRLQ VEHPVTECITGLDLV QEMIRVAKGYPLRH KQADIRINGWAVECR VYAEDPYKSFGLPSI GRLSQYQEPLHLPGV RVDSGIQPGSDISIYY DPMISKLITYGSDRTE ALKRMADALDNYVI RGVTHNIALLREVIIN SRFVKGDISTKFLSDV YPDGFKGHMLTKSE KNQLLAIASSLFVAF QLRAQHFQENSRMP VIKPDIANWELSVKL HDKVHTVVASNNGS VFSVEVDGSKLNVTS TWNLASPLLSVSVDG TQRTVQCLSREAGGN MSIQFLGTVYKVNIL TRLAAELNKFMLEK VTEDTSSVLRSPMPG VVVAVSVKPGDAVA | AUGGCCGGCUUCUG GGUUGGCACCGCCC CUCUCGUGGCCGCA GGAAGGAGGGGCAG GUGGCCUCCACAGC AGCUUAUGUUGUCC GCCGCCCUCAGAAC ACUCAAGCACGUGC UAUACUACAGCAGA CAGUGCUUGAUGGU GUCCAGAAAUCUGG GCAGCGUAGGUUAU GACCCUAACGAGAA GACCUUCGACAAGA UCCUGGUGGCUAAC AGGGGAGAAAUCGC CUGUAGGGUCAUUA GAACCUGCAAGAAG AUGGGAAUCAAGAC CGUCGCUAUCCACU CUGACGUUGAUGCA AGCAGCGUGCACGU CAAGAUGGCUGAUG AGGCUGUCUGCGUC GGUCCUGCUCCAAC AUCUAAGAGCUACC UGAACAUGGACGCU AUCAUGGAGGCCAU UAAGAAGACAAGGG CCCAGGCCGUGCAC CCUGGAUACGGCUU CCUCAGCGAGAAUA AGGAGUUCGCAAGA UGUCUCGCCGCCGA GGACGUCGUGUUCA UAGGCCCUGACACC CACGCCAUCCAGGC AAUGGGCGAUAAGA UCGAGUCCAAGCUG UUAGCAAAGAAGGC CGAAGUGAACACCA UUCCUGGCUUCGAU GGCGUCGUGAAGGA CGCUGAGGAGGCAG UGAGAAUCGCCAGA GAGAUCGGAUACCC | GGGAAA UAAGAG AGAAAA GAAGAG UAAGAA GAAAUA UAAGAG UAAGAG CCACC | UGAUAA UAGGCU GGAGCC UCGGUG GCCAUG CUUCUU GCCCCU UGGGCC UCCCCC CAGCCC CUCCUC CCCUUC CUGCAC CCGUAC CCCCGU GGUCUU UGAAUA AAGUCU GAGUGG GCGGC | SEQ ID NO: 61 consists from 5' to 3' end: 5' UTR of SEQ ID NO: 3, ORF Sequence of SEQ ID NO: 55, and 3' UTR of SEQ ID NO: 150 |

-continued

| | CONSTRUCT SEQUENCES | | | | |
| --- | --- | --- | --- | --- | --- |
| | By "G5" is meant that all uracils (U) in the mRNA are replaced by N1-methylpseudouracils. | | | | |
| mRNA Name | ORF Sequence (Amino Acid) | ORF Sequence (Nucleotide) | 5' UTR Sequence | 3' UTR Sequence | Construct Sequence |
| | EGQEICVIEAMKMQN SMTAGKTGTVKSVH CQAGDTVGEGDLLV ELE | UGUGAUGAUCAAGG CCUCUGCCGGAGGC GGAGGCAAGGGCAU GAGGAUUGCCUGGG AUGACGAAGAGACG CGUGACGGCUUCCG ACUGAGCUCUCAGG AGGCUGCCUCUUCU UUCGGAGACGAUAG GCUGCUGAUCGAGA AGUUCAUCGACAAC CCUCGGCACAUCGA GAUCCAGGUGCUCG GUGACAAGCAUGGA AAUGCCCUGUGGCU GAACGAGCGGGAGU GCUCUAUUCAGAGA AGAAACCAGAAGGU GGUGGAGGAGGCCC CUAGCAUCUUCUUA GACGCUGAAACUCG GAGAGCCAUGGGCG AGCAGGCCGUGGCG CUGGCUAGAGCCGU GAAGUACAGCAGUG CAGGCACAGUGGAG UUCCUGGUGGAUAG CAAGAAGAAUUUCU ACUUCCUGGAGAUG AAUACCAGGCUGCA GGUGGAGCACCCGG UGACGGAGUGCAUC ACAGGCCUGGACCU GGUCCAAGAAAUGA UCAGAGUGGCCAAG GGCUACCCUCUGCG GCAUAAGCAGGCUG ACAUCCGGAUUAAC GGAUGGGCCGUAGA GUGCCGUGUUUAUG CCGAGGACCCUUAC AAGAGCUUCGGUUU GCCAAGCAUUGGCC GGCUGUCCCAGUAC CAAGAGCCACUGCA UCUGCCAGGCGUCA GGGUGGACAGCGGC AUCCAGCCAGGCUC UGACAUCAGCAUUU AUUACGACCCGAUG AUCAGCAAGCUGAU CACAUAUGGAUCCG AUAGAACCGAAGCC CUGAAGAGAAUGGC AGAUGCUCUGGACA ACUACGUGAUCAGG GGCGUGACCCACAA CAUCGCCCUGCUCA GGGAAGUGAUCAUU AAUAGCCGGUUCGU GAAGGGCGAUAUCA GCACCAAGUUCCUG UCAGACGUUUAUCC AGAUGGCUUCAAGG GACACAUGCUGACA AAGUCCGAGAAGAA UCAGCUCCUGGCCA UUGCCAGCUCUCUC UUCGUGGCCUUCCA GUUGAGAGCGCAGC ACUUCCAGGAGAAC AGUCGAAUGCCUGU CAUUAAGCCUGACA | | | |

-continued

| CONSTRUCT SEQUENCES | | | | | |
| --- | --- | --- | --- | --- | --- |
| By "G5" is meant that all uracils (U) in the mRNA are replaced by N1-methylpseudouracils. | | | | | |
| mRNA Name | ORF Sequence (Amino Acid) | ORF Sequence (Nucleotide) | 5' UTR Sequence | 3' UTR Sequence | Construct Sequence |
| | | UCGCCAAUUGGGAG | | | |
| | | CUGAGCGUGAAGCU | | | |
| | | CCACGACAAGGUCC | | | |
| | | ACACUGUCGUGGCC | | | |
| | | AGCAACAACGGCUC | | | |
| | | AGUGUUCAGCGUGG | | | |
| | | AAGUCGACGGCUCC | | | |
| | | AAGCUCAAUGUGAC | | | |
| | | CUCCACUUGGAACC | | | |
| | | UGGCUUCCCCACUU | | | |
| | | CUGUCUGUGAGCGU | | | |
| | | GGACGGCACUCAGC | | | |
| | | GGACGGUGCAAUGU | | | |
| | | CUGAGCAGGGAAGC | | | |
| | | CGGCGGCAAUAUGA | | | |
| | | GCAUCCAAUUCCUC | | | |
| | | GGAACCGUGUACAA | | | |
| | | GGUUAACAUCCUUA | | | |
| | | CGCGACUGGCCGCU | | | |
| | | GAGCUGAAUAAGUU | | | |
| | | CAUGCUGGAGAAGG | | | |
| | | UGACCGAGGACACC | | | |
| | | UCUAGCGUGCUGCG | | | |
| | | GAGCCCUAUGCCAG | | | |
| | | GAGUGGUGGUGGCC | | | |
| | | GUGUCCGUGAAGCC | | | |
| | | UGGAGACGCCGUGG | | | |
| | | CCGAAGGCCAGGAA | | | |
| | | AUUUGCGUCAUCGA | | | |
| | | AGCCAUGAAGAUGC | | | |
| | | AGAACAGCAUGACC | | | |
| | | GCCGGCAAGACCGG | | | |
| | | AACGGUUAAGUCUG | | | |
| | | UCCACUGCCAGGCC | | | |
| | | GGCGACACCGUGGG | | | |
| | | AGAGGGUGACCUCC | | | |
| | | UGGUUGAGCUGGAG | | | |
| SEQ ID NO: | 1 | 56 | 3 | 150 | 62 |
| LX-hPCCA-01-019 (hPCCA; G5; SE#10) Cap: C1 PolyA tail: 100 nt | MAGFWVGTAPLVAA GRRGRWPPQQLMLS AALRTLKHVLYYSR QCLMVSRNLGSVGY DPNEKTFDKILVANR GEIACRVIRTCKKMG IKTVAIHSDVDASSV HVKMADEAVCVGPA PTSKSYLNMDAIMEA IKKTRAQAVHPGYGF LSENKEFARCLAAED VVFIGPDTHAIQAMG DKIESKLLAKKAEVN TIPGFDGVVKDAEEA VRIAREIGYPVMIKAS AGGGKGMRIAWDD EETRDGFRLSSQEAA SSFGDDRLLIEKFIDN PRHIEIQVLGDKHGN ALWLNERECSIQRRN QKVVEEAPSIFLDAE TRRAMGEQAVALAR AVKYSSAGTVEFLVD SKKNFYFLEMNTRLQ VEHPVTECITGLDLV QEMIRVAKGYPLRH KQADIRINGWAVECR VYAEDPYKSFGLPSI GRLSQYQEPLHLPGV RVDSGIQPGSDISIYY DPMISKLITYGSDRTE ALKRMADALDNYVI | AUGGCCGGCUUCUG GGUGGGCACCGCCC CCCUUGUCGCAGCA GGAAGGCGGGGCCG GUGGCCUCCCCAGC AGUUAAUGCUUAGC GCCGCCCUCCGCAC CCUCAAGCACGAUCC UCUACUACUCCCGC CAGUGCCUCAUGGU AUCCCGCAACCUCG GCUCCGUCGGCUAC GACCCCAACGAGAA GACCUUCGACAAGA UCCUCGUCGCCAAC CGCGGCGAGAUCGC CUGCCGCGUCAUCC GCACCUGCAAGAAG AUGGGCAUCAAGAC CGUCGCCAUCCACU CCGACGUCGACGCC UCCUCCGUCCACGU CAAGAUGGCCGACG AGGCCGUCUGCGUC GGCCCCGCCCCCAC CUCCAAGUCCUACC UCAACAUGGACGCC AUCAUGGAGGCCAU CAAGAAGACCCGCG CCCAGGCCGUCCAC CCCGGCUACGGCUU CCUCUCCGAGAACA | GGGAAA UAAGAG AGAAAA GAAGAG UAAGAA GAAAUA UAAGAG CCACC | UGAUAA UAGGCU GGAGCC UCGGUG GCCAUG CUUCUU GCCCCU UGGGCC UCCCCU CAGCCC CUCCUC CCCUUC CUGCAC CCGUAC CCCCGU GGUCUU UGAAUA AAGUCU GAGUGG GCGGC | SEQ ID NO: 62 consists from 5' to 3' end: 5' UTR of SEQ ID NO: 3, ORF Sequence of SEQ ID NO: 56, and 3' UTR of SEQ ID NO: 150 |

-continued

| | | CONSTRUCT SEQUENCES | | | |
|---|---|---|---|---|---|
| By "G5" is meant that all uracils (U) in the mRNA are replaced by N1-methylpseudouracils. | | | | | |
| mRNA Name | ORF Sequence (Amino Acid) | ORF Sequence (Nucleotide) | 5' UTR Sequence | 3' UTR Sequence | Construct Sequence |
| | RGVTHNIALLREVIIN | AGGAGUUCGCCCGC | | | |
| | SRFVKGDISTKFLSDV | UGCCUCGCCGCCGA | | | |
| | YPDGFKGHMLTKSE | GGACGUCGUCUUCA | | | |
| | KNQLLAIASSLFVAF | UCGGCCCUGACACC | | | |
| | QLRAQHFQENSRMP | CACGCAAUUCAGGC | | | |
| | VIKPDIANWELSVKL | CAUGGGUGACAAGA | | | |
| | HDKVHTVVASNNGS | UUGAGUCCAAGCUC | | | |
| | VFSVEVDGSKLNVTS | CUCGCCAAGAAGGC | | | |
| | TWNLASPLLSVSVDG | CGAGGUCAACACCA | | | |
| | TQRTVQCLSREAGGN | UCCCCGGCUUCGAC | | | |
| | MSIQFLGTVYKVNIL | GGCGUCGUCAAGGA | | | |
| | TRLAAELNKFMLEK | UGCUGAAGAGGCAG | | | |
| | VTEDTSSVLRSPMPG | UCCGCAUCGCCAGA | | | |
| | VVVAVSVKPGDAVA | GAGAUAGGCUACCC | | | |
| | EGQEICVIEAMKMQN | CGUCAUGAUCAAGG | | | |
| | SMTAGKTGTVKSVH | CCUCCGCCGGCGGC | | | |
| | CQAGDTVGEGDLLV | GGAGGAAAGGGCAU | | | |
| | ELE | GCGGAUCGCAUGGG | | | |
| | | ACGACGAGGAAACC | | | |
| | | CGCGACGGUUUCCG | | | |
| | | CCUCUCCUCCCAGG | | | |
| | | AGGCCGCCUCCAGU | | | |
| | | UUCGGCGACGACAG | | | |
| | | ACUCUUGAUCGAGA | | | |
| | | AGUUCAUCGACAAC | | | |
| | | CCCCGCCACAUCGA | | | |
| | | GAUCCAGGUCCUCG | | | |
| | | GAGAUAAGCACGGC | | | |
| | | AACGCCCUCUGGCU | | | |
| | | CAACGAGCGCGAGU | | | |
| | | GCUCCAUCCAGCGC | | | |
| | | CGCAACCAGAAGGU | | | |
| | | CGUGGAGGAGGCCC | | | |
| | | CCUCCAUCUUCCUC | | | |
| | | GACGCAGAAACAAG | | | |
| | | GCGCGCGAUGGGAG | | | |
| | | AGCAGGCAGUGGCC | | | |
| | | CUUGCCAGGGCCGU | | | |
| | | CAAGUACUCCUCCG | | | |
| | | CAGGUACCGUCGAG | | | |
| | | UUCCUCGUGGACUC | | | |
| | | CAAGAAGAACUUCU | | | |
| | | ACUUCUUGGAGAUG | | | |
| | | AACACACGACUGCA | | | |
| | | GGUCGAGCAUCCUG | | | |
| | | UAACCGAGUGCAUC | | | |
| | | ACCGGCCUCGACCU | | | |
| | | CGUCCAGGAGAUGA | | | |
| | | UCCGCGUUGCCAAG | | | |
| | | GGCUACCCUCUCCG | | | |
| | | CCACAAGCAGGCCG | | | |
| | | ACAUCCGCAUCAAC | | | |
| | | GGCUGGGCUGUGGA | | | |
| | | AUGUCGGGUGUAUG | | | |
| | | CCGAGGAUCCCUAC | | | |
| | | AAGUCCUUCGGCCU | | | |
| | | GCCAUCUAUUGGCA | | | |
| | | GACUAUCGCAGUAC | | | |
| | | CAGGAGCCCCUCCA | | | |
| | | CCUCCCCGGCGUGC | | | |
| | | GCGUUGACUCUGGC | | | |
| | | AUCCAGCCCGGCUC | | | |
| | | CGACAUCAGCAUCU | | | |
| | | ACUAUGAUCCGAUG | | | |
| | | AUCAGCAAGCUUAU | | | |
| | | CACCUAUGGCUCAG | | | |
| | | ACCGCACCGAGGCG | | | |
| | | CUGAAGCGCAUGGC | | | |
| | | UGACGCCCUCGACA | | | |
| | | ACUAUGUUAUCCGG | | | |
| | | GGCGUCACCCACAA | | | |
| | | CAUCGCACUCCUAC | | | |
| | | GGGAGGUCAUCAUC | | | |

CONSTRUCT SEQUENCES
By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | AACUCCCGCUUCGU GAAGGGUGACAUCU CCACCAAGUUCUUG AGUGACGUGUACCC UGACGGCUUCAAGG GCCACAUGCUCACC AAGUCCGAGAAGAA CCAACUGCUGGCUA UCGCCAGCAGUCUC UUCGUCGCCUUCCA GCUGAGGGCCCAGC ACUUCCAAGAGAAU AGCAGGAUGCCCGU CAUCAAGCCCGACA UCGCCAACUGGGAG CUCUCCGUCAAGCU CCACGACAAGGUCC ACACCGUCGUCGCA UCCAACAACGGAUC UGUGUUCUCCGUCG AGGUCGACGGAUCU AAGCUGAACGUCAC AAGCACUUGGAACC UCGCCUCCCCCCUG CUUUCAGUGAGCGU GGACGGCACCCAGC GCACCGUGCAGUGC CUGAGCCGCGAGGC GGGGAGGCAACAUGU CGAUACAGUUCCUG GGCACAGUGUACAA GGUGAAUAUCCUGA CAAGACUGGCUGCU GAGCUCAACAAGUU CAUGCUCGAGAAGG UCACCGAGGACACU UCUUCGGUGCUCCG CUCCCCCAUGCCUG GAGUGGUUGUGGCC GUGUCAGUAAAGCC AGGCGACGCUGUUG CCGAGGGUCAGGAA AUCUGCGUCAUCGA GGCCAUGAAGAUGC AGAACUCCAUGACG GCCGGCAAGACGGG CACUGUCAAGUCUG UGCAUUGCCAGGCC GGAGACACUGUGGG CGAGGGCGACCUAC UGGUUGAGCUCGAG | | | |

| SEQ ID NO: | 15 | 196 | 199 | 178 | 200 |
|---|---|---|---|---|---|
| SE_PCCB_026 (hPCCB; G5) Cap: C1 PolyA tail: 100 nt | MAAALRVAAVGARL SVLASGLRAAVRSLC SQATSVNERIENKRR TALLGGGQRRIDAQH KRGKLTARERISLLL DPGSFVESDMFVEHR CADFGMAADKNKFP GDSVVTGRGRINGRL VYVFSQDFTVFGGSL SGAHAQKICKIMDQA ITVGAPVIGLNDSGG ARIQEGVESLAGYAD IFLRNVTASGVIPQISL IMGPCAGGAVYSPAL TDFTFMVKDTSYLFI TGPDVVKSVTNEDVT QEELGGAKTHTTMS GVAHRAFENDVDAL | AUGGCCGCAGCCCU CAGAGUGGCCGUCG UGGGAGCCAGACUC AGCGUGCUCGCCUC AGGCCUGCGGGCCG CAGUCAGAAGCCUG UGCAGCCAGGCAAC CUCAGUGAACGAGA GAAUCGAGAACAAG AGACGGACCGCCCU GCUGGGUGGCGGGC AAAGAAGAAUUGAC GCCCAGCACAAGAG AGGCAAGCUGACCG CCCGCGAGCGCAUC AGCCUGCUGCUGGA CCCCGGCAGCUUCG UGGAGAGCGACAUG | AGGAAA UAAGAG AGAAAA GAAGAG UAAGAA GAAAUA UAAGAG CCACC | UGAUAA UAGUCC AUAAAG UAGGAA ACACUA CAGCUG GAGCCU CGGUGG CCUAGC UUCUUG CCCCUU GGGCCU CCAUAA AGUAGG AAACAC UACAUC CCCCCA GCCCCU | SEQ ID NO: 200 consists from 5' to 3' end: 5' UTR of SEQ ID NO: 199, ORF Sequence of SEQ ID NO: 196, and 3' UTR of SEQ ID NO: 178 |

-continued

CONSTRUCT SEQUENCES
By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | CNLRDFFNYLPLSSQ | UUCGUGGAGCAUCG | | CCUCCC | |
| | DPAPVRECHDPSDRL | GUGUGCCGACUUCG | | CUUCCU | |
| | VPELDTIVPLESTKAY | GCAUGGCCGCCGAC | | GCACCC | |
| | NMVDIIHSVVDEREF | AAGAACAAGUUCCC | | GUACCC | |
| | FEIMPNYAKNIIVGFA | CGGCGACAGCGUGG | | CCUCCA | |
| | RMNGRTVGIVGNQP | UGACCGGCAGAGGC | | UAAAGU | |
| | KVASGCLDINSSVKG | AGAAUCAACGGCAG | | AGGAAA | |
| | ARFVRFCDAFNIPLIT | ACUGGUGUACGUGU | | CACUAC | |
| | FVDVPGFLPGTAQEY | UCUCACAAGACUUU | | AGUGGU | |
| | GGIIRHGAKLLYAFA | ACCGUCUUCGGAGG | | CUUUGA | |
| | EATVPKVTVITRKAY | AUCCCUGUCAGGGG | | AUAAAG | |
| | GGAYDVMSSKHLCG | CUCACGCCCAGAAG | | UCUGAG | |
| | DTNYAWPTAEIAVM | AUCUGCAAGAUCAU | | UGGGCG | |
| | GAKGAVEIIFKGHEN | GGACCAGGCCAUCA | | GC | |
| | VEAAQAEYIEKFANP | CCGUGGGCGCUCCC | | | |
| | FPAAVRGFVDDIIQPS | GUGAUCGGCCUGAA | | | |
| | STRARICCDLDVLAS | CGACAGCGGAGGCG | | | |
| | KKVQRPWRKHANIP | CCAGGAUCCAAGAG | | | |
| | L | GGAGUGGAGUCCCU | | | |
| | | GGCCGGCUACGCCG | | | |
| | | ACAUCUUCCUGAGA | | | |
| | | AACGUGACCGCCUC | | | |
| | | GGGCGUGAUCCCAC | | | |
| | | AGAUCUCCCUGAUC | | | |
| | | AUGGGACCCUGCGC | | | |
| | | CGGCGGGGCCGUCU | | | |
| | | ACAGCCCUGCCCUG | | | |
| | | ACCGACUUCACCUU | | | |
| | | CAUGGUGAAGGACA | | | |
| | | CCAGCUACCUGUUC | | | |
| | | AUCACCGGCCCCGA | | | |
| | | CGUGGUCAAGAGCG | | | |
| | | UGACCAACGAGGAC | | | |
| | | GUGACCCAGGAGGA | | | |
| | | GCUCGGCGGAGCCA | | | |
| | | AGACUCACACAACC | | | |
| | | AUGUCCGGCGUCGC | | | |
| | | UCAUAGGGCCUUCG | | | |
| | | AGAACGACGUGGAC | | | |
| | | GCCCUGUGCAACCU | | | |
| | | GAGAGACUUCUUCA | | | |
| | | ACUACCUGCCAUUG | | | |
| | | AGCAGCCAGGAUCC | | | |
| | | CGCCCCUGUGAGAG | | | |
| | | AGUGCCACGACCCC | | | |
| | | AGCGACAGACUGGU | | | |
| | | GCCCGAGCUGGACA | | | |
| | | CCAUCGUGCCCCUG | | | |
| | | GAGAGCACCAAGGC | | | |
| | | CUACAACAUGGUGG | | | |
| | | ACAUCAUCCACAGC | | | |
| | | GUGGUGGACGAGAG | | | |
| | | AGAGUUCUUCGAGA | | | |
| | | UCAUGCCCAACUAC | | | |
| | | GCCAAGAACAUCAU | | | |
| | | CGUGGGCUUCGCCA | | | |
| | | GAAUGAACGGCAGA | | | |
| | | ACCGUGGGCAUUGU | | | |
| | | GGGCAACCAGCCCA | | | |
| | | AGGUCGCCAGCGGC | | | |
| | | UGCCUCGACAUCAA | | | |
| | | CAGCAGCGUGAAGG | | | |
| | | GCGCCAGAUUCGUG | | | |
| | | AGAUUCUGCGACGC | | | |
| | | CUUCAACAUACCUC | | | |
| | | UGAUCACCUUUGUG | | | |
| | | GACGUGCCUGGUUU | | | |
| | | CCUCCCGGGCACCG | | | |
| | | CCCAAGAAUACGGU | | | |
| | | GGCAUCAUCAGACA | | | |
| | | CGGCGCCAAGCUGC | | | |
| | | UGUACGCCUUCGCC | | | |
| | | GAGGCCACCGUGCC | | | |

-continued

| CONSTRUCT SEQUENCES | | | | | |
|---|---|---|---|---|---|
| By "G5" is meant that all uracils (U) in the mRNA are replaced by N1-methylpseudouracils. | | | | | |
| mRNA Name | ORF Sequence (Amino Acid) | ORF Sequence (Nucleotide) | 5' UTR Sequence | 3' UTR Sequence | Construct Sequence |
| | | CAAGGUGACCGUUA UCACCCGCAAAGCC UACGGCGGCGCCUA CGACGUGAUGAGCA GCAAGCACCUGUGU GGCGACACCAAUUA CGCCUGGCCCACCG CCGAGAUCGCCGUC AUGGGCGCGAAAGG AGCCGUGGAGAUCA UCUUCAAGGGCCAC GAGAACGUGGAGGC CGCCCAGGCCGAGU ACAUCGAGAAGUUC GCCAACCCCUUCCC UGCCGCCGUGAGGG GCUUCGUCGACGAU AUCAUCCAGCCCAG CUCCACCCGCGCCA GAAUUUGUUGCGAC CUGGACGUGCUGGC CAGCAAGAAGGUGC AAAGACCCUGGAGA AAGCACGCCAACAU CCCGCUG | | | |
| SEQ ID NO: | 15 | 197 | 199 | 178 | 201 |
| SE_PCCB_027 (hPCCB; G5) Cap: C1 PolyA tail: 100 nt | MAAALRVAAVGARL SVLASGLRAAVRSLC SQATSVNERIENKRR TALLGGGQRRIDAQH KRGKLTARERISLLL DPGSFVESDMFVEHR CADFGMAADKNKFP GDSVVTGRGRINGRL VYVFSQDFTVFGGSL SGAHAQKICKIMDQA ITVGAPVIGLNDSGG ARIQEGVESLAGYAD IFLRNVTASGVIPQISL IMGPCAGGAVYSPAL TDFTFMVKDTSYLFI TGPDVVKSVTNEDVT QEELGGAKTHTTMS GVAHRAFENDVDAL CNLRDFFNYLPLSSQ DPAPVRECHDPSDRL VPELDTIVPLESTKAY NMVDIIHSVVDEREF FEIMPNYAKNIIVGFA RMNGRTVGIVGNQP KVASGCLDINSSVKG ARFVRFCDAFNIPLIT FVDVPGFLPGTAQEY GGIIRHGAKLLYAFA EATVPKVTVITRKAY GGAYDVMSSKHLCG DTNYAWPTAEIAVM GAKGAVEIIFKGHEN VEAAQAEYIEKFANP FPAAVRGFVDDIIQPS STRARICCDLDVLAS KKVQRPWRKHANIP L | AUGGCCGCAGCCCU CAGAGUGGCUGCCG UGGGGAGCCAGACUC AGCGUGCUGCGCCUC AGGCCUGCGGGCCG CAGUCAGAAGCCUG UGCAGCCAGGCAAC CUCAGUGAACGAGA GAAUCGAGAACAAG AGACGGACCGCCCU GCUGGGUGGCGGGC AAAGAAGAAUUGAC GCCCAGCACAAGAG AGGCAAGCUGACCG CCCGCGAGCGCAUC AGCCUGCUGCUGGA CCCCGGCAGCUUCG UGGAGAGCGACAUG UUCGUGGAGCAUCG GUGUGCCGACUUCG GCAUGGCCGCCGAC AAGAACAAGUUCCC CGGCGACAGCGUGG UGACCGGCAGAGGC AGAAUCAACGGCAG ACUGGUGUACGUGU UCUCACAAGACUUU ACCGUCUUCGGAGG AUCCCUGUCAGGGG CUCACGCCCAGAAG AUCUGCAAGAUCAU GGACCAGGCCAUCA CCGUGGGCGCUCCC GUGAUCGGCCUGAA CGACAGCGGAGGCG CCAGGAUCCAAGAG GGAGUGGAGUCCCU GGCCGGCUACGCCG ACAUCUUCCUGAGA AACGUGACCGCCUC GGGCGUGAUCCCAC AGAUCUCCCUGAUC AUGGGACCCUGCGC CGGCGGGGCCGUCU | AGGAAA UAAGAG AGAAAA GAAGAG UAAGAA GAAAUA UAAGAG CCACC | UGAUAA UAGUCC AUAAAG UAGGAA ACACUA CAGCUG GAGCCU CGGUGG CCUAGC UUCUUG CCCCUU GGGCCU CCAUAA AGUAGG AAACAC UACAUC CCCCCA GCCCCU CCUCCC CUUCCU GCACCC GUACCC CCUCCA UAAAGU AGGAAA CACUAC AGUGGU CUUUGA AUAAAG UCUGAG UGGGCG GC | SEQ ID NO:201 consists from 5' to 3' end: 5' UTR of SEQ ID NO: 199, ORF Sequence of SEQ ID NO:197, and 3' UTR of SEQ ID NO:178 |

-continued

| CONSTRUCT SEQUENCES |
|---|
| By "G5" is meant that all uracils (U) in the mRNA are replaced by N1-methylpseudouracils. |

| mRNA Name | ORF Sequence (Amino Acid) | ORF Sequence (Nucleotide) | 5' UTR Sequence | 3' UTR Sequence | Construct Sequence |
|---|---|---|---|---|---|
| | | ACAGCCCUGCCCUG | | | |
| | | ACCGACUUCACCUU | | | |
| | | CAUGGUGAAGGACA | | | |
| | | CCAGCUACCUGUUC | | | |
| | | AUCACCGGCCCCGA | | | |
| | | CGUGGUCAAGAGCG | | | |
| | | UGACCAACGAGGAC | | | |
| | | GUGACCCAGGAGGA | | | |
| | | GCUCGGCGGAGCCA | | | |
| | | AGACUCACACAACC | | | |
| | | AUGUCCGGCGUCGC | | | |
| | | UCAUAGGGCCUUCG | | | |
| | | AGAACGACGUGGAC | | | |
| | | GCCCUGUGCAACCU | | | |
| | | GAGAGACUUCUUCA | | | |
| | | ACUACCUGCCAUUG | | | |
| | | AGCAGCCAGGAUCC | | | |
| | | CGCCCCUGUGAGAG | | | |
| | | AGUGCCACGACCCC | | | |
| | | AGCGACAGACUGGU | | | |
| | | GCCCGAGCUGGACA | | | |
| | | CCAUCGUGCCCCUG | | | |
| | | GAGAGCACCAAGGC | | | |
| | | CUACAACAUGGUGG | | | |
| | | ACAUCAUCCACAGC | | | |
| | | GUGGUGGACGAGAG | | | |
| | | AGAGUUCUUCGAGA | | | |
| | | UCAUGCCCAACUAC | | | |
| | | GCCAAGAACAUCAU | | | |
| | | CGUGGGCUUCGCCA | | | |
| | | GAAUGAACGGCAGA | | | |
| | | ACCGUGGGCAUUGU | | | |
| | | GGGCAACCAGCCCA | | | |
| | | AGGUCGCCAGCGGC | | | |
| | | UGCCUCGACAUCAA | | | |
| | | CAGCAGCGUGAAGG | | | |
| | | GCGCCAGAUUCGUG | | | |
| | | AGAUUCUGCGACGC | | | |
| | | CUUCAACAUACCUC | | | |
| | | UGAUCACCUUUGUG | | | |
| | | GACGUGCCUGGUUU | | | |
| | | CCUCCCGGGCACCG | | | |
| | | CCCAAGAAUACGGU | | | |
| | | GGCAUCAUCAGACA | | | |
| | | CGGCGCCAAGCUGC | | | |
| | | UGUACGCCUUCGCC | | | |
| | | GAGGCCACCGUGCC | | | |
| | | CAAGGUGACCGUUA | | | |
| | | UCACCCGCAAAGCC | | | |
| | | UACGGCGGCGCCUA | | | |
| | | CGACGUGAUGAGCA | | | |
| | | GCAAGCACCUGUGU | | | |
| | | GGCGACACCAAUUA | | | |
| | | CGCCUGGCCCACCG | | | |
| | | CCGAGAUCGCCGUC | | | |
| | | AUGGGCGCGAAAGG | | | |
| | | AGCCGUGGAGAUCA | | | |
| | | UCUUCAAGGGCCAC | | | |
| | | GAGAACGUGGAGGC | | | |
| | | CGCCCAGGCCGAGU | | | |
| | | ACAUCGAGAAGUUC | | | |
| | | GCCAACCCCUUCCC | | | |
| | | UGCCGCCGUGAGGG | | | |
| | | GCUUCGUCGACGAU | | | |
| | | AUCAUCCAGCCCAG | | | |
| | | CUCCACCCGCGCCA | | | |
| | | GAAUCUGCUGCGAC | | | |
| | | CUGGACGUGCUGGC | | | |
| | | CAGCAAGAAGGUGC | | | |
| | | AAAGACCCUGGAGA | | | |
| | | AAGCACGCCAACAU | | | |
| | | CCCGCUG | | | |

| CONSTRUCT SEQUENCES | | | | | |
| --- | --- | --- | --- | --- | --- |
| By "G5" is meant that all uracils (U) in the mRNA are replaced by N1-methylpseudouracils. | | | | | |
| mRNA Name | ORF Sequence (Amino Acid) | ORF Sequence (Nucleotide) | 5' UTR Sequence | 3' UTR Sequence | Construct Sequence |
| SEQ ID NO: | 15 | 198 | 199 | 178 | 202 |
| SE_PCCB_028 (hPCCB; G5) Cap: C1 PolyA tail: 100 nt | MAAALRVAAVGARL SVLASGLRAAVRSLC SQATSVNERIENKRR TALLGGGQRRIDAQH KRGKLTARERISLLL DPGSFVESDMFVEHR CADFGMAADKNKFP GDSVVTGRGRINGRL VYVFSQDFTVFGGSL SGAHAQKICKIMDQA ITVGAPVIGLNDSGG ARIQEGVESLAGYAD IFLRNVTASGVIPQISL IMGPCAGGAVYSPAL TDFTFMVKDTSYLFI TGPDVVKSVTNEDVT QEELGGAKTHTTMS GVAHRAFENDVDAL CNLRDFFNYLPLSSQ DPAPVRECHDPSDRL VPELDTIVPLESTKAY NMVDIIHSVVDEREF FEIMPNYAKNIIVGFA RMNGRTVGIVGNQP KVASGCLDINSSVKG ARFVRFCDAFNIPLIT FVDVPGFLPGTAQEY GGIIRHGAKLLYAFA EATVPKVTVITRKAY GGAYDVMSSKHLCG DTNYAWPTAEIAVM GAKGAVEIIFKGHEN VEAAQAEYIEKFANP FPAAVRGFVDDIIQPS STRARICCDLDVLAS KKVQRPWRKHANIP L | AUGGCCGCAGCCCU CAGAGUGGCUGCCG UGGGAGCCAGACUC AGCCGUGCUCGCCUC AGGCCUGCGGGCCG CAGUCAGAAGCCUG UGCAGCCAGGCAAC CUCAGUGAACGAGA GAAUCGAGAACAAG AGACGGACCGCCCU GCUGGGUGGCGGGC AAAGAAGAAUUGAC GCCCAGCACAAGAG AGGCAAGCUGACCG CCCGCGAGCGCAUC AGCCUGCUGCUGGA CCCCGGCAGCUUCG UGGAGAGCGACAUG UUCGUGGAGCAUCG GUGUGCCGACUUCG GCAUGGCCGCCGAC AAGAACAAGUUCCC CGGCGACAGCGUGG UGACCGGCAGAGGC AGAAUCAACGGCAG ACUGGUGUACGUGU UCUCACAAGACUUU ACCGUCUUCGGAGG AUCCCUGUCAGGGG CUCACGCCCAGAAG AUCUGCAAGAUCAU GGACCAGGCCAUCA CCGUGGGCGCUCCC GUGAUCGGCCUGAA CGACAGCGGAGGCG CCAGGAUCCAAGAG GGAGUGGAGUCCCU GGCCGGCUACGCCG ACAUCUUCCUGAGA AACGUGACCGCCUC GGGCGUGAUCCCAC AGAUCUCCCUGAUC AUGGGACCCUGCGC CGGCGGGGCCGUCU ACAGCCCUGCCCUG ACCGACUUCACCUU CAUGGUGAAGGACA CCAGCUACCUGUUC AUCACCGGCCCCGA CGUGGUCAAGAGCG UGACCAACGAGGAC GUGACCCAGGAGGA GCUCGGCGGAGCCA AGACUCACACAACC AUGUCCGGCGUCGC UCAUAGGGCCUUCG AGAACGACGUGGAC GCCCUGUGCAACCU GAGAGACUUCUUCA ACUACCUGCCAUUG AGCAGCCAGGAUCC CGCCCCUGUGAGAG AGUGCCACGACCCC AGCGACAGACUGGU GCCCGAGCUGGACA CCAUCGUGCCCCUG GAGAGCACCAAGGC CUACAACAUGGUGG ACAUCAUCCACAGC GUGGUGGACGAGAG | AGGAAA UAAGAG AGAAAA GAAGAG UAAGAA GAAAUA UAAGAG CCACC | UGAUAA UAGUCC AUAAAG UAGGAA ACACUA CAGCUG GAGCCU CGGUGG CCUAGC UUCUUG CCCCUU GGGCCU CCAUAA AGUAGG AAACAC UACAUC CCCCCA GCCCCU CCUCCC CUUCCU GCACCC GUACCC CCUCCA UAAAGU AGGAAA CACUAC AGUGGU CUUUGA AUAAAG UCUGAG UGGGCG GC | SEQ ID NO: 202 consists from 5' to 3' end: 5' UTR of SEQ ID NO: 199, ORF Sequence of SEQ ID NO: 198, and 3' UTR of SEQ ID NO: 178 |

-continued

CONSTRUCT SEQUENCES
By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | AGAGUUCUUCGAGA | | | |
| | | UCAUGCCCAACUAC | | | |
| | | GCCAAGAACAUCAU | | | |
| | | CGUGGGCUUCGCCA | | | |
| | | GAAUGAACGGCAGA | | | |
| | | ACCGUGGGCAUUGU | | | |
| | | GGGCAACCAGCCCA | | | |
| | | AGGUCGCCAGCGGC | | | |
| | | UGCCUCGACAUCAA | | | |
| | | CAGCAGCGUGAAGG | | | |
| | | GCGCCAGAUUCGUG | | | |
| | | AGAUUCUGCGACGC | | | |
| | | CUUCAACAUACCUC | | | |
| | | UGAUCACCUUUGUG | | | |
| | | GACGUGCCUGGUUU | | | |
| | | CCUCCCGGGCACCG | | | |
| | | CCCAAGAAUACGGU | | | |
| | | GGCAUCAUCAGACA | | | |
| | | CGGCGCCAAGCUGC | | | |
| | | UGUACGCCUUCGCC | | | |
| | | GAGGCCACCGUGCC | | | |
| | | CAAGGUGACCGUUA | | | |
| | | UCACCCGCAAAGCC | | | |
| | | UACGGCGGCGCCUA | | | |
| | | CGACGUGAUGAGCA | | | |
| | | GCAAGCACCUGUGU | | | |
| | | GGCGACACCAAUUA | | | |
| | | CGCCUGGCCCACCG | | | |
| | | CCGAGAUCGCCGUC | | | |
| | | AUGGGCGCGAAAGG | | | |
| | | AGCCGUGGAGAUCA | | | |
| | | UCUUCAAGGGCCAC | | | |
| | | GAGAACGUGGAGGC | | | |
| | | CGCCCAGGCCGAGU | | | |
| | | ACAUCGAGAAGUUC | | | |
| | | GCCAACCCCUUCCC | | | |
| | | UGCCGCCGUGAGGG | | | |
| | | GCUUCGUCGACGAU | | | |
| | | AUCAUCCAGCCCAG | | | |
| | | CUCCACCCGCGCCA | | | |
| | | GGAUUUGCUGCGAC | | | |
| | | CUGGACGUGCUGGC | | | |
| | | CAGCAAGAAGGUGC | | | |
| | | AAAGACCCUGGAGA | | | |
| | | AAGCACGCCAACAU | | | |
| | | CCCGCUG | | | |

| SEQ ID NO: | 1 | 11 | 199 | 178 | 203 |
|---|---|---|---|---|---|
| SE_PCCA_ 018_ 3xmiR142_ AGG (hPCCA; G5) Cap: C1 PolyA tail: 100 nt | MAGFWVGTAPLVAA GRRGRWPPQQLMLS AALRTLKHVLYYSR QCLMVSRNLGSVGY DPNEKTFDKILVANR GEIACRVIRTCKKMG IKTVAIHSDVDASSV HVKMADEAVCVGPA PTSKSYLNMDAIMEA IKKTRAQAVHPGYGF LSENKEFARCLAAED VVFIGPDTHAIQAMG DKIESKLLAKKAEVN TIPGFDGVVKDAEEA VRIAREIGYPVMIKAS AGGGGKGMRIAWDD EETRDGFRLSSQEAA SSFGDDRLLIEKFIDN PRHIEIQVLGDKHGN ALWLNERECSIQRRN QKVVEEAPSIFLDAE TRRAMGEQAVALAR AVKYSSAGTVEFLVD | AUGGCCGGCUUCUG GGUCGGCACAGCCC CUCUGGUGGCAGCC GGCAGAAGAGGACG GUGGCCUCCCCAGC AACUGAUGCUGAGC GCCGCCUUGAGAAC CCUGAAGCACGUGC UGUACUACAGCAGA CAGUGCCUGAUGGU GAGCAGAAAUCUGG GCAGCGUGGGGUAC GAUCCCAACGAGAA GACCUUCGAUAAGA UUCUGGUCGCGAAU AGAGGCGAGAUCGC CUGCAGGGUGAUCA GAACCUGCAAGAAG AUGGGCAUCAAGAC CGUGGCCAUCCAUU CGGACGUCGACGCG AGCAGCGUUCACGU GAAGAUGGCAGACG | AGGAAA UAAGAG AGAAAA GAAGAG UAAGAA GAAAUA UAAGAG CCACC | UGAUAA UAGUCC AUAAAG UAGGAA ACACUA CAGCUG GAGCCU CGGUGG CCUAGC UUCUUG CCCCUU GGGCCU CCAUAA AGUAGG AAACAC UACAUC CCCCCA GCCCCU CCUCCC CUUCCU GCACCC GUACCC CCUCCA | SEQ ID NO: 203 consists from 5' to 3' end: 5' UTR of SEQ ID NO: 199, ORF Sequence of SEQ ID NO: 11, and 3' UTR of SEQ ID NO: 178 |

-continued

CONSTRUCT SEQUENCES

By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | SKKNFYFLEMNTRLQ | AGGCCGUGUGCGUG | | UAAAGU | |
| | VEHPVTECITGLDLV | GGACCCGCCCCGAC | | AGGAAA | |
| | QEMIRVAKGYPLRH | CAGCAAGAGCUACC | | CACUAC | |
| | KQADIRINGWAVECR | UGAACAUGGACGCC | | AGUGGU | |
| | VYAEDPYKSFGLPSI | AUCAUGGAGGCCAU | | CUUUGA | |
| | GRLSQYQEPLHLPGV | CAAGAAGACCCGCG | | AUAAAG | |
| | RVDSGIQPGSDISIYY | CUCAAGCCGUGCAC | | UCUGAG | |
| | DPMISKLITYGSDRTE | CCGGGCUACGGCUU | | UGGGCG | |
| | ALKRMADALDNYVI | UCUGAGCGAGAACA | | GC | |
| | RGVTHNIALLREVIIN | AGGAAUUCGCCAGG | | | |
| | SRFVKGDISTKFLSDV | UGUCUCGCCGCCGA | | | |
| | YPDGFKGHMLTKSE | GGACGUAGUCUUCA | | | |
| | KNQLLAIASSLFVAF | UCGGCCCUGAUACG | | | |
| | QLRAQHFQENSRMP | CACGCGAUCCAGGC | | | |
| | VIKPDIANWELSVKL | CAUGGGCGACAAGA | | | |
| | HDKVHTVVASNNGS | UCGAGAGCAAACUG | | | |
| | VFSVEVDGSKLNVTS | CUGGCCAAGAAAGC | | | |
| | TWNLASPLLSVSVDG | AGAAGUCAACACCA | | | |
| | TQRTVQCLSREAGGN | UCCCCGGCUUCGAC | | | |
| | MSIQFLGTVYKVNIL | GGCGUGGUGAAGGA | | | |
| | TRLAAELNKFMLEK | CGCCGAAGAGGCUG | | | |
| | VTEDTSSVLRSPMPG | UCCGCAUCGCCAGA | | | |
| | VVVAVSVKPGDAVA | GAGAUCGGCUACCC | | | |
| | EGQEICVIEAMKMQN | UGUGAUGAUAAAG | | | |
| | SMTAGKTGTVKSVH | GCUAGCGCUGGAGG | | | |
| | CQAGDTVGEGDLLV | UGGCGGAAAGGGCA | | | |
| | ELE | UGAGAAUCGCCUGG | | | |
| | | GACGACGAGGAGAC | | | |
| | | UAGAGACGGCUUCA | | | |
| | | GACUGUCCUCCCAG | | | |
| | | GAGGCCGCCAGCUC | | | |
| | | CUUCGGAGACGACA | | | |
| | | GACUGCUGAUCGAG | | | |
| | | AAGUUCAUCGACAA | | | |
| | | CCCCAGACACAUCG | | | |
| | | AAAUCCAGGUGCUC | | | |
| | | GGUGACAAGCACGG | | | |
| | | GAACGCCCUGUGGC | | | |
| | | UGAACGAGAGAGAG | | | |
| | | UGCAGCAUCCAGAG | | | |
| | | AAGAAACCAGAAGG | | | |
| | | UGGUGGAGGAGGCG | | | |
| | | CCGAGCAUCUUUCU | | | |
| | | GGACGCGGAGACAA | | | |
| | | GGAGAGCGAUGGGC | | | |
| | | GAACAGGCCGUCGC | | | |
| | | CCUAGCAAGAGCCG | | | |
| | | UGAAGUACUCCAGU | | | |
| | | GCCGGAACCGUCGA | | | |
| | | GUUUCUUGUCGACA | | | |
| | | GCAAGAAGAAUUUC | | | |
| | | UACUUCCUGGAGAU | | | |
| | | GAACACCAGGCUGC | | | |
| | | AGGUGGAGCAUCCC | | | |
| | | GUGACAGAGUGCAU | | | |
| | | CACUGGACUGGAUC | | | |
| | | UGGUGCAGGAGAUG | | | |
| | | AUCAGGGUGGCCAA | | | |
| | | GGGCUAUCCCCUGA | | | |
| | | GACACAAGCAGGCC | | | |
| | | GACAUCAGAAUCAA | | | |
| | | CGGCUGGGCCGUGG | | | |
| | | AGUGCAGAGUGUAC | | | |
| | | GCCGAGGACCCCUA | | | |
| | | CAAGAGCUUCGGCC | | | |
| | | UGCCCAGCAUCGGC | | | |
| | | AGACUGAGCCAGUA | | | |
| | | CCAGGAGCCCCUGC | | | |
| | | ACCUGCCCGGCGUG | | | |
| | | AGAGUGGACAGCGG | | | |
| | | CAUCCAACCGGGGA | | | |
| | | GCGAUAUCAGCAUC | | | |
| | | UACUACGACCCCAU | | | |

-continued

CONSTRUCT SEQUENCES
By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | GAUCAGCAAGCUGA | | | |
| | | UAACCUACGGCAGC | | | |
| | | GACAGAACCGAGGC | | | |
| | | CCUGAAGAGAAUGG | | | |
| | | CCGACGCCCUGGAC | | | |
| | | AACUACGUGAUCAG | | | |
| | | AGGCGUGACCCACA | | | |
| | | ACAUCGCCCUGCUG | | | |
| | | AGAGAGGUGAUCAU | | | |
| | | CAACUCGAGGUUCG | | | |
| | | UGAAAGGCGACAUC | | | |
| | | AGCACCAAGUUCCU | | | |
| | | GAGCGACGUGUAUC | | | |
| | | CCGACGGAUUCAAA | | | |
| | | GGUCACAUGCUGAC | | | |
| | | CAAGAGCGAGAAGA | | | |
| | | ACCAGCUGCUGGCC | | | |
| | | AUCGCCUCAUCCCU | | | |
| | | GUUCGUGGCCUUCC | | | |
| | | AGCUGAGAGCCCAG | | | |
| | | CACUUCCAGGAGAA | | | |
| | | CAGCAGAAUGCCCG | | | |
| | | UGAUCAAGCCCGAC | | | |
| | | AUCGCCAACUGGGA | | | |
| | | GCUGAGCGUGAAGC | | | |
| | | UGCACGACAAGGUG | | | |
| | | CACACUGUCGUUGC | | | |
| | | CAGCAACAACGGCU | | | |
| | | CCGUGUUCAGCGUA | | | |
| | | GAGGUGGACGGAUC | | | |
| | | UAAGCUGAACGUGA | | | |
| | | CCUCCACCUGGAAC | | | |
| | | CUGGCAAGCCCUCU | | | |
| | | CCUGUCAGUGAGCG | | | |
| | | UGGACGGCACCCAG | | | |
| | | AGAACCGUGCAGUG | | | |
| | | UCUGUCCCGCGAGG | | | |
| | | CCGGCGGAAACAUG | | | |
| | | AGCAUCCAGUUCCU | | | |
| | | GGGCACCGUGUACA | | | |
| | | AGGUGAACAUCCUG | | | |
| | | ACCAGACUGGCCGC | | | |
| | | CGAGCUGAACAAGU | | | |
| | | UCAUGCUGGAGAAA | | | |
| | | GUGACGGAGGAUAC | | | |
| | | CAGCUCCGUGCUGA | | | |
| | | GAAGCCCCAUGCCC | | | |
| | | GGAGUGGUGGUGGC | | | |
| | | CGUUUCCGUGAAAC | | | |
| | | CUGGUGACGCCGUG | | | |
| | | GCCGAGGGCAAGA | | | |
| | | GAUCUGCGUGAUCG | | | |
| | | AGGCCAUGAAGAUG | | | |
| | | CAGAAUUCCAUGAC | | | |
| | | CGCCGGAAAGACCG | | | |
| | | GCACCGUCAAAUCA | | | |
| | | GUGCACUGCCAGGC | | | |
| | | GGGCGACACAGUGG | | | |
| | | GUGAGGGCGACCUG | | | |
| | | CUGGUGGAGCUGGA | | | |
| | | G | | | |
| SEQ ID NO: | 15 | 23 | 199 | 178 | 204 |
| SE_PCCB_ 018_ 3xmiR142_ AGG (hPCCB; G5) Cap: C1 | MAAALRVAAVGARL SVLASGLRAAVRSLC SQATSVNERIENKRR TALLGGGQRRIDAQH KRGKLTARERISLLL DPGSFVESDMFVEHR CADFGMAADKNKFP | AUGGCCGCAGCCCU CAGAGUGGCUGCCG UGGGAGCCAGACUC AGCGUGCUCGCCUC AGGCCUGCGGGCCG CAGUCAGAAGCCUG UGCAGCCAGGCAAC | AGGAAA UAAGAG AGAAA GAAGAG UAAGAA GAAAUA UAAGAG | UGAUAA UAGUCC AUAAAG UAGGAA ACACUA CAGCUG GAGCCU | SEQ ID NO: 204 consists from 5' to 3' end: 5' UTR of SEQ ID |

-continued

CONSTRUCT SEQUENCES
By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| PolyA tail: 100 nt | GDSVVTGRGRINGRL VYVFSQDFTVFGGSL SGAHAQKICKIMDQA ITVGAPVIGLNDSGG ARIQEGVESLAGYAD IFLRNVTASGVIPQISL IMGPCAGGAVYSPAL TDFTFMVKDTSYLFI TGPDVVKSVTNEDVT QEELGGAKTHTTMS GVAHRAFENDVDAL CNLRDFFNYLPLSSQ DPAPVRECHDPSDRL VPELDTIVPLESTKAY NMVDIIHSVVDEREF FEIMPNYAKNIIVGFA RMNGRTVGIVGNQP KVASGCLDINSSVKG ARFVRFCDAFNIPLIT FVDVPGFLPGTAQEY GGIIRHGAKLLYAFA EATVPKVTVITRKAY GGAYDVMSSKHLCG DTNYAWPTAEIAVM GAKGAVEIIFKGHEN VEAAQAEYIEKFANP FPAAVRGFVDDIIQPS STRARICCDLDVLAS KKVQRPWRKHANIP L | CUCAGUGAACGAGA GAAUCGAGAACAAG AGACGGACCGCCCU GCUGGGUGGCGGGC AAAGAAGAAUUGAC GCCCAGCACAAGAG AGGCAAGCUGACCG CCCGCGAGCGCAUC AGCCUGCUGCUGGA CCCCGGCAGCUUCG UGGAGAGCGACAUG UUCGUGGAGCAUCG GUGUGCCGACUUCG GCAUGGCCGCCGAC AAGAACAAGUUCCC CGGCGACAGCGUGG UGACCGGCAGAGGC AGAAUCAACGGCAG ACUGGUGUACGUGU UCUCACAAGACUUU ACCGUCUUCGGAGG AUCCCUGUCAGGGG CUCACGCCCAGAAG AUCUGCAAGAUCAU GGACCAGGCCAUCA CCGUGGGCGCUCCC GUGAUCGGCCUGAA CGACAGCGGAGGCG CCAGGAUCCAAGAG GGAGUGGAGUCCCU GGCCGGCUACGCCG ACAUCUUCCUGAGA AACGUGACCGCCUC GGGCGUGAUCCCAC AGAUCUCCCUGAUC AUGGGACCCUGCGC CGGCGGGGCCGUCU ACAGCCCUGCCCUG ACCGACUUCACCUU CAUGGUGAAGGACA CCAGCUACCUGUUC AUCACCGGCCCCGA CGUGGUCAAGAGCG UGACCAACGAGGAC GUGACCCAGGAGGA GCUCGGCGGAGCCA AGACUCACACAACC AUGUCCGGCGUCGC UCAUAGGGCCUUCG AGAACGACGUGGAC GCCCUGUGCAACCU GAGAGACUUCUUCA ACUACCUGCCAUUG AGCAGCCAGGAUCC CGCCCCUGUGAGAG AGUGCCACGACCCC AGCGACAGACUGGU GCCCGAGCUGGACA CCAUCGUGCCCCUG GAGAGCACCAAGGC CUACAACAUGGUGG ACAUCAUCCACAGC GUGGUGGACGAGAG AGAGUUCUUCGAGA UCAUGCCCAACUAC GCCAAGAACAUCAU CGUGGGCUUCGCCA GAAUGAACGGCAGA ACCGUGGGCAUUGU GGGCAACCAGCCCA AGGUCGCCAGCGGC UGCCUCGACAUCAA CAGCAGCGUGAAGG | CCACC | CGGUGG CCUAGC UUCUUG CCCCUU GGGCCU CCAUAA AGUAGG AAACAC UACAUC CCCCCA GCCCCU CCUCCC CUUCCU GCACCC GUACCC CCUCCA UAAAGU AGGAAA CACUAC AGUGGU CUUUGA AUAAAG UCUGAG UGGGCG GC | NO: 199, ORF Sequence of SEQ ID NO: 23, and 3' UTR of SEQ ID NO: 178 |

-continued

| CONSTRUCT SEQUENCES | | | | | |
| By "G5" is meant that all uracils (U) in the mRNA are replaced by N1-methylpseudouracils. | | | | | |
| mRNA Name | ORF Sequence (Amino Acid) | ORF Sequence (Nucleotide) | 5' UTR Sequence | 3' UTR Sequence | Construct Sequence |
| | | GCGCCAGAUUCGUG AGAUUCUGCGACGC CUUCAACAUACCUC UGAUCACCUUUGUG GACGUGCCUGGUUU CCUCCCGGGCACCG CCCAAGAAUACGGU GGCAUCAUCAGACA CGGCGCCAAGCUGC UGUACGCCUUCGCC GAGGCCACCGUGCC CAAGGUGACCGUUA UCACCCGCAAAGCC UACGGCGGCGCCUA CGACGUGAUGAGCA GCAAGCACCUGUGU GGCGACACCAAUUA CGCCUGGCCCACCG CCGAGAUCGCCGUC AUGGGCGCGAAAGG AGCCGUGGAGAUCA UCUUCAAGGGCCAC GAGAACGUGGAGGC CGCCCAGGCCGAGU ACAUCGAGAAGUUC GCCAACCCCUUCCC UGCCGCCGUGAGGG GCUUCGUCGACGAU AUCAUCCAGCCCAG CUCCACCCGCGCCA GAAUCUGUUGCGAC CUGGACGUGCUGGC CAGCAAGAAGGUGC AAAGACCCUGGAGA AAGCACGCCAACAU CCCGCUG | | | |

| SEQ ID NO: | 15 | 25 | 199 | 178 | 205 |
|---|---|---|---|---|---|
| SE_PCCB_ 020_ 3xmiR142_ AGG (hPCCB; G5) Cap: C1 PolyA tail: 100 nt | MAAALRVAAVGARL SVLASGLRAAVRSLC SQATSVNERIENKRR TALLGGGQRRIDAQH KRGKLTARERISLLL DPGSFVESDMFVEHR CADFGMAADKNKFP GDSVVTGRGRINGRL VYVFSQDFTVFGGSL SGAHAQKICKIMDQA ITVGAPVIGLNDSGG ARIQEGVESLAGYAD IPLRNVTASGVIPQISL IMGPCAGGAVYSPAL TDFTFMVKDTSYLFI TGPDVVKSVTNEDVT QEELGGAKTHTTMS GVAHRAFENDVDAL CNLRDFFNYLPLSSQ DPAPVRECHDPSDRL VPELDTIVPLESTKAY NMVDIIHSVVDEREF FEIMPNYAKNIIVGFA RMNGRTVGIVGNQP KVASGCLDINSSVKG ARFVRFCDAFNIPLIT FVDVPGFLPGTAQEY GGIIRHGAKLLYAFA EATVPKVTVITRKAY GGAYDVMSSKHLCG DTNYAWPTAEIAVM GAKGAVEIIFKGHEN VEAAQAEYIEKFANP | AUGGCGGCGGCAUU ACGGGUGGCGGCGG UCGGGGCAAGGCUC AGCGUGCUGGCCAG CGGCCUGAGAGCCG CCGUGAGAAGCCUG UGCAGCCAGGCCAC CAGCGUGAACGAGA GAAUCGAGAACAAG AGAAGAACCGCCCU GCUGGGCGGCGGCC AGAGAAGAAUCGAC GCCCAGCACAAGAG AGGCAAGCUGACCG CCAGAGAGAGAAUC AGCCUGCUGCUGGA CCCCGGCAGCUUCG UGGAGAGCGACAUG UUCGUGGAGCACAG GUGCGCCGACUUCG GCAUGGCCGCCGAC AAGAACAAGUUCCC CGGCGACAGCGUGG UGACCGGCAGAGGC AGAAUCAACGGCAG ACUGGUGUACGUGU UCAGCCAGGACUUC ACCGUGUUCGGCGG CAGCCUGAGCGGCG CCCACGCCCAGAAG AUCUGCAAGAUCAU GGACCAGGCCAUCA CCGUGGGCGCGCCC | AGGAAA UAAGAG AGAAAA GAAGAG UAAGAA GAAAUA UAAGAG CCACC | UGAUAA UAGUCC AUAAAG UAGGAA ACACUA CAGCUG GAGCCU CGGUGG CCUAGC UUCUUG CCCCUU GGGCCU CCAUAA AGUAGG AAACAC UACAUC CCCCCA GCCCCU CCUCCC CUUCCU GCACCC GUACCC CCUCCA UAAAGU AGGAAA CACUAC AGUGGU CUUUGA AUAAAG UCUGAG UGGGCG GC | SEQ ID NO: 205 consists from 5' to 3' end: 5' UTR of SEQ ID NO: 199, ORF Sequence of SEQ ID NO: 25, and 3' UTR of SEQ ID NO: 178 |

| | CONSTRUCT SEQUENCES | | | | |
|---|---|---|---|---|---|
| By "G5" is meant that all uracils (U) in the mRNA are replaced by N1-methylpseudouracils. | | | | | |
| mRNA<br>Name | ORF Sequence<br>(Amino Acid) | ORF Sequence<br>(Nucleotide) | 5' UTR<br>Sequence | 3' UTR<br>Sequence | Construct<br>Sequence |
| | FPAAVRGFVDDIIQPS<br>STRARICCDLDVLAS<br>KKVQRPWRKHANIP<br>L | GUGAUCGGCCUGAA<br>CGACAGCGGCGGCG<br>CCAGAAUCCAGGAG<br>GGCGUGGAGAGCCU<br>GGCCGGCUACGCCG<br>ACAUCUUCCUGAGA<br>AACGUGACCGCCAG<br>CGGCGUGAUCCCAC<br>AGAUCAGCCUGAUC<br>AUGGGCCCCUGCGC<br>CGGCGGCGCCGUGU<br>ACAGCCCCGCCCUG<br>ACCGACUUCACCUU<br>CAUGGUGAAGGACA<br>CCAGCUACCUGUUC<br>AUCACCGGCCCCGA<br>CGUGGUGAAGAGCG<br>UGACCAACGAGGAC<br>GUGACCCAGGAGGA<br>GCUGGGCGGCGCCA<br>AGACCCACACCACC<br>AUGAGCGGCGUGGC<br>CCACAGAGCCUUCG<br>AGAACGACGUGGAC<br>GCCCUGUGCAACCU<br>GAGAGACUUCUUCA<br>ACUACCUGCCCCUG<br>AGCAGCCAGGACCC<br>CGCGCCCGUGAGAG<br>AGUGCCACGACCCC<br>AGCGACAGACUGGU<br>GCCCGAGCUGGACA<br>CCAUCGUGCCCCUG<br>GAGAGCACCAAGGC<br>CUACAACAUGGUGG<br>ACAUCAUCCACAGC<br>GUGGUGGACGAGAG<br>AGAGUUCUUCGAGA<br>UCAUGCCCAACUAC<br>GCCAAGAACAUCAU<br>CGUGGGCUUCGCCA<br>GAAUGAACGGCAGA<br>ACCGUGGGCAUCGU<br>GGGCAACCAGCCCA<br>AGGUGGCCAGCGGC<br>UGCCUGGACAUCAA<br>CAGCAGCGUGAAGG<br>GCGCCAGAUUCGUG<br>AGAUUCUGCGACGC<br>CUUCAACAUCCCUC<br>UGAUCACCUUCGUG<br>GACGUGCCCGGCUU<br>CCUGCCCGGCACCG<br>CCCAGGAGUACGGC<br>GGCAUCAUCAGACA<br>CGGCGCCAAGCUGC<br>UGUACGCCUUCGCC<br>GAGGCCACCGUGCC<br>CAAGGUGACCGUGA<br>UCACCAGAAAGGCC<br>UACGGCGGCGCCUA<br>CGACGUGAUGAGCA<br>GCAAGCACCUGUGC<br>GGCGACACCAACUA<br>CGCCUGGCCCACCG<br>CCGAGAUCGCCGUG<br>AUGGGCGCCAAGGG<br>CGCCGUGGAGAUCA<br>UCUUCAAGGGCCAC<br>GAGAACGUGGAGGC<br>CGCCCAGGCCGAGU<br>ACAUCGAGAAGUUC<br>GCCAACCCCUUCCC | | | |

-continued

CONSTRUCT SEQUENCES
By "G5" is meant that all uracils (U) in the mRNA are replaced by N1-methylpseudouracils.

| mRNA Name | ORF Sequence (Amino Acid) | ORF Sequence (Nucleotide) | 5' UTR Sequence | 3' UTR Sequence | Construct Sequence |
|---|---|---|---|---|---|
| | | CGCCGCCGUGAGAG GCUUCGUGGACGAC AUCAUCCAGCCCAG CAGCACCAGAGCCA GAAUCUGCUGCGAC CUGGACGUGCUGGC CAGCAAGAAGGUGC AGAGACCCUGGAGA AAGCACGCCAACAU CCCUCUG | | | |

EXAMPLES

Example 1: Chimeric Polynucleotide Synthesis

A. Triphosphate Route

Two regions or parts of a chimeric polynucleotide can be joined or ligated using triphosphate chemistry. According to this method, a first region or part of 100 nucleotides or less can be chemically synthesized with a 5' monophosphate and terminal 3'desOH or blocked OH. If the region is longer than 80 nucleotides, it can be synthesized as two strands for ligation.

If the first region or part is synthesized as a non-positionally modified region or part using in vitro transcription (IVT), conversion the 5'monophosphate with subsequent capping of the 3' terminus can follow. Monophosphate protecting groups can be selected from any of those known in the art.

The second region or part of the chimeric polynucleotide can be synthesized using either chemical synthesis or IVT methods. IVT methods can include an RNA polymerase that can utilize a primer with a modified cap. Alternatively, a cap of up to 80 nucleotides can be chemically synthesized and coupled to the IVT region or part.

It is noted that for ligation methods, ligation with DNA T4 ligase, followed by treatment with DNAse should readily avoid concatenation.

The entire chimeric polynucleotide need not be manufactured with a phosphate-sugar backbone. If one of the regions or parts encodes a polypeptide, then such region or part can comprise a phosphate-sugar backbone.

Ligation can then be performed using any known click chemistry, orthoclick chemistry, solulink, or other bioconjugate chemistries known to those in the art.

B. Synthetic Route

The chimeric polynucleotide can be made using a series of starting segments. Such segments include:

(a) Capped and protected 5' segment comprising a normal 3'OH (SEG. 1)

(b) 5' triphosphate segment which can include the coding region of a polypeptide and comprising a normal 3'OH (SEG. 2)

(c) 5' monophosphate segment for the 3' end of the chimeric polynucleotide (e.g., the tail) comprising cordycepin or no 3'OH (SEG. 3)

After synthesis (chemical or IVT), segment 3 (SEG. 3) can be treated with cordycepin and then with pyrophosphatase to create the 5'monophosphate.

Segment 2 (SEG. 2) can then be ligated to SEG. 3 using RNA ligase. The ligated polynucleotide can then be purified and treated with pyrophosphatase to cleave the diphosphate. The treated SEG.2-SEG. 3 construct is then purified and SEG. 1 is ligated to the 5' terminus. A further purification step of the chimeric polynucleotide can be performed.

Where the chimeric polynucleotide encodes a polypeptide, the ligated or joined segments can be represented as: 5' UTR (SEG. 1), open reading frame or ORF (SEG. 2) and 3' UTR+PolyA (SEG. 3).

The yields of each step can be as much as 90-95%.

Example 2: PCR for cDNA Production

PCR procedures for the preparation of cDNA can be performed using 2x KAPA HIFI™ HotStart ReadyMix by Kapa Biosystems (Woburn, MA). This system includes 2× KAPA ReadyMix12.5 µl; Forward Primer (10 µM) 0.75 µl; Reverse Primer (10 µM) 0.75 µl; Template cDNA –100 ng; and dH$_2$O diluted to 25.0 µl. The PCR reaction conditions can be: at 95° C. for 5 min. and 25 cycles of 98° C. for 20 sec, then 58° C. for 15 sec, then 72° C. for 45 sec, then 72° C. for 5 min. then 4° C. to termination.

The reverse primer of the instant invention can incorporate a poly-T$_{120}$ for a poly-A$_{120}$ in the mRNA. Other reverse primers with longer or shorter poly(T) tracts can be used to adjust the length of the poly(A) tail in the polynucleotide mRNA.

The reaction can be cleaned up using Invitrogen's PURE-LINK™ PCR Micro Kit (Carlsbad, CA) per manufacturer's instructions (up to 5 µg). Larger reactions will require a cleanup using a product with a larger capacity. Following the cleanup, the cDNA can be quantified using the NANO-DROP™ and analyzed by agarose gel electrophoresis to confirm the cDNA is the expected size. The cDNA can then be submitted for sequencing analysis before proceeding to the in vitro transcription reaction.

Example 3: In Vitro Transcription (IVT)

The in vitro transcription reactions can generate polynucleotides containing uniformly modified polynucleotides. Such uniformly modified polynucleotides can comprise a region or part of the polynucleotides of the invention. The input nucleotide triphosphate (NTP) mix can be made using natural and un-natural NTPs.

A typical in vitro transcription reaction can include the following:

1 Template cDNA—1.0 μg 2 10× transcription buffer (400 mM Tris-HCl pH 8.0, 190 mM MgCl₂, 50 mM DTT, 10 mM Spermidine)—2.0 μl 3 Custom NTPs (25 mM each)—7.2 μl 4 RNase Inhibitor—20 U 5 T7 RNA polymerase—3000 U 6 dH₂O—Up to 20.0 μl. and 7 Incubation at 37° C. for 3 hr-5 hrs.

The crude IVT mix can be stored at 4° C. overnight for cleanup the next day. 1 U of RNase-free DNase can then be used to digest the original template. After 15 minutes of incubation at 37° C., the mRNA can be purified using Ambion's MEGACLEAR™ Kit (Austin, TX) following the manufacturer's instructions. This kit can purify up to 500 μg of RNA. Following the cleanup, the RNA can be quantified using the NanoDrop and analyzed by agarose gel electrophoresis to confirm the RNA is the proper size and that no degradation of the RNA has occurred.

Example 4: Enzymatic Capping

Capping of a polynucleotide can be performed with a mixture includes: IVT RNA 60 μg-180 μg and dH₂O up to 72 μl. The mixture can be incubated at 65° C. for 5 minutes to denature RNA, and then can be transferred immediately to ice.

The protocol can then involve the mixing of 10× Capping Buffer (0.5 M Tris-HCl (pH 8.0), 60 mM KCl, 12.5 mM MgCl₂) (10.0 μl); 20 mM GTP (5.0 μl); 20 mM S-Adenosyl Methionine (2.5 μl); RNase Inhibitor (100 U); 2'-O-Methyltransferase (400U); Vaccinia capping enzyme (Guanylyl transferase) (40 U); dH₂O (Up to 28 μl); and incubation at 37° C. for 30 minutes for 60 μg RNA or up to 2 hours for 180 μg of RNA.

The polynucleotide can then be purified using Ambion's MEGACLEAR™ Kit (Austin, TX) following the manufacturer's instructions. Following the cleanup, the RNA can be quantified using the NANODROP™ (ThermoFisher, Waltham, MA) and analyzed by agarose gel electrophoresis to confirm the RNA is the proper size and that no degradation of the RNA has occurred. The RNA product can also be sequenced by running a reverse-transcription-PCR to generate the cDNA for sequencing.

Example 5: PolyA Tailing Reaction

Without a poly-T in the cDNA, a poly-A tailing reaction must be performed before cleaning the final product. This can be done by mixing Capped IVT RNA (100 μl); RNase Inhibitor (20 U); 10× Tailing Buffer (0.5 M Tris-HCl (pH 8.0), 2.5 M NaCl, 100 mM MgCl₂)(12.0 μl); 20 mM ATP (6.0 μl); Poly-A Polymerase (20 U); dH₂O up to 123.5 μl and incubating at 37° C. for 30 min. If the poly-A tail is already in the transcript, then the tailing reaction can be skipped and proceed directly to cleanup with Ambion's MEGA-CLEAR™ kit (Austin, TX) (up to 500 μg). Poly-A Polymerase is, in some cases, a recombinant enzyme expressed in yeast.

It should be understood that the processivity or integrity of the polyA tailing reaction does not always result in an exact size polyA tail. Hence polyA tails of approximately between 40-200 nucleotides, e.g., about 40, 50, 60, 70, 80, 90, 91, 92, 93, 94, 95, 96, 97, 98, 99, 100, 101, 102, 103, 104, 105, 106, 107, 108, 109, 110, 150-165, 155, 156, 157, 158, 159, 160, 161, 162, 163, 164 or 165 are within the scope of the invention.

Example 6: Natural 5' Caps and 5' Cap Analogues

5'-capping of polynucleotides can be completed concomitantly during the in vitro-transcription reaction using the following chemical RNA cap analogs to generate the 5'-guanosine cap structure according to manufacturer protocols: 3'-O-Me-m7G(5')ppp(5') G [the ARCA cap]; G(5') ppp(5')A; G(5')ppp(5')G; m7G(5')ppp(5')A; m7G(5')ppp (5')G (New England BioLabs, Ipswich, MA). 5'-capping of modified RNA can be completed post-transcriptionally using a Vaccinia Virus Capping Enzyme to generate the "Cap 0" structure: m7G(5')ppp(5')G (New England Bio-Labs, Ipswich, MA). Cap 1 structure can be generated using both Vaccinia Virus Capping Enzyme and a 2'-O methyl-transferase to generate: m7G(5')ppp(5')G-2'-O-methyl. Cap 2 structure can be generated from the Cap 1 structure followed by the 2'-O-methylation of the 5'-antepenultimate nucleotide using a 2'-O methyl-transferase. Cap 3 structure can be generated from the Cap 2 structure followed by the 2'-O-methylation of the 5'-preantepenultimate nucleotide using a 2'-O methyl-transferase. Enzymes can be derived from a recombinant source.

When transfected into mammalian cells, the modified mRNAs can have a stability of between 12-18 hours or more than 18 hours, e.g., 24, 36, 48, 60, 72 or greater than 72 hours.

Example 7: Capping Assays

A. Protein Expression Assay

Polynucleotides encoding a polypeptide, containing any of the caps taught herein, can be transfected into cells at equal concentrations. After 6, 12, 24 and 36 hours post-transfection, the amount of protein secreted into the culture medium can be assayed by ELISA. Synthetic polynucleotides that secrete higher levels of protein into the medium would correspond to a synthetic polynucleotide with a higher translationally-competent Cap structure.

B. Purity Analysis Synthesis

Polynucleotides encoding a polypeptide, containing any of the caps taught herein, can be compared for purity using denaturing Agarose-Urea gel electrophoresis or HPLC analysis. Polynucleotides with a single, consolidated band by electrophoresis correspond to the higher purity product compared to polynucleotides with multiple bands or streaking bands. Synthetic polynucleotides with a single HPLC peak would also correspond to a higher purity product. The capping reaction with a higher efficiency would provide a more pure polynucleotide population.

C. Cytokine Analysis

Polynucleotides encoding a polypeptide, containing any of the caps taught herein, can be transfected into cells at multiple concentrations. After 6, 12, 24 and 36 hours post-transfection the amount of pro-inflammatory cytokines such as TNF-alpha and IFN-beta secreted into the culture medium can be assayed by ELISA. Polynucleotides resulting in the secretion of higher levels of pro-inflammatory cytokines into the medium would correspond to polynucleotides containing an immune-activating cap structure.

D. Capping Reaction Efficiency

Polynucleotides encoding a polypeptide, containing any of the caps taught herein, can be analyzed for capping reaction efficiency by LC-MS after nuclease treatment.

Nuclease treatment of capped polynucleotides would yield a mixture of free nucleotides and the capped 5'-5-triphosphate cap structure detectable by LC-MS. The amount of capped product on the LC-MS spectra can be expressed as a percent of total polynucleotide from the reaction and would correspond to capping reaction efficiency. The cap structure with higher capping reaction efficiency would have a higher amount of capped product by LC-MS.

Example 8: Agarose Gel Electrophoresis of Modified RNA or RT PCR Products

Individual polynucleotides (200-400 ng in a 20 μl volume) or reverse transcribed PCR products (200-400 ng) can be loaded into a well on a non-denaturing 1.2% Agarose E-Gel (Invitrogen, Carlsbad, CA) and run for 12-15 minutes according to the manufacturer protocol.

Example 9: Nanodrop Modified RNA Quantification and UV Spectral Data

Modified polynucleotides in TE buffer (1 μl) can be used for Nanodrop UV absorbance readings to quantitate the yield of each polynucleotide from a chemical synthesis or in vitro transcription reaction.

Example 10: Formulation of Modified mRNA Using Lipidoids

Polynucleotides can be formulated for in vitro experiments by mixing the polynucleotides with the lipidoid at a set ratio prior to addition to cells. In vivo formulation can require the addition of extra ingredients to facilitate circulation throughout the body. To test the ability of these lipidoids to form particles suitable for in vivo work, a standard formulation process used for siRNA-lipidoid formulations can be used as a starting point. After formation of the particle, polynucleotide can be added and allowed to integrate with the complex. The encapsulation efficiency can be determined using a standard dye exclusion assays.

Example 11: Method of Screening for Protein Expression

A. Electrospray Ionization

A biological sample that can contain proteins encoded by a polynucleotide administered to the subject can be prepared and analyzed according to the manufacturer protocol for electrospray ionization (ESI) using 1, 2, 3 or 4 mass analyzers. A biologic sample can also be analyzed using a tandem ESI mass spectrometry system.

Patterns of protein fragments, or whole proteins, can be compared to known controls for a given protein and identity can be determined by comparison.

B. Matrix-Assisted Laser Desorption/Ionization

A biological sample that can contain proteins encoded by one or more polynucleotides administered to the subject can be prepared and analyzed according to the manufacturer protocol for matrix-assisted laser desorption/ionization (MALDI).

Patterns of protein fragments, or whole proteins, can be compared to known controls for a given protein and identity can be determined by comparison.

C. Liquid Chromatography-Mass Spectrometry-Mass Spectrometry

A biological sample, which can contain proteins encoded by one or more polynucleotides, can be treated with a trypsin enzyme to digest the proteins contained within. The resulting peptides can be analyzed by liquid chromatography-mass spectrometry-mass spectrometry (LC/MS/MS). The peptides can be fragmented in the mass spectrometer to yield diagnostic patterns that can be matched to protein sequence databases via computer algorithms. The digested sample can be diluted to achieve 1 ng or less starting material for a given protein. Biological samples containing a simple buffer background (e.g., water or volatile salts) are amenable to direct in-solution digest; more complex backgrounds (e.g., detergent, non-volatile salts, glycerol) require an additional clean-up step to facilitate the sample analysis.

Patterns of protein fragments, or whole proteins, can be compared to known controls for a given protein and identity can be determined by comparison.

Example 12: Synthesis of mRNA Encoding PCCA and PCCB

Sequence optimized polynucleotides encoding PCCA polypeptides, i.e., SEQ ID NOs: 1, or PCCB polypeptides, i.e., SEQ ID NOs: 15, were synthesized and characterized as described in Examples 1 to 11. mRNA's encoding human PCCA isoform 1 and human PCCB isoform 1 were prepared for the Examples described below, and were synthesized and characterized as described in Examples 1 to 11.

An mRNA encoding human PCCA can be constructed, e.g., by using the ORF sequences provided in SEQ ID NOs: 2 and 5-14. An mRNA encoding human PCCB can be constructed, e.g., by using the ORF sequences provided in SEQ ID NO: 16-27, 196, 197, and 198. The mRNA sequence includes both 5' and 3' UTR regions flanking the ORF sequence (nucleotide). In an exemplary construct, the 5' UTR and 3' UTR sequences are SEQ ID NO: 3 and SEQ ID NO: 4, respectively (see Sequence Listing).

```
5'UTR:
                                        (SEQ ID NO: 3)
GGGAAAUAAGAGAGAAAAGAAGAGUAAGAAGAAAUAUAAGAGCCACC

3'UTR:
                                        (SEQ ID NO: 4)
UGAUAAUAGGCUGGAGCCUCGGUGGCCUAGCUUCUUGCCCCUUGGGCCUC

CCCCCAGCCCCUCCUCCCCUUCCUGCACCCGUACCCCCUCCAUAAAGUAG

GAAACACUACAGUGGUCUUUGAAUAAAGUCUGAGUGGGCGGC
```

In another exemplary construct, the 5' UTR and 3' UTR sequences are as follows:

```
5'UTR:
                                       (SEQ ID NO: 88)
UCAAGCUUUUGGACCCUCGUACAGAAGCUAAUACGACUCACUAUAGGGAA

AUAAGAGAGAAAAGAAGAGUAAGAAGAAAUAUAAGAGCCACC

3'UTR:
                                      (SEQ ID NO: 150)
UGAUAAUAGGCUGGAGCCUCGGUGGCCAUGCUUCUUGCCCCUUGGGCCUC

CCCCCAGCCCCUCCUCCCCUUCCUGCACCCGUACCCCCGUGGUCUUUGAA

UAAAGUCUGAGUGGGCGGC
```

In another exemplary construct, the 5' UTR and 3' UTR sequences are as follows:

```
5' UTR:
                              (SEQ ID NO: 3)
GGGAAAUAAGAGAGAAAAGAAGAGUAAGAAGAAAUAUAAGAGCCACC

3'UTR:
                              (SEQ ID NO: 178)
UGAUAAUAGUCCAUAAAGUAGGAAACACUACAGCUGGAGCCUCGGUG

GCCUAGCUUCUUGCCCCUUGGGCCUCCAUAAAGUAGGAAACACUACA

UCCCCCCAGCCCCUCCUCCCCUUCCUGCACCCGUACCCCCUCCAUAA

AGUAGGAAACACUACAGUGGUCUUUGAAUAAAGUCUGAGUGGGCGGC
```

In another exemplary construct, the 5' UTR and 3' UTR sequences are as follows:

```
5' UTR:
                              (SEQ ID NO: 64)
GGGAAAUAAGAGAGAAAAGAAGAGUAAGAAGAAAUAUAAGAGCCACC

3'UTR:
                              (SEQ ID NO: 112)
UGAUAAUAGUCCAUAAAGUAGGAAACACUACAGCUGGAGCCUCGGUG

GCCUAGCUUCUUGCCCCUUGGGCCUCCCCCCAGCCCCUCCUCCCCUU

CCUGCACCCGUACCCCCGCAUUAUUACUCACGGUACGAGUGGUCUU

UGAAUAAAGUCUGAGUGGGCGGC
```

In another exemplary construct, the 5' UTR and 3' UTR sequences are as follows:

```
5'UTR:
                              (SEQ ID NO: 3)
GGGAAAUAAGAGAGAAAAGAAGAGUAAGAAGAAAUAUAAGAGCCACC

3'UTR:
                              (SEQ ID NO: 112)
UGAUAAUAGUCCAUAAAGUAGGAAACACUACAGCUGGAGCCUCGGUGGCC

UAGCUUCUUGCCCCUUGGGCCUCCCCCCAGCCCCUCCUCCCCUUCCUGCA

CCCGUACCCCCGCAUUAUUACUCACGGUACGAGUGGUCUUUGAAUAAAG

UCUGAGUGGGCGGC
```

In another exemplary construct, the 5' UTR and 3' UTR sequences are as follows:

```
5'UTR:
                              (SEQ ID NO: 199)
AGGAAAUAAGAGAGAAAAGAAGAGUAAGAAGAAAUAUAAGAGCCACC

3'UTR:
                              (SEQ ID NO: 4)
UGAUAAUAGGCUGGAGCCUCGGUGGCCUAGCUUCUUGCCCCUUGGGCCUC

CCCCCAGCCCCUCCUCCCCUUCCUGCACCCGUACCCCCUCCAUAAAGUAG

GAAACACUACAGUGGUCUUUGAAUAAAGUCUGAGUGGGCGGC
```

In another exemplary construct, the 5' UTR and 3' UTR sequences are as follows:

```
5'UTR:
                              (SEQ ID NO: 199)
AGGAAAUAAGAGAGAAAAGAAGAGUAAGAAGAAAUAUAAGAGCCACC
```

-continued
```
3'UTR:
                              (SEQ ID NO: 178)
UGAUAAUAGUCCAUAAAGUAGGAAACACUACAGCUGGAGCCUCGGUGGCC

UAGCUUCUUGCCCCUUGGGCCUCCAUAAAGUAGGAAACACUACAUCCCCC

CAGCCCCUCCUCCCCUUCCUGCACCCGUACCCCCUCCAUAAAGUAGGAAA

CACUACAGUGGUCUUUGAAUAAAGUCUGAGUGGGCGGC
```

In another exemplary construct, the 5' UTR and 3' UTR sequences are as follows:

```
5'UTR:
                              (SEQ ID NO: 199)
AGGAAAUAAGAGAGAAAAGAAGAGUAAGAAGAAAUAUAAGAGCCACC

3'UTR:
                              (SEQ ID NO: 112)
UGAUAAUAGUCCAUAAAGUAGGAAACACUACAGCUGGAGCCUCGGUGGCC

UAGCUUCUUGCCCCUUGGGCCUCCCCCCAGCCCCUCCUCCCCUUCCUGCA

CCCGUACCCCCCGCAUUAUUACUCACGGUACGAGUGGUCUUUGAAUAAAG

UCUGAGUGGGCGGC
```

The PCCA and PCCB mRNA sequences were prepared as modified mRNA. Specifically, during in vitro translation, modified mRNA can be generated using N1-methyl-pseudouridine-5'-Triphosphate or 5-methoxy-UTP to ensure that the mRNAs contain 100% N1-methyl-pseudouridine or 5-methoxy-uridine instead of uridine. Further, PCCA/PCCB-mRNA can be synthesized with a primer that introduces a polyA-tail, and a Cap 1 structure is generated on both mRNAs using Vaccinia Virus Capping Enzyme and a 2'-O methyl-transferase to generate: m7G(5')ppp(5')G-2'-O-methyl.

Example 13: Detecting Endogenous PCCA/PCCB Expression In Vitro

PCCA and PCCB expression is characterized in a variety of cell lines derived from both mice and human sources. Cell are cultured in standard conditions and cell extracts are obtained by placing the cells in lysis buffer. For comparison purposes, appropriate controls are also prepared. To analyze PCCA and PCCB expression, lysate samples are prepared from the tested cells and mixed with lithium dodecyl sulfate sample loading buffer and subjected to standard Western blot analysis. For detection of PCCA, the antibody used is a commercial anti-PCCA antibody. A commercial anti-PCCB antibody is used for detection of PCCB. For detection of a load control, the antibody used is anti-citrate synthase (rabbit polyclonal; ab96600; Abcam). To examine the localization of endogenous PCCA or PCCB, immunofluorescence analysis is performed on cells. PCCA expression is detected using a commercial anti-PCCA antibody, while PCCB expression is detected using a commercial PCCB antibody. The location of specific organelles can be detected with existing commercial products. For example, mitochondria can be detected using Mitotracker, and the nucleus can be stained with DAPI. Image analysis is performed on a Zeiss ELYRA imaging system.

Endogenous PCCA expression in vehicle control-transfected cells can be used as a comparator group to determine changes in PCCA expression resulting from transfection with mRNAs comprising nucleic acids encoding PCCA. Likewise, endogenous PCCB expression in vehicle control-transfected cells can be used as a comparator group to determine changes in PCCB expression resulting from transfection with mRNAs comprising nucleic acids encoding PCCB.

Example 14: In Vitro Expression of PCCA/PCCB in Cells

To measure in vitro expression of human PCCA and PCCB in a mouse or human liver cell line, Hepa1-6 cells (ATCC® HB-8064™), PCCA-deficient Hep3B cells, PCCB-deficient Hep3B cells, or patient fibroblasts are used. Cells are seeded on 6-well plates (BD Biosciences, San Jose, USA) one day prior to transfection. mRNA formulations comprising wild type or sequence optimized human PCCA and PCCB, or a GFP control, are transfected using 1 or 2 μg mRNA and 3 or 6 μL Lipofectamin MessagerMax in 100 μL OPTI-MEM per well and incubated.

After 24 and 48 hours, the cells in each well are lysed using a consistent amount of lysis buffer. Appropriate controls are used, including actin (detected using anti-B-actin mouse monoclonal antibody #3700; Cell Signaling Technology). Protein concentrations of each are determined using a BCA assay according to manufacturer's instructions. To analyze PCCA and PCCB expression, equal loads of each lysate (i.e. 40 μg) are prepared in a loading buffer and subjected to standard Western blot analysis. For detection of PCCA, PCCB and control, commercial antibodies are used according to the manufacturer's instructions.

Example 15: In Vitro PCC Activity in Cells

An in vitro PCC activity assay is performed to determine whether PCCA or PCCB exogenously-expressed after introduction of mRNA comprising a PCCA or PCCB sequence is active.

A. Expression Assay

Hepa 1-6 cells, PCCA-deficient or PCCB-deficient patient fibroblasts cells are transfected with mRNA formulations comprising human PCCA or PCCB, or a GFP control. Cells are transfected with Lipofectamin-MessagerMax and lysed as described in Example 14 above. Appropriate controls are also prepared.

B. Activity Assay

To assess whether exogenous PCCA and PCCB can form functional PCC complex, an in vitro activity assay was performed using transfected Hepa 1-6 cells, PCCA-deficient or PCCB-deficient patient fibroblasts lysates as the source of enzymatic activity. To begin, lysate is mixed with PCC substrates, ATP, propionyl CoA, and 14C radioisotope labeled sodium bicarbonate. The reaction mixture was incubated at 37C for 15 min in a Thermo-mixer. The reaction was stopped by 5% TCA and vortexing. The reaction tubes were then centrifuged at 13,000 g for 5 min, and the supernatant was collected for quantification of radioisotope labeled enzymatic products methylmalonyl-CoA resulting from the activity of PCC protein complex using Microbeta2 scintillation counter according to the manufacturers' recommendations.

Example 16: Human PCCA and PCCB Mutant and Chimeric Constructs

A polynucleotide of the present invention can comprise at least a first region of linked nucleotides encoding human PCCA or PCCB, which can be constructed, expressed, and characterized according to the examples above. Similarly, the polynucleotide sequence can contain one or more mutations that results in the expression of a PCCA or PCCB with increased or decreased activity. Furthermore, the polynucleotide sequence encoding PCCA or PCCB can be part of a construct encoding a chimeric fusion protein.

Example 17: Production of Nanoparticle Compositions

A. Production of Nanoparticle Compositions

Nanoparticles can be made with mixing processes such as microfluidics and T-junction mixing of two fluid streams, one of which contains the polynucleotide and the other has the lipid components.

Lipid compositions are prepared by combining an ionizable amino lipid disclosed herein, e.g., a lipid according to Formula (I) such as Compound II or a lipid according to Formula (III) such as Compound VI, a phospholipid (such as DOPE or DSPC, obtainable from Avanti Polar Lipids, Alabaster, AL), a PEG lipid (such as 1,2-dimyristoyl-sn-glycerol methoxypolyethylene glycol, also known as PEG-DMG, obtainable from Avanti Polar Lipids, Alabaster, AL), and a structural lipid (such as cholesterol, obtainable from Sigma-Aldrich, Taufkirchen, Germany, or a corticosteroid (such as prednisolone, dexamethasone, prednisone, and hydrocortisone), or a combination thereof) at concentrations of about 50 mM in ethanol. Solutions should be refrigerated for storage at, for example, −20° C. Lipids are combined to yield desired molar ratios and diluted with water and ethanol to a final lipid concentration of between about 5.5 mM and about 25 mM.

Nanoparticle compositions including a polynucleotide and a lipid composition are prepared by combining the lipid solution with a solution including the a polynucleotide at lipid composition to polynucleotide wt:wt ratios between about 5:1 and about 50:1. The lipid solution is rapidly injected using a NanoAssemblr microfluidic based system at flow rates between about 10 ml/min and about 18 ml/min into the polynucleotide solution to produce a suspension with a water to ethanol ratio between about 1:1 and about 4:1.

For nanoparticle compositions including an RNA, solutions of the RNA at concentrations of 0.1 mg/ml in deionized water are diluted in 50 mM sodium citrate buffer at a pH between 3 and 4 to form a stock solution.

Nanoparticle compositions can be processed by dialysis to remove ethanol and achieve buffer exchange. Formulations are dialyzed twice against phosphate buffered saline (PBS), pH 7.4, at volumes 200 times that of the primary product using Slide-A-Lyzer cassettes (Thermo Fisher Scientific Inc., Rockford, IL) with a molecular weight cutoff of 10 kD. The first dialysis is carried out at room temperature for 3 hours. The formulations are then dialyzed overnight at 4° C. The resulting nanoparticle suspension is filtered through 0.2 μm sterile filters (Sarstedt, Nümbrecht, Germany) into glass vials and sealed with crimp closures. Nanoparticle composition solutions of 0.01 mg/ml to 0.10 mg/ml are generally obtained.

The method described above induces nano-precipitation and particle formation. Alternative processes including, but not limited to, T-junction and direct injection, can be used to achieve the same nano-precipitation.

B. Characterization of Nanoparticle Compositions

A Zetasizer Nano ZS (Malvern Instruments Ltd, Malvern, Worcestershire, UK) can be used to determine the particle size, the polydispersity index (PDI) and the zeta potential of the nanoparticle compositions in 1×PBS in determining particle size and 15 mM PBS in determining zeta potential.

Ultraviolet-visible spectroscopy can be used to determine the concentration of a polynucleotide (e.g., RNA) in nanoparticle compositions. 100 µL of the diluted formulation in 1×PBS is added to 900 µL of a 4:1 (v/v) mixture of methanol and chloroform. After mixing, the absorbance spectrum of the solution is recorded, for example, between 230 nm and 330 nm on a DU 800 spectrophotometer (Beckman Coulter, Beckman Coulter, Inc., Brea, CA). The concentration of polynucleotide in the nanoparticle composition can be calculated based on the extinction coefficient of the polynucleotide used in the composition and on the difference between the absorbance at a wavelength of, for example, 260 nm and the baseline value at a wavelength of, for example, 330 nm.

For nanoparticle compositions including an RNA, a QUANT-IT™ RIBOGREEN® RNA assay (Invitrogen Corporation Carlsbad, CA) can be used to evaluate the encapsulation of an RNA by the nanoparticle composition. The samples are diluted to a concentration of approximately 5 µg/mL in a TE buffer solution (10 mM Tris-HCl, 1 mM EDTA, pH 7.5). 50 µL of the diluted samples are transferred to a polystyrene 96 well plate and either 50 µL of TE buffer or 50 µL of a 2% Triton X-100 solution is added to the wells. The plate is incubated at a temperature of 37° C. for 15 minutes. The RIBOGREEN® reagent is diluted 1:100 in TE buffer, and 100 µL of this solution is added to each well. The fluorescence intensity can be measured using a fluorescence plate reader (Wallac Victor 1420 Multilablel Counter; Perkin Elmer, Waltham, MA) at an excitation wavelength of, for example, about 480 nm and an emission wavelength of, for example, about 520 nm. The fluorescence values of the reagent blank are subtracted from that of each of the samples and the percentage of free RNA is determined by dividing the fluorescence intensity of the intact sample (without addition of Triton X-100) by the fluorescence value of the disrupted sample (caused by the addition of Triton X-100).

Exemplary formulations of the nanoparticle compositions are presented in the Table 6 below. The term "Compound" refers to an ionizable lipid such as MC3, Compound II, or Compound VI. "Phospholipid" can be DSPC or DOPE. "PEG-lipid" can be PEG-DMG or Compound I.

TABLE 6

Exemplary Formulations of Nanoparticles

| Composition (mol %) | Components |
| --- | --- |
| 40:20:38.5:1.5 | Compound:Phospholipid:Chol:PEG-lipid |
| 45:15:38.5:1.5 | Compound:Phospholipid:Chol:PEG-lipid |
| 50:10:38.5:1.5 | Compound:Phospholipid:Chol:PEG-lipid |
| 55:5:38.5:1.5 | Compound:Phospholipid:Chol:PEG-lipid |
| 60:5:33.5:1.5 | Compound:Phospholipid:Chol:PEG-lipid |
| 45:20:33.5:1.5 | Compound:Phospholipid:Chol:PEG-lipid |
| 50:20:28.5:1.5 | Compound:Phospholipid:Chol:PEG-lipid |
| 55:20:23.5:1.5 | Compound:Phospholipid:Chol:PEG-lipid |
| 60:20:18.5:1.5 | Compound:Phospholipid:Chol:PEG-lipid |
| 40:15:43.5:1.5 | Compound:Phospholipid:Chol:PEG-lipid |
| 50:15:33.5:1.5 | Compound:Phospholipid:Chol:PEG-lipid |
| 55:15:28.5:1.5 | Compound:Phospholipid:Chol:PEG-lipid |
| 60:15:23.5:1.5 | Compound:Phospholipid:Chol:PEG-lipid |
| 40:10:48.5:1.5 | Compound:Phospholipid:Chol:PEG-lipid |
| 45:10:43.5:1.5 | Compound:Phospholipid:Chol:PEG-lipid |
| 55:10:33.5:1.5 | Compound:Phospholipid:Chol:PEG-lipid |
| 60:10:28.5:1.5 | Compound:Phospholipid:Chol:PEG-lipid |
| 40:5:53.5:1.5 | Compound:Phospholipid:Chol:PEG-lipid |
| 45:5:48.5:1.5 | Compound:Phospholipid:Chol:PEG-lipid |
| 50:5:43.5:1.5 | Compound:Phospholipid:Chol:PEG-lipid |
| 40:20:40:0 | Compound:Phospholipid:Chol:PEG-lipid |
| 45:20:35:0 | Compound:Phospholipid:Chol:PEG-lipid |
| 50:20:30:0 | Compound:Phospholipid:Chol:PEG-lipid |
| 55:20:25:0 | Compound:Phospholipid:Chol:PEG-lipid |
| 60:20:20:0 | Compound:Phospholipid:Chol:PEG-lipid |

TABLE 6-continued

Exemplary Formulations of Nanoparticles

| Composition (mol %) | Components |
| --- | --- |
| 40:15:45:0 | Compound:Phospholipid:Chol:PEG-lipid |
| 45:15:40:0 | Compound:Phospholipid:Chol:PEG-lipid |
| 50:15:35:0 | Compound:Phospholipid:Chol:PEG-lipid |
| 55:15:30:0 | Compound:Phospholipid:Chol:PEG-lipid |
| 60:15:25:0 | Compound:Phospholipid:Chol:PEG-lipid |
| 40:10:50:0 | Compound:Phospholipid:Chol:PEG-lipid |
| 45:10:45:0 | Compound:Phospholipid:Chol:PEG-lipid |
| 50:10:40:0 | Compound:Phospholipid:Chol:PEG-lipid |
| 55:10:35:0 | Compound:Phospholipid:Chol:PEG-lipid |
| 60:10:30:0 | Compound:Phospholipid:Chol:PEG-lipid |

Example 18: In Vivo PCCA Expression and PCC Activity in an Animal Model

To assess the ability of PCCA-containing mRNAs to facilitate PCCA expression in vivo, mRNA encoding human PCCA is introduced into an animal model of Propionic Acidemia (PA).

A genetic mouse model of PA is the Pcca$^{-/-}$ (A138T) hypomorphic mouse (Guenzel et al., Mol. Ther., 1316-1323, 2013). Pcca$^{-/-}$ knockout mice lacking PCCA protein exhibit substantial increases in C3 and methylcitric acid, and die within 36 hours of birth (Miyazaki et al., J. Biol. Chem., 35995-35999, 2001). Because these null mutant animals die shortly after birth, they are difficult to use for testing intravenous injection therapies. By contrast, Pcca$^{-/-}$ (A138T) mice have been engineered to express a mutant human PCCA that was identified previously in human PA patients with mild-to-moderate symptoms. The mutant PCCA protein has an A138T substitution that causes protein instability and reduces protein levels relative to wild type protein. Pcca$^{-/-}$ (A138T) mice have approximately 2-5% of wild type PCC activity (about 2% of wild-type PCC activity in liver), exhibit delayed growth throughout neonatal development, are smaller than their littermates, and have elevated disease-associated metabolites (PA biomarkers), including propionyl-L-camitine (C3; produced by the addition of carnitine to propionyl-CoA) normalized to acetylcarnitine (C2), 2-methylcitric acid (2MC; a toxin produced by the combination of propionyl-CoaA and oxaloacetate), and 3-hydroxypropionic acid (3-HP), consistent with biochemical presentation in human patients. Pcca$^{-/-}$ (A138T) mice also exhibit elevated plasma ammonia levels, similar to PA presentation in humans, where hyperammonia is common and mild-to-moderate ammonia elevations may present chronically or during acute metabolic decompensations in patients. Pcca$^{-/-}$ (A138T) mice also have increased heart mass, similar to PA patients who can have delayed growth and cardiomyopathy. However, the small amount of PCC enzyme activity in these mice allows them to survive to adulthood (they exhibit only marginally decreased survival over 3 months following birth). Female Pcca$^{-/-}$ (A138T) mice have consistently higher biomarker levels than male mutant mice, although the reason for this remains unclear. Pcca$^{-/-}$ (A138T) hypomorphic mice are injected intravenously with 0.1-2 mg/kg of either control mRNA (GFP or Luciferase) or human PCCA mRNA. The mRNA is formulated in lipid nanoparticles (Compound II/PEG-DMG) for delivery into the mice. Mice are sacrificed after 24 or 48 hrs and PCCA protein levels in liver lysates are determined by Western Blot and liquid chromatography-mass spectrometry-mass spectrometry (LC/MS/MS). PCC enzymatic activity is determined using MicroBeta2, as described in Example 15. Citrate synthase expression is examined for use as a protein loading control. Treatment with mRNA encoding PCCA is expected to reliably induce expression of PCCA and activity of PCC. Blood levels of propionyl-L-carnitine/acetyl-L-carnitine (C3/C2), 2-methylcitiric acid (2-MC), 3-hydroxypropionic acid (3-HP), and ammonia are measured as PA markers.

Example 19: Assessing Duration of Biochemical Response Due to Administration of PCCA mRNA in Pcca$^{-/-}$ (A138T) Hypomorphic Mice The levels of PA markers C3/C2 and 2-MC in dried blood spots (DBS) collected from Pcca$^{-/-}$ (A138T) hypomorphic mice was measured-4 (4 days before administration), 2, 7, 10, 14, 21, and 24 days following two doses of intravenous injection of 1-methyl-pseudouridine modified mRNA encoding human PCCA or wild type human PCCA mRNA at 1 mg/kg. The modified PCCA mRNA constructs used for injections are represented by SEQ ID NOs: 38 and 57-59. The mRNA was formulated in lipid nanoparticles (MC3) for delivery into the mice. PBS or control mRNA encoding GFP was also injected into Pcca$^{-/-}$ (A138T) hypomorphic mice. The mRNA encoding human PCCA was IV injected at 1 mg/kg a second time 22 days after the first injection. At day 24, blood was drawn and tissue was harvested. C3/C2 and 2-MC blood levels were measured for each time point using LC-MS/MS.

Figure 1B:
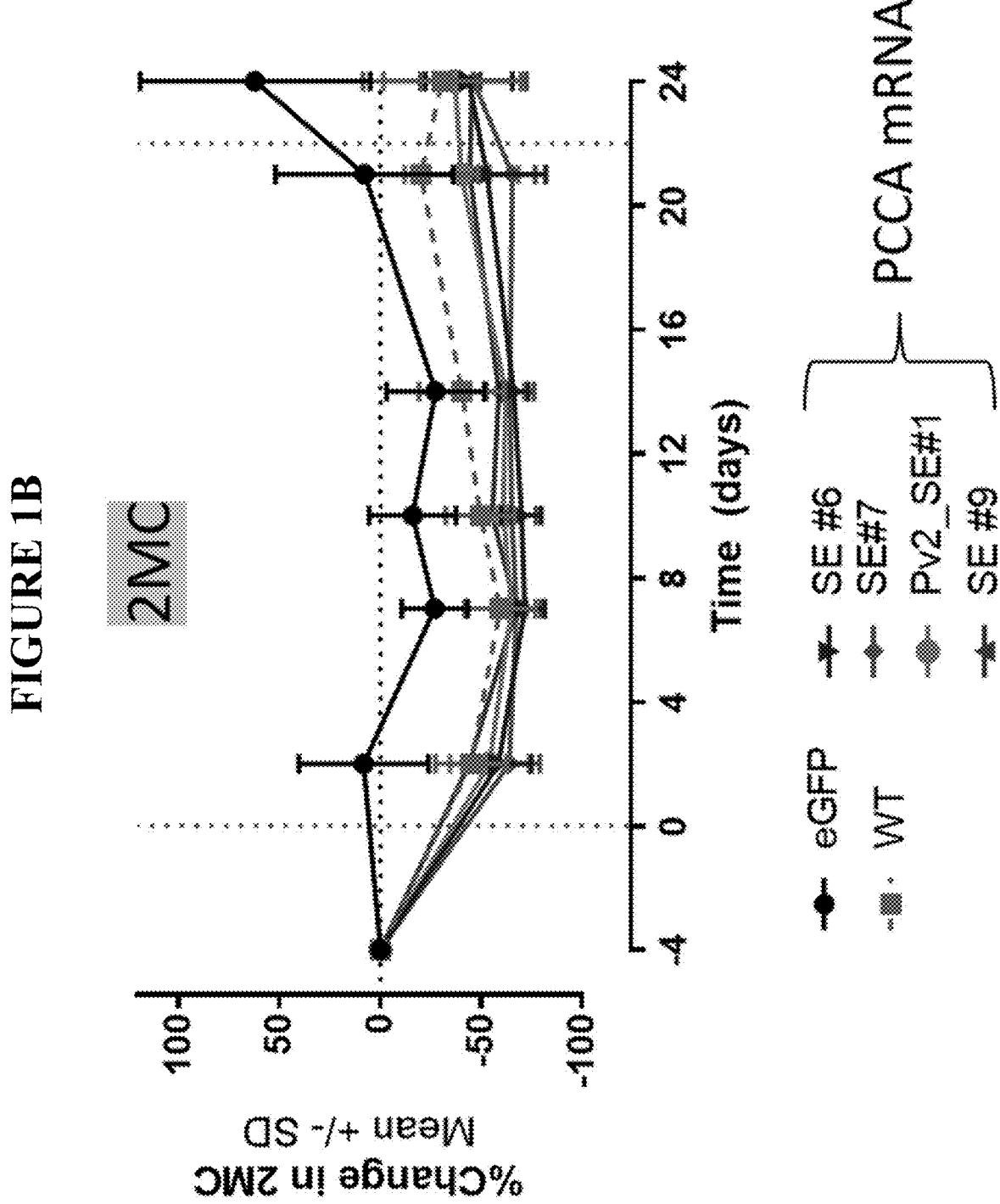
FIG. 1B shows the percent change in 2-methylcitric acid (2-MC) levels measured in Pcca$^{-/-}$ (A138T) mice at mice at 2, 7, 14, 21, and 24 days following intravenous injection of modified human PCCA mRNA constructs or eGFP mRNA control.

A significant decrease in blood C3/C2 and 2-MC levels in Pcca$^{-/-}$ (A138T) hypomorphic mice was observed over the course of the entire 21 days after single IV injection of mRNA encoding human PCCA relative to hypomorphic mice that received an IV injection of eGFP control mRNA. As shown in FIG. 1A, C3/C2 levels decreased in hypomorphic mice administered human PCCA mRNA, while C3/C2 levels in hypomorphic mice administered control mRNA remained elevated. Up to a 70% reduction in C3/C2 levels in DBS was observed at around day 2. FIG. 1B shows that 2-MC levels decreased in hypomorphic mice that had been administered mRNA encoding PCCA. An up to 60% reduction in 2-MC levels in DBS was observed at about day 2.

Example 20: In Vivo Ammonia Reduction in an Animal Model

Figure 2A:
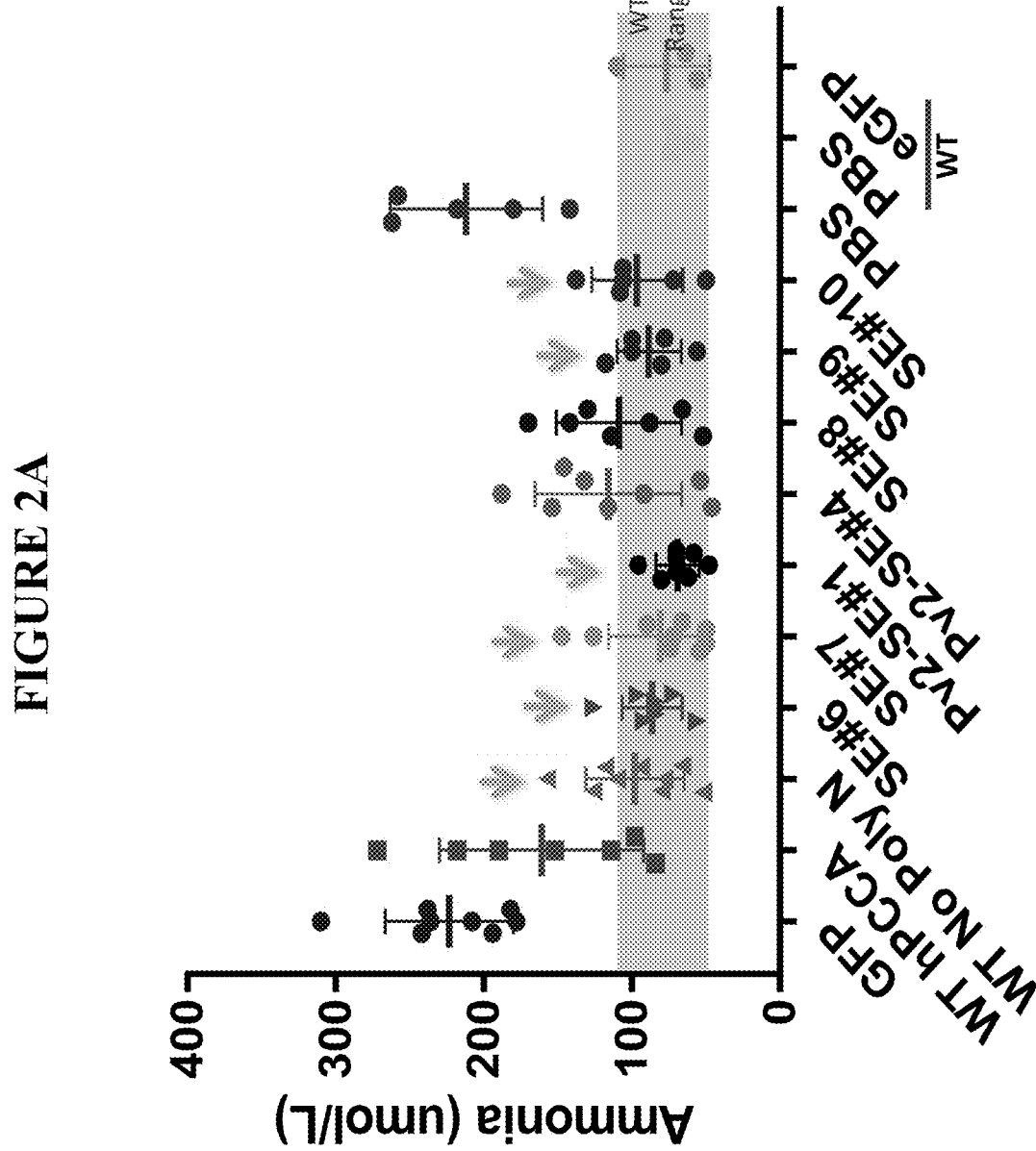
FIG. 2A is a graph showing the levels of plasma ammonia (μmol/L) in Pcca$^{-/-}$ (A138T) mice at 21 days following single intravenous injection of modified human PCCA mRNA or control mRNA.

Levels of ammonia, a disease-associated metabolite that accumulates in PA patients due to secondary inhibition of ureagenesis, particularly during acute metabolic decompensations, was measured in plasma from Pcca$^{-/-}$ (A138T) hypomorphic mice 21 days after a single IV injection of 1-methyl-pseudouridine modified mRNA encoding human PCCA at 1 mg/kg or control mRNA encoding GFP. The modified PCCA constructs used for injections are represented by SEQ ID NOs:38 and 57-62. The mRNA was formulated in lipid nanoparticles (MC3) for delivery into the mice. Ammonia levels were measured using a clinical analyzer (see Pesh-Imam et al, Clin. Chem., 1978, 24(11):2044-2046, herein incorporated by reference in its entirety). The lower limit of quantification (LLOQ) was 23.4 μmol/L for ammonia assays. Plasma samples with hemolysis were removed from the analysis. As shown in FIG. 2A, several of the PCCA mRNA constructs reduced ammonia levels to within the range of wild-type ammonia levels at 21 days after a single IV administration relative to control mRNA or PBS alone.

Figure 2B:
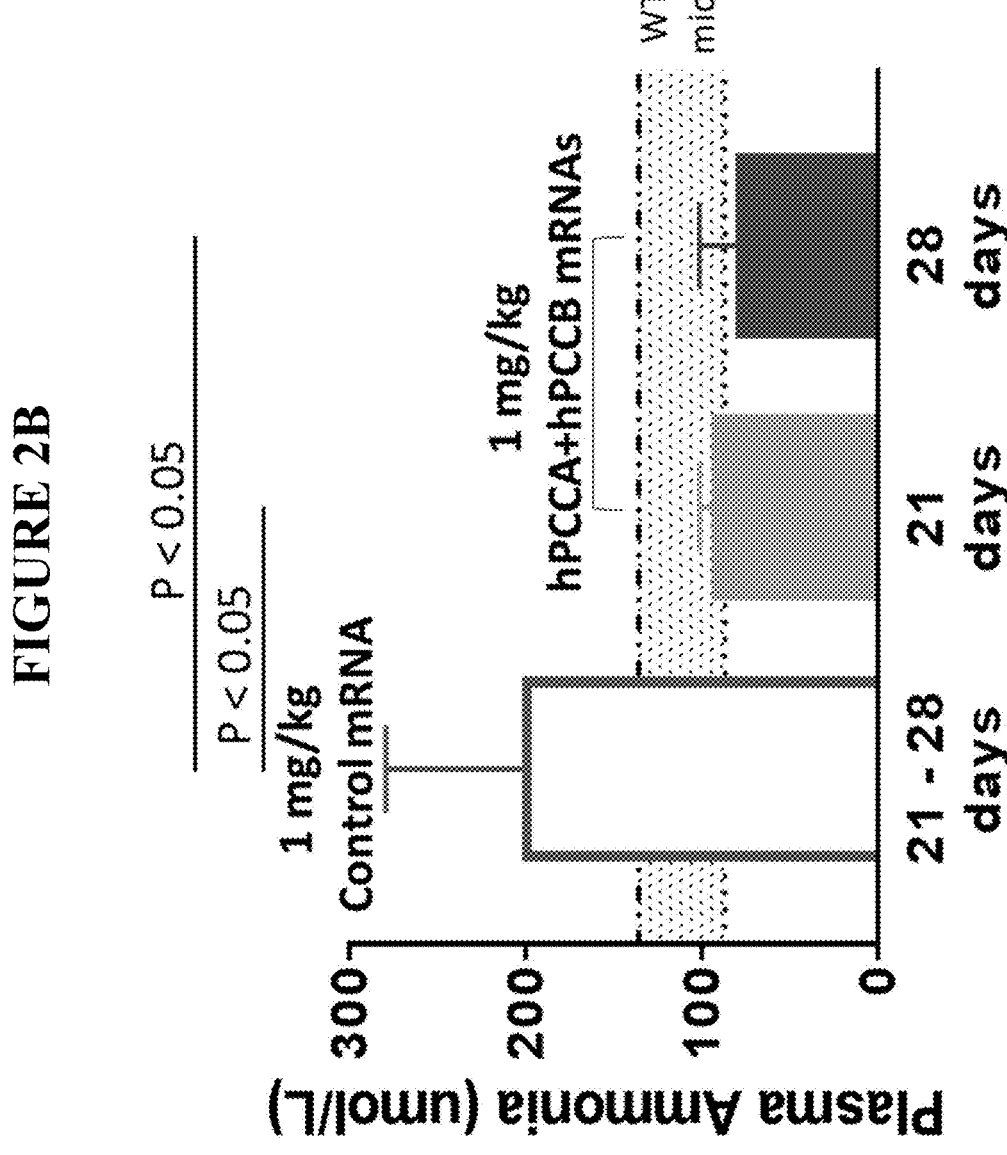
FIG. 2B is a bar graph showing plasma ammonia levels (μmol/L) in Pcca$^{-/-}$ (A138T) mice at 3 weeks and 4 weeks following single intravenous injection of modified human PCCA and PCCB mRNAs or control mRNA.

The levels of ammonia in the plasma of Pcca$^{-/-}$ (A138T) hypomorphic mice were also measured 21 days (3 weeks) and 28 days (4 weeks) after a single IV injection of 1-methyl-pseudouridine modified mRNAs encoding human PCCA and PCCB (PCCA_18, SEQ ID NO:35; and PCCB_18, SEQ ID NO:46, respectively) at 1 mg/kg or control mRNA encoding luciferase (n=4-5/group) The results were compared to ammonia levels in wild-type FVB mice. As shown in FIG. 2B, ammonia levels decreased approximately 2-fold in mice injected with a single dose of mRNAs encoding PCCA and PCCB at 21 days (3 weeks) and 28 days (4 weeks) post-injection relative to controls. These results suggest that injection of PCCA and PCCB mRNAs result in a PD response in Pcca$^{-/-}$ (A138T) hypomorphic mice due to the production of functional PCC enzyme to correct the underlying metabolic defect.

The effects of co-administering PCCA and PCCB mRNAs on plasma ammonia levels are compared to the effects on ammonia levels that result from administering carglumic acid to mice. Pcca$^{-/-}$ (A138T) hypomorphic mice are injected with 1-methyl-pseudouridine modified mRNAs encoding human PCCA and PCCB (or control mRNA encoding Luciferase), or are administered carglumic acid. Ammonia levels in the mice injected with mRNAs and the mice administered carglumic acid are then monitored and compared.

Example 21: PCCB Mutant Animal Model

A mouse model is used that is hypomorphic for PCCB gene expression. Hypomorphic pccb mutant mice are expected to exhibit symptoms of propionic academia, show increases in C3, 3HP and 2-methylcitric acid. Modified mRNA encoding human PCCB and/or PCCA is intravenously injected into this mutant mouse model to test PCCB and PCCA expression and PCC activity. The levels of PA biomarkers (2-MC, C3/C2, and 3-HP) are also tested in hypomorphic pccb mice.

Wild-type CD-1 mice are injected with 5×10$^{11}$ units per mouse of either rAAV2/8-shRNA1-EF1a-ZsGreen-ShRNA2 (sequences provided below) or rAAV2/8-EF1a-ZsGreen empty control virus. Three different cohorts of mice are sacrificed at 1, 2, and 3 weeks post-dosing to examine the PCCA and PCCB mRNA levels by q-PCR or bDNA assay, PCCA and PCCB protein levels by capillary electrophoresis (CE) and LC-MS/MS, and PCC activity in liver. This is to determine how long it takes for the shRNA to take effect, and how much reduction in PCCB is achieved. PCCA mRNA and/or protein levels might be affected after PCCB is knocked down as a reduction of PCC complex formation may de-stabilize PCCA as well.

```
siRNA:
UUUAAUUAGCUCAUAAUUC shRNA1:
agatctGAATTATGAGCTAATTAAAtacctgacccataTTTAATTAGCTC
ATAATTCTTTTTggtacc shRNA2:
ctcgagaagaaggtatattgctgttgacagtgagcgACGAATTATGAGCT
AATTAAAtagtgaagcttcagatgtaTTTAATTAGCTCATAATTCGCtgc
ctactgcctcggacttcaaggggtcagtcagaattc
```

Figure 3:
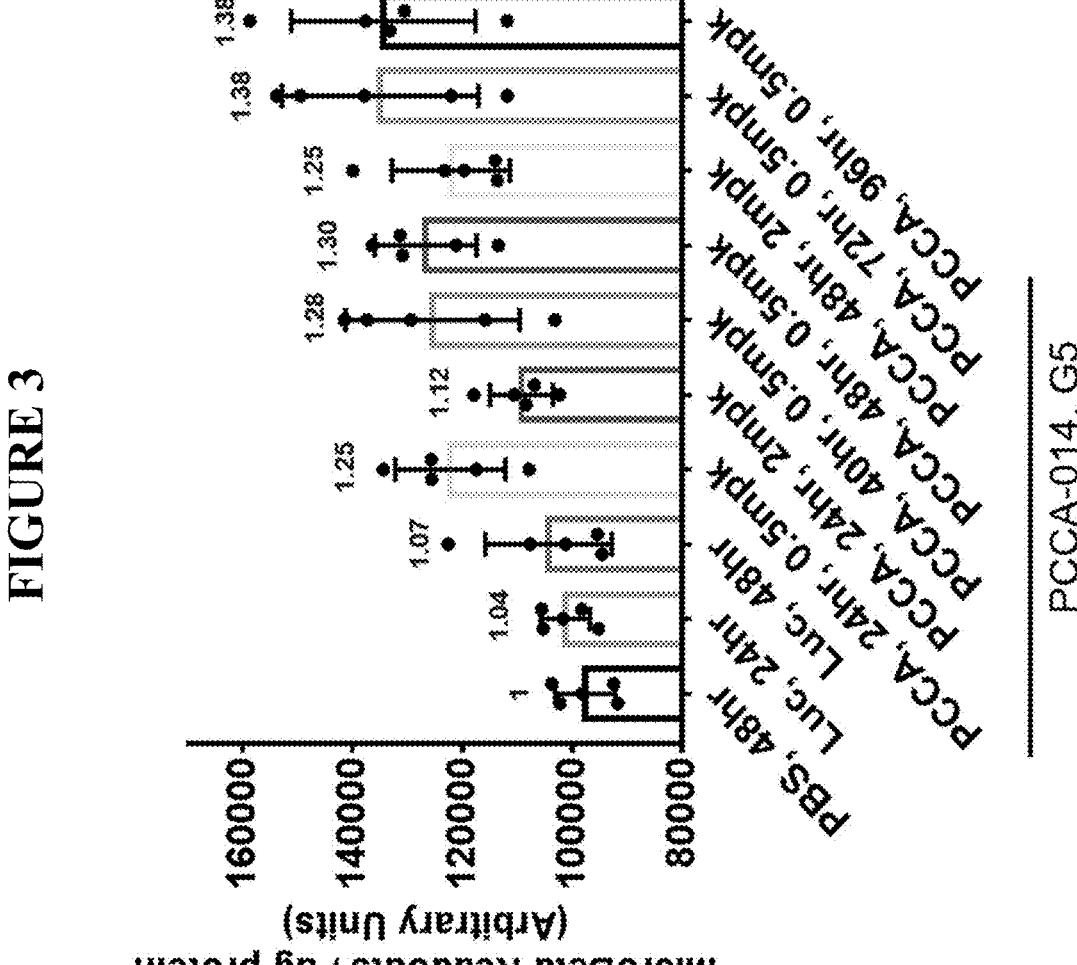
FIG. 3 is a bar graph showing PCC activity (MicroBeta readout/μg protein) in wild-type CD-1 mice at 24, 40, 48, 72, or 96 hours following single intravenous injection of a modified human PCCA mRNA or control mRNA.

Example 22: In Vivo Dosing in Wild-Type Mice Administered mRNA Encoding Human PCCA To determine the dose of PCCA mRNA that could effectively increase PCC activity in vivo, a single IV tail vein injection of either 0.5 mg/kg or 2 mg/kg of 1-methyl-pseudouridine modified mRNA encoding human PCCA (PCCA-014; SEQ ID NO:38) was administered to wild-type CD-1 mice. The mRNA was formulated in lipid nanoparticles (Compound II/PEG-DMG) for delivery into mice. PCC activity was assessed 24 hours, 48 hours, 72 hours, or 96 hours after mRNA administration using a Microbeta2 scintillation counter, as described in Example 15, on mitochondrial fractions isolated from liver lysates collected from the mouse. 5 µg of mitochondrial matrix protein was loaded to the PCC reaction. Control mice were administered PBS or a luciferase construct. FIG. 3 shows that a single 0.5 mg/kg dose of PCCA mRNA produced higher PCC activity than a single 2 mg/kg dose of PCCA mRNA at 24 hours and 48 hours following administration. PCC activity increased over time, and reached its maximum level at 72 hours following mRNA administration.

Figure 4:
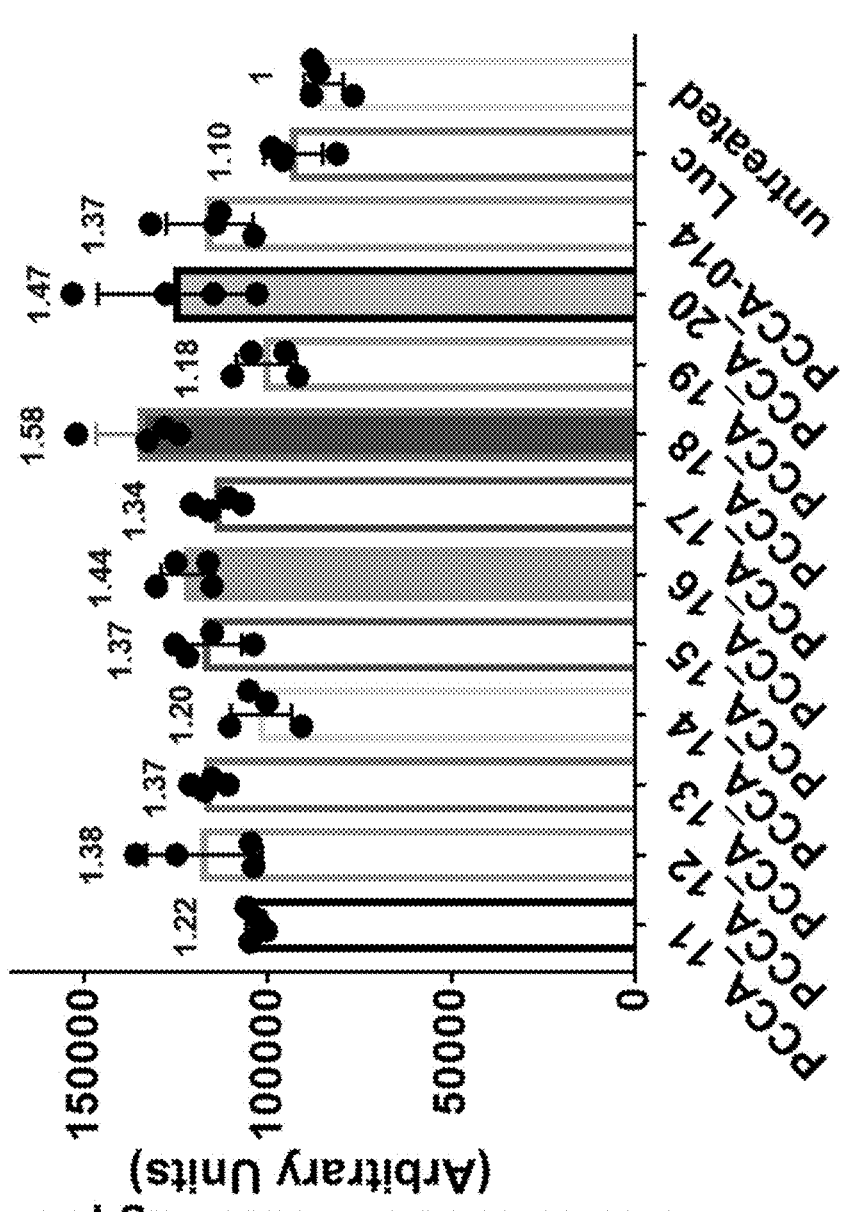
FIG. 4 is a bar graph showing PCC activity (MicroBeta readout/μg protein) in wild-type FVB mice at 72 hours following single intravenous injection of modified human PCCA mRNAs or control mRNA.
Figure 5:
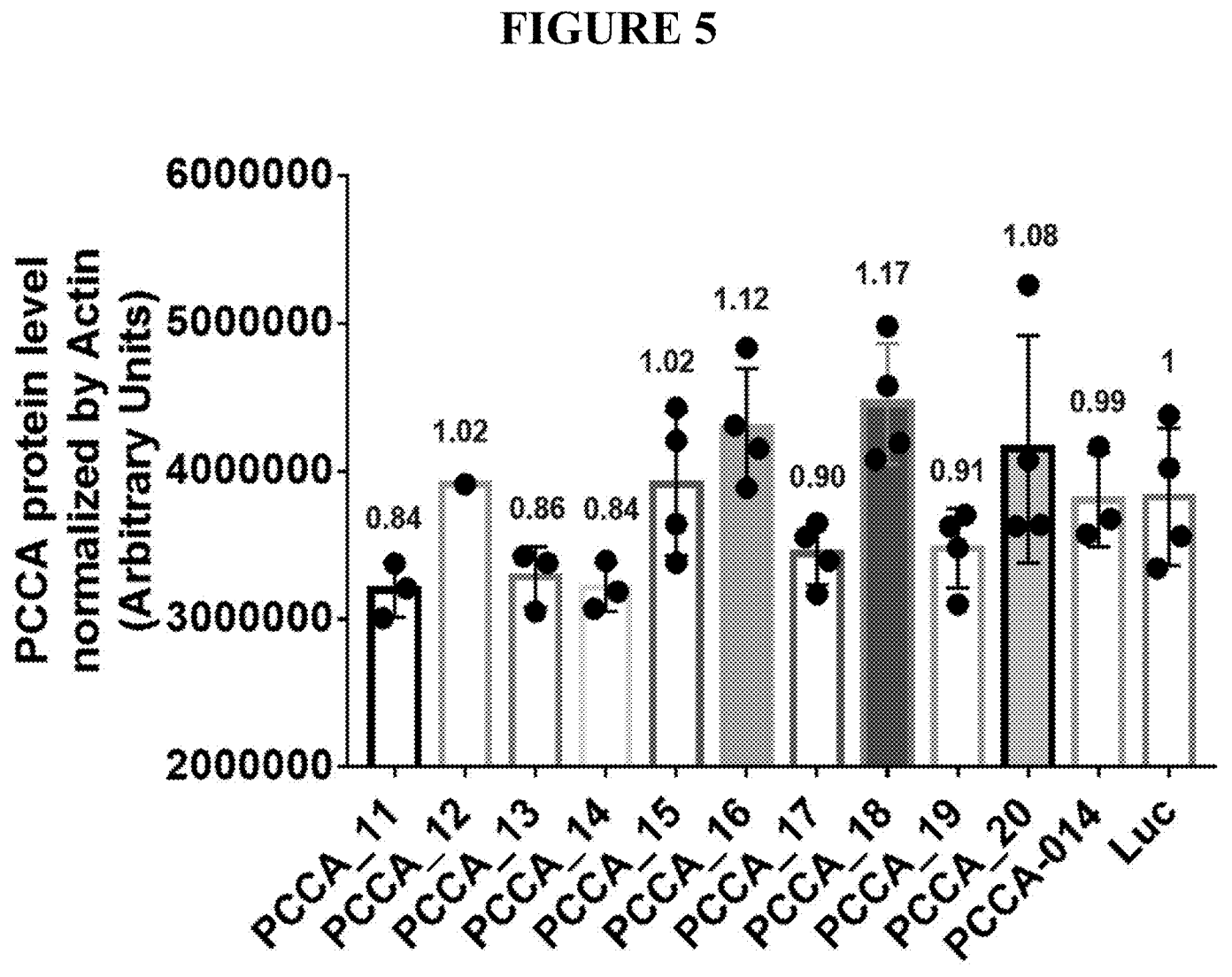

Example 23: PCC Activity and PCCA Protein Expression in Wild-Type Mice Administered a Single Dose of mRNA Encoding Human PCCA To test the ability of 1-methyl-pseudouridine modified mRNA constructs to express PCCA and increase PCC activity in vivo, a single 0.5 mg/kg dose of each construct (PCCA_11 to PCCA_20 and PCCA-014, represented by SEQ ID NOs: 28-38, respectively) was IV administered to wild-type FVB mice via tail vein injection. The mRNA was formulated in lipid nanoparticles (Compound II/PEG-DMG) for delivery into mice. PCCA expression was determined by capillary electrophoresis on mitochondrial fractions isolated from liver lysates collected from the mouse. PCC activity was assessed 72 hours after mRNA administration using a Microbeta2 scintillation counter, as described in Example 15, on mouse liver mitochondrial fractions. 5 µg of mitochondrial matrix protein was loaded to the PCC reaction. Control mice were administered a luciferase construct or left untreated. FIG. 4 shows that the PCCA mRNA constructs increased PCC activity 72 hours after a single administration relative to controls. FIG. 5 shows that mRNA encoding PCCA can increase the expression of PCCA after a single administration in mice. Some of the mRNA constructs that increased PCC activity at higher levels (see FIG. 4) produced greater PCCA expression levels in vivo (see FIG. 5), including the PCCA_16, PCCA_18, and PCCA_20 constructs. PCCA_18 was selected to use in subsequent in vivo studies.

Figure 6:
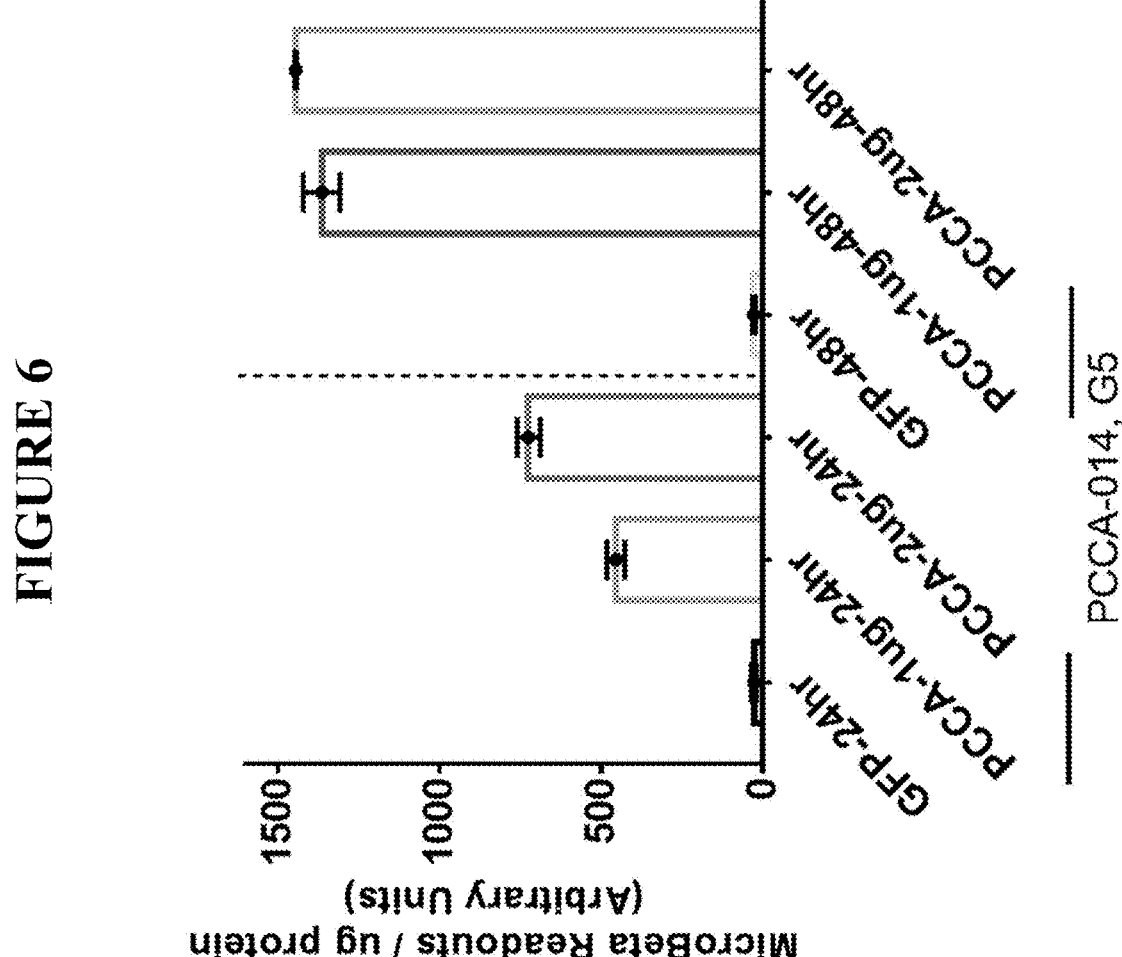
FIG. 6 is a bar graph showing PCC activity (MicroBeta readout/μg protein) in GM371 PCCA-deficient patient fibroblasts transfected with a modified human PCCA mRNA or control mRNA at 24- or 48-hours post-transfection.

Example 24: In Vitro PCC Activity and PCCA/PCCB Expression in PCCA-Deficient Patient Fibroblasts Transfected with mRNA Encoding Human PCCA PCC activity was measured in GM371 PCCA-deficient patient fibroblasts 24 hours or 48 hours after transfection with 1 µg or 2 µg of 1-methyl-pseudouridine modified mRNA encoding human PCCA (PCCA-014; SEQ ID NO: 38), or a GFP control. PCC activity was assessed as described in Example 15. 30 µg of protein was loaded to the PCC reaction. FIG. 6 shows that PCCA mRNA increased PCC activity in PCCA-deficient patient fibroblasts.

Figures 7A, 7B:
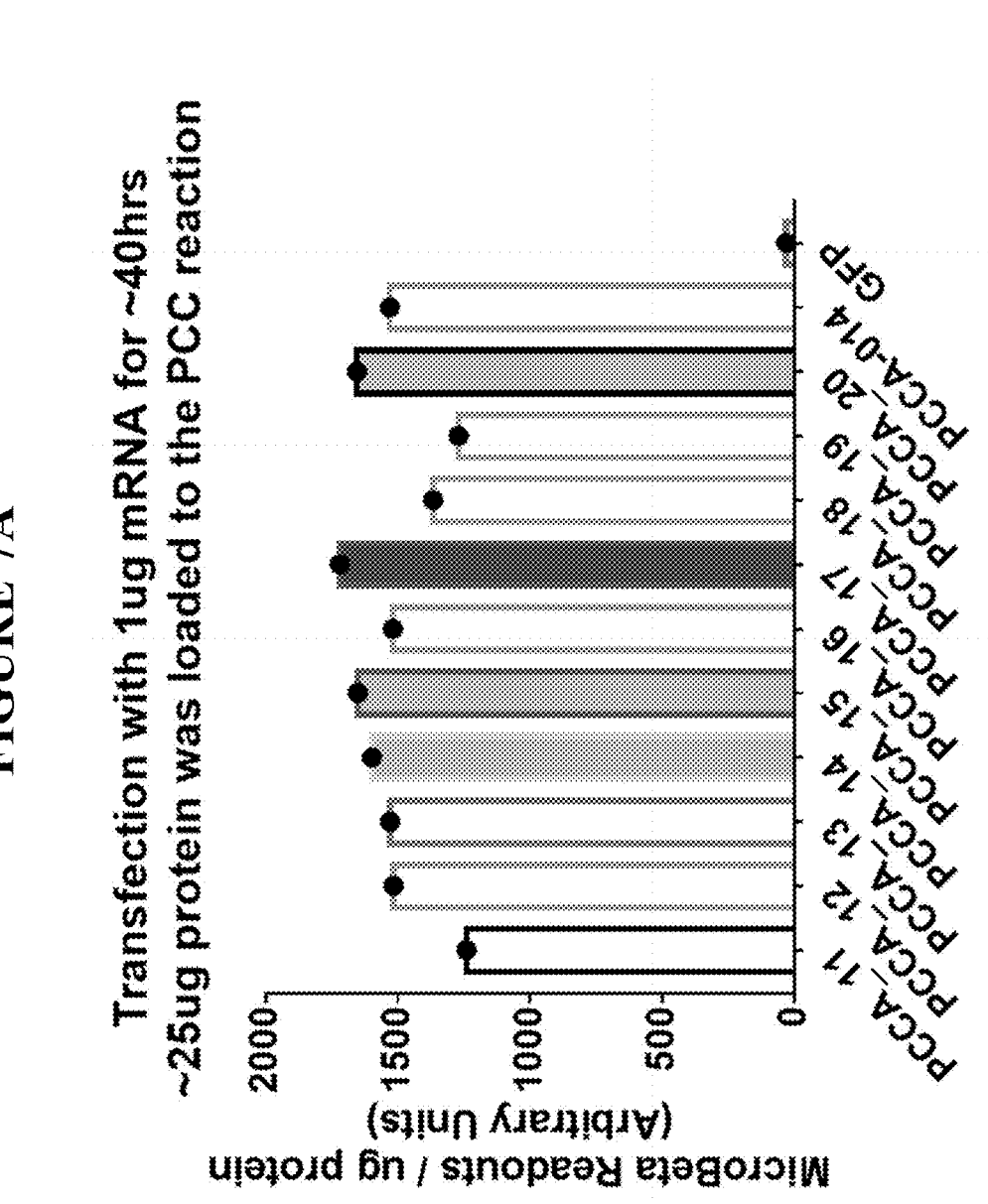
FIG. 7A is a bar graph showing PCC activity (MicroBeta readout/μg protein) in GM371 PCCA-deficient patient fibroblasts transfected with modified human PCCA mRNAs or control mRNA at 40-hours post-transfection.
FIG. 7B shows the PCC activity levels produced by each PCCA mRNA construct of FIG. 7A relative to the PCC activity level produced by the control mRNA (ratio to GFP).

GM371 PCCA-deficient patient fibroblasts (Coriell Institute) were transfected with 1 µg of 1-methyl-pseudouridine modified mRNA constructs encoding PCCA (PCCA_11 to PCCA_20 and PCCA-014, represented by SEQ ID NOs: 28-38, respectively), or a GFP control. PCC activity was tested as described in Example 15, in the cells harvested approximately 40 hours after transfection. About 25 µg of protein was loaded to the PCC reaction. FIG. 7A shows that PCC activity increased upon transfection with any of the PCCA mRNA constructs. FIG. 7B provides the PCC activity levels for each of the PCCA mRNA constructs relative to the GFP control.

Figure 8A:
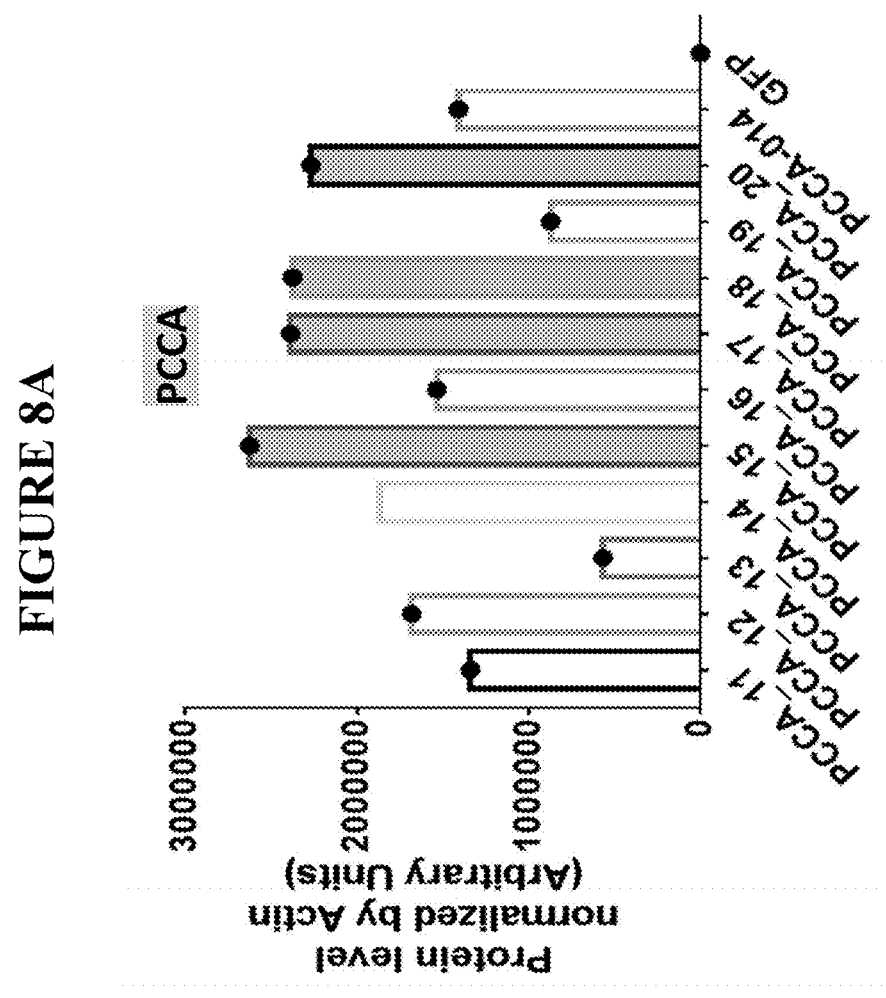
FIG. 8A is a bar graph showing PCCA expression levels (Western blots assessed with capillary electrophoresis, normalized to actin levels) in GM371 PCCA-deficient patient fibroblasts transfected with modified human PCCA mRNAs or control mRNA.
Figure 8B:
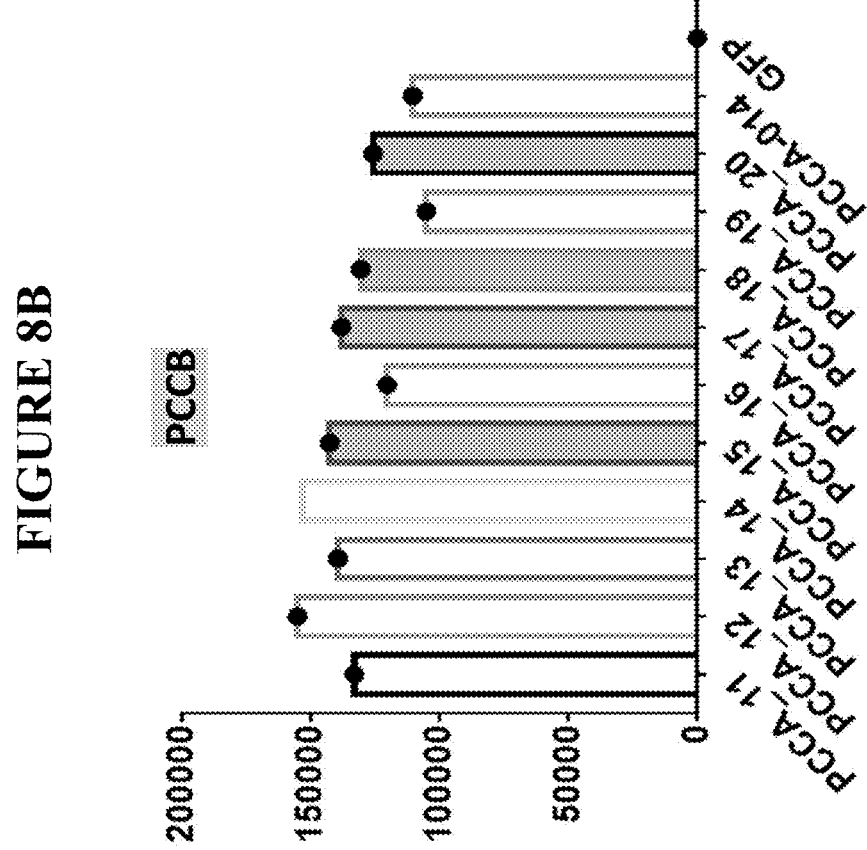
FIG. 8B is a bar graph showing PCCB expression levels (Western blots assessed with capillary electrophoresis, normalized to actin levels) in GM371 PCCA-deficient patient fibroblasts transfected with modified human PCCA mRNAs or control mRNA.

PCCA and PCCB expression levels were tested in the GM371 PCCA-deficient patient fibroblasts transfected with the different mRNA constructs encoding PCCA, or a GFP control using capillary electrophoresis, as described in Examples 14 and 15. Since the PCCB protein requires PCCA for stability, PCCB is also deficient in PCCA-deficient fibroblasts. FIG. 8A shows that mRNA encoding PCCA can increase the expression of PCCA in patient-derived fibroblasts. Some of the mRNA constructs that increased PCC complex activity at higher levels (see FIGS. 7A and 7B) produced greater PCCA expression levels in cells. FIG. 8B shows PCCB expression levels were increased in patient-derived fibroblasts transfected with PCCA mRNA relative to control.

Figure 9:
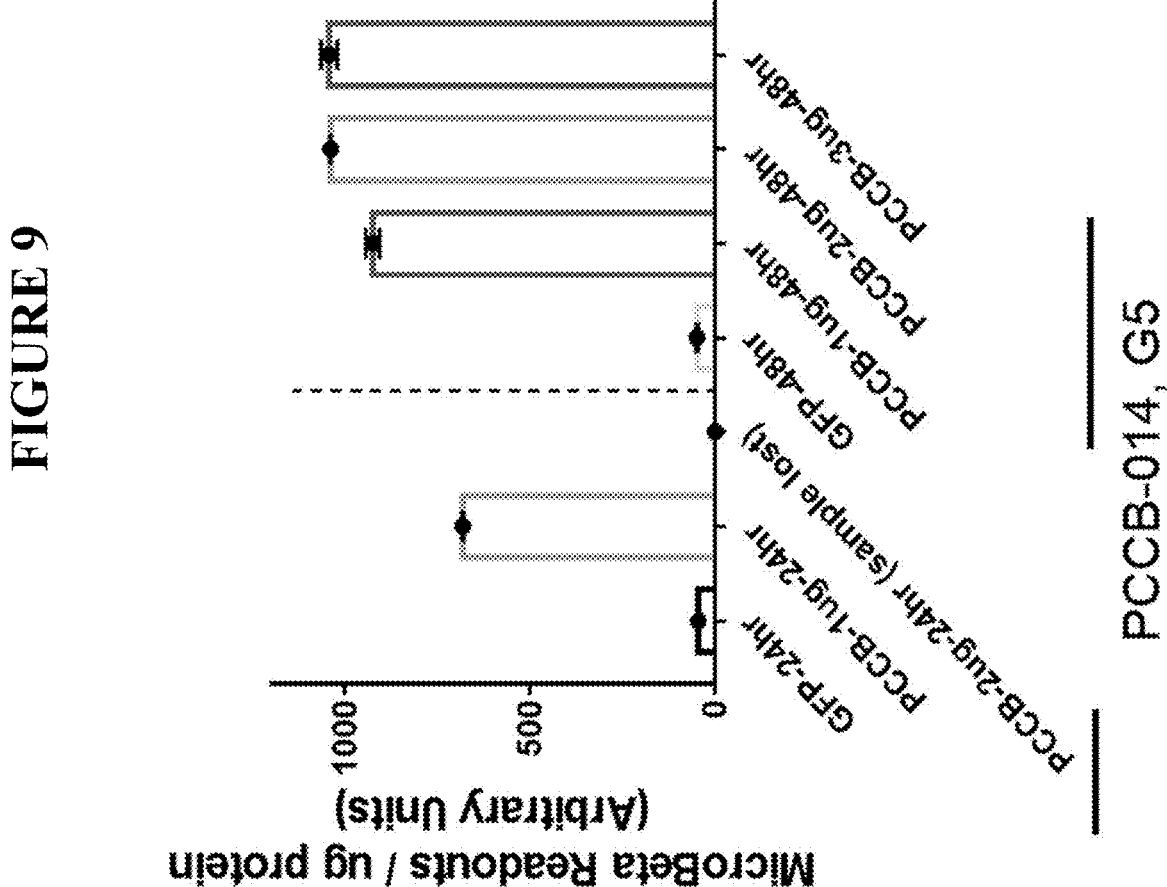
FIG. 9 is a bar graph showing PCC activity (MicroBeta readout/μg protein) in GM1298 PCCB-deficient patient fibroblasts transfected with a modified human PCCB mRNA or control mRNA at 24- or 48-hours post-transfection.

Example 25: In Vitro PCC Activity and PCCA/PCCB Expression in PCCB-Deficient Patient Fibroblasts Transfected with mRNA Encoding Human PCCB PCC activity was measured in GM1298 PCCB-deficient patient fibroblasts (Coriell Institute) 24 hours or 48 hours after transfection with 1 µg, 2 µg or 3 µg of 1-methyl-pseudouridine modified mRNA encoding human PCCB (PCCB-014; SEQ ID NO: 49), or a GFP control. PCC activity was assessed as described in Example 15. 30 µg of protein was loaded to the PCC reaction. FIG. 9 shows that PCCB mRNA increased PCC activity in PCCB-deficient patient fibroblasts.

Figure 10:
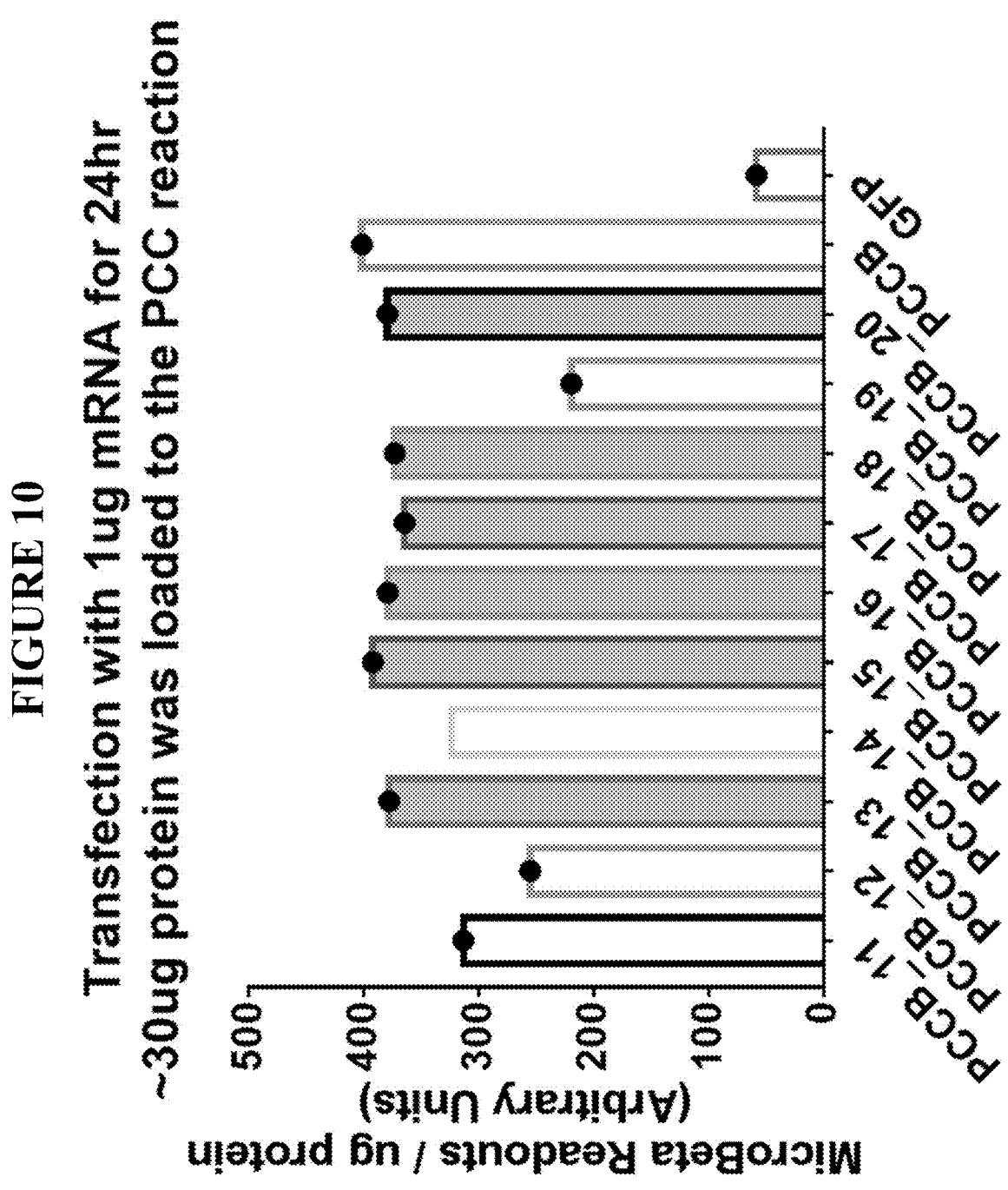
FIG. 10 is a bar graph showing PCC activity (MicroBeta readout/μg protein) in GM1298 PCCB-deficient patient fibroblasts transfected with modified human PCCB mRNAs or control mRNA at 24-hours post-transfection.

GM1298 PCCB-deficient patient fibroblasts were transfected with 1 µg of 1-methyl-pseudouridine modified mRNA constructs encoding human PCCB (PCCB_11 to PCCB_20 and PCCB-014, represented by SEQ ID NOs: 39-49, respectively), or a GFP control. PCC activity was tested as described in Example 15, in the cells harvested approximately 24 hours after transfection. About 30 µg of protein was loaded to the PCC reaction. FIG. 10 shows that PCC activity increased upon transfection with any of the PCCB mRNA constructs.

Figure 11C:
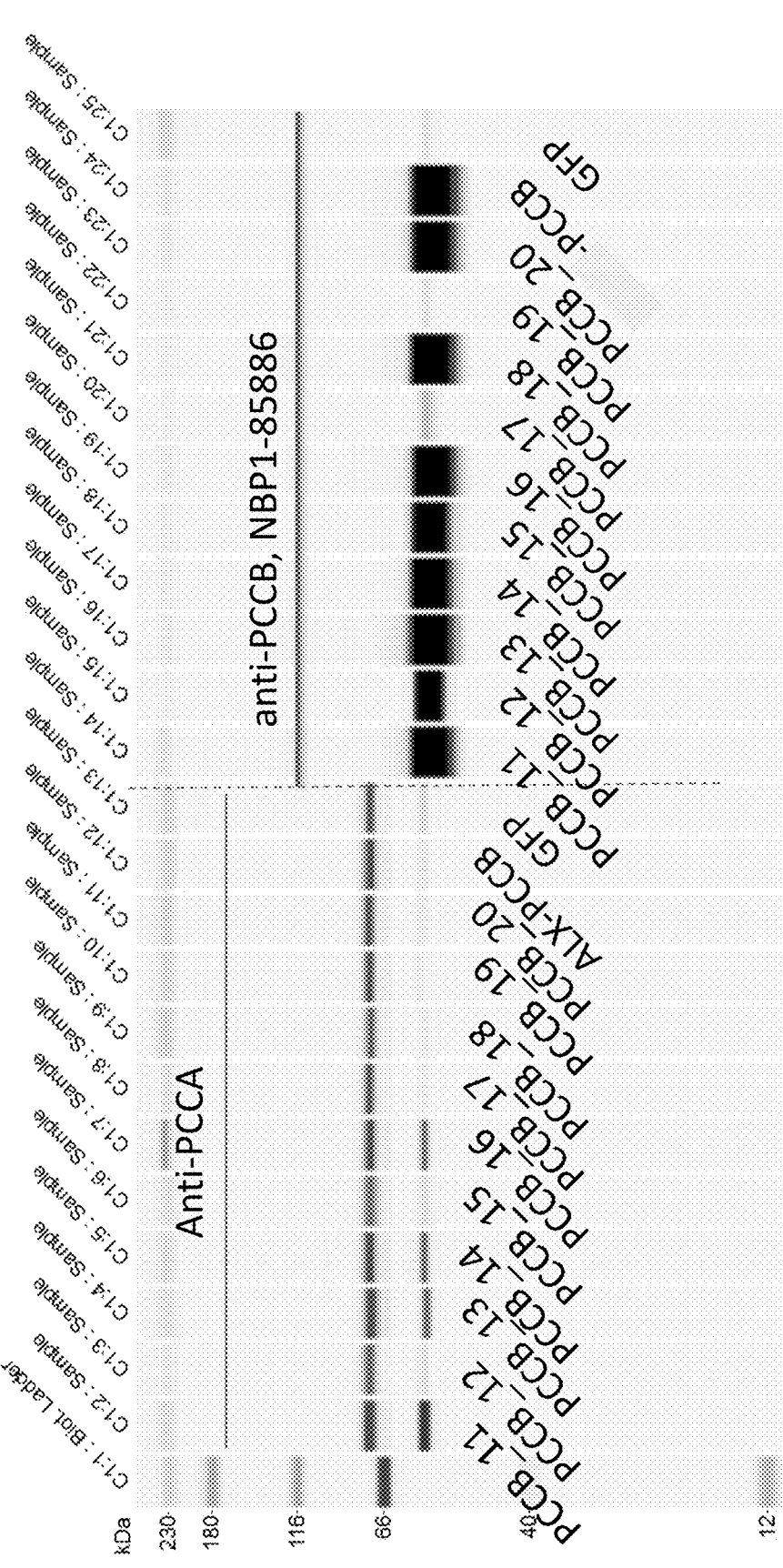
FIG. 11C shows the capillary electrophoresis images of Western blot assays to detect PCCA and PCCB expression levels in GM1298 PCCB-deficient patient fibroblasts transfected with modified human PCCB mRNAs or control mRNA.

PCCB and PCCA expression levels were tested in the GM1298 PCCB-deficient patient fibroblasts transfected with the different mRNA constructs encoding human PCCB, or a GFP control using capillary electrophoresis, as described in Examples 14 and 15. PCCA does not usually require PCCB for its stability, thus PCCB-deficient fibroblasts exhibit endogenous PCCA expression levels. FIG. 11A shows that mRNA encoding human PCCB can increase the expression of PCCB in patient-derived fibroblasts. FIG. 11B shows PCCA expression levels in patient-derived fibroblasts transfected with PCCB mRNA. FIG. 11C shows the capillary electrophoresis images showing PCCA and PCCB expression levels. PCCB_18 was selected for use in subsequent in vivo studies based on the results shown in FIG. 10 and FIG. 11A.

Figure 12A:
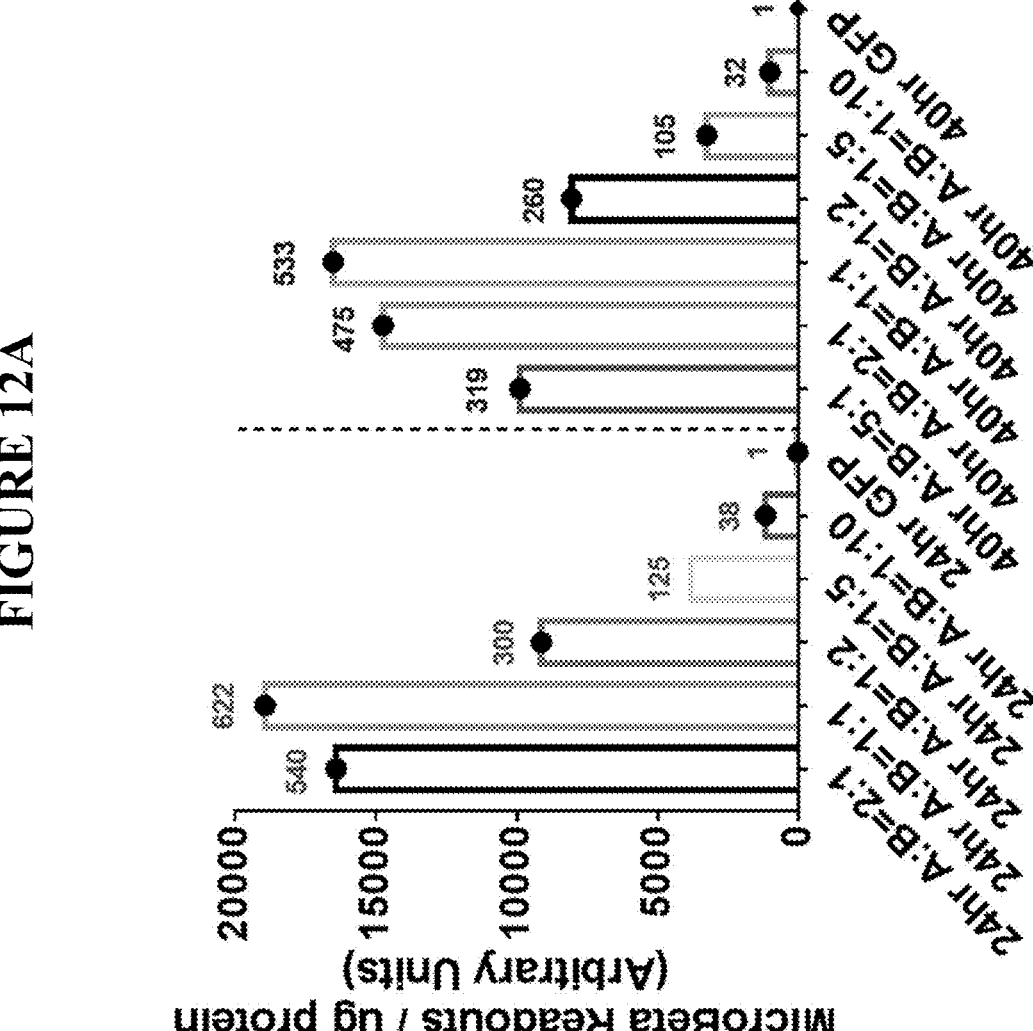
FIG. 12A is a bar graph showing PCC activity (MicroBeta readout/μg protein) in GM371 PCCA-deficient patient fibroblasts transfected with different ratios of a modified human PCCA mRNA and a modified human PCCB mRNA at 24- or 40-hours post-transfection.

Example 26: PCCA:PCCB Molar Ratio Titration in PCCA-Deficient Patient Fibroblasts Transfected with mRNAs Encoding Human PCCA and Human PCCB PCC activity was measured in GM371 PCCA-deficient patient fibroblasts 24 hours or 40 hours after transfection with 1-methyl-pseudouridine modified mRNAs encoding human PCCA (PCCA-014; SEQ ID NO: 38) and human PCCB (PCCB-014; SEQ ID NO: 49) at different molar ratios of PCCA:PCCB mRNA (A:B ratio). Transfection with a GFP mRNA was used as a control. Total mRNA in each ratio group was equalized to 1 μg of PCCA mRNA (molar amount). PCC activity was assessed as described in Example 15. Approximately 25 μg of protein was loaded to the PCC reaction. FIG. 12A shows that a PCCA:PCCB molar ratio of 1:1 (A:B ratio of 1:1) increased PCC activity the greatest in PCCA-deficient patient fibroblasts at both 24 and 40 hours after transfection.

PCCA and PCCB expression levels are also assayed in GM371 PCCA-deficient patient fibroblasts and/or PCCA KO Hep3B cells 24 hours and 48 hours after transfection with 1-methyl-pseudouridine modified mRNAs encoding human PCCA and human PCCB at different molar ratios of PCCA:PCCB mRNA (A:B ratio), or a GFP control, using capillary electrophoresis, as described in Examples 14 and 15. Transfecting cells with different molar ratios of PCCA:PCCB, including a 1:1 molar ratio of PCCA:PCCB, results in expression of both PCCA and PCCB.

Figure 12B:
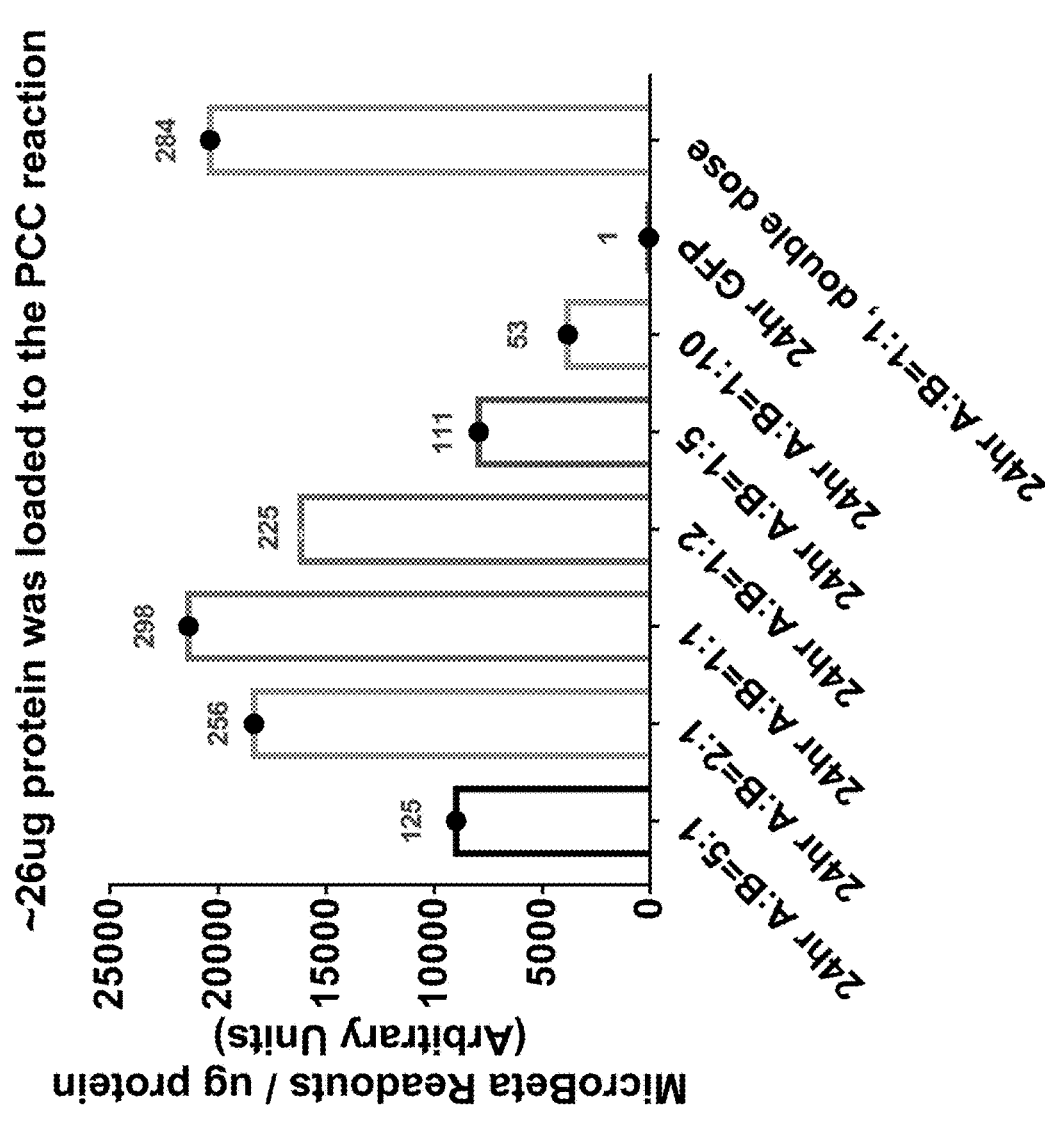
FIG. 12B is a bar graph showing PCC activity (MicroBeta readout/μg protein) in GM1298 PCCB-deficient patient fibroblasts transfected with different ratios of a modified human PCCA mRNA and a modified human PCCB mRNA at 24-hours post-transfection.

Example 27: PCCA:PCCB Molar Ratio Titration in PCCB-Deficient Patient Fibroblasts Transfected with mRNAs Encoding Human PCCA and Human PCCB PCC activity was measured in GM1298 PCCB-deficient patient fibroblasts 24 hours after transfection with 1-methyl-pseudouridine modified mRNAs encoding human PCCA (PCCA-014; SEQ ID NO: 38) and human PCCB (PCCB-014; SEQ ID NO: 49) at different molar ratios of PCCA:PCCB mRNA (A:B ratio). Transfection with a GFP mRNA was used as a control. Total mRNA in each ratio group was equalized to 1 μg of PCCA mRNA (molar amount), or 2 μg of PCCA mRNA (molar amount). PCC activity was assessed as described in Example 15. Approximately 26 μg of protein was loaded to the PCC reaction. FIG. 12B shows that a PCCA:PCCB molar ratio of 1:1 (A:B ratio of 1:1) increased PCC activity the greatest in PCCB-deficient patient fibroblasts at 24 after transfection.

Figure 13A:
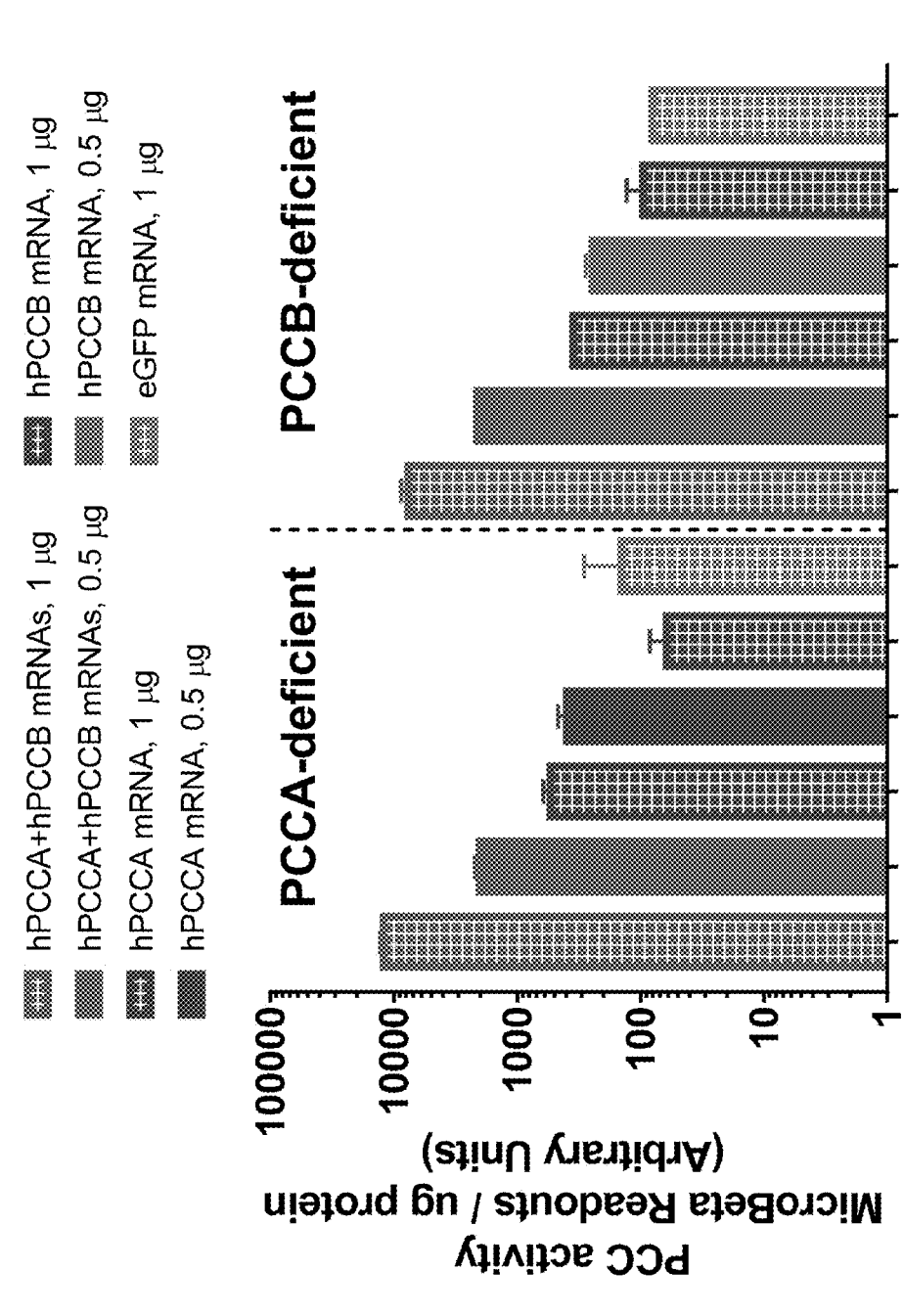
FIG. 13A is a bar graph showing PCC activity (MicroBeta readout/μg protein) in PCCA-deficient and PCCB-deficient patient fibroblasts transfected with 0.5 μg or 1 μg of modified human PCCA mRNA, modified human PCCB mRNA, both modified human PCCA and PCCB mRNAs, or 1 μg of control (eGFP) mRNA at 24-hours post-transfection.

Example 28: In Vitro PCC Activity in PCCA- and PCCB-Deficient Patient Fibroblasts Transfected with mRNAs Encoding Human PCCA and PCCB PCC activity was measured in human fibroblasts (3-4× $10^5$/well, n=2 per condition) isolated from a PCCA-deficient PA patient (GM371 PCCA-deficient patient fibroblasts, Coriell Institute) and a PCCB-deficient PA patient (GM1298 PCCB-deficient patient fibroblasts, Coriell Institute) 24 hours after transfection (with lipofectamine) with 0.5 or 1 μg of 1-methyl-pseudouridine modified mRNA encoding human PCCA (PCCA_18; SEQ ID NO:35) alone, mRNA encoding human PCCB (PCCB_18; SEQ ID NO:46) alone, or mRNAs encoding human PCCA (PCCA_18; SEQ ID NO:35) and PCCB (PCCB_18; SEQ ID NO:46) at a molar ratio of 1:1. Control cells were transfected with 1 μg of mRNA encoding GFP. PCC activity was measured in the transfected cell lysates using a radiometric activity assay as described in Example 15. Briefly, lysate was mixed with PCC substrates, ATP, propionyl CoA, and $^{14}C$ radioisotope labeled sodium bicarbonate. The reaction mixture was incubated at 37° C. for 15 minutes, followed by the addition of 5% TCA to stop the reaction, and was then centrifuged at 13,000 g for 5 minutes. Supernatant was collected for quantification of radioisotope labeled enzymatic products methylmalonyl-CoA using Microbeta2 scintillation counter. FIG. 13A shows that co-transfection of mRNAs encoding PCCA and PCCB at a molar ratio of 1:1 increased PCC enzyme activity at higher levels (5-25 fold higher) compared to the transfection of mRNA encoding PCCA or PCCB alone in both PCCA- and PCCB-deficient fibroblasts. These data suggest increased production of functional PCC enzyme due to transfection of both PCCA and PCCB mRNAs, compared to transfection of PCCA mRNA alone and PCCB mRNA alone in both subtypes (PCCA-deficient and PCCB-deficient).

Figure 13B:
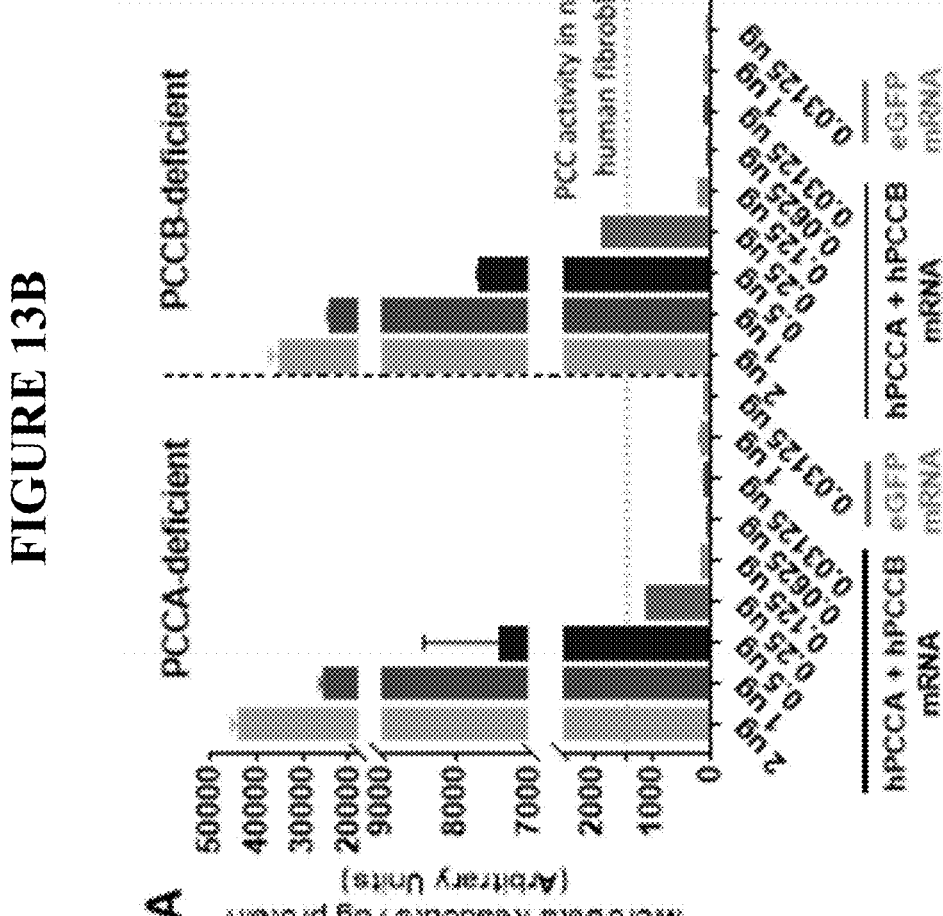
FIG. 13B is a bar graph showing PCC activity (MicroBeta readout/μg protein) in PCCA-deficient and PCCB-deficient patient fibroblasts transfected with different amounts (0.03125-2 μg) of modified human PCCA and PCCB mRNAs, or a control (eGFP) mRNA at 24-hours post-transfection.

PCC activity was also measured in human fibroblasts (3-4×$10^5$/well, n=2 per condition isolated from a PCCA-deficient PA patient (GM371 PCCA-deficient patient fibroblasts) and a PCCB-deficient PA patient (GM1298 PCCB-deficient patient fibroblasts) 24 hours after transfection (with lipofectamine) with 0.03125-2 μg of 1-methyl-pseudouridine modified mRNAs encoding human PCCA (PCCA_18; SEQ ID NO:35) and human PCCB (PCCB_18; SEQ ID NO:46) at a molar ratio of 1:1, or a GFP control mRNA. FIG. 13B shows a dose-dependent effect, wherein transfection with larger amounts of PCCA and PCCB mRNAs induced greater PCC activity levels in both PCCA- and PCCB-deficient fibroblasts. Transfection of cells with 2 μg of mRNAs led to the greatest PCC activity levels which started to plateau, but transfection with 0.5-1 μg of mRNAs was sufficient to induce PCC activity levels that are greater than the PCC activity levels in normal human fibroblasts. Transfection of PCCA and PCCB mRNAs across a range of concentrations resulted in similar PCC activity in patient fibroblasts obtained from both subtypes (PCCA-deficient and PCCB-deficient).

Figure 14:
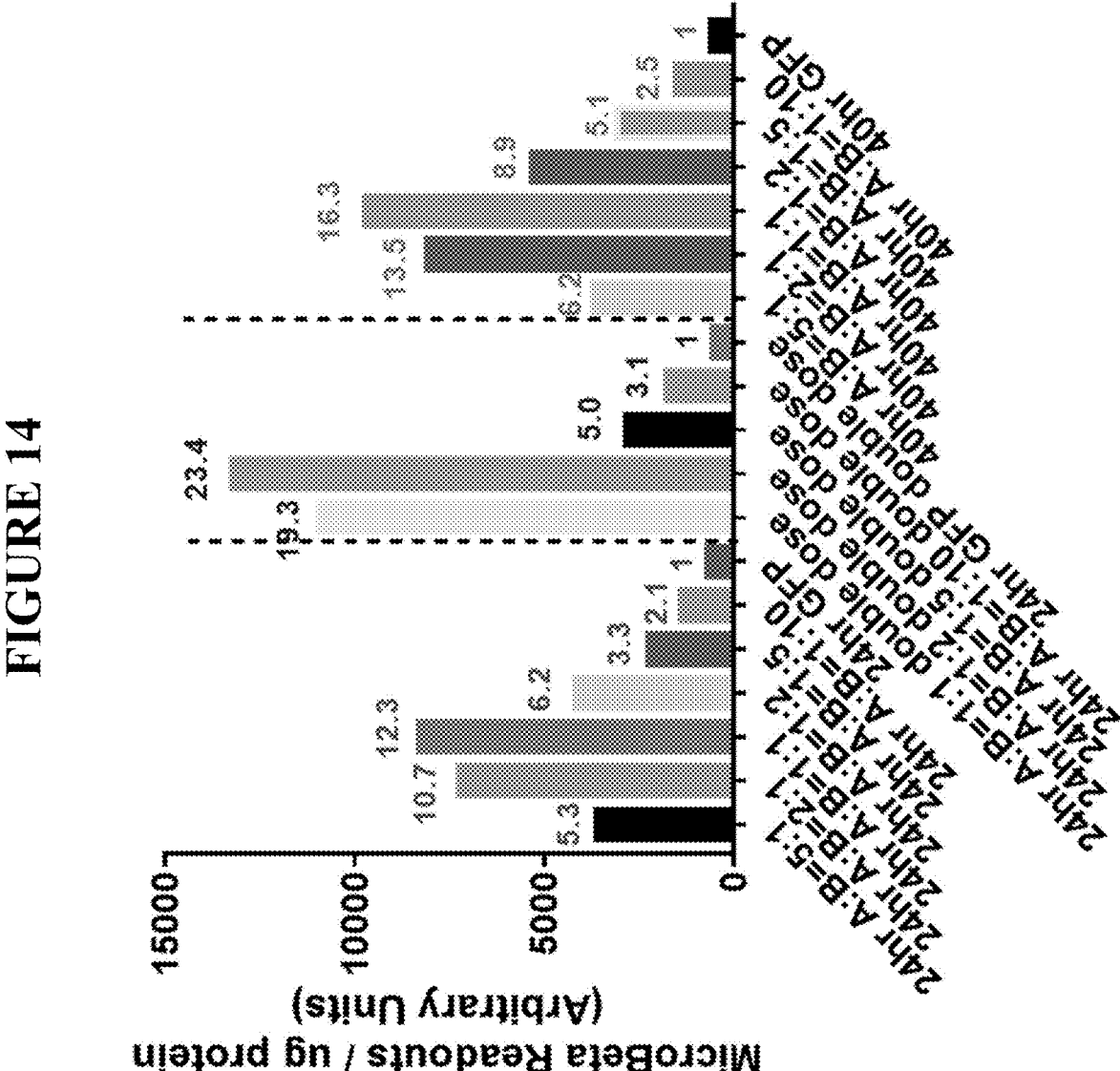
FIG. 14 is a bar graph showing PCC activity (MicroBeta readout/μg protein) in Hep1-6 liver cells transfected with different ratios of a modified human PCCA mRNA and a modified human PCCB mRNA at 24- or 40-hours post-transfection.

Example 29: PCCA:PCCB Molar Ratio Titration in Hepa1-6 Cells Transfected with mRNAs Encoding Human PCCA and Human PCCB PCC activity was measured in Hepa1-6 liver cells (ATCC® HB-8064TM) 24 hours or 40 hours after transfection with 1-methyl-pseudouridine modified mRNAs encoding human PCCA (PCCA-014; SEQ ID NO: 38) and human PCCB (PCCB-014; SEQ ID NO: 49) at different molar ratios of PCCA:PCCB mRNA (A:B ratio). Transfection with a GFP mRNA was used as a control. Total mRNA in each ratio group was equalized to 1 μg of PCCA mRNA (molar amount). In some cases, total mRNA in each ratio group was equalized to 2 μg of PCCA mRNA ("double dose"). PCC activity was assessed as described in Example 15. Approximately 25 μg of protein was loaded to the PCC reaction. FIG. 14 shows that a PCCA:PCCB molar ratio of 1:1 (A:B ratio of 1:1) increased PCC activity the greatest in Hepa1-6 liver cells at both 24 and 40 hours after transfection.

PCCA and PCCB expression levels are also assayed in Hepa1-6 and/or Hep3B (ATCC® HB-8064TM) liver cells 24 hours and 48 hours after transfection with 1-methyl-pseudouridine modified mRNAs encoding human PCCA and human PCCB at different molar ratios of PCCA:PCCB mRNA (A:B ratio), or a GFP control, using capillary electrophoresis, as described in Examples 14 and 15. Transfecting cells with different molar ratios of PCCA:PCCB, including a 1:1 molar ratio of PCCA:PCCB, results in expression or overexpression of both PCCA and PCCB.

Figure 15:
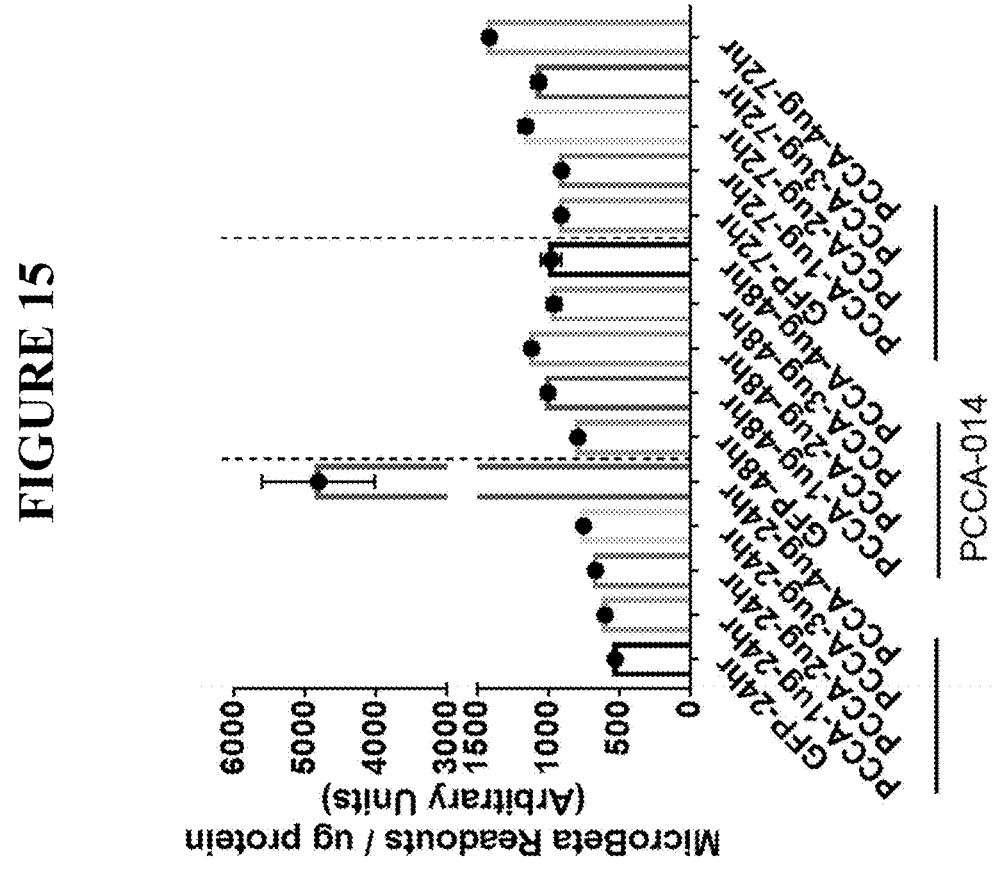
FIG. 15 is a bar graph showing PCC activity (MicroBeta readout/μg protein) in Hep1-6 liver cells transfected with a modified human PCCA mRNA or control mRNA at 24-, 48-, or 72-hours post-transfection.

Example 30: In Vitro PCC Activity and PCCA/PCCB Expression in Hepa1-6 Cells Transfected with mRNA Encoding Human PCCA PCC activity was measured in Hepa1-6 cells 24 hours, 48 hours or 72 hours after transfection with 1 µg, 2 µg, 3 µg, or 4 µg of 1-methyl-pseudouridine modified mRNA encoding human PCCA (PCCA-014; SEQ ID NO: 38), or a GFP control. PCC activity was assessed as described in Example 15. 30 µg of protein was loaded to the PCC reaction. FIG. 15 shows that PCCA mRNA alone did not significantly increased PCC activity in Hepa1-6 liver cells under most of the conditions tested.

Figures 16A, 16B:
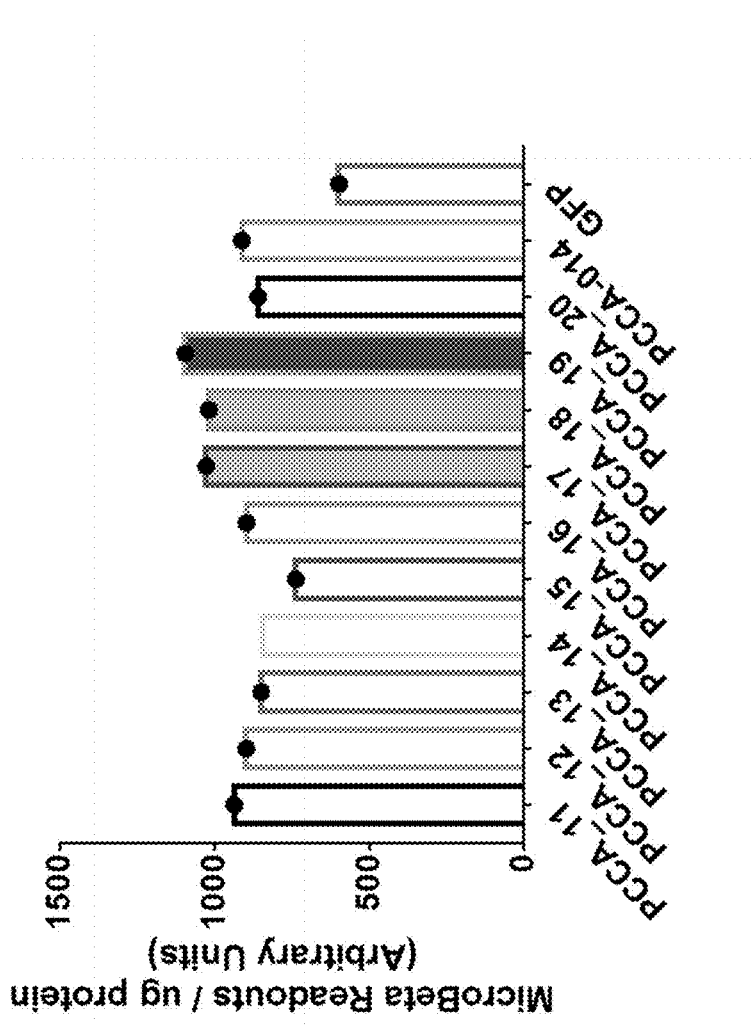
FIG. 16A is a bar graph showing PCC activity (MicroBeta readout/μg protein) in Hep1-6 liver cells transfected with 2 μg of modified human PCCA mRNAs or control mRNA at 48-hours post-transfection.
FIG. 16B shows the PCC activity levels produced by each PCCA mRNA construct of FIG. 16A relative to the PCC activity level produced by the control mRNA (ratio to GFP).

Hepa1-6 cells were transfected with 2 µg of 1-methyl-pseudouridine modified mRNA constructs encoding PCCA (PCCA_11 to PCCA_20 and PCCB-014, represented by SEQ ID NOs: 28-38, respectively), or a GFP control. PCC activity was tested as described in Example 15, in the cells approximately 48 hours after transfection. About 25 µg of protein was loaded to the PCC reaction. FIG. 16A shows that PCC activity increased mildly upon transfection with the PCCA mRNA constructs. FIG. 16B provides the PCC activity levels for each of the PCCA mRNA constructs relative to the GFP control.

Figure 17A:
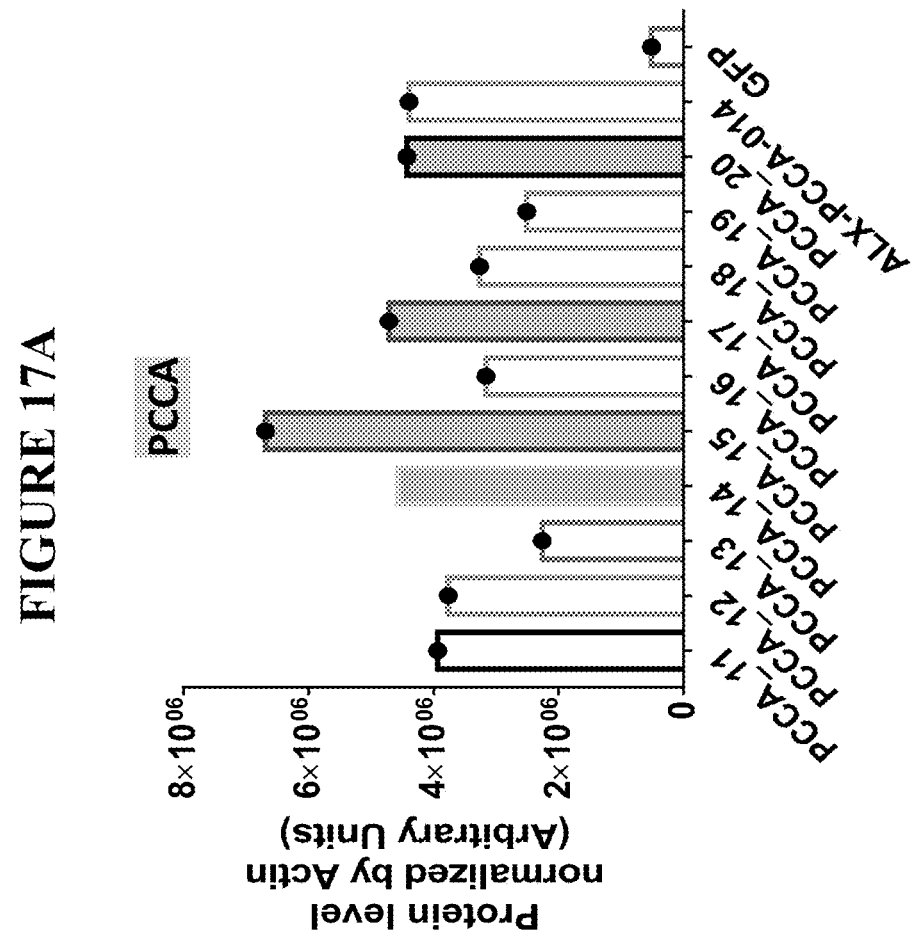
FIG. 17A is a bar graph showing PCCA expression levels (Western blots assessed with capillary electrophoresis, normalized to actin levels) in Hep1-6 liver cells transfected with modified human PCCA mRNAs or control mRNA.
Figure 17B:
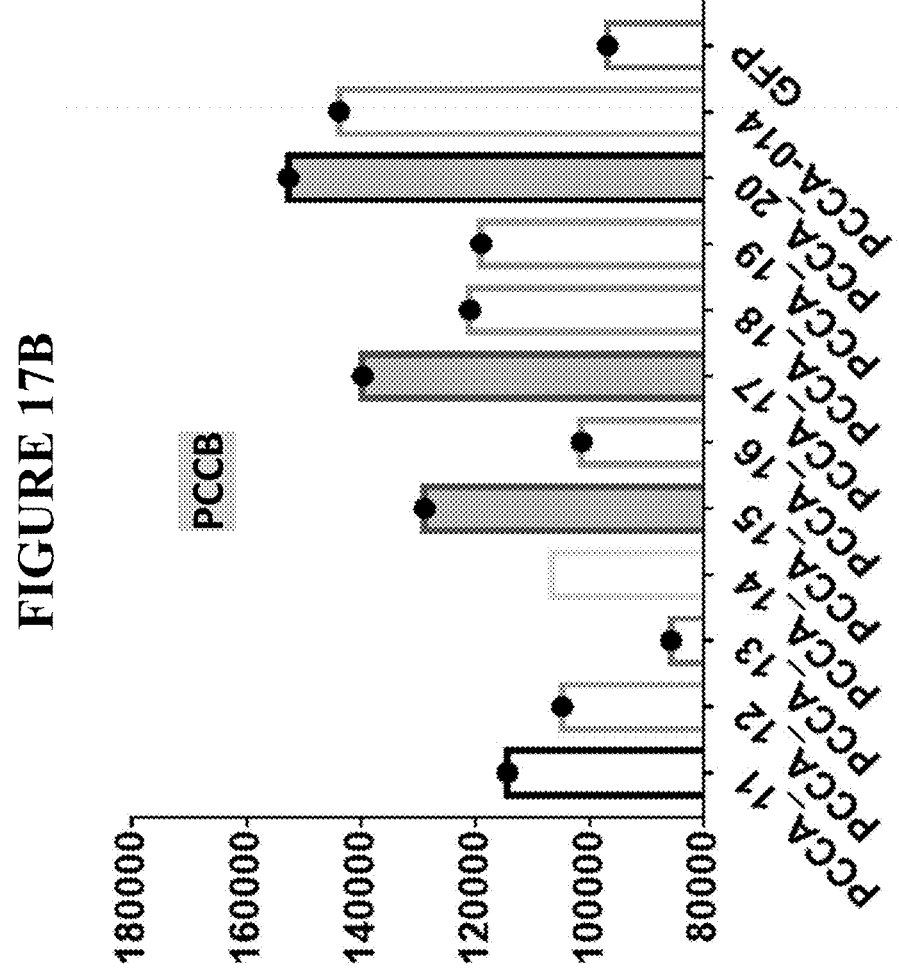
FIG. 17B is a bar graph showing PCCB expression levels (Western blots assessed with capillary electrophoresis, normalized to actin levels) in Hep1-6 liver cells transfected with modified human PCCA mRNAs or control mRNA.

PCCA and PCCB expression levels were tested in the Hepa1-6 transfected with the different mRNA constructs encoding human PCCA, or a GFP control using capillary electrophoresis, as described in Examples 14 and 15. FIG. 17A shows that mRNA encoding human PCCA can increase the expression of PCCA in Hepa1-6 cells. FIG. 17B shows PCCB expression levels in Hepa1-6 cells transfected with PCCA mRNA.

Figure 18:
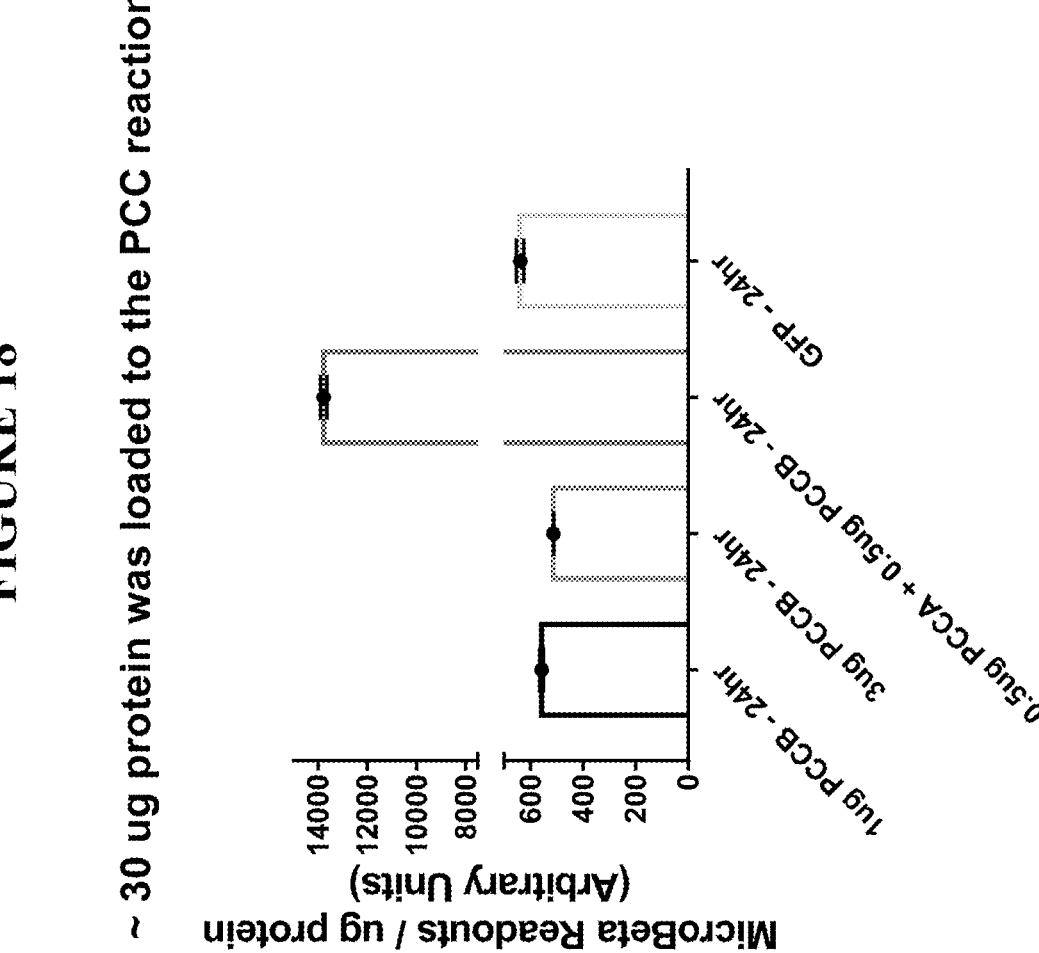
FIG. 18 is a bar graph showing PCC activity (MicroBeta readout/μg protein) in Hep1-6 liver cells transfected with a modified human PCCB mRNA or control mRNA at 24-hours post-transfection.

Example 31: In Vitro PCC Activity and PCCA/PCCB Expression in Hepa1-6 Cells Transfected with mRNA Encoding Human PCCB PCC activity was measured in Hepa1-6 cells 24 hours after transfection with 1 µg or 3 µg of 1-methyl-pseudouridine modified mRNA encoding human PCCB (PCCB-014; SEQ ID NO: 49), or a GFP control. In addition, 0.5 µg of mRNA encoding human PCCA (PCCA-014; SEQ ID NO: 38) and 0.5 µg of mRNA encoding PCCB (PCCB-014; SEQ ID NO: 49) were transfected into cells. PCC activity was assessed as described in Example 15. 30 µg of protein was loaded to the PCC reaction. FIG. 18 shows that there was no significant increase in PCC activity when PCCB mRNA was transfected alone, but PCC activity was markedly increased when PCCA and PCCB were transfected together.

Figure 19:
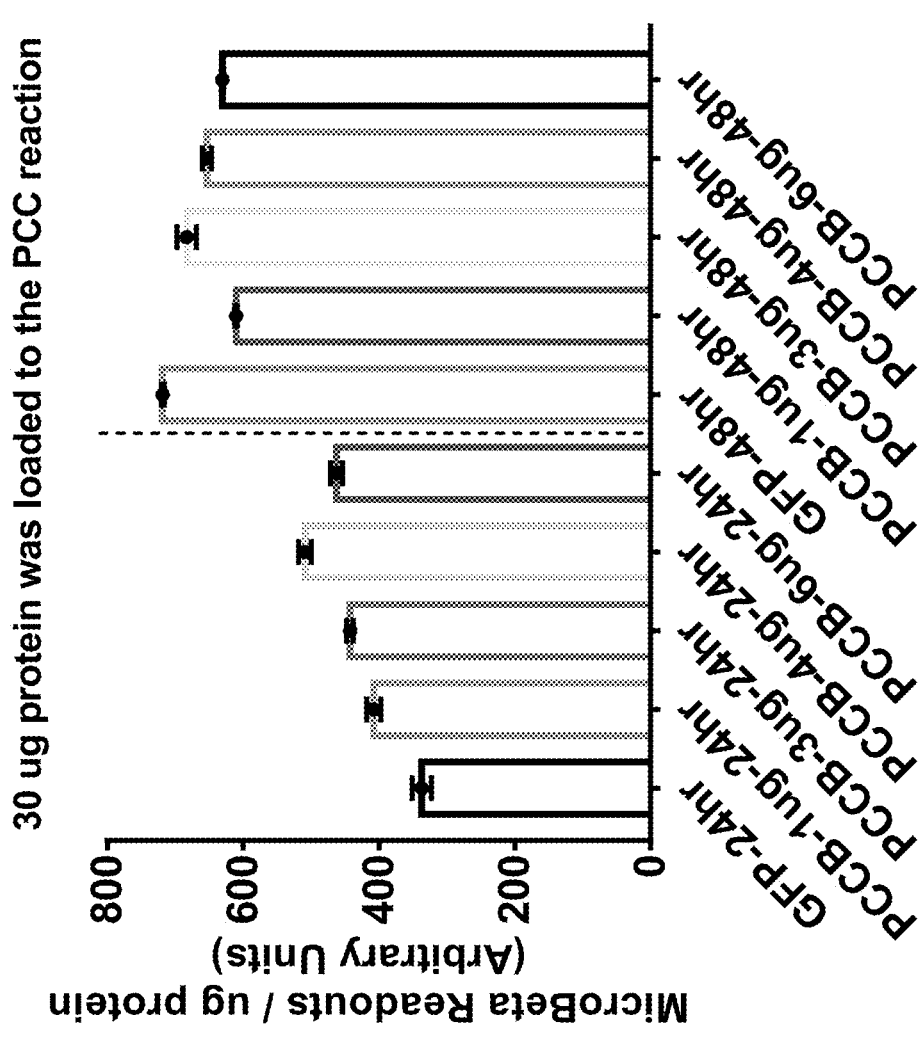
FIG. 19 is a bar graph showing PCC activity (MicroBeta readout/μg protein) in Hep1-6 liver cells transfected with modified human PCCB mRNAs or control mRNA at 24- or 48-hours post-transfection.

Hepa1-6 cells were transfected with 1 µg, 3 µg, 4 µg, or 6 µg of 1-methyl-pseudouridine modified mRNA constructs encoding PCCB (PCCB-014; SEQ ID NO: 49), or a GFP control. PCC activity was tested as described in Example 15, at 24 hours or 48 hours after transfection. About 30 µg of protein was loaded to the PCC reaction. FIG. 19 shows PCC activity upon transfection with PCCB mRNA.

Example 32: In Vivo Dose Dependent PCC Activity Due to Administration of PCCA and PCCB mRNAs in Pcca$^{-/-}$ (A138T) Hypomorphic Mice To determine whether the co-administration of PCCA and PCCB mRNAs can increase PCC activity in a dose dependent manner, 0.25 mg/kg, 0.5 mg/kg or 1 mg/kg of 1-methyl-pseudouridine modified PCCA and PCCB mRNAs encoding human PCCA (PCCA_18; SEQ ID NO:35) and human PCCB (PCCB_18; SEQ ID NO: 46) at a molar ratio of 1:1 were administered to male Pcca$^{-/-}$ (A138T) hypomorphic mice via a single IV bolus tail vein injection. The mRNAs were formulated in lipid nanoparticles (Compound II/PEG-DMG) for delivery into mice (n=4/group). As controls, 1 mg/kg of mRNA encoding luciferase was injected into Pcca$^{-/-}$ (A138T) hypomorphic mice or wild-type FVB mice (n=4) by single IV tail vein injection. Mice were bled 3 days prior to mRNA administration. Mice were sacrificed and hepatic PCC activity was assessed 2 days after IV injection using a Microbeta2 scintillation counter, as described in Example 15, on mitochondrial fractions isolated from liver lysates collected from the mouse. Protein expression of PCCA and PCCB in mitochondrial fractions isolated from livers of Pcca$^{-/-}$ (A138T) and WT mice was assessed using capillary electrophoresis and normalized to citrate synthase protein levels.

Figure 20A:
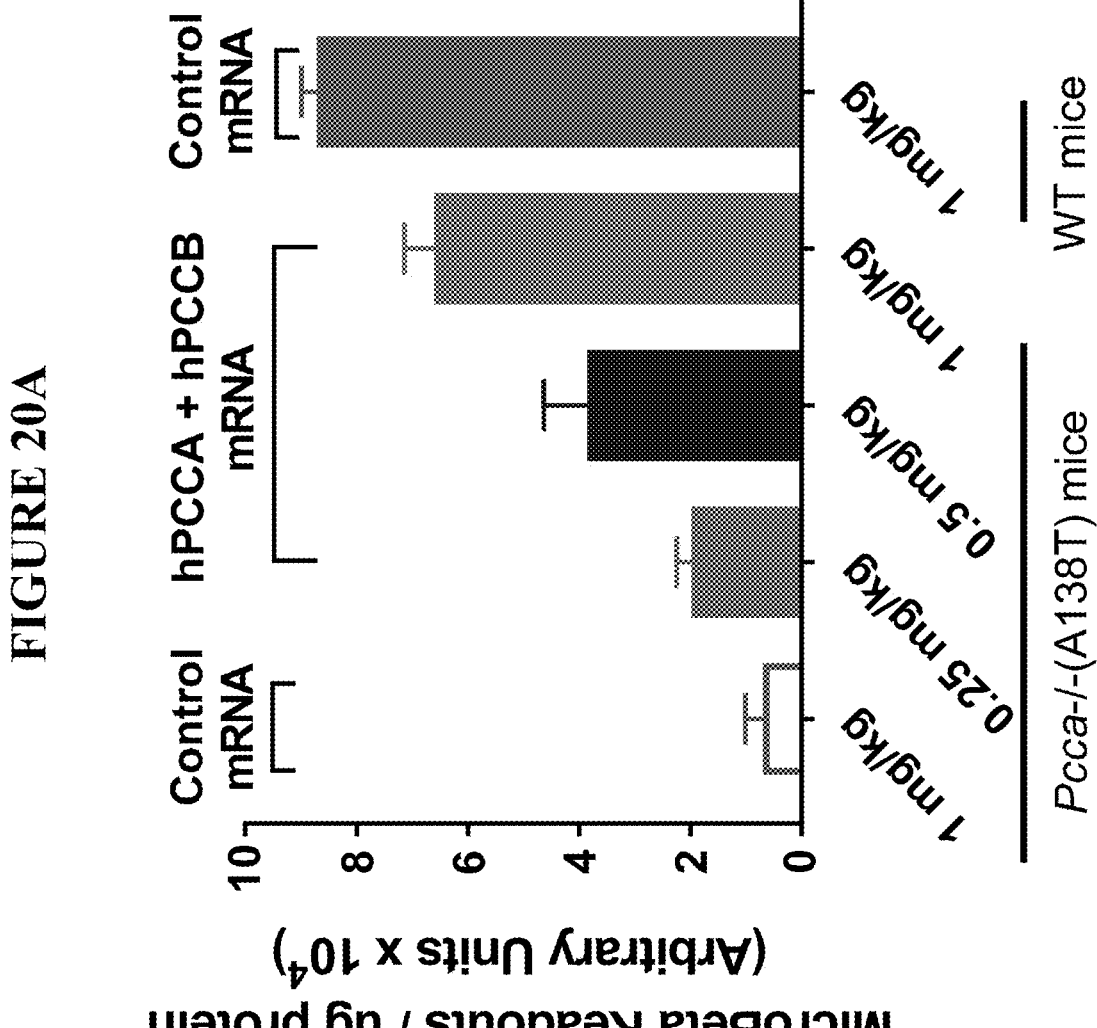
FIG. 20A is a bar graph showing PCC activity in Pcca$^{-/-}$ (A138T) mice at 2 days following a single intravenous injection of modified human PCCA mRNA and PCCB mRNA, or control mRNA.
Figure 20B:
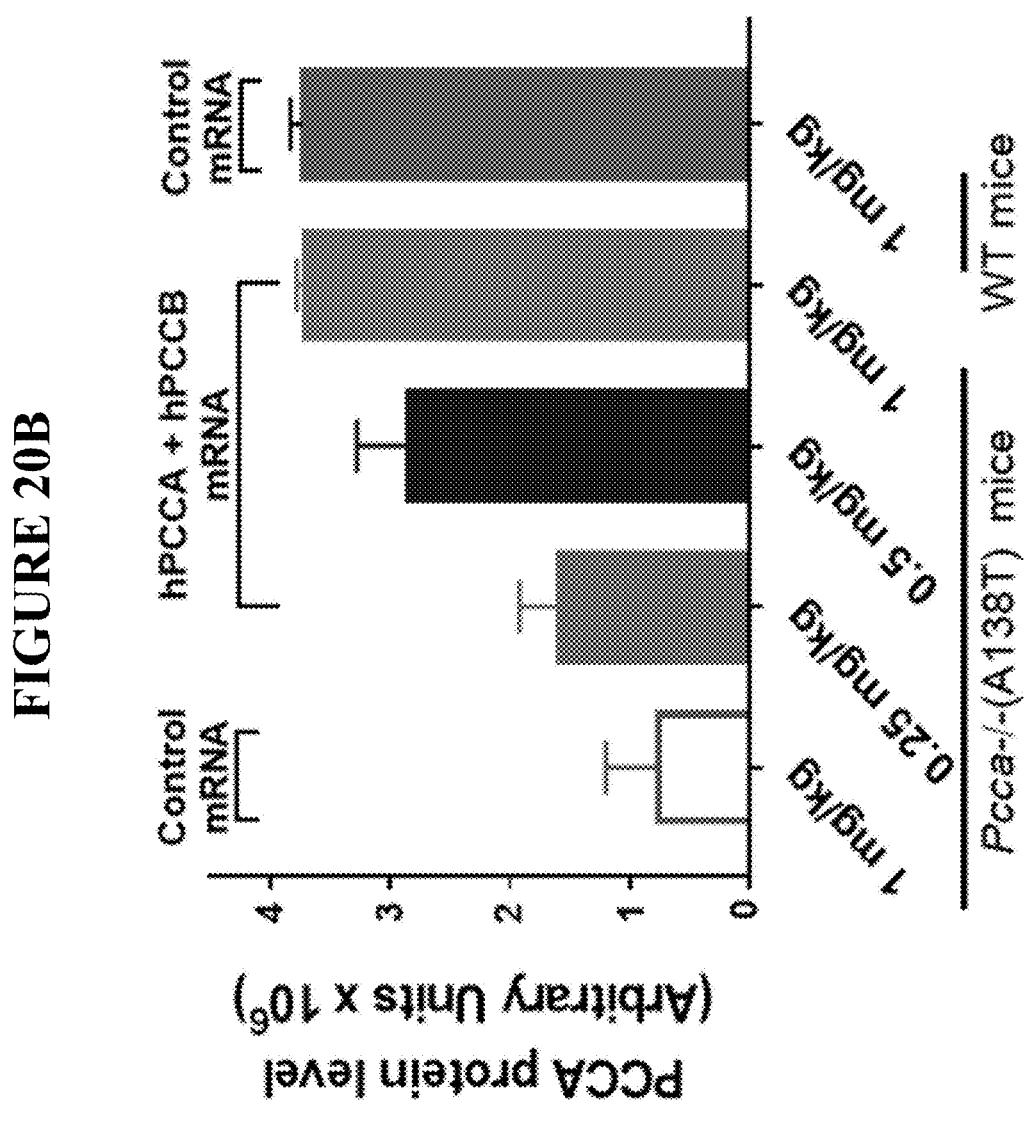
FIGS. 20B and 20C are bar graphs showing PCCA and PCCB protein levels (Western blots assessed with capillary electrophoresis), respectively, in Pcca$^{-/-}$ (A138T) mice at 2 days following a single intravenous injection of modified human PCCA mRNA and PCCB mRNA, or control mRNA.
Figure 20C:
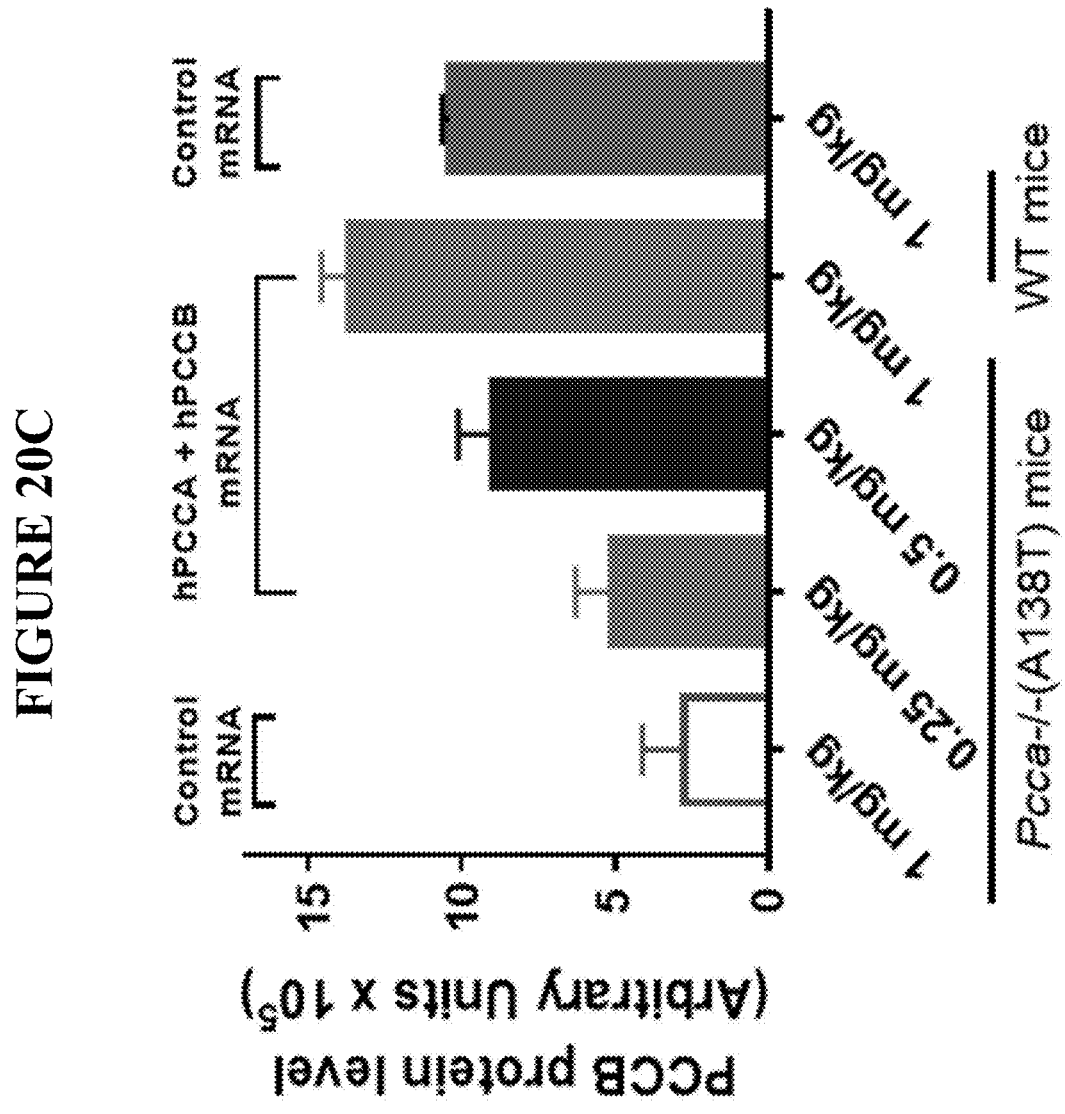

FIG. 20A shows a dose dependent effect associated with a single co-administration of PCCA and PCCB mRNAs in hypomorphic mice, such that higher doses of mRNAs result in greater hepatic PCC activity, compared to mice injected with control mRNA. Administration of 0.25 mg/kg of PCCA and PCCB mRNAs resulted in the lowest PCC activity and administration of 1 mg/kg of PCCA and PCCB mRNAs resulted in the highest PCC activity. Specifically, hepatic PCC enzyme activity was 22%, 44% and 76% of liver PCC activity levels observed in luciferase mRNA-administered wild-type mice at dose levels of 0.25, 0.5 and 1 mg/kg, respectively, two days after a single IV administration of PCCA and PCCB mRNAs in hypomorphic Pcca$^{-/-}$ (A138T) mice. FIGS. 20B and 20C show that hepatic PCCA and PCCB proteins levels assessed by capillary electrophoresis increased in a dose-dependent manner, respectively, 2 days after the human PCCA and PCCB mRNAs were administered in a single injection to Pcca$^{-/-}$ (A138T) mice.

To assess whether co-administration of PCCA and PCCB mRNAs has a dose dependent effect on 2-MC levels and C3/C2 levels, PA biomarkers, 0.25 mg/kg, 0.5 mg/kg or 1 mg/kg of 1-methyl-pseudouridine modified PCCA and PCCB mRNAs encoding human PCCA (PCCA_18; SEQ ID NO:35) and human PCCB (PCCB_18; SEQ ID NO:46) at a 1:1 molar ratio, or 1 mg/kg of mRNA encoding luciferase as a control, were administered to Pcca$^{-/-}$ (A138T) hypomorphic mice (n=4/group) via a single IV tail vein injection. The mice were pre-bled 3 days prior to administration of PCCA/PCCB mRNAs to determine baseline 2-MC and C3/C2 levels. The mRNAs were formulated in lipid nanoparticles (Compound II/PEG-DMG) for delivery into mice. The levels of 2-MC in plasma was measured 2 days after IV injection using LC-MS/MS, and compared to the 2-MC levels in pre-bleed plasma samples. The amount of C3 in dried blood spot (DBS) normalized to C2 ratio concentrations was also measured 2 days after IV injection by methanol extraction, enrichment via a cation exchange column and LC-MS analysis. The lower limit of quantification (LLOQ) was 0.5 µM for 2MC and 12 nM for C3 and C2 carnitines. P-values were obtained from paired-tests to compare means from pre-treatment vs. post-treatment metabolite concentrations.

Figure 20D:
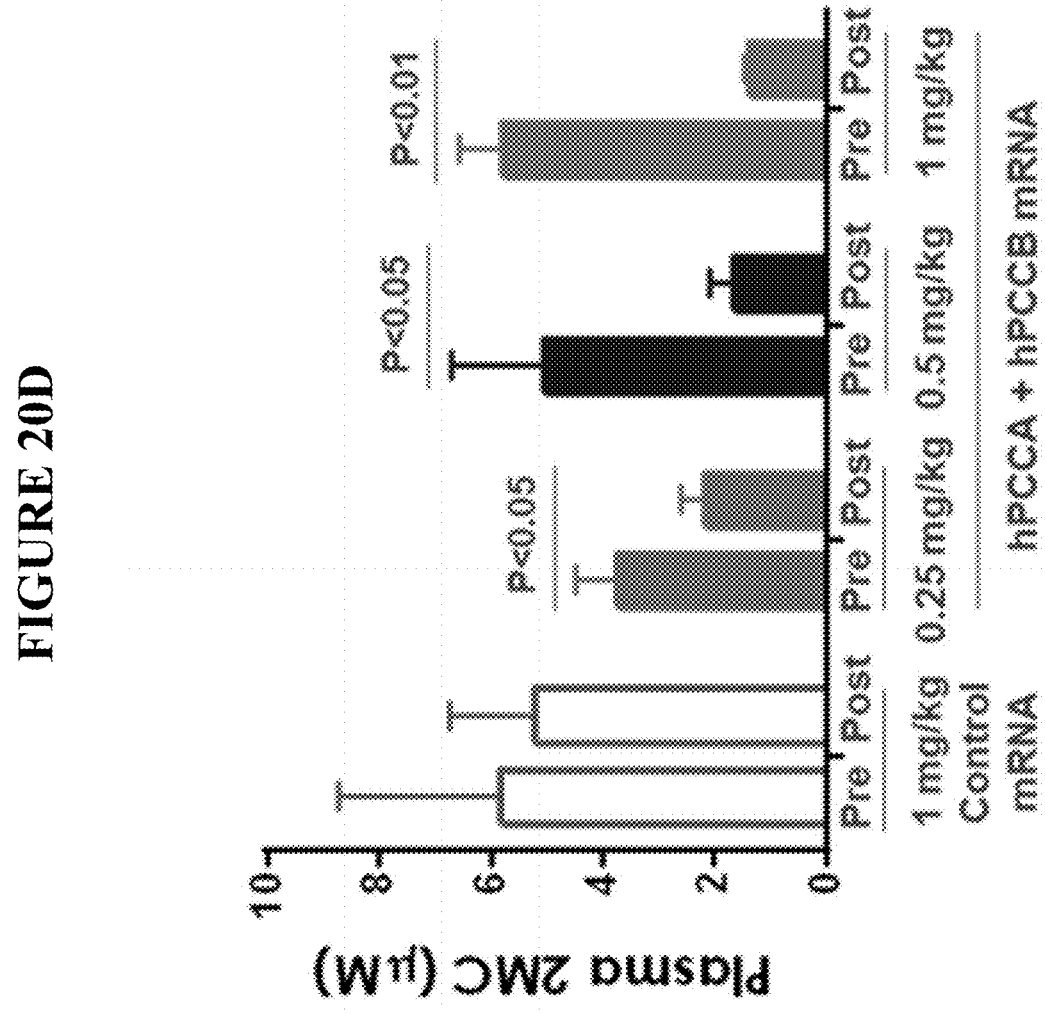
FIG. 20D is a bar graph showing the change in plasma 2-methylcitric acid (2-MC) levels measured in Pcca$^{-/-}$ (A138T) mice at 2 days following intravenous injection of modified human PCCA mRNA and PCCB mRNA, or control mRNA, relative to pre-bleed 2-MC levels.
Figure 20E:
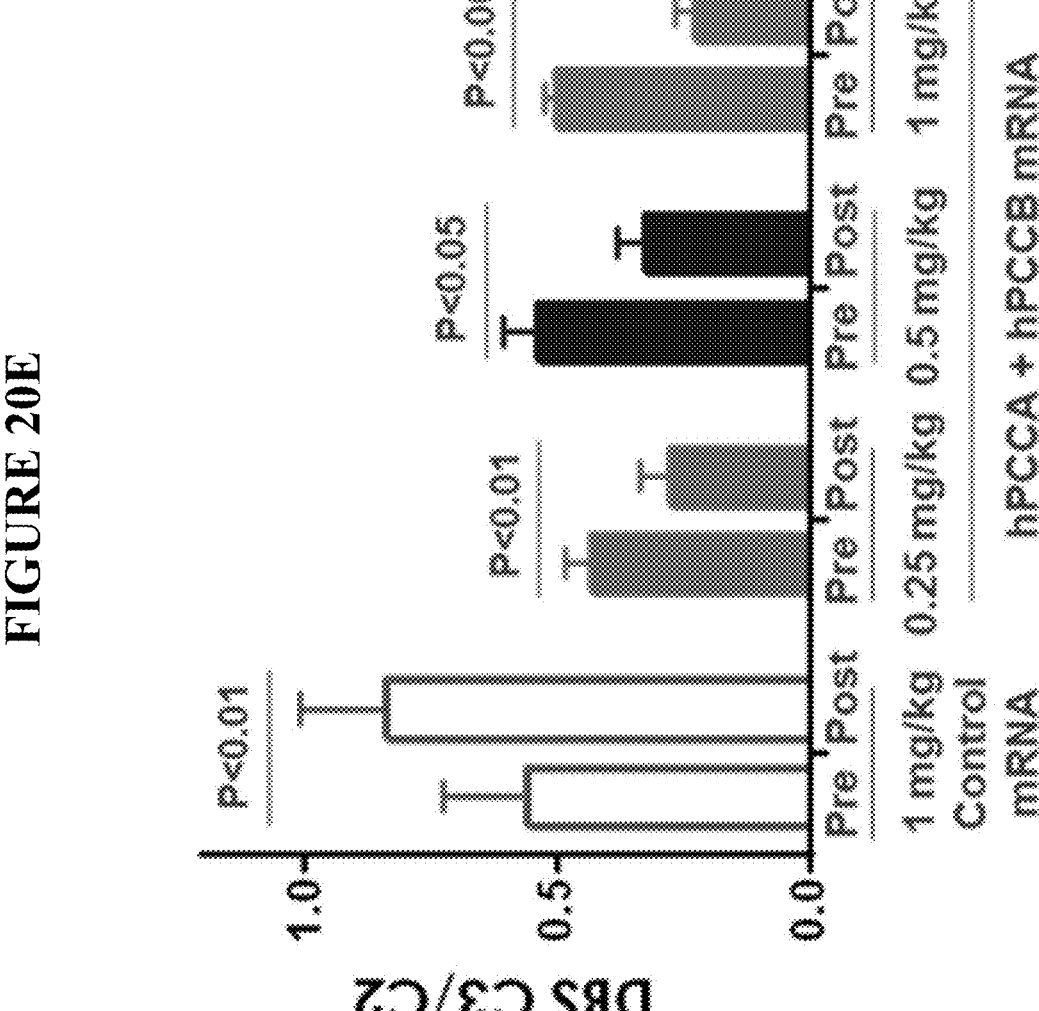
FIG. 20E is a bar graph showing the change in dried blood spot (DBS) propionyl-L-carnitine (C3) levels (normalized to acetyl-L-carnitine (C2) levels) measured in Pcca$^{-/-}$ (A138T) mice at 2 days following intravenous injection of modified human PCCA mRNA and PCCB mRNA, or control mRNA, relative to pre-bleed C3/C2 levels.

FIG. 20D shows that the co-administration of PCCA and PCCB mRNAs resulted in a dose dependent reduction of 2-MC plasma levels in hypomorphic mice, such that 1 mg/kg of PCCA and PCCB mRNAs reduces 2-MC levels the most. Plasma 2-MC decreased 42%, 65%, and 76% on average 2 days after a single injection of 0.25, 0.5, and 1 mg/kg of PCCA and PCCB mRNAs, respectively, to Pcca$^{-/-}$ (A138T) hypomorphic mice, compared to pre-treatment levels of 2-MC. FIG. 20E shows that C3/C2 carnitine ratio concentrations were similarly decreased by 37%, 39%, and 55% on average 2 days after a single injection of 0.25, 0.5, and 1 mg/kg of PCCA and PCCB mRNAs, respectively, compared to pre-treatment levels at these dose levels. By contrast, Pcca$^{-/-}$ (A138T) mice injected with 1 mg/kg of luciferase mRNA exhibited elevated plasma 2-MC concentrations and DBS C3/C2 carnitine ratio concentrations. Thus, a dose-dependent metabolic correction was observed, consistent with the observed hepatic activity of PCC (see FIG. 20A).

The results of these experiments showed that administration of mRNAs encoding human PCCA and PCCB can restore functional hepatic PCC enzyme.

Example 33: Repeat Dose Study Assessing Biochemical Response Due to Co-Administration of PCCA and PCCB mRNAs in Pcca$^{-/-}$ (A138T) Hypomorphic Mice Over Six Months A 6-month repeat dose study was performed to evaluate whether repeat IV administration of PCCA and PCCB mRNAs could improve the biochemical abnormalities, growth, and heart mass symptoms of PA. Pcca$^{-/-}$ (A138T) hypomorphic mice (females) were injected with 0.5 mg/kg or 1 mg/kg of 1-methyl-pseudouridine modified PCCA and PCCB mRNAs encoding human PCCA (PCCA_18; SEQ ID NO:35) and human PCCB (PCCB_18; SEQ ID NO:46), or with 1 mg/kg of mRNA encoding luciferase as a control. Mice were given six doses of mRNAs by IV tail vein injection as follows: a first dose at day 0, a second dose at day 49, a third dose at day 77, a fourth dose at day 107, a fifth dose at day 135, and a sixth dose at day 163. Mice were pre-bled four days before the first dose, and sacrificed for testing 48 hours after the final sixth dose was administered. The mRNAs were formulated in lipid nanoparticles (Compound II/PEG-DMG) for delivery into mice. The levels of PA biomarkers C3/C2 carnitine ratio, 2-MC, and 3-HP were measured in blood drawn from the mice over the course of 165 days using LC-MS/MS (n=6/group). The lower limit of quantification (LLOQ) was 0.5 µM for 2-MC and C3 and C2 carnitines, and 25 µM for 3-HP. For 3HP, values below LLOQ were reported as 25 µM; many of the PCCA and PCCB mRNA-treated mice were <LLOQ for plasma 3HP. Wild-type levels were below LLOQ for 2MC and 3HP, and 0.06±0.02 for C3/C2 carnitine ratio based on n=6 WT FVB mice. Table 7 provides an overview of the study design.

Figure 21A:
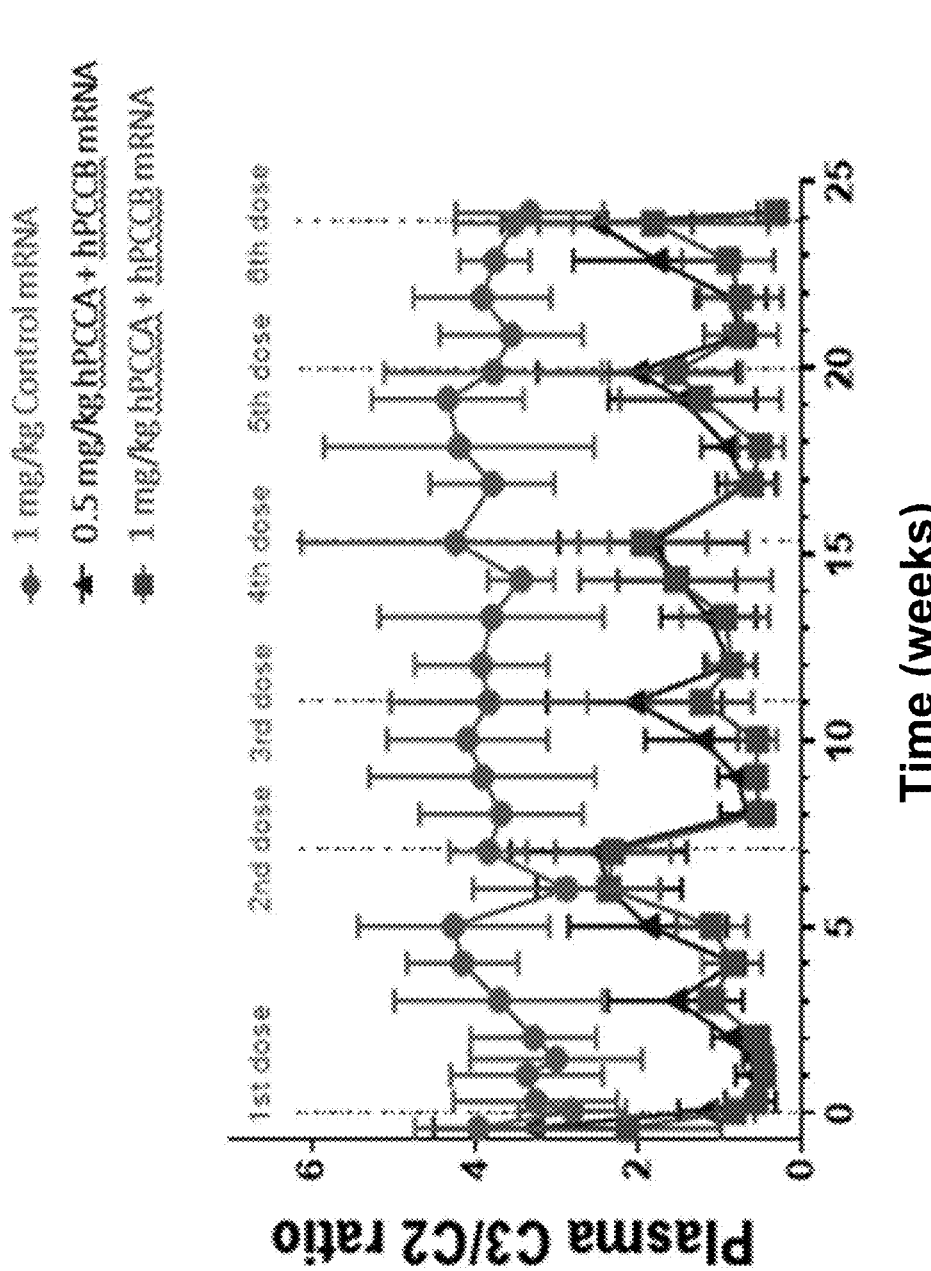
FIG. 21A is a graph showing propionyl-L-carnitine/acetyl-L-carnitine (C3/C2) levels measured in plasma collected from Pcca$^{-/-}$ (A138T) mice following 6 intravenous injections (at a dose of 0.5 mg/kg or 1 mg/kg of mRNAs per injection) of modified human PCCA mRNA and PCCB mRNA, or 1 mg/kg control mRNA in a 6-month pharmacology study.
Figure 21B:
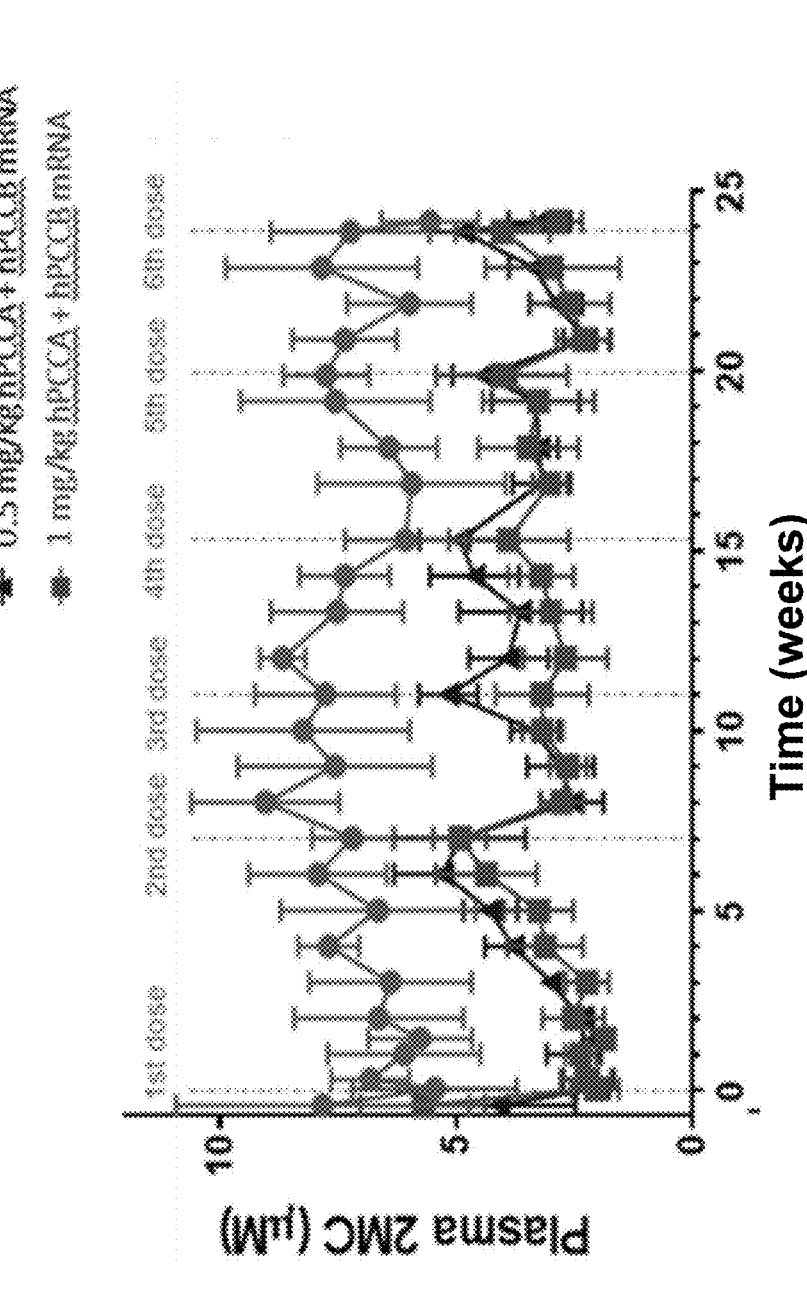
FIG. 21B is a graph showing 2-methylcitric acid (2-MC) levels measured in plasma collected from Pcca$^{-/-}$ (A138T) mice following 6 intravenous injections (at a dose of 0.5 mg/kg or 1 mg/kg of mRNAs per injection) of modified human PCCA mRNA and PCCB mRNA, or 1 mg/kg control mRNA in a 6-month pharmacology study.
Figure 21C:
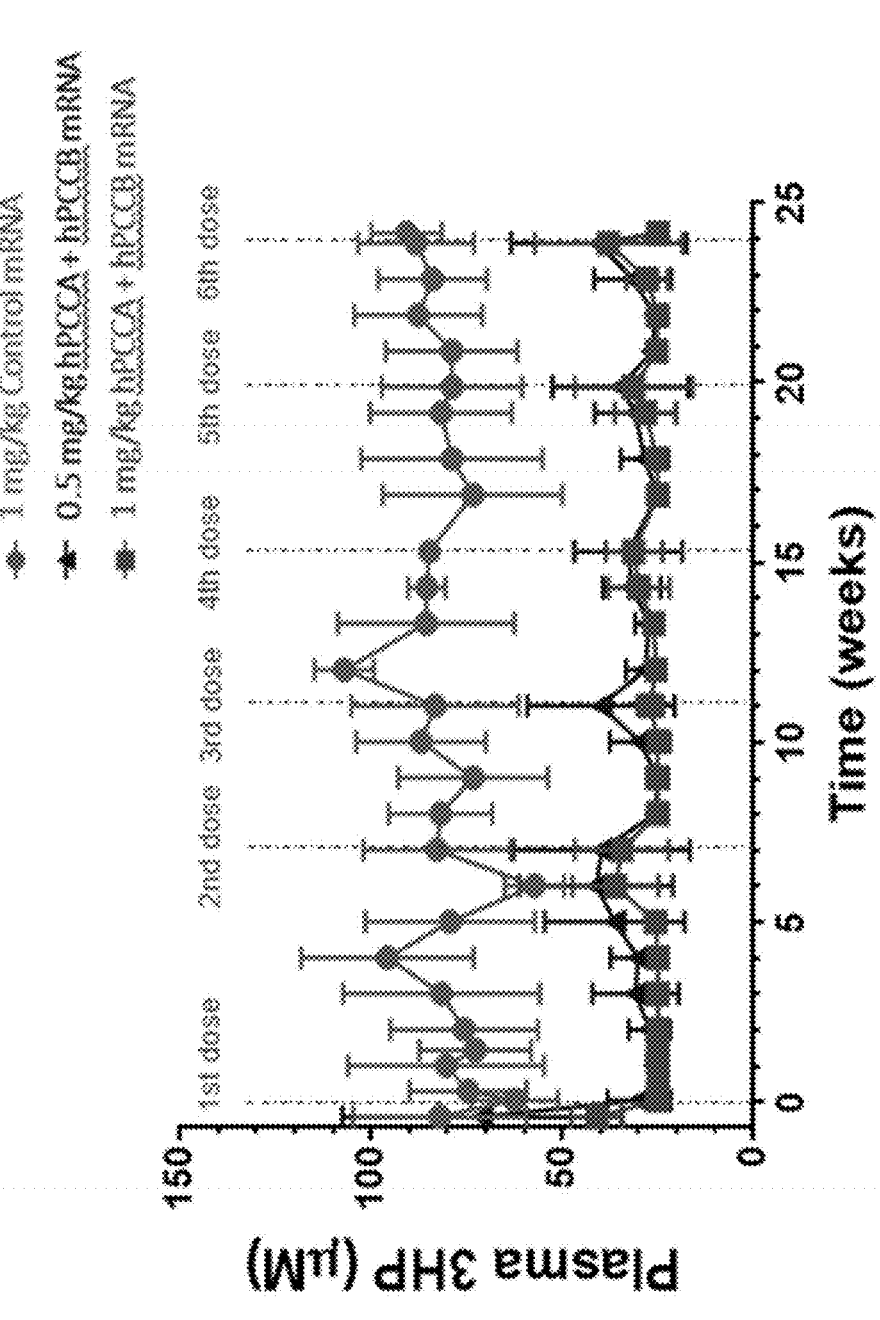
FIG. 21C is a graph showing 3-hydroxypropionic acid (3-HP) levels measured in plasma collected from Pcca$^{-/-}$ (A138T) mice following 6 intravenous injections (at a dose of 0.5 mg/kg or 1 mg/kg of mRNAs per injection) of modified human PCCA mRNA and PCCB mRNA, or 1 mg/kg of control mRNA in a 6-month pharmacology study.

A rapid and significant decrease (≥50%) in plasma C3/C2, 2-MC, and 3-HP levels in Pcca$^{-/-}$ (A138T) hypomorphic mice was observed as early as 6 hours after the first IV injection of the mRNAs encoding PCCA and PCCB relative to hypomorphic mice that received an IV injection of luciferase control mRNA, demonstrating a rapid metabolic correction in mice (see FIGS. 21A-C). These results were consistent with the results of a pharmacokinetic/pharmacodynamics study (see Example 34). A decrease in the biomarkers was sustained for about 2-3 weeks following injection, before biomarker concentrations began to rebound. Based on this duration of biochemical response, the dosing interval was determined to be monthly (i.e., dose administration every 4 weeks) for the remainder of the study.

As shown in FIG. 21A, C3/C2 plasma levels decreased in hypomorphic mice administered 0.5 mg/kg or 1.0 mg/kg of human PCCA and PCCB mRNAs, while C3/C2 levels in hypomorphic mice administered control mRNA remained elevated. There was a significant and sustained reduction in C3/C2 after each administered dose of mRNAs encoding human PCCA and PCCB. In contrast, mice injected with the luciferase control mRNA did not exhibit a C3/C2 metabolic response. FIG. 21B shows that there was a significant and sustained decrease in 2-MC plasma levels in Pcca$^{-/-}$ (A138T) hypomorphic mice that had been repeatedly administered mRNAs encoding human PCCA and PCCB. Administration of 0.5 mg/kg of PCCA and PCCB mRNAs resulted in about a 50% reduction in 2-MC levels (in µM). 2-MC levels started to rebound at approximately 20 days following the first dose of mRNAs, although the levels were still significantly lower than control through 49 days. 2-MC levels significantly decreased again following the second dose of mRNAs administered on day 49, and after each of the subsequent third, fourth, fifth, and sixth doses. FIG. 21C shows a significant and sustained reduction in 3-HP plasma levels, relative to control, after each administered dose of mRNAs encoding PCCA and PCCB, similar to what was observed for the 2-MC and C3/C2 biomarkers.

Thus, the results showed that a single dose of mRNAs encoding human PCCA and PCCB exhibited a long duration of action in Pcca$^{-/-}$ (A138T) hypomorphic mice, eliciting a biochemical response that lasted about 1 month. In addition, the results showed that repeat dosing of mRNAs encoding human PCCA and PCCB resulted in sustained efficacy. Co-administration of mRNAs encoding human PCCA and PCCB had a long duration of action since significant reductions in PA biomarkers (C3/C2, 2-MC, 3-HP) were observed over the course of 165 days in response to repeat doses of mRNAs compared to control mRNA (all p<0.001). A similar

TABLE 7

| Study Design of 6-Month Repeat Dose Pharmacology Study in PCCa$^{-/-}$ (A138T) mice | | | | | | | |
|---|---|---|---|---|---|---|---|
| Group | Mouse Model | Treatment | ROA | Dose Level | Dose Schedule | N | Sacrifice Time Point |
| 1 | Pcca$^{-/-}$ (A138T) | Luciferase mRNA | IV bolus | 1 mg/kg | Day 1*, | 6 | 6 months (2 |
| 2 | (female) | hPCCA + hPCCB mRNAs | | 0.5 mg/kg | Weeks 8, 12, 16, 20, 24 | 6 | days after the 6$^{th}$ |
| 3 | | hPCCA + hPCCB mRNAs | | 1 mg/kg | 6 | | injection) |
| 4 | WT (female) | N/A | N/A | N/A | N/A | 6 | N/A |

*Adaptive design to assess the duration of biochemical response (plasma 2MC, C3/C2 carnitine ratios and 3HP levels) due to human PCCA + PCCB mRNA after a single dose. The second dose was administered after plasma biomarker levels rebounded to basal pre-treatment levels. The subsequent dosing interval in the study was selected based on the duration of biochemical response observed after the first dose.

Bleeding schedule for Pcca$^{-/-}$ (A138T) mice: 3 days before, 6 hours and 2, 7, 10, 14, 21, 28, 35, 42, 49 days after the first injection, 1, 2, 3, 4 weeks after each injection of second through fifth doses, and 2 days after the sixth injection.

biomarker response across all three biomarkers was observed in the 0.5 mg/kg and 1 mg/kg dose level groups. This shows that mRNAs encoding for human PCCA and PCCB reconstitute an active and stable intracellular PCC complex in liver that results in a significant decrease in disease-associated biomarkers (i.e., 2-MC, C3/C2 and 3-HP lowered in a dose dependent manner) with a long duration of effect (i.e., biochemical response) in a mouse model for PA, and can be dosed repeatedly with sustained pharmacology.

Additional pharmacology endpoints were assessed at the end of the 6-month study to help determine the clinical outcome and safety profile of repeat dosing of mRNAs encoding human PCCA and PCCB. Mice were sacrificed 2 days following the last (sixth) dose of PCCA and PCCB mRNAs (n=6/group). Plasma ammonia levels were determined, as described in Example 20, and compared to ammonia levels in control mice. The LLOQ of plasma ammonia was 23.4 μmol/L. Body weight gain was also calculated as the body weight at the end of the study (6-month time point) minus the body weight at the beginning of the study (day 1). The heart weight of injected mice was also measured and compared to the heart weight of Pcca$^{-/-}$ (A138T) hypomorand maximum heart weight/body weight in n=6 wild-type age-matched female mice. P-value obtained from Dunnett's post-hoc multiple comparison test following a one-way ANOVA. Cardiomyopathy is frequently found in PA patients, and these findings suggest an amelioration of enlarged hearts in Pcca$^{-/-}$ (A138T) mice due to treatment with mRNAs encoding human PCCA and PCCB.

Clinical chemistry parameters were also assessed at the end of the 6-month study in the mRNA-injected Pcca (A138T) mice and in untreated age-matched wild-type mice. Plasma levels of ALT and AST were first measured by in-house clinical analyzer. Remaining plasma was used to measure GGT, triglycerides, cholesterol, bile acids and albumin measurement by clinical analyzer. Plasma from mice was collected with EDTA. Pcca$^{-/-}$ (A138T) mice injected with control mRNA had liver enzyme concentrations within normal range, similar to most PA patients. Table 8 provides the results of these measurements. Data is shown as mean±SD. One-way ANOVA analysis was performed, followed by Dunnett's multiple comparison tests to perform pairwise comparisons between all groups. An outlier in the untreated wild-type group was removed from statistical analyses for ALT and AST.  $p<0.01$ vs. control mRNA, * $p<0.001$ vs. control mRNA.

TABLE 8

| | Serum chemistry parameters from 6-month repeat dose study in Pcca$^{-/-}$(A138T) mice and untreated wild-type mice | | | |
| --- | --- | --- | --- | --- |
| | Control mRNA, 1 mg/kg (n = 6 Pcca$^{-/-}$ (A138T) mice) | hPCCA + hPCCB mRNA, 0.5 mg/kg (n = 6 Pcca$^{-/-}$ (A138T) mice) | hPCCA + hPCCB mRNA, 1 mg/kg (n = 5-6 Pcca$^{-/-}$ (A138T) mice) | Untreated WT (n = 4-6 WT mice) |
| ALT (U/L) | 133.83 ± 42.23 | 51.00 ± 18.75*** | 43.50 ± 15.98*** | 117.83 ± 129.35** |
| AST (U/L) | 115.17 ± 24.49 | 76.83 ± 19.18 | 79.33 ± 24.22 | 140.83 ± 95.50 |
| GGT (U/L) | 0 ± 0 | 0 ± 0 | 0 ± 0 | 0 ± 0 |
| Triglycerides (mg/dL) | 181.30 ± 130.03 | 145.00 ± 29.04 | 172.80 ± 33.06 | 347.25 ± 54.44 |
| Cholesterol (mg/dL) | 141.20 ± 15.24 | 125.70 ± 14.71 | 135.00 ± 18.97 | 182.75 ± 80.39 |
| Bile Acids (umol/L) | 5.18 ± 0.68 | 5.97 ± 3.50 | 5.26 ± 3.90 | 6.33 ± 2.53 |
| Albumin (g/dL) | 2.83 ± 0.22 | 3.03 ± 0.23 | 3.12 ± 0.09 | 2.90 ± 0.22 | phic mice and wild-type mice. Heart weight was determined as a ratio to body weight since the body weights of mice can differ.

Figure 22A:
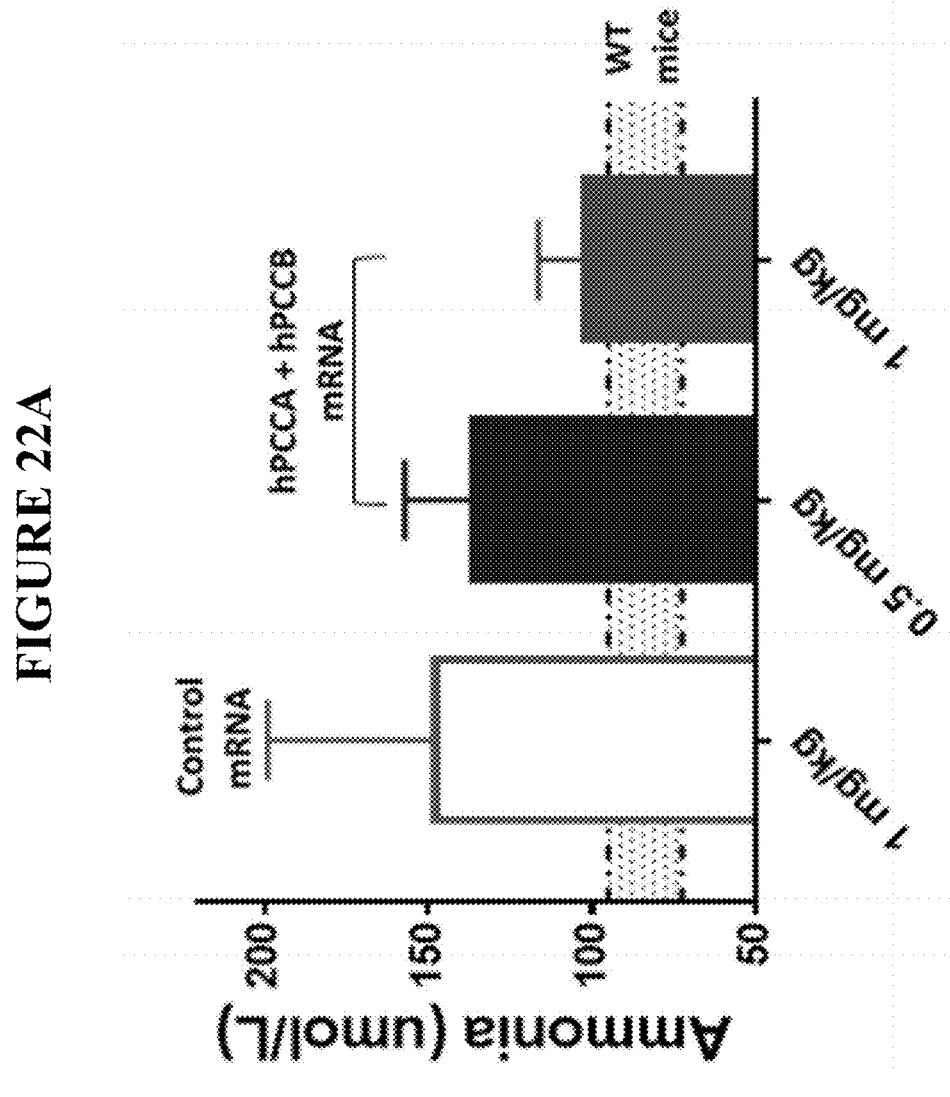
FIG. 22A is a bar graph showing plasma ammonia levels (μmol/L) measured in Pcca$^{-/-}$ (A138T) mice following 6 intravenous injections (at a dose of 0.5 mg/kg or 1 mg/kg of mRNAs per injection) of modified human PCCA mRNA and PCCB mRNA, or 1 mg/kg of control mRNA. The shaded bar indicates the minimum and maximum plasma ammonia levels observed in wild-type mice.
Figure 22B:
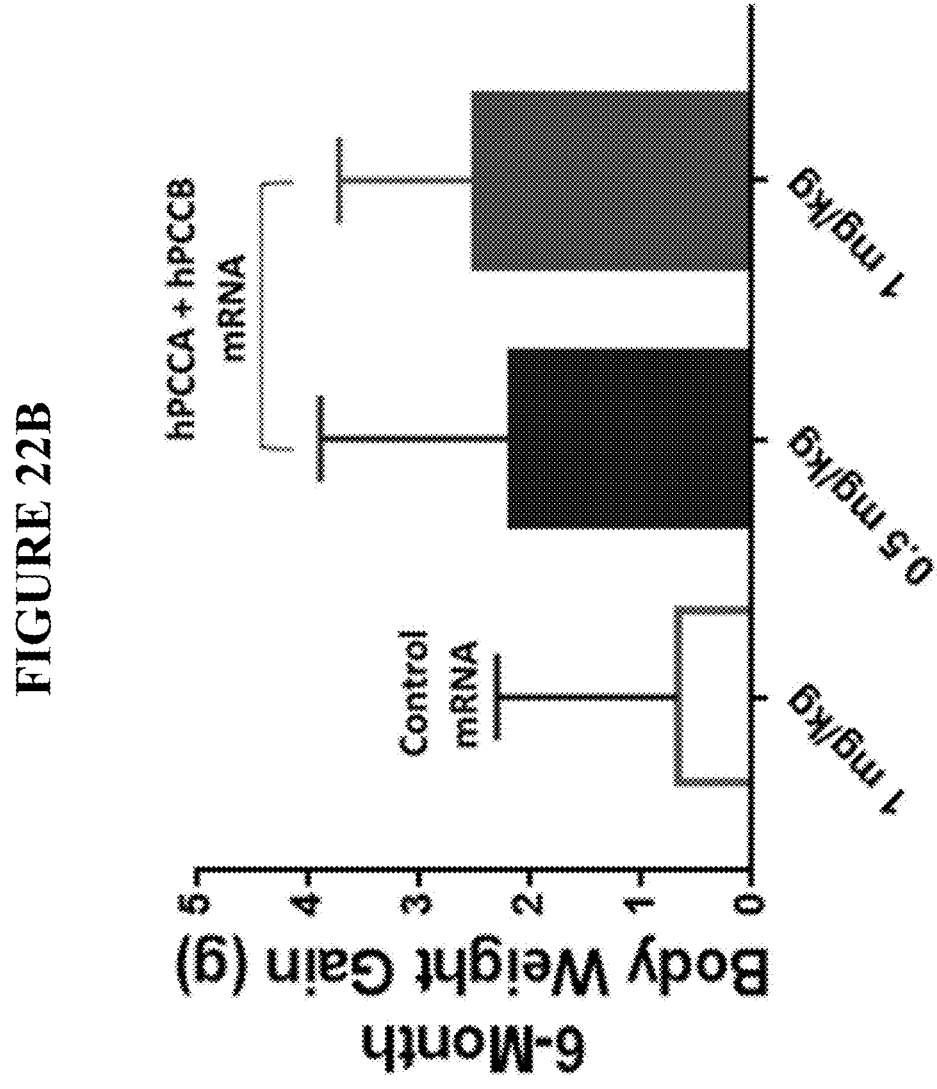
FIG. 22B is a bar graph showing body weight gain measured in Pcca$^{-/-}$ (A138T) mice following 6 intravenous injections (at a dose of 0.5 mg/kg or 1 mg/kg of mRNAs per injection) of modified human PCCA mRNA and PCCB mRNA, or 1 mg/kg of control mRNA.
Figure 22C:
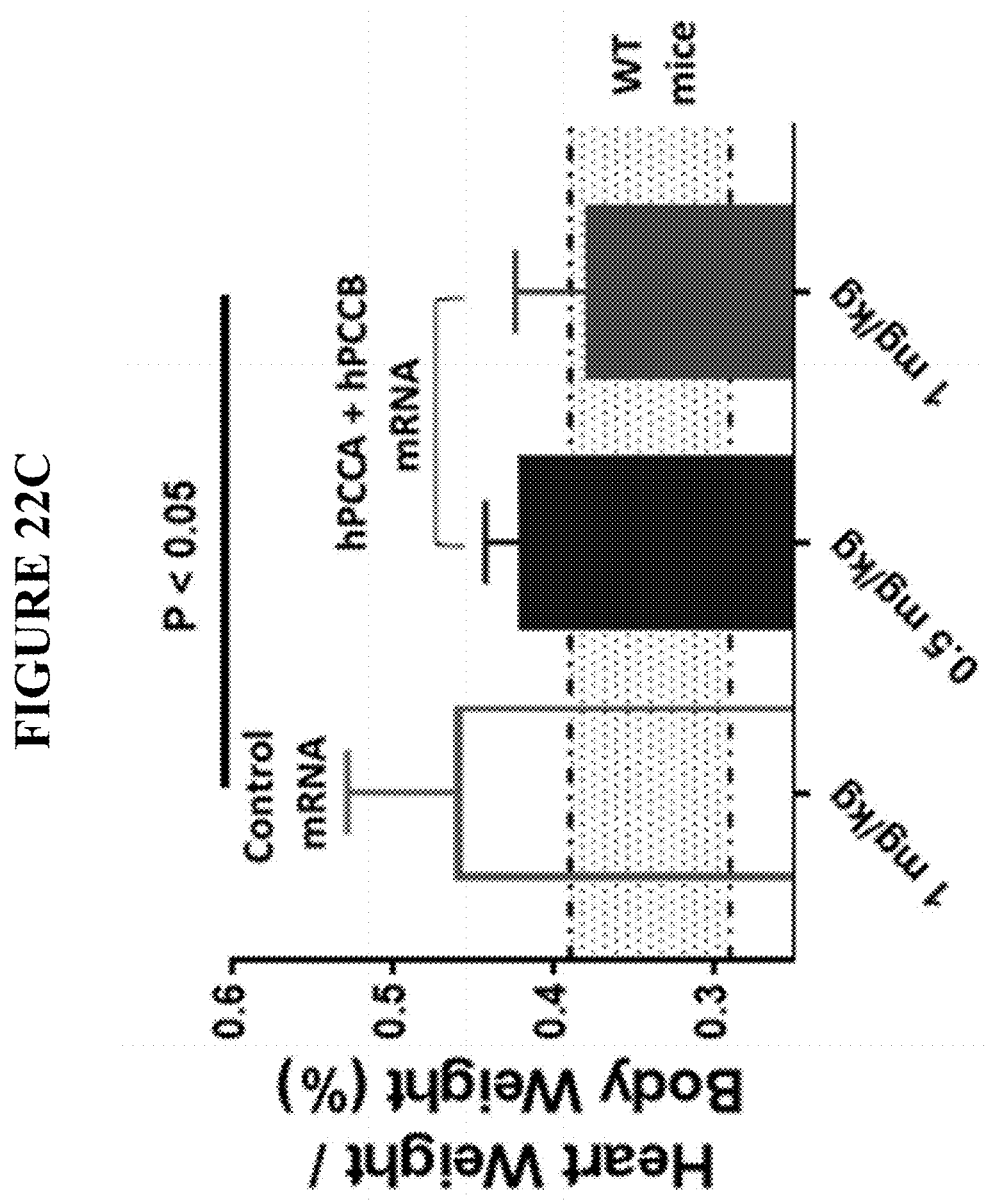
FIG. 22C is a bar graph showing heart weight (normalized to body weight) measured in Pcca$^{-/-}$ (A138T) mice following 6 intravenous injections (at a dose of 0.5 mg/kg or 1 mg/kg of mRNAs per injection) of modified human PCCA mRNA and PCCB mRNA, or 1 mg/kg of control mRNA. The shaded bar indicates the minimum and maximum heart weights (normalized to body weights) observed in wild-type mice

FIG. 22A shows that a dose-dependent decrease in plasma ammonia was observed in Pcca (A138T) mice administered human PCCA and PCCB mRNAs at the end of the study. Mice that were administered 1 mg/kg of the PCCA and PCCB mRNAs exhibited near wild-type levels of ammonia. The shaded bar for wild-type mice in FIG. 22A is the minimum and maximum ammonia level in n=6 wild-type age-matched female mice. FIG. 22B shows that Pcca$^{-/-}$ (A138T) mice injected with human PCCA and PCCB mRNAs (0.5 or 1 mg/kg) generally exhibited greater body weight gain at the end of the study compared to control mice administered 1 mg/kg of the luciferase mRNA. FIG. 22C shows that Pcca$^{-/-}$ (A138T) hypomorphic mice that were administered 1 mg/kg of mRNAs encoding human PCCA and PCCB exhibited a dose-dependent decrease in heart mass normalized to body weight compared to mice that were administered the control mRNA. Mice that received repeat administration of 1 mg/kg of the PCCA and PCCB mRNAs have significantly lower heart weights normalized to body weight compared to control mRNA-injected mice. The shaded bar for wild-type mice in FIG. 22C is the minimum Plasma ALT levels were significantly lower in the Pcca$^{-/-}$ (A138T) mice that were injected with human PCCA and PCCB mRNAs (both at the 0.5 mg/kg and 1 mg/kg doses) and in untreated wild-type mice compared to Pcca$^{-/-}$ (A138T) mice injected with control mRNA. The plasma ALT levels in the mice injected with the mRNAs encoding PCCA and PCCB were similar to levels reported in 8-week old wild-type (FVB) female mice (see http://jackson.jax.org/rs/444-BUH-304/images/physiological_data_001800.pdf), and were not significantly different from the plasma ALT levels in the age-matched untreated wild-type mice from the study. All other serum chemistry parameters (AST, GGT, triglycerides, cholesterol, bile acids, and albumin) were not statistically different between groups, although there was a trend towards lower AST in Pcca$^{-/-}$ (A138T) mice administered PCCA and PCCB mRNAs compared to the mice administered control mRNA. All clinical chemistry parameters were within the normal range observed in wild-type mice and thus these data suggest that administering human PCCA and PCCB mRNAs was well-tolerated in Pcca$^{-/-}$ (A138T) mice after the 6-month repeat dose study.

Example 34: Assessing Duration of Biochemical
Response Due to Co-Administration of PCCA and
PCCB mRNAs in Pcca$^{-/-}$ (A138T) Hypomorphic
Mice A study was conducted to characterize the pharmacokinetics (PK) of mRNA-encoded human PCCA and PCCB proteins and PCC enzyme activity in liver and the pharmacodynamic (PD) response. Pcca$^{-/-}$ (A138T) hypomorphic mice (mixed genders) were injected with a single dose of 1 mg/kg of 1-methyl-pseudouridine modified PCCA and PCCB mRNAs encoding human PCCA (PCCA_18; SEQ ID NO:35) and human PCCB (PCCB_18; SEQ ID NO:46), or with 1 mg/kg of mRNA encoding luciferase as a control, by IV tail vein injection. Previous studies showed no difference in hepatic PCCA and PCCB protein levels and PCC enzyme activity in Pcca$^{-/-}$ (A138T) mice administered luciferase mRNA in LNPs compared to PBS (data not shown). The mRNAs were formulated in lipid nanoparticles (Compound II/PEG-DMG) for delivery into mice. Mice were sacrificed at 6 hours, 24 hours, 48 hours, 7 days, 14 days, 21 days or 28 days following a single injection of mRNAs (n=3-4 mice per time point). For each time point, hepatic PCC activity was measured using a Microbeta2 scintillation counter, as described in Example 15, on mitochondrial fraction isolated from liver lysates. Plasma PA biomarkers (2-MC, C$_3$/C2 ratio, 3-HP, and ammonia) were also measured. Plasma levels of 2-MC, C3/C2 carnitine ratio, and 3-HP were measured using LC-MS/MS at each time point. The lower limit of quantification (LLOQ) was 0.5 µM for 2-MC and C3 and C2 carnitines, and 25 µM for 3-HP. Absolute quantification of human PCCA and PCCB proteins was also measured by LC-MS/MS. Homogenized mouse livers were spiked with isotopically labeled signature peptides (natural C and N atoms on lysine were replaced by 13C and 15N isotopes; Thermo Scientific Pierce) specific for human wild-type PCCA (AQAVHPGYGFLSENK, which does not recognize the human PCCA A138T mutant) and PCCB (TV-GIVGNQPK) as an internal standard. Mice administered the control luciferase mRNA were used to assess the baseline PCCA and PCCB protein levels and PCC enzyme activity in liver.

Figure 23A:
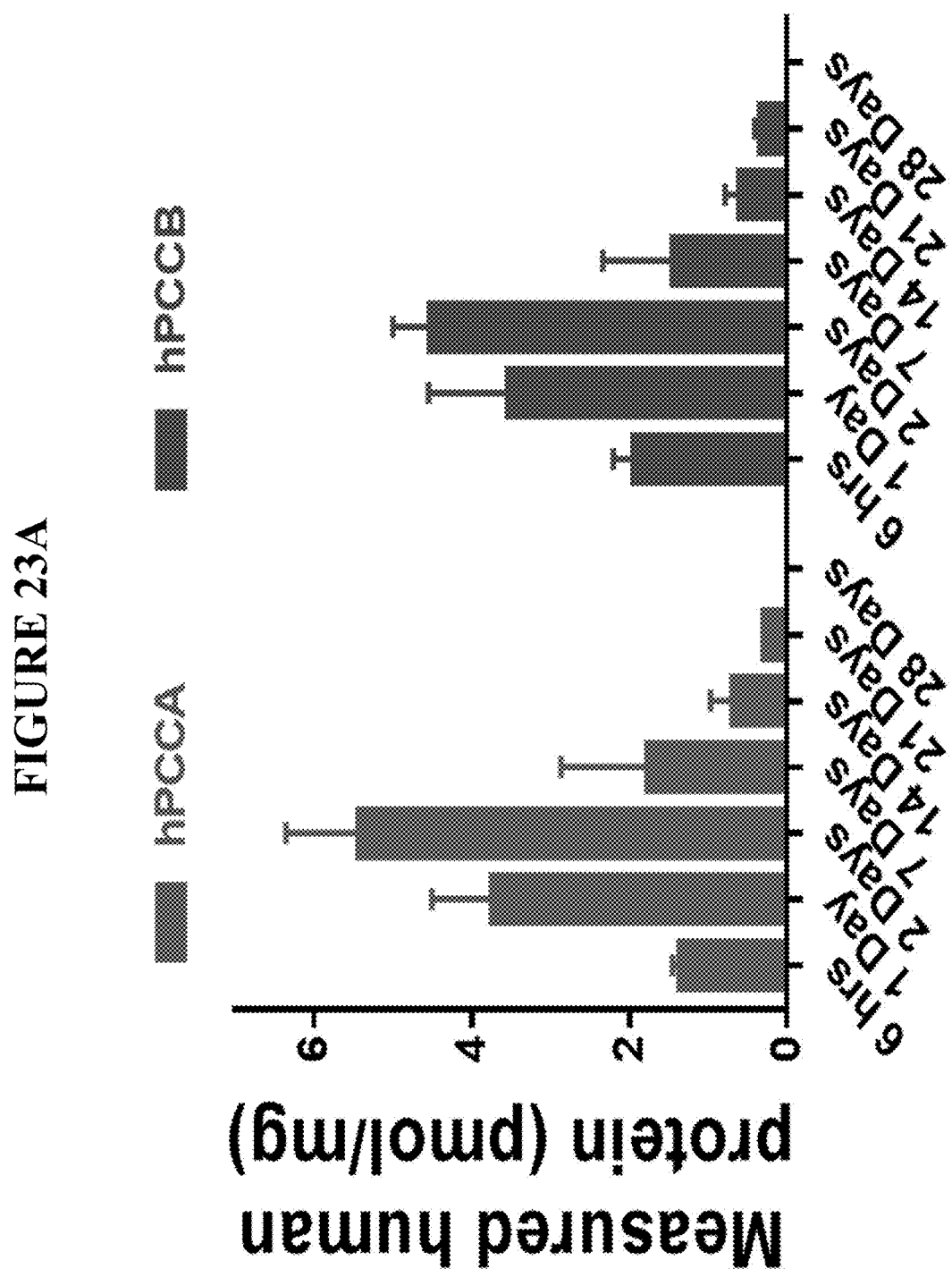
FIG. 23A is a bar graph showing the levels of human wild-type PCCA protein and human PCCB protein quantified by LC-MS/MS with human-specific peptides in Pcca$^{-/-}$ (A138T) mice at 6 hours and at 1, 2, 7, 14, 21, and 28 days following a single intravenous injection of 1 mg/kg modified human PCCA mRNA and PCCB mRNA, or control mRNA.
Figure 23B:
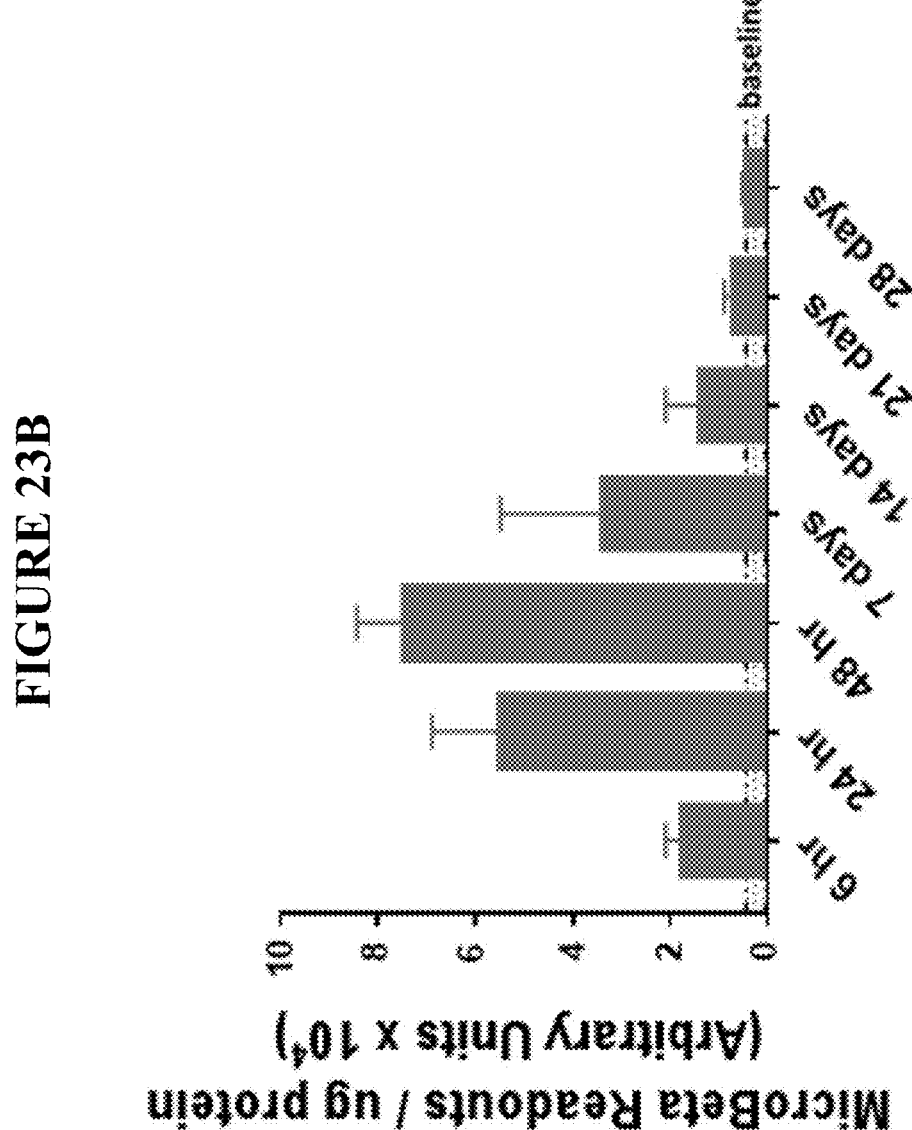
FIG. 23B is a bar graph showing PCC activity in Pcca$^{-/-}$ (A138T) mice at 6 hours and at 1, 2, 7, 14, 21, and 28 days following a single intravenous injection with 1 mg/kg modified human PCCA mRNA and PCCB mRNA, or control mRNA. The baseline shaded bar represents the range (minimum and maximum values) observed in Pcca$^{-/-}$ (A138T) mice injected with luciferase control mRNA.

FIG. 23A shows that PCCA protein levels were substantially increased as early as 6 hours (the first time point) after injection of PCCA and PCCB mRNAs, and peaked at 48 hours (Tmax), relative to PCCA protein levels in control mice injected with control mRNA (i.e., the baseline level which is below LLOQ). PCCA protein levels decreased to within control levels by 28 days following injection. PCCB protein levels exhibited a similar protein expression pattern and an approximate 1:1 molar ratio of PCCA/PCCB over the course of 28 days. PCCA and PCCB protein concentrations (pmol/mg tissue) were similar across the time course. LLOQ for PCCA and PCCB was 26 and 16 ng/mg tissue, respectively. All PCCA and PCCB protein values from luciferase mRNA-injected mice were below the LLOQ at all time points. FIG. 23B shows that hepatic PCC activity levels were higher in Pcca$^{-/-}$ (A138T) hypomorphic mice at 6 hours, 24 hours, 48 hours, 7 days, 14 days and 21 days following injection of PCCA and PCCB mRNAs relative to luciferase controls. PCC activity increased above background levels as early as 6 hours (the first time point) and peaked at 48-hours post-injection, reaching near wild-type levels (86.1% of wild-type levels), and fell within control mRNA levels (i.e., baseline) at 28 days post-injection. The kinetics of PCC enzyme activity in liver was consistent with the kinetics of the PCCA and PCCB proteins, and demonstrates restoration of functional PCC enzyme activity in a mouse model of PA. It is expected that PCC activity levels will not increase in the heart and brain tissue of mice injected with PCCA and PCCB mRNAs compared to controls.

Figure 23D:
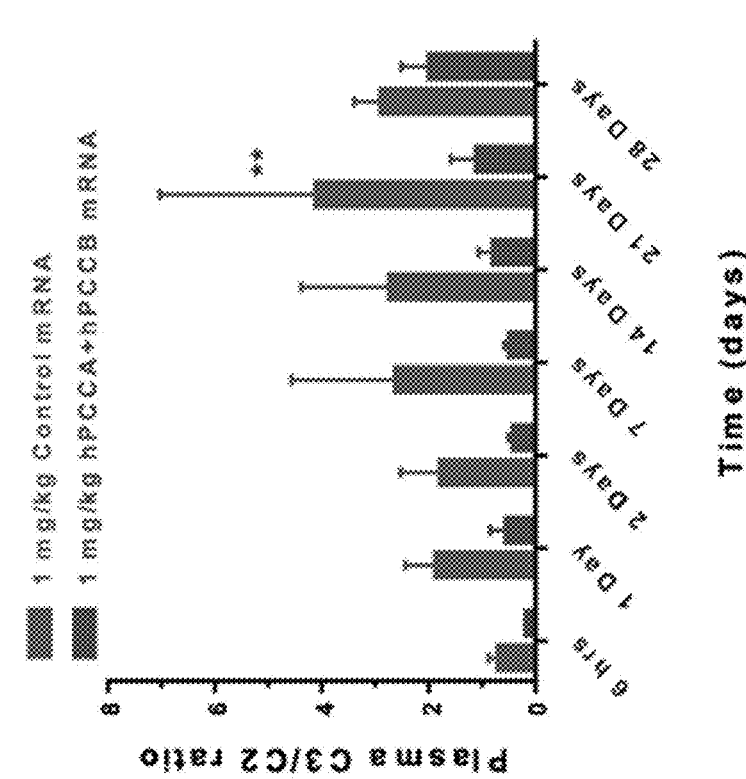
FIG. 23D is a bar graph showing plasma propionyl-L-carnitine/acetyl-L-carnitine (C3/C2) levels measured in Pcca$^{-/-}$ (A138T) mice at 6 hours and at 1, 2, 7, 14, 21, and 28 days following a single intravenous injection of 1 mg/kg modified human PCCA mRNA and PCCB mRNA, or control mRNA.
Figure 23C:
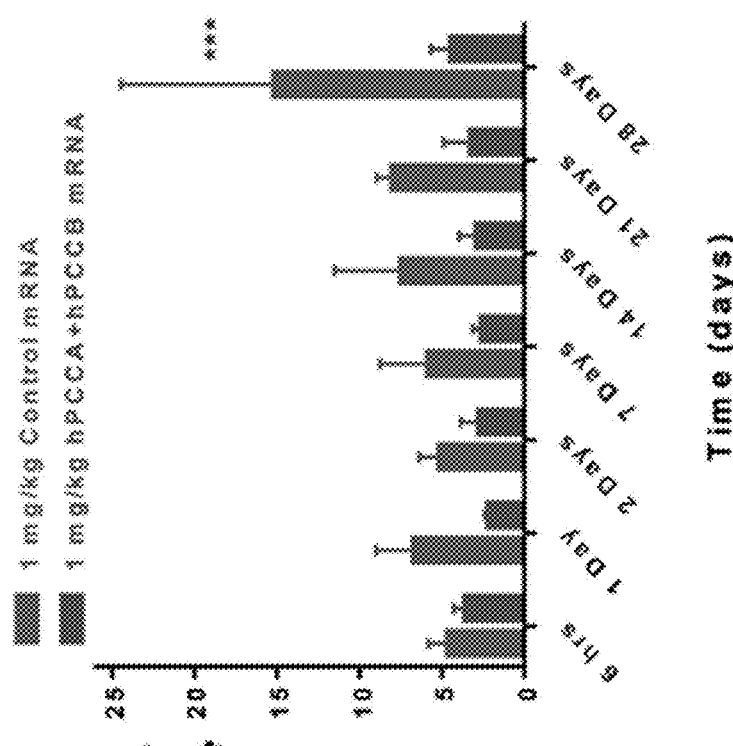
FIG. 23C is a bar graph showing plasma 2-methylcitric acid (2-MC) levels measured in Pcca$^{-/-}$ (A138T) mice at 6 hours and at 1, 2, 7, 14, 21, and 28 days following a single intravenous injection of 1 mg/kg modified human PCCA mRNA and PCCB mRNA, or control mRNA.
Figure 23E:
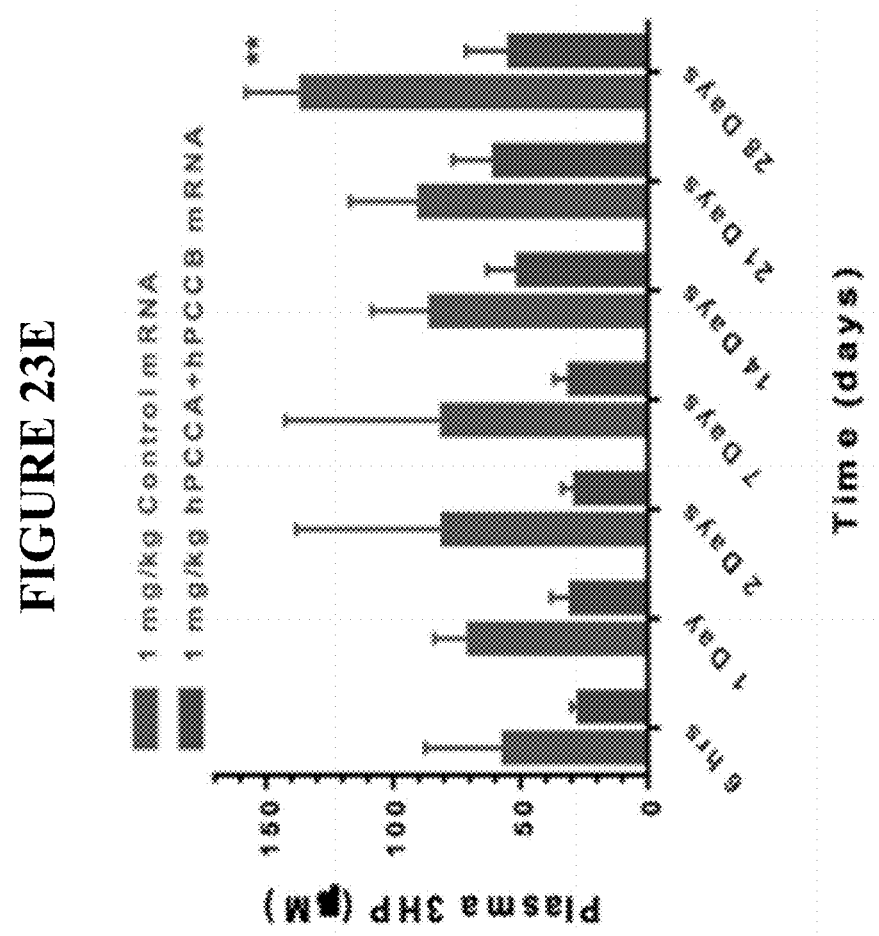
FIG. 23E is a bar graph showing plasma 3-hydroxypropionic (3-HP) levels measured in Pcca$^{-/-}$ (A138T) mice at 6 hours and at 1, 2, 7, 14, 21, and 28 days following a single intravenous injection of 1 mg/kg modified human PCCA mRNA and PCCB mRNA, or control mRNA.

FIG. 23C shows that plasma levels of 2-MC were reduced in mice sacrificed at 1, 2, 7, 14, 21, and 28 days after a single injection of mRNAs encoding PCCA and PCCB, showing that the combination of PCCA and PCCB mRNAs had a long duration of action in reducing 2-MC levels over at least 4 weeks. Indeed, there was a greater than 50% reduction in 2-MC levels in mice injected with PCCA and PCCB mRNAs compared to control mice at 28 days. FIG. 23D shows that plasma levels of C3/C2 were reduced at 6 hours, and 1, 2, 7, 14, and 21 days after a single injection of mRNAs encoding PCCA and PCCB, showing that the combination of PCCA and PCCB mRNAs had a long duration of action in reducing C3/C2 levels over at least 3 weeks. The C3/C2 ratio level was reduced by more than 50% as early as 6 hours after injection, indicating a rapid metabolic correction, but was similar to control levels at 28 days following injection. FIG. 23E shows 3-HP levels were much reduced over the course of 28 days following injection of PCCA and PCCB mRNAs. 3-HP levels were reduced by greater than 50% by 6 hours and at 28 days after injection relative to control. Thus, all plasma primary disease biomarkers (metabolites that accumulate in PA due to the metabolic block) that were examined were substantially lower in Pcca$^{-/-}$ (A138T) mice that were administered a single dose of PCCA and PCCB mRNAs relative to control. In addition, plasma ammonia, a secondary PA disease biomarker (which accumulates due to secondary inhibition of ureagenesis) was also significantly reduced in Pcca$^{-/-}$ (A138T) mice administered a single dose of PCCA and PCCB mRNAs relative to controls (see Example 20). Reduction of all of these PA biomarkers demonstrate a pharmacodynamics response in mice treated with PCCA and PCCB mRNAs due to the production of functional PCC enzyme, which corrects the underlying metabolic defect of PA.

2-MC levels were also measured in key disease-associated tissues (liver, heart, and brain) of mice at each time point (6 hours, 1 day, 2 days, 7 days, 14 days, 21 days, and 28 days) following mRNA injection using LC-MS/MS. Tissue samples (in milligrams) were homogenized in 4 volumes (in microliters) of water: acetonitrile (80:20, v/v) and tissue 2MC concentrations were quantified by LC-MS/MS. The LLOQ of 2MC in all tissues was 2.5 µM. Values below the LLOQ were reported as 2.5 µM (i.e. the LLOQ). P-values were obtained from Sidak's multiple comparison test to compare PCCA and PCCB mRNAs vs. control mRNA groups at each time point following a two-way ANOVA. *p<0.05, **p<0.01.

Figures 23F, 23G:
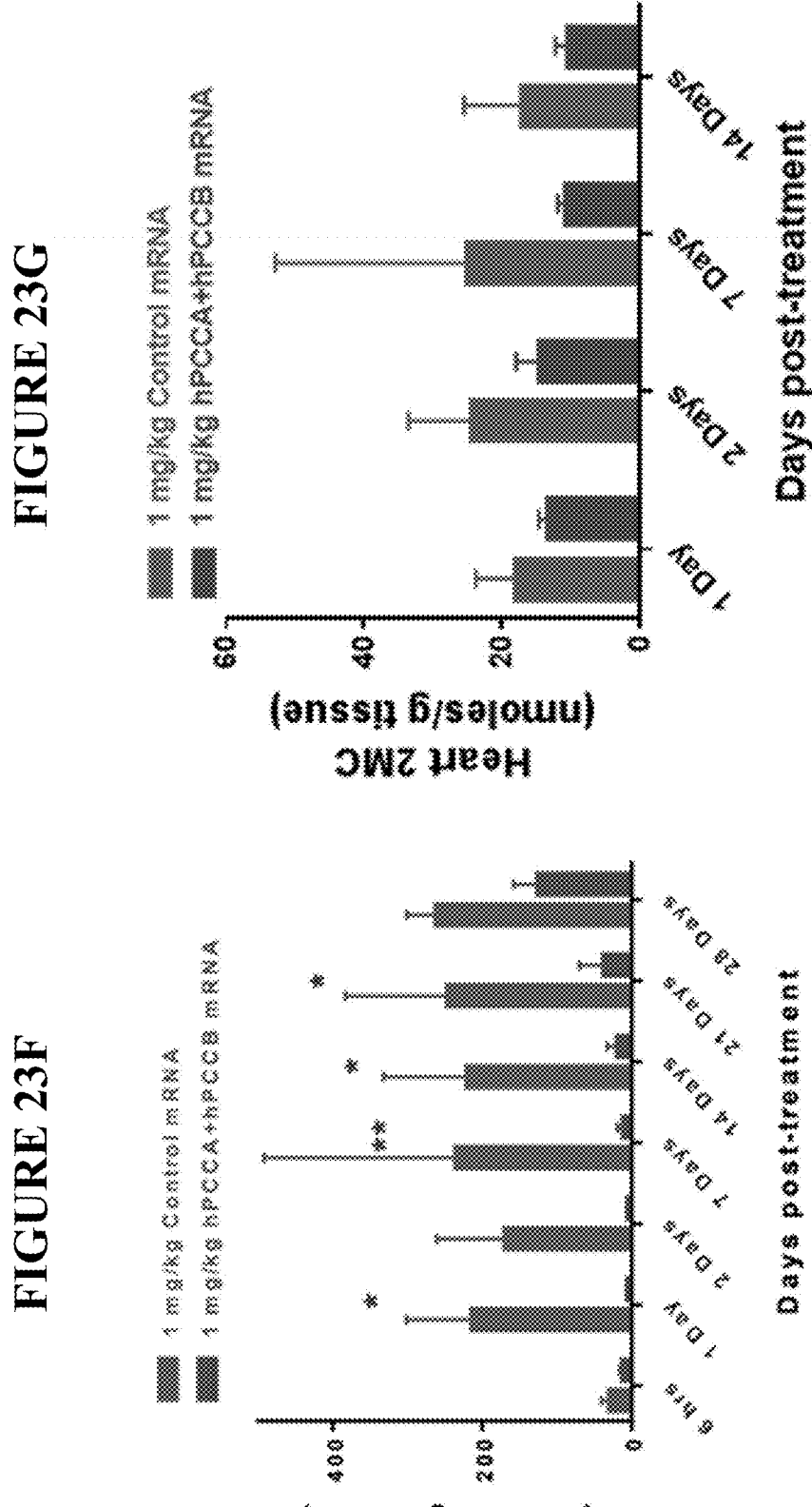
FIGS. 23F, 23G, and 23H are bar graphs showing the 2-methylcitric acid (2-MC) levels measured in the livers, hearts, and brains, respectively, of Pcca$^{-/-}$ (A138T) mice at 6 hours and at 1, 2, 7, 14, 21, and 28 days (at only 1, 2, 7, and 14 days in heart) following a single intravenous injection of 1 mg/kg modified human PCCA mRNA and PCCB mRNA, or control mRNA.
Figure 23H:
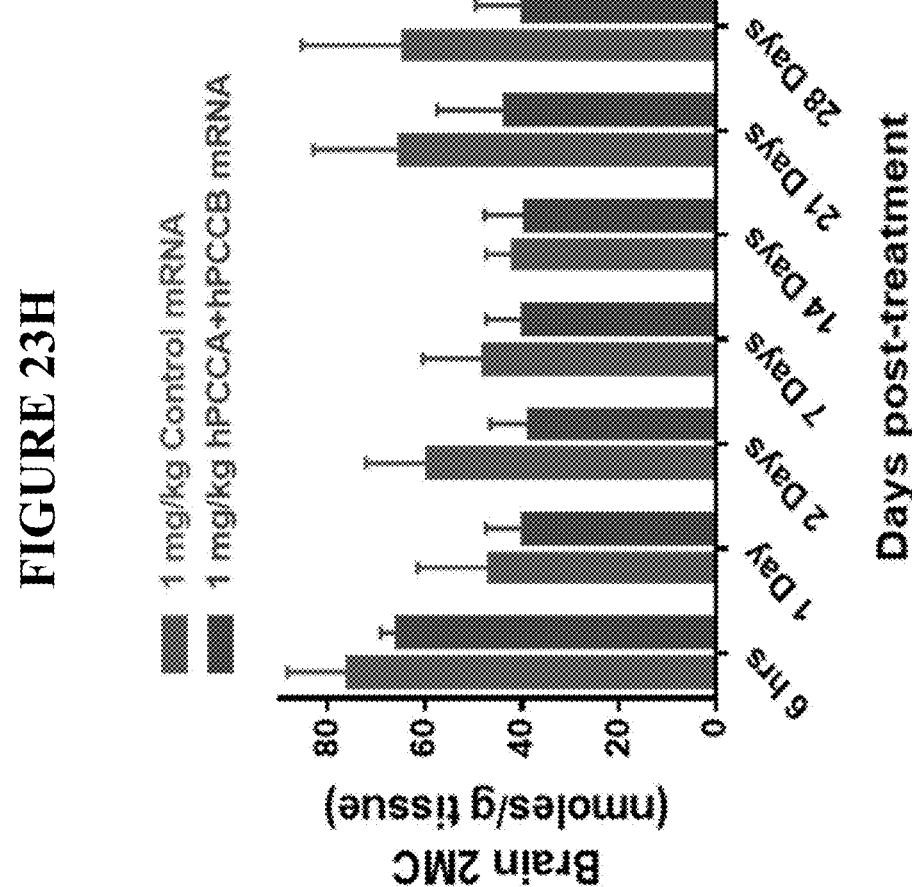

FIG. 23F shows that 2-MC levels were also reduced for at least 28 days in the livers of Pcca$^{-/-}$ (A138T) hypomorphic mice following a single injection of PCCA and PCCB mRNAs, relative to luciferase control mRNA. Indeed, 2-MC concentrations were substantially lower (≥85%) 1 to 21 days after injection; the reduction in liver 2-MC concentrations was statistically significant at all time point except for the 6-hour, 2-day, and 28-day time points. FIG. 23G shows that 2-MC levels were also reduced in the hearts of Pcca$^{-/-}$ (A138T) hypomorphic mice injected with PCCA and PCCB mRNAs, ranging from 27-58% lower on average in treated vs. control mice. FIG. 23H shows that brain 2-MC concentrations were 6-38% lower on average in mice administered PCCA and PCCB mRNAs compared to controls, but these differences were not statistically significant. C3/C2 and 3-HP levels will also be measured in the livers, hearts, and brains of Pcca$^{-/-}$ (A138T) hypomorphic mice following injection of PCCA and PCCB mRNA.

PCCA and PCCB protein expression levels are also measured in the tissues (liver and spleen) o fPcca$^{-/-}$ (A138T) hypomorphic mice that are administered 1 mg/kg of 1-methyl-pseudouridine modified PCCA and PCCB mRNAs encoding human PCCA (PCCA_18; SEQ ID NO: 35) and human PCCB (PCCB_18; SEQ ID NO: 46) at a 1:1 molar ratio, or with 1 mg/kg of mRNA encoding luciferase as a control, by a single IV tail vein injection. Protein levels are assessed by LC-MS/MS at 6 hours, 24 hours, 48 hours, 7 days, 14 days, 21 days and 28 days following injection.

Modified human PCCA and PCCB mRNA levels are also measured in the plasma and tissues (liver and spleen) of Pcca$^{-/-}$ (A138T) hypomorphic mice that are administered 1 mg/kg of 1-methyl-pseudouridine modified PCCA and PCCB mRNAs encoding human PCCA (PCCA_18; SEQ ID NO: 35) and human PCCB (PCCB_18; SEQ ID NO: 46) at a 1:1 molar ratio, or with 1 mg/kg of mRNA encoding luciferase as a control, by a single IV tail vein injection. The levels of mRNA encoding modified human PCCA and PCCB is assayed at 6 hours, 24 hours, 48 hours, and 7 days following injection of mice using a bDNA (as described in Cell Reports, 2017, 21:3548-58, which is herein incorporated by reference in its entirety) or qPCR assay. It is expected that modified human PCCA and PCCB mRNA levels will be detectable in the plasma and the tissues (liver, spleen) of mice post-injection.

Example 35: In Vivo Formation of PCC Dodecamer

The PCC holoenzyme is an alpha(6)beta(6) dodecamer with a molecular weight of approximately 800 kDa in humans. To determine if 1-methyl-pseudouridine modified PCCA and PCCB mRNAs encoding human PCCA (PCCA_18; SEQ ID NO: 35) and human PCCB (PCCB_18; SEQ ID NO: 46) can express PCCA and PCCB proteins that form a PCC dodecamer of the appropriate molecular weight, Pcca$^{-/-}$ (A138T) hypomorphic mice are injected with a single 1 mg/kg dose of mRNAs encoding human PCCA and PCCB via tail vein injection. Mitochondrial fractions of liver lysates are isolated from mice 2 days after injections, and proteins are separated by size exclusion chromatography using Superose 6 column (GE Healthcare) with a 500 ul loop. Fractions are then pooled and the protein concentrated. PCCA and PCCB expression and the enrichment of PCC complex in pooled fractions is assessed using capillary electrophoresis as described in Example 13 and PCC activity is assessed as described in Example 15. PCC complex formation can also be assessed by blue native-polyacrylamide gel followed by western blotting (as described in Jiang et al., J. Biol. Chem., 2005, 280(30):27719-27, which is herein incorporated by reference in its entirety). It is expected that the co-injection of PCCA and PCCB mRNAs will result in the formation of PCC complexes at a molecular weight of approximately 800 kDa in mitochondria, indicating that mRNA expressed human PCCA and PCCB can form dodecamers in mice.

Example 36: Assessing Cardiomyopathy in Pcca$^{-/-}$ (A138T) Hypomorphic Mice Cardiomyopathy is observed in human patients with propionic academia, and Pcca (A138T) hypomorphic mice have enlarged hearts relative to wild-type mice (Guenzel et al., Mol. Ther., 1316-1323, 2013, herein incorporated by reference in its entirety; see, also, Example 33, FIG. 22C). Heart weight is assessed in Pcca$^{-/-}$ (A138T) hypomorphic mice (compared to age- and gender-matched wild-type mice) to determine if these hypomorphic mice have cardiomyopathy. If increased heart weight (normalized to body weight) and cardiac hypertrophy is detected, then Pcca$^{-/-}$ (A138T) hypomorphic mice will be administered multiple doses (e.g., at 0.5 mg/kg or 1 mg/kg) of 1-methyl-pseudouridine modified PCCA and PCCB mRNAs encoding human PCCA and human PCCB, or mRNA encoding luciferase as a control, over a period of time, as described in Example 31, to determine if cardiomyopathy can be improved by administering PCCA and PCCB mRNAs.

Indeed, FIG. 22C of Example 33 shows that the hearts of Pcca$^{-/-}$ (A138T) hypomorphic mice are enlarged relative to wild-type mice, and repeat injection of mRNAs encoding PCCA and PCCB over about 165 days can decrease heart size in these mice.

Example 37: Assessing Liver Histology and Mitochondrial Function in Pcca$^{-/-}$ (A138T) Hypomorphic Mice Liver histology is determined in Pcca$^{-/-}$ (A138T) hypomorphic mice (compared to age-matched wild-type mice) by hematoxylin and eosin (H&E) staining. If liver pathology is detected, then Pcca$^{-/-}$ (A138T) hypomorphic mice will be administered multiple doses of 1-methyl-pseudouridine modified PCCA and PCCB mRNAs encoding human PCCA and human PCCB, or mRNA encoding luciferase as a control, over a period of time to determine if liver pathology can be improved by administering PCCA and PCCB mRNAs. It is expected that the livers of Pcca$^{-/-}$ (A138T) hypomorphic mice will not be significantly different than the livers of wild-type mice because ALT/AST levels were observed to not be significantly different in these mice (data not shown).

Mitochondrial dysfunction has also been reported in Pcca$^{-/-}$ (A138T) hypomorphic mice (Gallego-Villar et al., Free Radical Biology and Medicine, 96:1-12, 2016). Liver mitochondrial function is assessed in Pcca$^{-/-}$ (A138T) hypomorphic mice and compared to liver mitochondrial function in wild-type mice by XF$^e$ 96 Extracellular Flux Analyzer (Seahorse Bioscience). Pcca$^{-/-}$ (A138T) hypomorphic mice are then administered multiple doses of 1-methyl-pseudouridine modified PCCA and PCCB mRNAs encoding human PCCA and human PCCB, or mRNA encoding luciferase as a control, over a period of time, as described in Example 31, to determine if mitochondrial function can be improved by administering PCCA and PCCB mRNAs.

Figure 24A:
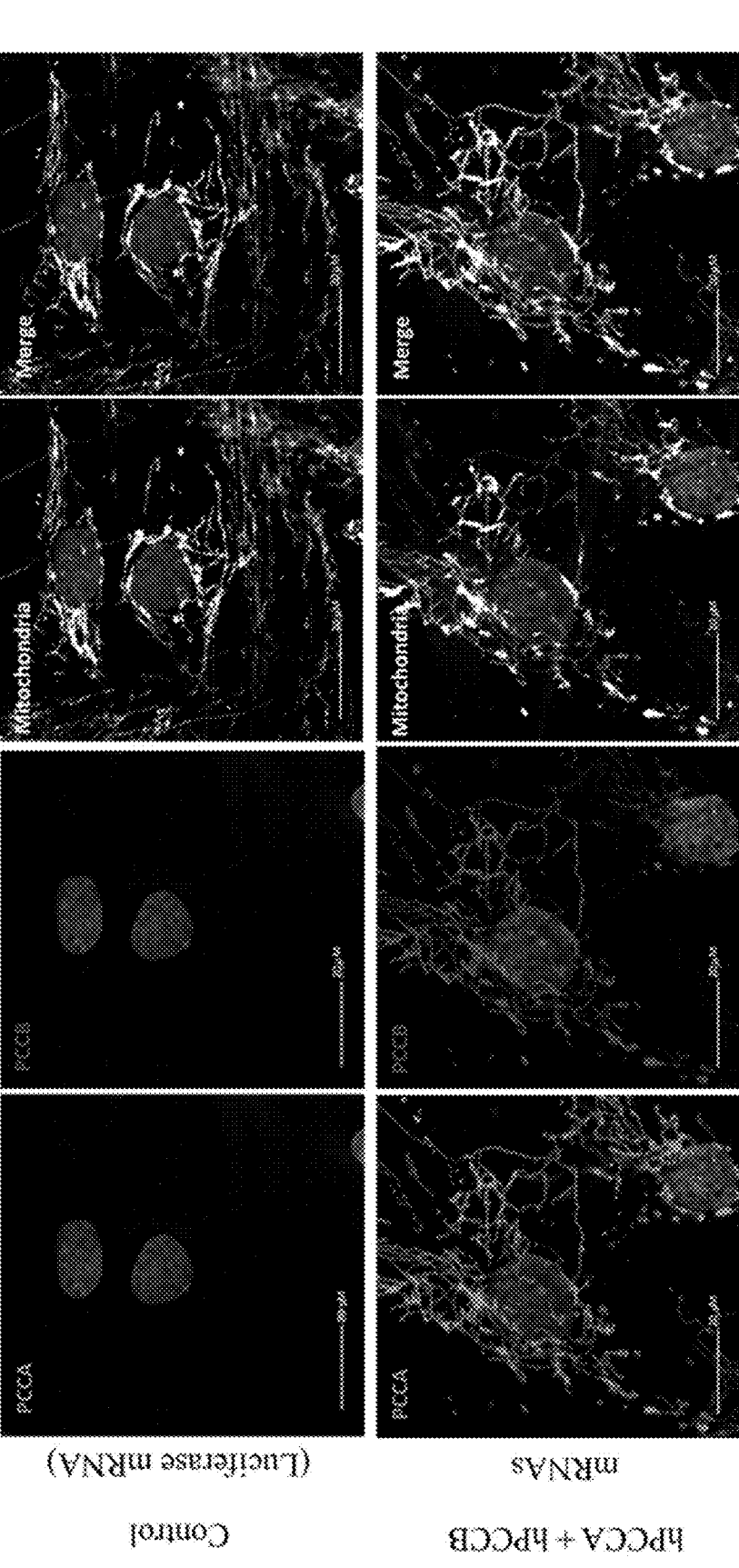
FIG. 24A shows immunofluorescence images showing the subcellular co-localization of human PCCA and human PCCB in mitochondria in GM371 PCCA-deficient patient fibroblasts transfected with 1 μg of modified human PCCA and PCCB mRNAs or control luciferase mRNA at 24-hours post-transfection.
Figure 24B:
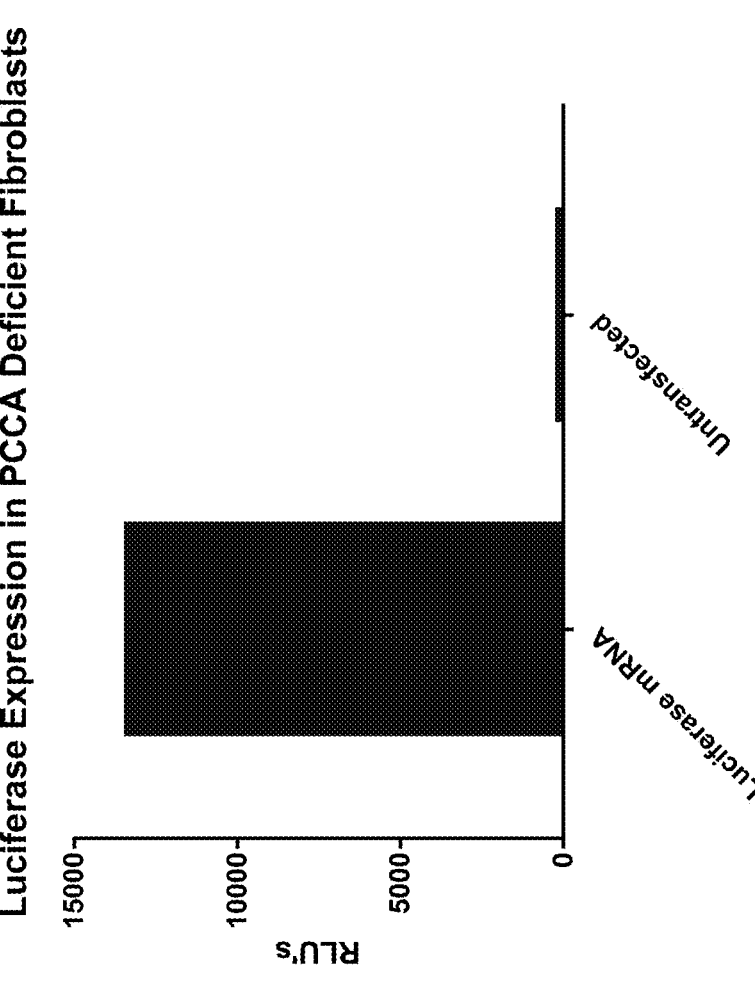
FIG. 24B is a bar graph showing marked luciferase expression in negative control cells that were transfected with mRNA encoding luciferase.

Example 38: Localization of PCCA/PCCB in PCCA-Deficient Patient Fibroblasts Transfected with mRNA Encoding Human PCCA/PCCB The subcellular co-localization of PCCA and PCCB proteins was examined in GM371 PCCA-deficient patient fibroblasts (9,000 cells/well on a 96-well plate) 24 hours after transfection with a total of 25 ng of 1-methyl-pseudouridine modified mRNAs encoding human PCCA (PCCA_18; SEQ ID NO: 35) and PCCB (PCCB_18; SEQ ID NO: 46), or a luciferase control. Commercial anti-PCCA monoclonal antibody (Santa Cruz #sc-393527) and anti-PCCB polyclonal antibody (Novus #NBP1-85886) were used to detect mRNA-expressed PCCA and PCCB using immunofluorescence microscopy. Mitotracker Red was used to confirm the identity of mitochondria and DAPI was used to stain nuclei. Image analysis was performed on a Zeiss ELYRA imaging system. As shown in FIG. 24A, PCCA and PCCB translated from the administered mRNAs co-localized with mitochondria in PCCA-deficient patient fibroblasts, showing that the mRNA-encoded proteins localized to the proper subcellular portions of the cells. These results also suggested that mRNA-expressed PCCA and PCCB form complexes in cells. There was no PAAC or PCCB staining in negative control cells that were transfected with mRNA encoding luciferase. FIG. 24B shows that there was marked luciferase expression in PCCA-deficient patient fibroblasts transfected with the luciferase mRNA.

Example 39: Pharmacology Study Using Different Lipid Nanoparticles

A one-month pharmacology study was conducted to evaluate the effects of formulating human PCCA (SE_P-CCA_018; SEQ ID NO:203) and PCCB mRNAs (SE_P-CCB_018; SEQ ID NO:204) in two different lipid nanoparticles (LNPs). The mRNAs were formulated at a molar ratio of 1:1 in either Compound II/PEG-DMG or Compound II/Compound I, and injected intravenously into Pcca (A138T) mice (n=6/group) in 2 0.5 mg/kg doses at day 0 and day 28. Control mice were injected with tris-sucrose buffer at day 0 and day 28. Plasma was collected prior to injections and on days 2, 8, 14, 21 and 28 days after the first IV dose, and 2 days after the second IV dose. Plasma 2-MC, C3/C2 camitine ratio and 3-HP concentrations were quantified by LC-MS/MS at each time point. Hepatic PCC activity was measured at sacrifice 2 days after the second dose. Data shown as mean±SD. The LLOQ was 0.5 μM for plasma 2-MC, C3 and C2 carnitines. The LLOQ for 3-HP was 25 or 50 μM for samples with no dilution or with 1:2 dilution. For 3-HP, values below the LLOQ were reported as 25 or 50 μM (i.e. the LLOQ) for samples with no dilution or with 1:2 dilution, respectively. Wild-type biomarker levels were below the LLOQ for plasma 2MC and 3HP, and 0.04±0.005 for plasma C3/C2 carnitine ratio based on n=6 wild-type mice.

Figures 25A, 25B:
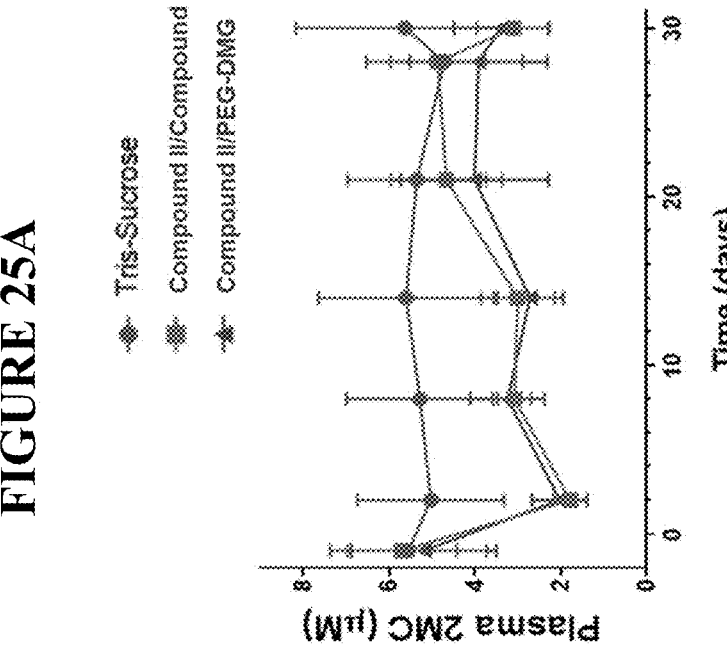
FIG. 25A is a graph showing plasma 2-MC levels measured over the course of 30 days in Pcca$^{-/-}$ (A138T) mice injected with two doses of modified human PCCA and PCCB mRNAs formulated in either Compound II/Compound I LNPs or Compound II/PEG-DMG LNPs, or tris-sucrose buffer control, at day 0 and day 28.
FIG. 25B is a graph showing plasma C3/C2 levels measured over the course of 30 days in Pcca$^{-/-}$ (A138T) mice injected with two doses of modified human PCCA and PCCB mRNAs formulated in either Compound II/Compound I LNPs or Compound II/PEG-DMG LNPs, or tris-sucrose buffer control, at day 0 and day 28.
Figures 25C, 25D:
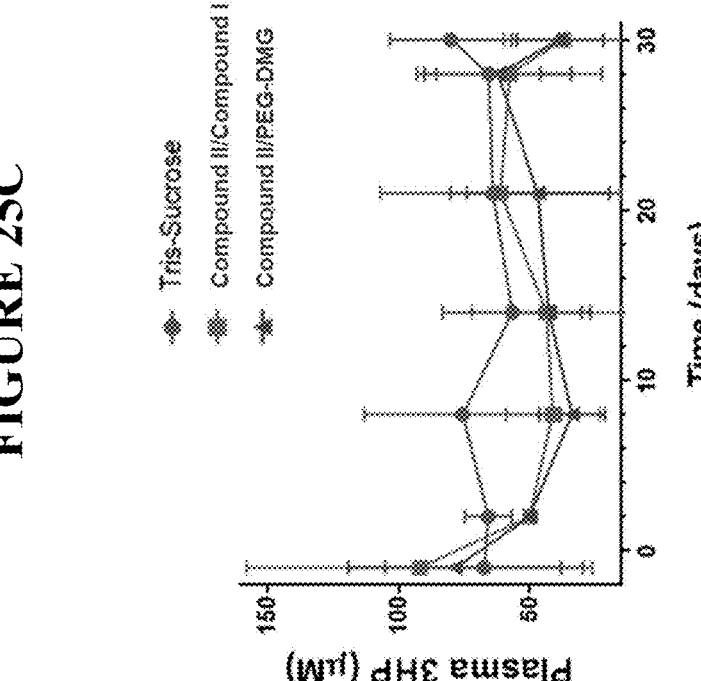
FIG. 25C is a graph showing plasma 3-HP levels measured over the course of 30 days in Pcca$^{-/-}$ (A138T) mice injected with two doses of modified human PCCA and PCCB mRNAs formulated in either Compound II/Compound I LNPs or Compound II/PEG-DMG LNPs, or tris-sucrose buffer control, at day 0 and day 28.
FIG. 25D is a bar graph showing PCC activity levels at day 30, measured in Pcca$^{-/-}$ (A138T) mice injected with two doses of modified human PCCA and PCCB mRNAs formulated in either Compound II/Compound I LNPs or Compound II/PEG-DMG LNPs, or tris-sucrose buffer control, at day 0 and day 28. PCC activity levels in wild-type mice 30 days after injection with tris-sucrose buffer control is also shown.

FIGS. 25A-C show that pharmacodynamics (PD) responses, defined by reductions in primary disease biomarkers (2-MC, C3/C2, 3-HP), were similar in Pcca$^{-/-}$ (A138T) mice that were administered human PCCA and PCCB mRNAs formulated in both LNPs (Compound II/PEG-DMG and Compound II/Compound I). The area under the effect curve (AUE) was slightly lower for the Compound II/Compound I formulation compared to the Compound II/PEG-DMG formulation. In contrast, consistent with previous experiments, no metabolic response was observed for mice administered buffer solution (tris-sucrose). Consistent with the lower AUE observed in the Compound II/Compound I LNP group, hepatic PCC activity was slightly lower in mice that received mRNAs formulated in Compound II/Compound I compared to PCC activity in mice that received PCCA and PCCB mRNAs formulated in Compound II/PEG-DMG (FIG. 25D). The duration of biochemical response across all biomarkers was approximately 4 weeks. These data demonstrate that PCCA and PCCB mRNAs formulated in either Compound II/PEG-DMG or Compound II/Compound I resulted in similar pharmacology results in Pcca$^{-/-}$ (A138T) mice.

It is to be appreciated that the Detailed Description section, and not the Summary and Abstract sections, is intended to be used to interpret the claims. The Summary and Abstract sections can set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

All publications, patent applications, patents, and other references mentioned herein are incorporated by reference in their entirety. In case of conflict, the present specification, including definitions, will control.

---

SEQUENCE LISTING

```
Sequence total quantity: 238
SEQ ID NO: 1              moltype = AA  length = 728
FEATURE                  Location/Qualifiers
source                   1..728
                         mol_type = protein
                         organism = Homo sapiens
SEQUENCE: 1
MAGFWVGTAP LVAAGRRGRW PPQQLMLSAA LRTLKHVLYY SRQCLMVSRN LGSVGYDPNE   60
KTFDKILVAN RGEIACRVIR TCKKMGIKTV AIHSDVDASS VHVKMADEAV CVGPAPTSKS  120
YLNMDAIMEA IKKTRAQAVH PGYGFLSENK EFARCLAAED VVFIGPDTHA IQAMGDKIES  180
KLLAKKAEVN TIPGFDGVVK DAEEAVRIAR EIGYPVMIKA SAGGGGKGMR IAWDDEETRD  240
GFRLSSQEAA SSFGDDRLLI EKFIDNPRHI EIQVLGDKHG NALWLNEREC SIQRRNQKVV  300
```

-continued

```
EEAPSIFLDA ETRRAMGEQA VALARAVKYS SAGTVEFLVD SKKNFYFLEM NTRLQVEHPV    360
TECITGLDLV QEMIRVAKGY PLRHKQADIR INGWAVECRV YAEDPYKSFG LPSIGRLSQY    420
QEPLHLPGVR VDSGIQPGSD ISIYYDPMIS KLITYGSDRT EALKRMADAL DNYVIRGVTH    480
NIALLREVII NSRFVKGDIS TKFLSDVYPD GFKGHMLTKS EKNQLLAIAS SLFVAFQLRA    540
QHFQENSRMP VIKPDIANWE LSVKLHDKVH TVVASNNGSV FSVEVDGSKL NVTSTWNLAS    600
PLLSVSVDGT QRTVQCLSRE AGGNMSIQFL GTVYKVNILT RLAAELNKFM LEKVTEDTSS    660
VLRSPMPGVV VAVSVKPGDA VAEGQEICVI EAMKMQNSMT AGKTGTVKSV HCQAGDTVGE    720
GDLLVELE                                                            728

SEQ ID NO: 2              moltype = RNA   length = 2184
FEATURE                   Location/Qualifiers
source                    1..2184
                          mol_type = other RNA
                          organism = synthetic construct
SEQUENCE: 2
atggccggat tctgggtcgg cacagcccct cttgtggccg cagggaggcg cggccgctgg    60
ccaccacagc agctgatgct gtctgccgcc ctgcggaccc tgaagcacgt gctgtactat    120
agcagacagt gtctgatggt gtccagaaac ctcggaacgc tgggctacga ccccaacgag    180
aagaccttcg acaagatcct ggtcgccaac cgcggcgaga tcgcttgccg ggtgatcagg    240
acctgtaaga agatgggcat caagaccgtg gccatccaca gcgacgtaga cgccagcagc    300
gtgcacgtca agatggccga cgaagcggtg tgcgtggggc ccgcccctac atccaagtcc    360
tatcttaaca tggacgccat catggaggcc atcaagaaga gagcccca agccgttcat    420
ccggggtacg gatttctgtc cgagaacaaa gagttcgcta ggtgcctcgc cgccgaaagc    480
gttgtcttca ttggtccaga cacccacgcc atccaggcta tgggcgataa gatcgagagc    540
aagctgctgg ctaagaaggc agaggtgaac accatccccg gattcgacgg agtggtcaaa    600
gacgcggagg aggccgtgag gatcgcgaga gagatcggat acccggtgat gatcaaggcc    660
tcagcaggcg gcggcggaaa gggaatgaga attgcctggg acgacgagga aacccgcgac    720
ggcttccggc tcagctccca ggaagcagct tctagctttg gcgacgatcg gctgctgatt    780
gagaaattca tcgataaccc cagacacata gagatccagg tgctgggtga caagcacggc    840
aacgccctgt ggctgaacga gagagagtgc tccattcaga ggaggaacca gaaggtggtt    900
gaggaggcgc ctagcatctt cctggacgct gaaacaagga gagccatggg tgagcaggcc    960
gtggccctgg ctcgcgccgt taagtatagc agcgccggca ccgtcgagtt cctggtggac    1020
tccaagaaga acttctattt cctggagatg aacacccgcc tgcaggtgga gcaccccgtc    1080
actgagtgta ttaccggcct cgacctggtc caggagatga tcagagtcgc caaggggtat    1140
cccctgcggc acaagcaggc agacatccgc atcaacggct gggccgtgga gtgcagagtg    1200
tacgccgagg acccctacaa gagcttcggc ctgccaagca tcggcagact gtctcagtac    1260
caagaacccc tgcacctgcc cggcgtgaga gtagacagcg gcattcagcc tggaagcgac    1320
attagcatct actacgaccc tatgatcagc aagctcatca cctacggttc tgaccggacc    1380
gaggccctga aacggatggc tgacgccctg gacaactacg tgatccgggg cgtgactcac    1440
aacatcgccc tcctgaggga agtcatcatc aacagccgat tcgtgaaggg agacatctcc    1500
accaagttcc tgagcgacgt gtaccctgac ggcttcaaag gccacatgct gaccaagagc    1560
gagaagaacc agctcctggc catcgccagt agcctgttcg tggccttcca gctgagggcc    1620
cagcactttc aggagaacag caggatgcca gtgattaagc ctgacatcgc caactgggag    1680
ctgtcagtca agctgcacga taaggtgcac acagtggtgg ccagcaataa cggctccgtg    1740
ttcagcgtcg aggtggacgg ctccaaactg aacgtcacca gcacctggaa tctgcctca    1800
cccttactga gcgtgtctgt ggacggcacc cagagaaccg tgcagtgttt gtctaggag    1860
gcaggcggca acatgtccat ccagtttctg ggaacagtgt acaaagtgaa tatcctgacc    1920
agactggccg ctgagctgaa caagttcatg cttgagaagg tgaccgagga tactagctcc    1980
gttctgagat cccctatgcc cggtgtggtc gtggcagtga gcgtgaagcc tggtgacgcg    2040
gtggcagagg tcaggagat ctgtgtcatt gaggctatga gatgcagaa tagcatgaca    2100
gccggtaaga ccgggacggt taaatccgtt cactgccagg ctggcgacac cgtgggcgag    2160
ggcgatctgt tagtggagct tgag                                         2184

SEQ ID NO: 3              moltype = RNA   length = 47
FEATURE                   Location/Qualifiers
source                    1..47
                          mol_type = other RNA
                          organism = synthetic construct
SEQUENCE: 3
gggaaataag agagaaaaga agagtaagaa gaaatataag agccacc                47

SEQ ID NO: 4              moltype = RNA   length = 142
FEATURE                   Location/Qualifiers
source                    1..142
                          mol_type = other RNA
                          organism = synthetic construct
SEQUENCE: 4
tgataatagg ctggagcctc ggtggcctag cttcttgccc cttgggcctc cccccagccc    60
ctcctcccct tcctgcaccc gtaccccctc cataaagtag gaaacactac agtggtcttt    120
gaataaagtc tgagtgggcg gc                                            142

SEQ ID NO: 5              moltype = RNA   length = 2184
FEATURE                   Location/Qualifiers
source                    1..2184
                          mol_type = other RNA
                          organism = synthetic construct
SEQUENCE: 5
atggcgggct tttgggtggg caccgcccca ctggtcgctg ccggcaggag aggacggtgg    60
ccaccccagc agctcatgct gagcgccgca ctcagaaccc tgaagcacgt gctgtactac    120
```

```
tcgcgacagt gccttatggt gtctaggaac ctgggctctg tcggctacga tccgaacgag  180
aagaccttcg acaagatcct ggtcgccaac aggggcgaaa tcgcctgtag agtcataagg  240
acctgtaaga agatgggcat caagaccgtg gctatccaca gcgacgtgga cgctagctcc  300
gtacacgtga agatggccga cgaggcagtg tgcgtgggtc cggctcccac ctccaagtcc  360
tacctgaaca tggacgccat catggaagcc atcaagaaga ctagagccca ggccgtgcac  420
ccaggctacg ggtttctctc cgagaataaa gagttcgcca ggtgcctggc tgccgaggac  480
gtggtgttta tcggacccga tactcacgcc atccaggcca tgggcgacaa gatagagtct  540
aagctgttgg ccaagaaagc tgaggtgaac accatccccg gcttcgacgg tgtggttaag  600
gacgccgagg aagctgtgcg catcgccagg gaaatcggct accccgtgat gatcaaggca  660
agtgcaggag gaggcggcaa agggatgaga atcgcctggg acgacgaaga aactagagac  720
ggtttccggc tgtcttccca ggaggctgca tcatcttttg gagacgatcg gttgctgatt  780
gagaagttta ttgacaaccc gcggcacatc gagatccagg tgctcggtga caagcacggc  840
aacgccctct ggctcaacga aagagagtgc agcattcagc gccggaacca gaaagtggtg  900
gaggaggctc ccagtatttt cctggacgcc gaaacccgga gagccatggg agagcaggcc  960
gtggctctcg ctagggcggt gaagtacagc tccgccggca cagtcgagtt cctggtggac  1020
tccaagaaga acttctactt cctggagatg aacacacagac tgcaggtgga gcatcccgtt  1080
accgagtgta taaccggcct ggatctggtc caggagatga tcagagtcgc caagggatat  1140
cccctaggc ataaacaggc cgacatcagg atcaacgcct gggccgtcga gtgccgggtg  1200
tacgctgagg accccttataa gagcttcggc ttaccatcca ttggcagact gtcccagtac  1260
caggaacctc tgcacttgcc cggagtgaga gtcgacagcg gcatccagcc cggcagcgac  1320
atctccatct actacgaccc catgatatca aagctgatca cctacggctc ggatagaaca  1380
gaggctctga agaggatggc tgacgccctg gacaactacg tgatccggg tgtgacacac  1440
aacattgccc tgctgaggga ggtgatcatc aatagccggt ttgtgaaggg tgatatttcc  1500
accaagttcc tgtctgacgt gtatccggac ggattcaagg gccacatgct gacaaagtcc  1560
gagaagaatc agctgctggc catagcttct tcactgttcg tggcctttca gctgagagct  1620
cagcacttcc aggagaactc aagaatgccc gtgatcaagc ctgatatcgc caattgggag  1680
ctgagcgtga agctgcacga caaggtacac acagtggtgg ccagcaacaa cggcagcgtg  1740
ttttccgtgg aggtagacgg aagcaaactg aacgtgacat ctacctggaa tctggcctct  1800
cctctgctga gtgttagcgt cgacggcacg cagagaactg tgcagtgcct gagccgggag  1860
gcgggcggaa acatgtcaat ccagtttctc ggcactgtct acaaggtcaa catcctgacc  1920
agactggctg ctgagctgaa taaattcatg ctcgagaagg tgaccgagga cacaagctcg  1980
gtgctcagaa gcccaatgcc cggcgtggtg gtcgccgtca gcgtcaagcc cggcgacgct  2040
gtggccgaag gccaggaaat ctgcgtcatc gaggcgatga agatgcagaa ttcaatgact  2100
gccgggaaga ccggcaccgt caagagcgtg cattgccagg caggggacac cgtgggcgaa  2160
ggggaccttc tggtggagct cgag                                          2184

SEQ ID NO: 6              moltype = RNA  length = 2184
FEATURE                  Location/Qualifiers
source                   1..2184
                         mol_type = other RNA
                         organism = synthetic construct SEQUENCE: 6
atggccggct tctgggtggg caccgcaccc ctcgtggccg ccggcagaag aggcaggtgg  60
cctccccagc agctgatgct gagcgccgcc ctgcggaccc tgaagcacgt gctgtactac  120
agccggcagt gcctgatggt gagccggaac ctgggcagcg tgggctacga ccccaacgag  180
aagaccttcg acaagatttt ggtggcaaac cggggcgaga tcgcctgccg ggtgatccgg  240
acctgcaaga agatgggcat caagaccgtg gccatccaca gcgacgtgga cgccagcagc  300
gtgcacgtga agatggccga cgaggccgtg tgcgtcggcc ccgccccctac cagcaagagc  360
tacctgaaca tggacgcgat catggaggcc atcaagaaga cccggggccca ggccgtgcac  420
cccggctacg gcttcctgag cgagaacaag gagttcgccc ggtgcctggc cgcagaggac  480
gtggtgttca tcggccccga cacccacgcc atccaggcca tgggcgacaa gatcgagagc  540
aagctgctgg ccaagaaggc cgaggtgaac accatccccg gcttcgacgg cgtggtgaag  600
gacgccgagg aagctgtgcg gatcgcccgg gagatcggct accccgtgat gatcaaggcc  660
agcgccggag gcgaggcaa gggcatgaga atcgcttggg acgacgagga caagagac  720
ggctttcggc tgagcagcca ggaggcagcg agcagcttcg gcgacgaccg gctgctgatc  780
gagaagttca tcgacaaccc tcggcacatc gagatccagg tgctgggaga caagcacggc  840
aacgccctgt ggctgaacga gcgggagtgc agcatccagc ggcggaacca gaaggtggtg  900
gaggaggccc ctagcatctt cctggacgct gaaaccagga gagccatggg agagcaggcc  960
gttgccctgg cccgggccgt gaagtactct agcgctggca ccgtggagtt cctggttgac  1020
tctaagaaga acttctattt tctggagatg aacacccggc tgcaggtgga gcaccccgtc  1080
accgagtgca tcaccggcct ggacctggtc caggagatga tccgcgtggc taagggctac  1140
cctctgcggc acaagcaggc tgacatccgg atcaacggct gggccgtaga gtgccgtgtc  1200
tacgccgagg accccctacaa gtccttcggc ctgccatcca tcggcaggct gtcccagtac  1260
caggagcacc tgcacctgcc cggcgtgcga gtggataacg gcattcagcc cggcagcgac  1320
atcagcatct actacgaccc tatgatctcc aagctaatca cctacggcag cgatcggacc  1380
gaggccctga gagaatggc tgacgccctg gacaactacg tgatcagagg cgtgacccac  1440
aacatcgccc tgctgcggga ggtgatcatc aacagccggt cgtgaaggg cgatatcagc  1500
accaagtttc tgtccgacgt ttaccccgac ggcttcaagg gccacatgct gaccaagagc  1560
gagaagaacc agctgctcgc catcgcaagc tccctgttcg tggccttcca gctgcgagca  1620
cagcacttcc aggagaatag tagaatgccc gtgatcaagc ccgacatcgc caactgggag  1680
ctgagcgtga agctgcacga caaggtgcac accgttgtgg ctagcaacaa cggttctgtg  1740
ttcagcgtga aggtggacgg tagcaaactg aacgtgacca gcacctggaa cctgcctca  1800
ccactgctca gcgtgagcgt ggacggaacc agcggaccg tgcagtgcct cagccgggaa  1860
gccggcggaa acatgagcat tcagtttctc ggcactgtgt acaaggtgaa tatcctgacc  1920
aggctggccg ctgagctgaa caagttcatg ctggagaagg tgacagagga cactagcagc  1980
gttctgcgga gccccatgcc aggggtggtg gtcgccgtta gcgtcaagcc tggcgacgct  2040
gtggccgagg ccaggagat ctgcgtgatc gaggccatga agatgcagaa cagcatgacc  2100
gccggcaaga ctggcacagt gaagtcagtg cactgccagg ccggcgacac cgtgggcgag  2160
ggcgacctgc tggtggagct ggag                                          2184
```

```
SEQ ID NO: 7            moltype = RNA  length = 2184
FEATURE                 Location/Qualifiers
source                  1..2184
                        mol_type = other RNA
                        organism = synthetic construct
SEQUENCE: 7
atggccggct tctgggtggg caccgcaccc ctggtggctg ctgggagacg gggacggtgg   60
cctcctcagc agctgatgct gagcgccgcc ctgcggaccc tgaagcacgt gctgtactac  120
agccggcagt gcctgatggt gagccggaac ctgggcagcg tgggctacga ccccaacgag  180
aagaccttcg acaagatcct ggtcgccaac cggggcgaga tcgcctgccg ggtgatccgg  240
acctgcaaga agatggggcat caagaccgtg gccatccaca gcgacgtgga cgccagcagc  300
gtgcacgtga agatggccga cgaggccgtg tgcgtgggcc ctgcgcctac cagcaagagc  360
tacctgaaca tggacgctat catggaggcc atcaagaaga cccgggccca ggccgtgcac  420
cccggctacg gcttcctgag cgagaacaag gagttcgccc ggtgcctggc agcagaggac  480
gtggtgttca tcggccccga cacccacgcc atccaggcca tgggagacaa gattgagagc  540
aagctgctgg ccaagaaggc cgaggtgaac accatccccg gcttcgacgg cgtggtgaag  600
gacgccgaag aggccgtccg gatcgcccgg gagatcggct acccgtgat gatcaaggcc  660
tccgccggtg gaggcggcaa gggcatgagg atcgcttggg acgacgagga gactagagac  720
ggctttcggc tgagcagcca ggaggcagcc agctcattcg gcgacgaccg gctgctgatc  780
gagaagttca tcgacaatcc acggcacatc gagatccagg tgctgggcga taaacacggc  840
aacgccctgt ggctgaacga gcgggagtgc agcatccagc ggcggaacca gaaggtggtg  900
gaggaggctc ctagcatctt ccttgacgcc gagacacgca gagctatggg cgagcaggct  960
gtggccctgg cccgggccgt gaagtactcc agtgctggca ccgtggagtt cctcgtggac  1020
agcaagaaga acttctactt cctcgagatg aacaccccgg tgcaggtgga gcaccccgtc  1080
accgagtgca tcaccggcct ggacctggtg caggagatga tccgtgtggc taagggctac  1140
cctctgcggc acaaacaggc cgacatccgg atcaacggct gggccgtcga gtgcagggtg  1200
tacgccgagg acccctacaa gagcttcggg ctgcctagca ttggcaggct cagccagtac  1260
caggagcccc tgcacctgcc cggcgtgagg gtcgactctg gcatacagcc cggcagcgac  1320
atcagcatct attacgatcc catgatcagc aaactgatca cctacggtag gaccgggacc  1380
gaggctctga agagaatggc cgacgccctg gacaactacg tgatacgggg cgtgacccac  1440
aacatcgccc tgctgcggga ggtgatcatc aacagccggt tcgtgaaggg cgatatctct  1500
accaagttcc tgtccgacgt gtaccccgac gggtttaagg gccacatgct gaccaagagt  1560
gagaagaaacc aactgcttgc catcgaagc agcctgttcg tggccttcca gctgcgagcc  1620
cagcacttcc aggagaactc ccggatgccc gtgatcaagc ccgacatcgc caactgggag  1680
ctgagcgtga agctgcacga caaggtgcac accgtggttg ccagcaacaa cggctcagtg  1740
ttcagcgtgg aggtggacgg ctctaagctc aacgtgacca gcacctggaa tctgccagc  1800
ccgctgctgt ctgtcagcgt cgacggcacc cagcggaccg tgcagtgtct gagccgggag  1860
gccggcggta acatgagcat tcagttcctg ggcactgtgt acaaagtgaa catcctgacc  1920
cgcctggctg cagagctgaa caagttcatg ctggagaagg tgaccgaaga cacatcaagc  1980
gtgctgcgga gccccatgcc tggcgtcgtg gtagccgtgt ccgtgaagcc cggcgacgcg  2040
gttgccgagg gccaggagat ctgcgtgatc gaggccatga agatgcagaa cagcatgacc  2100
gccggcaaga cgggaaccgt taagtccgtc cactgccagg ctggcgatac tgtgggcgag  2160
ggcgacctgc tggtggagct ggag                                         2184

SEQ ID NO: 8            moltype = RNA  length = 2184
FEATURE                 Location/Qualifiers
source                  1..2184
                        mol_type = other RNA
                        organism = synthetic construct
SEQUENCE: 8
atggccggct tctgggtggg caccgcccca ctggtggctg cgggcaggag gggcaggtgg   60
cctcctcagc agctgatgct gagcgccgcc ctccgcaccc tcaagcacgt cctctactac  120
tcccgccagt gcctcatggt gtcccgcaac ctcggctccg tcggctacga ccccaacgag  180
aagaccttcg acaagatcct cgtcgccaac cgcggcgaga tcgcctgccg cgtcatccgc  240
acctgcaaga agatgggcat caagaccgtc gccatccact ccgacgtcga cgcctcctcc  300
gtccacgtca gatggccga cgaggccgtc tgcgttggac ccgcccctac ctccaagtcc  360
tacctcaaca tggacgccat catggaggcc atcaagaaga cccgcgccca ggccgtccac  420
cccggctacg gcttcctctc cgagaacaag gagttcgcca gatgcctggc tgccgaggac  480
gtcgtcttca tcggccctga cacccacgct atccaggcca tgggcgacaa gatagagtcc  540
aagctcctcg ccaagaaggc cgaggtcaac accatccccg gcttcgacgg cgtcgtcaag  600
gacgcggaag aggccgttcg catcgcccgg gaaatcggct accccgtcat gatcaaggcc  660
tccgccggtg gaggcggcaa gggcatgagg attgcctggg acgacgagga aacgagagac  720
ggtttccgcc tctcctccca ggaagccgca agctcattcg gcgacgatag actgctgatc  780
gagaagttca tcgacaatcc tcgccacatc gagatccagg tcctcggcga caaacacggc  840
aacgccctct ggctcaacga gcgcgagtgc tccatccagc gccgcaacca gaaggtcgtc  900
gaggaggcac cctccatctt cctcgacgcc gaaaccaggc gcgccatggg tgagcaggcc  960
gtggccctgg cccgagccgt caagtacagc tccgctggga ccgtcgagtt tctggttgac  1020
tccaagaaga acttctactt cctgatgatg aacacccgc tccaggtcga gcatcctgtc  1080
accgagtgca tcaccggcct cgacctcgtc caggagatga tccgagtggc caagggatac  1140
ccgctccgcc acaagcaggc tgacatccgg atcaacggct gggcggttga gtgtagggtg  1200
tacgctgaag acccctacaa gtctttcggc ctgcccagca tcggcagact gtcccagtac  1260
caggagcccc tccacctccc cggcgtgagg gtggactctg gcatccagcc cggctccgac  1320
atctccatct attacgatcc tatgatctca aagctgatca cctacggttc cgatcgcacc  1380
gaggctctga agcgcatggc tgacgccctc gacaactacg taatcagagg cgtcacccac  1440
aacatcgccc tcctgagaga ggtcatcatc aactcccgct tcgtgaaggg tgatatctct  1500
accaagtttc tgagcgacgt gtaccctgac gggttcaagg gccacatgct caccaagtcc  1560
gagaagaacc agctgctggc catagccagc agcctcttcg tcgccttcca gctgagagcc  1620
cagcacttcc aagagaattc tcgtatgccc gtcatcaagc ccgacatcgc caactgggag  1680
```

```
ctctccgtca agctccacga caaggtccac accgtggttg catccaacaa cggcagcgtg  1740
ttctccgtcg aggtcgacgg aagcaagctg aacgtcacct ctacctggaa cctcgcctct  1800
cccttctgt  ctgtgagcgt ggacggcacc cagcgcaccg tgcagtgcct gtcccgcgag  1860
gctggcggca acatgtccat tcaattcctg ggcactgtgt acaaggtgaa catcctgaca  1920
cggctcgcag ccgaactcaa caagttcatg ctcgagaaga tgaccgaaga caccagctcc  1980
gtgctccgca gccctatgcc cggggtggtc gtggccgtgt ccgtcaaacc cggcgacgtg  2040
gtggcggagg gacaggagat ctgcgtcatc gaggccatga agatgcagaa ctccatgacg  2100
gcggggaaga ccgaacagt  caagagcgtg cattgccaag ccggcgatac cgtcggcgag  2160
ggcgacttgc tggtggagct cgag                                         2184
```

```
SEQ ID NO: 9              moltype = RNA  length = 2184
FEATURE                   Location/Qualifiers
source                    1..2184
                          mol_type = other RNA
                          organism = synthetic construct
SEQUENCE: 9
atggccggct tctgggtggg caccgcgccc ctggtggccg ccggccggcg gggccggtgg  60
ccaccccagc agctgatgct gagcgccgcc ctgcggaccc tgaagcacgt gctgtactac  120
agccggcagt gcctgatggt gagccggaac ctgggcagcg tgggctacga ccccaacgag  180
aagaccttcg acaagatcct ggtggccaac cggggcgaga tcgcctgccg ggtgatccgg  240
acctgcaaga agatgggcat caagaccgtg gccatccaca gcgacgtgga cgccagcagc  300
gtgcacgtga agatggccga cgaggccgtg tgcgtgggcc ccgcgcccac cagcaagagc  360
tacctgaaca tggacgccat catggaggcc atcaagaaga cccgggccca ggccgtgcac  420
cccggctacg gcttcctgag cgagaacaag gagttcgccc ggtgcctggc cgccgaggac  480
gtggtgttca tcgcccccga cacccacgcc atccaggcca tgggcgacaa gatcgagagc  540
aagctgtgg  ccaagaaggc cgaggtgaac accatcccgc gcttcgacgg cgtggtgaag  600
gacgccgagg aggccgtgcg gatcgcccgg gagatcggct accccgtgat gatcaaggcc  660
agcgccggcg gcggcggcaa gggcatgcgg atcgcctggg acgacgagga gacccgggac  720
ggcttccggc tgagcagcca ggaggccgcc agcagcttcg gcgacgaccg gctgctgatc  780
gagaagttca tcgacaaccc acggcacatc gagatccagg tgctgggcga caagcacgc  840
aacgccctgt ggctgaacga gcgggagtgc agcatccagc ggcggaacca gaaggtggtg  900
gaggaggcgc ccagcatctt cctggacgcc gagacccggc gggccatggg cgagcaggcc  960
gtggccctgg cccgggccgt gaagtacagc agcgccggca ccgtggagtt cctggtggac  1020
agcaagaaga acttctactt cctggagatg aacacccggc tgcaggtgga gcaccccgtg  1080
accgagtgca tcaccggcct ggacctggtg caggagatga tccgggtggc caagggctac  1140
ccgctgcggc acaagcaggc cgacatccgg atcaacggct gggccgtgga gtgccgggtg  1200
tacgccgagg accctacaa  gagcttcggc ctgccagca  tcggccggct gagccagtac  1260
caggagcccg tgcacctgcc cggcgtgcgg gtggacagcg gcatccagcc cggcagcgac  1320
atcagcatct actacgaccc catgatcagc aagctgatca cctacggcag cgacggcacc  1380
gaggccctga agcggatggc cgacgccctg gacaactacg tgatccgggg cgtgacccac  1440
aacatcgccc tgctgcggga ggtgatcatc aacagccggt tcgtgaaggg cgacatcagc  1500
accaagttcc tgagcgacgt gtaccccgac ggcttcaagg ccacatgct  gaccaagagc  1560
gagaagaacc agctgctggc catcgccagc agcctgttcg tggccttcca gctgcgggcc  1620
cagcacttcc aggagaacag ccggatgccc gtgatcaagc ccgacatcgc caactgggag  1680
ctgagcgtga agctgcacga caaggtgcac accgtggtgg ccagcaacaa cggcagcgtg  1740
ttcagcgtga aggtggacgg cagcaagctg aacgtgacca gcacctggaa cctggccagc  1800
cctctgctga gcgtgagcgt ggacggcacc cagcggaccg tgcagtgcct gagccgggag  1860
gccggcggca acatgagcat ccagttcctg ggcaccgtgt acaaggtgaa catcctgacc  1920
cggctggccg ccgagctgaa caagttcatg ctggagaagg tgaccgagga caccagcagc  1980
gtgctgcgga gccccatgcc cggcgtggtg gtggccgtga gcgtgaagcc cggcgacgcc  2040
gtggccgagg gccaggagat ctgcgtgatc gaggccatga agatgcagaa cagcatgacc  2100
gccggcaaga ccggcaccgt gaagagcgtg cactgccagg ccggcgacac cgtgggcgag  2160
ggcgacctgc tggtggagct ggag                                         2184
```

```
SEQ ID NO: 10             moltype = RNA  length = 2184
FEATURE                   Location/Qualifiers
source                    1..2184
                          mol_type = other RNA
                          organism = synthetic construct
SEQUENCE: 10
atggccggct tctgggtcgg caccgcccca ctcgtggcag ccggcagaag aggccggtgg  60
cctccccagc agctgatgct gagcgccgcc ctgagaaccc tgaagcacgt gctgtactac  120
agcagacagt gcctgatggt gagcagaaat ctgggatctg tcgggtacga ccccaacgag  180
aagaccttcg acaagatcct ggtggccaac agaggcgaga tcgcctgcag agtgatcaga  240
acctgcaaga agatgggcat caagaccgtg gccatccaca gcgacgtgga cgcgtccagc  300
gtgcacgtga agatggccga cgaggccgtg tgcgtaggcc ccgctcccac cagcaagagc  360
tacctgaaca tggacgccat catggaggcc atcaagaaga ccagagccca ggctgtgcat  420
cccggctacg gcttcctgag cgagaacaag gagttcgcca ggtgtctggc tgccgaagac  480
gtcgtgttca tcgcccccga cacccacgcc atccaggcca tgggtgataa gatcgagagc  540
aaactgctgg ccaagaaggc cgaggtgaac accatccccg cttcgacgg  cgtggtgaaa  600
gacgccgagg aggcagtgag aatcgcccga gagatcggct accccgtgat gatcaaggcc  660
agcgcaggtg cggaggcaa  gggcatgagg attgcctggg acgacgaaga gacgagggac  720
gggttccgac tgagcagcca ggaggccgcc agctccttcg gcgacgacag actgctgatc  780
gagaagttca tcgacaaccc cagacacatc gagatacagg tgctcggaga caagcacgc  840
aacgccctgt ggctgaacga gagagagtgc agcatccaga aagaaacca  gaaggtggtg  900
gaggaggccc catcaatctt cctcgacgcc gaaaccagac gggccatggg agagcaagcc  960
gtggcactgg ctagggccgt gaagtacagc tccgccggaa ccgtggagtt tctggtcgac  1020
tccaagaaga acttctactt cctggagatg aatacccgtc tgcaggtgga gcaccccgtg  1080
accgagtgca tcaccggtct ggacctggtg caggagatga tcagagtggc caagggctac  1140
```

-continued

```
cctctgagac acaagcaggc cgacatcaga atcaacggct gggccgtgga gtgcagagtg  1200
tacgccgagg acccctacaa gagcttcggc ctgcccagca tcggcagact gagccagtac  1260
caggagcccc tgcacctgcc cggcgtgaga gtggacagcg gcatccagcc cggctctgac  1320
atctccatat actacgaccc catgatcagc aagctcatca cctacggcag cgacagaacc  1380
gaggccctga agagaatggc cgacgccctg gacaactacg tgatcagagg cgtgacccac  1440
aacatcgccc tgctgagaga ggtgatcatc aacagcagat tcgtgaaggg cgacatcagc  1500
accaagttcc tgagcgacgt gtaccccgac ggcttcaagg gccacatgct gaccaagagc  1560
gagaagaacc agcttctggc aatcgcctcc agcctgttcg tggccttcca gctgagagcc  1620
cagcacttcc aggagaacag cagaatgccc gtgatcaagc ccgacatcgc caactgggag  1680
ctgagcgtga agctgcacga caaggtccat acggtggtcg ccagcaacaa cggcagcgtg  1740
ttcagcgtgg aggtggacgg cagcaagctg aacgtgacca gcacctggaa cctcgcctca  1800
 cccctcctga gcgtcagcgt cgacggcacc cagagaaccg tgcagtgtct gagcagagag  1860
gcaggcggca acatgagcat ccagttcctg ggcaccgtgt acaaggtgaa catcctgacc  1920
agactggccg ccgagctgaa caagttcatg ctggagaagg tgaccgagga caccagcagc  1980
gtgctgagaa gccccatgcc cggagtggtg gtggccgtga gcgtgaaacc gggtgacgca  2040
gtggccgagg gccaggagat ctgcgtgatc gaggccatga agatgcagaa cagcatgacg  2100
gccggaaaga ccggcaccgt gaagtccgtg cactgccaag ccggcgatac cgtgggcgag  2160
ggcgacctcc tcgtcgagct ggag                                        2184
```

SEQ ID NO: 11  moltype = RNA length = 2184
FEATURE     Location/Qualifiers
source      1..2184
          mol_type = other RNA
          organism = synthetic construct
SEQUENCE: 11

```
atggccggct tctgggtcgg cacagcccct ctggtggcag ccggcagaag aggacggtgg  60
cctccccagc aactgatgct gagcgccgcc ctgagaaccc tgaagcacgt gctgtactac  120
agcagacagt gcctgatggt gagcagaaat ctgggcagcg tggggtacga tcccaacgag  180
aagaccttcg ataagattct ggtcgcgaat agaggcgaga tcgcctgcag ggtgatcaga  240
acctgcaaga agatgggcat caagaccgtg gccatccatt cggacgtcga cgcgagcagc  300
gttcacgtga gatggccaga cgaggccgtg tgcgtgggac ccgccccgac cagcaagagc  360
tacctgaaca tggacgccat catggaggcc atcaagaaga cccgcgctca gccgtgcac   420
ccgggctacg gctttctgag cgagaacaag gaattcgcca ggtgtctcgc cgccgaggac  480
gtagtcttca tcggccctga tacgcacgcg atccaggcca tgggcgacaa gatcgagagc  540
aaactgctgg ccaagaaagc agaagtcaac accatccccg gcttcgacgg cgtggtgaag  600
gacgccgaag aggctgtccg catcgccaga gagatcggct accctgtgat gataaaggct  660
agcgctggag gtggcggaaa gggcatgaga atcgcctggg acgacgagga gactagagac  720
ggcttcagac tgtcctccca ggaggccgcc agctccttcg gagacgacag actgctgatc  780
gagaagttca tcgacaaccc cagacacatc gaaatccagt tgctcggtga caagcacgag  840
aacgccctgt ggctgaacga gagagagtgc agcatccaga gaagaaacca gaaggtggtg  900
gaggaggcgc cgagcatctt tctggacgcg gagacaagga gagcgatggg cgaacaggcc  960
gtcgccctag caagagccgt gaagtactcc agtgccggaa ccgtcgagtt tcttgtcgac  1020
agcaagaaga atttctactt cctggaatga aacaccaggc tgcaggtgga gcatcccgtg  1080
acagagtgca tcactggact ggatctggtc caggagatga tcagggtggc caagggctat  1140
ccctgagac acaagcaggc cgacatcaga atcaacggct gggccgtgga gtgcagagtg   1200
tacgccgagg acccctacaa gagcttcggc ctgcccagca tcggcagact gagccagtac  1260
caggagcccc tgcacctgcc cggcgtgaga gtggacagcg gcatccaacc ggggagcgat  1320
atcagcatct actacgaccc catgatcagc aagctgataa cctacggcag cgacagaacc  1380
gaggccctga agagaatggc cgacgccctg gacaactacg tgatcagagg cgtgacccac  1440
aacatcgccc tgctgagaga ggtgatcatc aactcgaggt cgtgaaagg cgacatcagc   1500
accaagttcc tgagcgacgt gtatcccgac ggattcaaag gtcacatgct gaccaagagc  1560
gagaagaacc agctgctggc catcgcctca tccctgttcg tggccttcca gctgagagcc  1620
cagcacttcc aggagaacag cagaatgccc gtgatcaagc ccgacatcgc caactgggag  1680
ctgagcgtga agctgcacga caaggtgcac actgtcgttg ccagcaacaa cggctccgtg  1740
ttcagcgtag aggtggacgg atctaagctg aacgtgacct ccacctggaa cctggcaagc  1800
cctctcctgt cagtgagcgt ggacggcacc cagagaaccg tgcagtgtct gtcccgcgag  1860
gccggcggaa acatgagcat ccagttcctg ggcaccgtgt acaaggtgaa catcctgacc  1920
agactggccg ccgagctgaa caagttcatg ctggagaaag tgacggagga taccagctcc  1980
gtgctgagaa gccccatgcc cggagtggtg gtggccgttt ccgtgaaacc tggtgacgcc  2040
gtggccgagg ggcaagagat ctgcgtgatc gaggccatga agatgcagaa ttccatgacc  2100
gccggaaaga ccggcaccgt caaatcagtg cactgccagg cgggcgacac agtgggtgag  2160
ggcgacctgc tggtggagct ggag                                        2184
```

SEQ ID NO: 12  moltype = RNA length = 2184
FEATURE     Location/Qualifiers
source      1..2184
          mol_type = other RNA
          organism = synthetic construct
SEQUENCE: 12

```
atggccgggt tctgggtggg gaccgcccca ctcgtggccg ccgggaggag agggaggtgg  60
ccaccgcaac aactaatgct aagcgccgcc ctacggaccc taaagcacgt actatactac  120
agcaggcagt gcctaatggt gagcaggaac ctagggagcg tggggtacga tccaaacgag  180
aagaccttcg ataagatact agtggccaat agaggggaga tcgcctgcag agtgataagg  240
acctgcaaga agatggggat caagaccgtg gccatacaca gcgacgtgga cgccagcagc  300
gtgcacgtga gatggccga cgaggccgtg tgtgtggggc agcccccaac cagcaagagc  360
tacctaaaca tggacgcgat aatggaggca atcaagaaga ccagagcgca gccgtgcac   420
cctgggtacg ggttcctatc cgagaacaag gagttcgcca ggtgcctagc cgcggaggac  480
gtggttttta tagggccaga tacgcacgcc atccaagcca tgggagataa gatcgagagc  540
aagctactag ccaagaaggc cgaggtgaac accataccag ggttcgacgg ggtggtgaag  600
```

```
gacgccgagg aggccgtgag gattgccagg gagatagggt acccagtgat gataaaggcc   660
tctgccggtg gaggagggaa ggggatgcgg atagcctggg acgacgagga gacgagggac   720
ggcttcaggc taagcagcca agaggccgcc tctagcttcg gggacgatag gctactaata   780
gagaagttca tagataaccc aaggcacata gagatacaag tactagggga taaacacggt   840
aacgccctgt ggctcaacga gagagagtgc agcatacaaa ggaggaacca gaaggtggtt   900
gaggaggcgc caagcatctt cctagacgcc gagacacgga gggcgatggg agaacaggcc   960
gtggccctag ccagggccgt taagtactca agcgcaggga ccgtggagtt cctagtggat  1020
agcaagaaga acttctactt cctcgagatg aataccaggc tacaagtgga gcacccagta  1080
accgagtgca tcacggggct cgatctagtg caagagatga taagggtggc caaggggtat  1140
ccactaaggc acaagcaagc ggatataagg ataaacgggt gggccgttga gtgcagggtg  1200
tacgccgagg atccctacaa gtccttcggg ctaccaagca tagggaggct atctcaatac  1260
caagagccac tacacctacc aggggtgagg gttgatagcg ggatccaacc agggtctgat  1320
ataagcatct actacgatcc catgatatct aagctaataa cctacgggag cgacaggacg  1380
gaggccctaa agaggatggc ggacgcccta gataactacg tgatacgcgg ggtgacccac  1440
aacattgccc tactaaggga ggtgatcata aattctaggt tcgtgaaggg agatatatca  1500
acgaagtttc taagcgacgt ttacccagac gggttcaagg ggcacatgct aaccaagagc  1560
gagaagaatc aactgctcgc catcgcctca tcactattcg tggccttcca actaagggcc  1620
caacacttcc aagagaatag ccggatgcct gtgataaagc cagatatagc caattgggaa  1680
ctaagcgtga agctccacga taaggtgcac accgtggtgg ccagcaacaa cggatctgtg  1740
ttcagcgtgg aggtggacgg tagcaagctc aacgtgacca gcacctggaa tctagccagc  1800
ccactactga gcgtcagcgt tgacgggacc caaaggaccg tgcagtgctt gagcagggag  1860
gccggaggga atatgtccat tcaattccta gggacggtct acaaggtaaa catactaacc  1920
cgactagccg ccgagctcaa caagttcatg ctagagaagg tgaccgagga tacgtctagc  1980
gtgctacgta gcccaatgcc aggagtggta gttgccgtgt cagtgaagcc aggggacgcc  2040
gtagccgagg acaagagat ctgcgtgatc gaggccatga agatgcagaa tagcatgacc  2100
gcagggaaga cggggacggt gaagtctgtt cactgccaag ccggggatac cgtaggggag  2160
ggagatctac tcgtggagct agag                                          2184
```

```
SEQ ID NO: 13          moltype = RNA  length = 2184
FEATURE                Location/Qualifiers
source                 1..2184
                       mol_type = other RNA
                       organism = synthetic construct
SEQUENCE: 13
atggccggct tctgggtggg caccgcgccc ctggtggccg ccggcagaag aggcaggtgg   60
ccgccccagc agctgatgct gagcgccgcc ctgagaaccc tgaagcacgt gctgtactac  120
agcagacagt gcctgatggt gagcagaaac ctgggcagcg tgggctacga ccccaacgag  180
aagaccttcg acaagatcct ggtggccaac agaggcgaga tcgcctgcag agtgatcaga  240
acctgcaaga agatgggcat caagaccgtg gccatccaca gcgacgtgga cgccagcagc  300
gtgcacgtga agatggccga cgaggccgtg tgcgtgggcc ccgcgcccac cagcaagagc  360
tacctgaaca tggacgccat catggaggcc atcaagaaga ccagagccca ggccgtgcac  420
cccggctacg gcttcctgag cgagaacaag gagttcgcca ggtgcctggc cgccgaggac  480
gtggtgttca tcggccccga cacccacgcc atccaggcca gatcgagagc  540
aagctgctgg ccaagaaggc cgaggtgaac accatccccg gcttcgacgg cgtggtgaag  600
gacgccgagg aggccgtgag aatcgccaga gagatcggct accccgtgat gatcaaggcc  660
agcgccggcg gcggcggcaa gggcatgaga atcgcctggg acgacgagga ccagagac  720
ggcttcagac tgagcagcca ggaggccgcc agcagcttcg gcgacgacag actgctgatc  780
gagaagttca tcgacaaccc cagacacatc gagatccagg tgctgggcga caagcacggc  840
aacgccctgt ggctgaacga gagagagtgc agcatccaga aagaaaccca gaaggtggtg  900
gaggaggcgc ccagcatctt cctggacgcc gagaccagaa gagccatggg cgagcaggcc  960
gtggccagac cgagagccgt gaagtacagc agcgccggca ccgtggagtt cctggtggac  1020
agcaagaaga acttctactt cctggagatg aacaccagac tgcaggtgga gcaccccgtg  1080
accgagtgca tcaccggcct ggacctggtg caggagatga tcagagtggc caagggctac  1140
ccactgagac acaagcaggc cgacatcaga atcaacggct gggccgtgga gtgcagagtg  1200
tacgccgagg accctacaa gagcttcggc ctgcccagca tcggcagact gagccagtac  1260
caagaaccgt tacatctacc tggtgtccga gtggacagcg gcatccagcc cggcagcgac  1320
atcagcatct actacgaccc catgatcagc aagctgatca cctacggcag cgacagaacc  1380
gaggccctga gagaatggc cgacgccctg gacaactacg tgatcagagg cgtgacccac  1440
aacatcgccc tgctgagaga ggtgatcatc aacagcagat tcgtgaaggg cgacatcagc  1500
accaagttcc tgagcgacgt gtaccccgac ggcttcaagg gccacatgct gaccaagagc  1560
gagaagaacc agctgctggc catcgccagc agcctgttcg tggccttcca gctgagagcc  1620
cagcacttcc aggagaacag cagaatgccc gtgatcaagc ccgacatcgc caactgggag  1680
ctgagcgtga agctgcacga caaggtgcac accgtggtgg ccagcaacaa cggcagcgtg  1740
ttcagcgtgg aggtggacgg cagcaagctg aacgtgacca gcacctggaa cctgagcagc  1800
ccactgctga gcgtgagcgt ggacggcacc cagagaaccg tgcagtgcct gagcagagag  1860
gccggcggca acatgagcat ccagttcctg ggcaccgtgt acaaggtgaa catcctgacc  1920
agactggccg ccgagctgaa caagttcatg ctggagaagg tgaccgagga caccagcagc  1980
gtgctgagaa gccccatgcc cggcgtggtg gtggccgtga gcgtgaagcc cggcgacgcc  2040
gtggccgagg acaaggagat ctgcgtgatc gaggccatga agatgcagaa cagcatgacc  2100
gccggcaaga ccggcaccgt gaagagcgtg cactgccagg ccggcgacac cgtgggcgag  2160
ggcgacctgc tggtggagct ggag                                          2184
```

```
SEQ ID NO: 14          moltype = RNA  length = 2184
FEATURE                Location/Qualifiers
source                 1..2184
                       mol_type = other RNA
                       organism = synthetic construct
SEQUENCE: 14
atggcaggct tctgggttgg cactgcccca ctcgtggccg ccggcagaag gggaaggtgg   60
```

-continued

```
cctccccagc agctcatgct gtccgccgct ctgcgaaccc tgaagcacgt gctgtattat   120
agcaggcagt gcctcatggt ttcccggaac ctggggagcg tgggctatga ccctaatgag   180
aagactttcg acaagatcct ggtcgctaac agaggcgaga tcgcctgcag ggtgatcaga   240
acatgcaaga agatgggcat caagaccgtc gcgatccata gcgacgtgga tgccagcagc   300
gttcacgtca agatggccga cgaggctgtg tgcgtcggcc cgcccccaac ttccaagagc   360
tatctgaaca tggacgccat aatggaggct atcaagaaga ccagagccca ggcagttcat   420
cccggctacg gattcctgag cgagaacaag gagttcgcta gatgtctggc cgccgaagac   480
gtggtttttca tcggtccaga cacccatgcc atccaagcca tgggcgataa gatcgagagc   540
aagctcctgg ccaagaaggc cgaggtgaac accatccccg gcttcgatgg cgtggtgaag   600
gacgcggagg aggcagtgcg cattgccagg gagatcggct accccgtgat gatcaaggct   660
tccgcagggg gaggcggcaa aggcatgcgg attgcctggg atgatgaaga aaccagagat   720
ggcttcagac tgtcaagcca ggaggccgcc agcagcttcg gcgacgacag actgctgatc   780
gagaagttta tagataaccc ccgacacata gaaatccagg tgctgggaga caagcacggc   840
aacgctctgt ggctgaacga gcgggaatgc agtatccaga ggagaaacca aaggtggtt   900
gaggaggccc cctcaatctt cctggatgcc gagacaagac gcgccatggg tgagcaggct   960
gtagccctcg cccgtgccgt gaagtatagc agcgccggga cagtgagtt cttggtcgac   1020
tccaagaaga atttctattt tctggagatg aacactcggc tccaagtaga gcaccccgtg   1080
actgagtgca ttacaggcct tgatctggtg caggagatga ttagggttgc caagggctac   1140
cctctgcgcc acaagcaggc cgacatcagg atcaatggct gggctgtcga gtgtagggtg   1200
tacgcagagg acccgtacaa gagcttcggc cttccctcta ttggcaggct gagccagtac   1260
caggagcctc tgcacctacc cggcgttcgc gtggacagcg gtatccaacc aggctctgat   1320
atcagcattt attacgaccc aatgatctca aagctgatca catcggcag cgacagaacc   1380
gaggccctga agcgaatggc cgacgccctg gacaactacg tgatccgggg cgtcacacat   1440
aacattgccc tgctgagaga ggtgatcatt aattctcggt tcgtcaaagg cgacatcagc   1500
actaagtttc tgagcgacgt gtaccccgac gggtttaaag gccacatgct gacaaagagc   1560
gagaagaacc agttgctggc catcgcctct agcctgttcg tagccttcca gctgcgagca   1620
cagcacttcc aggagaatag cagaatgcca gtgatcaagc ccgacatcgc taactgggag   1680
ctgagcgtga agtccatga taaggtccac acagttgtgg ccagcaacaa cggctcagtg   1740
ttcagcgtgg aggtagacgg ctccaagctg aacgtgacca gcacttggaa tctggccagc   1800
ccctgcgtga gcgtgtccgt ggacggcacc cagagaaccg tgcagtgcct gagcagggag   1860
gccgggggca acatgtccat ccagtttctg gggaccgtct ataaggttaa catcctgact   1920
agactggcg ctgagcttaa caagtttatg ttagagaaag tgaccgagga tacaagcagc   1980
gtgctgcgta gccccatgcc tggcgtggtc gtggccgtga gcgtcaagcc aggcgatgca   2040
gtggctgagg gccaggagat ttgtgtgata gaggccatga agatgcagaa ctctatgacc   2100
gccggaaaga ctggcaccgt gaagtctgtc cattgtcagg ccgagacac cgtgggggaa   2160
ggagacctgc tcgtcgagct ggag   2184
```

```
SEQ ID NO: 15       moltype = AA  length = 539
FEATURE             Location/Qualifiers
source              1..539
                    mol_type = protein
                    organism = Homo sapiens
SEQUENCE: 15
MAAALRVAAV GARLSVLASG LRAAVRSLCS QATSVNERIE NKRRTALLGG GQRRIDAQHK   60
RGKLTARERI SLLLDPGSFV ESDMFVEHRC ADFGMAADKN KFPGDSVVTG RGRINGRLVY   120
VFSQDFTVFG GSLSGAHAQK ICKIMDQAIT VGAPVIGLND SGGARIQEGV ESLAGYADIF   180
LRNVTASGVI PQISLIMGPC AGGAVYSPAL TDFTFMVKDT SYLFITGPDV VKSVTNEDVT   240
QEELGGAKTH TTMSGVAHRA FENDVDALCN LRDFFNYLPL SSQDPAPVRE CHDPSDRLVP   300
ELDTIVPLES TKAYNMVDII HSVVDEREFF EIMPNYAKNI IVGFARMNGR TVGIVGNQPK   360
VASGCLDINS SVKGARFVRF CDAFNIPLIT FVDVPGFLPG TAQEYGGIIR HGAKLLYAFA   420
EATVPKVTVI TRKAYGGAYD VMSSKHLCGD TNYAWPTAEI AVMGAKGAVE IIFKGHENVE   480
AAQAEYIEKF ANPFPAAVRG FVDDIIQPSS TRARICCDLD VLASKKVQRP WRKHANIPL   539
```

```
SEQ ID NO: 16       moltype = RNA  length = 1617
FEATURE             Location/Qualifiers
source              1..1617
                    mol_type = other RNA
                    organism = synthetic construct
SEQUENCE: 16
atggccgccg cccttagggt cgcagccgtg ggcgctagac tgtcagtgct ggccagcggc   60
ctaagagccg ccgttaggag cctgtgcagc caggctacta gcgtgaacga gagaatagag   120
aacaaacgcc gtacagctct gctaggagga ggccagagac gtatcgacgc ccagcacaag   180
cggggcaagc tgaccgcccg ggagcgcatc agcctcctgc ttgaccccgg cagctttgtt   240
gagtcggaca tgttcgtgga gcaccggtgc gctgacttcg gcatggctgc cgacaagaac   300
aagttccccg gcgactccgt ggtgacagga aggggacgga tcaacggccg gctggtgtac   360
gtgttctctc aggacttcac tgtgttcggc ggctcccttt ctggcgccca cgcccagaag   420
atctgtaaga ttatggacca ggcaatcacc gtgggagctc ccgtcatcgg cctgaacgac   480
tcaggcggcg cccgaatcca ggagggcgtg gagagcctgg ccgggtacgc agacattttc   540
ctgagaaacg tgaccgctag cggcgttatc ccacagatca gcctgatcat gggaccttgc   600
gctgaggagg cagtctacag cccagccctg actgattta ccttcatggt gaaagacaca   660
agctacctgt tcatcactgg gccggacgta gttaagagtg tgactaacga ggacgtgacc   720
caggaggagc tgggcggagc caagacccat acgactatga gcggtgtggc gcaccgcgcc   780
ttcgagaacg acgtggacgc cctgtgcaat ctgcgcgact tcttcaatta cctgccctta   840
agcagccaag atcccgcacc cgtcgggagg tgccacgatc caagcgatag gctggtgccc   900
gagctggaca ccattgtgcc tctggagtca actaaggctt acaacatggt tgacatcatc   960
cacagcgtgg tcgacgagcg cgagttcttc gagatcatgc ccaactacgc gaagaatatc   1020
atcgtgggct ttgcccgcat gaacggccgg accgtcggga tcgtcggcaa tcaacctaag   1080
gtcgccagcg gttgcctgga catcaacagc tcggtgaagg gcgccaggtt cgttagattc   1140
tgcgacgctt tcaacatccc tctgatcact ttcgtagacg ttcccggctt cctccctggg   1200
```

-continued

```
accgcacagg agtacggagg aatcattagg cacggcgcca agctgctcta cgccttcgct   1260
gaggctaccg tgcctaaggt gaccgtgatc actaggaagg cctacggtgg cgcctacgac   1320
gtcatgagca gcaagcacct gtgtggagac acaaactacg cctggcccac agctgagatt   1380
gcggttatgg gagccaaggg cgccgtggag attattttca agggcacga gaacgtggag   1440
gccgcccagg ccgagtacat cgagaagttt gccaacccct tccctgccgc cgtgagagga   1500
tttgtggacg atattatcca gccctcctcc accagagcca ggatctgctg cgacctcgac   1560
gttttggcct cgaagaaggt gcaacggccc tggcgcaaac acgcaaacat cccgctg     1617
```

SEQ ID NO: 17          moltype = RNA  length = 1617
FEATURE                Location/Qualifiers
source                 1..1617
                       mol_type = other RNA
                       organism = synthetic construct
SEQUENCE: 17

```
atggccgccg ccctgagggt ggccgcagtc ggcgcacgac tctccgtgct ggctagcggc   60
ctgagagccg ctgtgcggag cctgtgctct caggctacgt cggttaacga gcgtatagag   120
aacaagcggc gcaccgctct ccttggcggc ggccagagga gaatagacgc ccagcataag   180
cgtggaaagc tgaccgccag agagagaata tcccttctcc tggatcccgg gtctttcgtg   240
gagagcgaca tgttcgtcga acacaggtgc gccgactttg ggatggctgc tgacaagaac   300
aagttccctg gagattcagt agtgacaggt aggggcagga tcaacggcag actggtctac   360
gtgtttccc aagatttcac cgtgttcggc ggcagcctga gcggcgctca cgcacagaag   420
atctgcaaga tcatggatca ggcaattaca gtgggcgccc ctgtgatcgg cctgaacgac   480
agtggcggcg cgagaattca ggagggagtg gaatctctgg ctgggtacgc cgacattttc   540
ctgcgaaacg tcacagccag cggggttatt ccccaaattt cgctcatcat ggggccttgc   600
gccggcggtg ctgtgtacag ccctgccctc accgacttca ccttcatggt gaaagacacc   660
tcctatctgt tcattacagg acccgacgtg gtgaaatccg tgacaaacga ggacgtgacc   720
caggaggaac tcggcggcgc taagacccac acaaccatgt caggcgttgc ccacagagcg   780
ttcgagaacg acgtggacgc tctgtgcaac ctgagagact tcttcaacta cctgcctctg   840
agctcgcagg acccagctcc cgtgcgggag tgtcacgatc ccagcgatcg tctggtgcct   900
gaactggaca caatcgttcc actggagtcc accaaggcct ataatatggt ggacattatc   960
cacagcgtgg tggacgaaag ggaattcttc gagatcatgc ccaattacgc caagaatatc   1020
atcgtgggct cgccagaat gaacggccgc accgtgggca tcgttggcaa tcaacctaag   1080
gtggccagcg gctgcctcga cattaacagc agtgtgaaag cgccagatt cgtgcggttt   1140
tgcgacgcct ttaatatccc tctgatcacc ttcgtggacg tgcccgggtt tctgccgggc   1200
accgcccagg agtacggagg gatcattaga cacggtgcta agctgctgta cgccttcgtc   1260
gaggccacag tgcccaaggt taccgttatc acacgcaaag cctacggcgg agcctacgac   1320
gtgatgagca gcaaacacct ctgtggcgac accaactacg cttggcccac agccgagatt   1380
gccgtgatgg gcgccaaggg cgctgtggag atcattttca aaggccacga gaacgtggag   1440
gctgcccagg ccgagtatat cgagaagttc gcaaacccct tcccagcagc agtgcgggat   1500
ttcgtcgacg acatcatcca gccttctagc accagggcaa gaatctgctg tgaccttgac   1560
gtgctcgcca gtaagaaggt ccagaggccg tggagaaagc acgctaacat tcccctg     1617
```

SEQ ID NO: 18          moltype = RNA  length = 1617
FEATURE                Location/Qualifiers
source                 1..1617
                       mol_type = other RNA
                       organism = synthetic construct
SEQUENCE: 18

```
atggccgccg ccctgcgggt tgcagccgtg ggcgcccggc tgagcgtgtt ggcctcaggg   60
ctgagagccg ctgtgcggag cctgtgcagc caggccacca gcgtgaacga gcggatcgag   120
aacaagcggc ggactgccct gctgggcggc ggccagagga gaatcgacgc ccagcacaag   180
cggggcaagc tgaccgcccg ggagaggatt agcctgctgc tggacccgg cagcttcgtg   240
gagagcgaca tgttcgtcga gcaccggtgc gccgacttcg gcatggcagc tgacaagaac   300
aagttccccg gcgacagcgt ggtgaccggc cggggccgga tcaacggccg gctggtgtac   360
gtgttcagcc aggacttcac cgtgttcggc ggcagcctga gcggcgccca cgcccagaag   420
atctgcaaga tcatggacca ggccatcact gtcggcgcac ccgtgatcgg cctgaacgac   480
agcggcggcg cacgtatcca ggagggtgta gaatctctgg ccggctacgc cgacatcttc   540
ctgcggaacg tgaccgcctc aggggtgatt cctcagatct cgctgatcat gggcccctgc   600
gccggaggtg ctgtgtacag ccccgccctg accgacttca cattcatggt gaaggacacc   660
agctacctgt tcatcaccgg ccccgacgtg gtgaaatctg tgaccaacga ggacgtgacc   720
caggaggagt taggaggcgc caagacccac accaccatga gtggcgtggc ccaccgggcc   780
ttcgagaacg acgtggacgc cctgtgcaac ctgcgggact tcttcaacta cctgcccctg   840
tcaagtcagg accccgctcc ggtacgggag tgccacgacc ccagcgatag actggtgccc   900
gagctggaca ccatcgtgcc cctggagagc accaaggcct acaacatggt ggacatcatc   960
cactctgtgg tagacgagcg gggagttctt cgagatcatgc ccaactacgc caagaacatc   1020
atcgtgggct ttgctcgcat gaacggtcgt accgttggta tcgtcggaaa ccagcccaag   1080
gtggcctccg gttgcctcga tatcaactcc agcgtaaagg cgctcggtt cgtgcggttc   1140
tgcgacgcct tcaacattcc actgatcaca ttcgtggacg tgcccggctt cctgcccggc   1200
accgcccagg agtacggcgg catcatccgg cacggagcaa agctgctgta cgccttcgtc   1260
gaggccaccg tgcctaaggt gaccgtgatc acccggaagg cctacggcgg cgcatacgac   1320
gtgatgagca gcaagcacct gtgcggcgac acaaattacg cttggcccac tgccgagatc   1380
gccgtgatgg tgctaaggg agccgtggag atcatcttca agggccacga gaacgtggag   1440
gcagcccagg ccgagtacat cgagaagttc gccaacccct ccccgccgc ggtccgcgga   1500
tttgttgacg atatcatcca gccccagcagc accggggccc gaatctgctg cgacctagac   1560
gtattggcct ctaagaaggt gcagcggccc tggcggaagc acgcaaacat cccactg     1617
```

SEQ ID NO: 19          moltype = RNA  length = 1617
FEATURE                Location/Qualifiers
source                 1..1617

-continued

```
                        mol_type = other RNA
                        organism = synthetic construct
SEQUENCE: 19
atggccgccg cgctcagagt tgccgcggtc ggcgcacgcc tgagcgtgct ggccagcggc    60
ctgcgtgcag cagtccggag cctgtgcagc caggccacca gcgtgaacga gcggatcgag   120
aacaagcggc ggaccgcact cctgggcggc ggtcaacgca ggattgacgc ccagcacaag   180
cggggcaagc tgaccgcccg ggagcggatt agcctgctgc tggacccggg cagcttcgtg   240
gagagcgaca tgtttgtcga acaccggtgc gccgacttcg gcatggccgc tgacaagaac   300
aagttccccg gcgacagcgt ggtgaccggc cggggccgga tcaacggccg gctggtgtac   360
gtgttcagcc aggacttcac cgtgttcggc ggcagcctga gcggcgccca cgcccagaag   420
atctgcaaga tcatggacca ggccatcacc gtgggtgctc cggtgatcgg cctgaacgac   480
tcaggaggtg cccggatcca ggagggagtg gaatctctgg ccggctacgc cgacatcttc   540
ctgcggaacg tgaccgctag cggcgtgata cctcaaattt ctctgatcat gggaccatgc   600
gctggcgggg ccgtgtacag ccccgccctg accgacttta cgttcatggt gaaggacacc   660
agctacctgt tcatcaccgg ccccgacgtg gtcaagtccg tgaccaacga ggacgtgacc   720
caggaggaac tcggtggggc caagacccac accaccatgt ccggcgttgc ccaccgggcc   780
ttcgagaacg acgtggacgc cctgtgcaac ctgcgggact tcttcaacta cctgcccctg   840
tcttcacaag atcctgctcc agtgcgggag tgccacgacc ccacgacgcc tttggtgccc   900
gagctggaca ccatcgtgcc cctggagagc accaaggcct acaacatggt ggacatcatc   960
cactccgttg tagacgagcg ggagttcttc gagatcatgc ccaactacgc caagaacatc  1020
atcgtgggct tcgcccgtat gaacggccgt accgtcggga ttgtggggaa ccagcccaag  1080
gttgcttctg ggtgcctaga catcaactca agcgtcaaga agccccggtt cgtgcggttc  1140
tgcgacgcct tcaacattcc cctgatcacg ttcgttgacg tgcccggctt cctgcccggc  1200
accgcccagg agtacggcgg catcatccgg cacggtgcca aactgctgta cgccttcgcc  1260
gaggccaccg ttcccaaggt gaccgtgatc acccggaaag cttacggagg ggcttacgac  1320
gtgatgacga gcaagcacct gtgcggcgac acaaattacg cttggcctac cgccgagatc  1380
gccgtgatgg gcgcaaaggg cgctgttgag atcatcttca agggccacga gaacgtggag  1440
gctgctcagg ccgagtacat cgagaagttc gccaacccct tccccgctgc cgtgcgggg t  1500
ttcgtggacg atattattca gcccagcagc acccgggcca gaatctgctg cgacctggac  1560
gtttttggcat caaagaaggt gcagcggccc tggcggaagc acgccaatat ccctctg     1617

SEQ ID NO: 20         moltype = RNA   length = 1617
FEATURE               Location/Qualifiers
source                1..1617
                      mol_type = other RNA
                      organism = synthetic construct
SEQUENCE: 20
atggccgccg cccttcgggt tgcagcggtc ggtgctcggc tgagcgtgct cgcttccggt    60
cttagggctg ctgtgcggag cctgtgcagc caggccacct ccgtcaacga gcgcatcgag   120
aacaagcgcc gcactgccct gctgggcgga ggccagaggc gaatcgacgc ccagcacaag   180
cgcggcaagc tcaccgccag ggaacggatc tccctcctcc tcgaccccgg ctccttcgtc   240
gagtccgaca tgttcgtaga acaccgctgc gccgacttcg gcatggccgc agacaagaac   300
aagttccccg gcgactccgt cgtcaccggc cgcggccgca tcaacggccg cctcgtctac   360
gtcttctccc aggacttcac cgtcttcggc ggctccctct ccggcgccca cgcccagaag   420
atctgcaaga tcatggacca ggccatcacc gtcggcgccc cggtcatcgg cctcaacgac   480
tccggcggc cccgcatcca ggagggagtc gaatccctcg ccggctacgc cgacatcttc   540
ctccgcaacg tcaccgcctc cggcgtcatc ccgcagatca gccttatcat gggccccctgc   600
gccggtggtg ctgtctacag tccggcccctc accgacttta cgttcatggt caaggacacc   660
tcctacctct tcatcactgg ccccgacgtc gtcaagtccg tcaccaacga ggacgtcacc   720
caggaggagc tgggaggcgc caagacccac accaccatgt ccggtgtggc ccaccgcgcc   780
ttcgagaacg acgttgacgc cctctgcaac ctccgcgact tcttcaacta ccttccactc   840
agctcacagg accctgctcc tgtacgcgag tgccacgacc cctccgacag gctggttccc   900
gagctcgaca ccatcgtgcc gctcgagtcc accaaggcct acaacatggt cgacatcatc  1020
catagcgtgg tcgacgagcg cgagttcttc gagatcatgc ccaactacgc caagaacatc  1020
atcgtggct tcgcgcggat gaacggcagg accgtcggta tagtcggcaa ccagcccaag  1080
gtcgccagcg ggtgcctaga tattaactcc tccgttaaag gggcaagatt cgtccgcttc  1140
tgcgacgcct tcaacatccc cttgattacc ttcgtggacg tccccggctt cctcccccgga  1200
acagcccagg agtacggcgg catcatccgc cacggtgcca aactcctcta cgccttcgcc  1260
gaggccaccg tccccaaagt gaccgtcatc acccggaaag cctacggagg cgcttacgac  1320
gtcatgtcct ccaagcacct ctgcggcgac accaattacg cttggcctac tgccgagatc  1380
gccgtcatgg gcgctaaagg agctgttgag ataatcttca agggccacga gaacgtgag  1440
gccgcgcagg ccgagtacat tgagaagttc gccaacccct tccccgcagc cgtccgcggt  1500
ttcgtggacg acattattca accttcttct acccgtgccc gtatctgctg cgacctggac  1560
gtgctcgcct ccaagaaggt ccagcgcccc tggcgcaagc acgccaatat cccactc     1617

SEQ ID NO: 21         moltype = RNA   length = 1617
FEATURE               Location/Qualifiers
source                1..1617
                      mol_type = other RNA
                      organism = synthetic construct
SEQUENCE: 21
atggccgccg ccctgcgggt ggccgccgtg ggcgcccggc tgagcgtgct ggccagcggc    60
ctgcgggccg ccgtgcggag cctgtgcagc caggccacca gcgtgaacga gcggatcgag   120
aacaagcggc ggaccgccct gctgggcggc ggccagaggc gaatcgacgc ccagcacaag   180
cggggcaagc tgaccgcccg ggagcggatc agcctgctgc tggacccggg cagcttcgtg   240
gagagcgaca tgttcgtgga gcaccggtgc gccgacttcg gcatggccgc cgacaagaac   300
aagttccccg gcgacagcgt ggtgaccggc cggggccgga tcaacggccg gctggtgtac   360
gtgttcagcc aggacttcac cgtgttcggc ggcagcctga gcggcgccca cgcccagaag   420
atctgcaaga tcatggacca ggccatcacc gtgggcgcgc ccgtgatcgg cctgaacgac   480
```

-continued

```
agcggcggcg cccggatcca ggagggcgtg gagagcctgg ccggctacgc cgacatcttc  540
ctgcggaacg tgaccgccag cggcgtgatc ccgcagatca gcctgatcat gggcccctgc  600
gccggcggcg ccgtgtacag ccccgccctg accgacttca ccttcatggt gaaggacacc  660
agctacctgt tcatcaccgg ccccgacgtg gtgaagagcg tgaccaacga ggacgtgacc  720
caggaggagc tgggcggcgc caagacccac accaccatga gcggcgtggc ccaccgggcc  780
ttcgagaacg acgtggacgc cctgtgcaac ctgcgggact tcttcaacta cctgcccctg  840
agcagccagg accccgcgcc cgtgcgggag tgccacgacc ccagcgaccg gctggtgccc  900
gagctggaca ccatcgtgcc cctggagagc accaaggcct acaacatggt ggacatcatc  960
cacagcgtgg tggacgagcg ggagttcttc gagatcatgc ccaactacgc caagaacatc  1020
atcgtgggct tcgcccggat gaacggccgg accgtgggca tcgtgggcaa ccagcccaag  1080
gtggccagcg gctgcctgga catcaacagc agcgtgaagg gcgcccggtt cgtgcggttc  1140
tgcgacgcct tcaacatccc actgatcacc ttcgtggacg tgcccggctt cctgcccggc  1200
accgcccagg agtacggcgg catcatccgg cacggcgcca agctgctgta cgccttcgcc  1260
gaggccaccg tgcccaaggt gaccgtgatc acccggaagg cctacggcgg agcctacgac  1320
gtgatgagca gcaagcacct gtgcggcgac accaactacg cctggcccac cgccgagatc  1380
gccgtgatgg gcgccaaggg cgccgtggag atcatcttca agggccacga gaacgtggag  1440
gccgcccagg ccgagtacat cgagaagttc gccaacccct ccccgccgc cgtgcggggc  1500
ttcgtggacg acatcatcca gcccagcagc accgggagc ggatctgctg cgacctggac  1560
gtgctggcca gcaagaaggt gcagcggccc tggcggaagc acgccaacat cccgctg     1617
```

SEQ ID NO: 22          moltype = RNA   length = 1617
FEATURE                Location/Qualifiers
source                 1..1617
                       mol_type = other RNA
                       organism = synthetic construct
SEQUENCE: 22

```
atggccgcgg ccctgcgggt cgcggccgtg ggagccagac tgtccgtgct agcctcaggg  60
ctgcgcgccg ctgtgagaag cctgtgcagc caggccacca gcgtgaacga gagaatcgag  120
aacaagagaa gaaccgctct gctgggtggc ggccagagaa gaatcgacgc ccagcacaag  180
agaggcaagc tgaccgccag agagagaatc agcctgctgc tggaccccgg cagcttcgtg  240
gagagcgaca tgttcgtgga gcaccgctgc gccgacttcg gcatggccgc cgacaagaac  300
aagttccccg gcgacagcgt ggtgaccggc agaggcagaa tcaacggcag actggtgtac  360
gtgttcagcc aggacttcac cgtgttcggc ggctccctga gcgggggcca cgcccagaag  420
atctgcaaga tcatggacca agccattacc gtgggcgctc ctgtgatcgg cctgaacgac  480
tccggcggcg cgaggatcca ggagggcgtg gaaagcctgg cgggttacgc cgacatcttc  540
ctgagaaacg tcaccgcatc cggagtgatt ccccagatca gcctgatcat gggtccctgc  600
gcgggcggag ccgtgtacag ccccgccctg accgacttca ccttcatggt gaaggacacc  660
agctacctgt tcatcaccgg ccccgacgtg gtcaagagcg tgaccaacga ggacgtgacc  720
caagaggcagc tcggaggcgc caagacccac accaccatga gcggcgtggc ccacagacca  780
ttcgagaacg acgtggacgc cctgtgcaac ctgagagact tcttcaacta cctgcccctg  840
agttctcagg atcctgcacc cgtgagagag tgccacgacc ccagcgacag actggtgccc  900
gagctggaca ccatcgtgcc cctggagagc accaaggcct acaacatggt ggacatcatc  960
cacagcgttg tggacgagag agagttcttc gagatcatgc ccaactacgc caagaacatc  1020
atcgtgggct cgccagaat gaacggcagg actgtgggaa tcgtgggcaa ccagcccaag  1080
gtggccagcg gctgcctgga catcaacagc agcgtgaagg gcgccagatt cgtgagattc  1140
tgcgacgcct tcaacatccc gctgatcaca ttcgtggacg ttcccggctt cctgcccggc  1200
acagcccagg agtacggcgg catcatcaga cacggcgcca agctgctgta cgccttcgcc  1260
gaggccaccg tgcccaaggt gaccgtgatc accagaaagg cctacggcgg agcttacgac  1320
gtgatgagca gcaagcacct gtgcggtgac actaactacg cctggccgac cgccgagatc  1380
gccgtgatgg gcgccaaagg ggccgtggag atcatcttca agggccacga gaacgtggag  1440
gccgcccagg ccgagtacat cgagaagttc gccaacccct ccccgccgc cgtgcagggt  1500
ttcgtggacg acatcatcca gccctcctcc accagagcca gaatctgctg cgacctggac  1560
gtactggcca gcaagaaggt gcaacgtccc tggagaaagc acgccaacat ccctctg     1617
```

SEQ ID NO: 23          moltype = RNA   length = 1617
FEATURE                Location/Qualifiers
source                 1..1617
                       mol_type = other RNA
                       organism = synthetic construct
SEQUENCE: 23

```
atggccgcag ccctcagagt ggctgccgtg ggagccagac tcagcgtgct cgcctcaggc  60
ctgcgggccg cagtcagaag cctgtgcagc caggcaacct cagtgaacga gagaatcgag  120
aacaagagac ggaccgccct gctgggtggc gggcaaagaa gaattgacgc ccagcacaag  180
agaggcaagc tgaccgcccg cgagcgcatc agcctgctgc tggaccccgg cagcttcgtg  240
gagagcgaca tgttcgtgga gcatcggtgt gccgacttcg gcatggccgc cgacaagaac  300
aagttcctccg gcgacagcgt ggtgaccggc agaggcagaa tcaacggcag actggtgtac  360
gtgttctcac aagactttac cgtcttcgga ggatccctgt caggggctca cgcccagaag  420
atctgcaaga tcatggacca ggccatcacc gtgggcgctc ccgtgatcgg cctgaacgac  480
agcggaggcg ccaggatcca agagggagtg agtccctgg ccggctacgc cgacatcttc  540
ctgagaaacg tgaccgcctc gggcgtgatc ccacagatct ccctgatcat gggaccctgc  600
gccggcgggg ccgtctacag ccctgccctg accgacttca ccttcatggt gaaggacacc  660
agctacctgt tcatcaccgg ccccgacgtg gtcaagagcg tgaccaacga ggacgtgacc  720
caggaggagc tcggcggagc caagactcac acaaccatgt ccggcgtcgc tcatagggc  780
ttcgagaacg acgtggacgc cctgtgcaac ctgagagact tcttcaacta cctgccattg  840
agcagccagg atcccgcccc tgtgagagag tgccacacc ccagcgacag actggtgccc  900
gagctggaca ccatcgtgcc cctggagagc accaaggcct acaacatggt ggacatcatc  960
cacagcgtgg tggacgagag agagttcttc gagatcatgc ccaactacgc caagaacatc  1020
atcgtgggct cgccagaat gaacggcaga accgtgggca ttgtgggcaa ccagcccaag  1080
gtcgccagcg gctgcctcga catcaacagc agcgtgaagg gcgccagatt cgtgagattc  1140
```

```
tgcgacgcct tcaacatacc tctgatcacc tttgtggacg tgcctggttt cctcccgggc  1200
accgcccaag aatacggtgg catcatcaga cacggcgcca agctgctgta cgccttcgcc  1260
gaggccaccg tgcccaaggt gaccgttatc acccgcaaag cctacggcgg cgcctacgac  1320
gtgatgagca gcaagcacct gtgtggcgac accaattacg cctggcccac cgccgagatc  1380
gccgtcatgg gcgcgaaagg agccgtggag atcatcttca agggccacga gaacgtggag  1440
gccgcccagg ccgagtacat cgagaagttc gccaacccct tccctgccgc cgtgaggggc  1500
ttcgtcgacg atatcatcca gcccagctcc acccgcgcca gaatctgttg cgacctggac  1560
gtgctggcca gcaagaaggt gcaaagaccc tggagaaagc acgccaacat cccgctg     1617
```

SEQ ID NO: 24         moltype = RNA   length = 1617  
FEATURE               Location/Qualifiers  
source                1..1617  
                       mol_type = other RNA  
                       organism = synthetic construct  
SEQUENCE: 24

```
atggccgccg ccctaagggt tgccgcagtt ggtgccaggc taagcgtgct agccagcggg  60
ctacgggcgg cggtaaggag cctgtgcagc caagccacca gcgtgaacga gaggatagag  120
aacaagagga ggaccgccct actaggcggt gggcaacggc ggatcgacgc ccaacacaag  180
aggggaaagc taaccgccag ggaaagaata agcctactac tagatccagg gagcttcgtg  240
gagagcgata tgtttgtgga gcacaggtgc gccgatttcg ggatggccgc agataagaac  300
aagttcccag gggatagcgt ggtgaccggg agaggaagga taaacgggag gctagtgtac  360
gtgttcagcc aagatttcac cgtgttcgga gggagcctaa gcggggccca cgcccagaag  420
atttgcaaga taatggatca agccataacc gttggagcgc cagtgatagg gctaaacgat  480
agcggtggag cccggatcca agaggcgtg gaatctctag ccgggtacgc cgatatattc  540
ctaaggaacg tgaccgcgtc tggtgtgata ccacaaatta gtctcataat ggggccttgc  600
gcaggagggg ctgtgtacag cccagcccta accgatttca cgttcatggt gaaggatacc  660
agctacctat tcataaccgg gccagacgtg gtaaagtccg tgaccaacga ggacgtgacc  720
caagaggaat taggaggagc caagacccac accaccatgt ccggggttgc ccacagggcc  780
ttcgagaacg acgtggacgc cctgtgcaac ctaagggatt tcttcaacta cctaccacta  840
tcttcccaag atcctgatcc agtgagggag tgccacgatc aagcgatag actggtccca  900
gagctagata ccatagtgcc actagagagc accaaggcct acaacatggt ggatataata  960
cactccgtgg tggacgagag ggagttcttc gagataatgc caaactacgc caagaacata  1020
atagtgggt tcgccaggat gaacgggcgt accgtgggga tagtaggaaa ccaaccaaag  1080
gtggcctctg ggtgcctaga tataaacagc tctgtcaagg gagcccgctt cgtgaggttc  1140
tgcgacgcct tcaacatacc tctaataaca ttcgttacg tgccagggtt cctaccaggg  1200
acggcacaag agtacggagg gataataagg cacgggcga agctactata cgccttcgcc  1260
gaggccaccg tgcctaaggt gaccgtgata accaggaagg cttacggagg ggcctacgac  1320
gtgatgagca gcaagcacct gtgcgggat accaactacg cgtggccaac cgccgagata  1380
gccgtgatgg gtgcaaaggg tgctgtggag ataatattca aggggcacga gaacgtggag  1440
gccgcgcagg ccgagtacat agagaagttc gccaacccat tcccagcagc ggtacggga  1500
tttgttgacg atatcattca accaagcagc acccgcgcga gaatttgctg cgacttagac  1560
gtgttagcga gcaagaaggt acaacggccc tggaggaagc acgctaacat cccacta     1617
```

SEQ ID NO: 25         moltype = RNA   length = 1617  
FEATURE               Location/Qualifiers  
source                1..1617  
                       mol_type = other RNA  
                       organism = synthetic construct  
SEQUENCE: 25

```
atggcggcgg cattacgggt ggcggcggtc ggggcaaggc tcagcgtgct ggccagcggc  60
ctgagacgg ccgtgagaag cctgtgcagc caggccacca gcgtgaacga gagaatcgag  120
aacaagagaa gaaccgccct gctgggcggc ggccagagaa gaatcgacgc ccagcacaag  180
agaggcaagc tgaccgccag agagagaatc agcctgctgc tggacccccgg cagcttcgtg  240
gagagcgaca tgttcgtgga gcacaggtgc gccgacttcg gcatggccgc cgacaagaac  300
aagttccccg gcgacagcgt ggtgaccggc agaggcagga tcaacggcag actggtgtac  360
gtgttcagcc aggacttcac cgtgttcggc ggcagcctga gcggcgccca cgcccagaag  420
atctgcaaga tcatggacca ggccatcacc gtgggcgcgc ccgtgatcgg cctgaacgac  480
agcggcggcc ccagaatcca ggaggcgtg gagagcctgg ccggctacgc cgacatcttc  540
ctgagaaacg tgaccgccag cggcgtgatc ccacagatca gcctgatcat gggccccctgc  600
gccggcggcg ccgtgtacag ccccgccctg accgacttca ccttcatggt gaaggacacc  660
agctacctgt tcatcaccgg ccccgacgtg gtgaagagcg tgaccaacga ggacgtgacc  720
caggaggagc tgggcggcgc caagacccac accaccatga gcggcgtggc ccacagagcc  780
ttcgagaacg acgtggacgc cctgtgcaac ctgagagact tcttcaacta cctgcccctg  840
agcagccagg accccgcgcc cgtgagagag tgccacgacc agcgcgacag actggtgccc  900
gagctggaca ccatcgtgcc cctggagagc accaaggcct acaacatggt ggacatcatc  960
cacagcgtgg tggacgagag agagttcttc gagatcatgc ccaactacgc caagaacatc  1020
atcgtgggct cgccagaat gaacggcaga accgtgggca tcgtgggcaa ccagcccaag  1080
gtggccagcg gctgcctgga catcaacagc agcgtgaagg cgccagatt cgtgagattc  1140
tgcgacgcct tcaacatccc tctgatcacc ttcgtgacg tgcccggctt cctgcccggc  1200
accgcccagg agtacggcgg catcatcaga cacggcgcca agctgctgta cgccttcgcc  1260
gaggccaccg tgcccaaggt gaccgtgatc accagaaagg cctacggcgg cgcctacgac  1320
gtgatgagca gcaagcacct gtgcggcgac accaactacg cctggcccac cgccgagatc  1380
gccgtgatgg gcgccaaggg cgccgtggag atcatcttca agggccacga gaacgtggag  1440
gccgcccagg ccgagtacat cgagaagttc gccaacccct tccccgccgc cgtgagaggc  1500
ttcgtggacg acatcatcca gcccagcagc accagagagc gaatctgctg cgacctggac  1560
gtgctggcca gcaagaaggt gcagagaccc tggagaaagc acgccaacat ccctctg     1617
```

SEQ ID NO: 26         moltype = RNA   length = 1617  
FEATURE               Location/Qualifiers -continued

```
source                  1..1617
                        mol_type = other RNA
                        organism = synthetic construct
SEQUENCE: 26
atggccgccg ccctgagagt ggccgctgtg ggcgccaggc tgagcgtgct cgctagcggc    60
ctgagagccg ccgttagaag cctgtgcagc caggccacct ccgtgaacga gaggatcgag   120
aataagagac gaaccgccct gctcggcggc ggccagagac gcatcgacgc ccagcacaag   180
cgaggtaagc tgacagccag gggagcgaatc agcctgctcc tggaccccgg aagcttcgtg   240
gaatccgaca tgttcgttga gcacagatgc gccgacttcg gcatggccgc cgacaagaac   300
aagtttccag gggactcagt ggtcaccgga agaggccgca tcaacggccg cctggtctac   360
gtgttctcac aggactttac agtgttcggc ggcagcctgt caggcgccca tgcccagaag   420
atctgcaaga tcatggatca ggccatcaca gtgggcgccc ccgtgatcgg tctgaacgac   480
tctggcggcg ccagaattca agagggcgtg gagagcctgg ccggttacgc cgacattttc   540
ctgaggaacg tcaccgccag cggcgtcatc ccccagatct ctctgatcat gggcccctgc   600
gctggcggcg ccgtgtacag ccccgccctg accgatttca ccttcatggt gaaggatacc   660
agctatctgt tcatcaccgg cccggatgtg gtgaagagtg tgaccaacga ggacgtgacc   720
caggaggagc tgggtggagc caagactcac acaaccatgt ccggcgtggc ccatcgagcc   780
tttgagaacg acgtcgacgc cctgtgtaac ctgagagact tcttcaatta cctgcccctg   840
agctcccagg accccgcccc agttagggag tgccacgatc cctccgaccg cctggtgccc   900
gagctggaca ccatcgtgcc cctggagagc accaaggcct acaacatggt ggatatcatc   960
catagcgtcg tcgacgagcg cgagttcttc gagatcatgc ccaactacgc caagaacatc  1020
atcgtgggct ttgccaggat gaacggccgc accgtgggca ttgtgggcaa ccagcccaag  1080
gtggcctctg gctgcctgga catcaacagc agcgtgaagg gtgctaggtt cgtgaggttc  1140
tgcgatgcct ttaacatccc acttatcacc ttcgttgatg tccctggctt cctgcctggc  1200
accgcccagg agtacggcgg catcatcaga catggtgcca agctgctgta cgccttcgcc  1260
gaggccaccg tgcccaaggt gaccgtgatt acccggaaag cctacggcgg cgcctacgac  1320
gtcatgagca gcaagcacct gtgcggcgac accaactacg cctggcccac cgccgagatc  1380
gccgtcatgg gcgccaaggg ggccgtcgag atcatcttca agggacacga gaacgtggag  1440
gccgctcagg ccgagtacat cgagaagttc gctaaccctt tccccgccgc tgttagagga  1500
ttcgtggatg acatcatcca gccaagcagc acccgggcca ggatctgctg tgacctggat  1560
gtgctggcta gcaagaaggt gcagagaccc tggagaaagc acgccaacat tcccctg     1617
```

```
SEQ ID NO: 27            moltype = RNA  length = 1617
FEATURE                 Location/Qualifiers
source                  1..1617
                        mol_type = other RNA
                        organism = synthetic construct
SEQUENCE: 27
atggccgccg ccctgagagt ggccgctgtg ggcgccaggc tgagcgtgct cgctagcggc    60
ctgagagccg ccgttagaag cctgtgcagc caggccacct ccgtgaacga gaggatcgag   120
aataagagac gaaccgccct gctcggcggc ggccagagac gcatcgacgc ccagcacaag   180
cgaggtaagc tgacagccag gggagcgaatc agcctgctcc tggaccccgg aagcttcgtg   240
gaatccgaca tgttcgttga gcacagatgc gccgacttcg gcatggccgc cgacaagaac   300
aagtttccag gggactcagt ggtcaccgga agaggccgca tcaacggccg cctggtctac   360
gtgttctcac aggactttac agtgttcggc ggcagcctgt caggcgccca tgcccagaag   420
atctgcaaga tcatggatca ggccatcaca gtgggcgccc ccgtgatcgg tctgaacgac   480
tctggcggcg ccagaattca agagggcgtg gagagcctgg ccggttacgc cgacattttc   540
ctgaggaacg tcaccgccag cggcgtcatc ccccagatct ctctgatcat gggcccctgc   600
gctggcggcg ccgtgtacag ccccgccctg accgatttca ccttcatggt gaaggatacc   660
agctatctgt tcatcaccgg cccggatgtg gtgaagagtg tgaccaacga ggacgtgacc   720
caggaggagc tgggtggagc caagactcac acaaccatgt ccggcgtggc ccatcgagcc   780
tttgagaacg acgtcgacgc cctgtgtaac ctgagagact tcttcaatta cctgcccctg   840
agctcccagg accccgcccc agttagggag tgccacgatc cctccgaccg cctggtgccc   900
gagctggaca ccatcgtgcc cctggagagc accaaggcct acaacatggt ggatatcatc   960
catagcgtcg tcgacgagcg cgagttcttc gagatcatgc ccaactacgc caagaacatc  1020
atcgtgggct tgccaggat gaacggccgc accgtgggca ttgtgggcaa ccagcccaag  1080
gtggcctctg gctgcctgga catcaacagc agcgtgaagg gtgctaggtt cgtgaggttc  1140
tgcgatgcct ttaacatccc acttatcacc ttcgttgatg tccctggctt cctgcctggc  1200
accgcccagg agtacggcgg catcatcaga catggtgcca agctgctgta cgccttcgcc  1260
gaggccaccg tgcccaaggt gaccgtgatt acccggaaag cctacggcgg cgcctacgac  1320
gtcatgagca gcaagcacct gtgcggcgac accaactacg cctggcccac cgccgagatc  1380
gccgtcatgg gcgccaaggg ggccgtcgag atcatcttca agggacacga gaacgtggag  1440
gccgctcagg ccgagtacat cgagaagttc gctaaccctt tccccgccgc tgttagagga  1500
ttcgtggatg acatcatcca gccaagcagc acccgggcca ggatctgctg tgacctggat  1560
gtgctggcta gcaagaaggt gcagagaccc tggagaaagc acgccaacat tcccctg     1617
```

```
SEQ ID NO: 28            moltype = RNA  length = 2373
FEATURE                 Location/Qualifiers
source                  1..2373
                        mol_type = other RNA
                        organism = synthetic construct
SEQUENCE: 28
gggaaataag agagaaaaga agagtaagaa gaaatataag agccaccatg gccggattct    60
gggtcggcac agcccctctt gtggccgcag ggaggcgcgg ccgctggcca ccacagcagc   120
tgatgctgtc tgccgccctg cggaccctga agcacgtgct gtactatagc agacagtgtc   180
tgatggtgtc cagaaacctc ggaagcgtgg gctacgaccc caacgagaag accttcgaca   240
agatcctggt cgccaaccgc ggcgagatcg cttgccgggt gatcaggacc tgtaagaaga   300
tgggcatcaa gaccgtggcc atccacacgc acgtagacgc cagcagcgtg cacgtcaaga   360
tggccgacga agcggtgtgc gtggggcccg cccctacatc caagtcctat cttaacatgg   420
```

```
acgccatcat ggaggccatc aagaagacta gagcccaagc cgttcatccg gggtacggat  480
ttctgtccga gaacaaagag ttcgctaggt gcctcgccgc cgaagacgtt gtcttcattg  540
gtccagacac ccacgccatc caggctatgg gcgataagat cgagagcaag ctgctggcta  600
agaaggcaga ggtgaacacc atccccggat tcgacggagt ggtcaaagac gcggaggagg  660
ccgtgaggat cgcgagagag atcggatacc cggtgatgat caaggcctca gcaggcggcg  720
gcggaaaggg aatgagaatt gcctgggacg acgaggaaac ccgcgacggc ttccggctca  780
gctcccagga agcagcttct agctttggcg acgatcggct gctgattgag aaattcatcg  840
ataacccccag acacatagag atccaggtgc tgggtgacaa gcacggcaac gccctgtggc  900
tgaacgagag agagtgctcc attcagagga ggaaccagaa ggtggttgag gaggcgccta  960
gcatcttcct ggacgctgaa acaaggagag ccatgggtga gcaggccgtg gccctggctc 1020
gcgccgttaa gtatagcagc gccggcaccg tcgagttcct ggtggactcc aagaagaact 1080
tctatttcct ggagatgaac acccgcctgc aggtggagca ccccgtcact gagtgtatta 1140
ccggcctcga cctggtccag gagatgatca gagtcgccaa ggggtatccc ctgcggcaca 1200
agcaggcaga catccgcatc aacggctggg ccgtgagtg cagagtgtac gccgaggacc 1260
cctacaagag cttcggcctg ccaagcatcg gcagactgtc tcagtaccaa gaaccccgc 1320
acctgcccgg cgtgagagta gacagcggca ttcagcctgg aagcgacatt agcatctact 1380
acgaccctat gatcagcaag ctcatcacct acggttctga ccggaccgag gccctgaaac 1440
ggatggctga cgccctggac aactacgtga tccggggcgt gactcacaac atcgccctcc 1500
tgagggaagt catcatcaac agccgattcg tgaaggggaga catctccacc aagttcctga 1560
gcgacgtgta ccctgacggc ttcaaaggcc acatgctgac caagagcgag aagaaccagc 1620
tcctggccat cgccagtagc ctgttcgtgg ccttccagct gagggcccag cactttcagg 1680
agaacagcag gatgccagtg attaagcctg acatcgccaa ctgggagctg tcagtcaagc 1740
tgcacgataa ggtgcacaca gtggtggcca gcaataacgg ctccgtgttc agcgtcgagg 1800
tggacggctc caaactgaac gtcaccagca cctggaatct ggcctcaccc ttactgagcg 1860
tgtctgtgga cggcacccag agaaccgtgc agtgtttgtc tagggaggca ggcggcaaca 1920
tgtccatcca gtttctggga acagtgtaca aagtgaatat cctgaccaga ctggccgctg 1980
agctgaacaa gttcatgctt gagaaggtga ccgaggatac tagctccgtt ctgagatccc 2040
ctatgcccgg tgtggtcgtg gcagtgagcg tgaagcctgg tgacgcggtg gcagagggtc 2100
aggagatctg tgtcattgag gctatgaaga tgcagaatag catgacagcc ggtaagaccg 2160
ggacggttaa atccgttcac tgccaggctg gcgcacaccg gggcgagggc gatctgttag 2220
tggagcttga gtgataatag gctggagcct cggtggccta gcttcttgcc ccttgggcct 2280
cccccagcc cctcctcccc ttcctgcacc cgtaccccct ccataaagta ggaaacacta 2340
cagtggtctt tgaataaagt ctgagtgggc ggc                              2373
```

SEQ ID NO: 29          moltype = RNA   length = 2373
FEATURE                Location/Qualifiers
source                 1..2373
                       mol_type = other RNA
                       organism = synthetic construct
SEQUENCE: 29

```
gggaaataag agagaaaaga agagtaagaa gaaatataag agccaccatg gcgggctttt   60
gggtgggcac cgcccactg gtcgctgccg gcaggagagg acggtggcca ccccagcagc  120
tcatgctgag cgccgcactc agaaccctga agcacgtgct gtactactcg cgacagtgac  180
ttatggtgtc taggaacctg ggctctgtcg gctacgatcc gaacgagaag accttcgaca  240
agatcctggt cgccaacagg ggcgaaatcg cctgtagagt cataaggacc tgtaagaaga  300
tgggcatcaa gaccgtggct atccacagcg acgtggacgc tagctccgta cacgtgaaga  360
tggccgacga ggcagtgtgc gtgggtccgg ctcccacctc caagtcctac ctgaacatgg  420
acgccatcat ggaagccatc aagaagacta gagcccaggc cgtgcaccca ggctacgggt  480
ttctctccga gaataaagag ttcgccaggt gcctggctgc cgaggacgtg gtgtttatcg  540
gacccgatac tcacgccatc caggccatgg gcgacaagat agagtctaag ctgttggcca  600
agaaagctga ggtgaacacc atccccggct tcgacggtgt ggttaaggac gccgaggaag  660
ctgtgcgcat cgccagggaa atcggctacc ccgtgatgat caaggcaagt gcaggaggag  720
gcggcaaagg gatgagaatc gcctgggacg acgaagaaac tagagacggt ttccggctgt  780
cttcccagga ggctgcatca tcttttggag acgatcggtt gctgattgag aagtttattg  840
acaacccgcg gcacatcgag atccaggtgc tcggtgacaa gcacggcaac gccctctggc  900
tcaacgaaag agagtgcagc attcagcgcc ggaaccagaa agtggtggag gaggctccca  960
gtatttcct ggacgccgaa acccggagag ccatgggaga gcaggctgtg gctctcgcta 1020
gggcggtgaa gtacagctcc gccggcacag tcgagttcct ggtggactcc aagaagaact 1080
tctacttcct ggagatgaac aaagactgc aggtggagca tcccgttacc gagtgtataa 1140
ccggcctgga tctggtccag gagatgatca gagtcgccaa gggatatccc cttaggcata 1200
aacaggccga catcaggatc aacggctggg ccgtcgagtg ccgggtgtac gctgaggacc 1260
cttataagag cttcggctta ccatccattg gcagactgtc ccagtaccag gaacctctgc 1320
acttgcccgg agtgagagtc gacagcggca tccagcccgg cagcgacatc tccatctact 1380
acgaccccat gatatcaaag ctgatcacct acggctcgga tagaacagag gccctgaaac 1440
ggatggctga cgccctggac aactacgtga tccggggtgt gacacacaac attgccctgc 1500
tgagggaggt gatcatcaat agccggtttg tgaagggtgta tatttccacc aagttcctgt 1560
ctgacgtgta tccggacgga ttcaagggcc acatgctgac aaagtccgag aagaatcagc 1620
tgctggccat agcttcttca ctgttcgtgg cctttcagct gagagctcag cacttccagg 1680
agaactcaag aatgcccgtg atcaagcctg atatcgccaa ttgggagctg agcgtgaagc 1740
tgcacgacaa ggtacacaca gtggtggcca gcaacaacgg cagcgtgttt tccgtggagg 1800
tagacggaag caaactgaac gtgacatcta cctggaatct ggcctctcct ctgctgagtg 1860
ttagcgtcga cggcacgcag agaactgtgc agtgcctgag ccgggaggcg gcggaaaca 1920
tgtcaatcca gtttctcggc actgtctaca aggtcaacat cctgaccaga ctggctgctg 1980
agctgaataa attcatgctc gagaaggtga ccgaggacac agctcggtg ctcagaagcc 2040
caatgcccgg cgtggtggtc gccgtcagcg tcaagcccgg cgacgctgtg gccgaaggcc 2100
aggaaatctg cgtcatcgag gcgatgaaga tgcagaattc aatgactgcc gggaagaccg 2160
gcaccgtcaa gagcgtgcat tgccaggcag gggacaccgt gggcgaaggg gaccttctgg 2220
tggagctcga gtgataatag gctggagcct cggtggccta gcttcttgcc ccttgggcct 2280
cccccagcc cctcctcccc ttcctgcacc cgtaccccct ccataaagta ggaaacacta 2340
```

-continued

```
cagtggtctt tgaataaagt ctgagtgggc ggc                                    2373

SEQ ID NO: 30           moltype = RNA   length = 2373
FEATURE                 Location/Qualifiers
source                  1..2373
                        mol_type = other RNA
                        organism = synthetic construct
SEQUENCE: 30
gggaaataag agagaaaaga agagtaagaa gaaatataag agccaccatg gccggcttct        60
gggtgggcac cgcacccctc gtggccgccg gcagaagagg caggtggcct ccccagcagc       120
tgatgctgag cgccgccctg cggaccctga agcacgtgct gtactacagc cggcagtgcc       180
tgatggtgag ccggaacctg ggcagcgtgg gctacgaccc caacgagaag accttcgaca       240
agattttggt ggcaaaccgg ggcgagatcg cctgccgggt gatccggacc tgcaagaaga       300
tgggcatcaa gaccgtggcc atccacagcg acgtggacgc cagcagcgtg cacgtgaaga       360
tggccgacga ggccgtgtgc gtcggcccccg ccctaccag caagagctac ctgaacatgg       420
acgcgatcat ggaggccatc aagaagaccc gggcccaggc cgtgcacccc ggctacggct       480
tcctgagcga gaacaaggag ttcgcccggt gcctggccgc agaggacgtg gtgttcatcg       540
gccccgacac ccacgccatc caggccatgg gcgacaagat cgagagcaag ctgctggcca       600
agaaggccga ggtgaacacc atccccggct tcgacggcgt ggtgaaggac gccgaggaag       660
ctgtgcggat cgcccgggag atcggctacc ccgtgatgat caaggccagc gccggaggcg       720
gaggcaaggg catgagaatc gcttgggacg acgaggagac aagagacggc tttcggctga       780
gcagccagga ggcagcgagc agcttcggcg acgaccggct gctgatcgag aagttcatcg       840
acaaccctcg gcacatcgag atccaggtgc tgggagacaa gcacgacaac gccctgtggc       900
tgaacgagcg ggagtgcagc atccagcggc ggaaccagaa ggtggtggag gaggccccta       960
gcatcttcct ggacgctgaa accaggagag ccatgggaga gcaggccgtt gccctggccc      1020
gggccgtgaa gtactctagc gctggcaccg tggagttcct ggttgactct aagaagaact      1080
tctattttct ggagatgaac acccggctgc aggtggagca ccccgtcacc gagtgcatca      1140
ccggcctgga cctggtgcag gagatgatcc gcgtggctaa gggctaccct ctgcggcaca      1200
agcaggctga catccggatc aacggctggg ccgtagagtg ccgtgtctac gccgaggacc      1260
cctacaagtc cttcggcctg ccatccatcg gcaggctggc ccagtaccag gagccctgc       1320
acctgcccgg cgtgcgagtg gatagcggca ttcagcccgg cagcgacatc agcatctact      1380
acgaccctat gatctccaag ctaatcacct acggcagcga tcggaccgag gccctgaaga      1440
gaatggctga cgccctggac aactacgtga tcagaggcgt gacccacaac atcgccctgc      1500
tgcgggaggt gatcatcaac agccggttcg tgaagggcga tatcagcacc aagtttctgt      1560
ccgacgttta ccccgacggc ttcaagggcc acatgctgac caagagcgag aagaaccagc      1620
tgctcgccat cgcaagctcc ctgttcgtgg ccttccagct gcgagcacag cacttccagg      1680
agaatagtag aatgcccgtg atcaagcccg acatcgccaa ctgggagctg agcgtgaagc      1740
tgcacgacaa ggtgcacacc gttgtggcta gcaacaacgg ttctgtgttc agcgtggagg      1800
tggacggtag caaactgaac gtgaccagca cctggaacct cgcctcacca ctgctcagcg      1860
tgagcgtgga cggaacccag cggaccgtgc agtgcctcag ccgggaagcc ggcggcaaca      1920
tgagcattca gtttctcggc actgtgtaca aggtgaatat cctgaccagg ctggccgctg      1980
agctgaacaa gttcatgctg gagaaggtga cagaggacac tagcagcgtt ctgcggagcc      2040
ccatgccagg ggtggtggtc gccgttagcg tcaagcctgg gccgaggcg gccgagggcc      2100
aggagatctg cgtgatcgag gccatgaaga tgcagaacga catgaccgcc ggcaagactg      2160
gcacagtgaa gtcagtgcac tgccaggccg gcgacaccgt gggcgagggc gacctgctgg      2220
tggagctgga gtgataatag gctggagcct cggtggccta gcttcttgcc ccttgggcct      2280
cccccagcc cctcctcccc ttcctgcacc cgtaccccct ccataaagta ggaaacacta      2340
cagtggtctt tgaataaagt ctgagtgggc ggc                                    2373

SEQ ID NO: 31           moltype = RNA   length = 2373
FEATURE                 Location/Qualifiers
source                  1..2373
                        mol_type = other RNA
                        organism = synthetic construct
SEQUENCE: 31
gggaaataag agagaaaaga agagtaagaa gaaatataag agccaccatg gccggcttct        60
gggtgggcac cgcacccctg gtggctgctg ggagacgggg acggtggcct cctcagcagc       120
tgatgctgag cgccgccctg cggaccctga agcacgtgct gtactacagc cggcagtgcc       180
tgatggtgag ccggaacctg ggcagcgtgg gctacgaccc caacgagaag accttcgaca       240
agatcctggt cgccaaccgg ggcgagatcg cctgccgggt gatccggacc tgcaagaaga       300
tgggcatcaa gaccgtggcc atccacagcg acgtggacgc cagcagcgtg cacgtgaaga       360
tggccgacga ggccgtgtgc gtgggccctg cgcctaccag caagagctac ctgaacatgg       420
acgctatcat ggaggccatc aagaagaccc gggcccaggc cgtgcacccc ggctacggct       480
tcctgagcga gaacaaggag ttcgcccggt gcctggccgc agaggacgtg gtgttcatcg       540
gccccgacac ccacgccatc caggccatgg gagacaagat tgagagcaag ctgctggcca       600
agaaggccga ggtgaacacc atccccggct tcgacggcgt ggtgaaggac gccgaagagg       660
ccgtccggat cgcccgggag atcggctacc cgtgatgat caaggcctcc gccggtggag       720
gcggcaaggg catgaggatc gcttgggacg acgaggagac tagacaggc tttcggctga       780
gcagccagga ggcagccagc tcattcggcg acgaccggct gctgatcgag aagttcatcg       840
acaatccacg gcacatcgag atccaggtgc tgggcgataa acacggcaac gccctgtggc       900
tgaacgagcg ggagtgcagc atccagcggc ggaaccagaa ggtggtggag gaggctccta       960
gcatcttcct tgacgccgag acacgcagag ctatgggcga gcaggctgtg gccctggccc      1020
gggccgtgaa gtactccagt gctggcaccg tggagttcct cgtggcagc aagaagaact      1080
tctacttcct cgagatgaac acccggctgc aggtggagca ccccgtcacc gagtgcatca      1140
ccggcctgga cctggtgcag gagatgatcc gtgtggctaa gggctaccct ctgcggcaca      1200
aacaggccga catccggatc aacggctggg ccgtcgagtg cagggtgtac gccgaggacc      1260
cctacaagag cttcggcctg cctagcattg gcaggctcag ccagtaccag gagcccctgc      1320
acctgcccgg cgtgagggtc gactctgca tacagcccgg cagcgacatc agcatctatt      1380
acgatcccat gatcagcaaa ctgatcacct acggtagcga ccgaccgag gctctgaaga      1440
```

-continued

```
gaatggccga cgccctggac aactacgtga tacggggcgt gacccacaac atcgccctgc    1500
tgcgggaggt gatcatcaac agccggttcg tgaagggcga tatctctacc aagttcctgt    1560
ccgacgtgta ccccgacggg tttaagggcc acatgctgac caagagtgag aagaaccaac    1620
tgcttgccat cgcaagcagc ctgttcgtgg ccttccagct gcgagcccag cacttccagg    1680
agaactcccg gatgcccgtg atcaagcccg acatcgccaa ctgggagctg agcgtgaagc    1740
tgcacgacaa ggtgcacacc gtggttgcca gcaacaacgg ctcagtgttc agcgtggagg    1800
tggacggctc taagctcaac gtgaccagca cctggaatct ggccagcccg ctgctgtctg    1860
tcagcgtcga cggcacccag cggaccgtgc agtgtctgag ccgggaggcc ggcggtaaca    1920
tgagcattca gttcctgggc actgtgtaca aagtgaacat cctgacccgc ctggctgcag    1980
agctgaacaa gttcatgctg gagaaggtga ccgaagacac atcaagcgtg ctgcggagcc    2040
ccatgcctgg cgtcgtggta gccgtgtccg tgaagcccgg cgacgcggtt gccgagggcc    2100
aggagatctg cgtgatcgag gccatgaaga tgcagaacag catgaccgcc ggcaagacgg    2160
gaaccgttaa gtccgtccac tgccaggctg gcgatactgt gggcgagggc gacctgctgg    2220
tggagctgga gtgataatag gctggagcct cggtggccta gcttcttgcc ccttgggcct    2280
cccccccagcc cctcctcccc ttcctgcacc cgtacccct ccataaagta ggaaacacta    2340
cagtggtctt tgaataaagt ctgagtgggc ggc                                 2373
```

SEQ ID NO: 32          moltype = RNA    length = 2373
FEATURE                Location/Qualifiers
source                 1..2373
                       mol_type = other RNA
                       organism = synthetic construct
SEQUENCE: 32

```
gggaaataag agagaaaaga agagtaagaa gaaatataag agccaccatg gccggcttct    60
gggtgggcac cgccccactg gtggctgcgg gcaggagggg caggtggcct cctcagcagc    120
tgatgctgag cgccgccctc cgcaccctca agcacgtgct ctactactcc cgccagtgcc    180
tcatggtgtc ccgcaacctc ggctccgtcg gctacgaccc caacgagaag accttcgaca    240
agatcctcgt cgccaaccgc ggcgagatcg cctgccgcgt catccgcacc tgcaagaaga    300
tgggcatcaa gaccgtcgcc atccactccg acgtcgacgc ctcctccgtc cacgtcaaga    360
tggccgacga ggccgtctgc gttggacccg ccctacctc caagtcctac ctcaacatgg    420
acgccatcat ggaggccatc aagaagaccc gcgcccaggc cgtccacccc ggctacggct    480
tcctctccga gaacaaggag ttcgccagat gcctggctgc cgaggacgtc gtcttcatcg    540
gccctgacac ccacgctatc caggccatgg gcgacaagat agagtccaag ctcctcgcca    600
agaaggccga ggtcaacacc atccccggct tcgacggcgt cgtcaaggac gcggaagagg    660
ccgttcgcat cgcccgggaa atcggctacc ccgtcatgat caaggcctcc gccggtggag    720
gcggcaaggg catgaggatt gcctgggacg acgaggaaac gagagacggt ttccgcctct    780
cctcccagga agccgcaagc tcattcggcg acgatagact gctgatcgag aagttcatcg    840
acaatcctcg ccacatcgag atccaggtcc tcggcgacaa acacggcaac gccctctggc    900
tcaacgagcg cgagtgctcc atccagcgcc gcaaccagaa ggtcgtcgag gaggcaccct    960
ccatcttcct cgacgccgaa accaggcgcg ccatgggtga gcaggccgtg gccctggccc    1020
gagccgtcaa gtacagctcc gctgggaccg tcgagtttct ggttgactcc aagaagaact    1080
tctacttcct ggagatgaac acccgcctcc aggtcgagca tcctgtgacc gagtgcatca    1140
ccggcctcga cctcgtccag gagatgatcc gagtggccaa gggtatacccg ctccgccaca    1200
agcaggctga catccgcatc aacggctggg cggttgagtg tagggtgtac gctgaagacc    1260
cctacaagtc tttcggcctg cccagcatcg gcagactgtc ccagtaccag gagcccctcc    1320
acctccccgg cgtgaggtg gactctggca tccagcccgg ctccgacatc tccatctatt    1380
acgatcctat gatctcaaag ctgatcacct acggttccga tcgcaccgag gctctgaagc    1440
gcatggctga cgccctcgac aactacgtaa tcagaggcgt cacccacaac atcgccctcc    1500
tgagagaggt catcatcaac tcccgcttcg tgaagggtga tatctctacc aagtttctga    1560
gcgacgtgta ccctgacggg ttcaagggcc acatgctcac caagtccgag aagaaccagc    1620
tgctgccat agccagcagc ctcttcgtcg ccttccagct gagagcccag cacttccaag    1680
agaattctcg tatgcccgtc atcaagcccg acatcgccaa ctgggagctc tccgtcaagc    1740
tccacgacaa ggtccacacc gtggttgcat ccaacaacgg cagcgtgttc tccgtcgagg    1800
tcgacggaag caagctgaac gtcacctcta cctggaacct cgcctctccc cttctgtctg    1860
tgagcgtgga cggcacccag cgcaccgtgc agtgcctgtc ccgcgaggct ggcggcaaca    1920
tgtccattca attcctgggc actgtgtaca aggtgaacat cctgacacg ctcgcagccg    1980
aactcaacaa gttcatgctc gagaaggtga ccgaagacac cagctccgtg ctccgcagcc    2040
ctatgcccgg ggtggtcgtg gccgtgtccg tcaaacccgg cgacgctgtg gcggagggac    2100
aggagatctg cgtgatcgag gccatgaaga tgcagaactg catgacggcg gggaagaccg    2160
gaacagtcaa gagcgtgcat tgccaagccg gcgataccgt cggcgagggc gacttgctgg    2220
tggagctcga gtgataatag gctggagcct cggtggccta gcttcttgcc ccttgggcct    2280
cccccccagcc cctcctcccc ttcctgcacc cgtacccct ccataaagta ggaaacacta    2340
cagtggtctt tgaataaagt ctgagtgggc ggc                                 2373
```

SEQ ID NO: 33          moltype = RNA    length = 2373
FEATURE                Location/Qualifiers
source                 1..2373
                       mol_type = other RNA
                       organism = synthetic construct
SEQUENCE: 33

```
gggaaataag agagaaaaga agagtaagaa gaaatataag agccaccatg gccggcttct    60
gggtgggcac cgcgcccctg gtggccgccg gccggcgggg ccggtggcca ccccagcagc    120
tgatgctgag cgccgcccctg cggacccctga agcacgtgct gtactacagc cggcagtgcc    180
tgatggtgag ccggaacctg ggcagcgtgg gctacgaccc caacgagaag accttcgaca    240
agatcctggt ggccaaccgg ggcgagatcg cctgccgggt gatccggacc tgcaagaaga    300
tgggcatcaa gaccgtggcc atccacacgc acgtggacgc cagcagcgtg cacgtgaaga    360
tggccgacga ggccgtgtgc gtgggcccc gccccaccag caagagctac ctgaacatgg    420
acgccatcat ggaggccatc aagaagaccc gggcccaggc cgtgcacccc ggctacggct    480
tcctgagcga gaacaaggag ttcgcccggt gcctggccgc cgaggacgtg gtgttcatcg    540
```

```
gccccgacac ccacgccatc caggccatgg gcgacaagat cgagagcaag ctgctggcca   600
agaaggccga ggtgaacacc atccccggct tcgacggccgt ggtgaaggac gccgaggagg   660
ccgtgcggat cgcccgggag atcggctacc ccgtgatgat caaggccagc gccggcggcg   720
gcggcaaggg catgcggatc gcctgggacg acgaggagac ccgggacggc ttccggctga   780
gcagccagga ggccgccagc agcttcggcg acgaccggct gctgatcgag aagttcatcg   840
acaacccacg gcacatcgag atccaggtgc tgggcgacaa gcacgtgcaac gccctgtggc   900
tgaacgagcg ggagtgcagc atccagcggc ggaaccagaa ggtggtggag gaggcgccca   960
gcatcttcct ggacgccgag acccggcggg ccatgggcga gcaggccgtg gccctggccc  1020
gggccgtgaa gtacagcagc gccggcaccg tggagttcct ggtggacagc aagaagaact  1080
tctacttcct ggagatgaac acccggctgc aggtggagca ccccgtgacc gagtgcatca  1140
ccggcctgga cctggtgcag gagatgatcc gggtggccaa gggctacccg ctgcggcaca  1200
agcaggccga catccggatc aacggctggg ccgtggagtg ccgggtgtac gccgaggacc  1260
cctacaagag cttcggcctg cccagcatcg gccggctgag ccagtaccag gagcccctgc  1320
acctgcccgg cgtgcgggtg gacagcggca tccagcccgg cagcgacatc agcatctact  1380
acgacccccat gatcagcaag ctgatcacct acggcagcga ccggaccgag gccctgaagc  1440
ggatggccga cgccctggac aactacgtga tccggggcgt gacccacaac atcgccctgc  1500
tgcgggaggt gatcatcaac agccggttcg tgaagggcga catcagcacc aagttcctga  1560
gcgacgtgta ccccgacggc ttcaagggcc acatgctgac caagagcgag aagaaccagc  1620
tgctggccat cgcccagcagc ctgttcgtgg ccttccagct gcgggcccag cacttccagg  1680
agaacagccg gatgcccgtg atcaagcccg acatcgccaa ctgggagctg agcgtgaagc  1740
tgcacgacaa ggtgcacacc gtggtggcca gcaacaacgg cagcgtgttc agcgtggagg  1800
tggacgagcag caagctgaac gtgaccagca cctggaacct ggccagccct ctgctgagcg  1860
tgagcgtgga cggcacccag cggaccgtgc agtgcctgag ccgggaggcc ggcggcaaca  1920
tgagcatcca gttcctgggc accgtgtaca aggtgaacat cctgacccgg ctggccgccg  1980
agctgaacaa gttcatgctg gagaaggtga ccgaggacac cagcagcgtg ctgcggagcc  2040
ccatgcccgg cgtggtggtg gccgtgagcg tgaagccgtg cgacgccgtg gccgagggcc  2100
aggagatctg cgtgatcgag gccatgaaga tgcagaacag catgaccgcc ggcaagaccc  2160
gcaccgtgaa gagcgtgcac tgccaggccg gcgacaccgt gggcgagggc gacctgctgg  2220
tggagctgga gtgataatag gctggagcct cggtggccta gcttcttgcc ccttgggcct  2280
cccccagcc cctcctcccc ttcctgcacc cgtacccct ccataaagta ggaaacacta  2340
cagtggtctt tgaataaagt ctgagtgggc ggc                                2373
```

SEQ ID NO: 34              moltype = RNA   length = 2373
FEATURE                    Location/Qualifiers
source                     1..2373
                           mol_type = other RNA
                           organism = synthetic construct
SEQUENCE: 34

```
gggaaataag agagaaaaga agagtaagaa gaaatataag agccaccatg gccggcttct    60
gggtcggcac cgccccactc gtggcagccg gcagaagagg ccggtggcct ccccagcagc   120
tgatgctgag cgccgccctg agaaccctga agcacgtgct gtactacagc agacagtgcc   180
tgatggtgag cagaaatctg ggatctgtcg ggtacgaccc caacgagaag accttcgaca   240
agatcctggt ggccaacaga ggcgagatcc cctgcagagt gatcagaacc tgcaagagga   300
tgggcatcaa gaccgtggcc atccacagcg acgtggacgc gtccagcgtg cacgtgaaga   360
tggccgacga ggccgtgtgc gtaggccccg ctcccaccag caagagctac ctgaacatgg   420
acgccatcat ggaggccatc aagaagacca gagcccaggc tgtgcatccc ggctacggct   480
tcctgagcga gaacaaggag ttcgccaggt gtctggctgc gtgaagacgtc gtgttcatcg   540
gccccgacac ccacgcgatc caggccatgg gtgataagat cgagagcaaa ctgctggcca   600
agaaggccga ggtgaacacc atccccggct tcgacggcgt ggtgaaagac gccgaggagg   660
cagtgagaat cgccagagag atcggctacc ccgtgatgat caaggccagc gcaggtggcg   720
gaggcaaggg catgaggatt gcctgggacg acgaagagac gagggacggg ttccgactga   780
gcagccagga ggccgccagc tccttcggcg acgacagact gctgatcgag aagttcatcg   840
acaacccccag acacatcgag atacaggtgc tcggagacaa gcacggcaac gccctgtggc   900
tgaacgagag agagtgcagc atccagagaa gaaaccagaa ggtggtggag gaggccccat   960
caatcttcct cgacgccgaa accagacggg ccatgggaga gcaggccgtg gcactggcta   1020
gggccgtgaa gtacagctcc gccgaaccgt ggagtttct ggtcgactcc aagaagaact   1080
tctacttcct ggagatgaat acccgtctgc aggtggagca ccccgtgacc gagtgcatca   1140
ccggtctgga cctggtgcag gagatgatca gagtggccaa gggctaccct ctgagacaca   1200
agcaggccga catcagaatc aacggctggg ccgtggagtg cagagtgtac gccgaggacc   1260
cctacaagag cttcggcctg cccagcatcg gcagactgag ccagtaccag gagcccctgc   1320
acctgcccgg cgtgagagtg gacagcggca tccagcccgg ctctgacatc tccatatact   1380
acgacccccat gatcagcaag ctcatcacct acggcagcga cagaaccgag gccctgaaga   1440
gaatggccga cgccctggac aactacgtga tcagaggcgt gacccacaac atcgccctgc   1500
tgagagaggt gatcatcaac agcagattcg tgaagggcga catcagcacc aagttcctga   1560
gcgacgtgta ccccgacggc ttcaagggcc acatgctgac caagagcgag aagaaccagc   1620
ttctggcaat cgcctccagc ctgttcgtgg ccttccagct gagagcccag cacttccagg   1680
agaacagcag aatgcccgtg atcaagcccg acatcgccaa ctgggagctg agcgtgaagc   1740
tgcacgacaa ggtccatacg gtggtcgcca gcaacaacgg cagcgtgttc agcgtggagg   1800
tggacgagcag caagctgaac gtgaccagca cctggaacct ggcctcaccc ctcctgagcg   1860
tcagcgtcga cggcacccag agaaccgtgc agtgtctgag cagagaggca ggcggcaaca   1920
tgagcatcca gttcctgggc accgtgtaca aggtgaacat cctgaccaga ctggccgccg   1980
agctgaacaa gttcatgctg gagaaggtga ccgaggacac cagcagcgtg ctgagaagcc   2040
ccatgcccgg agtggtggtg gccgtgagcg tgaaaccggt tgacgcagtg gccgagggcc   2100
aggagatctg cgtgatcgag gccatgaaga tgcagaacag catgaccgcc ggaaagaccc   2160
gcaccgtgaa gtccgtgcac tgccaagccg cgataccgt gggcgaggggc gacctcctcg   2220
tcgagctgga gtgataatag gctggagcct cggtggccta gcttcttgcc ccttgggcct   2280
cccccagcc cctcctcccc ttcctgcacc cgtacccct ccataaagta ggaaacacta   2340
cagtggtctt tgaataaagt ctgagtgggc ggc                                2373
```

```
SEQ ID NO: 35          moltype = RNA   length = 2373
FEATURE                Location/Qualifiers
source                 1..2373
                       mol_type = other RNA
                       organism = synthetic construct
SEQUENCE: 35
gggaaataag agagaaaaga agagtaagaa gaaatataag agccaccatg gccggcttct    60
gggtcggcac agcccctctg gtggcagccg gcagaagagg acggtggcct ccccagcaac   120
tgatggtgag cgccgccctg agaaccctga agcacgtgct gtactacagc agacagtgcc   180
tgatggtgag cagaaatctg ggcagcgtgg ggtacgatcc caacgagaag accttcgata   240
agattctggt cgcgaataga ggcgagatcg cctgcagggt gatcagaacc tgcaagaaga   300
tgggcatcaa gaccgtggcc atccattcgg acgtcgacgc gagcagcgtt cacgtgaaga   360
tggcagacga ggccgtgtgc gtgggacccg ccccgaccag caagagctac ctgaacatgg   420
acgccatcat ggaggccatc aagaagaccc gcgctcaagc cgtgcacccg ggctacggct   480
ttctgagcga gaacaaggaa ttcgccaggt gtctcgccgc cgaggacgta gtcttcatcg   540
gccctgatac gcacgcgatc caggccatgg gcgacaagat cgagagcaaa ctgctggcca   600
agaaagcaga agtcaacacc atccccggct tcgacggcgt ggtgaaggac gccgaagagg   660
ctgtccgcat cgccagagag atcggctacc ctgtgatgat aaaggctagc gctggaggtg   720
gcggaaaggg catgagaatc gcctgggacg acgaggagac tagagacggc ttcagactgt   780
cctcccagga ggccgccagc tccttcggag acgacagact gctgatcgag aagttcatcg   840
acaacccag acacatcgaa atccaggtgc tcggtgacaa gcacgggaac gccctgtggc   900
tgaacgagag agagtgcagc atccagagaa gaaaccagaa ggtggtggag gaggcgccga   960
gcatctttct ggacgcggag acaaggagag cgatgggcga acaggccgtc gccctagcaa  1020
gagccgtgaa gtactccagt gccggaaccg tcgagtttct tgtcgacagc aagaagaatt  1080
tctacttcct ggagatgaac accaggctgc aggtggagca tcccgtgaca gagtgcatca  1140
ctggactgga tctggtgcag gagatgatca gggtggccaa ggctatcccc ctgagacaca  1200
agcaggccga catcagaatc aacggctggg ccgtggagtg cagagtgtac gccgaggacc  1260
cctacaagag cttcggcctg cccagcatcg gcagactgag ccagtaccag gagcccctgc  1320
acctgcccgg cgtgagagtg gacagcggca tccaaccggg gagcgatatc agcatctact  1380
acgaccccat gatcagcaag ctgataacct acggcacgca cagaaccgag gccctgaaga  1440
gaatggccga cgccctggac aactacgtga tcagaggcgt gacccacaac atcgccctgc  1500
tgagagaggt gatcatcaac tcgaggttcg tgaaaggcga catcagcacc aagttcctga  1560
gcgacgtgta tcccgacgga ttcaaaggtc acatgctgac caagagcgag aagaaccagc  1620
tgctggccat cgcctcatcc ctgttcgtgg ccttccagct gagagcccag cacttccagg  1680
agaacagcag aatgcccgtg atcaagcccg acatcgccaa ctggggagctg agcgtgaagc  1740
tgcacgacaa ggtgcacact gtcgttgcca gcaacaacgg ctccgtgttc agcgtagagg  1800
tggacggatc taagctgaac gtgacctcca cctggaacct ggcaagccct ctcctgtcag  1860
tgagcgtgga cggcacccag agaaccgtgc agtgtctgtc ccgcgaggcc ggcggaaaca  1920
tgagcatcca gttcctgggc accgtgtaca aggtgaacat cctgaccaga ctggccgccg  1980
agctgaacaa gttcatgctg gagaaagtga cggaggatac cagctccgtg ctgagaagcc  2040
ccatgcccgg agtggtggtg gccgtttccg tgaaacctgg tgacgccgtg gccgaggggc  2100
aagagatctg cgtgatcgag gccatgaaga tgcagaattc catgaccgcc ggaaagaccg  2160
gcaccgtcaa atcagtgcac tgccaggcgg gcgacacagt gggtgaggge gacctgctga  2220
tggagctgga gtgataatag gctggagcct cggtggccta gcttcttgcc ccttgggcct  2280
ccccccagcc cctcctcccc ttcctgcacc cgtacccccc ccataaagta ggaaacacta  2340
cagtggtctt tgaataaagt ctgagtgggc ggc                              2373

SEQ ID NO: 36          moltype = RNA   length = 2373
FEATURE                Location/Qualifiers
source                 1..2373
                       mol_type = other RNA
                       organism = synthetic construct
SEQUENCE: 36
gggaaataag agagaaaaga agagtaagaa gaaatataag agccaccatg gccgggttct    60
gggtggggac cgccccactc gtggccgccg ggaggagagg gaggtggcca cgcaacaac   120
taatgctaag cgccgcccta cggaccctaa agcacgtact atactacagc aggcagtgcc   180
taatggtgag caggaaccta gggagcgtgg ggtacgatcc aaacgagaag accttcgata   240
agatactagt ggccaataga ggggagatcg cctgcagagt gataaggacc tgcaagaaga   300
tggggatcaa gaccgtggcc atacacagcg acgtggacgc cagcagcgtg cacgtgaaga   360
tggccgacga ggccgtgtgt gtggggccag ccccaaccag caagagctac ctaaacatgg   420
acgcgataat ggaggcaatc aagaagacca gagcgcaagc cgtgcaccct gggtacgggt   480
tcctatccga gaacaaggag ttcgccaggt gcctagccgc ggaggacgtg gttttcatag   540
ggccagatac gcacgccatc caagccatgg gagataagat cgagagcaag ctactagcca   600
agaaggcga ggtgaacacc ataccagggt tcgacggcgt ggtgaaggac gccgaggagg   660
ccgtgaggat tgccagggag atagggtacc cagtgatgat aaaggcctct gccggtggag   720
gagggaaggg gatgcggata gcctgggacg acgaggagac gaggacggc ttcaggctaa   780
gcagccaaga ggccgcctct agcttcgggg acgataggct actaatagag aagttcatag   840
ataacccaag gcacatagag atacaagtac taggggataa acacggtaac gccctgtggc   900
tcaacgagag agagtgcagc atacaaagga ggaaccagaa ggtggttgag gaggcgccaa   960
gcatcttcct agacgccgag acacggaggg cgatgggaga acaggccgtg gccctagcca  1020
gggccgttaa gtactcaagc gcagggaccg tggagttcct agtggatagc aagaagaact  1080
tctacttcct cgagatgaat accaggctac aagtggagca cccagtaacc gagtgcatca  1140
cggggctcga tctagtgcaa gagatgataa gggtggccaa ggggtatcca ctaaggcaca  1200
agcaagcgga tataaggata aacggctggg ccgttgagtg cagggtgtac gccgaggatc  1260
cctacaagtc cttcgggcta ccaagcatag gaggctatc tcaataccaa gagccactac  1320
acctaccagg ggtgagggtt gatagcggga tccaaccagg gtctgatata agcatctact  1380
acgatcccat gatatctaag ctaataacct acggagcga caggacggag gccctaaaga  1440
ggatggcgga cgccctagat aactacgtga tacgcggggg gacccacaac attgccctac  1500
taagggaggt gatcataaat tctaggttcg tgaagggaga tatatcaacg aagtttctaa  1560
```

```
gcgacgttta cccagacggg ttcaaggggc acatgctaac caagagcgag aagaatcaac   1620
tgctcgccat cgcctcatca ctattcgtgg ccttccaact aagggcccaa cacttccaag   1680
agaatagccg gatgcctgtg ataaagccag atatagccaa ttgggaacta agcgtgaagc   1740
tccacgataa ggtgcacacc gtggtggcca gcaacaacgg atctgtgttc agcgtggagg   1800
tggacggtag caagctcaac gtgaccagca cctggaatct agccagccca ctactgagcg   1860
tcagcgttga cgggacccaa aggaccgtgc agtgcttgag cagggaggcc ggagggaata   1920
tgtccattca attcctaggg acggtctaca aggtaaacat actaacccga ctagccgccg   1980
agctcaacaa gttcatgcta gagaaggtga ccgaggatac gtctagcgtg ctacgtagcc   2040
caatgccagg agtggtagtt gccgtgtcag tgaagccagg ggacgccgta gccgagggac   2100
aagagatctg cgtgatcgag gccatgaaga tgcagaatag catgaccgca gggaagacgg   2160
ggacggtgaa gtctgttcac tgccaagccg gggataccgt aggggaggga gatctactcg   2220
tggagctaga gtgataatag gctggagcct cggtggccta gcttcttgcc ccttgggcct   2280
ccccccagcc cctcctcccc ttcctgcacc cgtacccccct ccataaagta ggaaacacta   2340
cagtggtctt tgaataaagt ctgagtgggc ggc                                2373
```

SEQ ID NO: 37              moltype = RNA    length = 2373
FEATURE                    Location/Qualifiers
source                     1..2373
                           mol_type = other RNA
                           organism = synthetic construct
SEQUENCE: 37

```
gggaaataag agagaaaaga agagtaagaa gaaatataag agccaccatg gccggcttct   60
gggtgggcac cgcgcccctg gtggccgccg gcagaagagg caggtggccg ccccagcagc   120
tgatgctgag cgccgccctg agaaccctga agcacgtgct gtactacagc agacagtgcc   180
tgatggtgag cagaaacctg ggcagcgtgg gctacgaccc caacgagaag accttcgaca   240
agatcctggt ggccaacaga ggcgagatcg cctgcagagt gatcagaacc tgcaagaaga   300
tgggcatcaa gaccgtggcc atccacagcg acgtggacgc cagcagcgtg cacgtgaaga   360
tggccgacga ggccgtgtgc gtgggcccg cgcccaccag caagagctac ctgaacatgg   420
acgccatcat ggaggccatc aagaagacca gagcccaggc cgtgcacccc ggctacggct   480
tcctgagcga gaacaaggag ttcgccaggt gcctggccga gcagacgtg gtgttcatcg   540
gccccgacac ccacgccatc caggccatgg gcgacaagat cgagagcaag ctgctggcca   600
agaaggccga ggtgaacacc atcccggct tcgacggcgt ggtgaaggac gccgaggagg   660
ccgtgagaat cgccagagag atcggctacc ccgtgatgat caaggccagc gccggcggcg   720
gcggcaaggg catgagaatc gcctgggacg acgaggagac caagagactg ttcagactga   780
gcagccagga ggccgccagc agcttcggcg acgacagact gctgatcgag aagttcatcg   840
acaaccccag acacatcgag atccaggtgc tgggcgacaa gcacggcaac gccctgtggc   900
tgaacgagag agagtgcagc atccagagaa gaaaccagaa ggtggtggag gaggcgccca   960
gcatcttcct ggacgccgag accagaagag ccatgggcga gcaggccgtg gccctggcca   1020
gagccgtgaa gtacagcagc gccggcaccg tggagttcgt ggtggacgac aagaagaact   1080
tctacttcct ggagatgaac accagactgc aggtggagca ccccgtgacc gagtgcatca   1140
ccggcctgga cctggtgcag gagatgatca gagtggccaa gggctaccca ctgagacaca   1200
agcaggccga catcagaatc aacggctggg ccgtggagtg cagagtgtac gccgaggacc   1260
cctacaagag cttcggcctg cccagcatcg gcagactgag cgagactgac accgtgtac   1320
atctacctgg tgtccgagtg gacagcggca tccagcccgg cagcgacatc agcatctact   1380
acgaccccat gatcagcaag ctgatcacct acggcagcga cagaaccgag gccctgaaga   1440
gaatggccga cgccctggac aactacgtga tcagaggcgt gacccacaac atcgccctgc   1500
tgagagaggt gatcatcaac agcagattcg tgaaggccga catcagcacc aagttcctga   1560
gcgacgtgta ccccgacggc ttcaaggggc acatgctgac caagagcgag aagaaccagc   1620
tgctggccat cgccagcagc ctgttcgtgg ccttccagct gagagcccag cacttccagg   1680
agaacagcag aatgcccgtg atcaagcccg acatcgccaa ctgggagctg agcgtgaagc   1740
tgcacgacaa ggtgcacacc gtggtggcca gcaacaacgg cagcgtgttc agcgtggagg   1800
tggacggcag caagctgaac gtgaccagca cctggaacct ggccagccca ctgctgagcg   1860
tgagcgtgga cggcacccag agaaccgtgc agtgcctgag cagagaggcc ggcggcaaca   1920
tgagcatcca gttcctgggc accgtgtaca aggtgaacat cctgaccaga ctggccgccg   1980
agctgaacaa gttcatgctg gagaaggtga ccgaggacac cagcagcgtg ctgagaagcc   2040
ccatgcccgg cgtggtggtg gccgtgagcg tgaagcccgg cgacgccgtg gccgagggcc   2100
aggagatctg cgtgatcgag gccatgaaga tgcagaacag catgaccgcc ggcaagaccg   2160
gcaccgtgaa gagcgtgcac tgccaggccg gcgacaccgt gggcgagggc gacctgctgg   2220
tggagctgga gtgataatag gctggagcct cggtggccta gcttcttgcc ccttgggcct   2280
ccccccagcc cctcctcccc ttcctgcacc cgtacccccct ccataaagta ggaaacacta   2340
cagtggtctt tgaataaagt ctgagtgggc ggc                                2373
```

SEQ ID NO: 38              moltype = RNA    length = 2350
FEATURE                    Location/Qualifiers
source                     1..2350
                           mol_type = other RNA
                           organism = synthetic construct
SEQUENCE: 38

```
gggaaataag agagaaaaga agagtaagaa gaaatataag agccaccatg gcaggcttct   60
gggttggcac tgcccactc gtggccgccg gcagaagggg aaggtggcct ccccagcagc   120
tcatgctgtc cgccgctctg cgaaccctga agcacgtgct gtattatagc aggcagtgcc   180
tcatggtttc ccggaacctg gggagcgtgg gctatgaccc taatgagaag actttcgaca   240
agatcctggt cgctaacaga ggcgagatcg cctgcagggt gatcagaaca tgcaagaaga   300
tgggcatcaa gaccgtcgcg atccatagcg acgtggatgc cagcagcgtt cacgtcaaga   360
tggccgacga ggctgtgtgc gtcggcccg ccccaacttc caagagctat ctgaacatgg   420
acgccataat ggaggctatc aagaagacca gagcccaggc agttcatccc ggctacggat   480
tcctgagcga gaacaaggag ttcgctagat gtctggccgc cgaagacgtg gttttcatcg   540
gtccagacac ccatgccatc caagccatgg gcgataagat cgagagcaag ctcctggcca   600
agaaggccga ggtgaacacc atcccccggct tcgatggcgt ggtgaaggac gcggaggagg   660
```

```
cagtgcgcat tgccagggag atcggctacc ccgtgatgat caaggcttcc gcaggggggag  720
gcggcaaagg catgcggatt gcctgggatg atgaagaaac cagagatggc ttcagactgt  780
caagccagga ggccgccagc agcttcggcg acgacagact gctgatcgag aagtttatag  840
ataacccccg acacatagaa atccaggtgc tgggagacaa gcacggcaac gctctgtggc  900
tgaacgagcg ggaatgcagt atccagagga gaaaccagaa ggtggttgag gaggcccct  960
caatcttcct ggatgccgag acaagacgcg ccatgggtga gcaggctgta gccctcgccc 1020
gtgccgtgaa gtatagcagc gccgggacag tggagttctt ggtcgactcc aagaagaatt 1080
tctattttct ggagatgaac actcggctcc aagtagagca ccccgtgact gagtgcatta 1140
caggccttga tctggtgcag gagatgatta gggttgccaa gggctaccct ctgcgccaca 1200
agcaggccga catcaggatc aatggctggg ctgtcgagtg tagggtgtac gcagaggacc 1260
cgtacaagag cttcggcctt ccctctattg gcaggctgag ccagtaccag gagcctctgc 1320
acctacccgg cgttcgcgtg gacagcggta tccaaccagg ctctgatatc agcatttatt 1380
acgacccaat gatctcaaag ctgatcacat acggcagcga cagaaccgag gccctgaagc 1440
gaatggccga cgccctggac aactacgtga tccggggcgt cacacataac attgccctgc 1500
tgagagaggt gatcattaat tctcggttcg tcaaaggcga catcagcact aagtttctga 1560
gcgacgtgta ccccgacggg tttaaaggcc acatgctgac aaagagcgag aagaaccagt 1620
tgctggccat cgcctctagc ctgttcgtag ccttccagct gcgagcacag cacttccagg 1680
agaatagcag aatgccagtg atcaagcccg acatcgctaa ctgggagctg agcgtgaagc 1740
tccatgataa ggtccacaca gttgtggcca gcaacaacgg ctcagtgttc agcgtggagg 1800
tagacggctc caagctgaac gtgaccagca cttggaatct ggccagcccc ctgctgagcg 1860
tgtccgtgga cggcacccag agaaccgtgc agtgcctgag cagggaggcc gggggcaaca 1920
tgtccatcca gtttctgggg accgtctata aggttaacat cctgactaga ctggcggctg 1980
agcttaacaa gtttatgtta gagaaagtga ccgaggatac aagcagccgtg ctgcgtagcc 2040
ccatgcctgg cgtggtcgtg gccgtgagcg tcaagccagg cgatgcagtg gctgagggcc 2100
aggagatttg tgtgatagag gccatgaaga tgcagaactc tatgaccgcc ggaaagactg 2160
gcaccgtgaa gtctgtccat tgtcaggccg gagacaccgt gggggaagga gacctgctgg 2220
tcgagctgga gtgataatag gctggagcct cggtggccat gcttcttgcc ccttgggcct 2280
cccccagcc cctcctcccc ttcctgcacc cgtacccccg tggtctttga ataaagtctg 2340
agtgggcggc                                                       2350
```

```
SEQ ID NO: 39          moltype = RNA   length = 1806
FEATURE                Location/Qualifiers
source                 1..1806
                       mol_type = other RNA
                       organism = synthetic construct
SEQUENCE: 39
gggaaataag agagaaaaga agagtaagaa gaaatataag agccaccatg gccgccgccc   60
ttagggtcgc agccgtgggc gctagactgt cagtgctggc cagcggccta agagccgccg  120
ttaggagcct gtgcagccag gctactagcg tgaacgagag aatagagaac aaacgccgta  180
cagctctgct aggaggaggc cagagacgta tcgacgccca gcacaagcgg ggcaagctga  240
ccgcccggga gcgcatcagc ctcctgcttg accccggcag ctttgttgag tcggacatgt  300
tcgtggagca ccggtcgct gacttcggca tggctgccga caagaacaag ttccccggcg  360
actccgtggt gacaggaagg ggacggatca acggccggct ggtgtacgtg ttctctcagg  420
acttcactgt gttcggcggc tcccttttctg gcgcccacgc ccagaagatc tgtaagatta  480
tggaccaggc aatcaccgtg ggagctcccg tcatcggcct gaacgactca ggcggcgccc  540
gaatccagga gggcgtggag agcctggccg ggtacgcaga cattttcctg agaaacgtga  600
ccgctagcgg cgttatccca cagatcagcc tgatcatggg accttgcgct gggaggcag  660
tctacagccc agccctgact gattttacct tcatggtgaa agacacaagc tacctgttca  720
tcactgggcc ggacgtagtt aagagtgtga ctaacgagga cgtgacccag gaggagctgg  780
gcggagccaa gacccatacg actatgagcg gtgtggcgca ccgcgccttc gagaacgacg  840
tggacgccgt gtgcaatctg cgcgacttct tcaattacct gcccttaagc agccaagatc  900
ccgcacccgt gcgggagtgc cacgatccaa gcgataggct ggtgcccgag ctggacacca  960
ttgtgcctct ggagtcaact aaggcttaca acatggttga catcatccac agcgtggtcg 1020
acgagcgcga gttcttcgag atcatgccca actacgcgaa gaatatcatc gtgggctttg 1080
cccgcatgaa cggccggacc gtcgggatcg tcggcaatca acctaaggtc gccagcggtt 1140
gcctggacat caacagctcg gtgaagggcg ccaggttcgt tagattctgc gacgctttca 1200
acatccctct gatcactttc gtagacgttc ccggcttcct ccctgggacc gcacaggagt 1260
acggaggaat cattaggcac ggcgccaagc tgctctacgc cttcgctgag gctaccgtgc 1320
ctaaggtgac cgtgatcact aggaaggcct acggtggcgc ctacgacgtc atgagcagca 1380
agcacctgtg tggagacaca aactacgcct ggcccacagc tgagattgcg gttatgggag 1440
ccaagggcgc cgtggagatt attttcaagg ccacgagaa cgtggaggcc gcccaggccg 1500
agtacatcga gaagtttgcc aacccccttcc ctgccgccgt gagaggattt gtggacgata 1560
ttatccagcc ctcctccacc agagccagga tctgctgcga cctcgacgtt ttggcctcga 1620
agaaggtgca acggcccctgg cgcaaacacg caaacatccc gctgtgataa taggctggag 1680
cctcggtggc ctagcttctt gcccccttggg cctcccccca gcccctcctc ccctctgctgc 1740
acccgtaccc cctccataaa gtaggaaaca ctacagtggt ctttgaataa agtctgagtg 1800
ggcggc                                                           1806
```

```
SEQ ID NO: 40          moltype = RNA   length = 1806
FEATURE                Location/Qualifiers
source                 1..1806
                       mol_type = other RNA
                       organism = synthetic construct
SEQUENCE: 40
gggaaataag agagaaaaga agagtaagaa gaaatataag agccaccatg gccgccgccc   60
tgagggtggc cgcagtcggc gcacgactct ccgtgctggc tagcggcctg agagccgctg  120
tgcggagcct gtgctctcag gctacgtcgg ttaacgagcg tatagagaac aagcggcgca  180
ccgctctcct tggcggcggc cagaggagaa tagacgccca gcataagcgt ggaaagctga  240
ccgccagaga gagaatatcc cttctcctgg atcccgggtc tttcgtggag agcgacatgt  300
```

```
tcgtcgaaca caggtgcgcc gactttggga tggctgctga caagaacaag ttccctggag   360
attcagtagt gacaggtagg ggcaggatca acggcagact ggtctacgtg tttttcccaag   420
atttcaccgt gttcggcggc agcctgagcg gcgctcacgc acagaagatc tgcaagatca   480
tggatcaggc aattacagtg ggcgcccctg tgatcggcct gaacgacagt ggcggcgcga   540
gaattcagga gggagtggaa tctctggctg ggtacgccga catttcctg cgaaacgtca   600
cagccagcgg ggttattccc caaatttcgc tcatcatggg gccttgcgcc ggcggtgctg   660
tgtacagccc tgccctcacc gacttcacct tcatggtgaa agacacctcc tatctgttca   720
ttacaggacc cgacgtggtg aaatccgtga caaacgagga cgtgacccag gaggaactcg   780
gcggcgctaa gacccacaca accatgtcag gcgttgccca cagagcgttc gagaacgtca   840
tggacgctct gtgcaacctg agagacttct tcaactacct gcctctgagc tcgcaggacc   900
cagctcccgt gcgggagtgt cacgatccca gcgatcgtct ggtgcctgaa ctggacacaa   960
tcgttccact ggagtccacc aaggcctata atatggtgga cattatccac agcgtggtgg  1020
acgaaaggga attcttcgag atcatgccca attacgccaa gaatatcatc gtgggcttcg  1080
ccagaatgaa cggccgcacc gtgggcatcg ttggcaatca acctaaggtg gccagcgct  1140
gcctcgacat taacagcagt gtgaaaggcc ccagattcgt gcggtttttgc gacgcctta  1200
atatccctct gatcaccttc gtggacgtgc ccgggtttct gccgggcacc gcccaggagt  1260
acggagggat cattagacac ggtgctaagc tgctgtacgc cttcgccgag gccacagtgc  1320
ccaaggttac cgttatcaca cgcaaagcct acggcggagc ctacgacgtg atgagcagca  1380
aacacctctg tggcgacacc aactacgctt ggcccacagc cgagattgcc gtgatgggcg  1440
ccaagggcgc tgtgtggagatc attttcaaag gccacgagaa cgtggaggct gcccaggccg  1500
agtatatcga gaagttcgca aaccccttcc cagcagcagt gcggggcttc gtcgacgaca  1560
tcatccagcc ttctagcacc agggcaagaa tctgctgtga ccttgacgtg tcgccagta  1620
agaaggtcca gaggccgtgg agaaagcacg ctaacattcc cctgtgataa taggctggag  1680
cctcggtggc ctagcttctt gcccctttggg cctcccccca gcccctcctc cccttcctgc  1740
acccgtaccc cctccataaa gtaggaaaca ctacagtggt ctttgaataa agtctgagtg  1800
ggcggc                                                              1806
```

SEQ ID NO: 41          moltype = RNA  length = 1806
FEATURE                Location/Qualifiers
source                 1..1806
                       mol_type = other RNA
                       organism = synthetic construct
SEQUENCE: 41

```
gggaaataag agagaaaaga agagtaagaa gaaatataag agccaccatg gccgccgccc   60
tgcggggttgc agccgtgggc gcccggctga gcgtgttggc ctcagggctg agagccgctg  120
tgcggagcct gtgcagccag gccaccagcg tgaacgagcg gatcgagaac aagcggcgga  180
ctgccctgct gggcggcggg cagaggagaa tcgacgccca gcacaagcgg ggcaagctga  240
ccgcccggga gaggattagc ctgctgctgg acccccggcag cttcgtggag agcgacatgt  300
tcgtcgagca ccggtgcgcc gacttcggca tggcagctga caagaacaag ttcccgggcg  360
acagcgtggt gaccggccgg ggccggatca acggccggct ggtgtacgtg ttcagccagg   420
acttcaccgt gttcggcggc agcctgagcg gcgcccacgc ccagaagatc tgcaagatca   480
tggaccaggc catcactgtc ggcgcacccg tgatcggcct gaacgacagc ggcggcgcac   540
gtatccagga gggtgtagaa tctctggccg gctacgccga catcttcctg ggcaacgacg   600
ccgcctcagg ggtgattcct cagatctcgc tgatcatggg ccctgcgcc ggaggtgctg   660
tgtacagccc cgccctgacc gacttcacat tcatggtgaa ggacaccagc tacctgttca   720
tcaccggccc cgacgtggtg aaatctgtga ccaacgagga cgtgacccag gaggagttag   780
gaggcgccaa gacccacacc accatgagtg gcgtggccca ccgggccttc gagaacgacg   840
tggacgccct gtgcaacctg cgggacttct tcaactacct gccctgtca agtcaggacc   900
ccgctccggt acgggagtgc cacgaccca gcgatagact ggtgcccgag ctggacacca   960
tcgtgcccct ggagagcacc aaggcctaca acatggtgga catcatccac tctgtggtag  1020
acgagcggga gttcttcgag atcatgccca actacgccaa gaacatcatc gtgggcttca  1080
ctcgcatgaa cggtcgtacc gttggtatcg tcggaaacca gcccaaggtg gcctccggtt  1140
gcctcgatat caactccagc gtaaagggcg ctcggttcgt gcggttctgc gacgccttca  1200
acattccact gatcacattc gtggacgtgc ccggcttcct gccgggcacc gcccaggagt  1260
acggcggcat catccggcac ggagcaaagc tgctgtacgc cttcgccgag gccaccgtgc  1320
ctaaggtgac cgtgatcacc cggaaggcct acggcggcgc atacgacgtg atgagcagca  1380
agcacctgtg cggcgacaca aattacgctt ggcccactgc cgagatcgcc gtgatgggtg  1440
ctaagggagc cgtggagatc atcttcaagg ccacgagaa cgtggaggca gcccaggccg  1500
agtacatcga gaagttcgcc aacccctttcc ccgccgcggt ccgcggattt gttgacgata  1560
tcatccagcc cagcagcacc cgggcccgaa tctgctgca cctagacgta ttggcctcta  1620
agaaggtgca gcggccctgg cggaagcacg caaacatccc actgtgataa taggctggag  1680
cctcggtggc ctagcttctt gcccctttggg cctcccccca gcccctcctc cccttcctgc  1740
acccgtaccc cctccataaa gtaggaaaca ctacagtggt ctttgaataa agtctgagtg  1800
ggcggc                                                              1806
```

SEQ ID NO: 42          moltype = RNA  length = 1806
FEATURE                Location/Qualifiers
source                 1..1806
                       mol_type = other RNA
                       organism = synthetic construct
SEQUENCE: 42

```
gggaaataag agagaaaaga agagtaagaa gaaatataag agccaccatg gccgccgcgc   60
tcagagttgc cgcggtcggc gcacgcctga gcgtgctggc cagcggcctg cgtgcagcag   120
tccggagcct gtgcagccag gccaccagcg tgaacgagcg gatcgagaac aagcggcgga   180
ccgcactcct gggcggcggt caacgcagga ttgacgccca gcacaagcgg ggcaagctga   240
ccgcccggga gcggattagc ctgctgctgg acccccggcag cttcgtggag agcgacatgt   300
ttgtcgaaca ccggtgcgcc gacttcggca tggccgctga caagaacaag ttccccggcg   360
acagcgtggt gaccggccgg ggccggatca acggccggct ggtgtacgtg ttcagccagg   420
acttcaccgt gttcggcggc agcctgagcg gcgcccacgc ccagaagatc tgcaagatca   480
```

-continued

```
tggaccaggc catcaccgtg ggtgctccgg tgatcggcct gaacgactca ggaggtgccc      540
ggatccagga gggagtggaa tctctggccg gctacgccga catcttcctg cggaacgtga      600
ccgctagcgg cgtgatacct caaatttctc tgatcatggg accatgcgct ggcggggccg      660
tgtacagccc cgccctgacc gactttacgt tcatggtgaa ggacaccagc tacctgttca      720
tcaccggccc cgacgtggtc aagtccgtga ccaacgagga cgtgacccag gaggaactcg      780
gtggggccaa gacccacacc accatgtccg gcgttgccca ccgggccttc gagaacgacg      840
tggacgccct gtgcaacctg cgggacttct tcaactacct gcccctgtct tcacaagatc      900
ctgctccagt gcgggagtgc cacgacccca gcgaccgttt ggtgcccgag ctggacacca      960
tcgtgcccct ggagagcacc aaggcctaca acatggtgga catcatccac tccgttgtag     1020
acgagcggga gttcttcgag atcatgccca actacgccaa gaacatcatc gtgggcttcg     1080
cccgtatgaa cggccgtacc gtcgggattg tggggaacca gcccaaggtt gcttctgggt     1140
gcctagacat caactcaagc gtcaaagggg cccggttcgt gcggttctgc gacgccttca     1200
acattcccct gatcacgttc gttgacgtgc ccggcttcct gcccggcacc gcccaggagt     1260
acggcggcat catccggcac ggtgccaaac tgctgtacgc cttcgccgag gccaccgttc     1320
ccaaggtgac cgtgatcacc cggaaagctt acggagggc ttacgacgtg atgagcagca     1380
agcacctgtg cggcgacaca aattacgctt ggcctaccgc cgagatcgcc gtgatgggcg     1440
caaagggcgc tgttgagatc atcttcaagg gccacgagaa cgtggaggct gctcaggccg     1500
agtacatcga gaagttcgcc aaccccttcc ccgctgccgt gcggggtttc gtggacgata     1560
ttattcagcc cagcagcacc cgggccagaa tctgctgcga cctgggacgtt ttggcatcaa     1620
agaaggtgca gcggccctgg cggaagcacg ccaatatccc tctgtgataa taggctggag     1680
cctcggtggc ctagcttctt gcccccttggg cctccccca gccccctcctc cccttcctgc     1740
acccgtaccc cctccataaa gtaggaaaca ctacagtggt ctttgaataa agtctgagtg     1800
ggcggc                                                                 1806

SEQ ID NO: 43          moltype = RNA  length = 1806
FEATURE                Location/Qualifiers
source                 1..1806
                       mol_type = other RNA
                       organism = synthetic construct
SEQUENCE: 43
gggaaataag agagaaaaga agagtaagaa gaaatataag agccaccatg gccgccgccc       60
ttcgggttgc agcggtcggt gctcggctga gcgtgctcgc ttccggtctt agggctgctg      120
tgcggagcct gtgcagccag gccacctccg tcaacgagcg catcgagaac aagcgccgca      180
ctgccctgct gggcggaggc cagaggcgaa tcgacgcgca gcacaagcgc ggcaagctca      240
ccgccaggga acggatctcc ctcctcctcg accccggctc cttcgtcgag tccgacatgt      300
tcgtagaaca ccgctgcgcc gacttcggca tggccgcaga caagaacaag ttccccggcg      360
actccgtcgt caccggccgc ggccgcatca acggccgcct cgtctacgtc ttctcccagg      420
acttcaccgt cttcggcggc tccctctccg cgcccacgc ccagaagatc tgcaagatca      480
tggaccaggc catcaccgtc ggcgccccgg tcatcggcct caacgactcc ggcggcgcca      540
gcatccagga gggagtcgaa tccctcgccg gctacgccga catcttcctc cgcaacgtca      600
ccgcctccgg cgtcatcccg cagatcagcc ttatcatggg ccccctgcgc cggtggtgctg      660
tctacagtcc ggccctcacc gactttacgt tcatggtcaa ggacacctcc tacctcttca      720
tcactggccc cgacgtcgtc aagtccgtca ccaacgagga cgtcaccag gaggagctcg      780
gaggcgccaa gacccacacc accatgtccg gtgtggccca ccgcgccttc gagaacgacg      840
ttgacgccct ctgcaacctc cgcgacttct tcaactacct tccactcagc tcacaggacc      900
ctgctcctgt acgcgagtgc cacgacccct ccgacaggct ggttcccgag ctcgacacca      960
tcgtgccgct cgagtccacc aaggcctaca acatggtcga catcatccat agcgtggtcg     1020
acgagcgcga gttcttcgag atcatgccca actacgccaa gaacatcatc gtcggcttcg     1080
cgcggatgaa cggcaggacc gtcggtatag tcggcaacca gcccaaggtc gccagcgggt     1140
gcctagatat taactcctcc gttaaagggg caagattcgt ccgcttctgc gacgccttca     1200
acatcccctt gattaccttc gtggacgtcc ccggcttcct ccccggaaca gcccaggagt     1260
acggcggcat catccgccac ggtgccaaac tcctctacgc cttcgccgag gccaccgtcc     1320
ccaagtgac cgtcatcacc cgaaaggcct acggaggcgc ttacgacgtc atgtcctcca     1380
agcacctctg cggcgacacc aattacgctt ggcctactgc cgagatcgcc gtcatgggcg     1440
ctaaaggagc tgttgagata atcttcaagg gccacgagaa cgtcgaggcc gcgcaggccg     1500
agtacattga gaagttcgcc aaccccttcc ccgcagccgt ccgcggtttc gtggacgaca     1560
ttattcaacc ttcttctacc cgtgcccgta tctgctgcga cctggacgtg ctcgcctcca     1620
agaaggtcca gcgcccctgg cgcaagcacg ccaatatccc actctgataa taggctggag     1680
cctcggtggc ctagcttctt gccccttggg cctcccccca gcccctcctc cccttcctgc     1740
acccgtaccc cctccataaa gtaggaaaca ctacagtggt ctttgaataa agtctgagtg     1800
ggcggc                                                                 1806

SEQ ID NO: 44          moltype = RNA  length = 1806
FEATURE                Location/Qualifiers
source                 1..1806
                       mol_type = other RNA
                       organism = synthetic construct
SEQUENCE: 44
gggaaataag agagaaaaga agagtaagaa gaaatataag agccaccatg gccgccgccc       60
tgcgggtggc cgccgtgggc gcccggctga gcgtgctggc cagcggcctg cgggccgccg      120
tgcggagcct gtgcagccag gccaccagcg tgaacgagcg gatcgagaac aagcggcgga      180
ccgccctgct gggcggcggc cagcggcgga tcgacgccca gcacaagcgg ggcaagctga      240
ccgcccggga gcggatcagc ctgctgctgg accccggcag cttcgtggag agcgacatgt      300
tcgtggagca ccggtgcgcc gacttcggca tggccgccga caagaacaag ttccccggcg      360
acagcgtggt gaccggccgg ggcggatca acggccggct ggtgtacgtg ttcagccagg      420
acttcaccgt gttcggcggc agcctgagcg cgcccacgc ccagaagatc tgcaagatca      480
tggaccaggc catcaccgtg ggcgcgcccg tgatcggcct gaacgacagc ggcggcgccc      540
ggatccagga gggcgtggag agcctggccg gctacgccga catcttcctg cggaacgtga      600
ccgccagcgg cgtgatcccg cagatcagcc tgatcatggg cccctgcgcc ggcggcgccg      660
```

```
tgtacagccc cgccctgacc gacttcacct tcatggtgaa ggacaccagc tacctgttca      720
tcaccggccc cgacgtggtg aagagcgtga ccaacgagga cgtgacccag gaggagctgg      780
gcggcgccaa gacccacacc accatgagcg gcgtggccca ccgggccttc gagaacgacg      840
tggacgccct gtgcaacctg cgggacttct tcaactacct gcccctgagc agccaggacc      900
ccgcgcccgt gcgggagtgc cacgacccca gcgaccggct ggtgcccgag ctggacacca      960
tcgtgcccct ggagagcacc aaggcctaca acatggtgga catcatccac agcgtggtg     1020
acgagcggga gttcttcgag atcatgccca actacgccaa gaacatcatc gtgggcttcg     1080
cccggatgaa cggccggacc gtgggcatcg tgggcaacca gcccaaggtg gccagcggct     1140
gcctggacat caacagcagc gtgaagggcg cccggttcgt gcggttctgc gacgccttca     1200
acatcccact gatcaccttc gtggacgtgc ccggcttcct gcccggcacc gcccaggagt     1260
acggcggcat catccggcac ggcgccaagc tgctgtacgc cttcgccgag gccaccgtgc     1320
ccaaggtgac cgtgatcacc cggaaggcct acggcggcgc ctacgacgtg atgagcagca     1380
agcacctgtg cggcgacacc aactacgcct ggcccaccgc cgagatcgcc gtgatgggcg     1440
ccaagggcgc cgtggagatc atcttcaagg gccacgagaa cgtggaggcc gcccaggccg     1500
agtacatcga gaagttcgcc aacccccttcc ccgccgccgt gcggggcttc gtggacgaca     1560
tcatccagcc cagcagcacc cgggcccgga tctgctgcga cctggacgtg ctggccagca     1620
agaaggtgca gcggccctgg cggaagcacg ccaacatccc gctgtgataa taggctggag     1680
cctcggtggc ctagcttctt gcccccttggg cctcccccca gcccctcctc cccttcctgc     1740
acccgtaccc cctccataaa gtaggaaaca ctacagtggt cttttgaataa agtctgagtg     1800
ggcggc                                                                  1806
```

SEQ ID NO: 45         moltype = RNA   length = 1806
FEATURE               Location/Qualifiers
source                1..1806
                      mol_type = other RNA
                      organism = synthetic construct
SEQUENCE: 45

```
gggaaataag agagaaaaga agagtaagaa gaaatataag agccaccatg gccgcgcgccc      60
tgcgggtcgc ggccgtggga gccagactgt ccgtgctagc ctcagggctg cgcgccgctg     120
tgagaagcct gtgcagccag gccaccagcg tgaacgagaa catcgagaac aagagaagaa     180
ccgctctgct gggtggcggc cagagaagaa tcgacgccca gcacaagaga ggcaagctga     240
ccgccagaga gagaatcagc ctgctgctgg acccggcag cttcgtggag agcgacatgt     300
tcgtggagca ccgctgcgcc gacttcggca tggccgccga caagaacaag ttccccggcg     360
acagcgtggt gaccggcaga ggcagaatca acggcagact ggtgtacgtg ttcagccagg     420
acttcaccgt gttcggcggc tccctgagcg gggcccacgc ccagaagatc tgcaagatca     480
tggaccaagc cattaccgtg ggcgctcctg tgatcggcct gaacgactcc ggcggcgcga     540
ggatccagga gggcgtggaa agcctggcgg gttacgccga catcttcctg agaaacgtca     600
ccgcatccgg agtgatttcc cagatcagcc tgatcatggg tccctgcgcg ggcggagccg     660
tgtacagccc cgccctgacc gacttcacct tcatggtgaa ggacaccagc tacctgttca     720
tcaccggccc cgacgtggtc aagagcgtga ccaacgagga cgtgacccaa gaggagctcg     780
gaggcgccaa gacccacacc accatgagcg gcgtggccca cagagccttc gagaacgacg     840
tggacgccct gtgcaacctg agagacttct tcaactacct gcccctgagt tctcaggatc     900
ctgcaccgt gagagagtgc cacgacccca gcgaccggct ggtgcccgag ctggacacca     960
tcgtgcccct ggagagcacc aaggcctaca acatggtgga catcatccac agcgttgtgg     1020
acgagagaga gttcttcgag atcatgccca actacgccaa gaacatcatc gtgggcttcg     1080
ccagaatgaa cggcaggact gtgggaatcg tgggcaacca gcccaaggtg gccagcggct     1140
gcctggacat caacagcagc gtgaagggcg ccagattcgt gagattctgc gacgccttca     1200
acatcccgct gatcacattc gtggacgttc ccggcttcct gcccggcaca gcccaggagt     1260
acggcggcat catcagacac ggcgccaagc tgctgtacgc cttcgccgag gccaccgtgc     1320
ccaaggtgac cgtgatcacc agaaaggcct acggcggagc ttacgacgtg atgagcagca     1380
agcacctgtg cggtgacact aactacgcct ggccgaccgc cgagatcgcc gtgatgggcg     1440
ccaaaggggc cgtggagatc atcttcaagg gccacgagaa cgtggaggcc gcccaggccg     1500
agtacatcga gaagttcgcc aaccccttcc ccgccgccgt caggggtttc gtggacgaca     1560
tcatccagcc ctcctccacc agagccagaa tctgctgcga cctggacgta ctggccagca     1620
agaaggtgca acgtccctgg agaaagcacg ccaacatccc tctgtgataa taggctggag     1680
cctcggtggc ctagcttctt gccccttggg cctcccccca gcccctcctc cccttcctgc     1740
acccgtaccc cctccataaa gtaggaaaca ctacagtggt cttttgaataa agtctgagtg     1800
ggcggc                                                                  1806
```

SEQ ID NO: 46         moltype = RNA   length = 1806
FEATURE               Location/Qualifiers
source                1..1806
                      mol_type = other RNA
                      organism = synthetic construct
SEQUENCE: 46

```
gggaaataag agagaaaaga agagtaagaa gaaatataag agccaccatg gccgcagccc      60
tcagagtggc tgccgtggga gccagactca gcgtgctcgc ctcaggcctg cgggccgcag     120
tcagaagcct gtgcagccag gcaacctcag tgaacgagag aatcgagaac aagagacgga     180
ccgcccctgct gggtggcggg caaagaagaa ttgacgccca gcacaagaga ggcaagctga     240
ccgcccgcga gcgcatcagc ctgctgctgg acccggcag cttcgtggag agcgacatgt     300
tcgtggagca tcggtgtgcc gacttcggca tggccgccga caagaacaag ttccccggcg     360
acagcgtggt gaccggcaga ggcagaatca cggcagact ggtgtacgtg ttctcacaag     420
actttaccgt cttcggagga tccctgtcag gggctcacgc ccagaagatc tgcaagatca     480
tggaccaagc catcaccgtg ggcgctcccg tgatcggcct gaacgacagc ggaggcgca     540
ggatccaaga gggagtggag tccctggccg gctacgccga catcttcctg agaaacgtga     600
ccgcctcggg cgtgatccca cagatctccc tgatcatggg accctgcgcc ggcgggccg     660
tctacagccc tgccctgacc gacttcacct tcatggtgaa ggacaccagc tacctgttca     720
tcaccggccc cgacgtggtc aagagcgtga ccaacgagga cgtgacccag gaggagctcg     780
gcggagccaa gactcacaca accatgtccg gcgtcgctca tagggccttc gagaacgacg     840
```

-continued

```
tggacgccct gtgcaacctg agagacttct tcaactacct gccattgagc agccaggatc    900
ccgcccctgt gagagagtgc cacgacccca gcgacagact ggtgcccgag ctggacacca    960
tcgtgcccct ggagagcacc aaggcctaca acatggtgga catcatccac agcgtggtgg   1020
acgagagaga gttcttcgag atcatgccca actacgccaa gaacatcatc gtgggcttcg   1080
ccagaatgaa cggcagaacc gtgggcattg tgggcaacca gcccaaggtc gccagcggct   1140
gcctcgacat caacagcagc gtgaagggcg ccagattcgt gagattctgc gacgccttca   1200
acatacctct gatcaccttt gtggacgtgc ctggtttcct cccgggcacc gcccaagaat   1260
acggtggcat catcagacac ggcgccaagc tgctgtacgc cttcgccgag gccaccgtgc   1320
ccaaggtgac cgttatcacc cgcaaagcct acggcggcgc ctacgacgtg atgagcagca   1380
agcacctgtg tggcgacacc aattacgcct ggcccaccgc cgagatcgcc gtcatgggcg   1440
cgaaaggagc cgtggagatc atcttcaagg gccacgagaa cgtggaggcc gcccaggccg   1500
agtacatcga gaagttcgcc aaccccttcc ctgccgccgt gaggggcttc gtcgacgata   1560
tcatccagcc cagctccacc cgcgccagaa tctgttgcga cctggacgtg ctggccagca   1620
agaaggtgca aagaccctgg agaaagcacg ccaacatccc gctgtgataa taggctggag   1680
cctcggtggc ctagcttctt gcccttgggc cctccccca gccctcctc cccttcctgc   1740
acccgtaccc cctccataaa gtaggaaaca ctacagtggt ctttgaataa agtctgagtg   1800
ggcggc                                                              1806
```

SEQ ID NO: 47 　　　　　　moltype = RNA  length = 1806
FEATURE 　　　　　　　　　Location/Qualifiers
source 　　　　　　　　　　1..1806
　　　　　　　　　　　　　mol_type = other RNA
　　　　　　　　　　　　　organism = synthetic construct
SEQUENCE: 47

```
gggaaataag agagaaaaga agagtaagaa gaaatataag agccaccatg gccgccgccc    60
taagggttgc cgcagttggt gccaggctaa gcgtgctagc cagcgggcta gccagcgcgg   120
taaggagcct gtgcagccaa gccaccagcg tgaacgagag gatagagaac aagaggagga   180
ccgccctact aggcggtggg caacgccgga tcgacgccca acacaagagg ggaaagctaa   240
ccgccaggga aagaataagc ctactactag atccaggag cttcgtggag agcgatatgt   300
ttgtggagca caggtgcgcc gatttcggga tggccgcaga taagaacaag ttcccaggg   360
atagcgtggt gaccgggaga ggaaggataa acgggaggct agtgtacgtg ttcagccaag   420
atttcaccgt gttcggaggg agcctaagcg gggcccacgc ccagaagatt tgcaagataa   480
tggatcaagc cataaccgtt ggagcgccag tgataggct aaacgatagc ggtggagccc    540
ggatccaaga gggcgtggaa tctctagccg ggtacgccga tatattccta aggaacgtga   600
ccgcgtctgg tgtgatacca caaattagtc tcataatggg gccttgcgca ggagggggctg   660
tgtacagccc agccctaacc gatttcacgt tcatggtgaa ggataccagc tacctattca   720
taaccgggcc agacgtggta aagtccgtga ccaacgagga cgtgacccaa gaggaattag   780
gaggagccaa gacccacacc accatgtccg gggttgccca cagggccttc gagaacgacg   840
tggacgccgt gtgcaaccta agggatttct tcaactacct accactatct tcccaagatc   900
ctgccccagt gagggagtgc cacgatccaa gcgatagact ggtcccagag ctagatacca   960
tagtgccact agagagcacc aaggcctaca acatggtgga tataatacac tccgtggtgg   1020
acgagaggga gttcttcgag ataatgccaa actacgccaa gaacataata gtggggttcg   1080
ccaggatgaa cgggcgtacc gtggggatag taggaaacca accaaaggtg gcctctgggt   1140
gcctagatat aaacagctct gtcaagggag cccgcttcgt gaggttctgc gacgccttca   1200
acatacctct aataacattc gttgacgtgc cagggttcct accagggacg gcacaagagt   1260
acggagggat aataaggcac ggggcgaagc tactatacgc cttcgccgag gccaccgtgc   1320
ctaaggtgac cgtgataacc aggaaggctt acggaggggc ctacgacgtg atgagcagca   1380
agcacctgtg cggggatacc aactacgcgt ggccaaccgc cgagatagcc gtgatgggtg   1440
caaaggtgc tgtggagata atattcaagg gcacgagaa cgtggaggcc gcgcaggccg   1500
agtacataga gaagttcgcc aacccattcc cagcagcggc acgggatttt gttgacgata   1560
tcattcaacc aagcagcacc cgcgcgagaa tttgctgcga cttagacgtg ttagcgacta   1620
agaaggtaca acggccctgg aggaagcacg ctaacatccc actatgataa taggctggag   1680
cctcggtggc ctagcttctt gcccttgggc cctcccccca gccctcctc cccttcctgc   1740
acccgtaccc cctccataaa gtaggaaaca ctacagtggt ctttgaataa agtctgagtg   1800
ggcggc                                                              1806
```

SEQ ID NO: 48 　　　　　　moltype = RNA  length = 1806
FEATURE 　　　　　　　　　Location/Qualifiers
source 　　　　　　　　　　1..1806
　　　　　　　　　　　　　mol_type = other RNA
　　　　　　　　　　　　　organism = synthetic construct
SEQUENCE: 48

```
gggaaataag agagaaaaga agagtaagaa gaaatataag agccaccatg gcggcggcat    60
tacgggtggc ggcggtcggg gcaaggctca gcgtgctggc cagcggcctg agagccggcg   120
tgagaagcct gtgcagccag gccaccagcg tgaacgagag aatcgagaac aagagaagaa   180
ccgccctgct gggcggcggc cagagaagaa tcgacgccca gcacaagaga ggcaagctga   240
ccgccagaga gagaatcagc ctgctgctgg acccccgcag cttcgtggag agcgacatgt   300
tcgtggagca caggtgcgcc gacttcggca tggccgccga caagaacaag ttccccggcg   360
acagcgtggt gaccggcgga ggcagaatca acggcagact ggtgtacgtg ttcagccagg   420
acttcaccgt gttcggcggc agcctgagcg gcgcccacgc ccagaagatc tgcaagatca   480
tggaccaggc cataccgtg ggcgcgcccc tgatcggcct gaacgacagc ggcggcgcca   540
gaatccagga gggcgtggag agcctggccg gctacgccga catcttcctg agaaacgtga   600
ccgccagcgg cgtgatccca cagatcagcc tgatcatggg ccctgcgcc ggcggcgccg   660
tgtacagccc cgccctgacc gacttcacct tcatggtgaa ggacaccagc tacctgttca   720
tcaccggccc cgacgtggtg aagagcgtga ccaacgagga cgtgacccag gaggagctgg   780
gcggcgccaa gacccacacc accatgagcg gcgtggccca cagggccttc gagaacgacg   840
tggacgccct gtgcaacctg agagacttct tcaactacct gcccctgagc agccaggacc   900
ccgcgcccgt gagagagtgc cacgacccca gcgacagact ggtgcccgag ctggacacca   960
tcgtgcccct ggagagcacc aaggcctaca acatggtgga catcatccac agcgtggtgg   1020
```

-continued

```
acgagagaga gttcttcgag atcatgccca actacgccaa gaacatcatc gtgggcttcg   1080
ccagaatgaa cggcagaacc gtgggcatcg tgggcaacca gcccaaggtg gccagcggct   1140
gcctggacat caacagcagc gtgaagggcg ccagattcgt gagattctgc gacgccttca   1200
acatccctct gatcaccttc gtggacgtgc ccggcttcct gcccggcacc gcccaggagt   1260
acggcggcat catcagacac ggcgccaagc tgctgtatcgc cttcgccgag gccaccgtgc   1320
ccaaggtgac cgtgatcacc agaaaggcct acggcggcgc ctacgacgtg atgagcagca   1380
agcacctgtg cggcgacacc aactacgcct ggcccaccgc cgagatcgcc gtgatgggcg   1440
ccaagggcgc cgtggagatc atcttcaagg gccacgagaa cgtggaggcc gcccaggccg   1500
agtacatcga gaagttcgcc aacccettcc ccgccgccgt gagaggcttc gtggacgaca   1560
tcatccagcc cagcagcacc agagccagaa tctgctgcga cctggacgtg ctggccagca   1620
agaaggtgca gagaccctgg agaaagcacg ccaacatccc tctgtgataa taggctggag   1680
cctcggtggc ctagcttctt gcccettggg cctcccccca gcccctcctc cccttcctgc   1740
acccgtaccc cctccataaa gtaggaaaca ctacagtggt ctttgaataa agtctgagtg   1800
ggcggc                                                               1806
```

```
SEQ ID NO: 49          moltype = RNA  length = 1783
FEATURE                Location/Qualifiers
source                 1..1783
                       mol_type = other RNA
                       organism = synthetic construct
SEQUENCE: 49
gggaaataag agagaaaaga agagtaagaa gaaatataag agccaccatg gccgccgccc   60
tgagagtggc cgctgtgggc gccaggctga gcgtgctcgc tagcggcctg agagccgccg   120
ttagaagcct gtgcagccag gccacctccg tgaacgagag gatcgagaat aagagacgaa   180
ccgccctgct cggcggcggc cagagacgca tcgacgccca gcacaagcga ggtaagctga   240
cagccaggga gcgaatcagc ctgctcctgg accccggaag cttcgtggaa tccgacatgt   300
tcgttgagca cagatgcgcc gacttcggca tggccgccga caagaacaag tttccagggg   360
actcagtggt caccggaaga ggccgcatca acggccgcct ggtctacgtg ttctcacagg   420
actttacagt gttcggcggc agcctgtcag gcgcccatgc ccagaagatc tgcaagatca   480
tggatcaggc catcacagtg ggcgcccccg tgatcggtct gaacgactct ggcggcgcca   540
gaattcaaga gggcgtggag agcctggccg gttacgccga cattttcctg aggaacgtca   600
ccgccagcgg cgtcatcccc cagatctctc tgatcatggg cccctgcgct ggcggcgccg   660
tgtacagccc cgccctgacc gatttcacct tcatggtgaa ggataccagc tatctgttca   720
tcaccggcca ggatgtggtg aagagtgtga caacgagga cgtgacccag gaggagctgg   780
gtggagccaa gactcacaca accatgtccg gcgtggccca tcgagccttt gagaacgacg   840
tcgacgccct gtgtaacctg agagacttct tcaattacct gccctgagc tcccaggacc   900
ccgccccagt tagggagtgc cacgatccct ccgaccgcct ggtgcccgag ctggacacca   960
tcgtgcccct ggagagcacc aaggcctaca acatggtgga tatcatccat agcgtcgtcg   1020
acgagcgcga gttcttcgag atcatgccca actacgccaa gaacatcatc gtgggctttg   1080
ccaggatgaa cggccgcacc gtgggcattg tgggcaacca gcccaaggtg gcctctggct   1140
gcctggacat caacagcagc gtgaagggtg ctaggttcgt gaggttctgc gatgcctta   1200
acatcccact tatcaccttc gttgatgtcc ctggcttcct gcctggcacc gcccaggagt   1260
acggcggcat catcagacat ggtgccaagc tgctgtatgc cttcgccgag gccaccgtgc   1320
ccaaggtgac cgtgattacc cggaaagcct acggcggcgc ctacgacgtc atgagcagca   1380
agcacctgtg cggcgacacc aactacgcct ggcccaccgc cgagatcgcc gtcatgggcg   1440
ccaaggggc cgtcgagatc atcttcaagg gacacgagaa cgtggaggcc gctcaggccg   1500
agtacatcga gaagttcgct aacccettcc ccgccgctgt taggattcct gtggatgaca   1560
tcatccagcc aagcagcacc cgggccagga tctgctgtga cctggatgtg ctggctagca   1620
agaaggtgca gagaccctgg agaaagcacg ccaacattcc cctgtgataa taggctggag   1680
cctcggtggc catgcttctt gcccettggg cctcccccca gcccctcctc cccttcctgc   1740
acccgtaccc ccgtggtctt tgaataaagt ctgagtgggc ggc                     1783
```

```
SEQ ID NO: 50          moltype = RNA  length = 1783
FEATURE                Location/Qualifiers
source                 1..1783
                       mol_type = other RNA
                       organism = synthetic construct
SEQUENCE: 50
gggaaataag agagaaaaga agagtaagaa gaaatataag agccaccatg gccgccgccc   60
tgagagtggc cgctgtgggc gccaggctga gcgtgctcgc tagcggcctg agagccgccg   120
ttagaagcct gtgcagccag gccacctccg tgaacgagag gatcgagaat aagagacgaa   180
ccgccctgct cggcggcggc cagagacgca tcgacgccca gcacaagcga ggtaagctga   240
cagccaggga gcgaatcagc ctgctcctgg acccggaag cttcgtggaa tccgacatgt   300
tcgttgagca cagatgcgcc gacttcggca tggccgccga caagaacaag tttccagggg   360
actcagtggt caccggaaga ggccgcatca acggccgcct ggtctacgtg ttctcacagg   420
actttacagt gttcggcggc agcctgtcag gcgcccatgc ccagaagatc tgcaagatca   480
tggatcaggc catcacagtg ggcgcccccg tgatcggtct gaacgactct ggcggcgcca   540
gaattcaaga gggcgtggag agcctggccg gttacgccga cattttcctg aggaacgtca   600
ccgccagcgg cgtcatcccc cagatctctc tgatcatggg ccctgcgct ggcggcgccg   660
tgtacagccc cgccctgacc gatttcacct tcatggtgaa ggataccagc tatctgttca   720
tcaccggcca ggatgtggtg aagagtgtga caacgagga cgtgacccag gaggagctgg   780
gtggagccaa gactcacaca accatgtccg gcgtggccca tcgagccttt gagaacgacg   840
tcgacgccct gtgtaacctg agagacttct tcaattacct gccctgagc tcccaggacc   900
ccgccccagt tagggagtgc cacgatccct ccgaccgcct ggtgcccgag ctggacacca   960
tcgtgcccct ggagagcacc aaggcctaca acatggtgga tatcatccat agcgtcgtcg   1020
acgagcgcga gttcttcgag atcatgccca actacgccaa gaacatcatc gtgggctttg   1080
ccaggatgaa cggccgcacc gtgggcattg tgggcaacca gcccaaggtg gcctctggct   1140
gcctggacat caacagcagc gtgaagggtg ctaggttcgt gaggttctgc gatgcctta   1200
acatcccact tatcaccttc gttgatgtcc ctggcttcct gcctggcacc gcccaggagt   1260
```

-continued

```
acggcggcat catcagacat ggtgccaagc tgctgtacgc cttcgccgag gccaccgtgc    1320
ccaaggtgac cgtgattacc cggaaagcct acggcggcgc ctacgacgtc atgagcagca    1380
agcacctgtg cggcgacacc aactacgcct ggcccaccgc cgagatcgcc gtcatgggcg    1440
ccaaggggc cgtcgagatc atcttcaagg gacacgagaa cgtggaggcc gctcaggccg     1500
agtacatcga gaagttcgct aacccttcc ccgccgctgt tagaggattc gtggatgaca     1560
tcatccagcc aagcagcacc cgggccagga tctgctgtga cctggatgtg ctggctagca    1620
agaaggtgca gagaccctgg agaaagcacg ccaacattcc cctgtgataa taggctggag    1680
cctcggtggc catgcttctt gccccttggg cctcccccca gcccctcctc cccttcctgc    1740
acccgtaccc ccgtggtctt tgaataaagt ctgagtgggc ggc                      1783
```

```
SEQ ID NO: 51           moltype = RNA   length = 2184
FEATURE                 Location/Qualifiers
source                  1..2184
                        mol_type = other RNA
                        organism = synthetic construct
SEQUENCE: 51
atggccgggt tctgggtggg caccgccccc ctggtcgctg caggccggag gggcaggtgg    60
cccctcagc agctgatgct gagcgccgct cttcggacac tcaaacacgt gctgtactat      120
agcagacagt gcctgatggt gagtaggaac ctcggcagcg tggggtatga tcccaacgag    180
aagaccttcg acaagatcct ggtggcaaat cggggcgaga tcgcctgcag ggtgatcaga    240
acctgcaaga agatgggcat caagaccgtc gctattcaca gcgacgtgga tgcctcaagc    300
gtgcacgtga agatggcaga cgaagcagtg tgtgtgggcc ccgcccctac ttcaaagtcc    360
taccttaata tggacgcaat tatggaggca atcaagaaga ccagggctca agctgtgcat    420
ccaggatatg gcttcctgtc cgagaacaag gagttcgcca gatgcctggc agccgaggat    480
gtggtcttta tcggccctga tacacacgcc atccaggcta tggggataa gatcgagagt       540
aagctgctgg cgaagaaagc cgaggtgaac accattccgg gctttgacgg cgtggtgaag    600
gacgccgagg aggccgtgcg gatcgctagg gagatcggct accctgtgat gatcaaggct    660
tctgccggcg gaggcggaaa gggcatgcgt attgcttggg acgacgagga aacccgcgac    720
ggctttcggc tgagcagcca ggaagccgcc agtagctttg gcgatgaccg gcttcttata    780
gagaagttta tcgacaaccc cagacacatt gagatccgga tattgggcga taaacacgga    840
aatgcccttt ggctgaatga gagagaatgc tccatccaga gaaggaacca gaaggtggtg    900
gaggaggccc cctcaatctt cctggacgcc gagacccgta gagccatggg cgagcaggcc    960
gtggccctcg ccagagctgt gaagtattcc tctgctggca ccgtggagtt cttagtggat    1020
tccaagaaga acttctactt cctcgaagtg aataccagac tccaggtgga gcatcccgtc     1080
accgaatgca tcactggcct ggacctggtg caggagatga tcagagttgc taagggttac    1140
ccactgcgcc acaagcaggc tgacatcagg atcaacgggt gggcagtgga gtgcagagtg    1200
tatgctgagg acccctacaa gagcttcggc ctgccgagca tcggccggct gagccagtac    1260
caggaacccc tccacctgcc tggcgtacgg gtggacagtg gaatccagcc cggcagcgac    1320
atcagcattt attacgatcc catgatctcg aagttgatca cctatgggtc tgacagaacc    1380
gaggccctga gagaatggc cgacgcgctg gataactacg tgattcgggg agtgactcac     1440
aacatagctc tactgcgtga ggtcatcatc aatagcagat tcgtaaaggg cgacattagc    1500
accaagtttc tttccgacgt gtacccagac ggttttaagg acacatgct gacaaagtct      1560
gagaagaacc agctgctggc catagccagc agcctgttcg tggcctttca gctccgaacc    1620
caacacttcc aggagaacag cagaatgcca gtgatcaagc ctgacatcgc caactgggag    1680
ctgtctgtga aactgcacga caaggtgcat accgtcgtgg ccagcaacaa tggctccgtg    1740
ttctccgtgg aggtggatgg ctcaaagctg aacgtgacct cgacatggaa cctcgcctct    1800
cccctgctga gtgtgagcgt ggacggcaca cagagaacg tgcagtgcct ggtagagaa      1860
gcagggggca acatgtccat tcagtttctc ggcaccgtgt acaaggtcaa tattctcacc    1920
agactcgccg ccgagctgaa caagttcatg cttgagaagg tgaccgagga tactagttcc    1980
gtgctcagat cccctatgcc cggcgtggtg gtcgctgtgt ccgtcaagcc cggcgacgcc    2040
gtggccgagg gacaggagat ttgcgtgatt gaggctatga agatgcagaa tagcatgact    2100
gctggcaaga cgggcacagt gaagagcgtg cattgccagg caggcgacac agtgggcgaa    2160
ggagacctgc tggtcgagtt agag                                           2184
```

```
SEQ ID NO: 52           moltype = RNA   length = 2184
FEATURE                 Location/Qualifiers
source                  1..2184
                        mol_type = other RNA
                        organism = synthetic construct
SEQUENCE: 52
atggcaggct ctgggttgg cactgcccca ctcgtggccg ccggcagaag gggaaggtgg      60
cctccccagc agctcatgct gtccgccgct ctgcgaaccc tgaagcacgt gctgtattat    120
agcaggcagt gcctcatggt ttcccggaac ctggggagcg tgggctatga ccctaatgag    180
aagactttcg acaagatcct gatcgctaac agaggcgaga tcgcctgcag ggtgatcaga    240
acatgcaaga agatgggcat caagaccgtc gcgatccata gcgacgtgga tgccagcagc    300
gttcacgtca gatggccga cgaggctgtg tgcgtcggcc ccgccccaac ttccaagagc      360
tatctgaaca tggacgccat aatggaggct atcaagaaga ccagagccca ggcagttcat    420
cccggctacg gattcctgag cgagaacaag gagttcgcta gatgtctggc cgccgaagac    480
gtggttttca tcggtccaga cacccatgcc atccaagcca tgggcgataa gatcgagagc    540
aagctcctgg ccaagaaggc cgaggtgaac accatccccg gcttcgatgg cgtggtgaag    600
gacgcggagg aggcagtgcg cattgccagg gagatcggct accccgtgat gatcaaggct    660
tccgcagggg aggcggcaa aggcatgcgc attgcctggg atgatgaaga aaccagagat       720
ggcttcagac tgtcaagcca ggaggccgcc agcagcttcg gcgacgacag actgctgatc    780
gagaagttta tagataaccc ccgacacata gaaatccgga tgctgggaga caagcacgga     840
aacgctctgt ggctgaacga gcgggaatgc agtatccaga ggagaaacca gaaggtggtt    900
gaggaggccc cctcaatctt cctggatgcc gagacaagac gcgccatggg tgagcaggct    960
gtagccctcg cccgtgccgt gaagtatagc agcgccggga cagtggagtt cttggtcgac    1020
tccaagaaga atttctattt tctggagatg aacactcggc tccaagtaga gcaccccgtg    1080
actgagtgca ttacaggcct tgatctggtg caggagatga ttagggttgc caagggctac    1140
```

```
cctctgcgcc acaagcaggc cgacatcagg atcaatggct gggctgtcga gtgtagggtg  1200
tacgcagagg acccgtacaa gagcttcggc cttccctcta ttggcaggct gagccagtac  1260
caggagcctc tgcacctacc cggcgttcgc gtggacagcg gtatccaacc aggctctgat  1320
atcagcattt attacgaccc aatgatctca aagctgatca catacggcag cgacagaacc  1380
gaggccctga agcgaatgga ggacgccctg gacaactacg tgatccgggg cgtcacacat  1440
aacattgccc tgctgagaga ggtgatcatt aattctcggt tcgtcaaagg cgacatcagc  1500
actaagtttc tgagcgacgt gtaccccgac gggtttaaag gccacatgct gacaaagagc  1560
gagaagaacc agttgctggc catcgcctct agcctgttcg tagccttcca gctgcgagca  1620
cagcacttcc aggagaatag cagagtgcca gtgatcaagc ccgacatcgc taactgggag  1680
ctgagcgtga agctccatga taaggtccac acagttgtgg ccagcaacaa cggctcagtg  1740
ttcagcgtgg aggtagacgg ctccaagctg aacgtgacca gcacttggaa tctggccagc  1800
cccctgctga gcgtgtccgt ggacggcacc cagagaaccg tgcagtgcct gagcagggag  1860
gccgggggca acatgtccat ccagtttctg gggaccgtct ataaggttaa catcctgact  1920
agactggcgg ctgagcttaa caagtttatg ttagagaaag tgaccgagga tacaagcagc  1980
gtgctgcgta gccccatgcc tggcgtggtc gtggccgtga gcgtcaagcc aggcgatgca  2040
gtggctgagg gccaggagat ttgtgtgata gaggccatga agatgcagaa ctctatgacc  2100
gccggaaaga ctggcaccgt gaagtctgtc cattgtcagg ccggagacac cgtggggggaa  2160
ggagacctgc tcgtcgagct ggag                                         2184
```

SEQ ID NO: 53        moltype = RNA  length = 2184
FEATURE              Location/Qualifiers
source               1..2184
                     mol_type = other RNA
                     organism = synthetic construct
SEQUENCE: 53

```
atggccggct tctgggtggg caccgctcca ttggtggccg ccggcagacg gggccgctgg  60
cctcctcaac agcttatgtt atcagccgct ttgcggacct tgaagcacgt gctttactat  120
agcaggcagt gcctcatggt gtccaggaat ctcggcagcg tgggttacga tcctaacgag  180
aagaccttcg ataagatcct ggtagcaaac cgcggcgaga tcgcctgtag ggtgatcagg  240
acctgcaaga agatgggaat aaagaccgtg gccattcact ccgatgtgga ggccagcagc  300
gtgcacgtta agatggccga cgaggccgtg tgcgtgggcc ctgcccctac tagcaagtct  360
tacctgaaca tggacgccat catggaggcc atcaagaaga ccagagccca ggccgttcat  420
ccaggatacg gcttcctgag cgagaacaag gaattcgcca ggtgcctggc ggccgaagat  480
gtggtgttca tcggtccaga cacacacgcc atccaagcca tgggcgacaa gatcgagagc  540
aagctgctgt ctaagaaggc cgaggtcaac acaatccctg gcttcgacgg tgtcgtgaag  600
gatgccgagg aggccgtgcg gatcgcccgt gagattggct atccagtgat gatcaaggcc  660
tccgccggag gaggcggcaa gggcatgaga atcgcgtggg acgacgagga aactagagac  720
ggattccgcc tgagcagtca ggaggccgct agcagcttcg gcgacgatag actgctgatc  780
gagaagttca tcgacaaccc aagacacatc gagatccaag tgttaggcga taagcacggc  840
aatgccctct ggctgaatga gcgggagtgc agcattcagc ggagaaatca gaaggtggtg  900
gaggaggctc catccatttt cctcgacgcc gagactagaa gggcaatggg cgaacaagct  960
gttgccctgg caagagccgt gaagtactct agcgccggca ccgtcgagtt cctggtcgac  1020
agcaagaaga acttctactt cctggaatga aacacaagac tgcaggtgga acaccctgtc  1080
accgagtgca taacaggcct ggaccttgtg caggagatga ttaggtggc caagggatac  1140
cctctgcgcc acaagcaggc cgacatccgg atcaacggct gggccgtgga gtgccgagtc  1200
tacgccgagg atccttacaa gagcttcggc ttgcctagca tcggcaggct gagccagtat  1260
caggagccgc tgcacctgcc tggtgttaga gtggactcag gaatccagcc gggcagcgac  1320
atcagcatct actatgaccc gatgatctcc aagctcatta cctacggctc tgacagaaca  1380
gaagctctga gcgcatggc tgacgccctg gacaactacg tgatcagagg cgtgacccac  1440
aatatcgccc tgctgcggga ggtgatcatc aattcccgtt cgtgaaggg cgatatcagc  1500
acaaagttcc ttagcgatgt ctaccctgac ggcttcaagg gccacatgct gactaagagc  1560
gagaagaacc agctcctggc catcgcatca agcctcttcg tcgccttcca gctgcgggct  1620
cagcacttcc aggagaacag ccggatgcca gtgatcaagc cagacatcgc caactgggag  1680
ctttctgtca agctgcacga caaggtgcat acagtcgtgg cttctaacaa tggcagcgtc  1740
ttctccgtgg aggtcgacgg atcaaagctg aacgtgacca gcacctggaa tctggccagc  1800
cctcttctca gcgtgtccgt ggacggaacc cagagaaccg tgcagtgtct gagtagagag  1860
gccggcggca acatgagcat acagttcctg ggcaccgtgt acaaggtcaa catcctgacc  1920
aggctggctc cggagctgaa caagttcatg ttggagaagg tgacggagga cacctctagc  1980
gtgctgcgaa gccctatgcc gggtgtcgta gtggctgtga gcgtcaagcc aggcgacgcc  2040
gtggcagagg gccaagagat ttgtgttatt gaggcaatga agatgcagaa tagcatgacc  2100
gccggcaaga ccggcactgt gaagtccgtt cactgccagg ccggcgatac cgtgggtgag  2160
ggcgacttgc tcgtggagtt ggaa                                         2184
```

SEQ ID NO: 54        moltype = RNA  length = 2184
FEATURE              Location/Qualifiers
source               1..2184
                     mol_type = other RNA
                     organism = synthetic construct
SEQUENCE: 54

```
atggccgggt tctgggtggg caccgccccc ctggtcgctg caggccggag gggcaggtgg  60
cccccctcagc agctgatgct gagcgccgct cttcggacac tcaaacacgt gctgtactat  120
agcagacagt gcctgatggt gagtaggaac ctcggcagcg tggggtatga tcccaacgag  180
aagaccttcg acaagatcct gatcgcaaat cggggcgaga tcgcctgcag ggtgatcaga  240
acctgcaaga agatgggcat caagaccgtc gctattcaca gcgacgtgga tgcctcaagc  300
gtgcacgtga agatggcaga cgaagcagtc tgtgtgggcc ccgcccctac ttcaaagtcc  360
taccttaata tggacgcaat tatggaggca atcaagaaga ccaggggctca agctgtgcat  420
ccaggatatg gcttcctgtc cgagaacaag gagttcgcca gatgcctggc agccgaggat  480
gtggtctttta tcggccctga tacacacgcc atccaggcta tgggggataa gatcgagagt  540
aagctgctgg cgaagaaagc cgaggtgaac accattccgg gctttgacgg cgtggtgaag  600
```

-continued

```
gacgccgagg aggccgtgcg gatcgctagg gagatcggct accctgtgat gatcaaggct   660
tctgccggcg gaggcggaaa gggcatgcgt attgcttggg acgacgagga aacccgcgac   720
ggctttcggc tgagcagcca ggaagccgcc agtagctttg gcgatgaccg gcttcttata   780
gagaagttta tcgacaaccc cagacacatt gagatccagg tattgggcga taaacacgga   840
aatgcccttt ggctgaatga gagagaatgc tccatccaga gaaggaacca gaaggtggtg   900
gaggaggccc cctcaatctt cctggacgcc gagacccgta gagccatggg cgagcaggcc   960
gtggccctcg ccagagctgt gaagtattcc tctgctggca ccgtggagtt cttagtggat  1020
tccaagaaga acttctactt cctcgagatg aataccagac tccaggtgga gcatcccgtc  1080
accgaatgca tcactggcct ggacctggtg caggagatga tcagagttgc taagggttac  1140
ccactgcgcc acaagcaggc tgacatcagg atcaacggt gggcagtgga gtgcagagtg  1200
tatgctgagg acccctacaa gagcttcggc ctgccgagca tcggccggct gagccagtac  1260
caggaacccc tccacctgcc tggcgtacgg gtggacagtg gaatccagcc cggcagcgac  1320
atcagcattt attacgatcc catgatctcg aagttgatca cctatgggtc tgacagaacc  1380
gaggccctga agagaatgga ggacgcgctg gataactacg tgattcgggg agtgactcac  1440
aacatagctc tactgcgtga ggtcatcatc aatagcagat tcgtaaaggg cgacattagc  1500
accaagtttc tttccgacgt gtacccagac ggttttaagg gacacatgct gacaaagtct  1560
gagaagaacc agctgctggc catagccagc agcctgttcg tggcctttca gctccgagcc  1620
caacacttcc aggagaacag cagagtgcca gtgatcaagc ctgacatcgc caactgggag  1680
ctgtctgtga aactcacga caaggtgcat accgtcgtgg ccagcaacaa tggctccgtg  1740
ttctccgtgg aggtggatgg ctcaaagctg aacgtgacct cgacatggaa cctcgcctct  1800
cccctgctga gtgtgagcgt ggacggcaca cagagaaccg tgcagtgcct gagtagagaa  1860
gcaggggca acatgtccat tcagtttctc ggcaccgtgt acaaggtcaa tattctcacc  1920
agactcgccg ccgagctgaa caagttcatg cttgagaagg tgaccgagga tactagttcc  1980
gtgctcagat cccctatgcc cggcgtggtg gtcgctgtgt ccgtcaagcc cggcgacgcc  2040
gtggccgagg acaggagat ttgcgtgatt gaggctatga agatgcagaa tagcatgact  2100
gctggcaaga cgggcacagt gaagagcgtg cattgccagg caggcgacac agtgggcgaa  2160
ggagacctgc tggtcgagtt agag                                         2184
```

```
SEQ ID NO: 55          moltype = RNA  length = 2184
FEATURE                Location/Qualifiers
source                 1..2184
                       mol_type = other RNA
                       organism = synthetic construct
SEQUENCE: 55
atggccggct tctgggttgg caccgcccct ctcgtggccg caggaaggag gggcaggtgg   60
cctccacagc agcttatgtt gtccgccgcc ctcagaacac tcaagcacgt gctatactac  120
agcagacagt gcttgatggt gtccagaaat ctgggcagcg taggttatga ccctaacgag  180
aagaccttcg acaagatcct ggtggctaac aggggagaaa tcgcctgtag ggtcattaga  240
acctgcaaga agatgggaat caagaccgtc gctatccact ctgacgttga tgcaagcagc  300
gtgcacgtca agatggctga tgaggctgtc tgcgtcggtc ctgctccaac atctaagagc  360
tacctgaaca tggacgctat catggaggcc attaagaaga caagggccca ggccgtgcac  420
cctggatacg gcttcctcag cgagaataag gagttcgcaa gatgtctcgc cgccgaggac  480
gtcgtgttca taggccctga cacccacgcc atccaggcaa tgggcgataa gatcgagtcc  540
aagctgttag caaagaaggc cgaagtgaac accattcctg gcttcgatgc gtcgtgaag  600
gacgctgagg aggcagtgag aatcgccaga gagatcggat accctgtgat gatcaaggcc   660
tctgccggag gcgaggcaa gggcatgagg attgcctggg atgacgaaga gacgcgtgac   720
ggcttccgac tgagctctca ggaggctgcc tcttctttcg gacgatag gctgctgatc   780
gagaagttca tcgacaaccc tcggcacatc gagatccagg tgctcggtga caagcatgga   840
aatgccctgt ggctgaacga gcgggagtgc tctattcaga gaagaaacca gaaggtggtg   900
gaggaggccc ctagcatctt cttagacgct gaaactcgga gagccatggg cgagcaggcc   960
gtggccctga ctagagccgt gaagtacagc agtgcaggca cagtggagtt cctggtggat  1020
agcaagaaga atttctactt cctggagatg aataccaggc tgcaggtgga gcacccggtg  1080
acggagtgca tcacaggcct ggacctggtc caagaaatga tcagagtggc caagggctac  1140
cctctgcggc ataagcaggc tgacatccgg attaacggat gggccgtaga gtgccgtgtt  1200
tatgccgagg acccttacaa gagcttcggt ttgccaagca ttggccggat gtcccagtac  1260
caagagccac tgcatctgcc aggcgtcagg gtggacagcg gcatccagcc aggctctgac  1320
atcagcattt attacgaccc gatgatcagc aagctgatca catatggatc cgatagaacc  1380
gaagccctga agagaatggc agatgctctg gacaactacg tgatcagggg cgtgacccac  1440
aacatcgccc tgctcaggga agtgatcatt aatagccggt tcgtgaaggg cgatatcagc  1500
accaagttcc tgtcagacgt ttatccagat ggcttcaagg gacacatgct gacaaagtct  1560
gagaagaatc agctcctggc cattgccagc tctctcttcg tggccttcca gttgagagcg  1620
cagcacttcc aggagaacag tcgaatgcct gtcattaagc ctgacatcgc caattgggag  1680
ctgagcgtga agctccacga caaggtccac actgtcgtgg ccagcaacaa cggctcagtg  1740
ttcagcgtga agtcgacgg ctccaagctc aatgtgacct ccacttggaa cctggcttcc  1800
ccacttctgt ctgtgagcgt ggacggcact cagcggacgg tgcaatgtct gagcagggaa  1860
gccggcggca atatgagcat ccaattcctc ggaaccgtgt acaaggttaa catccttacg  1920
cgactggccg ctgagctgaa taagttcatg ctggagaagg tgaccgagga cacctctagc  1980
gtgctgcgga gccctatgcc aggagtggtg gtggccgtgt ccgtgaagcc tggagacgcc  2040
gtggccgaag gccaggaaat ttgcgtcatc gaagccatga agatgcagaa cagcatgacc  2100
gccggcaaga ccggaacggt taagtctgtc cactgccagg ccggcgacac cgtgggagag  2160
ggtgacctcc tggttgagct ggag                                         2184
```

```
SEQ ID NO: 56          moltype = RNA  length = 2184
FEATURE                Location/Qualifiers
source                 1..2184
                       mol_type = other RNA
                       organism = synthetic construct
SEQUENCE: 56
atggccggct tctgggtggg caccgccccc cttgtcgcag caggaaggcg gggccggtgg   60
```

-continued

```
cctccccagc agttaatgct tagcgccgcc ctccgcaccc tcaagcacgt cctctactac  120
tcccgccagt gcctcatggt atcccgcaac ctcggctccg tcggctacga ccccaacgag  180
aagaccttcg acaagatcct cgtcgccaac cgcggcgaga tcgcctgccg cgtcatccgc  240
acctgcaaga agatgggcat caagaccgtc gccatccact ccgacgtcga cgcctcctcc  300
gtccacgtca agatggccga cgaggccgtc tgcgtcggcc cgcccccac ctccaagtcc  360
tacctcaaca tggacgccat catggaggcc atcaagaaga cccgcgccca ggccgtccac  420
cccggctacg gcttcctctc cgagaacaag gagttcgccc gctgcctcgc cgccgaggac  480
gtcgtcttca tcggccctga cacccacgca attcaggcca tgggtgacaa gattgagtcc  540
aagctcctcg ccaagaaggc cgaggtcaac accatcccg gcttcgacgg cgtcgtcaag  600
gatgctgaag aggcagtccg catcgccaga gagataggct accccgtcat gatcaaggcc  660
tccgccggcg gcggaggaaa gggcatgcgc atcgcatggg acgacgagga aacccgcgac  720
ggtttccgcc tctcctccca ggaggccgcc tccagtttcg gcgacgacag actcttgatc  780
gagaagttca tcgacaaccc ccgccacatc gagatccagg tcctcggaga taagcacggc  840
aacgccctct ggctcaacga gcgcgagtgc tccatccagc gccgcaacca gaaggtcgtg  900
gaggaggccc cctccatctt cctcgacgca gaaacaaggc gcgcgatggg agagcaggca  960
gtggcccttg ccagggccgt caagtactcc tccgcaggta ccgtcgagtt cctcgtggac  1020
tccaagaaga acttctactt cttggagatg aacacacgac tgcaggtcga gcatcctgta  1080
accgagtgca tcaccggcct cgacctcgtc caggagatga tccgcgttgc caagggctac  1140
cctctccgcc acaagcaggc cgacatccgc atcaacggct gggctgtgga atgtcgggtg  1200
tatgccgagg atccctacaa gtccttcggc ctgccatcta ttggcagact atcgcagtac  1260
caggagcccc tccacctccc cggcgtgcgc gttgactctg gcatccagcc cggctccgac  1320
atcagcatct actatgatcc gatgatcagc aagcttatca cctatggctc agaccgcacc  1380
gaggcgctga gcgcatggc tgacgccctc gacaactatg ttatccgggg cgtcacccac  1440
aacatcgcac tcctacggga ggtcatcatc aactcccgct tcgtgaaggg tgacatctcc  1500
accaagttct tgagtgacgt gtaccctgac ggcttcaagg gccacatgct caccaagtcc  1560
gagaagaacc aactgctggc tatcgccagc agtctcttcg tcgccttcca gctgagggcc  1620
cagcacttcc aagagaatag caggatgccc gtcatcaagc ccgacatcgc caactgggag  1680
ctctccgtca agtccacga caaggtccac accgtcgtcg catccaacaa cggatctgtg  1740
ttctccgtcg aggtcgacgg atctaagctg aacgtcacaa gcacttggaa cctcgcctcc  1800
cccctgcttt cagtgagcgt ggacggcacc cagcgcaccg tgcagtgcct gagccgcgag  1860
gcggggaggca acatgtcgat acagttcctg ggcacagtgt acaaggtgaa tatcctgaca  1920
agactggctg ctgagctcaa caagttcatg ctcgagaagg tcaccgagga cacttcttcg  1980
gtgctccgct cccccatgcc tggagtggtt gtggccgtgt cagtaaagcc aggcgacgct  2040
gttgccgagg tcaggaaat ctgcgtcatc gaggccatga agatgcagaa ctccatgacg  2100
gccggcaaga cgggcactgt caagtctgtg cattgccagg ccgagacac tgtgggcgag  2160
ggcgacctac tggttgagct cgag                                          2184
```

SEQ ID NO: 57          moltype = RNA  length = 2350
FEATURE                Location/Qualifiers
source                 1..2350
                       mol_type = other RNA
                       organism = synthetic construct
SEQUENCE: 57

```
gggaaataag agagaaaaga agagtaagaa gaaatataag agccaccatg gccgggttct  60
gggtgggcac cgcccccctg gtcgctgcag gccggagggg caggtggccc cctcagcagc  120
tgatgctgag cgccgctctt cggacactca aacacgtgct gtactatagc agacagtgcc  180
tgatggtgag taggaacctc ggcagcgtgg ggtatgatcc caacgagaag accttcgaca  240
agatcctggt ggcaaatcgg ggcgagatcg cctgcagggt gatcagaacc tgcaagaaga  300
tgggcatcaa gaccgtcgct attcacagcg acgtggatgc ctcaagcgtg cacgtgaaga  360
tggcagacga agcagtgtgt gtgggccccg ccctacttc aaagtcctac cttaatatgg  420
acgcaattat ggaggcaatc aagaagacca gggctcaagc tgtgcatcca ggatatggct  480
cctgtccga gaacaaggag ttcgccagat gcctggcagc cgaggatgtg gtctttatcg  540
gccctgatac acacgccatc caggctatgg gggataagat cgagagtaag ctgctggcga  600
agaaagccga ggtgaacacc attccggggct ttgacggcgt ggtgaaggac gccgaggagg  660
ccgtgcggat cgctagggag atcggctacc ctgtgatgat caaggcttct gccggcggag  720
gcggaaaggg catgcgtatt gcttgggacg acgaggaaac ccgcgacggc tttcggctga  780
gcagccagga agccgccagt agctttggcg atgaccggct tcttatagag aagtttatcg  840
acaaccccag acacattgag atccaggtat gggcgataa acacgaaat gcccctttggc  900
tgaatgagag agaatgctcc atccagagaa ggaaccagaa ggtggtggga gaggcccccat  960
caatcttcct ggacgccgag accgtagag ccatgggcga gcaggccgtg gccctcgcca  1020
gagctgtgaa gtattcctct gctggcaccg tggagttctt agtggattcc aagaagaact  1080
tctacttcct cgagatgaat accagactcc aggtggagca tccgtcacc gaatgcatca  1140
ctggcctgga cctggtgcag gagatgatca gagttgctaa gggttaccca ctgcgccaca  1200
agcaggctga catcaggatc aacggtgggg cagtggagtg cagagtgtat gctgaggacc  1260
cctacaagag cttcggcctg ccgagcatcg gccggctgaa ccagtaccag gaaccctcc  1320
acctgctgg cgtacgggtg gacagtggaa tccagcccgg cagcgacatc agcatttatt  1380
acgatcccat gatctcgaag ttgatcacct atgggtctga cagaaccgag gccctgaaga  1440
gaatggccga cgcgctggat aactacgtga ttcggggagt gactcacaac atagctctac  1500
tgcgtgaggt catcatcaat agcagattcg taaagggcga cattagcacc aagtttcttt  1560
ccgacgtgta cccagacggt tttaaggac acatgctgac aaagtctgag aagaaccagc  1620
tgctggccat agccagcagc ctgttcgtgg cctttcagct ccgagcccaa cacttccagg  1680
agaacagcag aatgccagtg atcaagcctg acatcgccaa ctgggagctg tctgtgaaac  1740
tgcacgacaa ggtgcatacc gtcgtggcca gcaacaatgg ctccgtgttc tccgtggagg  1800
tggatggctc aaagctgaac gtgacctcga catggaacct cgcctctccc ctgctgagtg  1860
tgagcgtgga cggcacacag agaaccgtgc agtgcctgag tagagaagca gggggcaaca  1920
tgtccattca gtttctcggc accgtgtaca aggtcaatat tctcaccaga ctcgccgccg  1980
agctgaacaa gttcatgctt gagaaggtga ccgaggatac tagttccgtg ctcagatccc  2040
ctatgcccgt cgtggtggtc gctgtgtccg tcaagcccgg cgacgccgtg gccgaggac  2100
aggagatttg cgtgattgag gctatgaaga tgcagaatag catgactgct ggcaagacgg  2160
```

```
gcacagtgaa gagcgtgcat tgccaggcag gcgacacagt gggcgaagga gacctgctgg   2220
tcgagttaga gtgataatag gctggagcct cggtggccat gcttcttgcc ccttgggcct   2280
cccccagcc cctcctcccc ttcctgcacc cgtacccccg tggtctttga ataaagtctg   2340
agtgggcggc                                                          2350

SEQ ID NO: 58             moltype = RNA   length = 2350
FEATURE                   Location/Qualifiers
source                    1..2350
                          mol_type = other RNA
                          organism = synthetic construct
SEQUENCE: 58
gggaaataag agagaaaaga agagtaagaa gaaatataag agccaccatg gcaggcttct   60
gggttggcac tgccccactc gtggccgccg gcagaagggg aaggtggcct ccccagcagc   120
tcatgctgtc cgccgctctg cgaaccctga agcacgtgct gtattatagc aggcagtgcc   180
tcatggtttc ccggaacctg gggagcgtgg gctatgaccc taatgagaag actttcgaca   240
agatcctgat cgctaacaga ggcgagatcg cctgcagggt gatcagaaca tgcaagaaga   300
tgggcatcaa gaccgtcgcg atccatagcg acgtggatgc cagcagcgtt cacgtcaaga   360
tggccgacga ggctgtgtgc gtcggccccg ccccaacttc caagagctat ctgaacatag   420
acgccataat ggaggctatc aagaagacca gagcccaggc agttcatccc ggctacggat   480
tcctgagcga gaacaaggag ttcgctagat gtctggccgc cgaagacgtg gttttcatcg   540
gtccagacac ccatgccatc caagccatgg gcgataagat cgagagcaag ctcctggcca   600
agaaggccga ggtgaacacc atccccggct tcgatgacgt ggtgaaggac gcggaggagg   660
cagtgcgcat tgccagggag atcggctacc ccgtgatgat caaggcttcc gcagggggag   720
gcggcaaagg catgcggatt gcctgggatg atgaagaaac cagagatggc ttcagactgt   780
caagccagga ggccgccagc agcttcggcg acgacagact gctgatcgag aagtttatag   840
ataacccccg acacatagaa atccaggtgc tgggagacaa gcacggcaac gctctgtgac   900
tgaacgagcg ggaatgcagt atccagagga gaaaccagaa ggtggttgag gaggccccct   960
caatcttcct ggatgccgag acaagacgcg ccatgggtga gcaggctgta gccctcgccc   1020
gtgccgtgaa gtatagcagc gccgggacag tggagttctt ggtcgactcc aagaagaatt   1080
tctattttct ggagatgaac actctggctcc aagtagagca ccccgtgact gagtgcatta   1140
caggccttga tctggtgcag gagatgatta gggttgccaa gggctaccct ctgcgccaca   1200
agcaggccga catcaggatc aatggctggg ctgtcgagtg tagggtgtac gcagaggacc   1260
cgtacaagag cttcggcctt ccctctattg gcaggctgag ccagtaccag gagcctctgc   1320
acctacccgg cgttcgcgtg gacagcggta tccaaccagg ctctgatatc agcatttatt   1380
acgacccaat gatctcaaag ctgatcacat acggcagcga cagaaccgag gccctgaagc   1440
gaatggagga cgccctggac aactacgtga tccggggcgt cacacataac attgccctgc   1500
tgagagaggt gatcattaat tctcggttcg tcaaaggcga catcagcact aagtttctga   1560
gcgacgtgta ccccgacggg tttaaaggcc acatgctgac aaagagcgag aagaaccagt   1620
tgctggccat cgcctctagc ctgttcgtag ccttccagct gcgagcacag cacttccagg   1680
agaatagcag agtgccagtg atcaagcccg acatcgctaa ctgggagctg agcgtggaagc   1740
tccatgataa ggtccacaca gttgtggcca gcaacaacgg ctcagtgttc agcgtggagg   1800
tagacggctc caagctgaac gtgaccagca cttggaatct ggccagcccc ctgctgagcg   1860
tgtccgtgga cggcacccag agaaccgtgc agtgcctgag cagggaggcc gggggcaaca   1920
tgtccatcca gtttctgggg accgtctata aggttaacat cctgactaga ctggcggctg   1980
agcttaacaa gtttatgtta gagaaagtga ccgaggatac aagcagcgtg ctgcgtagcc   2040
ccatgcctgg cgtggtcgtg gccgtgagcg tcaagccagg cgatgcagtg gctgagggcc   2100
aggagatttg tgtgatagag gccatgaaga tgcagaactc tatgaccgcc ggaaagactg   2160
gcaccgtgaa gtctgtccat tgtcaggccg gagacaccgt gggggaagga gacctgctcg   2220
tcgagctgga gtgataatag gctggagcct cggtggccat gcttcttgcc ccttgggcct   2280
cccccagcc cctcctcccc ttcctgcacc cgtaccccg tggtctttga ataaagtctg   2340
agtgggcggc                                                          2350

SEQ ID NO: 59             moltype = RNA   length = 2350
FEATURE                   Location/Qualifiers
source                    1..2350
                          mol_type = other RNA
                          organism = synthetic construct
SEQUENCE: 59
gggaaataag agagaaaaga agagtaagaa gaaatataag agccaccatg gccggcttct   60
gggtggggcac cgctccattg gtggccgccg gcagacgggg ccgctggcct cctcaacagc   120
ttatgttatc agccgctttg cggaccttga agcacgtgct ttactatagc aggcagtgcc   180
tcatggtgtc caggaatctc ggcagcgtgg gttacgatcc taacgagaag accttcgata   240
agatcctggt agcaaaccgc ggcgagatcg cctgtagggt gatcaggacc tgcaagaaga   300
tgggaataaa gaccgtggcc attcactccg atgtggacgc cagcagcgtg cacgttaaga   360
tggccgacga ggccgtgtgc gtgggccctg ccctactag caagtcttac ctgaacatgg   420
acgccatcat ggaggccatc aagaagacca gagcccaggc cgttcatcca ggatacggct   480
tcctgagcga gaacaaggaa ttcgccaggt gcctggcggc cgaagatgtg gtgttcatcg   540
gtccagacac acacgccatc caagccatgg gcgacaagat cgagagcaag ctgctggcta   600
agaaggccga ggtcaacaca atccctggct cgcagtgcgt cgtgaaggat gccgaggagg   660
ccgtgcggat cgcccgtgag attggctatc cagtgatgat caaggcctcc gccgaggag   720
gcggcaaggg catgagaatc gcgtgggacg acaggaaac tagagacgga ttcgcctga   780
gcagtcagga ggccgctagc agcttcggcg acgatagact gctgatcgag aagttcatcg   840
acaacccaag acacatcgag atccaagtgt taggcgataa gcacggcaat gccctctggc   900
tgaatgagcg ggagtgcagc attcagcgga gaaatcagaa ggtggtggag gaggctccat   960
ccattttcct cgacgccgag actagaaggg caatggcgga acaagctgtt gccctggcaa   1020
gagccgtgaa gtactctagc gccggcaccg tcgagttcct ggtcgacagc aagaagaact   1080
tctacttcct ggagatgaac acaagactgc aggtggaaca ccctgtcacc gagtgcataa   1140
caggcctgga ccttgtgcag gagatgatta ggggtggcca gggataccct ctgcgccaca   1200
agcaggccga catccggatc aacggctggg ccgtggagtg ccgagtctac gccgaggatc   1260
```

-continued

```
cttacaagag cttcggcttg cctagcatcg gcaggctgag ccagtatcag gagccgctgc   1320
acctgcctgg tgttagagtg gactcaggaa tccagccggg cagcgacatc agcatctact   1380
atgacccgat gatctccaag ctcattacct acggctctga cagaacagaa gctctgaagc   1440
gcatggctga cgccctggac aactacgtga tcagaggcgt gacccacaat atcgccctgc   1500
tgcgggaggt gatcatcaat tcccgtttcg tgaagggcga tatcagcaca aagttcctta   1560
gcgatgtcta ccctgacggc ttcaaggggc acatgctgac taagagcgag aagaaccagc   1620
tcctggccat cgcatcaagc ctcttcgtcg ccttccagct gcgggctcag cacttccagg   1680
agaacagccg gatgccagtg atcaagccag acatcgccaa ctgggagctt tctgtcaagc   1740
tgcacgacaa ggtgcataca gtcgtggctt ctaacaatgg cagcgtcttc tccgtggagg   1800
tcgacgggatc aaagctgaac gtgaccagca cctggaatct ggccagccct cttctcagcg   1860
tgtccgtgga cggaacccag agaaccgtgc agtgtctgag tagagaggcc ggcggcaaca   1920
tgagcataca gttcctgggc accgtgtaca aggtcaacat cctgaccagg ctggctgcgg   1980
agctgaacaa gttcatgttg gagaaggtga cggaggacac ctctagcgtg ctgcgaagcc   2040
ctatgccggg tgtcgtagtg gctgtgagcg tgaagccagg cgacgccgtg gcagagggcc   2100
aagagatttg tgttattgag gcaatgaaga tgcagaatag catgaccgcc ggcaagaccg   2160
gcactgtgaa gtccgttcac tgccaggccg gcgataccgt gggtgagggc gacttgctcg   2220
tggagttgga atgataatag gctggagcct cggtggccat gcttcttgcc ccttgggcct   2280
cccccagcc cctcctcccc ttcctgcacc cgtacccccg tggtctttga ataaagtctg   2340
agtgggcggc                                                         2350
```

```
SEQ ID NO: 60          moltype = RNA  length = 2350
FEATURE                Location/Qualifiers
source                 1..2350
                       mol_type = other RNA
                       organism = synthetic construct
SEQUENCE: 60
gggaaataag agagaaaaga agagtaagaa gaaatataag agccaccatg gccgggttct   60
gggtgggcac cgcccccctg gtcgctgcag gccggagggg caggtggccc cctcagcagc   120
tgatgctgag cgccgctctt cggacactca aacacgtgct gtactatagc agacagtgcc   180
tgatggtgag taggaacctc ggcagcgtgg ggtatgatcc caacgagaag accttcgaca   240
agatcctgat cgcaaatcgg ggcgagatcg cctgcagggt gatcagaacc tgcaagaaga   300
tgggcatcaa gaccgtcgct attcacagcg acgtggatgc ctcaagcgtg cacgtgaaga   360
tggcagacga agcagtgtgt gtgggccccg cccctacttc aaagtcctac cttaatatgg   420
acgcaattat ggaggcaatc aagaagacca gggctcaagc tgtgtcatcca ggatatggct   480
tcctgtccga gaacaaggag ttcgccagat gcctggcagc cgaggatgtg gtctttatcg   540
gccctgatac acacgccatc caggctatgg gggataagat cgagagtaag ctgctggcga   600
agaaagccga ggtgaacacc attccgggct ttgacggcgt ggtgaaggac gccgaggagg   660
ccgtgcggat cgctagggag atcggctacc ctgtgatgat caaggcttct gccggcggag   720
gcggaaaggg catgcgtatt gcttgggacg acgaggaaac ccgcgacggc tttcggctgg   780
gcagccagga agccgccagt agctttggcg atgaccggct tcttatagag aagtttatcg   840
acaaccccag acacattgag atccaggtat tgggcgataa acacgaaat gcccctttggc   900
tgaatgagag agaatgctcc atccagagaa ggaaccagaa ggtggtggag gaggcccct   960
caatcttcct ggacgccgag acccgtagag ccatgggacg gcaggccgtg gccctcgcca   1020
gagctgtgaa gtattcctct gctggcaccg tggagttctt agtggattcc aagaagaact   1080
tctacttcct cgagatgaat accagactcc aggtggagca tcccgtcacc gaatgcatca   1140
ctggcctgga cctggtgcag gagatgatca gagttgctaa gggttacca ctgcgccaca   1200
agcaggctga catcaggatc aacggtgg cagtggagtg cagagtgtat gctgaggacc   1260
cctacaagag cttcggcctg ccgagcatcg gccggctgag ccagtaccag gaaccctcc   1320
acctgcctgg cgtacgggtg gacagtggaa tccagcccgg cagcgacatc agcatttatt   1380
acgatcccat gatctcgaag ttgatcacct atgggtctga cagaaccgag gccctgaaga   1440
gaatgggaga cgcgctggat aactacgtga ttcggggagt gactcacaac atagctctac   1500
tgcgtgaggt catcatcaat agcagattcg taaagggcga cattagcacc aagtttcttt   1560
ccgacgtgta cccagacggt tttaagggac acatgctgac aaagtctgag aagaaccagc   1620
tgctggccat agccagcagc ctgttcgtgg cctttcagct ccgagcccaa cacttccagg   1680
agaacagcag agtgccagtg atcaagcctg acatcgccaa ctgggagctg tctgtgaaac   1740
tgcacgacaa ggtgcatacc gtcgtggcca gcaacaatgg ctccgtgttc tccgtggagg   1800
tggatggctc aaagctgaac gtgacctcga catggaacct cgcctctccc ctgctgagtg   1860
tgagcgtgga cggcacacag agaaccgtgc agtgcctgag tagagaagca gggggcaaca   1920
tgtccattca gtttctcggc accgtgtaca aggtcaatat tctcaccaga ctcgccgccg   1980
agctgaacaa gttcatgctt gagaaggtga ccgaggatac tagttccgtg ctcagatccc   2040
ctatgcccgg cgtggtggtc gctgtgtccg tcaagcccgg cgacgccgtg gccgagggac   2100
aggagatttg cgtgattgag gctatgaaga tgcagaatag catgactgct ggcaagacgg   2160
gcacagtgaa gagcgtgcat tgccaggcag gcgacacagt gggcgaagga gacctgctgg   2220
tcgagttaga gtgataatag gctggagcct cggtggccat gcttcttgcc ccttgggcct   2280
cccccagcc cctcctcccc ttcctgcacc cgtacccccg tggtctttga ataaagtctg   2340
agtgggcggc                                                         2350
```

```
SEQ ID NO: 61          moltype = RNA  length = 2350
FEATURE                Location/Qualifiers
source                 1..2350
                       mol_type = other RNA
                       organism = synthetic construct
SEQUENCE: 61
gggaaataag agagaaaaga agagtaagaa gaaatataag agccaccatg gccggcttct   60
gggttggcac cgcccctctc gtggccgcag gaaggagggg caggtggcct ccacagcagc   120
ttatgttgtc cgccgccctc agaacactca agcacgtgct atactacagc agacagtgct   180
tgatggtgtc cagaaatctg ggcagcgtag gttatgaccc caacgagaag accttcgaca   240
agatcctggt ggctaacagg ggagaaatcg cctgtagggt cattagaacc tgcaagaaga   300
tgggaatcaa gaccgtcgct atccactctg acgttgatgc aagcagcgtg cacgtcaaga   360
```

-continued

```
tggctgatga ggctgtctgc gtcggtcctg ctccaacatc taagagctac ctgaacatgg   420
acgctatcat ggaggccatt aagaagacaa gggcccaggc cgtgcaccct ggatacggct   480
tcctcagcga gaataaggag ttcgcaagat gtctcgccgc cgaggacgtc gtgttcatag   540
gccctgacac ccacgccatc caggcaatgg gcgataagat cgagtccaag ctgttagcaa   600
agaaggccga agtgaacacc attcctggct tcgatgacgt cgtgaaggac gctgaggagg   660
cagtgagaat cgccagagag atcggatacc ctgtgatgat caaggcctct gccggaggcg   720
gaggcaaggg catgaggatt gcctgggatg acgaagagac gcgtgacggc ttccgactga   780
gctctcagga ggctgcctct tctttcggag acgataggct gctgatcgag aagttcatcg   840
acaaccctcg gcacatcgag atccaggtgc tcggtgacaa gcatggaaat gccctgtggc   900
tgaacgagcg ggagtgctct attcagagaa gaaaccagaa ggtggtggag gaggccccta   960
gcatcttctt agacgctgaa actcggagag ccatgggcga gcaggccgtg gcgctggcta  1020
gagccgtgaa gtacagcagt gcaggcacag tggagttcct ggtggatagc aagaagaatt  1080
tctacttcct ggagatgaat accaggctgc aggtggagca cccggtgacg gagtgcatca  1140
caggcctgga cctggtccaa gaaatgatca gagtggccaa gggctaccct ctgcggcata  1200
agcaggctga catccggatt aacggatggg ccgtagagtg ccgtgtttat gccgaggacc  1260
cttacaagag cttcggtttg ccaagcattg gccggctgtc ccagtaccaa gagccactgc  1320
atctgccagg cgtcagggtg gacagcggca tccagccagg ctctgacatc agcatttatt  1380
acgacccgat gatcagcaag ctgatcacat atggatccga tagaaccgaa gccctgaaga  1440
gaatggcaga tgctctggac aactacgtga tcaggggcgt gacccacaac atcgccctgc  1500
tcagggaagt gatcattaat agccggttcg tgaagggcga tatcagcacc aagttcctgt  1560
cagacgttta tccagatggc ttcaagggac acatgctgac aaagtccgag aagaatcagc  1620
tcctggccat tgccagctct ctcttcgtgg ccttccagtt gagagcgcaa gccttccagg  1680
agaacagtcg aatgcctgtc attaagcctg acatcgccaa ttgggagctg agcgtggaagc  1740
tccacgacaa ggtccacact gtcgtggcca gcaacaacgg ctcagtgttc agcgtggaag  1800
tcgacggctc caagctcaat gtgacctcca cttggaacct ggcttcccca cttctgtctg  1860
tgagcgtgga cggcactcag cggacggtgc aatgtctgga cagggaagcc ggcggcaata  1920
tgagcatcca attcctcgga accgtgtaca aggttaacat ccttacgcga ctggccgctg  1980
agctgaataa gttcatgctg gagaaggtga ccgaggacac ctctagcgtg ctgcggagcc  2040
ctatgccagg agtggtggtg gccgtgtccg tgaagcctgg agacgccgtg gccgaaggcc  2100
aggaaatttg cgtcatcgaa gccatgaaga tgcagaacag catgaccgcc ggcaagaccg  2160
gaacggttaa gtctgtccac tgccaggccg gcgcacaccgt gggagagggt gacctcctgg  2220
ttgagctgga gtgataatag gctggagcct cggtggccat gcttcttgcc ccttgggcct  2280
cccccagcc cctcctcccc ttcctgcacc cgtaccccg tggtctttga ataaagtctg  2340
agtgggcggc                                                         2350
```

SEQ ID NO: 62          moltype = RNA  length = 2350
FEATURE                Location/Qualifiers
source                 1..2350
                       mol_type = other RNA
                       organism = synthetic construct
SEQUENCE: 62

```
gggaaataag agagaaaaga agagtaagaa gaaatataag agccaccatg gccggcttct    60
gggtgggcac cgccccccctt gtcgcagcag gaaggcgggg ccggtggcct ccccagcagt   120
taatgcttag cgccgccctc cgcaccctca agcacgtcct ctactactcc cgccagtgcc   180
tcatggtatc ccgcaacctc ggctccgtcg gctacgaccc caacgagaag accttcgaca   240
agatcctcgt cgccaaccgc ggcgagatcg cctgccgcgt catccgcacc tgcaagaaga   300
tgggcatcaa gaccgtcgcc atccactccg acgtcgacgc ctcctccgtc cacgtcaaga   360
tggccgacga ggccgtctgc gtcggccccg cccccacctc caagtcctac ctcaacatgg   420
acgccatcat ggaggccatc aagaagaccc gcgcccaggc cgtccacccc ggctacggct   480
tcctctccga gaacaaggag ttcgcccgct gcctcgccgc cgaggacgtc gtcttcatcg   540
gccctgacac ccacgcaatt caggccatgg gtgacaagat tgagtccaag ctcctcgcca   600
agaaggccga ggtcaacacc atccccggct tcgacgacgt cgtcaaggat gctgaagagg   660
cagtccgcat cgccagagag ataggctacc ccgtcatgat caaggcctcc gccggcggcg   720
gaggcaaggg catgcggatc gcatgggacg acgaggaaac ccgcgacggt ttccgcctct   780
cctcccagga ggccgcctcc agtttcgggcg acgacagact cttgatcgag aagttcatcg   840
acaaccccccg cccacatcgag atccaggtcc tcggagataa gcacggcaac gccctctggc   900
tcaacgagcg cgagtgctcc atccagcgcc gcaaccagaa ggtcgtggag gaggcccccct   960
ccatcttcct cgacgcagaa acaaggcgcg cgatggggaga gcaggcagtg gcccttgcca  1020
gggccgtcaa gtactcctcc gcaggtaccg tcgagttcct cgtggactcc aagaagaact  1080
tctacttctt ggagatgaac acacgactgc aggtcgagca tcctgtaacc gagtgcatca  1140
ccggcctcga cctcgtccag gagatgatcc gcgttgccaa gggctaccct ctccgccaca  1200
agcaggccga catccgcatc aacggctggg ctgtggaatg tcgggtgtat gccgaggatc  1260
cctacaagtc cttcggcctg ccatctattg gcagactatc gcagtaccag gagccctcc   1320
acctccccgg cgtgcgcgtt gactctggca tccagccca tcgagcatctact  1380
atgatccgat gatcagcaag cttatcacct atggctcaga ccgcaccgag gcgctgaagc  1440
gcatggctga cgccctcgac aactatgtta tccggggcgt cacccacaac atcgcactcc  1500
tacgggaggt catcatcaac tcccgcttcg tgaagggtga catctccacc aagttcttga  1560
gtgacgtgta ccctgacggc ttcaagggcc acatgctcac caagtccgag aagaaccaac  1620
tgctggctat cgccagcagt ctcttcgtcg ccttccagct gagggcccag cacttccaag  1680
agaatagcag gatgcccgtc atcaagcccg acatcgccaa ctgggagctc tccgtcaagc  1740
tccacgacaa ggtccacacc gtcgtcgcat ccaacaacgg atctgtgttc tccgtcgagg  1800
tcgacggatc taagctgaac gtcacaagca cttggaacct cgcctcccccc ctgctttcag  1860
tgagcgtgga cggcacccag cgcaccgtgc agtgcctgag ccgcgaggcg ggaggcaaca  1920
tgtcgatca gttcctgggc acagtgtaca aggtgaatat cctgacaaga ctggctgctg  1980
agctcaacaa gttcatgctc gagaaggtca ccgaggacac ttcttcggtg ctccgctccc  2040
ccatgcctgg agtggttgtg gccgtgtcag taaagccagg cgacgctgtt gccgagggtc  2100
aggaaatctg cgtcatcgag gccatgaaga tgcagaactc catgacggcc ggcaagacgg  2160
gcactgtcaa gtctgtgcat tgccaggccg agacactgt gggcgagggc gacctactgg  2220
ttgagctcga gtgataatag gctggagcct cggtggccat gcttcttgcc ccttgggcct  2280
```

```
ccccccagcc cctcctcccc ttcctgcacc cgtacccccg tggtctttga ataaagtctg   2340
agtgggcggc                                                          2350

SEQ ID NO: 63          moltype = RNA  length = 2419
FEATURE                Location/Qualifiers
source                 1..2419
                       mol_type = other RNA
                       organism = synthetic construct
SEQUENCE: 63
gggaaataag agagaaaaga agagtaagaa gaaatataag agccaccatg gccggcttct   60
gggtcggcac agcccctctg gtggcagccg gcagaagagg acggtggcct ccccagcaac   120
tgatgctgag cgccgccctg agaaccctga agcacgtgct gtactacagc agacagtgcc   180
tgatggtgag cagaaatctg ggcagcgtgg ggtacgatcc caacgagaag accttcgata   240
agattctggt cgcgaataga ggcgagatcc cctgcagggt gatcagaacc tgcaagaaga   300
tgggcatcaa gaccgtggcc atccattcgg acgtcgacgc gagcagcgtt cacgtgaaga   360
tggcagacga ggccgtgtgc gtgggacccg ccccgaccag caagagctac ctgaacatgg   420
acgccatcat ggaggccatc aagaagaccc gcgctcaagc cgtgcacccg ggctacggct   480
ttctgagcga gaacaaggaa ttcgccaggt gtctcgccgc gaggacgta gtcttcatcg   540
gccctgatac gcacgcgatc caggccatgg gcgacaagat cgagagcaaa ctgctggcca   600
agaaagcaga agtcaacacc atccccggct tcgacggcgt ggtgaaggac gccgaagagg   660
ctgtccgcat cgccagagag atcggctacc ctgtgatgat aaaggctagc gctggaggtg   720
gcggaaaggg catgagaatc gcctgggacg acgaggagac tagagacggc ttcagactgt   780
cctcccagga ggccgccagc tccttcggag acgacagact gctgatcgag aagttcatcg   840
acaaccccag acacatcgaa atccaggtgc tcggtgacaa gcacgggaac gccctgtggc   900
tgaacgagag agagtgcagc atccagagaa gaaaccagaa ggtggtggag gaggcgccga   960
gcatctttct ggacgcggag acaaggagag cgatggccga gatgg cccgtc gccctagcaa   1020
gagccgtgaa gtactccagt gccggaaccg tcgagtttct tgtcgacagc aagaagaatt   1080
tctacttcct ggagatgaac accaggctgc aggtggagca tcccgtgaca gagtgcatca   1140
ctggactgga tctggtgcag gagatgatca gggtggccaa gggctatccc ctgagacaca   1200
agcaggccga catcgagatc aacaggctgg ccgtggagtg cagagtgtac gccgaggacc   1260
cctacaagag cttcggcctg cccagcatcg gcagactgag ccagtaccag gagcccctgc   1320
acctgcccgg cgtgagagtg gacagcggca tccaaccggg gagcgatatc agcatctact   1380
acgaccccat gatcagcaag ctgataacct acggcagcga cagaaccgag gccctgaaga   1440
gaatggccga cgccctggac aactacgtga tcagaggcgt gacccacaac atcgccctgc   1500
tgagagaggt gatcatcaac tcgaggttcg tgaaaggcac catcagcacc aagttcctga   1560
gcgacgtgta tcccgacgga ttcaaaggtc acatgctgac caagagcgag aagaaccagc   1620
tgctggccat cgcctcatcc ctgttcgtgg ccttccagct gagagcccag cacttccagg   1680
agaacagcag aatgcccgtg atcaagcccg acatcgccaa ctgggagctg agcgtgaagc   1740
tgcacgacaa ggtgcacact gtcgttgcca gcaacaacgg ctccgtgttc agcgtagagg   1800
tggacggatc taagctgaac gtgacctcca cctggaacct ggcaagccct ctcctgtcag   1860
tgagcgtgga cggcacccag agaaccgtgc agtgtctgtc ccgcgaggcc ggcggaaaca   1920
tgagcatcca gttcctgggc accgtgtaca aggtgaacat cctgaccaga ctggccgccg   1980
agctgaacaa gttcatgctg gagaaagtga cggaggatac cagctccgtg ctgagaagcc   2040
ccatgcccgg agtggtggtg gccgtttccg tgaaacctgg tgacgccgtg gccgaggggc   2100
aagagatctg cgtgatcgag gccatgaaga tgcagaattc catgaccgcc ggaaagaccg   2160
gcaccgtcaa atcagtgcac tgccaggcgg gcgacacagt gggtgagggc gacctgctgg   2220
tggagctgga gtgataatag tccataaagt aggaaacact acagctggag cctcggtggc   2280
ctagcttctt gccccttggg cctccataaa gtaggaaaca ctacatcccc ccagcccctc   2340
ctccccttcc tgcacccgta ccccctccat aaagtaggaa acactacagt ggtctttgaa   2400
taaagtctga gtgggcggc                                                2419

SEQ ID NO: 64          moltype = DNA  length = 47
FEATURE                Location/Qualifiers
source                 1..47
                       mol_type = other DNA
                       organism = synthetic construct
SEQUENCE: 64
gggaaataag agagaaaaga agagtaagaa gaaatataag agccacc                 47

SEQ ID NO: 65          moltype = RNA  length = 2395
FEATURE                Location/Qualifiers
source                 1..2395
                       mol_type = other RNA
                       organism = synthetic construct
SEQUENCE: 65
gggaaataag agagaaaaga agagtaagaa gaaatataag agccaccatg gccggcttct   60
gggtcggcac agcccctctg gtggcagccg gcagaagagg acggtggcct ccccagcaac   120
tgatgctgag cgccgccctg agaaccctga agcacgtgct gtactacagc agacagtgcc   180
tgatggtgag cagaaatctg ggcagcgtgg ggtacgatcc caacgagaag accttcgata   240
agattctggt cgcgaataga ggcgagatcc cctgcagggt gatcagaacc tgcaagaaga   300
tgggcatcaa gaccgtggcc atccattcgg acgtcgacgc gagcagcgtt cacgtgaaga   360
tggcagacga ggccgtgtgc gtgggacccg ccccgaccag caagagctac ctgaacatgg   420
acgccatcat ggaggccatc aagaagaccc gcgctcaagc cgtgcacccg ggctacggct   480
ttctgagcga gaacaaggaa ttcgccaggt gtctcgccgc gaggacgta gtcttcatcg   540
gccctgatac gcacgcgatc caggccatgg gcgacaagat cgagagcaaa ctgctggcca   600
agaaagcaga agtcaacacc atccccggct tcgacggcgt ggtgaaggac gccgaagagg   660
ctgtccgcat cgccagagag atcggctacc ctgtgatgat aaaggctagc gctggaggtg   720
gcggaaaggg catgagaatc gcctgggacg acgaggagac tagagacggc ttcagactgt   780
cctcccagga ggccgccagc tccttcggag acgacagact gctgatcgag aagttcatcg   840
```

```
acaaccccag acacatcgaa atccaggtgc tcggtgacaa gcacgggaac gccctgtggc    900
tgaacgagag agagtgcagc atccagagaa gaaaccagaa ggtggtggag gaggcgccga    960
gcatctttct ggacgcggag acaaggagag cgatgggcga acaggccgtc gccctagcaa   1020
gagccgtgaa gtactccagt gccggaaccg tcgagtttct tgtcgacagc aagaagaatt   1080
tctacttcct ggagatgaac accaggctgc aggtggagca tcccgtgaca gagtgcatca   1140
ctggactgga tctggtgcag gagatgatca gggtggccaa gggctatccc ctgagacaca   1200
agcaggccga catcagaatc aacggctggg ccgtggagtg cagagtgtac gccgaggacc   1260
cctacaagag cttcggcctg cccagcatcg gcagactgag ccagtaccag gagcccctgc   1320
acctgcccgg cgtgagagtg gacagcggca tccaaccggg gagcgatatc agcatctact   1380
acgaccccat gatcagcaag ctgataacct acggcagcga cagaaccgag gccctgaaga   1440
gaatggccga cgccctggac aactacgtga tcagaggcgt gacccacaac atcgccctgc   1500
tgagagaggt gatcatcaac tcgaggttcg tgaaagcga catcagcacc aagttcctga   1560
gcgacgtgta tcccgacgga ttcaaaggtc acatgctgac caagagcgag aagaaccagc   1620
tgctggccat cgcctcatcc ctgttcgtgg ccttccagct gagagcccag cacttccagg   1680
agaacagcag aatgcccgtg atcaagcccg acatcgccaa ctgggagctg agcgtgaagc   1740
tgcacgacaa ggtgcacact gtcgttgcca gcaacaacgg ctccgtgttc agcgtagagg   1800
tggacggatc taagctgaac gtgacctcca cctggaacct ggcaagccct ctcctgtcag   1860
tgagcgtgga cggcacccag agaaccgtgc agtgtctgtc ccgcgaggcc ggcggaaaca   1920
tgagcatcca gttcctgggc accgtgtaca aggtgaacat cctgaccaga ctggccgccg   1980
agctgaacaa gttcatgctg gagaaagtga cggaggatac cagctccgtg ctgagaagcc   2040
ccatgcccgg agtggtggtg gccgtttccg tgaaacctgg tgacgccgtg gccgaggggc   2100
aagagatctg cgtgaattgc gccatgaaga tgcagaattc catgaccgcc ggaaagaccg   2160
gcaccgtcaa atcagtgcac tgccaggcgg cgcacacagt gggtgagggc gacctgctgg   2220
tggagctgga gtgataatag tccataaagt aggaaacact acagctggag cctcggtggc   2280
ctagcttctt gccccttggg cctccccca gccctcctc cccttcctgc acccgtaccc    2340
cccgcattat tactcacggt acgagtggtc tttgaataaa gtctgagtgg cggc         2395
```

SEQ ID NO: 66              moltype = RNA   length = 1852
FEATURE                    Location/Qualifiers
source                     1..1852
                           mol_type = other RNA
                           organism = synthetic construct
SEQUENCE: 66

```
gggaaataag agagaaaaga agagtaagaa gaaatataag agccaccatg gccgcagccc     60
tcagagtggc tgccgtggga gccagactca gcgtgctcgc ctcaggcctg cgggccgcag    120
tcagaagcct gtgcagccag gcaacctcag tgaacgagag aatcgagaac aagagacgga    180
ccgccctgct gggtggcggg caaagaagaa ttgacgccca gcacaagaga ggcaagctga    240
ccgcccgcga gcgcatcagc ctgctgctgg accccggcag cttcgtggag agcgacatgt    300
tcgtgagca tcggtgtgcc gacttcggca tggccgccga caagaacaag ttccccggcg    360
acagcgtggt gaccggcaga ggcagaatca acggcagact ggtgtacgtg ttctcacaag    420
actttaccgt cttcggagga tccctgtcag gggctcacgc ccagaagatc tgcaagatca    480
tggaccaggc catcaccgtg ggcgctcccg tgatcggcct gaacgacagc ggaggcgcca    540
ggatccaaga gggagtggag tccctggccg gctacgccga catcttcctg agaaacgtga    600
ccgcctcggg cgtgatccca cagatctccc tgatcatggg accctgcgcc ggcgggggcg    660
tctacagccc tgccctgacc gacttcacct tcatggtgaa ggacaccagc tacctgttca    720
tcaccggccc cgacgtggtc aagagcgtga ccaacgagga cgtgacccag gaggagctcg    780
gcggagccaa gactcacaca accatgtccg gcgtcgctca tagggccttc gagaacgacg    840
tggacgccct gtgcaacctg agagacttct tcaactacct gccattgagc agccaggatc    900
ccgcccctgt gagagagtgc cacgacccca gcgacagact ggtgcccgag ctggacacca    960
tcgtgcccct ggagagcacc aaggcctaca acatggtgga catcatccac agcgtggtgg   1020
acgagagaga gttcttcgag atcatgccca actacgccaa gaacatcatc gtgggcttcg   1080
ccagaatgaa cggcagaacc gtgggcattg tgggcaacca gcccaaggtc gccagcggct   1140
gcctcgacat caacagcagc gtgaagggcg ccagattcgt gagattctgc gacgccttca   1200
acatacctct gatcaccttt gtggacgtgc ctggtttcct cccgggcacc gcccaagaat   1260
acggtggcat catcagacac ggcgccaagc tgctgtaccg cttcgccgag gccaccgtgc   1320
ccaaggtgac cgttatcacc cgcaaagcct acggcggcgc ctacgacgtg atgagcagca   1380
agcacctgtg tggcgacacc aattacgcct ggcccaccgc cgagatcgcc gtcatgggcg   1440
cgaaaggagc cgtggagatc atcttcaagg ccacgagaa cgtggaggcc gcccaggccg   1500
agtacatcga gaagttcgcc aaccccttcc ctgccgccg gagggggttc gtcgacgata   1560
tcatccagcc cagctccacc cgcgccagaa tctgttgcga cctggacgtg ctggccagca   1620
agaaggtgca aagaccctgg agaaagcacg ccaacatccc gctgtgataa tagtccataa   1680
agtaggaaac actacagctg gagcctcggt ggcctagctt cttgcccctt gggcctccat   1740
aaagtaggaa acactacatc cccccagccc ctcctcccct tcctgcaccc gtaccccctc   1800
cataaagtag gaaacactac agtggtcttt gaataaagtc tgagtgggcg gc           1852
```

SEQ ID NO: 67              moltype = RNA   length = 1828
FEATURE                    Location/Qualifiers
source                     1..1828
                           mol_type = other RNA
                           organism = synthetic construct
SEQUENCE: 67

```
gggaaataag agagaaaaga agagtaagaa gaaatataag agccaccatg gccgcagccc     60
tcagagtggc tgccgtggga gccagactca gcgtgctcgc ctcaggcctg cgggccgcag    120
tcagaagcct gtgcagccag gcaacctcag tgaacgagag aatcgagaac aagagacgga    180
ccgccctgct gggtggcggg caaagaagaa ttgacgccca gcacaagaga ggcaagctga    240
ccgcccgcga gcgcatcagc ctgctgctgg accccggcag cttcgtggag agcgacatgt    300
tcgtggagca tcggtgtgcc gacttcggca tggccgccga caagaacaag ttccccggcg    360
acagcgtggt gaccggcaga ggcagaatca acggcagact ggtgtacgtg ttctcacaag    420
actttaccgt cttcggagga tccctgtcag gggctcacgc ccagaagatc tgcaagatca    480
```

```
tggaccaggc catcaccgtg ggcgctcccg tgatcggcct gaacgacagc ggaggcgcca    540
ggatccaaga gggagtggag tccctggccg gctacgccga catcttcctg agaaacgtga    600
ccgcctcggg cgtgatccca cagatctccc tgatcatggg accctgcgcc ggcggggccg    660
tctacagccc tgccctgacc gacttcacct tcatggtgaa ggacaccagc tacctgttca    720
tcaccggccc cgacgtggtc aagagcgtga ccaacgagga cgtgacccag gaggagctcg    780
gcggagccaa gactcacaca accatgtccg gcgtcgctca tagggccttc gagaacgacg    840
tggacgccct gtgcaacctg agagacttct tcaactacct gccattgagc agccaggatc    900
ccgcccctgt gagagagtgc cacgaccccca gcgacagact ggtgcccgag ctggacacca    960
tcgtgcccct ggagagcacc aaggcctaca acatggtgga catcatccac agcgtggtgg   1020
acgagagaga gttcttcgag atcatgccca actacgccaa gaacatcatc gtgggcttcg   1080
ccagaatgaa cggcagaacc gtgggcattg tgggcaacca gcccaaggtc gccagcggct   1140
gcctcgacat caacagcagc gtgaagggcg ccagattcgt gagattctgc gacgccttca   1200
acatacctct gatcaccttt gtggacgtgc ctggtttcct cccgggcacc gcccaagaat   1260
acggtggcat catcagacac ggcgccaagc tgctgtacgc cttcgccgag gccaccgtgc   1320
ccaaggtgac cgttatcacc cgcaaagcct acggcggcgc ctacgacgtg atgagcagca   1380
agcacctgtg tggcgacacc aattacgcct ggcccaccgc cgagatcgcc gtcatgggcg   1440
cgaaaggagc cgtggagatc atcttcaagg ccacgagaa cgtggaggcc gcccaggccg   1500
agtacatcga gaagttcgcc aacccacttcc ctgccgccgt gagggggcttc gtcgacgata   1560
tcatccagcc cagctccacc cgcgccagaa tctgttgcga cctggacgtg ctggccagca   1620
agaaggtgca agaccctggg agaaagcacg ccaacatccc gctgtgataa tagtccataa   1680
agtaggaaac actacagctg gagcctcggt ggcctagctt cttgcccctt gggcctcccc   1740
ccagcccctc ctcccttcc tgcaccccgta ccccccgcat tattactcac ggtacgagtg   1800
gtctttgaat aaagtctgag tgggcggc                                     1828
```

```
SEQ ID NO: 68           moltype =   length =
SEQUENCE: 68
000

SEQ ID NO: 69           moltype =   length =
SEQUENCE: 69
000

SEQ ID NO: 70           moltype =   length =
SEQUENCE: 70
000

SEQ ID NO: 71           moltype =   length =
SEQUENCE: 71
000

SEQ ID NO: 72           moltype =   length =
SEQUENCE: 72
000

SEQ ID NO: 73           moltype =   length =
SEQUENCE: 73
000

SEQ ID NO: 74           moltype =   length =
SEQUENCE: 74
000

SEQ ID NO: 75           moltype =   length =
SEQUENCE: 75
000

SEQ ID NO: 76           moltype =   length =
SEQUENCE: 76
000

SEQ ID NO: 77           moltype =   length =
SEQUENCE: 77
000

SEQ ID NO: 78           moltype =   length =
SEQUENCE: 78
000

SEQ ID NO: 79           moltype =   length =
SEQUENCE: 79
000

SEQ ID NO: 80           moltype =   length =
SEQUENCE: 80
000

SEQ ID NO: 81           moltype =   length =
SEQUENCE: 81
000
```

```
SEQ ID NO: 82          moltype =   length =
SEQUENCE: 82
000

SEQ ID NO: 83          moltype =   length =
SEQUENCE: 83
000

SEQ ID NO: 84          moltype =   length =
SEQUENCE: 84
000

SEQ ID NO: 85          moltype =   length =
SEQUENCE: 85
000

SEQ ID NO: 86          moltype = AA   length = 5
FEATURE                Location/Qualifiers
source                 1..5
                       mol_type = protein
                       organism = synthetic construct
SEQUENCE: 86
GGGGS                                                               5

SEQ ID NO: 87          moltype =   length =
SEQUENCE: 87
000

SEQ ID NO: 88          moltype = RNA   length = 92
FEATURE                Location/Qualifiers
source                 1..92
                       mol_type = other RNA
                       organism = synthetic construct
SEQUENCE: 88
tcaagctttt ggaccctcgt acagaagcta atacgactca ctatagggaa ataagagaga   60
aaagaagagt aagaagaaat ataagagcca cc                                 92

SEQ ID NO: 89          moltype = RNA   length = 47
FEATURE                Location/Qualifiers
source                 1..47
                       mol_type = other RNA
                       organism = synthetic construct
SEQUENCE: 89
gggagatcag agagaaaaga agagtaagaa gaaatataag agccacc                 47

SEQ ID NO: 90          moltype = RNA   length = 42
FEATURE                Location/Qualifiers
source                 1..42
                       mol_type = other RNA
                       organism = synthetic construct
SEQUENCE: 90
gggagacaag cttggcattc cggtactgtt ggtaaagcca cc                      42

SEQ ID NO: 91          moltype =   length =
SEQUENCE: 91
000

SEQ ID NO: 92          moltype =   length =
SEQUENCE: 92
000

SEQ ID NO: 93          moltype = RNA   length = 47
FEATURE                Location/Qualifiers
source                 1..47
                       mol_type = other RNA
                       organism = synthetic construct
SEQUENCE: 93
gggaattaac agagaaaaga agagtaagaa gaaatataag agccacc                 47

SEQ ID NO: 94          moltype = RNA   length = 47
FEATURE                Location/Qualifiers
source                 1..47
                       mol_type = other RNA
                       organism = synthetic construct
SEQUENCE: 94
gggaaattag acagaaaaga agagtaagaa gaaatataag agccacc                 47

SEQ ID NO: 95          moltype = RNA   length = 47
```

-continued

```
FEATURE                  Location/Qualifiers
source                   1..47
                         mol_type = other RNA
                         organism = synthetic construct
SEQUENCE: 95
gggaaataag agagtaaaga acagtaagaa gaaatataag agccacc                    47

SEQ ID NO: 96            moltype = RNA   length = 47
FEATURE                  Location/Qualifiers
source                   1..47
                         mol_type = other RNA
                         organism = synthetic construct
SEQUENCE: 96
gggaaaaaag agagaaaaga agactaagaa gaaatataag agccacc                    47

SEQ ID NO: 97            moltype = RNA   length = 47
FEATURE                  Location/Qualifiers
source                   1..47
                         mol_type = other RNA
                         organism = synthetic construct
SEQUENCE: 97
gggaaataag agagaaaaga agagtaagaa gatatataag agccacc                    47

SEQ ID NO: 98            moltype = RNA   length = 47
FEATURE                  Location/Qualifiers
source                   1..47
                         mol_type = other RNA
                         organism = synthetic construct
SEQUENCE: 98
gggaaataag agacaaaaca agagtaagaa gaaatataag agccacc                    47

SEQ ID NO: 99            moltype = RNA   length = 47
FEATURE                  Location/Qualifiers
source                   1..47
                         mol_type = other RNA
                         organism = synthetic construct
SEQUENCE: 99
gggaaattag agagtaaaga acagtaagta gaattaaaag agccacc                    47

SEQ ID NO: 100           moltype = RNA   length = 47
FEATURE                  Location/Qualifiers
source                   1..47
                         mol_type = other RNA
                         organism = synthetic construct
SEQUENCE: 100
gggaaataag agagaataga agagtaagaa gaaatataag agccacc                    47

SEQ ID NO: 101           moltype = RNA   length = 47
FEATURE                  Location/Qualifiers
source                   1..47
                         mol_type = other RNA
                         organism = synthetic construct
SEQUENCE: 101
gggaaataag agagaaaaga agagtaagaa gaaaattaag agccacc                    47

SEQ ID NO: 102           moltype = RNA   length = 47
FEATURE                  Location/Qualifiers
source                   1..47
                         mol_type = other RNA
                         organism = synthetic construct
SEQUENCE: 102
gggaaataag agagaaaaga agagtaagaa gaaatttaag agccacc                    47

SEQ ID NO: 103           moltype =     length =
SEQUENCE: 103
000

SEQ ID NO: 104           moltype = RNA   length = 142
FEATURE                  Location/Qualifiers
source                   1..142
                         mol_type = other RNA
                         organism = synthetic construct
SEQUENCE: 104
tgataatagt ccataaagta ggaaacacta cagctggagc ctcggtggcc atgcttcttg      60
cccccttgggc ctcccccccag cccctcctcc ccttcctgca cccgtacccc cgtggtcttt   120
gaataaagtc tgagtgggcg gc                                              142

SEQ ID NO: 105           moltype = RNA   length = 142
FEATURE                  Location/Qualifiers
```

-continued

```
source                   1..142
                         mol_type = other RNA
                         organism = synthetic construct
SEQUENCE: 105
tgataatagg ctggagcctc ggtggctcca taaagtagga aacactacac atgcttcttg    60
cccttgggc ctcccccag ccctcctcc ccttcctgca cccgtacccc cgtggtcttt      120
gaataaagtc tgagtgggcg gc                                            142

SEQ ID NO: 106          moltype = RNA   length = 142
FEATURE                 Location/Qualifiers
source                  1..142
                        mol_type = other RNA
                        organism = synthetic construct
SEQUENCE: 106
tgataatagg ctggagcctc ggtggccatg cttcttgccc cttccataaa gtaggaaaca    60
ctacatgggc ctcccccag ccctcctcc ccttcctgca cccgtacccc cgtggtcttt     120
gaataaagtc tgagtgggcg gc                                            142

SEQ ID NO: 107          moltype = RNA   length = 142
FEATURE                 Location/Qualifiers
source                  1..142
                        mol_type = other RNA
                        organism = synthetic construct
SEQUENCE: 107
tgataatagg ctggagcctc ggtggccatg cttcttgccc cttgggcctc ccccagtcc     60
ataaagtagg aaacactaca ccctcctcc ccttcctgca cccgtacccc cgtggtcttt    120
gaataaagtc tgagtgggcg gc                                            142

SEQ ID NO: 108          moltype = RNA   length = 142
FEATURE                 Location/Qualifiers
source                  1..142
                        mol_type = other RNA
                        organism = synthetic construct
SEQUENCE: 108
tgataatagg ctggagcctc ggtggccatg cttcttgccc cttgggcctc ccccagccc     60
ctcctcccct tctccataaa gtaggaaaca ctacactgca cccgtacccc cgtggtcttt   120
gaataaagtc tgagtgggcg gc                                            142

SEQ ID NO: 109          moltype = RNA   length = 142
FEATURE                 Location/Qualifiers
source                  1..142
                        mol_type = other RNA
                        organism = synthetic construct
SEQUENCE: 109
tgataatagg ctggagcctc ggtggccatg cttcttgccc cttgggcctc ccccagccc     60
ctcctcccct tcctgcaccc gtacccctc cataaagtag gaaacactac agtggtcttt    120
gaataaagtc tgagtgggcg gc                                            142

SEQ ID NO: 110          moltype = RNA   length = 142
FEATURE                 Location/Qualifiers
source                  1..142
                        mol_type = other RNA
                        organism = synthetic construct
SEQUENCE: 110
tgataatagg ctggagcctc ggtggccatg cttcttgccc cttgggcctc ccccagccc     60
ctcctcccct tcctgcaccc gtaccccgt ggtctttgaa taaagttcca taaagtagga    120
aacactacac tgagtgggcg gc                                            142

SEQ ID NO: 111          moltype = RNA   length = 164
FEATURE                 Location/Qualifiers
source                  1..164
                        mol_type = other RNA
                        organism = synthetic construct
SEQUENCE: 111
tgataatagt ccataaagta ggaaacacta cagctggagc ctcggtggcc atgcttcttg    60
cccttgggc ctcccccag ccctcctcc ccttcctgca cccgtacccc ccgcattatt      120
actcacggta cgagtggtct ttgaataaag tctgagtggg cggc                    164

SEQ ID NO: 112          moltype = RNA   length = 164
FEATURE                 Location/Qualifiers
source                  1..164
                        mol_type = other RNA
                        organism = synthetic construct
SEQUENCE: 112
tgataatagt ccataaagta ggaaacacta cagctggagc ctcggtggcc tagcttcttg    60
cccttgggc ctcccccag ccctcctcc ccttcctgca cccgtacccc ccgcattatt      120
actcacggta cgagtggtct ttgaataaag tctgagtggg cggc                    164

SEQ ID NO: 113          moltype =    length =
```

```
SEQUENCE: 113
000

SEQ ID NO: 114          moltype = RNA   length = 87
FEATURE                 Location/Qualifiers
source                  1..87
                        mol_type = other RNA
                        organism = synthetic construct
SEQUENCE: 114
gacagtgcag tcacccataa agtagaaagc actactaaca gcactggagg gtgtagtgtt   60
tcctacttta tggatgagtg tactgtg                                      87

SEQ ID NO: 115          moltype = RNA   length = 23
FEATURE                 Location/Qualifiers
source                  1..23
                        mol_type = other RNA
                        organism = synthetic construct
SEQUENCE: 115
tgtagtgttt cctactttat gga                                          23

SEQ ID NO: 116          moltype = RNA   length = 23
FEATURE                 Location/Qualifiers
source                  1..23
                        mol_type = other RNA
                        organism = synthetic construct
SEQUENCE: 116
tccataaagt aggaaacact aca                                          23

SEQ ID NO: 117          moltype = RNA   length = 21
FEATURE                 Location/Qualifiers
source                  1..21
                        mol_type = other RNA
                        organism = synthetic construct
SEQUENCE: 117
cataaagtag aaagcactac t                                            21

SEQ ID NO: 118          moltype = RNA   length = 21
FEATURE                 Location/Qualifiers
source                  1..21
                        mol_type = other RNA
                        organism = synthetic construct
SEQUENCE: 118
agtagtgctt tctactttat g                                            21

SEQ ID NO: 119          moltype = RNA   length = 85
FEATURE                 Location/Qualifiers
source                  1..85
                        mol_type = other RNA
                        organism = synthetic construct
SEQUENCE: 119
cgctggcgac gggacattat tacttttggt acgcgctgtg acacttcaaa ctcgtaccgt   60
gagtaataat gcgccgtcca cggca                                        85

SEQ ID NO: 120          moltype = RNA   length = 22
FEATURE                 Location/Qualifiers
source                  1..22
                        mol_type = other RNA
                        organism = synthetic construct
SEQUENCE: 120
tcgtaccgtg agtaataatg cg                                           22

SEQ ID NO: 121          moltype = RNA   length = 22
FEATURE                 Location/Qualifiers
source                  1..22
                        mol_type = other RNA
                        organism = synthetic construct
SEQUENCE: 121
cgcattatta ctcacggtac ga                                           22

SEQ ID NO: 122          moltype = RNA   length = 21
FEATURE                 Location/Qualifiers
source                  1..21
                        mol_type = other RNA
                        organism = synthetic construct
SEQUENCE: 122
cattattact tttggtacgc g                                            21

SEQ ID NO: 123          moltype = RNA   length = 21
FEATURE                 Location/Qualifiers
```

-continued

```
source                  1..21
                        mol_type = other RNA
                        organism = synthetic construct
SEQUENCE: 123
cgcgtaccaa aagtaataat g                                          21

SEQ ID NO: 124          moltype =   length =
SEQUENCE: 124
000

SEQ ID NO: 125          moltype =   length =
SEQUENCE: 125
000

SEQ ID NO: 126          moltype =   length =
SEQUENCE: 126
000

SEQ ID NO: 127          moltype =   length =
SEQUENCE: 127
000

SEQ ID NO: 128          moltype =   length =
SEQUENCE: 128
000

SEQ ID NO: 129          moltype =   length =
SEQUENCE: 129
000

SEQ ID NO: 130          moltype =   length =
SEQUENCE: 130
000

SEQ ID NO: 131          moltype =   length =
SEQUENCE: 131
000

SEQ ID NO: 132          moltype =   length =
SEQUENCE: 132
000

SEQ ID NO: 133          moltype =   length =
SEQUENCE: 133
000

SEQ ID NO: 134          moltype = RNA   length = 133
FEATURE                 Location/Qualifiers
source                  1..133
                        mol_type = other RNA
                        organism = synthetic construct
SEQUENCE: 134
gctggagcct cggtggccat gcttcttgcc ccttgggcct cccccagcc cctcctcccc  60
ttcctgcacc cgtacccct ccataaagta ggaaacacta cagtggtctt tgaataaagt  120
ctgagtgggc ggc                                                   133

SEQ ID NO: 135          moltype = RNA   length = 22
FEATURE                 Location/Qualifiers
source                  1..22
                        mol_type = other RNA
                        organism = synthetic construct
SEQUENCE: 135
cctctgaaat tcagttcttc ag                                          22

SEQ ID NO: 136          moltype = RNA   length = 22
FEATURE                 Location/Qualifiers
source                  1..22
                        mol_type = other RNA
                        organism = synthetic construct
SEQUENCE: 136
tgagaactga attccatggg tt                                          22

SEQ ID NO: 137          moltype = RNA   length = 22
FEATURE                 Location/Qualifiers
source                  1..22
                        mol_type = other RNA
                        organism = synthetic construct
SEQUENCE: 137
ctcctacata ttagcattaa ca                                          22
```

-continued

```
SEQ ID NO: 138            moltype = RNA   length = 23
FEATURE                   Location/Qualifiers
source                    1..23
                          mol_type = other RNA
                          organism = synthetic construct
SEQUENCE: 138
ttaatgctaa tcgtgatagg ggt                                        23

SEQ ID NO: 139            moltype = RNA   length = 22
FEATURE                   Location/Qualifiers
source                    1..22
                          mol_type = other RNA
                          organism = synthetic construct
SEQUENCE: 139
ccagtattaa ctgtgctgct ga                                         22

SEQ ID NO: 140            moltype = RNA   length = 22
FEATURE                   Location/Qualifiers
source                    1..22
                          mol_type = other RNA
                          organism = synthetic construct
SEQUENCE: 140
tagcagcacg taaatattgg cg                                         22

SEQ ID NO: 141            moltype = RNA   length = 21
FEATURE                   Location/Qualifiers
source                    1..21
                          mol_type = other RNA
                          organism = synthetic construct
SEQUENCE: 141
caacaccagt cgatgggctg t                                          21

SEQ ID NO: 142            moltype = RNA   length = 22
FEATURE                   Location/Qualifiers
source                    1..22
                          mol_type = other RNA
                          organism = synthetic construct
SEQUENCE: 142
tagcttatca gactgatgtt ga                                         22

SEQ ID NO: 143            moltype = RNA   length = 22
FEATURE                   Location/Qualifiers
source                    1..22
                          mol_type = other RNA
                          organism = synthetic construct
SEQUENCE: 143
tgtcagtttg tcaaataccc ca                                         22

SEQ ID NO: 144            moltype = RNA   length = 22
FEATURE                   Location/Qualifiers
source                    1..22
                          mol_type = other RNA
                          organism = synthetic construct
SEQUENCE: 144
cgtgtatttg acaagctgag tt                                         22

SEQ ID NO: 145            moltype = RNA   length = 22
FEATURE                   Location/Qualifiers
source                    1..22
                          mol_type = other RNA
                          organism = synthetic construct
SEQUENCE: 145
tggctcagtt cagcaggaac ag                                         22

SEQ ID NO: 146            moltype = RNA   length = 22
FEATURE                   Location/Qualifiers
source                    1..22
                          mol_type = other RNA
                          organism = synthetic construct
SEQUENCE: 146
tgcctactga gctgatatca gt                                         22

SEQ ID NO: 147            moltype = RNA   length = 21
FEATURE                   Location/Qualifiers
source                    1..21
                          mol_type = other RNA
                          organism = synthetic construct
SEQUENCE: 147
```

-continued

```
ttcacagtgg ctaagttccg c                                             21

SEQ ID NO: 148          moltype = RNA   length = 22
FEATURE                 Location/Qualifiers
source                  1..22
                        mol_type = other RNA
                        organism = synthetic construct
SEQUENCE: 148
agggcttagc tgcttgtgag ca                                            22

SEQ ID NO: 149          moltype = RNA   length = 141
FEATURE                 Location/Qualifiers
source                  1..141
                        mol_type = other RNA
                        organism = synthetic construct
SEQUENCE: 149
tgataatagg ctggagcctc ggtggccatg cttcttgccc cttgggcctc ccccagccc    60
ctcctcccct tcctgcaccc gtacccccg cattattact cacggtacga gtggtctttg    120
aataaagtct gagtgggcgg c                                             141

SEQ ID NO: 150          moltype = RNA   length = 119
FEATURE                 Location/Qualifiers
source                  1..119
                        mol_type = other RNA
                        organism = synthetic construct
SEQUENCE: 150
tgataatagg ctggagcctc ggtggccatg cttcttgccc cttgggcctc ccccagccc    60
ctcctcccct tcctgcaccc gtaccccgt ggtctttgaa taaagtctga gtgggcggc    119

SEQ ID NO: 151          moltype =   length =
SEQUENCE: 151
000

SEQ ID NO: 152          moltype =   length =
SEQUENCE: 152
000

SEQ ID NO: 153          moltype = RNA   length = 23
FEATURE                 Location/Qualifiers
source                  1..23
                        mol_type = other RNA
                        organism = synthetic construct
SEQUENCE: 153
ttaatgctaa ttgtgatagg ggt                                           23

SEQ ID NO: 154          moltype = RNA   length = 23
FEATURE                 Location/Qualifiers
source                  1..23
                        mol_type = other RNA
                        organism = synthetic construct
SEQUENCE: 154
acccctatca caattagcat taa                                           23

SEQ ID NO: 155          moltype = RNA   length = 188
FEATURE                 Location/Qualifiers
source                  1..188
                        mol_type = other RNA
                        organism = synthetic construct
SEQUENCE: 155
tgataatagt ccataaagta ggaaacacta cagctggagc ctcggtggcc atgcttcttg    60
ccccttgggc ctccataaag taggaaacac tacatccccc cagcccctcc tcccttcct    120
gcacccgtac ccctccata aagtaggaaa cactacagtg gtctttgaat aaagtctgag    180
tgggcggc                                                            188

SEQ ID NO: 156          moltype = RNA   length = 140
FEATURE                 Location/Qualifiers
source                  1..140
                        mol_type = other RNA
                        organism = synthetic construct
SEQUENCE: 156
tgataatagg ctggagcctc ggtggccatg cttcttgccc cttgggcctc ccccagccc    60
ctcctcccct tcctgcaccc gtaccccag tagtgctttc tactttatgg tggtctttga    120
ataaagtctg agtgggcggc                                               140

SEQ ID NO: 157          moltype = RNA   length = 182
FEATURE                 Location/Qualifiers
source                  1..182
                        mol_type = other RNA
                        organism = synthetic construct
```

```
SEQUENCE: 157
tgataataga gtagtgcttt ctactttatg gctggagcct cggtggccat gcttcttgcc    60
ccttgggcca gtagtgcttt ctactttatg tcccccagc cctcctccc cttcctgcac   120
ccgtacccc agtagtgctt tctactttat ggtggtcttt gaataaagtc tgagtgggcg   180
gc                                                                 182

SEQ ID NO: 158            moltype = RNA   length = 184
FEATURE                   Location/Qualifiers
source                    1..184
                          mol_type = other RNA
                          organism = synthetic construct
SEQUENCE: 158
tgataataga gtagtgcttt ctactttatg gctggagcct cggtggccat gcttcttgcc    60
ccttgggcct ccataaagta ggaaacacta catccccca gccctcctc cccttcctgc   120
acccgtaccc ccagtagtgc tttctacttt atggtggtct ttgaataaag tctgagtggg   180
cggc                                                               184

SEQ ID NO: 159            moltype = RNA   length = 142
FEATURE                   Location/Qualifiers
source                    1..142
                          mol_type = other RNA
                          organism = synthetic construct
SEQUENCE: 159
tgataatagg ctggagcctc ggtggccatg cttcttgccc cttgggcctc ccccagccc    60
ctcctcccct tcctgcaccc gtaccccac ccctatcaca attagcatta agtggtcttt   120
gaataaagtc tgagtgggcg gc                                            142

SEQ ID NO: 160            moltype = RNA   length = 188
FEATURE                   Location/Qualifiers
source                    1..188
                          mol_type = other RNA
                          organism = synthetic construct
SEQUENCE: 160
tgataataga ccctatcac aattagcatt aagctggagc ctcggtggc atgcttcttg    60
cccttgggc caccctatc acaattagca ttaatcccc cagccctcc tccccttcct   120
gcacccgtac ccccacccct atcacaatta gcattaagtg gtctttgaat aaagtctgag   180
tgggcggc                                                           188

SEQ ID NO: 161            moltype = RNA   length = 188
FEATURE                   Location/Qualifiers
source                    1..188
                          mol_type = other RNA
                          organism = synthetic construct
SEQUENCE: 161
tgataataga ccctatcac aattagcatt aagctggagc ctcggtggcc atgcttcttg    60
cccttgggc ctccataaag taggaaacac tacatccccc cagccctcc tccccttcct   120
gcacccgtac ccccacccct atcacaatta gcattaagtg gtctttgaat aaagtctgag   180
tgggcggc                                                           188

SEQ ID NO: 162            moltype =    length =
SEQUENCE: 162
000

SEQ ID NO: 163            moltype =    length =
SEQUENCE: 163
000

SEQ ID NO: 164            moltype = RNA   length = 142
FEATURE                   Location/Qualifiers
source                    1..142
                          mol_type = other RNA
                          organism = synthetic construct
SEQUENCE: 164
tgataatagg ctggagcctc ggtggccatg cttcttgccc cttgggcctc cataaagtag    60
gaaacactac atcccccag ccctcctcc ccttcctgca cccgtacccc cgtggtcttt   120
gaataaagtc tgagtgggcg gc                                            142

SEQ ID NO: 165            moltype = RNA   length = 70
FEATURE                   Location/Qualifiers
source                    1..70
                          mol_type = other RNA
                          organism = synthetic construct
SEQUENCE: 165
gggaaataag agtccataaa gtaggaaaca ctacaagaaa agaagagtaa gaagaaatat    60
aagagccacc                                                          70

SEQ ID NO: 166            moltype = RNA   length = 70
FEATURE                   Location/Qualifiers
source                    1..70
```

```
                            mol_type = other RNA
                            organism = synthetic construct
SEQUENCE: 166
gggaaataag agagaaaaga agagtaatcc ataaagtagg aaacactaca gaagaaatat   60
aagagccacc                                                         70

SEQ ID NO: 167          moltype = RNA  length = 70
FEATURE                 Location/Qualifiers
source                  1..70
                        mol_type = other RNA
                        organism = synthetic construct
SEQUENCE: 167
gggaaataag agagaaaaga agagtaagaa gaaatataat ccataaagta ggaaacacta   60
cagagccacc                                                         70

SEQ ID NO: 168          moltype =   length =
SEQUENCE: 168
000

SEQ ID NO: 169          moltype = RNA  length = 181
FEATURE                 Location/Qualifiers
source                  1..181
                        mol_type = other RNA
                        organism = synthetic construct
SEQUENCE: 169
tgataataga gtagtgcttt ctactttatg gctggagcct cggtggccat gcttcttgcc   60
ccttgggcca gtagtgcttt ctactttatg tcccccagc ccctctcccc ttcctgcacc  120
cgtaccccca gtagtgcttt ctactttatg gtggtctttg aataaagtct gagtgggcgg  180
c                                                                 181

SEQ ID NO: 170          moltype =   length =
SEQUENCE: 170
000

SEQ ID NO: 171          moltype =   length =
SEQUENCE: 171
000

SEQ ID NO: 172          moltype =   length =
SEQUENCE: 172
000

SEQ ID NO: 173          moltype =   length =
SEQUENCE: 173
000

SEQ ID NO: 174          moltype =   length =
SEQUENCE: 174
000

SEQ ID NO: 175          moltype = RNA  length = 119
FEATURE                 Location/Qualifiers
source                  1..119
                        mol_type = other RNA
                        organism = synthetic construct
SEQUENCE: 175
tgataatagg ctggagcctc ggtggcctag cttcttgccc cttgggcctc ccccagccc   60
ctcctcccct tcctgcaccc gtaccccgt ggtctttgaa taaagtctga gtgggcggc  119

SEQ ID NO: 176          moltype =   length =
SEQUENCE: 176
000

SEQ ID NO: 177          moltype = RNA  length = 141
FEATURE                 Location/Qualifiers
source                  1..141
                        mol_type = other RNA
                        organism = synthetic construct
SEQUENCE: 177
tgataatagg ctggagcctc ggtggcctag cttcttgccc cttgggcctc ccccagccc   60
ctcctcccct tcctgcaccc gtacccccg cattattact cacggtacga gtggtctttg  120
aataaagtct gagtgggcgg c                                           141

SEQ ID NO: 178          moltype = RNA  length = 188
FEATURE                 Location/Qualifiers
source                  1..188
                        mol_type = other RNA
                        organism = synthetic construct
SEQUENCE: 178
```

```
tgataatagt ccataaagta ggaaacacta cagctggagc ctcggtggcc tagcttcttg    60
ccccttgggc ctccataaag taggaaacac tacatccccc cagcccctcc tcccttcct    120
gcacccgtac cccctccata aagtaggaaa cactacagtg gtctttgaat aaagtctgag    180
tgggcggc                                                             188

SEQ ID NO: 179          moltype = RNA   length = 142
FEATURE                 Location/Qualifiers
source                  1..142
                        mol_type = other RNA
                        organism = synthetic construct
SEQUENCE: 179
tgataatagt ccataaagta ggaaacacta cagctggagc ctcggtggcc tagcttcttg    60
ccccttgggc ctcccccag cccctcctcc ccttcctgca cccgtacccc cgtggtcttt    120
gaataaagtc tgagtgggcg gc                                              142

SEQ ID NO: 180          moltype = RNA   length = 142
FEATURE                 Location/Qualifiers
source                  1..142
                        mol_type = other RNA
                        organism = synthetic construct
SEQUENCE: 180
tgataatagg ctggagcctc ggtggctcca taaagtagga aacactacac tagcttcttg    60
ccccttgggc ctcccccag cccctcctcc ccttcctgca cccgtacccc cgtggtcttt    120
gaataaagtc tgagtgggcg gc                                              142

SEQ ID NO: 181          moltype = RNA   length = 142
FEATURE                 Location/Qualifiers
source                  1..142
                        mol_type = other RNA
                        organism = synthetic construct
SEQUENCE: 181
tgataatagg ctggagcctc ggtggcctag cttcttgccc cttgggcctc cataaagtag    60
gaaacactac atcccccag ccctcctcc ccttcctgca cccgtacccc cgtggtcttt    120
gaataaagtc tgagtgggcg gc                                              142

SEQ ID NO: 182          moltype = RNA   length = 142
FEATURE                 Location/Qualifiers
source                  1..142
                        mol_type = other RNA
                        organism = synthetic construct
SEQUENCE: 182
tgataatagg ctggagcctc ggtggcctag cttcttgccc cttgggcctc ccccagccc    60
ctcctcccct tcctgcaccc gtaccccac ccctatcaca attagcatta agtggtcttt    120
gaataaagtc tgagtgggcg gc                                              142

SEQ ID NO: 183          moltype = RNA   length = 188
FEATURE                 Location/Qualifiers
source                  1..188
                        mol_type = other RNA
                        organism = synthetic construct
SEQUENCE: 183
tgataataga cccctatcac aattagcatt aagctggagc ctcggtggcc tagcttcttg    60
ccccttgggc cacccctatc acaattagca ttaatccccc cagcccctcc tcccttcct    120
gcacccgtac ccccacccct atcacaatta gcattaagtg gtctttgaat aaagtctgag    180
tgggcggc                                                             188

SEQ ID NO: 184          moltype = RNA   length = 188
FEATURE                 Location/Qualifiers
source                  1..188
                        mol_type = other RNA
                        organism = synthetic construct
SEQUENCE: 184
tgataataga cccctatcac aattagcatt aagctggagc ctcggtggcc tagcttcttg    60
ccccttgggc ctccataaag taggaaacac tacatccccc cagcccctcc tcccttcct    120
gcacccgtac ccccacccct atcacaatta gcattaagtg gtctttgaat aaagtctgag    180
tgggcggc                                                             188

SEQ ID NO: 185          moltype = DNA   length = 18
FEATURE                 Location/Qualifiers
source                  1..18
                        mol_type = other DNA
                        organism = synthetic construct
SEQUENCE: 185
attgggcacc cgtaaggg                                                    18

SEQ ID NO: 186          moltype = AA   length = 25
FEATURE                 Location/Qualifiers
source                  1..25
                        mol_type = protein
```

-continued

```
                                  organism = synthetic construct
SEQUENCE: 186
GSGVKQTLNF DLLKLAGDVE SNPGP                                      25

SEQ ID NO: 187          moltype = AA   length = 21
FEATURE                 Location/Qualifiers
source                  1..21
                        mol_type = protein
                        organism = synthetic construct
SEQUENCE: 187
GSGEGRGSLL TCGDVEENPG P                                          21

SEQ ID NO: 188          moltype = AA   length = 22
FEATURE                 Location/Qualifiers
source                  1..22
                        mol_type = protein
                        organism = synthetic construct
SEQUENCE: 188
GSGATNFSLL KQAGDVEENP GP                                         22

SEQ ID NO: 189          moltype = AA   length = 23
FEATURE                 Location/Qualifiers
source                  1..23
                        mol_type = protein
                        organism = synthetic construct
SEQUENCE: 189
GSGQCTNYAL LKLAGDVESN PGP                                        23

SEQ ID NO: 190          moltype = RNA   length = 54
FEATURE                 Location/Qualifiers
source                  1..54
                        mol_type = other RNA
                        organism = synthetic construct
SEQUENCE: 190
gggaaataag agagaaaaga agagtaagaa gaaatataag accccggcgc cacc      54

SEQ ID NO: 191          moltype = RNA   length = 57
FEATURE                 Location/Qualifiers
source                  1..57
                        mol_type = other RNA
                        organism = synthetic construct
SEQUENCE: 191
gggaaataag agagaaaaga agagtaagaa gaaatataag accccggcgc cgccacc   57

SEQ ID NO: 192          moltype =    length =
SEQUENCE: 192
000

SEQ ID NO: 193          moltype =    length =
SEQUENCE: 193
000

SEQ ID NO: 194          moltype = RNA   length = 10
FEATURE                 Location/Qualifiers
source                  1..10
                        mol_type = other RNA
                        organism = synthetic construct
SEQUENCE: 194
ccccggcgcc                                                       10

SEQ ID NO: 195          moltype =    length =
SEQUENCE: 195
000

SEQ ID NO: 196          moltype = RNA   length = 1617
FEATURE                 Location/Qualifiers
source                  1..1617
                        mol_type = other RNA
                        organism = synthetic construct
SEQUENCE: 196
atggccgcag ccctcagagt ggctgccgtg ggagccagac tcagcgtgct cgcctcaggc   60
ctgcgggccg cagtcagaag cctgtgcagc caggcaacct cagtgaacga gagaatcgag  120
aacaagagac ggaccgccct gctgggtggc gggcaaagaa gaattgacgc ccagcacaag  180
agaggcaagc tgaccgcccg cgagcgcatc agcctgctgc tggaccccgg cagcttcgtg  240
gagagcgaca tgttcgtgga gcatcggtgt gccgacttcg gcatggccgc cgacaagaac  300
aagttccccg gcgacagcgt ggtgaccggc agaggcagaa tcaacggcag actggtgtac  360
gtgttctcac aagactttac cgtcttcgga ggatccctgt caggggctca cgcccagaag  420
atctgcaaga tcatggacca ggccatcacc gtggccgctc ccgtgatcgg cctgaacgac  480
agcggaggcg ccaggatcca agaggggagtg gagtccctgg ccggctacgc cgacatcttc  540
```

```
ctgagaaacg tgaccgcctc gggcgtgatc ccacagatct ccctgatcat gggaccctgc    600
gccggcgggg ccgtctacag ccctgccctg accgacttca ccttcatggt gaaggacacc    660
agctacctgt tcatcaccgg ccccgacgtg gtcaagagcg tgaccaacga ggacgtgacc    720
caggaggagc tcggcggagc caagactcac acaaccatgt ccggcgtcgc tcatagggcc    780
ttcgagaacg acgtggacgc cctgtgcaac ctgagagact tcttcaacta cctgccattg    840
agcagccagg atcccgcccc tgtgagagag tgccacgacc ccagcgacag actggtgccc    900
gagctggaca ccatcgtgcc cctggagagc accaaggcct acaacatggt ggacatcatc    960
cacagcgtgg tggacgagag agagttcttc gagatcatgc ccaactacgc caagaacatc   1020
atcgtgggct tcgccagaat gaacggcaga accgtgggca ttgtgggcaa ccagcccaag   1080
gtcgccagcg gctgcctcga catcaacagc agcgtgaagg cgccagatt cgtgagattc   1140
tgcgacgcct tcaacatacc tctgatcacc tttgtggacg tgcctggttt cctcccgggc   1200
accgcccaag aatacggtgg catcatcaga cacggcgcca agctgctgta cgccttcgcc   1260
gaggccaccg tgcccaaggt gaccgttatc acccgcaaag cctacggcgg cgcctacgac   1320
gtgatgagca gcaagcacct gtgtggcgac accaattacg cctggcccac cgccgagatc   1380
gccgtcatgg gcgcgaaagg agccgtggag atcatcttca agggccacga gaacgtggag   1440
gccgcccagg ccgagtacat cgagaagttc gccaaccccct ccctgccgc cgtgaggggc   1500
ttcgtcgacg atatcatcca gcccagctcc acccgcgcca gaatttgttg cgacctggac   1560
gtgctggcca gcaagaaggt gcaaagaccc tggagaaagc acgccaacat cccgctg      1617
```

```
SEQ ID NO: 197          moltype = RNA  length = 1617
FEATURE                 Location/Qualifiers
source                  1..1617
                        mol_type = other RNA
                        organism = synthetic construct
SEQUENCE: 197
atggccgcag ccctcagagt ggctgccgtg ggagccagac tcagcgtgct cgcctcaggc     60
ctgcgggccg cagtcagaag cctgtgcagc caggcaacct cagtgaacga gagaatcgag    120
aacaagagac ggaccgccct gctgggtggc gggcaaagaa gaattgacgc ccagcacaag    180
agaggcaagc tgaccgcccg cgagcgcatc agcctgctgc tggaccccgg cagcttcgtg    240
gagagcgaca tgttcgtgga gcatcggtgt gccgacttcg gcatggccgc cgacaagaac    300
aagttccccg gcgacagcgt ggtgaccggc agaggcagaa tcaacggcag actggtgtac    360
gtgttctcac aagactttac cgtcttcgga ggatccctgt caggggctca cgcccagaag    420
atctgcaaga tcatggacca ggccatcacc gtgggcgctc ccgtgatcgg cctgaacgac    480
agcggaggcg ccaggatcca agagggagtg gagtccctgg ccggctacgc cgacatcttc    540
ctgagaaacg tgaccgcctc gggcgtgatc ccacagatct ccctgatcat gggaccctgc    600
gccggcgggg ccgtctacag ccctgccctg accgacttca ccttcatggt gaaggacacc    660
agctacctgt tcatcaccgg ccccgacgtg gtcaagagcg tgaccaacga ggacgtgacc    720
caggaggagc tcggcggagc caagactcac acaaccatgt ccggcgtcgc tcatagggcc    780
ttcgagaacg acgtggacgc cctgtgcaac ctgagagact tcttcaacta cctgccattg    840
agcagccagg atcccgcccc tgtgagagag tgccacgacc ccagcgacag actggtgccc    900
gagctggaca ccatcgtgcc cctggagagc accaaggcct acaacatggt ggacatcatc    960
cacagcgtgg tggacgagag agagttcttc gagatcatgc ccaactacgc caagaacatc   1020
atcgtgggct tcgccagaat gaacggcaga accgtgggca ttgtgggcaa ccagcccaag   1080
gtcgccagcg gctgcctcga catcaacagc agcgtgaagg cgccagatt cgtgagattc   1140
tgcgacgcct tcaacatacc tctgatcacc tttgtggacg tgcctggttt cctcccgggc   1200
accgcccaag aatacggtgg catcatcaga cacggcgcca agctgctgta cgccttcgcc   1260
gaggccaccg tgcccaaggt gaccgttatc acccgcaaag cctacggcgg cgcctacgac   1320
gtgatgagca gcaagcacct gtgtggcgac accaattacg cctggcccac cgccgagatc   1380
gccgtcatgg gcgcgaaagg agccgtggag atcatcttca agggccacga gaacgtggag   1440
gccgcccagg ccgagtacat cgagaagttc gccaacccct ccctgccgc cgtgaggggc   1500
ttcgtcgacg atatcatcca gcccagctcc acccgcgcca gaatctgctg cgacctggac   1560
gtgctggcca gcaagaaggt gcaaagaccc tggagaaagc acgccaacat cccgctg      1617
```

```
SEQ ID NO: 198          moltype = RNA  length = 1617
FEATURE                 Location/Qualifiers
source                  1..1617
                        mol_type = other RNA
                        organism = synthetic construct
SEQUENCE: 198
atggccgcag ccctcagagt ggctgccgtg ggagccagac tcagcgtgct cgcctcaggc     60
ctgcgggccg cagtcagaag cctgtgcagc caggcaacct cagtgaacga gagaatcgag    120
aacaagagac ggaccgccct gctgggtggc gggcaaagaa gaattgacgc ccagcacaag    180
agaggcaagc tgaccgcccg cgagcgcatc agcctgctgc tggaccccgg cagcttcgtg    240
gagagcgaca tgttcgtgga gcatcggtgt gccgacttcg gcatggccgc cgacaagaac    300
aagttccccg gcgacagcgt ggtgaccggc agaggcagaa tcaacggcag actggtgtac    360
gtgttctcac aagactttac cgtcttcgga ggatccctgt caggggctca cgcccagaag    420
atctgcaaga tcatggacca ggccatcacc gtgggcgctc ccgtgatcgg cctgaacgac    480
agcggaggcg ccaggatcca agagggagtg gagtccctgg ccggctacgc cgacatcttc    540
ctgagaaacg tgaccgcctc gggcgtgatc ccacagatct ccctgatcat gggaccctgc    600
gccggcgggg ccgtctacag ccctgccctg accgacttca ccttcatggt gaaggacacc    660
agctacctgt tcatcaccgg ccccgacgtg gtcaagagcg tgaccaacga ggacgtgacc    720
caggaggagc tcggcggagc caagactcac acaaccatgt ccggcgtcgc tcatagggcc    780
ttcgagaacg acgtggacgc cctgtgcaac ctgagagact tcttcaacta cctgccattg    840
agcagccagg atcccgcccc tgtgagagag tgccacgacc ccagcgacag actggtgccc    900
gagctggaca ccatcgtgcc cctggagagc accaaggcct acaacatggt ggacatcatc    960
cacagcgtgg tggacgagag agagttcttc gagatcatgc ccaactacgc caagaacatc   1020
atcgtgggct tcgccagaat gaacggcaga accgtgggca ttgtgggcaa ccagcccaag   1080
gtcgccagcg gctgcctcga catcaacagc agcgtgaagg cgccagatt cgtgagattc   1140
tgcgacgcct tcaacatacc tctgatcacc tttgtggacg tgcctggttt cctcccgggc   1200
```

-continued

```
accgcccaag aatacggtgg catcatcaga cacggcgcca agctgctgta cgccttcgcc   1260
gaggccaccg tgcccaaggt gaccgttatc acccgcaaag cctacggcgg cgcctacgac   1320
gtgatgagca gcaagcacct gtgtggcgac accaattacg cctggcccac cgccgagatc   1380
gccgtcatgg gcgcgaaagg agccgtggag atcatcttca agggcacga gaacgtggag    1440
gccgcccagg ccgagtacat cgagaagttc gccaacccct tccctgccgc cgtgaggggc   1500
ttcgtcgacg atatcatcca gcccagctcc acccgcgcca ggatttgctg cgacctggac   1560
gtgctggcca gcaagaaggt gcaaagaccc tggagaaagc acgccaacat cccgctg     1617
```

```
SEQ ID NO: 199        moltype = RNA  length = 47
FEATURE               Location/Qualifiers
source                1..47
                      mol_type = other RNA
                      organism = synthetic construct
SEQUENCE: 199
aggaaataag agagaaaaga agagtaagaa gaaatataag agccacc                47
```

```
SEQ ID NO: 200        moltype = RNA  length = 1852
FEATURE               Location/Qualifiers
source                1..1852
                      mol_type = other RNA
                      organism = synthetic construct
SEQUENCE: 200
aggaaataag agagaaaaga agagtaagaa gaaatataag agccaccatg gccgcagccc   60
tcagagtggc tgccgtggga gccagactca gcgtgctcgc ctcaggcctg cgggccgcag   120
tcagaagcct gtgcagccag gcaacctcag tgaacgagag aatcgagaac aagagacgga   180
ccgccctgct gggtggcggg caaagaagaa ttgacgccca gcacaagaga gccaagctga   240
ccgcccgcga gcgcatcagc ctgctgctgg accccggcag cttcgtggag agcgacatgt   300
tcgtggagca tcggtgtgcc gacttcggca tggccgccga caagaacaag ttccccggcg   360
acagcgtggt gaccggcaga ggcagaatca acggcagact ggtgtacgtg ttctcacaag   420
actttaccgt cttcggagga tccctgtcag gggctcacgc ccagaagatc tgcaagatca   480
tggaccaggc catcaccgtg ggcgctcccg tgatcggcct gaacgacagc ggaggcgcca   540
ggatccaaga gggagtggag tccctggccg gctacgccga catcttcctg agaaacgtga   600
ccgcctcggg cgtgatccca cagatctccc tgatcatggg accctgcgcc ggcggggccg   660
tctacagccc tgccctgacc gacttcacct tcatggtgaa ggacaccagc tacctgttca   720
tcaccggccc cgacgtggtc aagagcgtga ccaacgagga cgtgacccag gaggagctcg   780
gcggagccaa gactcacaca accatgtccg cgtcgctca tagggccttc gagaacgacg    840
tggacgccct gtgcaacctg agagacttct tcaactacct gccattgagc agccaggatc   900
ccgcccctgt gagagagtgc cacgacccca cgcgacagact ggtgcccgag ctggacacca   960
tcgtgcccct ggagagcacc aaggcctaca acatggtgga catcatccac agcgtggtgg   1020
acgagagaga gttcttcgag atcatgccca actacgccaa gaacatcatc gtgggcttcg   1080
ccagaatgaa cggcagaacc gtgggcattg tgggcaacca gcccaaggtc gccagcggct   1140
gcctcgacat caacagcagc gtgaagggcg ccagattcgt gagattctgc gacgccttca   1200
acatacctct gatcaccttt gtggacgtgc ctggtttcct cccgggcacc gcccaagaat   1260
acggtggcat catcagacac ggcgccaagc tgctgtacgc cttcgccgag gccaccgtgc   1320
ccaaggtgac cgttatcacc cgcaaagcct acggcggcgc ctacgacgtg atgagcagca   1380
agcacctgtg tggcgacacc aattacgcct ggcccaccgc cgagatcgcc gtcatgggcg   1440
cgaaaggagc cgtggagatc atcttcaagg gccacgaaga cgtggaggcc gcccaggccg   1500
agtacatcga gaagttcgcc aacccccttcc ctgccgccgt gaggggcttc gtcgacgata   1560
tcatccagcc cagctccacc cgcgccagaa tttgttgcga cctggacgtg ctggccagca   1620
agaaggtgca aagaccctgg agaaagcacg ccaacatccc gctgtgataa tagtccataa   1680
agtaggaaac actacagctg gagcctcggt ggcctagctt cttgcccctt gggcctccat   1740
aaagtaggaa acactacatc cccccagccc ctcctcccct tcctgcaccc gtaccccctc   1800
cataaagtag gaaacactac agtggtcttt gaataaagtc tgagtgggcg gc           1852
```

```
SEQ ID NO: 201        moltype = RNA  length = 1852
FEATURE               Location/Qualifiers
source                1..1852
                      mol_type = other RNA
                      organism = synthetic construct
SEQUENCE: 201
aggaaataag agagaaaaga agagtaagaa gaaatataag agccaccatg gccgcagccc   60
tcagagtggc tgccgtggga gccagactca gcgtgctcgc ctcaggcctg cgggccgcag   120
tcagaagcct gtgcagccag gcaacctcag tgaacgagag aatcgagaac aagagacgga   180
ccgccctgct gggtggcggg caaagaagaa ttgacgccca gcacaagaga gccaagctga   240
ccgcccgcga gcgcatcagc ctgctgctgg accccggcag cttcgtggag agcgacatgt   300
tcgtggagca tcggtgtgcc gacttcggca tggccgccga caagaacaag ttccccggcg   360
acagcgtggt gaccggcaga ggcagaatca acggcagact ggtgtacgtg ttctcacaag   420
actttaccgt cttcggagga tccctgtcag gggctcacgc ccagaagatc tgcaagatca   480
tggaccaggc catcaccgtg ggcgctcccg tgatcggcct gaacgacagc ggaggcgcca   540
ggatccaaga gggagtggag tccctggccg gctacgccga catcttcctg agaaacgtga   600
ccgcctcggg cgtgatccca cagatctccc tgatcatggg accctgcgcc ggcggggccg   660
tctacagccc tgccctgacc gacttcacct tcatggtgaa ggacaccagc tacctgttca   720
tcaccggccc cgacgtggtc aagagcgtga ccaacgagga cgtgacccag gaggagctcg   780
gcggagccaa gactcacaca accatgtccg cgtcgctca tagggccttc gagaacgacg    840
tggacgccct gtgcaacctg agagacttct tcaactacct gccattgagc agccaggatc   900
ccgcccctgt gagagagtgc cacgacccca cgcgacagact ggtgcccgag ctggacacca   960
tcgtgcccct ggagagcacc aaggcctaca acatggtgga catcatccac agcgtggtgg   1020
acgagagaga gttcttcgag atcatgccca actacgccaa gaacatcatc gtgggcttcg   1080
ccagaatgaa cggcagaacc gtgggcattg tgggcaacca gcccaaggtc gccagcggct   1140
```

```
gcctcgacat caacagcagc gtgaagggcg ccagattcgt gagattctgc gacgccttca   1200
acatacctct gatcaccttt gtggacgtgc ctggtttcct cccgggcacc gcccaagaat   1260
acggtggcat catcagacac ggcgccaagc tgctgtacgc cttcgccgag gccaccgtgc   1320
ccaaggtgac cgttatcacc cgcaaagcct acggcggcgc ctacgacgtg atgagcagca   1380
agcacctgtg tggcgacacc aattacgcct ggcccaccgc cgagatcgcc gtcatgggcg   1440
cgaaaggagc cgtggagatc atcttcaagg gccacgagaa cgtggaggcc gcccaggccg   1500
agtacatcga gaagttcgcc aaccccttcc ctgccgccgt gaggggcttc gtcgacgata   1560
tcatccagcc cagctccacc cgcgccagaa tctgctgcga cctggacgtg ctggccagca   1620
agaaggtgca aagaccctgg agaaagcacg ccaacatccc gctgtgataa tagtccataa   1680
agtaggaaac actacagctg gagcctcggt ggcctagctt cttgcccctt gggcctccat   1740
aaagtaggaa acactacatc cccccagccc ctcctcccct tcctgcaccc gtaccccctc   1800
cataaagtag gaaacactac agtggtcttt gaataaagtc tgagtgggcg gc           1852
```

SEQ ID NO: 202        moltype = RNA  length = 1852
FEATURE               Location/Qualifiers
source                1..1852
                      mol_type = other RNA
                      organism = synthetic construct
SEQUENCE: 202

```
aggaaataag agagaaaaga agagtaagaa gaaatataag agccaccatg gccgcagccc   60
tcagagtggc tgccgtggga gccagactca gcgtgctcgc ctcaggcctg cgggccgcag   120
tcagaagcct gtgcagccag gcaacctcag tgaacgagag aatcgagaac aagagacgga   180
ccgccctgct gggtggcggg caaagaagaa ttgacgccca gcacaagaga ggcaagctga   240
ccgcccgcga gcgcatcagc ctgctgctgg accccggcag cttcgtggag agcgacatgt   300
tcgtggagca tcggtgtgcc gacttcggca tggccgccga caagaacaag ttccccggcg   360
acagcgtggt gaccggcaga ggcagaatca acggcacgac tggtgtacgt g ttctcacaag   420
actttaccgt cttcggagga tccctgtcag gggctcacgc ccagaagatc tgcaagatca   480
tggaccaggc catcaccgtg ggcgctcccg tgatcggcct gaacgacagc ggaggcgcca   540
ggatccaaga gggagtggag tccctggccg gctacgccga catcttcctg agaaacgtga   600
ccgcctcggg cgtgatccca cagatctccc tgatcatggg accctgcgcc ggcggggccg   660
tctacagccc tgccctgacc gacttcacct tcatggtgag ggacaccagc tacctgttca   720
tcaccggccc cgacgtggtc aagagcgtga ccaacgagga cgtgacccag gaggagctcg   780
gcggagccaa gactcacaca accatgtccg gcgtcgctca tagggccttc gagaacgacg   840
tggacgccct gtgcaacctg agagacttct tcaactacct gccattgagc agccaggatc   900
ccgcccctgt gagagagtgc cacgacccca gcgacagact ggtgcccgag ctggacacca   960
tcgtgcccct ggagagcacc aaggcctaca acatggtgga catcatccac agcgtggtgg   1020
acgagagaga gttcttcgag atcatgccca actacgccaa gaacatcatc gtgggcttcg   1080
ccagaatgaa cggcagaacc gtgggcattg tgggcaacca gcccaaggtc gccagcggct   1140
gcctcgacat caacagcagc gtgaagggcg ccagattctg cgacgccttca gacgccttca   1200
acatacctct gatcaccttt gtggacgtgc ctggtttcct cccgggcacc gcccaagaat   1260
acggtggcat catcagacac ggcgccaagc tgctgtacgc cttcgccgag gccaccgtgc   1320
ccaaggtgac cgttatcacc cgcaaagcct acggcggcgc ctacgacgtg atgagcagca   1380
agcacctgtg tggcgacacc aattacgcct ggcccaccgc cgagatcgcc gtcatgggcg   1440
cgaaaggagc cgtggagatc atcttcaagg gccacgagaa cgtggaggcc gcccaggccg   1500
agtacatcga gaagttcgcc aacccettcc ctgccgccgt gaggggcttc gtcgacgata   1560
tcatccagcc cagctccacc cgcgccagga tttgctgcga cctggacgtg ctggccagca   1620
agaaggtgca aagaccctgg agaaagcacg ccaacatccc gctgtgataa tagtccataa   1680
agtaggaaac actacagctg gagcctcggt ggcctagctt cttgcccctt gggcctccat   1740
aaagtaggaa acactacatc cccccagccc ctcctcccct tcctgcaccc gtaccccctc   1800
cataaagtag gaaacactac agtggtcttt gaataaagtc tgagtgggcg gc           1852
```

SEQ ID NO: 203        moltype = RNA  length = 2419
FEATURE               Location/Qualifiers
source                1..2419
                      mol_type = other RNA
                      organism = synthetic construct
SEQUENCE: 203

```
aggaaataag agagaaaaga agagtaagaa gaaatataag agccaccatg gccggcttct   60
gggtcggcac agcccctctg gtggcagccg gcagaagagg acggtggcct ccccagcaac   120
tgatgctgag cgccgccctg agaaccctga agcacgtgct gtactacagc agacagttcc   180
tgatggtgag cagaaatctg ggcagcgtgg ggtacgatcc caacgagaag accttcgata   240
agattctggt cgcgaataga ggcgagatcg cctgcagggt gatcagaacc tgcaagaaga   300
tgggcatcaa gaccgtggcc atccattcgg acgtcgacgc gagcagcgtt cacgtgaaga   360
tggcagacga ggccgtgtgc gtgggacccg ccccgaccag caagagctac ctgaacatgt   420
acgccatcat ggaggccatc aagaagaccc gcgctcaagc cgtgcacccg ggctacggct   480
ttctgagcga gaacaaggaa ttcgccaggt gtctcgccgc cgaggacgta gtcttcatcg   540
gccctgatac gcacgcgatc caggccatgg gcgacaagat cgagagcaaa ctgctggcca   600
agaaagcaga agtcaacacc atccccggct tcgacggcgt ggtgaaggac gccgaagagg   660
ctgtccgcat cgccagagga atcggctacc ctgtgatgat aaaggctagc gctggaggtg   720
gcggaaaggg catgagaatc gcctgggacg acgaggagac tagagacggc ttcagactgt   780
cctcccagga ggccgccagc tccttcggag acgacagact gctgatcgag aagttcatcg   840
acaaccccag acacatcgaa atccaggtgc tcggtgacaa gcacgggaac gccctgtggc   900
tgaacgagag agagtgcagc atccagagaa gaaaccagaa ggtggtggag gaggcgccga   960
gcatctttct ggacgcggag acaaggagag cgatgggcga caagatcggc gcctagcaa   1020
gagccgtgaa gtactccagt gccggaaccg tcgagtttct tgtcgacagc aagaagaatt   1080
tctacttcct ggagatgaac accaggctgc aggtggagca tcccgtgaca gagtgcatca   1140
ctggactgga tctggtgcag gagatgatca gggtggccaa gggctatccc ctgagacaca   1200
agcaggccga catcagaatc aacggctggg ccgtggagtg cagagtgtac gccgaggacc   1260
cctacaagag cttcggcctg cccagcatcg gcagactgag ccagtaccag gagcccctgc   1320
```

```
acctgcccgg cgtgagagtg gacagcggca tccaaccggg gagcgatatc agcatctact   1380
acgacccat  gatcagcaag ctgataacct acggcagcga cagaaccgag gccctgaaga   1440
gaatggccga cgccctggac aactacgtga tcagaggcgt gacccacaac atcgccctgc   1500
tgagagaggt gatcatcaac tcgaggttcg tgaaaggcga catcagcacc aagttcctga   1560
gcgacgtgta tcccgacgga ttcaaaggtc acatgctgac caagagcgac aagaaccagc   1620
tgctggccat cgcctcatcc ctgttcgtgg ccttccagct gagagcccag cacttccagg   1680
agaacagcag aatgcccgtg atcaagcccg acatcgccaa ctgggagctg agcgtgaagc   1740
tgcacgacaa ggtgcacact gtcgttgcca gcaacaacgg ctccgtgttc agcgtagagg   1800
tggacggatc taagctgaac gtgacctcca cctggaacct ggcaagccct ctcctgtcag   1860
tgagcgtgga cggcacccag agaaccgtgc agtgtctgtc ccgcgaggcc ggcggaaaca   1920
tgagcatcca gttcctgggc accgtgtaca aggtgaacat cctgaccaga ctggccgccg   1980
agctgaacaa gttcatgctg gagaaagtga cggaggatac cagctccgtg ctgagaagcc   2040
ccatgcccgg agtggtggtg gccgtttccg tgaaacctgg tgacgccgtg gccgaggggc   2100
aagagatctg cgtgaatcga gccatgaaga tgcagaattc catgaccgcc ggaaagaccg   2160
gcaccgtcaa atcagtgcac tgccaggcgg gcgacacagt gggtgagggc gacctgctgg   2220
tggagctgga gtgataatag tccataaagt aggaaacact acagctggag cctcggtggc   2280
ctagcttctt gcccttggg  cctccataaa gtaggaaaca ctacatcccc ccagcccctc   2340
ctcccttcc  tgcacccgta cccctcat  aaagtaggaa acactacagt ggtctttgaa   2400
taaagtctga gtgggcggc                                                2419

SEQ ID NO: 204       moltype = RNA  length = 1852
FEATURE              Location/Qualifiers
source               1..1852
                     mol_type = other RNA
                     organism = synthetic construct
SEQUENCE: 204
aggaaataag agagaaaaga agagtaagaa gaaatataag agccaccatg gccgcagccc   60
tcagagtggc tgccgtggga gccagactca gcgtgctcgc ctcaggcctg cgggccgcag   120
tcagaagcct gtgcagccag gcaacctcag tgaacgagag aatcgagaac aagagacgga   180
ccgccctgct gggtggcggg caaagaagaa ttgacgccca gcacaagaga ggcaagctga   240
ccgcccgcga gcgcatcagc ctgctgctgg accccggcag cttcgtggag agcgacatgt   300
tcgtggagca tcggtgtgcc gacttcggca tggccgccga caagaacaag ttccccggcg   360
acagcgtggt gaccggcaga ggcagaatca acggcagact ggtgtacgtg ttctcacaag   420
actttaccgt cttcggagga tccctgtcag gggctcacgc ccagaagatc tgcaagatca   480
tggaccaggc catcaccgtg ggcgctcccg tgatcggcat gaacgacagc ggaggcgcca   540
ggatccaaga gggagtggag tccctggccg gctacgccga catcttcctg agaaacgtga   600
ccgcctcggg cgtgatccca cagatctccc tgatcatggg accctgcgcc ggcgggggccg   660
tctacagccc tgccctgacc gacttcacct tcatggtgaa ggacaccagc tacctgttca   720
tcaccggccc cgacgtggtc aagagcgtga ccaacgagga cgtgacccag gaggagctcg   780
gcggagccaa gactcacaca accatgtccg gcgtcgctca tagggccttc gagaacgacg   840
tggacgccct gtgcaacctg agagacttct tcaactacct gccattgagc agccaggatc   900
ccgcccctgt gagagagtgc cacgacccca gcgacagact ggtgcccgag ctggacacca   960
tcgtgcccct ggagagcacc aaggcctaca acatggtgga catcatccac agcgtggtg   1020
acgagagaga gttcttcgag atcatgccca actacgccaa gaacatcatc gtgggcttcg   1080
ccagaatgaa cggcagaacc gtgggcattg tgggcaacca gcccaaggtc gccagcggct   1140
gcctcgacat caacagcagc gtgaagggcg ccagattcgt gagattctgc gacgccttca   1200
acatcctct  gatcacctt  gtggacgtgc ctggtttcct cccgggcacc gcccaagaat   1260
acggtggcat catcagacac ggcgccaagc tgctgtacgc cttcgccgag gccaccgtgc   1320
ccaaggtgac cgttatcacc cgcaaagcct acggcggcgc ctacgacgtg atgagcagca   1380
agcacctgtg tggcgacacc aattacgcct ggcccaccgc cgagatcgcc gtcatggcg   1440
cgaaaggagc cgtggagatc atcttcaagg gccacgagaa cgtggaggcc gcccaggccg   1500
agtacatcga gaagttcgcc aacccccttcc ctgccgccgt gaggggcttc gtcgacgata   1560
tcatccagcc cagctccacc cgcgccagaa tctgttgcga cctggacgtg ctggccagca   1620
agaaggtgca aagaccctgg agaaagcacg ccaacatccc gctgtgataa tagtccataa   1680
agtaggaaac actacagctg gagcctcggt ggcctagctt cttgcccctt gggcctccat   1740
aaagtaggaa acactacatc ccccagccc ctcctcccct tcctgcaccc gtacccctc   1800
cataaagtag gaaacactac agtggtcttt gaataaagtc tgagtgggcg gc           1852

SEQ ID NO: 205       moltype = RNA  length = 1852
FEATURE              Location/Qualifiers
source               1..1852
                     mol_type = other RNA
                     organism = synthetic construct
SEQUENCE: 205
aggaaataag agagaaaaga agagtaagaa gaaatataag agccaccatg gcggcggcat   60
tacgggtggc ggcggtcggg gcaaggctca gcgtgctggc cagcggcctg agagccgccg   120
tgagaagcct gtgcagccag gccaccagcg tgaacgagag aatcgagaac aagagaagaa   180
ccgccctgct gggcggcggc cagagaagaa tcgacgccca gcacaagaga ggcaagctga   240
ccgccagaga gagaatcagc ctgctgctgg accccggcag cttcgtggag agcgacatgt   300
tcgtggagca caggtgcgcc gacttcggca tggccgccga caagaacaag ttccccggcg   360
acagcgtggt gaccggcaga ggcagaatca acggcagact ggtgtacgtg ttcagccagg   420
acttcaccgt gttcggcggc agcctgagcg gcgcccacgc ccagaagatc tgcaagatca   480
tggaccaggc catcaccgtg ggcgcgcccg tgatcggcct gaacgacagc ggcggcgcca   540
gaatccagga gggcgtggag agcctggccg gctacgccga catcttcctg agaaacgtga   600
ccgccagcgg cgtgatccca cagatcagcc tgatcatggg ccctgcgcc ggcggcgccg   660
tgtacagccc cgccctgacc gacttcacct tcatggtgaa ggacaccagc tacctgttca   720
tcaccggccc cgacgtggtg aagagcgtga ccaacgagga cgtgacccag gaggagctgg   780
gcggcgccaa gacccacacc accatgagcg gcgtggccca cagagccttc gagaacgacg   840
tggacgccct gtgcaacctg agagacttct tcaactacct gcccctgagc agccaggacc   900
```

-continued

```
ccgcgcccgt gagagagtgc cacgacccca gcgacagact ggtgcccgag ctggacacca    960
tcgtgcccct ggagagcacc aaggcctaca acatggtgga catcatccac agcgtggtgg    1020
acgagagaga gttcttcgag atcatgccca actacgccaa gaacatcatc gtgggcttcg    1080
ccagaatgaa cggcagaacc gtgggcatcg tgggcaacca gcccaaggtg gccagcggct    1140
gcctggacat caacagcagc gtgaagggcg ccagattcgt gagattctgc gacgccttca    1200
acatccctct gatcaccttc gtggacgtgc ccggcttcct gcccggcacc gcccaggagt    1260
acggcggcat catcagacac ggcgccaagc tgctgtacgc cttcgccgag gccaccgtgc    1320
ccaaggtgac cgtgatcacc agaaaggcct acggcggcgc ctacgacgtg atgagcagca    1380
agcacctgtg cggcgacacc aactacgcct ggcccaccgc cgagatcgcc gtgatgggcg    1440
ccaagggcgc cgtggagatc atcttcaagg gccacgagaa cgtggaggcc gcccaggccg    1500
agtacatcga gaagttcgcc aaccccttcc ccgccgccgt gagaggcttc gtggacgaca    1560
tcatccagcc cagcagcacc agagccgaaa tctgctgcga cctggacgtg ctggccagca    1620
agaaggtgca gagaccctgg agaaagcacg ccaacatccc tctgtgataa tagtccataa    1680
agtaggaaac actacagctg gagcctcggt ggctagctt cttgcccctt gggcctccat    1740
aaagtaggaa acactacatc cccccagccc ctcctcccct tcctgcaccc gtacccctc    1800
cataaagtag gaaacactac agtggtcttt gaataaagtc tgagtgggcg gc           1852
```

```
SEQ ID NO: 206          moltype = RNA   length = 57
FEATURE                 Location/Qualifiers
source                  1..57
                        mol_type = other RNA
                        organism = synthetic construct
SEQUENCE: 206
aggaaataag agagaaaaga agagtaagaa gaaatataag accccggcgc cgccacc       57
```

```
SEQ ID NO: 207          moltype = RNA   length = 141
FEATURE                 Location/Qualifiers
source                  1..141
                        mol_type = other RNA
                        organism = synthetic construct
SEQUENCE: 207
tgataatagg ctggagcctc ggtggccatg cttcttgccc cttgggcctc ccccagccc    60
ctcctcccct tcctgcaccc gtaccccca aacaccattg tcacactcca gtggtctttg    120
aataaagtct gagtgggcgg c                                              141
```

```
SEQ ID NO: 208          moltype = RNA   length = 141
FEATURE                 Location/Qualifiers
source                  1..141
                        mol_type = other RNA
                        organism = synthetic construct
SEQUENCE: 208
tgataatagg ctggagcctc ggtggcctag cttcttgccc cttgggcctc ccccagccc    60
ctcctcccct tcctgcaccc gtaccccca aacaccattg tcacactcca gtggtctttg    120
aataaagtct gagtgggcgg c                                              141
```

```
SEQ ID NO: 209          moltype = RNA   length = 66
FEATURE                 Location/Qualifiers
source                  1..66
                        mol_type = other RNA
                        organism = synthetic construct
SEQUENCE: 209
ggaagcggag ctactaactt cagcctgctg aagcaggctg agacgtgga ggagaaccct    60
ggacct                                                               66
```

```
SEQ ID NO: 210          moltype = RNA   length = 108
FEATURE                 Location/Qualifiers
source                  1..108
                        mol_type = other RNA
                        organism = synthetic construct
SEQUENCE: 210
tccggactca gatccgggga tctcaaaatt gtcgctcctg tcaaacaaac tcttaacttt    60
gatttactca aactggctgg ggatgtagaa agcaatccag gtccactc                108
```

```
SEQ ID NO: 211          moltype = RNA   length = 41
FEATURE                 Location/Qualifiers
source                  1..41
                        mol_type = other RNA
                        organism = synthetic construct
SEQUENCE: 211
gggaaataag agagaaaaga agagtaagaa gaaatataag a                        41
```

```
SEQ ID NO: 212          moltype = DNA   length = 100
FEATURE                 Location/Qualifiers
source                  1..100
                        mol_type = other DNA
                        organism = synthetic construct
SEQUENCE: 212
aaaaaaaaaa aaaaaaaaaa aaaaaaaaaa aaaaaaaaaa aaaaaaaaaa aaaaaaaaaa    60
aaaaaaaaaa aaaaaaaaaa aaaaaaaaaa aaaaaaaaaa                          100
```

-continued

```
SEQ ID NO: 213            moltype = AA   length = 21
FEATURE                   Location/Qualifiers
source                    1..21
                          mol_type = protein
                          organism = Homo sapiens
SEQUENCE: 213
QQIIGWAQWL PLVISALWEA E                                               21

SEQ ID NO: 214            moltype = DNA   length = 150
FEATURE                   Location/Qualifiers
misc_feature              1..150
                          note = /note="This sequence may encompass 50-150
                           nucleotides"
source                    1..150
                          mol_type = other DNA
                          organism = synthetic construct
SEQUENCE: 214
aaaaaaaaaa aaaaaaaaaa aaaaaaaaaa aaaaaaaaaa aaaaaaaaaa aaaaaaaaaa   60
aaaaaaaaaa aaaaaaaaaa aaaaaaaaaa aaaaaaaaaa aaaaaaaaaa aaaaaaaaaa   120
aaaaaaaaaa aaaaaaaaaa aaaaaaaaaa                                     150

SEQ ID NO: 215            moltype = DNA   length = 150
FEATURE                   Location/Qualifiers
misc_feature              1..150
                          note = /note="This sequence may encompass 75-150
                           nucleotides"
source                    1..150
                          mol_type = other DNA
                          organism = synthetic construct
SEQUENCE: 215
aaaaaaaaaa aaaaaaaaaa aaaaaaaaaa aaaaaaaaaa aaaaaaaaaa aaaaaaaaaa   60
aaaaaaaaaa aaaaaaaaaa aaaaaaaaaa aaaaaaaaaa aaaaaaaaaa aaaaaaaaaa   120
aaaaaaaaaa aaaaaaaaaa aaaaaaaaaa                                     150

SEQ ID NO: 216            moltype = DNA   length = 150
FEATURE                   Location/Qualifiers
misc_feature              1..150
                          note = /note="This sequence may encompass 85-150
                           nucleotides"
source                    1..150
                          mol_type = other DNA
                          organism = synthetic construct
SEQUENCE: 216
aaaaaaaaaa aaaaaaaaaa aaaaaaaaaa aaaaaaaaaa aaaaaaaaaa aaaaaaaaaa   60
aaaaaaaaaa aaaaaaaaaa aaaaaaaaaa aaaaaaaaaa aaaaaaaaaa aaaaaaaaaa   120
aaaaaaaaaa aaaaaaaaaa aaaaaaaaaa                                     150

SEQ ID NO: 217            moltype = DNA   length = 150
FEATURE                   Location/Qualifiers
misc_feature              1..150
                          note = /note="This sequence may encompass 90-150
                           nucleotides"
source                    1..150
                          mol_type = other DNA
                          organism = synthetic construct
SEQUENCE: 217
aaaaaaaaaa aaaaaaaaaa aaaaaaaaaa aaaaaaaaaa aaaaaaaaaa aaaaaaaaaa   60
aaaaaaaaaa aaaaaaaaaa aaaaaaaaaa aaaaaaaaaa aaaaaaaaaa aaaaaaaaaa   120
aaaaaaaaaa aaaaaaaaaa aaaaaaaaaa                                     150

SEQ ID NO: 218            moltype = DNA   length = 120
FEATURE                   Location/Qualifiers
misc_feature              1..120
                          note = /note="This sequence may encompass 90-120
                           nucleotides"
source                    1..120
                          mol_type = other DNA
                          organism = synthetic construct
SEQUENCE: 218
aaaaaaaaaa aaaaaaaaaa aaaaaaaaaa aaaaaaaaaa aaaaaaaaaa aaaaaaaaaa   60
aaaaaaaaaa aaaaaaaaaa aaaaaaaaaa aaaaaaaaaa aaaaaaaaaa aaaaaaaaaa   120

SEQ ID NO: 219            moltype = DNA   length = 130
FEATURE                   Location/Qualifiers
misc_feature              1..130
                          note = /note="This sequence may encompass 90-130
                           nucleotides"
source                    1..130
```

```
                        mol_type = other DNA
                        organism = synthetic construct
SEQUENCE: 219
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120
aaaaaaaaaa                                                         130

SEQ ID NO: 220           moltype = AA  length = 4
FEATURE                  Location/Qualifiers
source                   1..4
                         mol_type = protein
                         organism = unidentified
SEQUENCE: 220
NPGP                                                                4

SEQ ID NO: 221           moltype = RNA  length = 30
FEATURE                  Location/Qualifiers
misc_feature             1..30
                         note = /note="This sequence may encompass 1-10 'ccg'
                          repeating units"
source                   1..30
                         mol_type = other RNA
                         organism = synthetic construct
SEQUENCE: 221
ccgccgccgc cgccgccgcc gccgccgccg                                   30

SEQ ID NO: 222           moltype = RNA  length = 24
FEATURE                  Location/Qualifiers
misc_feature             1..24
                         note = /note="This sequence may encompass 2-8 'ccg'
                          repeating units"
source                   1..24
                         mol_type = other RNA
                         organism = synthetic construct
SEQUENCE: 222
ccgccgccgc cgccgccgcc gccg                                         24

SEQ ID NO: 223           moltype = RNA  length = 18
FEATURE                  Location/Qualifiers
misc_feature             1..18
                         note = /note="This sequence may encompass 3-6 'ccg'
                          repeating units"
source                   1..18
                         mol_type = other RNA
                         organism = synthetic construct
SEQUENCE: 223
ccgccgccgc cgccgccg                                                18

SEQ ID NO: 224           moltype = RNA  length = 15
FEATURE                  Location/Qualifiers
misc_feature             1..15
                         note = /note="This sequence may encompass 4-5 'ccg'
                          repeating units"
source                   1..15
                         mol_type = other RNA
                         organism = synthetic construct
SEQUENCE: 224
ccgccgccgc cgccg                                                   15

SEQ ID NO: 225           moltype = RNA  length = 15
FEATURE                  Location/Qualifiers
misc_feature             1..15
                         note = /note="This sequence may encompass 1-5 'ccg'
                          repeating units"
source                   1..15
                         mol_type = other RNA
                         organism = synthetic construct
SEQUENCE: 225
ccgccgccgc cgccg                                                   15

SEQ ID NO: 226           moltype = RNA  length = 12
FEATURE                  Location/Qualifiers
source                   1..12
                         mol_type = other RNA
                         organism = synthetic construct
SEQUENCE: 226
ccgccgccgc cg                                                      12

SEQ ID NO: 227           moltype = RNA  length = 15
```

-continued

```
FEATURE            Location/Qualifiers
source             1..15
                   mol_type = other RNA
                   organism = synthetic construct
SEQUENCE: 227
ccgccgccgc cgccg                                              15

SEQ ID NO: 228     moltype = RNA  length = 30
FEATURE            Location/Qualifiers
misc_feature       1..30
                   note = /note="This sequence may encompass 1-10 'gcc'
                    repeating units"
source             1..30
                   mol_type = other RNA
                   organism = synthetic construct
SEQUENCE: 228
gccgccgccg ccgccgccgc cgccgccgcc                              30

SEQ ID NO: 229     moltype = DNA  length = 120
FEATURE            Location/Qualifiers
source             1..120
                   mol_type = other DNA
                   organism = synthetic construct
SEQUENCE: 229
aaaaaaaaaa aaaaaaaaaa aaaaaaaaaa aaaaaaaaaa aaaaaaaaaa aaaaaaaaaa  60
aaaaaaaaaa aaaaaaaaaa aaaaaaaaaa aaaaaaaaaa aaaaaaaaaa aaaaaaaaaa  120

SEQ ID NO: 230     moltype = DNA  length = 120
FEATURE            Location/Qualifiers
source             1..120
                   mol_type = other DNA
                   organism = synthetic construct
SEQUENCE: 230
tttttttttt tttttttttt tttttttttt tttttttttt tttttttttt tttttttttt  60
tttttttttt tttttttttt tttttttttt tttttttttt tttttttttt tttttttttt  120

SEQ ID NO: 231     moltype = RNA  length = 19
FEATURE            Location/Qualifiers
source             1..19
                   mol_type = other RNA
                   organism = synthetic construct
SEQUENCE: 231
tttaattagc tcataattc                                         19

SEQ ID NO: 232     moltype = DNA  length = 68
FEATURE            Location/Qualifiers
source             1..68
                   mol_type = other DNA
                   organism = synthetic construct
SEQUENCE: 232
agatctgaat tatgagctaa ttaaatacct gacccatatt taattagctc ataattcttt  60
ttggtacc                                                     68

SEQ ID NO: 233     moltype = DNA  length = 136
FEATURE            Location/Qualifiers
source             1..136
                   mol_type = other DNA
                   organism = synthetic construct
SEQUENCE: 233
ctcgagaaga aggtatattg ctgttgacag tgagcgacga attatgagct aattaaatag  60
tgaagcttca gatgtattta attagctcat aattcgctgc ctactgcctc ggacttcaag  120
gggtcagtca gaattc                                            136

SEQ ID NO: 234     moltype = AA  length = 15
FEATURE            Location/Qualifiers
source             1..15
                   mol_type = protein
                   organism = Homo sapiens
SEQUENCE: 234
AQAVHPGYGF LSENK                                              15

SEQ ID NO: 235     moltype = AA  length = 10
FEATURE            Location/Qualifiers
source             1..10
                   mol_type = protein
                   organism = Homo sapiens
SEQUENCE: 235
TVGIVGNQPK                                                   10
```

```
SEQ ID NO: 236          moltype = AA  length = 4
FEATURE                 Location/Qualifiers
source                  1..4
                        mol_type = protein
                        organism = synthetic construct
SEQUENCE: 236
GGGS                                                                    4

SEQ ID NO: 237          moltype = AA  length = 20
FEATURE                 Location/Qualifiers
SITE                    1..20
                        note = /note="This sequence may encompass 2-5 'Gly Gly Gly
                         Ser' repeating units"
source                  1..20
                        mol_type = protein
                        organism = synthetic construct
SEQUENCE: 237
GGGSGGGSGG GSGGGSGGGS                                                   20

SEQ ID NO: 238          moltype = AA  length = 728
FEATURE                 Location/Qualifiers
source                  1..728
                        mol_type = protein
                        organism = synthetic construct
SEQUENCE: 238
MAGFWVGTAP LVAAGRRGRW PPQQLMLSAA LRTLKHVLYY SRQCLMVSRN LGSVGYDPNE  60
KTFDKILIAN RGEIACRVIR TCKKMGIKTV AIHSDVDASS VHVKMADEAV CVGPAPTSKS  120
YLNMDAIMEA IKKTRAQAVH PGYGFLSENK EFARCLAAED VVFIGPDTHA IQAMGDKIES  180
KLLAKKAEVN TIPGFDGVVK DAEEAVRIAR EIGYPVMIKA SAGGGGKGMR IAWDDEETRD  240
GFRLSSQEAA SSFGDDRLLI EKFIDNPRHI EIQVLGDKHG NALWLNEREC SIQRRNQKVV  300
EEAPSIFLDA ETRRAMGEQA VALARAVKYS SAGTVEFLVD SKKNFYFLEM NTRLQVEHPV  360
TECITGLDLV QEMIRVAKGY PLRHKQADIR INGWAVECRV YAEDPYKSFG LPSIGRLSQY  420
QEPLHLPGVR VDSGIQPGSD ISIYYDPMIS KLITYGSDRT EALKRMEDAL DNYVIRGVTH  480
NIALLREVII NSRFVKGDIS TKFLSDVYPD GFKGHMLTKS EKNQLLAIAS SLFVAFQLRA  540
QHFQENSRVP VIKPDIANWE LSVKLHDKVH TVVASNNGSV FSVEVDGSKL NVTSTWNLAS  600
PLLSVSVDGT QRTVQCLSRE AGGNMSIQFL GTVYKVNILT RLAAELNKFM LEKVTEDTSS  660
VLRSPMPGVV VAVSVKPGDA VAEGQEICVI EAMKMQNSMT AGKTGTVKSV HCQAGDTVGE  720
GDLLVELE                                                            728
```

What is claimed is:

1. A messenger RNA (mRNA) comprising:

(i) a 5'-terminal cap;

(ii) a 5' untranslated region (UTR);

(iii) an open reading frame (ORF) encoding the propionyl-CoA carboxylase alpha (PCCA) polypeptide set forth in SEQ ID NO:1, wherein the ORF has at least 93% sequence identity to the nucleic acid sequence set forth in SEQ ID NO:11;

(iv) a 3' UTR; and (v) a poly-A-region.

2. The mRNA of claim 1, wherein the ORF has at least 95% sequence identity to the nucleic acid sequence set forth in SEQ ID NO:11.

3. The mRNA of claim 1, wherein the ORF has at least 98% sequence identity to the nucleic acid sequence set forth in SEQ ID NO:11.

4. The mRNA of claim 1, wherein the ORF has at least 99% sequence identity to the nucleic acid sequence set forth in SEQ ID NO:11.

5. The mRNA of claim 1, wherein the ORF has the nucleic acid sequence set forth in SEQ ID NO: 11.

6. The mRNA of claim 1, wherein the 5' UTR comprises the nucleic acid sequence set forth in SEQ ID NO:199.

7. The mRNA of claim 1, wherein the 3' UTR comprises the nucleic acid sequence set forth in SEQ ID NO:178.

8. The mRNA of claim 1, wherein the 5' UTR comprises the nucleic acid sequence set forth in SEQ ID NO:199, and wherein the 3' UTR comprises the nucleic acid sequence set forth in SEQ ID NO:178.

9. The mRNA of claim 1, comprising the nucleic acid sequence set forth in SEQ ID NO:203.

10. The mRNA of claim 1, wherein the poly-A region is at least 100 nucleotides in length.

11. The mRNA of claim 1, wherein all of the uracils are N1-methylpseudouracils.

12. The mRNA of claim 5, wherein the poly-A region is at least 100 nucleotides in length.

13. The mRNA of claim 5, wherein all of the uracils are N1-methylpseudouracils.

14. The mRNA of claim 9, wherein the poly-A region is at least 100 nucleotides in length.

15. The mRNA of claim 9, wherein all of the uracils are N1-methylpseudouracils.

16. The mRNA of claim 14, wherein all of the uracils are N1-methylpseudouracils.

17. A pharmaceutical composition comprising a first mRNA and a second mRNA, wherein the first mRNA comprises (i) a first 5'-terminal cap, (ii) a first 5' UTR, (iii) a first ORF encoding the PCCA polypeptide set forth in SEQ ID NO:1, wherein the ORF has at least 93% sequence identity to the nucleic acid sequence set forth in SEQ ID NO:11, (iv) a first 3' UTR, and (v) a first poly-A-region, and wherein the second mRNA comprises (i) a second 5'-terminal cap, (ii) a second 5' UTR, (iii) a second ORF encoding the PCCB polypeptide set forth in SEQ ID NO:15, wherein the ORF has at least 93% sequence identity to the nucleic acid sequence set forth in SEQ ID NO:25, (iv) a second 3' UTR, and (v) a second poly-A-region.

18. The pharmaceutical composition of claim 17, wherein the first ORF has at least 95% sequence identity to the nucleic acid sequence set forth in SEQ ID NO: 11, and wherein the second ORF has at least 95% sequence identity to the nucleic acid sequence set forth in SEQ ID NO:25.

19. The pharmaceutical composition of claim 17, wherein the first ORF has at least 98% sequence identity to the nucleic acid sequence set forth in SEQ ID NO: 11, and wherein the second ORF has at least 98% sequence identity to the nucleic acid sequence set forth in SEQ ID NO:25.

20. The pharmaceutical composition of claim 17, wherein the first ORF has at least 99% sequence identity to the nucleic acid sequence set forth in SEQ ID NO: 11, and wherein the second ORF has at least 99% sequence identity to the nucleic acid sequence set forth in SEQ ID NO:25.

21. The pharmaceutical composition of claim 17, wherein the first ORF has to the nucleic acid sequence set forth in SEQ ID NO:11, and wherein the second ORF has the nucleic acid sequence set forth in SEQ ID NO:25.

22. The pharmaceutical composition of claim 17, wherein the first 5' UTR comprises the nucleic acid sequence set forth in SEQ ID NO: 199, wherein the first 3' UTR comprises the nucleic acid sequence set forth in SEQ ID NO:178, wherein the second 5' UTR comprises the nucleic acid sequence set forth in SEQ ID NO: 199, and wherein the second 3' UTR comprises the nucleic acid sequence set forth in SEQ ID NO:178.

23. The pharmaceutical composition of claim 17, wherein the first mRNA comprises the nucleic acid sequence set forth

32. The pharmaceutical composition of claim 31, wherein the lipid nanoparticle comprises an ionizable lipid, a structural lipid, a phospholipid, and a polyethylene glycol (PEG)-modified lipid.

33. The pharmaceutical composition of claim 32, wherein the ionizable lipid is (Compound II)

or a salt thereof, wherein the structural lipid is cholesterol, wherein the phospholipid is 1,2-distearoyl-sn-glycero-3-phosphocholine (DSPC) or 1,2-dioleoyl-sn-glycero-3-phosphoethanolamine (DOPE), and wherein the PEG-modified lipid is 1,2-dimyristoyl-sn-glycerol methoxypolyethylene glycol (PEG-DMG) or Compound I (Compound I)

in SEQ ID NO:203, and wherein the second mRNA comprises the nucleic acid sequence set forth in SEQ ID NO:205.

24. The pharmaceutical composition of claim 17, wherein the first poly-A region is at least 100 nucleotides in length, and wherein the second poly-A region is at least 100 nucleotides in length.

25. The pharmaceutical composition of claim 17, wherein all of the uracils of the first mRNA are N1-methylpseudouracils, and wherein all of the uracils of the second mRNA are N1-methylpseudouracils.

26. The pharmaceutical composition of claim 21, wherein the first poly-A region is at least 100 nucleotides in length, and wherein the second poly-A region is at least 100 nucleotides in length.

27. The pharmaceutical composition of claim 21, wherein all of the uracils of the first mRNA are N1-methylpseudouracils, and wherein all of the uracils of the second mRNA are N1-methylpseudouracils.

28. The pharmaceutical composition of claim 23, wherein the first poly-A region is at least 100 nucleotides in length, and wherein the second poly-A region is at least 100 nucleotides in length.

29. The pharmaceutical composition of claim 23, wherein all of the uracils of the first mRNA are N1-methylpseudouracils, and wherein all of the uracils of the second mRNA are N1-methylpseudouracils.

30. The pharmaceutical composition of claim 28, wherein all of the uracils of the first mRNA are N1-methylpseudouracils, and wherein all of the uracils of the second mRNA are N1-methylpseudouracils.

31. The pharmaceutical composition of claim 17, wherein the first mRNA and the second mRNA are encapsulated into a lipid nanoparticle.

34. The pharmaceutical composition of claim 21, wherein the first mRNA and the second mRNA are encapsulated into a lipid nanoparticle.

35. The pharmaceutical composition of claim 34, wherein the lipid nanoparticle comprises an ionizable lipid, a structural lipid, a phospholipid, and a polyethylene glycol (PEG)-modified lipid.

36. The pharmaceutical composition of claim 35, wherein the ionizable lipid is (Compound II)

or a salt thereof, wherein the structural lipid is cholesterol, wherein the phospholipid is 1,2-distearoyl-sn-glycero-3-phosphocholine (DSPC) or 1,2-dioleoyl-sn-glycero-3-phosphoethanolamine (DOPE), and wherein the PEG-modified lipid is 1,2-dimyristoyl-sn-glycerol methoxypolyethylene glycol (PEG-DMG) or Compound I (Compound I)

37. The pharmaceutical composition of claim 25, wherein the first mRNA and the second mRNA are encapsulated into a lipid nanoparticle.

38. The pharmaceutical composition of claim 37, wherein the lipid nanoparticle comprises an ionizable lipid, a structural lipid, a phospholipid, and a polyethylene glycol (PEG)-modified lipid.

39. The pharmaceutical composition of claim 38, wherein the ionizable lipid is (Compound II)

or a salt thereof, wherein the structural lipid is cholesterol, wherein the phospholipid is 1,2-distearoyl-sn-glycero-3-phosphocholine (DSPC) or 1,2-dioleoyl-sn-glycero-3-phosphoethanolamine (DOPE), and wherein the PEG-modified lipid is 1,2-dimyristoyl-sn-glycerol methoxypolyethylene glycol PEG-DMG) or Compound I (Compound I)

40. The pharmaceutical composition of claim 27, wherein the first mRNA and the second mRNA are encapsulated into a lipid nanoparticle.

41. The pharmaceutical composition of claim 40, wherein the lipid nanoparticle comprises an ionizable lipid, a structural lipid, a phospholipid, and a polyethylene glycol (PEG)-modified lipid.

42. The pharmaceutical composition of claim 41, wherein the ionizable lipid is (Compound II)

or a salt thereof, wherein the structural lipid is cholesterol, wherein the phospholipid is 1,2-distearoyl-sn-glycero-3-phosphocholine (DSPC) or 1,2-dioleoyl-sn-glycero-3-phosphoethanolamine (DOPE), and wherein the PEG-modified lipid is 1,2-dimyristoyl-sn-glycerol methoxypolyethylene glycol (PEG-DMG) or Compound I 497 498

(Compound I)

\* \* \* \* \*